United States Patent
Schoenbrunner et al.

(10) Patent No.: US 7,148,049 B2
(45) Date of Patent: Dec. 12, 2006

(54) THERMOSTABLE OR THERMOACTIVE DNA POLYMERASE MOLECULES WITH ATTENUATED 3'-5' EXONUCLEASE ACTIVITY

(75) Inventors: Nancy J. Schoenbrunner, Moraga, CA (US); Thomas W. Myers, Alameda, CA (US); David H. Gelfand, Oakland, CA (US)

(73) Assignee: Roche Molecular Systems, Inc., Alameda, CA (US)

( * ) Notice: Subject to any disclaimer, the term of this patent is extended or adjusted under 35 U.S.C. 154(b) by 500 days.

(21) Appl. No.: 10/401,403

(22) Filed: Mar. 26, 2003

(65) Prior Publication Data

US 2004/0005599 A1     Jan. 8, 2004

Related U.S. Application Data

(60) Provisional application No. 60/369,815, filed on Apr. 2, 2002.

(51) Int. Cl.
*C12N 9/12*         (2006.01)

(52) U.S. Cl. ..................... 435/194; 435/196
(58) Field of Classification Search ............... None
See application file for complete search history.

(56) References Cited

U.S. PATENT DOCUMENTS

| | | | |
|---|---|---|---|
| 5,420,029 A | 5/1995 | Gelfand et al. | 435/194 |
| 5,948,614 A * | 9/1999 | Chatterjee | 435/6 |
| 6,218,150 B1 | 4/2001 | Uemori et al. | 435/91.1 |
| 6,228,628 B1 | 5/2001 | Gelfand et al. | 435/194 |

OTHER PUBLICATIONS

American Type Culture Collection webpage (http://www.atcc.org/common/catalog/wordSearch/results.cfm).*

* cited by examiner

*Primary Examiner*—James Martinell
(74) *Attorney, Agent, or Firm*—Townsend and Townsend and Crew LLP; Christopher Sappenfield

(57) ABSTRACT

The present invention provides thermostable or thermoactive DNA polymerases with attenuated 3'-5' exonuclease activity, methods for their synthesis, methods for their use, kits comprising the polymerases, nucleic acids encoding the polymerases and cells comprising such a nucleic acid. The DNA polymerases of the invention are useful in many recombinant DNA techniques, such as nucleic acid amplification by the polymerase chain reaction. The DNA polymerases of the invention allow higher fidelity replication and amplification of a template DNA sequence, allow less degradation of primers and/or more efficient use of deoxynucleotide triphosphates and are in general more efficient and less costly to make and use.

3 Claims, 30 Drawing Sheets

Figure 1A: Amino Acid Sequence Tma DNA Polymerase (SEQ ID NO:85)

```
  1  MARLFLFDGT ALAYRAYYAL DRSLSTSTGI PTNATYGVAR MLVRFIKDHI
 51  IVGKDYVAVA FDKKAATFRH KLLETYKAQR PKTPDLLIQQ LPYIKKLVEA
101  LGMKVLEVEG YEADDIIATL AVKGLPLFDE IFIVTGDKDM LQLVNEKIKV
151  WRIVKGISDL ELYDAQKVKE KYGVEPQQIP DLLALTGDEI DNIPGVTGIG
201  EKTAVQLLEK YKDLEDILNH VRELPQKVRK ALLRDRENAI LSKKLAILET
251  NVPIEINWEE LRYQGYDREK LLPLLKELEF ASIMKELQLY EESEPVGYRI
301  VKDLVEFEKL IEKLRESPSF AIDLETSSLD PFDCDIVGIS VSFKPKEAYY
351  IPLHHRNAQN LDEKEVLKKL KEILEDPGAK IVGQNLKFDY KVLMVKGVEP
401  VPPYFDTMIA AYLLEPNEKK FNLDDLALKF LGYKMTSYQE LMSFSFPLFG
451  FSFADVPVEK AANYSCEDAD ITYRLYKTLS LKLHEADLEN VFYKIEMPLV
501  NVLARMELNG VYVDTEFLKK LSEEYGKKLE ELAEEIYRIA GEPFNINSPK
551  QVSRILFEKL GIKPRGKTTK TGDYSTRIEV LEELAGEHEI IPLILEYRKI
601  QKLKSTYIDA LPKMVNPKTG RIHASFNQTG TATGRLSSSD PNLQNLPTKS
651  EEGKEIRKAI VPQDPNWWIV SADYSQIELR ILAHLSGDEN LLRAFEEGID
701  VHTLTASRIF NVKPEEVTEE MRRAGKMVNF SIIYGVTPYG LSVRLGVPVK
751  EAEKMIVNYF VLYPKVRDYI QRVVSEAKEK GYVRTLFGRK RDIPQLMARD
801  RNTQAEGERI AINTPIQGTA ADIIKLAMIE IDRELKERKM RSKMIIQVHD
851  ELVFEVPNEE KDALVELVKD RMTNVVKLSV PLEVDVTIGK TWS
```

Figure 1B: Nucleic Acid Sequence of Tma DNA Polymerase (SEQ ID NO:87)

```
   1  ATGGCGAGAC TATTTCTCTT TGATGGAACT GCTCTGGCCT ACAGAGCGTA
  51  CTATGCGCTC GATAGATCGC TTTCTACTTC CACCGGCATT CCCACAAACG
 101  CCACATACGG TGTGGCGAGG ATGCTGGTGA GATTCATCAA GACCATATC
 151  ATTGTCGGAA AAGACTACGT TGCTGTGGCT TTCGACAAAA AAGCTGCCAC
 201  CTTCAGACAC AAGCTCCTCG AGACTTACAA GGCTCAAAGA CCAAAGACTC
 251  CGGATCTCCT GATTCAGCAG CTTCCGTACA TAAAGAAGCT GGTCGAAGCC
 301  CTTGGAATGA AAGTGCTGGA GGTAGAAGGA TACGAAGCGG ACGATATAAT
 351  TGCCACTCTC GCTGTGAAGG GGCTTCCGCT TTTTGATGAA ATATTCATAG
 401  TGACCGGAGA TAAAGACATG CTTCAGCTTG TGAACGAAAA GATCAAGGTG
 451  TGGCGAATCG TAAAAGGGAT ATCCGATCTG GAACTTTACG ATGCGCAGAA
 501  GGTGAAGGAA AAATACGGTG TTGAACCCCA GCAGATCCCG GATCTTCTGG
 551  CTCTAACCGG AGATGAAATA GACAACATCC CCGCTGTAAC TGGGATAGGT
 601  GAAAAGACTG CTGTTCAGCT TCTAGAGAAG TACAAAGACC TCGAAGACAT
 651  ACTGAATCAT GTTCGCGAAC TTCCTCAAAA GGTGAGAAAA GCCCTGCTTC
 701  GAGACAGAGA AAACGCCATT CTCAGCAAAA AGCTGGCGAT TCTGGAAACA
 751  AACGTTCCCA TTGAAATAAA CTGGGAAGAA CTTCGCTACC AGGGCTACGA
 801  CAGAGAGAAA CTCTTACCAC TTTTGAAAGA ACTGGAATTC GCATCCATCA
 851  TGAAGGAACT TCAACTGTAC GAAGAGTCCG AACCCGTTGG ATACAGAATA
 901  GTGAAAGACC TAGTGGAATT TGAAAAACTC ATAGAGAAAC TGAGAGAATC
 951  CCCTTCGTTC GCCATAGATC TTGAGACGTC TTCCCTCGAT CCTTTCGACT
1001  GCGACATTGT CGGTATCTCT GTGTCTTTCA AACCAAAGGA AGCGTACTAC
1051  ATACCACTCC ATCATAGAAA CGCCCAGAAC CTGGACGAAA AAGAGGTTCT
1101  GAAAAAGCTC AAAGAAATTC TGGAGGACCC CGGAGCAAAG ATCGTTGGTC
1151  AGAATTTGAA ATTCGATTAC AAGGTGTTGA TGGTGAAGGG TGTTGAACCT
1201  GTTCCTCCTT ACTTCGACAC GATGATAGCG GCTTACCTTC TTGAGCCGAA
1251  CGAAAAGAAG TTCAATCTGG ACGATCTCGC ATTGAAATTT CTTGGATACA
1301  AAATGACATC TTACCAAGAG CTCATGTCCT TCTCTTTTCC GCTGTTTGGT
1351  TTCAGTTTTG CCGATGTTCC TGTAGAAAAA GCAGCGAACT ACTCCTGTGA
1401  AGATGCAGAC ATCACCTACA GACTTTACAA GACCCTGAGC TTAAAACTCC
1451  ACGAGGCAGA TCTGGAAAAC GTGTTCTACA AGATAGAAAT GCCCCTTGTG
```

FIG 1B (Continued)

```
1501  AACGTGCTTG CACGGATGGA ACTGAACGGT GTGTATGTGG ACACAGAGTT
1551  CCTGAAGAAA CTCTCAGAAG AGTACGGAAA AAAACTCGAA GAACTGGCAG
1601  AGGAAATATA CAGGATAGCT GGAGAGCCGT TCAACATAAA CTCACCGAAG
1651  CAGGTTTCAA GGATCCTTTT TGAAAAACTC GGCATAAAAC CACGTGGTAA
1701  AACGACGAAA ACGGGAGACT ATTCAACACG CATAGAAGTC CTCGAGGAAC
1751  TTGCCGGTGA ACACGAAATC ATTCCTCTGA TTCTTGAATA CAGAAAGATA
1801  CAGAAATTGA AATCAACCTA CATAGACGCT CTTCCCAAGA TGGTCAACCC
1851  AAAGACCGGA AGGATTCATG CTTCTTTCAA TCAAACGGGG ACTGCCACTG
1901  GAAGACTTAG CAGCAGCGAT CCCAATCTTC AGAACCTCCC GACGAAAAGT
1951  GAAGAGGGAA AAGAAATCAG GAAAGCGATA GTTCCTCAGG ATCCAAACTG
2001  GTGGATCGTC AGTGCCGACT ACTCCCAAAT AGAACTGAGG ATCCTCGCCC
2051  ATCTCAGTGG TGATGAGAAT CTTTTGAGGG CATTCGAAGA GGGCATCGAC
2101  GTCCACACTC TAACAGCTTC CAGAATATTC AACGTGAAAC CCGAAGAAGT
2151  AACCGAAGAA ATGCGCCGCG CTGGTAAAAT GGTTAATTTT TCCATCATAT
2201  ACGGTGTAAC ACCTTACGGT CTGTCTGTGA GGCTTGGAGT ACCTGTGAAA
2251  GAAGCAGAAA AGATGATCGT CAACTACTTC GTCCTCTACC CAAAGGTGCG
2301  CGATTACATT CAGAGGGTCG TATCGGAAGC GAAAGAAAAA GGCTATGTTA
2351  GAACGCTGTT TGGAAGAAAA AGAGACATAC CACAGCTCAT GGCCCGGGAC
2401  AGGAACACAC AGGCTGAAGG AGAACGAATT GCCATAAACA CTCCCATACA
2451  GGGTACAGCA GCGGATATAA TAAAGCTGGC TATGATAGAA ATAGACAGGG
2501  AACTGAAAGA AAGAAAAATG AGATCGAAGA TGATCATACA GGTCCACGAC
2551  GAACTGGTTT TTGAAGTGCC CAATGAGGAA AAGGACGCGC TCGTCGAGCT
2601  GGTGAAAGAC AGAATGACGA ATGTGGTAAA GCTTTCAGTG CCGCTCGAAG
2651  TGGATGTAAC CATCGGCAAA ACATGGTCGT GA
```

Figure 2: Sequence from the region of the Tne DNA Polymerase 3'-5' Exonuclease Domain (SEQ ID NO:88)

```
292   EAEPTGYEIV KDHKTFEDLI EKLKEVPSFA LDLETSSLDP FNCEIVGISV SFKPKTAYYI

352   PLHHRNAQNL DETLVLSKLK EILEDPSSKI VGQNLKYDYK VLMVKGISPV YPHFDTMIAA

412   YLLEPNEKKF NLEDLSLKFL GYKMTSYQEL MSFSSPLFGF SFADVPVDKA ANYSCEDADI

472   TYRLYKILSM KLHEAE  487
```

Figure 3: Sequence from the region of the Taf DNA Polymerase 3'-5' Exonuclease Domain (SEQ ID NO:89)

```
293   KLEKEYILVD  NEDKLKKLAE  EIEKYKTFSI  DTETTSLDPF  EAKLVGISIS  TMEGKAYYIP

353   VSHFGAKNIS  KSLIDKFLKQ  ILQEKDYNIV  GQNLKFDYEI  FKSMGFSPNV  PHFDTMIAAY

413   LLNPDEKRFN  LEELSLKYLG  YKMISFDELV  NENVPLFGND  FSYVPLERAV  EYSCEDADVT

473   YRIFRKLGRK  IYENE  487
```

Figure 4A: Amino acid sequence of CS5 DNA Polymerase (SEQ ID NO:90)

```
  1  MKAMLPLFEP KGRVLLVDGH HLAYRTFFAL KGLTTSRGEP VQAVYGFAKS
 51  LLKALKEDGY KAVFVVFDAK APSFRHEAYE AYKAGRAPTP EDFPRQLALI
101  KELVDLLGFT RLEVPGFEAD DVLATLAKKA EREGYEVRIL TADRDLYQLV
151  SDRVAVLHPE GHLITPEWLW EKYGLKPEQW VDFRALVGDP SDNLPGVKGI
201  GEKTALKLLK EWGSLENILK NLDRVKPESV RERIKAHLED LKLSLELSRV
```

Z05   → →  Tma
```
251  RSDLPLEVDF ARRREPDREG LRAFLERLEF GSLLHEFGLL EESEPVGYRI
```

A
```
301  VKDLVEFEKL IEKLRESPSF AIDLETSSLD PFDCDIVGIS VSFKPKEAYY
```

AA    E
```
351  IPLHHRNAQN LDEKEVLKKL KEILEDPGAK IVGQNLKFDY KVLMVKGVEP
401  VPPYFDTMIA AYLLEPNEKK FNLDDLALKF LGYKMTSYQE LMSFSFPLFG
```

A
```
451  FSFADVPVEK AANYSCEDAD ITYRLYKTLS LKLHEADLEN VFYKIEMPLV
501  NVLARMELNG VYVDTEFLKK LSEEYGKKLE ELAEEIYRIA GEPFNINSPK
551  QVSRILFEKL GIKPRGKTTK TGDYSTRIEV LEELAGEHEI IPLILEYRKI
601  QKLKSTYIDA LPKMVNPKTG RIHASFNQTG TATGRLSSSD PNLQNLPTKS
651  EEGKEIRKAI VPQDPNWWIV SADYSQIELR ILAHLSGDEN LLRAFEEGID
701  VHTLTASRIF NVKPEEVTEE MRRAGKMVNF SIIYGVTPYG LSVRLGVPVK
751  EAEKMIVNYF VLYPKVRDYI QRVVSEAKEK GYVRTLFGRK RDIPQLMARD
801  RNTQAEGERI AINTPIQGTA ADIIKLAMIE IDRELKERKM RSKMIIQVHD
851  ELVFEVPNEE KDALVELVKD RMTNVVKLSV PLEVDVTIGK TWS
```

FIGURE 4B: Nucleic Acid Sequence OF CS5 DNA Polymerase (SEQ ID NO:106)

```
   1  ATGAAAGCTA TGTTACCATT ATTCGAACCC AAAGGCCGGG TCCTCCTGGT
  51  GGACGGCCAC CACCTGGCCT ACCGCACCTT CTTCGCCCTG AAGGGCCTCA
 101  CCACGAGCCG GGGCGAACCG GTGCAGGCGG TTTACGGCTT CGCCAAGAGC
 151  CTCCTCAAGG CCCTGAAGGA GGACGGGTAC AAGGCCGTCT TCGTGGTCTT
 201  TGACGCCAAG GCCCCTTCCT TCCGCCACGA GGCCTACGAG GCCTACAAGG
 251  CAGGCCGCGC CCCGACCCCC GAGGACTTCC CCCGGCAGCT CGCCCTCATC
 301  AAGGAGCTGG TGGACCTCCT GGGGTTTACT CGCCTCGAGG TTCCGGGCTT
 351  TGAGGCGGAC GACGTCCTCG CCACCCTGGC CAAGAAGGCG GAAAGGGACG
 401  GGTACGAGGT GCGCATCCTC ACCGCCGACC GGGACCTTTA CCAGCTCGTC
 451  TCCGACCGCG TCGCCGTCCT CCACCCCGAG GGCCACCTCA TCACCCCGGA
 501  GTGGCTTTGG GAGAAGTACG GCCTTAAGCC GGAGCAGTGG GTGGACTTCC
 551  GCGCCCTCGT GGGGGACCCC TCCGACAACC TCCCCGGGGT CAAGGGCATC
 601  GGGGAGAAGA CCGCCCTCAA GCTCCTCAAG GAGTGGGGAA GCCTGGAAAA
 651  TATCCTCAAG AACCTGGACC GGGTGAAGCC GGAAAGCGTC CGGGAAAGGA
 701  TCAAGGCCCA CCTGGAAGAC CTTAAGCTCT CCTTGGAGCT TTCCCGGGTG
 751  CGCTCGGACC TCCCCCTGGA GGTGGACTTC GCCCGGAGGC GGGAGCCTGA
 801  CCGGGAAGGG CTTCGGGCCT TTTTGGAGCG CTTGGAGTTC GGCAGCCTCC
 851  TCCACGAGTT CGGCCTTCTA GAGGAGTCCC AACCCGTTGG GTACCGTATA
 901  GTTAAAGACC TGGTTGAATT TGAAAAACTC ATAGAGAAAC TGAGAGAATC
 951  TCCTTCGTTC GCTATCGATT TGGAAACTAG TTCCCTCGAT CCTTTCGACT
1001  GCGACATTGT CGGTATCTCT GTGTCTTTCA AACCAAAGGA AGCGTACTAC
1051  ATACCACTCC ATCATAGAAA CGCCCAGAAC CTGGACGAAA AGAGGTTCT
1101  GAAAAAGCTC AAAGAAATTC TGGAGGACCC CGGAGCAAAG ATCGTTGGTC
1151  AGAATTTGAA ATTCGATTAC AAGGTGTTGA TGGTGAAGGG TGTTGAACCT
1201  GTTCCTCCTT ACTTCGACAC GATGATAGCG GCTTACCTTC TTGAGCCGAA
1251  CGAAAAGAAG TTCAATCTGG ACGATCTCGC ATTGAAATTT CTTGGATACA
1301  AAATGACATC TTACCAAGAG CTCATGTCCT TCTCTTTTCC GCTGTTTGGT
1351  TTCAGTTTTG CCGATGTTCC TGTAGAAAAA GCAGCGAACT ACTCCTGTGA
1401  AGATGCAGAC ATCACCTACA GACTTTACAA GACCCTGAGC TTAAAACTCC
1451  ACGAGGCAGA TCTGGAAAAC GTGTTCTACA AGATAGAAAT GCCCCTTGTG
```

FIGURE 4B (Continued)

```
1501  AACGTGCTTG CACGGATGGA ACTGAACGGT GTGTATGTGG ACACAGAGTT
1551  CCTGAAGAAA CTCTCAGAAG AGTACGGAAA AAAACTCGAA GAACTGGCAG
1601  AGGAAATATA CAGGATAGCT GGAGAGCCGT TCAACATAAA CTCACCGAAG
1651  CAGGTTTCAA GGATCCTTTT TGAAAAACTC GGCATAAAAC CACGTGGTAA
1701  AACGACGAAA ACGGGAGACT ATTCAACACG CATAGAAGTC CTCGAGGAAC
1751  TTGCCGGTGA ACACGAAATC ATTCCTCTGA TTCTTGAATA CAGAAAGATA
1801  CAGAAATTGA AATCAACCTA CATAGACGCT CTTCCCAAGA TGGTCAACCC
1851  AAAGACCGGA AGGATTCATG CTTCTTTCAA TCAAACGGGG ACTGCCACTG
1901  GAAGACTTAG CAGCAGCGAT CCCAATCTTC AGAACCTCCC GACGAAAAGT
1951  GAAGAGGGAA AAGAAATCAG GAAAGCGATA GTTCCTCAGG ATCCAAACTG
2001  GTGGATCGTC AGTGCCGACT ACTCCCAAAT AGAACTGAGG ATCCTCGCCC
2051  ATCTCAGTGG TGATGAGAAT CTTTTGAGGG CATTCGAAGA GGGCATCGAC
2101  GTCCACACTC TAACAGCTTC CAGAATATTC AACGTGAAAC CCGAAGAAGT
2151  AACCGAAGAA ATGCGCCGCG CTGGTAAAAT GGTTAATTTT TCCATCATAT
2201  ACGGTGTAAC ACCTTACGGT CTGTCTGTGA GGCTTGGAGT ACCTGTGAAA
2251  GAAGCAGAAA AGATGATCGT CAACTACTTC GTCCTCTACC CAAAGGTGCG
2301  CGATTACATT CAGAGGGTCG TATCGGAAGC GAAAGAAAAA GGCTATGTTA
2351  GAACGCTGTT TGGAAGAAAA AGAGACATAC CACAGCTCAT GGCCCGGGAC
2401  AGGAACACAC AGGCTGAAGG AGAACGAATT GCCATAAACA CTCCCATACA
2451  GGGTACAGCA GCGGATATAA TAAAGCTGGC TATGATAGAA ATAGACAGGG
2501  AACTGAAAGA AGAAAAATG AGATCGAAGA TGATCATACA GGTCCACGAC
2551  GAACTGGTTT TTGAAGTGCC CAATGAGGAA AAGGACGCGC TCGTCGAGCT
2601  GGTGAAAGAC AGAATGACGA ATGTGGTAAA GCTTTCAGTG CCGCTCGAAG
2651  TGGATGTAAC CATCGGCAAA ACATGGTCGT GA
```

Figure 5A: Amino Acid Sequence CS6 DNA Polymerase (SEQ ID NO:107)

```
  1  MKAMLPLFEP KGRVLLVDGH HLAYRTFFAL KGLTTSRGEP VQAVYGFAKS
 51  LLKALKEDGY KAVFVVFDAK APSFRHEAYE AYKAGRAPTP EDFPRQLALI
101  KELVDLLGFT RLEVPGFEAD DVLATLAKKA EREGYEVRIL TADRDLYQLV
151  SDRVAVLHPE GHLITPEWLW EKYGLKPEQW VDFRALVGDP SDNLPGVKGI
201  GEKTALKLLK EWGSLENILK NLDRVKPESV RERIKAHLED LKLSLELSRV
```

```
                                             Z05    → →   Tma
251  RSDLPLEVDF ARRREPDREG LRAFLERLEF GSLLHEFGLL EESEPVGYRI
                                 DEE
                                 DDE
                                 DKE
                                 DNE
                                 DQE
                                 DHE
                                 DLD
                                 ELD
                                 ELE
301  VKDLVEFEKL IEKLRESPSF AIALATSSLD PFDCDIVGIS VSFKPKEAYY
351  IPLHHRNAQN LDEKEVLKKL KEILEDPGAK IVGQNLKFDY KVLMVKGVEP
```

```
401  VPPYFDTMIA AYLLEPNEKK FNLDDLALKF LGYKMTSYQE LMSFSFPLFG
451  FSFADVPVEK AANYSCEDAD ITYRLYKTLS LKLHEADLEN VFYKIEMPLV
501  NVLARMELNG VYVDTEFLKK LSEEYGKKLE ELAEEIYRIA GEPFNINSPK
551  QVSRILFEKL GIKPRGKTTK TGDYSTRIEV LEELAGEHEI IPLILEYRKI
601  QKLKSTYIDA LPKMVNPKTG RIHASFNQTG TATGRLSSSD PNLQNLPTKS
651  EEGKEIRKAI VPQDPNWWIV SADYSQIELR ILAHLSGDEN LLRAFEEGID
701  VHTLTASRIF NVKPEEVTEE MRRAGKMVNF SIIYGVTPYG LSVRLGVPVK
751  EAEKMIVNYF VLYPKVRDYI QRVVSEAKEK GYVRTLFGRK RDIPQLMARD
801  RNTQAEGERI AINTPIQGTA ADIIKLAMIE IDRELKERKM RSKMIIQVHD
851  ELVFEVPNEE KDALVELVKD RMTNVVKLSV PLEVDVTIGK TWS
```

Figure 5B: Nucleic Acid Sequence CS6 DNA Polymerase (SEQ ID NO:129)

```
   1 ATGAAAGCTA TGTTACCATT ATTCGAACCC AAAGGCCGGG TCCTCCTGGT
  51 GGACGGCCAC CACCTGGCCT ACCGCACCTT CTTCGCCCTG AAGGGCCTCA
 101 CCACGAGCCG GGGCGAACCG GTGCAGGCGG TTTACGGCTT CGCCAAGAGC
 151 CTCCTCAAGG CCCTGAAGGA GGACGGGTAC AAGGCCGTCT TCGTGGTCTT
 201 TGACGCCAAG GCCCCTTCCT TCCGCCACGA GGCCTACGAG GCCTACAAGG
 251 CAGGCCGCGC CCCGACCCCC GAGGACTTCC CCCGGCAGCT CGCCCTCATC
 301 AAGGAGCTGG TGGACCTCCT GGGGTTTACT CGCCTCGAGG TTCCGGGCTT
 351 TGAGGCGGAC GACGTCCTCG CCACCCTGGC CAAGAAGGCG GAAAGGGAGG
 401 GGTACGAGGT GCGCATCCTC ACCGCCGACC GGGACCTTTA CCAGCTCGTC
 451 TCCGACCGCG TCGCCGTCCT CCACCCCGAG GGCCACCTCA TCACCCCGGA
 501 GTGGCTTTGG GAGAAGTACG GCCTTAAGCC GGAGCAGTGG GTGGACTTCC
 551 GCGCCCTCGT GGGGGACCCC TCCGACAACC TCCCCGGGGT CAAGGGCATC
 601 GGGGAGAAGA CCGCCCTCAA GCTCCTCAAG GAGTGGGGAA GCCTGGAAAA
 651 TATCCTCAAG AACCTGGACC GGGTGAAGCC GGAAAGCGTC CGGGAAAGGA
 701 TCAAGGCCCA CCTGGAAGAC CTTAAGCTCT CCTTGGAGCT TTCCCGGGTG
 751 CGCTCGGACC TCCCCCTGGA GGTGGACTTC GCCCGGAGGC GGGAGCCTGA
 801 CCGGGAAGGG CTTCGGGCCT TTTTGGAGCG CTTGGAGTTC GGCAGCCTCC
 851 TCCACGAGTT CGGCCTTCTA GAGGAGTCCG AACCCGTTGG GTACCGTATA
 901 GTTAAAGACC TGGTTGAATT TGAAAAACTC ATAGAGAAAC TGAGAGAATC
 951 TCCTTCGTTC GCGATCGCTC TTGCGACTAG TTCCCTCGAT CCTTTCGACT
1001 GCGACATTGT CGGTATCTCT GTGTCTTTCA AACCAAAGGA AGCGTACTAC
1051 ATACCACTCC ATCATAGAAA CGCCCAGAAC CTGGACGAAA AGAGGTTCT
1101 GAAAAGCTC AAAGAAATTC TGGAGGACCC CGGAGCAAAG ATCGTTGGTC
1151 AGAATTTGAA ATTCGATTAC AAGGTGTTGA TGGTGAAGGG TGTTGAACCT
1201 GTTCCTCCTT ACTTCGACAC GATGATAGCG GCTTACCTTC TTGAGCCGAA
1251 CGAAAAGAAG TTCAATCTGG ACGATCTCGC ATTGAAATTT CTTGGATACA
1301 AAATGACATC TTACCAAGAG CTCATGTCCT TCTCTTTTCC GCTGTTTGGT
1351 TTCAGTTTTG CCGATGTTCC TGTAGAAAAA GCAGCGAACT ACTCCTGTGA
1401 AGATGCAGAC ATCACCTACA GACTTTACAA GACCCTGAGC TTAAAACTCC
1451 ACGAGGCAGA TCTGGAAAAC GTGTTCTACA AGATAGAAAT GCCCCTTGTG
```

FIGURE 5B (Continued)

```
1501  AACGTGCTTG CACGGATGGA ACTGAACGGT GTGTATGTGG ACACAGAGTT
1551  CCTGAAGAAA CTCTCAGAAG AGTACGGAAA AAAACTCGAA GAACTGGCAG
1601  AGGAAATATA CAGGATAGCT GGAGAGCCGT TCAACATAAA CTCACCGAAG
1651  CAGGTTTCAA GGATCCTTTT TGAAAAACTC GGCATAAAAC CACGTGGTAA
1701  AACGACGAAA ACGGGAGACT ATTCAACACG CATAGAAGTC CTCGAGGAAC
1751  TTGCCGGTGA ACACGAAATC ATTCCTCTGA TTCTTGAATA CAGAAAGATA
1801  CAGAAATTGA AATCAACCTA CATAGACGCT CTTCCCAAGA TGGTCAACCC
1851  AAAGACCGGA AGGATTCATG CTTCTTTCAA TCAAACGGGG ACTGCCACTG
1901  GAAGACTTAG CAGCAGCGAT CCCAATCTTC AGAACCTCCC GACGAAAAGT
1951  GAAGAGGGAA AAGAAATCAG GAAAGCGATA GTTCCTCAGG ATCCAAACTG
2001  GTGGATCGTC AGTGCCGACT ACTCCCAAAT AGAACTGAGG ATCCTCGCCC
2051  ATCTCAGTGG TGATGAGAAT CTTTTGAGGG CATTCGAAGA GGGCATCGAC
2101  GTCCACACTC TAACAGCTTC CAGAATATTC AACGTGAAAC CCGAAGAAGT
2151  AACCGAAGAA ATGCGCCGCG CTGGTAAAAT GGTTAATTTT TCCATCATAT
2201  ACGGTGTAAC ACCTTACGGT CTGTCTGTGA GGCTTGGAGT ACCTGTGAAA
2251  GAAGCAGAAA AGATGATCGT CAACTACTTC GTCCTCTACC CAAAGGTGCG
2301  CGATTACATT CAGAGGGTCG TATCGGAAGC GAAAGAAAAA GGCTATGTTA
2351  GAACGCTGTT TGGAAGAAAA AGAGACATAC CACAGCTCAT GGCCCGGGAC
2401  AGGAACACAC AGGCTGAAGG AGAACGAATT GCCATAAACA CTCCCATACA
2451  GGGTACAGCA GCGGATATAA TAAAGCTGGC TATGATAGAA ATAGACAGGG
2501  AACTGAAAGA AAGAAAAATG AGATCGAAGA TGATCATACA GGTCCACGAC
2551  GAACTGGTTT TTGAAGTGCC CAATGAGGAA AAGGACGCGC TCGTCGAGCT
2601  GGTGAAAGAC AGAATGACGA ATGTGGTAAA GCTTTCAGTG CCGCTCGAAG
2651  TGGATGTAAC CATCGGCAAA ACATGGTCGT GA
```

Figure 6A: Amino acid sequence of CS7 DNA Polymerase (SEQ ID NO:130)

```
  1  MKAMLPLFEP KGRVLLVDGH HLAYRTFFAL KGLTTSRGEP VQAVYGFAKS

51  LLKALKEDGY KAVFVVFDAK APSFRHEAYE AYKAGRAPTP EDFPRQLALI

101  KELVDLLGFT RLEVPGFEAD DVLATLAKKA EREGYEVRIL TADRDLYQLV

151  SDRVAVLHPE GHLITPEWLW EKYGLKPEQW VDFRALVGDP SDNLPGVKGI

201  GEKTALKLLK EWGSLENILK NLDRVKPESV RERIKAHLED LKLSLELSRV

Z05  → →   Tma
251  RSDLPLEVDF ARRREPDREG LRAFLERLEF GSLLHEFGLL EESEPVGYRI

A
301  VKDLVEFEKL IEKLRESPSF AIDLETSSLD PFDCDIVGIS VSFKPKEAYY

AA       E
351  IPLHHRNAQN LDEKEVLKKL KEILEDPGAK IVGQNLKFDY KVLMVKGVEP

401  VPPYFDTMIA AYLLEPNEKK FNLDDLALKF LGYKMTSYQE LMSFSFPLFG

A                   Tma  → →   Z05
451  FSFADVPVEK AANYSCEDAD ITYRLYKTLS LKLHEEKLLW LYQEVEKPLS

501  RVLAHMEATG VRLDVAYLKA LSLELAEEIR RLEEEVFRLA GHPFNLNSRD

551  QLERVLFDEL RLPALGKTQK TGKRSTSAAV LEALREAHPI VEKILQHREL

601  TKLKNTYVDP LPGLVHPRTG RLHTRFNQTA TATGRLSSSD PNLQNIPIRT

651  PLGQRIRRAF VAEAGWALVA LDYSQIELRV LAHLSGDENL IRVFQEGKDI

701  HTQTASWMFG VSPEAVDPLM RRAAKTVNFG VLYGMSAHRL SQELAIPYEE

751  AVAFIERYFQ SFPKVRAWIE KTLEEGRKRG YVETLFGRRR YVPDLNARVK

801  SVREAAERMA FNMPVQGTAA DLMKLAMVKL FPHLREMGAR MLLQVHDELL

851  LEAPQARAEE VAALAKEAME KAYPLAVPLE VEVGIGEDWL SAKG
```

Figure 6B: Nucleic Acid Sequence of CS7 DNA Polymerase (SESQ ID NO:147)

```
   1  ATGAAAGCTA TGTTACCATT ATTCGAACCC AAAGGCCGGG TCCTCCTGGT
  51  GGACGGCCAC CACCTGGCCT ACCGCACCTT CTTCGCCCTG AAGGGCCTCA
 101  CCACGAGCCG GGGCGAACCG GTGCAGGCGG TTTACGGCTT CGCCAAGAGC
 151  CTCCTCAAGG CCCTGAAGGA GGACGGGTAC AAGGCCGTCT TCGTGGTCTT
 201  TGACGCCAAG GCCCCTTCCT TCCGCCACGA GGCCTACGAG GCCTACAAGG
 251  CAGGCCGCGC CCCGACCCCC GAGGACTTCC CCCGGCAGCT CGCCCTCATC
 301  AAGGAGCTGG TGGACCTCCT GGGGTTTACT CGCCTCGAGG TTCCGGGCTT
 351  TGAGGCGGAC GACGTCCTCG CCACCCTGGC CAAGAAGGCG GAAAGGGAGG
 401  GGTACGAGGT GCGCATCCTC ACCGCCGACC GGGACCTTTA CCAGCTCGTC
 451  TCCGACCGCG TCGCCGTCCT CCACCCCGAG GGCCACCTCA TCACCCCGGA
 501  GTGGCTTTGG GAGAAGTACG GCCTTAAGCC GGAGCAGTGG GTGGACTTCC
 551  GCGCCCTCGT GGGGGACCCC TCCGACAACC TCCCCGGGGT CAAGGGCATC
 601  GGGGAGAAGA CCGCCCTCAA GCTCCTCAAG GAGTGGGGAA GCCTGGAAAA
 651  TATCCTCAAG AACCTGGACC GGGTGAAGCC GGAAAGCGTC CGGGAAAGGA
 701  TCAAGGCCCA CCTGGAAGAC CTTAAGCTCT CCTTGGAGCT TTCCCGGGTG
 751  CGCTCGGACC TCCCCCTGGA GGTGGACTTC GCCCGGAGGC GGGAGCCTGA
 801  CCGGGAAGGG CTTCGGGCCT TTTTGGAGCG CTTGGAGTTC GGCAGCCTCC
 851  TCCACGAGTT CGGCCTTCTA GAGGAGTCCG AACCCGTTGG GTACCGTATA
 901  GTTAAAGACC TGGTTGAATT TGAAAAACTC ATAGAGAAAC TGAGAGAATC
 951  TCCTTCGTTC GCTATCGATT TGGAAACTAG TTCCCTCGAT CCTTTCGACT
1001  GCGACATTGT CGGTATCTCT GTGTCTTTCA AACCAAAGGA AGCGTACTAC
1051  ATACCACTCC ATCATAGAAA CGCCCAGAAC CTGGACGAAA AAGACGTTCT
1101  GAAAAAGCTC AAAGAAATTC TGGAGGACCC CGGAGCAAAG ATCGTTGGTC
1151  AGAATTTGAA ATTCGATTAC AAGGTGTTGA TGGTGAAGGG TGTTGAACCT
1201  GTTCCTCCTT ACTTCGACAC GATGATAGCG GCTTACCTTC TTGAGCCGAA
1251  CGAAAAGAAG TTCAATCTGG ACGATCTCGC ATTGAAATTT CTTGGATACA
1301  AAATGACATC TTACCAAGAG CTCATGTCCT TCTCTTTTCC GCTGTTTGGT
1351  TTCAGTTTTG CCGATGTTCC TGTAGAAAAA GCAGCGAACT ACTCCTGTGA
1401  AGATGCAGAC ATCACCTACA GACTTTACAA GACCCTGAGC TTAAAACTCC
1451  ACGAGGAAAA GCTTCTTTGG CTCTACCAAG AGGTGGAAAA GCCCCTCTCC
```

FIGURE 6B (Continued)

```
1501 CGGGTCCTGG CCCACATGGA GGCCACCGGG GTAAGGCTGG ACGTGGCCTA

1551 TCTAAAGGCC CTTTCCCTGG AGCTTGCGGA GGAGATTCGC CGCCTCGAGG

1601 AGGAGGTCTT CCGCCTGGCG GGCCACCCCT TCAACCTGAA CTCCCGTGAC

1651 CAGCTAGAGC GGGTGCTCTT TGACGAGCTT AGGCTTCCCG CCCTGGGCAA

1701 GACGCAAAAG ACGGGGAAGC GCTCCACCAG CGCCGCGGTG CTGGAGGCCC

1751 TCAGGGAGGC CCACCCCATC GTGGAGAAGA TCCTCCAGCA CCGGGAGCTC

1801 ACCAAGCTCA GAACACCTA CGTGGACCCC CTCCCGGGCC TCGTCCACCC

1851 GAGGACGGGC CGCCTCCACA CCCGCTTCAA CCAGACAGCC ACGGCCACGG

1901 GAAGGCTCTC TAGCTCCGAC CCCAACCTGC AGAACATCCC CATCCGCACC

1951 CCCTTGGGCC AGAGGATCCG CCGGGCCTTC GTGGCCGAGG CGGGATGGGC

2001 GTTGGTGGCC CTGGACTATA GCCAGATAGA GCTCCGGGTC CTCGCCCACC

2051 TCTCCGGGGA CGAGAACCTG ATCAGGGTCT TCCAGGAGGG GAAGGACATC

2101 CACACCCAGA CCGCAAGCTG GATGTTCGGC GTCTCCCCGG AGGCCGTGGA

2151 CCCCCTGATG CGCCGGGCGG CCAAGACGGT GAACTTCGGC GTCCTCTACG

2201 GCATGTCCGC CCATAGGCTC TCCCAGGAGC TTGCCATCCC CTACGAGGAG

2251 GCGGTGGCCT TTATAGAGCG CTACTTCCAA AGCTTCCCCA AGGTGCGGGC

2301 CTGGATAGAA AAGACCCTGG AGGAGGGGAG GAAGCGGGGC TACGTGGAAA

2351 CCCTCTTCGG AAGAAGGCGC TACGTGCCCG ACCTCAACGC CCGGGTGAAG

2401 AGCGTCAGGG AGGCCGCGGA GCGCATGGCC TTCAACATGC CCGTCCAGGG

2451 CACCGCCGCC GACCTCATGA AGCTCGCCAT GGTGAAGCTC TTCCCCCACC

2501 TCCGGGAGAT GGGGGCCCGC ATGCTCCTCC AGGTCCACGA CGAGCTCCTC

2551 CTGGAGGCCC CCCAAGCGCG GGCCGAGGAG GTGGCGGCTT TGGCCAAGGA

2601 GGCCATGGAG AAGGCCTATC CCCTCGCCGT GCCCCTGGAG GTGGAGGTGG

2651 GGATCGGGGA GGACTGGCTT TCCGCCAAGG GCTGA
```

Figure 7A: Amino acid sequence of CS8 DNA Polymerase (SEQ ID NO:148)

```
  1  MKAMLPLFEP KGRVLLVDGH HLAYRTFFAL KGLTTSRGEP VQAVYGFAKS
 51  LLKALKEDGY KAVFVVFDAK APSFRHEAYE AYKAGRAPTP EDFPRQLALI
101  KELVDLLGFT RLEVPGFEAD DVLATLAKKA EREGYEVRIL TADRDLYQLV
151  SDRVAVLHPE GHLITPEWLW EKYGLKPEQW VDFRALVGDP SDNLPGVKGI
201  GEKTALKLLK EWGSLENILK NLDRVKPESV RERIKAHLED LKLSLELSRV
                                              Z05  → →  Tma
251  RSDLPLEVDF ARRREPDREG LRAFLERLEF GSLLHEFGLL EESEPVGYRI
                     DEE
                     DDE
                     DKE
                     DNE
                     DQE
                     DHE
                     DLD
                     ELD
                     ELE
301  VKDLVEFEKL IEKLRESPSF AIALATSSLD PFDCDIVGIS VSFKPKEAYY
351  IPLHHRNAQN LDEKEVLKKL KEILEDPGAK IVGQNLKFDY KVLMVKGVEP
401  VPPYFDTMIA AYLLEPNEKK FNLDDLALKF LGYKMTSYQE LMSFSFPLFG
                                   Tma  → →  Z05
451  FSFADVPVEK AANYSCEDAD ITYRLYKTLS LKLHEEKLLW LYQEVEKPLS
501  RVLAHMEATG VRLDVAYLKA LSLELAEEIR RLEEEVFRLA GHPFNLNSRD
551  QLERVLFDEL RLPALGKTQK TGKRSTSAAV LEALREAHPI VEKILQHREL
601  TKLKNTYVDP LPGLVHPRTG RLHTRFNQTA TATGRLSSSD PNLQNIPIRT
651  PLGQRIRRAF VAEAGWALVA LDYSQIELRV LAHLSGDENL IRVFQEGKDI
701  HTQTASWMFG VSPEAVDPLM RRAAKTVNFG VLYGMSAHRL SQELAIPYEE
751  AVAFIERYFQ SFPKVRAWIE KTLEEGRKRG YVETLFGRRR YVPDLNARVK
801  SVREAAERMA FNMPVQGTAA DLMKLAMVKL FPHLREMGAR MLLQVHDELL
851  LEAPQARAEE VAALAKEAME KAYPLAVPLE VEVGIGEDWL SAKG
```

Figure 7B: Nucleic Acid Sequence of CS8 DNA Polymerase (SESQ ID NO: 171)

```
   1  ATGAAAGCTA TGTTACCATT ATTCGAACCC AAAGGCCGGG TCCTCCTGGT
  51  GGACGGCCAC CACCTGGCCT ACCGCACCTT CTTCGCCCTG AAGGGCCTCA
 101  CCACGAGCCG GGGCGAACCG GTGCAGGCGG TTTACGGCTT CGCCAAGAGC
 151  CTCCTCAAGG CCCTGAAGGA GGACGGGTAC AAGGCCGTCT TCGTGGTCTT
 201  TGACGCCAAG GCCCCTTCCT TCCGCCACGA GGCCTACGAG GCCTACAAGG
 251  CAGGCCGCGC CCCGACCCCC GAGGACTTCC CCGGCAGCT CGCCCTCATC
 301  AAGGAGCTGG TGGACCTCCT GGGGTTTACT CGCCTCGAGG TTCCGGGCTT
 351  TGAGGCGGAC GACGTCCTCG CCACCCTGGC CAAGAAGGCG AAAGGGAGG
 401  GGTACGAGGT GCGCATCCTC ACCGCCGACC GGGACCTTTA CCAGCTCGTC
 451  TCCGACCGCG TCGCCGTCCT CCACCCCGAG GGCCACCTCA TCACCCCGGA
 501  GTGGCTTTGG GAGAAGTACG GCCTTAAGCC GGAGCAGTGG GTGGACTTCC
 551  GCGCCCTCGT GGGGACCCC TCCGACAACC TCCCCGGGGT CAAGGGCATC
 601  GGGGAGAAGA CCGCCCTCAA GCTCCTCAAG GAGTGGGGAA GCCTGGAAAA
 651  TATCCTCAAG AACCTGGACC GGGTGAAGCC GGAAAGCGTC CGGGAAAGGA
 701  TCAAGGCCCA CCTGGAAGAC CTTAAGCTCT CCTTGGAGCT TTCCCGGGTG
 751  CGCTCGGACC TCCCCCTGGA GGTGGACTTC GCCCGGAGGC GGGAGCCTGA
 801  CCGGGAAGGG CTTCGGGCCT TTTTGGAGCG CTTGGAGTTC GGCAGCCTCC
 851  TCCACGAGTT CGGCCTTCTA GAGGAGTCCG AACCCGTTGG GTACCGTATA
 901  GTTAAAGACC TGGTTGAATT TGAAAAACTC ATAGAGAAAC TGAGAGAATC
 951  TCCTTCGTTC GCGATCGCTC TTGCGACTAG TTCCCTCGAT CCTTTCGACT
1001  GCGACATTGT CGGTATCTCT GTGTCTTTCA AACCAAAGGA AGCGTACTAC
1051  ATACCACTCC ATCATAGAAA CGCCCAGAAC CTGGACGAAA AAGAGGTTCT
1101  GAAAAAGCTC AAAGAAATTC TGGAGGACCC CGGAGCAAAG ATCGTTGGTC
1151  AGAATTTGAA ATTCGATTAC AAGGTGTTGA TGGTGAAGGG TGTTGAACCT
1201  GTTCCTCCTT ACTTCGACAC GATGATAGCG GCTTACCTTC TTGAGCCGAA
1251  CGAAAAGAAG TTCAATCTGG ACGATCTCGC ATTGAAATTT CTTGGATACA
1301  AAATGACATC TTACCAAGAG CTCATGTCCT TCTCTTTTCC GCTGTTTGGT
1351  TTCAGTTTTG CCGATGTTCC TGTAGAAAAA GCAGCGAACT ACTCCTGTGA
1401  AGATGCAGAC ATCACCTACA GACTTTACAA GACCCTGAGC TTAAAACTCC
1451  ACGAGGAAAA GCTTCTTTGG CTCTACCAAG AGGTGGAAAA GCCCCTCTCC
```

FIGURE 7B (Continued)

```
1501  CGGGTCCTGG CCCACATGGA GGCCACCGGG GTAAGGCTGG ACGTGGCCTA
1551  TCTAAAGGCC CTTTCCCTGG AGCTTGCGGA GGAGATTCGC CGCCTCGAGG
1601  AGGAGGTCTT CCGCCTGGCG GGCCACCCCT TCAACCTGAA CTCCCGTGAC
1651  CAGCTAGAGC GGGTGCTCTT TGACGAGCTT AGGCTTCCCG CCCTGGGCAA
1701  GACGCAAAAG ACGGGGAAGC GCTCCACCAG CGCCGCGGTG CTGGAGGCCC
1751  TCAGGGAGGC CCACCCCATC GTGGAGAAGA TCCTCCAGCA CCGGGAGCTC
1801  ACCAAGCTCA AGAACACCTA CGTGGACCCC CTCCCGGGCC TCGTCCACCC
1851  GAGGACGGGC CGCCTCCACA CCCGCTTCAA CCAGACAGCC ACGGCCACGG
1901  GAAGGCTCTC TAGCTCCGAC CCCAACCTGC AGAACATCCC CATCCGCACC
1951  CCCTTGGGCC AGAGGATCCG CCGGGCCTTC GTGGCCGAGG CGGGATGGGC
2001  GTTGGTGGCC CTGGACTATA GCCAGATAGA GCTCCGGGTC CTCGCCCACC
2051  TCTCCGGGGA CGAGAACCTG ATCAGGGTCT TCCAGGAGGG GAAGGACATC
2101  CACACCCAGA CCGCAAGCTG GATGTTCGGC GTCTCCCCGG AGGCCGTGGA
2151  CCCCCTGATG CGCCGGGCGG CCAAGACGGT GAACTTCGGC GTCCTCTACG
2201  GCATGTCCGC CCATAGGCTC TCCCAGGAGC TTGCCATCCC CTACGAGGAG
2251  GCGGTGGCCT TTATAGAGCG CTACTTCCAA AGCTTCCCCA AGGTGCGGGC
2301  CTGGATAGAA AAGACCCTGG AGGAGGGGAG GAAGCGGGGC TACGTGGAAA
2351  CCCTCTTCGG AAGAAGGCGC TACGTGCCCG ACCTCAACGC CCGGGTGAAG
2401  AGCGTCAGGG AGGCCGCGGA GCGCATGGCC TTCAACATGC CCGTCCAGGG
2451  CACCGCCGCC GACCTCATGA AGCTCGCCAT GGTGAAGCTC TTCCCCACC
2501  TCCGGGAGAT GGGGGCCCGC ATGCTCCTCC AGGTCCACGA CGAGCTCCTC
2551  CTGGAGGCCC CCAAGCGCG  GGCCGAGGAG GTGGCGGCTT TGGCCAAGGA
2601  GGCCATGGAG AAGGCCTATC CCCTCGCCGT GCCCCTGGAG GTGGAGGTGG
2651  GGATCGGGGA GGACTGGCTT TCCGCCAAGG GCTGA
```

Figure 8

```
     {Tth}   AACRDGRVHR  AA........  ..........  .......DPL  AG........  ..........
...LKDLKEV  RGLLAKDLAV  LA........  ..........
     {Tca}   AACRDGRVHR  AA........  ..........  .......DPL  AG........  ..........
...LKDLKEV  RGLLAKDLAV  LA........  ..........
     {Z05}   AACKEGRVHR  AK........  ..........  .......DPL  AG........  ..........
...LKDLKEV  RGLLAKDLAV  LA........  ..........
     {Taq}   AAARGGRVHR  AP........  ..........  .......EPY  KA........  ..........
...LRDLKEA  RGLLAKDLSV  LA........  ..........
     {Tfl}   AGAWEGRLHR  AQ........  ..........  .......DPL  RG........  ..........
...LRDLKGV  RGILAKDLAV  LA........  ..........
     {Tfi}   AGAKEGRVHR  AE........  ..........  .......DPV  GA........  ..........
...LKDLKEI  RGLLAKDLSV  LA........  ..........
   {Sps17}   AGAKEGRVHR  AE........  ..........  .......DPV  GA........  ..........
...LKDLKEI  RGLLAKDLSV  LA........  ..........
     {Dra}   TK.KEQKALE  KA........  ..........  ..........  ..........  ..........
...QKDAEKA  RAKLREQFPA  TVDEAEFVGQ  RTVTAAAAKA
 {HSP-B-7}   NRLRDATLHG  VA........  ..........  .......LAV  ASDRAVWLEL  GGSLFLPEPL
TRLLNDPQRA  RAVVWDLKTEC  LL........  ..........
     {Bst}   .......ALV  VEVVGDNYHH  APIVGIALAN  ERGRFFLRP.  ..........  .ETALADPKF
LAWLGDETKK  KTMFDSKRAA  VA........  ..........
     {Bca}   .......ALV  VEVVEENYHD  APIVGIAVVN  EHGRFFLRP.  ..........  .ETALADPQF
VAWLGDETKK  KSMFDSKRAA  VA........  ..........
  {E.coli}   EK.APVFAFD  TETDSLDNIS  ANLVGLSFAI  EPGVAAYIPV  AHDYLDAPDQ  ISRERALELL
KPLLEDEKAL  KVGQNLKYDR  GI........  ..........
     {Tma}   RE.SPSFAID  LETSSLDPFD  CDIVGISVSF  KPKEAYYIPL  HH...RNAQN  LDEKEVLKKL
KEILEDPGAK  IVGQNLKFDY  KV........  ..........
     {Tne}   KE.VPSFALD  LETSSLDPFN  CEIVGISVSF  KPKTAYYIPL  HHRNAHNLDE  T...LVLSKL
KEILEDPSSK  IVGQNLKYDY  KV........  ..........
     {Taf}   EK.YKTFSID  TETTSLDPFE  AKLVGISIST  MEGKAYYIPV  SH...FGAKN  ISKSLIDKFL
KQILQEKDYN  IVGQNLKFDY  EI........  ..........
   {HSP-A}   LACSGIVAWD  TETTSLDPRD  AQLVGIGCCW  SERDVAYLPI  GH...RQGSN  LDWNLVKQSL
QPIWEDPSRP  KSLQNCKYDL  SI........  ..........
                            Exo I Motif
Exo II Motif {Tth}   ....SR.EGL  DLVPGD.DPM  LLAYLLDPSN  TT......PE  ..........  ..........
...GVARRYG  .GEWTEDAAH  RALLSERLHR  NLLKRLEGEE
     {Tca}   ....SR.EGL  DLVPGD.DPM  LLAYLLDPSN  TTPE......  ..........  ..........
...GVARRYG  .GEWTEDAAH  RALLSERLHR  NLLKRLQGEE
     {Z05}   ....LR.EGL  DLAPSD.DPM  LLAYLLDPSN  TT......PE  ..........  ..........
...GVARRYG  .GEWTEDAAH  RALLAERLQQ  NLLERLKGEE
     {Taq}   ....LR.EGL  GLPPGD.DPM  LLAYLLDPSN  TT......PE  ..........  ..........
...GVARRYG  .GEWTEEAGE  RAALSERLFA  NLWGRLEGEE
     {Tfl}   ....LR.EGL  DLFPED.DPM  LLAYLLDPSN  TTPE......  ..........  ..........
...GVARRYG  .GEWTEDAGE  RALLAERLFQ  TLKERLKGEE
     {Tfi}   ....LR.EGR  EIPPGD.DPM  LLAYLLDPGN  TN......PE  ..........  ..........
...GVARRYG  .GEWKEDAAA  RALLSERLWQ  ALYPRVAEEE
   {Sps17}   ....LR.EGR  EIPPGD.DPM  LLAYLLDPGN  TN......PE  ..........  ..........
...GVARRYG  .GEWKEDAAA  RALLSERLWQ  ALYPRVAEEE
     {Dra}   LAAHLSVRGT  VVEPGD.DPL  LYAYLLDPAN  TNMPV.....  ..........  ..........
....VAKRYL  DREWPADAPT  RAAITGHLVR  ELPPLLDDAR
 {HSP-B-7}   ....LRGAGI  DARPAHFDAL  LAAYLWQPSR  AAYTLDWLCE  ..........  ..........
...DVLRLRL  .PDDPDARPA  AEACALLMLQ  PRLRDILHRE
     {Bst}   ....LKWKGI  ELRGVVFDLL  LAAYLLDPAQ  AAGDVAAVAK  MHQYEAVRSD  EAVYGKGAKR
TVPD.....E  .PTLAEHLAR  KAAAIWALEE  PLMDELRRNE
     {Bca}   ....LKWKGI  ELCGVSFDLL  LAAYLLDPAQ  GVDDVAAAAK  MKQYEAVRPD  EAVYGKGAKR
AVPD.....E  .PVLAEHLVR  KAAAIWALER  PFLDELRRNE
  {E.coli}   ....LANYGI  ELRGIAFDTM  LESYILNSVA  GRHDMDSLAE  RWLKHKTITF  EEIAGKGKNQ
L..TFNQIAL  .EEAGRYAAE  DADVTLQLHL  KMWPDLQKHK
     {Tma}   ....LMVKGV  EPVPPYFDTM  IAAYLLEPNE  KKFNLDDLAL  KFLGYKMTSY  QELMSFSFPL
FGFSFADVPV  .EKAANYSCE  DADITYRLYK  TLSLKLHEAD
     {Tne}   ....LMVKGI  SPVYPHFDTM  IAAYLLEPNE  KKFNLEDLSL  KFLGYKMTSY  QELMSFSSPL
FGFSFADVPV  .DKAAEYSCE  DADITYRLYK  ILSMKLHEAE
     {Taf}   ....FKSMGF  SPNVPHFDTM  IAAYLLNPDE  KRFNLEELSL  KYLGYKMISF  DELVNENVPL
FGNDFSYVPL  .ERAVEYSCE  DADVTYRIFR  KLGRKIYENE
   {HSP-A}   ....FRAHGI  RLQGIQFDPM  LASYVLNP.E  ASHNLADLAA  TYLNLPTTAS  HELLGK....
.AESIADLPI  .PKVAEYCGT  DAYCAYRLVP  ILTEKLQQTD
                            Exo IIa Motif
Exo III Motif
```

Figure 11A

Multiple Sequence Alignment of Family B DNA-Dependent DNA Polymerases

Alignment performed with XSAE

Tgo: Thermococcus gorgonarius pol (SEQ ID NO:191)
Pfu: Pyrococcus furiosus (SEQ ID NO:192)
Tsp: Thermus sp. 9oN-7 (SEQ ID NO:193)
Tli: Thermococcus litoralis (SEQ ID NO:194)
Mvo: Methanococcus voltae (SEQ ID NO:195)
RB69: Bacteriophage RB69 (SEQ ID NO:196)
T4: Bacteriophage T4 (SEQ ID NO:197)
Eco: E. coli Pol II (SEQ ID NO:198)
Pol_Delta: Human Pol d (SEQ ID NO:199)
KOD: Pyrococcus kodakaraensis (SEQ ID NO:200)
PabI: Pyrococcus abyssei (SEQ ID NO:201)
PocI: Pyrococcus occultum (SEQ ID NO:202)

Residues in bold are novel potential targets identified via structure-based approach.

```
              1                                                    50
       tgo MI........ .....LDTDY ........IT E.......... ..........
       pfu MI........ .....LDVDY ........IT E.......... ..........
       tsp MI........ .....LDTDY ........IT E.......... ..........
       tli MI........ .....LDTDY ........IT K.......... ..........
       mvo MD........ .....LD..Y ........NS K.......... ..........
      RB69 MK........ .....EFYLT ........VE Q.......... ..........
        T4 MK........ .....EFYIS ........IE T.......... ..........
       Eco M......... .....AQAGF ........IL TRH....WRD T.........
 Pol_Delta MD.......G KRRPGPGPGV ........PP KRARGGLWDD DDAPWPSQFE
       KOD MI........ .....LDTDY ........IT E.......... ..........
      PabI MP........ .....EAIEF VLLDSSYEIV G.......... ..........
      PocI M......... ....TETIEF VLLDSSYEIL G.......... ..........

51                                                   100
       tgo .......... .......... .......... ......DGKP VIRIFKKENG
       pfu .......... .......... .......... ......EGKP VIRLFKKENG
       tsp .......... .......... .......... ......NGKP VIRVFKKENG
       tli .......... .......... .......... ......DGKP IIRIFKKENG
       mvo .......... .......... .......... ......D..L CIDMYYKNCG
      RB69 .......... .......... .......... ......IGDS IFERYIDSNG
        T4 .......... .......... .......... ......VGNN IVERYIDENG
       Eco .......... .......... .......... .....PQGTE VSFWLATDNG
 Pol_Delta EDLALMEEME AEHRLQEQEE EELQSVLEGV ADGQVPPSAI DPRWLRPTPP
       KOD .......... .......... .......... ......DGKP VIRIFKKENG
      PabI .......... .......... .......... ......KEPV IILWGVTLDG
      PocI .......... .......... .......... ......KEPV VILWGITLDG 101                                                  150
       tgo ....EFK... ...IDYDRNF EPYIYA.... ......LLKD D..SAIED..
       pfu ....KFK... ...IEHDRTF RPYIYA.... ......LLRD D..SKIEE..
       tsp ....EFK... ...IEYDRTF EPYFYA.... ......LLKD D..SAIED..
       tli ....EFK... ...IELDPHF QPYIYA.... ......LLKD D..SAIEE..
       mvo LKKPEIN... ...LQKECEF KPYFVDTSE PKEIYDYLDG L..NQEID..
      RB69 .....RE... ...RTREVEY KPSLFA.... .......HCP E..SQATK..
        T4 .....KE... ...RTREVEY LPTMFR.... .......HCK E..E..SK..
```

FIGURE 11B

```
       Eco ....PLQ...  ..VTLAPQES VAFI.P.... ........AD Q..VPRAQH.
 Pol_Delta ....ALDPQT  EPLIFQQLEI DHYVGP.... ........AQ P..VPGGPPP
       KOD ....EFK...  ...IEYDRTF EPYFYA.... ......LLKD D..SAIEE..
      PabI ....KRI...  ...VLLDRRF RPYFYA.... ......LISR DYEGKAEE..
      PocI ....KRV...  ...VLLDHRF RPYFYA.... ......LIAR GYEDMVEE..

151                                                  200
       tgo ......VKKI TAE.RHGTTV .......... .......... R....VVRAE
       pfu ......VKKI TGE.RHGKIV .......... .......... R....IVDVE
       tsp ......VKKV TAK.RHGTVV .......... .......... K....VKRAE
       tli ......IKAI KGE.RHGKTV .......... .......... R....VLDAV
       mvo ......LKKL EPEFENNTSL .......... .......... KVQDLITNIE
      RB69 ......YFDI YG..KPCTRK .......... .......... L....FANMR
        T4 ......YKDI YG..KNCAPQ .......... .......... K....FPSMK
       Eco .......ILQG ....EQGFRL .......... .........T P.....LALK
 Pol_Delta SRGSVPVLRA FGVTDEGFSV CCHIHGFAPY FYTPAPPGFG P.....EHMG
       KOD ......VKKI TAE.RHGTVV .......... .......... T....VKRVE
      PabI ......VVAA IRRLSMAKSP .......... .......... .....IIEAK
      PocI ......IAAS IRRLSVVKSP .......... .......... .....IIDAK 201                                                  250
       tgo KVKK...... .......... .......... ........KF L..GRPIE..
       pfu KVEK...... .......... .......... ........KF L..GKPIT..
       tsp KVQK...... .......... .......... ........KF L..GRPIE..
       tli KVRK...... .......... .......... ........KF L..GREVE..
       mvo IIEK...... .......... .......... ....IVYSDY ILNGKDISEV
      RB69 DASQ...... .......... .......... .......... ..........
        T4 DARD...... .......... .......... .......... ..........
       Eco DFHRQ..... .......... .......... .......... ..........
 Pol_Delta DLQRELNLAI SRDSRGGREL TGPAVLAVEL CSRE...... ..........
       KOD KVQK...... .......... .......... ........KF L..GRPVE..
      PabI VVSK...... .......... .......... .......... ..........
      PocI PLDK...... .......... .......... .......... ..........

251                                                  300
       tgo .......... VWKLYFTHP. .......... .......... .QDVPAIRDK
       pfu .......... VWKLYLEHP. .......... .......... .QDVPTIREK
       tsp .......... VWKLYFNHP. .......... .......... .QDVPAIRDR
       tli .......... VWKLIFEHP. .......... .......... .QDVPAMRGK
       mvo SDFKNKKERK ICKVYVKYP. .......... .......... .NHVKIIREY
      RB69 .......... .WIKRMEDI. .......... .......... .GLEALGMDD
        T4 .......... .WMKRMEDI. .......... .......... .GLEALGMND
       Eco .......... ..PVYGLYC. .......... .......... .RAHRQLMNY
 Pol_Delta .......... ..SMFGYHG. .......... .......... .HGPSPFLRI
       KOD .......... VWKLYFTHP. .......... .......... .QDVPAIRDK
      PabI .......... ...KYFGRP. .......... RKAVKVTTVI PESVREYREA
      PocI .......... ...RYFGRP. .......... RKAVKITTMI PESVRHYREA 301                                                  350
       tgo I......... ..KEHPAVVD I......... .YEYDIPFAK RYLIDK....
       pfu V......... ..REHPAVVD I......... .FEYDIPFAK RYLIDK....
       tsp I......... ..RAHPAVVD I......... .YEYDIPFAK RYLIDK....
       tli I......... ..REHPAVVD I......... .YEYDIPFAK RYLIDK....
       mvo F......... ..KE...FGK S......... .YEFDIPFLR RYMIDQ....
      RB69 F......... ..KL.AYLSD T......... .YNYEIKYDH TKI.......
        T4 F......... ..KL.AYISD T......... .YGSEIVYDR KFV.......
       Eco E......... .KRLREGGVT V......... .YEADVRPPE RYLMER....
 Pol_Delta TVALPRLVAP ARRLLEQGIR VAGLGTPSFA PYEANVDFEI RFMVDT....
       KOD I......... ..REHPAVID I......... .YEYDIPFAK RYLIDK....
      PabI V......... ..KKLEGVED S......... .LEADIRFAM RYLIDK....
```

FIGURE 11C

```
      PocI V.........  ..KKIEGVED S.........  .LEADIRFAM RYLIDK....

351                                                   400
       tgo ..........  ..........  ..........  ........GL  ..........
       pfu ..........  ..........  ..........  ........GL  ..........
       tsp ..........  ..........  ..........  ........GL  ..........
       tli ..........  ..........  ..........  ........GL  ..........
       mvo ..........  ..........  ..........  ........DI  ..........
      RB69 ..........  ..........  ..........  ..........  ..........
        T4 ..........  ..........  ..........  ..........  ..........
       Eco ..........  ..........  ..........  ........FI  ..........
 Pol_Delta ..........  ..........  ..........  ........DI  ..........
       KOD ..........  ..........  ..........  ........GL  ..........
      PabI ..........  ..........  ..........  ........KL  YPFTAYRVRA
      PocI ..........  ..........  ..........  ........RL  YPFTVYRIPV 401                                                   450
       tgo ..........  ..........  ..........  .........I  ..........
       pfu ..........  ..........  ..........  .........I  ..........
       tsp ..........  ..........  ..........  .........I  ..........
       tli ..........  ..........  ..........  .........I  ..........
       mvo ..........  ..........  ..........  .........V  ..........
      RB69 ..........  ..........  ..........  ..........  ..........
        T4 ..........  ..........  ..........  ..........  ..........
       Eco ..........  ..........  ..........  .........T  SPVWVEGDMH  N.........
 Pol_Delta ..........  ..........  ..........  .........V  GCNWLELPAG  KYALRLKEKA
       KOD ..........  ..........  ..........  .........V  ..........
      PabI ENAGRSPGFR  VDSVYTIVED  PEPIADITSI  ..........  ..........
      PocI EDAGRNPGFR  VDRVYKVAGD  PEPLADITRI  DL........  ..........

451                                                   500
       tgo ..........  ..........  .......PM.  .........E  GDEELKMLAF
       pfu ..........  ..........  .......PM.  .........E  GEEELKILAF
       tsp ..........  ..........  .......PM.  .........E  GDEELTMLAF
       tli ..........  ..........  .......PM.  .........E  GDEELKLLAF
       mvo ..........  ..........  .......PSA  KYSEDNKIDN  SIPELNCIAF
      RB69 ..........  ..........  ..........  ..........  .....RVANF
        T4 ..........  ..........  ..........  ..........  .....RVANC
       Eco ......GTIV  NARLKPHPDY  RP.....P..  ..........  ....LKWVSI
 Pol_Delta TQCQLEADVL  WSDVVSHPPE  GPWQRIAP..  ..........  ....LRVLSF
       KOD ..........  ..........  .......PM.  .........E  GDEELKMLAF
      PabI ..........  ..........  ..........  ..........  DIPEMRVLAF
      PocI ..........  ..........  ..........  ..........  ..PPMRLVAF 501                                                   550
       tgo DIETL....Y  HEG..EEFAE  GPIL......  ....MISYAD  EEGARVITWK
       pfu DIETL....Y  HEG..EEFGK  GPII......  ....MISYAD  ENEAKVITWK
       tsp DIETL....Y  HEG..EEFGT  GPIL......  ....MISYAD  GSEARVITWK
       tli DIETF....Y  HEG..DEFGK  GEII......  ....MISYAD  EEEARVITWK
       mvo DMELY....C  KKE..PNAKK  DPII......  ....MVNLFS  KDYQKVITYK
      RB69 DIEVTSPDGF  PEPSQAKHPI  DAITHYDSID  DRFYVFDLLN  SPYGNVEEWS
        T4 DIEVTG.DKF  PDPMKAEYEI  DAITHYDSID  DRFYVFDLLN  SMYGSVSKWD
       Eco DIETT....R  HGELYCIGLE  ACGQ......  ....RIVYML  GPENGDASSL
 Pol_Delta DIECA....G  RKGIFPEPER  DPVI......  ....QICSLG  LRWGEPEPFL
       KOD DIETL....Y  HEG..EEFAE  GPIL......  ....MISYAD  EEGARVITWK
      PabI DIEV.....Y  SKRGSPNPSR  DPVI......  ....IISIKD  SKGNEKL...
      PocI DIEV.....Y  SRRGSPNPAR  DPVI......  ....IVSLRD  SEGKERLI..

551                                                   600
       tgo ..........  .....NIDL.  ......P.Y..  .VDVV.....  STEKEMIKRF
```

FIGURE 11D

```
       pfu ..........  .....NIDL.  ......P.Y..  .VEVV.....  SSEREMIKRF
       tsp ..........  .....KIDL.  ......P.Y..  .VDVV.....  STEKEMIKRF
       tli ..........  .....NIDL.  ......P.Y..  .VDVV.....  SNEREMIKRF
       mvo ..........  .....KFEN.  .....SEYNG  CVDYV.....  KDEKELIQKT
      RB69 IEIAAKLQEQ  GGDEVPSEI.  ..........  .IDKIIYMPF  DNEKELLMEY
        T4 AKLAAKLDCE  GGDEVPQEI.  ..........  .LDRVIYMPF  DNERDMLMEY
       Eco ..........  .....DFEL.  ..........  ..EYV.....  ASRPQLLEKL
 Pol_Delta ..........  .....RLALT  LRPCAPILGA  KVQSY.....  EKEEDLLQAW
       KOD ..........  .....NVDL.  ......P.Y..  .VDVV.....  STEREMIKRF
      PabI ..........  ......LEA.  ..........  ..NNY.....  .DDRNVLREF
      PocI ..........  .....EAEG.  ..........  ..........  HDDRRVLREF 601                                             650
       tgo LKVVKEKDPD  VLITYNGDNF  DFAYLKKRSE  KL....GVK.  FIL.......
       pfu LRIIREKDPD  IIVTYNGDSF  DFPYLAKRAE  KL....GIK.  LTI.......
       tsp LRVVREKDPD  VLITYNGDNF  DFAYLKKRCE  EL....GIK.  FTL.......
       tli VQVVKEKDPD  VIITYNGDNF  DLPYLIKRAE  KL....GVR.  LVL.......
       mvo IEILKQYD..  VIYTYNGDNF  DFPYLKKRAN  IY....EIE.  LDF.......
      RB69 LNFWQQKTPV  ILTGWNVESF  DIPYVYNRIK  NIFGESTAKR  LS........
        T4 INLWEQKRPA  IFTGWNIEGF  DVPYIMNRVK  MILGERSMKR  FS........
       Eco NAWFANYDPD  VIIGWNVVQF  DLRMLQKHAE  RY....RLP.  LRL.......
 Pol_Delta STFIRIMDPD  VITGYNIQNF  DLPYLISRAQ  TL....KVQT  FPFLGRVAGL
       KOD LRVVKEKDPD  VLITYNGDNF  DFAYLKKRCE  KL....GIN.  FAL.......
      PabI IEYIRSFDPD  IIVGYNSNNF  DWPYLIERAH  RI....GVK.  LDV.......
      PocI VEYVRAFDPD  IIVGYNSNHF  DWPYLMERAR  RL....GIK.  LDV.......

651                                             700
       tgo ...GREG..S  EPKIQRM...  GDRFAVEVKG  RIHFDLYPVI  RR.TI.NLPT
       pfu ...GRDG..S  EPKMQRI...  GDMTAVEVKG  RIHFDLYHVI  TR.TI.NLPT
       tsp ...GRDG..S  EPKIQRM...  GDRFAVEVKG  RIHFDLYPVI  RR.TI.NLPT
       tli ...GRDKEHP  EPKIQRM...  GDSFAVEIKG  RIHFDLFPVV  RR.TI.NLPT
       mvo ...DNASNSQ  QPQIIKISKG  GINRKSKIPG  IIHIDLYPIA  RK.LL.NLTK
      RB69 ....PHRKTR  VKVIENMY..  GSREIITLFG  ISVLDYIDLY  KKFSFTNQPS
        T4 ....PIGRVK  SKLIQNMY..  GSKEIYSIDG  VSILDYLDLY  KKFAFTNLPS
       Eco ...GRDNSEL  EWREHGFK..  NGVFFAQAKG  RLIIDGIEAL  KS.AFWNFSS
 Pol_Delta CSNIRDSSFQ  SKQTGRR...  .DTKVVSMVG  RVQMDMLQVL  LR.EY.KLRS
       KOD ...GRDG..S  EPKIQRM...  GDRFAVEVKG  RIHFDLYPVI  RR.TI.NLPT
      PabI ....TRRVGA  EPSMSVY...  ...GHVSVQG  RLNVDLYNYV  E..EMHEIKV
      PocI ....TRRVGA  EPTTSVY...  ...GHVSVQG  RLNVDLYDYA  E..EMPEIKM 701                                             750
       tgo YTLEAVYEAI  FGQPKEKVYA  EE...IAQAW  ETGEGLER..  ......VARY
       pfu YTLEAVYEAI  FGKPKEKVYA  DE...IAKAW  ESGENLER..  ......VAKY
       tsp YTLEAVYEAV  FGKPKEKVYA  EE...IAQAW  ESGEGLER..  ......VARY
       tli YTLEAVYEAV  LGKTKSKLGA  EE...IAAIW  ETEESMKK..  ......LAQY
       mvo YKLENVVQEL  FKINKEAVDY  GD...IPKMW  ETEDT..T..  ......LLRY
      RB69 YSLDYISEFE  LNVGKLK.YD  GP...ISKLR  ESNHQR....  ......YISY
        T4 FSLESVAQHE  TKKGKLP.YD  GP...INKLR  ETNHQR....  ......YISY
       Eco FSLETVAQEL  LGEGKS....  .....IDNPW  DRMDEIDRRF  AEDKPALATY
 Pol_Delta HTLNAVSFHF  LGEQKEDVQH  SI...ITDLQ  NGNDQTRRR.  ......LAVY
       KOD YTLEAVYEAV  FGQPKEKVYA  EE...ITTAW  ETGENLER..  ......VARY
      PabI KTLEEVAEYL  GVMRKSERVL  IEWWRIPDYW  DDEKKRPL..  ......LKRY
      PocI KTLEEVAEYL  GVMKKSERVI  IEWWRIPEYW  DDEKKRQL..  ......LERY 751                                             800
       tgo SMEDAKVTYE  L..GKEFFPM  ..EAQLSRLV  GQSL.WDVSR  SSTGNLVEWF
       pfu SMEDAKATYE  L..GKEFLPM  ..EIQLSRLV  GQPL.WDVSR  SSTGNLVEWF
       tsp SMEDAKVTYE  L..GREFFPM  ..EAQLSRLI  GQSL.WDVSR  SSTGNLVEWF
       tli SMEDARATYE  L..GKEFFPM  ..EAELAKLI  GQSV.WDVSR  SSTGNLVEWY
       mvo AYEDALYTYK  M..GNYFLPL  ..EIMFSRIV  NQPL.YDTSR  MNSSQMVEFL
```

FIGURE 11E

```
      RB69  NIIDVYRVLQ  IDAKRQFINL  ..SLDMGYYA  KIQIQSVFSP  IKTWDAI...
        T4  NIIDVESVQA  IDKIRGFIDL  ..VLSMSYYA  KMPFSGVMSP  IKTWDAI...
       Eco  NLKDCELVTQ  IFHKTEIMPF  ....LLERAT  VNGLPVDRHG  GSVAAFGHLY
 Pol_Delta  CLKDAYLPLR  L..LERLMVL  VNAVEMARVT  GVPLSYLLSR  GQQVKVVS.Q
       KOD  SMEDAKVTYE  L..GKEFLPM  ..EAQLSRLI  GQSL.WDVSR  SSTGNLVEWF
      PabI  ALDDVRATYG  L..AEKILPF  ..AIQLSTVT  GVPLD.QVGA  MGVGFRLEWY
      PocI  ALDDVRATYG  L..AEKMLPF  ..AIQLSTVT  GVPLD.QVGA  MGVGFRLEWY 801                                                 850
       tgo  ...LLRKAYE  RNELAPNKPD  ERELARR.RE  SYAGGYVKEP  ERGLWE.NIV
       pfu  ...LLRKAYE  RNEVAPNKPS  EEEYQRRLRE  SYTGGFVKEP  EKGLWE.NIV
       tsp  ...LLRKAYK  RNELAPNKPD  ERELARR.RG  GYAGGYVKEP  ERGLWD.NIV
       tli  ...LLRVAYA  RNELAPNKPD  EEEYKRRLRT  TYLGGYVKEP  EKGLWE.NII
       mvo  ...LLKRSFE  QNMISPNRPS  SSSYRERAKF  SYEGGYVREP  LKGIQE.DIV
      RB69  ...IFNSLKE  QNKVIPQGRS  HPV......Q  PYPGAFVKEP  IPNRYK.YVM
        T4  ...IFNSLKG  EHKVIPQQGS  HVK......Q  SFPGAFVFEP  KPIARR.YIM
       Eco  FPRMHRAGYV  APNLGEVPPH  ASP.......  ...GGYVMDS  RPGLYD.SVL
 Pol_Delta  ...LLRQAMH  EGLLMPVVKS  EGG......E  DYTGATVIEP  LKGYYDVPIA
       KOD  ...LLRKAYE  RNELAPNKPD  EKELARR.RQ  SYEGGYVKEP  ERGLWE.NIV
      PabI  ...LMRAAHD  MNELVPNRVK  RRE......E  SYKGAVVLKP  LKGVHE.NVV
      PocI  ...LMRAAYD  MNELVPNRVE  RRG......E  SYKGAVVLKP  LKGVHE.NVV 851                                                 900
       tgo  YLDFRSLYPS  IIITHNVSP.  ...DTL..NR  EGC.......  .EEYD...VA
       pfu  YLDFRALYPS  IIITHNVSP.  ...DTL..NL  EGC.......  .KNYD...IA
       tsp  YLDFRSLYPS  IIITHNVSP.  ...DTL..NR  EGC.......  .KEYD...VA
       tli  YLDFRSLYPS  IIVTHNVSP.  ...DTL..EK  EGC.......  .KNYD...VA
       mvo  SLDFMSLYPS  ILISHNISP.  ...ETV..I.  ..........  ...YE....EK
      RB69  SFDLTSLYPS  IIRQVNISP.  ...ETI..A.  ..........  .GTFK...VA
        T4  SFDLTSLYPS  IIRQVNISP.  ...ETI..R.  ..........  .GQFK...VH
       Eco  VLDYKSLYPS  IIRTFLIDPV  GLVEGM..AQ  PD........  .PEHS...TE
 Pol_Delta  TLDFSSLYPS  IMMAHNLCY.  ...TTL..LR  PGTAQKLGLT  EDQF....IR
       KOD  YLDFRSLYPS  IIITHNVSP.  ...DTL..NR  EGC.......  .KEYD...VA
      PabI  VLDFSSMYPN  IMIKYNVGP.  ...DTIIDDP  SEC.......  .EKYSGCYVA
      PocI  VLDFSSMYPS  IMIKYNVGP.  ...DTIVDDP  SEC.......  .PKYGGCYVA 901                                                 950
       tgo  P.........  ..........  QVGHKFCKDF  P..GFIPSLL  GDLLEERQK.
       pfu  P.........  ..........  QVGHKFCKDI  P..GFIPSLL  GHLLEERQK.
       tsp  P.........  ..........  EVGHKFCKDF  P..GFIPSLL  GDLLEERQK.
       tli  P.........  ..........  IVGYRFCKDF  P..GFIPSIL  GDLIAMRQD.
       mvo  E.........  ..........  RENMEL....  ...GIIPKTL  NELLSRRKH.
      RB69  PLHDYINAVA  ERPSDVYSCS  PNGMMYYKDR  D..GVVPTEI  TKVFNQRKEH
        T4  PIHEYIAGTA  PKPSDEYSCS  PNGWMYDKHQ  E..GIIPKEI  AKVFFQRKDW
       Eco  G.........  ..........  FLDAWFSREK  H...CLPEIV  TNIWHGRDE.
 Pol_Delta  T.........  ..........  PTGDEFVKTS  VRKGLLPQIL  ENLLSARKR.
       KOD  P.........  ..........  QVGHRFCKDF  P..GFIPSLL  GDLLEERQK.
      PabI  P.........  ..........  EVGHMFRRSP  S..GFFKTVL  ENLIALRKQ.
      PocI  P.........  ..........  EVGHRFRRSP  P..GFFKTVL  ENLLKLRRQ.

951                                                1000
       tgo  ..........  ...VKKKMKA  .TIDPIEKKL  ....LDYR..  ..........
       pfu  ..........  ...IKTKMKE  .TQDPIEKIL  ....LDYR..  ..........
       tsp  ..........  ...IKRKMKA  .TVDPLEKKL  ....LDYR..  ..........
       tli  ..........  ...IKKKMKS  .TIDPIEKKM  ....LDYR..  ..........
       mvo  ..........  ...IKMLLKD  .KIQKNEFDE  EYSRLEHE..  ..........
      RB69  KGYMLAAQRN  GEIIKEALHN  .PNLSVDEPL  D...VDYRFD  FSDEIKEKIK
        T4  KKKMFAEEMN  AEAIKKIIMK  .GAGSCSTKP  E...VERYVK  FSDDFLNELS
       Eco  ..........  ...AKRQGNK  .PLSQ.....  ..........  ..........
 Pol_Delta  ..........  ...AKAELAK  .ETDPLRRQV  ....LDGR..  ..........
```

FIGURE 11F

```
        KOD  ..........  ...IKKKMKA  .TIDPIERKL  ....LDYR..  ..........
        PabI ..........  ...VREKMKE  FPPDSPEYRI  ....YDER..  ..........
        PocI ..........  ...VKEKMKE  FPPDSPEYRL  ....YDER..  ..........

1001                                                  1050
        tgo  ..........  ..........  ....QRAIKI  LANSFYGYYG  YAKARWYCKE
        pfu  ..........  ..........  ....QKAIKL  LANSFYGYYG  YAKARWYCKE
        tsp  ..........  ..........  ....QRAIKI  LANSFYGYYG  YAKARWYCKE
        tli  ..........  ..........  ....QRAIKL  LANSYYGYMG  YPKARWYSKE
        mvo  ..........  ..........  ....QKSIKV  LANSHYGYLA  FPMARWYSDK
       RB69  KLSAKSLNEM  LFRAQRTEVA  GMTAQINRKL  LINSLYGALG  NVWFRYYDLR
         T4  NYTESVLNSL  IEECEKAATL  ANTNQLNRKI  LINSLYGALG  NIHFRYYDLR
        Eco  ..........  ..........  ......ALKI  IMNAFYGVLG  TTACRFFDPR
   Pol_Delta ..........  ..........  ....QLALKV  SANSVYGFTG  AQVGKLPCLE
        KOD  ..........  ..........  ....QRAIKI  LANSYYGYYG  YARARWYCKE
        PabI ..........  ..........  ....QKALKV  LANASYGYMG  WVHARWYCKR
        PocI ..........  ..........  ....QKALKV  LANASYGYMG  WSHARWYCKR 1051                                                  1100
        tgo  CAESVTAWGR  ..........  .QYIETTIRE  IEEKF....G  F....KVLYA
        pfu  CAESVTAWGR  ..........  .KYIELVWKE  LEEKF....G  F....KVLYI
        tsp  CAESVTAWGR  ..........  .EYIEMVIRE  LEEKF....G  F....KVLYA
        tli  CAESVTAWGR  ..........  .HYIEMTIRE  IEEKF....G  F....KVLYA
        mvo  CAEMVTGLGR  ..........  .KYIQETIEK  AEE.F....G  F....KVIYA
       RB69  NATAITTFGQ  MALQWIERKV  NEYLNEVCGT  EGEAF.....  ......VLYG
         T4  NATAITIFGQ  VGIQWIARKI  NEYLNKVCGT  NDEDF.....  ......IAAG
        Eco  LASSITMRGH  ..........  .QIMRQTKAL  IEAQ.....G  Y....DVIYG
   Pol_Delta ISQSVTGFGR  ..........  .QMIEKTKQL  VESKYTVENG  YSTSAKVVYG
        KOD  CAESVTAWGR  ..........  .EYITMTIKE  IEEKY....G  F....KVIYS
        PabI CAEAVTAWGR  ..........  ..NLILSAIE  YARKL....G  L....KVIYG
        PocI CAEAVTAWGR  ..........  ..NLILTAIE  YARKL....G  L....KVIYG 1101                                                  1150
        tgo  DTDGFFAT..  ..........  ..........  IPGADAET.V  KKKAKE....
        pfu  DTDGLYAT..  ..........  ..........  IPGGESEE.I  KKKALE....
        tsp  DTDGLHAT..  ..........  ..........  IPGADAET.V  KKKAKE....
        tli  DTDGFYAT..  ..........  ..........  IPGEKPEL.I  KKKAKE....
        mvo  DTDGFYAKWD  YDKLQKGKKE  ENDKSDKLSN  LPKLSKEE.L  IILTKK....
       RB69  DTDSIYVS..  ..........  ..........  .ADKIIDKVG  ESKFRDTNHW
         T4  DTDSVYVC..  ..........  ..........  .VDKVIEKVG  LDRFKEQNDL
        Eco  DTDSTFVW..  ..........  ..........  LKGAHSEEEA  AKIGRA....
   Pol_Delta DTDSVMCR..  ..........  ..........  FGVSSVAE.A  MALGRE....
        KOD  DTDGFFAT..  ..........  ..........  IPGADAET.V  KKKAME....
        PabI DTDSLFVT..  ..........  ..........  ........YD  IEKVKK....
        PocI DTDSLFVV..  ..........  ..........  ........YD  KEKVEK....

1151                                                  1200
        tgo  ..FLDYINA.  ........KL  PGLLELEYEG  F..YKR....  ..........
        pfu  ..FVKYINS.  ........KL  PGLLELEYEG  F..YKR....  ..........
        tsp  ..FLKYINP.  ........KL  PGLLELEYEG  F..YVR....  ..........
        tli  ..FLNYINS.  ........KL  PGLLELEYEG  F..YLR....  ..........
        mvo  ..FLKGINE.  ........EL  PEGMELEFEG  H..FKR....  ..........
       RB69  VDFLDKFAR.  .......ERM  EPAIDRGFRE  MCEYMNNKQH  LMFMDREAIA
         T4  VEFMNQFGK.  .......KKM  EPMIDVAYRE  LCDYMNNREH  LMHMDREAIS
        Eco  ..LVQHVNAW  WAETLQKQRL  TSALELEYET  H..FCR....  ..........
   Pol_Delta ..AADWVSG.  ........HF  PSPIRLEFEK  V..YFP....  ..........
        KOD  ..FLKYINA.  ........KL  PGALELEYEG  F..YKR....  ..........
        PabI ..LIEFVEK.  ........QL  G..FEIKIDK  V..YKR....  ..........
        PocI ..LIEFVEK.  ..........  ELGFEIKIDK  I..YKK....  ..........
```

FIGURE 11G

```
              1201                                                  1250
        tgo   ..........  GFFVT.....  ...KKKYAVI  ......D...  ......EED.
        pfu   ..........  GFFVT.....  ...KKRYAVI  ......D...  ......EEG.
        tsp   ..........  GFFVT.....  ...KKKYAVI  ......D...  ......EEG.
        tli   ..........  GFFVT.....  ...KKRYAVI  ......D...  ......EEG.
        mvo   ..........  GLFVT.....  ...KKKYALI  ......E...  ......DDG.
       RB69   GPPLGSKGIG  GFWTG.....  ...KKRYAL.  ......NVWD  MEGTRYAEP.
         T4   CPPLGSKGVG  GFWKA.....  ...KKRYAL.  ......NVYD  MEDKRFAEP.
        Eco   ..........  FLMPTIRGAD  TGSKKRYAGL  ......I...  ......QEGD
   Pol_Delta  ..........  YLLIS.....  ...KKRYAGL  LFSSRPD...  ......AHD.
        KOD   ..........  GFFVT.....  ...KKKYAVI  ......D...  ......EEG.
        PabI  ..........  VFFTEA....  ...KKRYVGL  ..........  .....LEDG.
        PocI  ..........  VFFTEA....  ...KKRYVGL  ..........  .....LEDG.

1251                                                  1300
        tgo   ..KITTRGLE  IVRRDWSEIA  KETQARVLEA  ILKHGDVEEA  VRIVKEVTEK
        pfu   ..KVITRGLE  IVRRDWSEIA  KETQARVLET  ILKHGDVEEA  VRIVKEVIQK
        tsp   ..KITTRGLE  IVRRDWSEIA  KETQARVLEA  ILKHGDVEEA  VRIVKEVTEK
        tli   ..RITTRGLE  VVRRDWSEIA  KETQAKVLEA  ILKEGSVEKA  VEVVRDVVEK
        mvo   ..HIVVKGLE  VVRRDWSNIA  KDTQQAVIRA  LLEDGDVNLA  KKIIKNTIDN
       RB69   ..KLKIMGLE  TQKSSTPKAV  QKALKECIRR  MLQEGE.ESL  QEYFKEFEKE
         T4   ..HLKIMGME  TQQSSTPKAV  QEALEESIRR  ILQEGE.ESV  QEYYKNFEKE
        Eco   KQRMVFKGLE  TVRTDWTPLA  QQFQQELYLR  IFRNEPYQE.  ..YVRETIDK
   Pol_Delta  ..RMDCKGLE  AVRRDNCPLV  ANLVTASLRR  LLIDRDPEGA  VAHAQDVISD
        KOD   ..KITTRGLE  IVRRDWSEIA  KETQARVLEA  LLKDGDVEKA  VRIVKEVTEK
        PabI  ..RMDIVGFE  AVRGDWCELA  KEVQEKVAEI  ILKTGDINRA  ISYIREVVRK
        PocI  ..RIDIVGFE  AVRGDWCELA  KEVQEKAAEI  VLNTGNVDKA  ISYIREVIKQ 1301                                                  1350
        tgo   LSKYE.VPPE  KLVIYEQITR  .DLKDYKATG  PHVAVAKRLA  .ARGIK....
        pfu   LANYE.IPPE  KLAIYEQITR  .PLHEYKAIG  PHVAVAKKLA  .AKGVK....
        tsp   LSKYE.VPPE  KLVIHEQITR  .DLRDYKATG  PHVAVAKRLA  .ARGVK....
        tli   IAKYR.VPLE  KLVIHEQITR  .DLKDYKAIG  PHVAIAKRLA  .ARGIK....
        mvo   LKKGN.IDKN  DLLIHTQLTK  .NIEEYKSTA  PHIEVAKKIK  .QRGDS....
       RB69   FRQLNYISIA  SVSSANNIAK  YDVGGFPGPK  CPFHIRGILT  YNRAIKGNID
         T4   YRQLDYKVIA  EVKTANDIAK  YDDKGWPGFK  CPFHIRGVLT  YRRAVSG.LG
        Eco   LMAGE.LD.A  RLVYRKRLRR  .PLSEYQRNV  PPHVRAARLA  .DEENQ....
   Pol_Delta  LLCNR.IDIS  QLVITKELTR  .AASDYAGKQ  AHVELAERMR  .KRDPG....
        KOD   LSKYE.VPPE  KLVIHEQITR  .DLKDYKATG  PHVAVAKRLA  .ARGVK....
        PabI  LREGK.IPIT  KLVIWKTLTK  .RIEEYEHEA  PHVTAARRMK  .EAGYD....
        PocI  LREGK.VPIT  KLIIWKTLSK  .RIEEYEHDA  PHVMAARRMK  .EAGYE....

1351                                                  1400
        tgo   .IRP..GTVI  SYIVLKGSGR  IGDRAIPFDE  FDPAKHKY..  DAEYYIENQV
        pfu   .IKP..GMVI  GYIVLRGDGP  ISNRAILAEE  YDPKKHKY..  DAEYYIENQV
        tsp   .IRP..GTVI  SYIVLKGSGR  IGDRAIPADE  FDPTKHRY..  DAEYYIENQV
        tli   .VKP..GTII  SYIVLKGSGK  ISDRVILLTE  YDPRKHKY..  DPDYYIENQV
        mvo   .VRV..GDVI  SYIIVKGSRS  ISERAELL.E  YAGD...Y..  DINYYIDNQV
       RB69   APQVVEGEKV  YVLPLREGNP  FGDKCIAWPS  GTEITDLIKD  DVLHWMDYTV
         T4   VAPILDGNKV  MVLPLREGNP  FGDKCIAWPS  GTELPKEIRS  DVLSWIDHST
        Eco   .KR...GRPL  QY......QN  RGTIKYVWTT  TGPEPPGL..  .PTFTTGLRT
   Pol_Delta  .SAPSLGDRV  PYVIISAAKG  VAAYMKSEDP  LFVLEHSLPI  DTQYYLEQQL
        KOD   .IRP..GTVI  SYIVLKGSGR  IGDRAIPFDE  FDPTKHKY..  DAEYYIENQV
        PabI  .VAP..GDKI  GYIIVKGHGS  ISSRAYPYFM  VDSSKV....  DTEYYIDHQI
        PocI  .VSP..GDKV  GYIVVKGSGS  VSSRAYPYFM  VDPSTI....  DVNYYIDHQI 1401                                                  1450
        tgo   L..PAVERIL  R.........  ..........  ..........  ...AFG....
        pfu   L..PAVLRIL  E.........  ..........  ..........  ...GFG....
        tsp   L..PAVERIL  K.........  ..........  ..........  ...AFG....
```

FIGURE 11H

```
       tli L..PAVLRIL E.........  ..........  ..........  ...AFG....
       mvo L..PPVIRIM E.........  ..........  ..........  ...SLG....
      RB69 LLEKTFIKPL E.........  ..........  ..........  ...GFT....
        T4 LFQKSFVKPL A.........  ..........  ..........  ...GMC....
       Eco L..SDPP...  ..........  ..........  ..........  ..........
 Pol_Delta A..KPLLRIF EPILGEGRAE AVLLRGDHTR CKTVLTGKVG GLLAFAKRRN
       KOD L..PAVERIL R.........  ..........  ..........  ...AFG....
      PabI V..PAAMRIL S.........  ..........  ..........  ...YFGV...
      PocI V..PAALRIL S.........  ..........  ..........  ...YFGV...

1451                                                  1500
       tgo ..........  ..........  ......YRKE  ..........  ..........
       pfu ..........  ..........  ......YRKE  ..........  ..........
       tsp ..........  ..........  ......YRKE  ..........  ..........
       tli ..........  ..........  ......YRKE  ..........  ..........
       mvo ..........  ..........  ......ISED  ..........  ..........
      RB69 ..........  ..........  .......SAA  ..........  ..........
        T4 ..........  ..........  .......ESA  ..........  ..........
       Eco ..........  ..........  ..........  ..........  ..........
 Pol_Delta CCIGCRTVLS HQGAVCEFCQ PRESELYQKE VSHLNALEER FSRLWTQCQR
       KOD ..........  ..........  ......YRKE  ..........  ..........
      PabI ..........  ..........  ......TEKQ L.........  ..........
      PocI ..........  ..........  ......TEKQ L.........  ..........

1501                                                  1550
       tgo ..........  ..........  ........DL.  .......RYQ KTRQVGLG..
       pfu ..........  ..........  ........DL.  .......RYQ KTRQVGLT..
       tsp ..........  ..........  ........DL.  .......RYQ KTKQVGLG..
       tli ..........  ..........  ........DL.  .......RYQ SSKQTGLD..
       mvo ..........  ..........  ........EL.  .......K.N SGKQFKLDQF
      RB69 ..........  ..........  ..........  .......KLD YEKKASLF..
        T4 ..........  ..........  ..........  .......GMD YEEKASLD..
       Eco ..........  ..........  ..........  .........A TTRGGGNT..
 Pol_Delta CQGSLHEDVI CTSRDCPIFY MRKKVRKDLE DQEQLLRRFG PPGPEAWT..
       KOD ..........  ..........  ........DL.  .......RYQ KTRQVGLS..
      PabI ..........  ..........  ..........  .......KAA SSGHRSLF..
      PocI ..........  ..........  ..........  .......KAA ATVQRSLF..

1551                                                  1600
       tgo ..AWLKPK..  ..........  ..........  ..........  ..........
       pfu ..SWLNIK..  ..........  ..........  ..........  ..........
       tsp ..AWLKVK..  ..........  ..........  ..........  ..........
       tli ..AWLKR...  ..........  ..........  ..........  ..........
       mvo MTPWRKIN..  ..........  ..........  ..........  ..........
      RB69 ..DMFDF...  ..........  ..........  ..........  ..........
        T4 ..FLFG....  ..........  ..........  ..........  ..........
       Eco ..PFY.....  ..........  ..........  ..........  ..........
 Pol_Delta ..PWRKINGW ITHFXLLSEQ XENCESSEQX ENCEINALIG NMENTSETGT
       KOD ..AWLKPK..  ..........  ..........  ..........  ..........
      PabI ..DFFAAK..  ..........  ..........  ..........  ..........
      PocI ..DFFASK..  ..........  ..........  ..........  ..........

1601                                                  1650
       tgo ..........  ..........  ..........  ..........  ..........
       pfu ..........  ..KSTPWRKI NGWITHFXLL SEQXENCESS EQXENCEINA
       tsp ..........  ..........  ..........  ..........  ..........
       tli ..........  ..........  ..........  ..........  ..........
       mvo ..........  ..........  ..........  ..........  ..........
      RB69 ..........  ..........  ..........  ..........  ..........
        T4 ..........  ..........  ..........  ..........  ..........
```

FIGURE 11I

```
       Eco  ..........  ..........  ..........  ..........  ..........
 Pol_Delta  GCGLASTSRS  PA........  ..........  ..........  ..........
       KOD  ..........  ..........  ..........  ..........  ..........
      PabI  ..........  ..........  ..........  ..........  ..........
      PocI  ..........  ..........  ..........  ..........  ..........

1651                                                    1700
       tgo  ..........  ..........  ..........  ..........  ..........
       pfu  LIGNMENTSE  TGTRCHESEQ  XENCEANALY  SISWEINTER  FACEMAINPA
       tsp  ..........  ..........  ..........  ..........  .........G
       tli  ..........  ..........  ..........  ..........  ..........
       mvo  ..........  ..........  ..........  ..........  .........G
      RB69  ..........  ..........  ..........  ..........  ..........
        T4  ..........  ..........  ..........  ..........  ..........
       Eco  ..........  ..........  ..........  ..........  ..........
 Pol_Delta  ..........  ..........  ..........  ..........  ..........
       KOD  ..........  ..........  ..........  ..........  .........G
      PabI  ..........  ..........  ..........  ..........  ..........
      PocI  ..........  ..........  ..........  ..........  ..........

1701                                                    1750
       tgo  ..........  ..........  ..........  ..........  ..........
       pfu  ..........  ..........  ..........  ..........  ..........
       tsp  ..........  ..........  ..........  ..........  ..........
       tli  ..........  ..........  ..........  ..........  ..........
       mvo  WITHFXLLSE  QXENCESSEQ  XENCEINALI  GNMENTSETG  TGCGLASTSR
      RB69  ..........  ..........  ..........  ..........  ..........
        T4  ..........  ..........  ..........  ..........  ..........
       Eco  ..........  ..........  ..........  ..........  ..........
 Pol_Delta  ..........  ..........  ..........  ..........  ..........
       KOD  ..........  ..........  ..........  ..........  ..........
      PabI  ..........  ..........  ..........  ..........  ..........
      PocI  ..........  ..........  ..........  ..........  ..........

17511755
       tgo  ...T.    (SEQ ID NO:191)
       pfu  ...GE    (SEQ ID NO:192)
       tsp  ...KK    (SEQ ID NO:193)
       tli  .....    (SEQ ID NO:194)
       mvo  SPAGE    (SEQ ID NO:195)
      RB69  .....    (SEQ ID NO:196)
        T4  .....    (SEQ ID NO:197)
       Eco  .....    (SEQ ID NO:198)
 Pol_Delta  ...GE    (SEQ ID NO:199)
       KOD  ...T.    (SEQ ID NO:200)
      PabI  ...KX    (SEQ ID NO:201)
      PocI  ...KX    (SEQ ID NO:202)
```

THERMOSTABLE OR THERMOACTIVE DNA POLYMERASE MOLECULES WITH ATTENUATED 3'-5' EXONUCLEASE ACTIVITY

This application claims the benefit of priority under 35 U.S.C. §119 (e) of U.S. Provisional Application No. 60/369, 815, filed Apr. 2, 2002, the contents of which are hereby incorporated by reference therein.

FIELD OF THE INVENTION

The present invention relates to thermostable or thermoactive DNA polymerases with attenuated 3'-5' exonuclease ("proofreading") activity, methods for their synthesis, methods for their use, and kits comprising them. The enzymes are useful in many recombinant DNA techniques, especially nucleic acid amplification by the polymerase chain reaction (PCR).

BACKGROUND OF THE INVENTION

DNA polymerases synthesize DNA molecules in the 5' to 3' direction from deoxynucleoside triphosphates (nucleotides) using a complementary template DNA strand and a primer by successively adding nucleotides to the free 3'-hydroxyl group of the growing strand. The template strand determines the order of addition of nucleotides via Watson-Crick base pairing. In cells, DNA polymerases are involved in DNA repair synthesis and replication. See, e.g., Kornberg et al., 1992, *DNA Synthesis*, W. H. Freeman, New York; Alberts et al., 1994, Molecular Biology of the Cell, 3d ed., Garland Press, New York.

Many molecular cloning techniques and protocols involve the synthesis of DNA in in vitro reactions catalyzed by DNA polymerases. For example, DNA polymerases are used in DNA labelling and DNA sequencing reactions, using either $^{35}$S-, $^{32}$P-, $^{33}$P- or fluorescently-labelled nucleotides. One of the most versatile and widely-used DNA synthesis techniques, the polymerase chain reaction (PCR) technique, is disclosed in U.S. Pat. Nos. 4,683,202; 4,683,195; 4,800,159; and 4,965,188, and discussed in *PCR Strategies*, 1995 Innis et al. (eds.), Academic Press, Inc., incorporated herein by reference in their entireties.

The best characterized DNA polymerase is *Escherichia coli* DNA polymerase I (Eco Pol I). Eco Pol I and several DNA polymerases homologous to it have three enzymatic functions: i) a 5'-3' exonuclease activity, ii) a 3'-5' exonuclease activity and iii) a DNA synthesis activity. The latter two functions are located toward the carboxy terminus of the protein, within a 'Klenow' fragment (Eco Pol I K). Enzyme preparations of Eco Pol I can be treated with subtilisin to yield a Eco Pol I K minus the 5'-3' exonuclease activity. See Brown et al., 1982, J Biol. Chem. 257: 1965–72; Joyce et al., 1982, J. Biol. Chem. 257: 1958–64; Joyce et al., 1983, Proc Natl Acad Sci USA 80: 1830–34; Klenow et al., 1970, Proc. Natl. Acad. Sci. USA 65: 168–75; Kornberg, 1974; Setlow, P. et al., 1972, J. Biol. Chem. 247: 224–31; Setlow et al., 1972, J. Biol. Chem. 247: 232–40; Steitz et al., 1987, in Protein Engineering, Chap. 20, pp. 227–35 Oxender et al. (eds). Alan R. Liss, New York.

Crystal structure analysis of Eco Pol I K has shown that its peptide chain is folded into two distinct domains, with the smaller domain, of 200 amino acid residues, being the 3'-5' exonuclease domain and the other domain, of 400 amino acid residues, being the DNA synthesis domain. See Ollis et al., 1985, Nature 313:762–66. The active sites of the 3'-5' exonuclease and DNA synthesis activities are separated by about 30 angstroms. See id. The DNA synthesis active site binds to double-stranded DNA containing a single-stranded 5' extension and deoxynucleoside triphosphate (dNTP) whereas the 3'-5' exonuclease active site binds to single-stranded DNA and deoxynucleoside monophosphate (dNMP). See id. The existence of a conserved 3'-5' exonuclease active site present in a number of DNA polymerases was predicted by Bernat et al., 1989, Cell 59: 219–28; Blanco et al., 1992, Gene 112: 139–44; Reha-Krantz, 1992, Gene 112: 133–37.

The DNA synthesis domain of Eco Pol I has been cloned, expressed, and characterized independently of the 3'-5' and 5'-3' exonuclease domains. As discussed above, the DNA synthesis domain contains approximately 400 amino acids. There is 50-fold less polymerase activity in the DNA synthesis domain than in the Eco Pol I K. See Derbyshire et al., 1993, Nucleic Acids Res. 21:5439–48.

Thermostable and thermoactive DNA polymerases derived from a variety of organisms have been described extensively in the literature. Particular examples include DNA polymerases from a variety of species of the eubacterial genus *Thermus*, see U.S. Pat. No. 5,466,591, in particular from *Thermus aquaticus* (Taq DNA polymerase) described in U.S. Pat. Nos. 4,889,818, 5,352,600 and 5,079, 352, and the DNA polymerase from the eubacterial species *Thermotoga maritima* (Tma DNA polymerase) described in U.S. Pat. Nos. 5,374,553 and 5,420,029.

Both *E. coli*, a mesophile, and *T. maritima*, a thermophile, are eubacteria. Like *E. coli* DNA polymerase I, Tma DNA polymerase has both a 5'-3' exonuclease activity and a 3'-5' exonuclease activity. In contrast, DNA polymerases from *Thermus* species, which also are thermophilic eubacteria, possess only 5'-3' exonuclease activity. A review of thermostable and thermoactive DNA polymerases and their associated activities is found in Abramson, 1995, in *PCR Strategies*, Innis et al. (eds), Academic Press, Inc. Mutant forms of a number of archae and eubacterial thermostable or thermoactive DNA polymerases that lack a 3'-5' exonuclease activity are described in U.S. Pat. Nos. 6,015,668, 5,939, 301, 5,988,614, 5,882,904, 5,489,523.

While Eco Pol I and Tma DNA polymerase have the same three enzymatic activities, and the same general domain structure, they are very different enzymes. For example, Eco Pol I and Tma DNA polymerase have very different amino acid sequences. In particular, even when gaps are introduced into their sequences to optimize their alignment, the 3'-5' exonuclease domains of these two proteins are only about 33% identical. Further, the two enzymes exhibit different specific activities and differing resistance to chemical denaturing conditions. As these differences are observed in purified enzymes removed from their natural in vivo environments, they must be caused by differences in the amino acid sequences of the enzymes themselves.

The 3'-5' exonuclease activity "proofreads" the nascent DNA strand as it is synthesized and preferentially removes nucleotides from it that are mismatched with the template strand, thus increasing the fidelity of DNA synthesis. However, the presence of a robust 3'-5' exonuclease activity can be problematic for in vitro polymerization reactions, particularly PCR, in which the presence of a 3'-5' exonuclease activity lowers the efficiency of the amplification. See Barnes, 1994, Proc. Natl. Acad. Sci. USA 91:2216–20.

Attempts have been made to avoid the deleterious effects of 3'-5' exonuclease activity by using a DNA polymerase enzyme that lacks a 3'-5' exonuclease activity. Taq polymerase naturally lacks this activity. Other DNA polymerases have been genetically engineered to eliminate it. See, e.g., U.S. Pat. Nos. 6,015,668, 5,939,301, 5,988,614, 5,882,904 and 5,489,523. These enzymes work in applications where higher fidelity of replication is unnecessary, for example, in a PCR used to amplify a template for DNA sequencing reactions, size analysis, restriction enzyme analysis or probe-based analyses.

However, other polymerization reactions, e.g., PCR to amplify a DNA fragment for cloning, require a higher level of fidelity. In an effort to reduce the problems associated with the 3'-5' exonuclease activity while retaining its benefits, mixtures of two different DNA polymerases have been used. One polymerase in the mix has a wild-type level of 3'-5' exonuclease activity. The other lacks this activity. The ratio of the two polymerases is manipulated to produce the desired ratio of 3'-5' exonuclease to DNA polymerase activities. See Cheng et al., 1994, Proc. Natl. Acad. Sci. USA 91:5695–99; Barnes, 1994, Proc. Natl. Acad. Sci. USA 91:2216–20; Cheng, 1995, "Longer PCR Amplifications" in PCR Strategies (Innis et al., eds), Academic Press, San Diego 313–24; Cheng et al., 1995, PCR Meth. Applic. 4:294–98; U.S. Pat. Nos. 5,512,462, 5,436,149 and 5,556,772 and PCT Pat. App. Pub. WO 94/26766. While this blending technique can be used to achieve the desired amount of 3'-5' exonuclease activity, it is expensive, time consuming, and must be optimized on a batch-by-batch basis. It requires the DNA polymerase activities and 3'-5' exonuclease activities of each enzyme preparation to be carefully calibrated so that the two polymerases can be mixed in the right amounts to produce the desired ratio of 3'-5' exonuclease activity to DNA polymerase activity. Thus, there is a need in the art for a rapid and economical method of producing a DNA polymerase reagent with a desired level of 3'-5' exonuclease activity and a desired ratio of 3'-5' exonuclease to DNA polymerase activities.

SUMMARY OF THE INVENTION

The present invention describes the surprising generation of a thermostable or thermoactive DNA polymerase with an attenuated 3'-5' exonuclease activity. The attenuated 3'-5' exonuclease activity makes such enzymes useful in a wide range of polymerization reactions.

In one aspect, the present invention provides an isolated thermostable or thermoactive DNA polymerase exhibiting attenuated 3'-5' exonuclease activity. In one embodiment, the thermostable or thermoactive polymerase is a modified thermostable or thermoactive DNA polymerase. In another embodiment, the modified thermostable DNA polymerase is a mutant thermostable DNA polymerase. In another embodiment, the modified thermostable or thermoactive DNA polymerase has a 3'-5' exonuclease activity of between about 0.1% and about 65% of that of a corresponding unmodified thermostable or thermoactive DNA polymerase, wherein exonuclease activity is determined using the Standard Assay described in Example 3. In another embodiment, the modified thermostable or thermoactive DNA polymerase has a 3'-5' exonuclease activity of between about 1% and about 30% of that of a corresponding unmodified thermostable or thermoactive DNA polymerase. In another embodiment, the modified thermostable or thermoactive DNA polymerase has a 3'-5' exonuclease activity of between about 3% and about 20% of that of a corresponding unmodified thermostable or thermoactive DNA polymerase. In another embodiment, the modified thermostable or thermoactive DNA polymerase has a 3'-5' exonuclease activity of between about 3% and about 10% of that of a corresponding unmodified thermostable or thermoactive DNA polymerase. In another embodiment, the modified thermostable or thermoactive DNA polymerase has a 3'-5' exonuclease activity of between about 3% and about 5% of that of a corresponding unmodified thermostable or thermoactive DNA polymerase.

In another aspect, the present invention provides an isolated thermostable or thermoactive DNA polymerase having 6.5 units or less, but more than 0, units (U)/pmol 3'-5' exonuclease activity, measured using the Standard Assay described below in Example 3. In one embodiment, the modified thermostable or thermoactive DNA polymerase has a 3'-5' exonuclease activity of between about 0.4 and 3.0 U/pmol. In another embodiment, the modified thermostable or thermoactive DNA polymerase has a 3'-5' exonuclease activity of between about 0.4 and 1.6 U/pmol.

In another aspect, the present invention provides an isolated thermostable or thermoactive DNA polymerase, wherein the thermostable or thermoactive DNA polymerase has a 5'-3' DNA polymerase activity and a 3'-5' exonuclease activity and the ratio of the polymerase activity to the exonuclease activity is greater than 1. In one embodiment, the thermostable or thermoactive DNA polymerase has a ratio of 5'-3' DNA polymerase activity to 3'-5' exonuclease activity between about 3.0 and 50. In another embodiment, the thermostable or thermoactive DNA polymerase has a ratio of 5'-3' DNA polymerase activity to 3'-5' exonuclease activity between about 6.0 and 25.0.

In another aspect, the thermostable or thermoactive DNA polymerase has an attenuated 3'-5' exonuclease activity. In one embodiment, the thermostable or thermoactive DNA polymerase is a modified thermostable or thermoactive DNA polymerase. In another embodiment, the modified thermostable DNA polymerase is a mutant thermostable DNA polymerase.

In another aspect, the invention provides a modified thermostable or thermoactive DNA polymerase wherein either the ssDNA or the dsDNA 3'-5' exonuclease activity is preferentially attenuated. In one embodiment, the modified thermostable DNA polymerase is a mutant thermostable DNA polymerase.

In another aspect, the thermostable or thermoactive DNA polymerase with attenuated 3'-5' exonuclease activity is derived from a thermophilic eubacterium in the genus *Thermotoga*. In yet another aspect, the thermophilic eubacterium is *Thermotoga maritima* (Tma). In another aspect, the thermophilic eubacterium is *Thermotoga neapolitana*.

In one aspect, the thermostable or thermoactive DNA polymerase with attenuated 3'-5' exonuclease activity is derived from a thermophilic eubacterium in the genus *Thermosipho*. In one embodiment, the thermophilic eubacterium is *Thermosipho africanus*.

In another aspect, the thermostable or thermoactive DNA polymerase with attenuated 3'-5' exonuclease activity is derived from a thermophilic eubacterium in the genus *Aquifex*. In one embodiment, the thermophilic eubacterium is *Aquifex pyrophilus*. In another embodiment, the thermophilic eubacterium is *Aquifex aeolieus*.

In another aspect, the thermostable or thermoactive DNA polymerase with attenuated 3'-5' exonuclease activity is derived from a thermophilic archae in the genus *Thermococcus*. In one embodiment, the thermophilic archae is *Thermococcus barossi*. In another embodiment, the thermophilic archae is *Thermococcus litoralis*. In another embodiment, the thermophilic archae is *Thermococcus gorgonarius* ("Tgo").

In another aspect, the thermostable or thermoactive DNA polymerase with attenuated 3'-5' exonuclease activity is derived from a thermophilic archae in the genus *Pyrococcus*. In one embodiment, the thermophilic archae is *Pyrococcus furiosus*. In another embodiment, the thermophilic archae is *Pyrococcus* sp. GB-D. In another embodiment, the thermophilic archae is *Pyrococcus woesei*. In another embodiment, the thermophilic archae is *Pyrococcus abyssi*.

In another aspect, the thermostable or thermoactive DNA polymerase with attenuated 3'-5' exonuclease activity is derived from a thermophilic archae in the genus *Pyrodictium*. In one embodiment, the thermophilic archae is *Pyrodictium abyssi*. In another embodiment, the thermophilic archae is *Pyrodictium occultum*.

In another aspect, the invention provides an isolated thermostable or thermoactive DNA polymerase comprising a 3'-5' exonuclease domain and exhibiting an attenuated 3'-5' exonuclease activity of about 6.5 or less, but greater than 0, U/pmol, measured using the Standard Assay of Example 3, wherein said 3'-5' exonuclease domain comprises the sequence motif:

(a) An EXO I motif having the formula $DX_1EX_2X_3SX_4$, wherein
  D is an aspartate residue,
  $X_1$ is any amino acid residue, or no residue,
  E is a glutamate residue,
  $X_2$ is any amino acid residue,
  $X_3$ is any amino acid residue,
  S is a serine residue, and
  $X_4$ is any amino acid residue, or
(b) An EXO II motif having the formula $X_5X_6X_7X_8X_9X_{10}X_{11}X_{12}X_{13}X_{14}$ (SEQ ID NO:1), wherein
  $X_5$ is any amino acid residue,
  $X_6$ is any amino acid residue,
  $X_7$ is a cysteine or a leucine residue,
  $X_8$ is any amino acid residue,
  $X_9$ is a phenylalanine or a tyrosine residue,
  $X_{10}$ is any amino acid residue,
  $X_{11}$ is any amino acid residue,
  $X_{12}$ is any amino acid residue,
  $X_{13}$ is an isoleucine or valine residue, and
  $X_{14}$ is a leucine or phenylalanine residue, or
(c) An EXO IIa motif having the formula $DX_{15}X_{16}X_{17}X_{18}X_{19}YX_{20}X_{21}X_{22}X_{23}$ (SEQ ID NO:2), wherein
  D is an aspartate residue,
  $X_{15}$ is a proline, an alanine, a leucine or a threonine residue,
  $X_{16}$ is a leucine or a methionine residue,
  $X_{17}$ is a leucine or an isoleucine residue,
  $X_{18}$ is any amino acid residue,
  $X_{19}$ is an alanine or a serine residue,
  Y is a tyrosine residue,
  $X_{20}$ is a leucine, an isoleucine or a valine residue,
  $X_{21}$ is a leucine or a tryptophan residue,
  $X_{22}$ is an aspartate residue, an asparagine residue, a glutamate residue or a glutamine residue, and
  $X_{23}$ is a proline or a serine residue, or
(d) An EXO III motif having the formula $X_{24}X_{25}X_{26}X_{27}X_{28}X_{29}X_{30}X_{31}X_{32}X_{33}X_{34}X_{35}X_{36}$ (SEQ ID NO:3), wherein
  $X_{24}$ is a proline or an alanine residue,
  $X_{25}$ is any amino acid residue,
  $X_{26}$ is a glutamate, an aspartate or a proline residue,
  $X_{27}$ is a lysine, an arginine or glutamate residue,
  $X_{28}$ is any amino acid residue,
  $X_{29}$ is any amino acid residue,
  $X_{30}$ is a glutamate, an arginine or an asparagine residue,
  $X_{31}$ is any amino acid residue,
  $X_{32}$ is a serine, an alanine or cysteine residue,
  $X_{33}$ is any amino acid residue,
  $X_{34}$ is a glutamate or a threonine residue,
  $X_{35}$ is any amino acid residue, and
  $X_{36}$ is an alanine residue.

In another aspect, the invention provides an isolated thermostable or thermoactive DNA polymerase comprising a 3'-5' exonuclease domain and having a 5'-3' polymerase activity and an attenuated 3'-5' exonuclease activity wherein the ratio of said 5'-3' polymerase activity in U/pmol, measured using the polymerase assay in Example 3, to said 3'-5' exonuclease activity in U/pmol, measured as described using the Standard Assay in Example 3, is between about 1 and 100 and said 3'-5' exonuclease domain comprises the sequence motif (a) An EXO I motif having the formula $DX_1EX_2X_3SX_4$, wherein
  D is an aspartate residue,
  $X_1$ is any amino acid residue, or no residue,
  E is a glutamate residue,
  $X_2$ is any amino acid residue,
  $X_3$ is any amino acid residue,
  S is a serine residue, and
  $X_4$ is any amino acid residue, or
(b) An EXO II motif having the formula $X_5X_6X_7X_8X_9X_{10}X_{11}X_{12}X_{13}X_{14}$ (SEQ ID NO:1), wherein
  $X_5$ is any amino acid residue,
  $X_6$ is any amino acid residue,
  $X_7$ is a cysteine or a leucine residue,
  $X_8$ is any amino acid residue,
  $X_9$ is a phenylalanine or a tyrosine residue,
  $X_{10}$ is any amino acid residue,
  $X_{11}$ is any amino acid residue,
  $X_{12}$ is any amino acid residue,
  $X_{13}$ is an isoleucine or valine residue, and
  $X_{14}$ is a leucine or phenylalanine residue, or
(c) An EXO IIa motif having the formula $DX_{15}X_{16}X_{17}X_{18}X_{19}YX_{20}X_{21}X_{22}X_{23}$ (SEQ ID NO:2), wherein
  D is an aspartate residue,
  $X_{15}$ is a proline, an alanine, a leucine or a threonine residue,
  $X_{16}$ is a leucine or a methionine residue,
  $X_{17}$ is a leucine or an isoleucine residue,
  $X_{18}$ is any amino acid residue,
  $X_{19}$ is an alanine or a serine residue,
  Y is a tyrosine residue,
  $X_{20}$ is a leucine, an isoleucine or a valine residue,
  $X_{21}$ is a leucine or a tryptophan residue,
  $X_{22}$ is an aspartate residue, an asparagine residue, a glutamate residue or a glutamine residue, and
  $X_{23}$ is a proline or a serine residue, or
(d) An EXO m motif having the formula $X_{24}X_{25}X_{26}X_{27}X_{28}X_{29}X_{30}X_{31}X_{32}X_{33}X_{34}X_{35}X_{36}$ (SEQ ID NO:3), wherein
  $X_{24}$ is a proline or an alanine residue,
  $X_{25}$ is any amino acid residue,
  $X_{26}$ is a glutamate, an aspartate or a proline residue,
  $X_{27}$ is a lysine, an arginine or glutamate residue,
  $X_{28}$ is any amino acid residue,
  $X_{29}$ is any amino acid residue,
  $X_{30}$ is a glutamate, an arginine or an asparagine residue,
  $X_{31}$ is any amino acid residue,
  $X_{32}$ is a serine, an alanine or cysteine residue,
  $X_{33}$ is any amino acid residue, $X_{34}$ is a glutamate or a threonine residue,
$X_{35}$ is any amino acid residue, and
$X_{36}$ is an alanine residue.

In yet another aspect, the invention provides a modified thermostable or thermoactive DNA polymerase wherein said modified polymerase comprises a 3'-5' exonuclease domain, has about 0.1% to 65% of the 3'-5' exonuclease activity of the thermostable DNA polymerase before modification and said 3'-5' exonuclease domain comprises the sequence motif (a) An EXO I motif having the formula $DX_1EX_2X_3SX_4$, wherein
D is an aspartate residue,
$X_1$ is any amino acid residue, or no residue,
E is a glutamate residue,
$X_2$ is any amino acid residue,
$X_3$ is any amino acid residue,
S is a serine residue, and
$X_4$ is any amino acid residue, or (b) An EXO II motif having the formula $X_5X_6X_7X_8X_9X_{10}X_{11}X_{12}X_{13}X_{14}$ (SEQ ID NO:1), wherein
$X_5$ is any amino acid residue,
$X_6$ is any amino acid residue,
$X_7$ is a cysteine or a leucine residue,
$X_8$ is any amino acid residue,
$X_9$ is a phenylalanine or a tyrosine residue,
$X_{10}$ is any amino acid residue,
$X_{11}$ is any amino acid residue,
$X_{12}$ is any amino acid residue,
$X_{13}$ is an isoleucine or valine residue, and
$X_{14}$ is a leucine or phenylalanine residue, or (c) An EXO IIa motif having the formula $DX_{15}X_{16}X_{17}X_{18}X_{19}YX_{20}X_{21}X_{22}X_{23}$ (SEQ ID NO:2), wherein
D is an aspartate residue,
$X_{15}$ is a proline, an alanine, a leucine or a threonine residue,
$X_{16}$ is a leucine or a methionine residue,
$X_{17}$ is a leucine or an isoleucine residue,
$X_{18}$ is any amino acid residue,
$X_{19}$ is an alanine or a serine residue,
Y is a tyrosine residue,
$X_{20}$ is a leucine, an isoleucine or a valine residue,
$X_{21}$ is a leucine or a tryptophan residue,
$X_{22}$ is an aspartate residue, an asparagine residue, a glutamate residue or a glutamine residue, and
$X_{23}$ is a proline or a serine residue, or (d) An EXO m motif having the formula $X_{24}X_{25}X_{26}X_{27}X_{28}X_{29}X_{30}X_{31}X_{32}X_{33}X_{34}X_{35}X_{36}$ (SEQ ID NO:3), wherein
$X_{24}$ is a proline or an alanine residue,
$X_{25}$ is any amino acid residue,
$X_{26}$ is a glutamate, an aspartate or a proline residue,
$X_{27}$ is a lysine, an arginine or glutamate residue,
$X_{28}$ is any amino acid residue,
$X_{29}$ is any amino acid residue,
$X_{30}$ is a glutamate, an arginine or an asparagine residue,
$X_{31}$ is any amino acid residue,
$X_{32}$ is a serine, an alanine or cysteine residue,
$X_{33}$ is any amino acid residue,
$X_{34}$ is a glutamate or a threonine residue,
$X_{35}$ is any amino acid residue, and
$X_{36}$ is an alanine residue.

In one aspect, the 3'-5' exonuclease domain of an isolated thermostable or thermoactive DNA polymerase of the invention comprises an EXO I, EXO II, EXO IIa, or EXO III domain having any combination of particular amino acid residues consistent with the above formulae.

In another aspect, the 3'-5' exonuclease domain of an isolated thermostable or thermoactive DNA polymerase of the the invention comprises at least two, three or each of said sequence motifs (a), (b), (c) and (d), in an amino-terminal to carboxy-terminal order.

In another aspect, a modified thermostable or thermoactive DNA polymerase of the invention comprises a 3'-5' exonuclease domain and exhibits an attenuated 3'-5' exonuclease activity of about 6.5 or less, but greater than 0, U/pmol, measured using the Standard Assay of Example 3, below, wherein said 3'-5' exonuclease domain has greater than about 80% but less than 100% sequence identity to the 3'-5' exonuclease domain that is underlined in FIG. 1A (SEQ ID NO:85).

In another aspect, a modified thermostable or thermoactive DNA polymerase of the invention comprises a 3'-5' exonuclease domain and exhibits an attenuated 3'-5' exonuclease activity of about 6.5 or less, but greater than 0, U/pmol, measured using the Standard Assay of Example 3, below, wherein said modified DNA polymerase has greater than about 80% but less than 100% sequence identity to the sequence of FIG. 1A (SEQ ID NO:85).

In another aspect, a modified thermostable or thermoactive DNA polymerase of the invention comprises a 3'-5' exonuclease domain and exhibits an attenuated 3'-5' exonuclease activity of about 6.5 or less, but greater than 0, U/pmol, measured using the Standard Assay of Example 3, below, wherein said 3'-5' exonuclease domain has greater than about 80% but less than 100% sequence identity to the 3'-5' exonuclease domain of an unmodified Tne DNA polymerase. In one embodiment, the 3'-5' exonuclease domain of the unmodified Tne DNA polymerase comprises the sequence shown in FIG. 2 (SEQ ID NO:88).

In another aspect, a modified thermostable or thermoactive DNA polymerase of the invention comprises a 3'-5' exonuclease domain and exhibits an attenuated 3'-5' exonuclease activity of about 6.5 or less, but greater than 0, U/pmol, measured using the Standard Assay of Example 3, below, wherein said DNA polymerase has greater than about 80% but less than 100% sequence identity to the amino acid sequence of an unmodified Tne DNA polymerase. The amino acid sequence of an unmodified Tne DNA polymerase can, for example, comprise the amino acid sequence of a Tne polymerase provided in U.S. Pat. No. 5,948,614.

In another aspect, a modified thermostable or thermoactive DNA polymerase of the invention comprises a 3'-5' exonuclease domain and exhibits an attenuated 3'-5' exonuclease activity of about 6.5 or less, but greater than 0, U/pmol, measured using the Standard Assay of Example 3, below, wherein said 3'-5' exonuclease domain has greater than about 80% but less than 100% sequence identity to the 3'-5' exonuclease domain of an unmodified Taf DNA polymerase. In one embodiment, the 3'-5' exonuclease domain of the unmodified Taf DNA polymerase comprises the sequence shown in FIG. 3 (SEQ ID NO:89).

In another aspect, a modified thermostable or thermoactive DNA polymerase of the invention comprises a 3'-5' exonuclease domain and exhibits an attenuated 3'-5' exonuclease activity of about 6.5 or less, but greater than 0, U/pmol, measured using the Standard Assay of Example 3, below, wherein said DNA polymerase has greater than about 80% but less than 100% sequence identity to the amino acid sequence of an unmodified Taf DNA polymerase. The amino acid sequence of the unmodified Taf DNA polymerase can, for example, comprise the amino acid sequence of a Taf DNA polymerase provided in U.S. Pat. No. 5,968,799.

In another aspect, the 3'-5' exonuclease domain of a thermostable or thermoactive DNA polymerase of the invention comprises an EXO I motif wherein
$DX_1EX_2X_3SX_4$, wherein
D is an aspartate residue,
$X_1$ is any amino acid residue, or no residue,
E is a glutamate residue,
$X_2$ is a threonine residue,
$X_3$ is any amino acid residue,
S is a serine residue, and
$X_4$ is any amino acid residue (SEQ ID NO:4);

or wherein
D is an aspartate residue,
$X_1$ is any amino acid residue, or no residue,
E is a glutamate residue,
$X_2$ is a threonine residue,
$X_3$ is a threonine residue,
S is a serine residue, and
$X_4$ is a leucine residue (SEQ ID NO:5);

or wherein
D is an aspartate residue,
$X_1$ is any amino acid residue, or no residue,
E is a glutamate residue,
$X_2$ is a threonine residue,
$X_3$ is any amino acid residue,
S is a serine residue, and
$X_4$ is a leucine residue (SEQ ID NO:6);

or wherein
D is an aspartate residue,
$X_1$ is any amino acid residue, or no residue,
E is a glutamate residue,
$X_2$ is any amino acid residue,
$X_3$ is any amino acid residue,
S is a serine residue, and
$X_4$ is a leucine residue (SEQ ID NO:7);

or wherein
D is an aspartate residue,
$X_1$ is any amino acid residue, or no residue,
E is a glutamate residue,
$X_2$ is any amino acid residue,
$X_3$ is a threonine residue,
S is a serine residue, and
$X_4$ is a leucine residue (SEQ ID NO:8);

or wherein
D is an aspartate residue,
$X_1$ is a leucine residue,
E is a glutamate residue,
$X_2$ a threonine residue,
$X_3$ is a serine residue,
S is a serine residue, and
$X_4$ is a leucine residue (SEQ ID NO:9).

In another aspect, the 3'-5' exonuclease domain of a thermostable or thermoactive DNA polymerase of the invention comprises an EXO II motif wherein
$X_5$ is any amino acid residue,
$X_6$ is any amino acid residue,
$X_7$ is a cysteine or a leucine residue,
$X_8$ is a lysine residue,
$X_9$ is a phenylalanine or a tyrosine residue,
$X_{10}$ is any amino acid residue,
$X_{11}$ is any amino acid residue,
$X_{12}$ is any amino acid residue,
$X_{13}$ is an isoleucine or a valine residue and
$X_{14}$ is a leucine or phenylalanine amino acid residue (SEQ ID NO:10);

or wherein
$X_5$ is an uncharged polar residue,
$X_6$ is any amino acid residue,
$X_7$ is a cysteine or a leucine residue,
$X_8$ is a lysine residue,
$X_9$ is a phenylalanine or a tyrosine residue,
$X_{10}$ is any amino acid residue,
$X_{11}$ is any amino acid residue,
$X_{12}$ is any amino acid residue,
$X_{13}$ is an isoleucine or a valine residue and
$X_{14}$ is a leucine or phenylalanine amino acid residue (SEQ ID NO:11);

or wherein
$X_5$ is an uncharged polar residue,
$X_6$ is an uncharged polar residue,
$X_7$ is a cysteine or a leucine residue,
$X_8$ is a lysine residue,
$X_9$ is a phenylalanine or a tyrosine residue,
$X_{10}$ is any amino acid residue,
$X_{11}$ is any amino acid residue,
$X_{12}$ is any amino acid residue,
$X_{13}$ is an isoleucine or a valine residue and
$X_{14}$ is a leucine or phenylalanine amino acid residue (SEQ ID NO:12);

or wherein
$X_5$ is an uncharged polar residue,
$X_6$ is an uncharged polar residue,
$X_7$ is a cysteine or a leucine residue,
$X_8$ is a lysine residue,
$X_9$ is a phenylalanine or a tyrosine residue,
$X_{10}$ is an acidic residue,
$X_{11}$ is any amino acid residue,
$X_{12}$ is any amino acid residue,
$X_{13}$ is an isoleucine or a valine residue and
$X_{14}$ is a leucine or phenylalanine amino acid residue (SEQ ID NO:13);

or wherein
$X_5$ is an uncharged polar residue,
$X_6$ is an uncharged polar residue,
$X_7$ is a cysteine or a leucine residue,
$X_8$ is a lysine residue,
$X_9$ is a phenylalanine or a tyrosine residue,
$X_{10}$ is an acidic residue,
$X_{11}$ is any amino acid residue,
$X_{12}$ is any amino acid residue,
$X_{13}$ is an isoleucine or a valine residue and
$X_{14}$ is a leucine or a phenylalanine residue (SEQ ID NO:14);

or wherein
$X_5$ is a glutamine residue,
$X_6$ is an asparagine residue,
$X_7$ is a cysteine or a leucine residue,
$X_8$ is a lysine residue,
$X_9$ is a phenylalanine or a tyrosine residue,
$X_{10}$ is an aspartate residue,
$X_{11}$ is any amino acid residue,
$X_{12}$ is any amino acid residue,
$X_{13}$ is an isoleucine or a valine residue and
$X_{14}$ is a leucine or phenylalanine residue (SEQ ID NO:15);

or wherein
- $X_5$ is a glutamine residue,
- $X_6$ is an asparagine residue,
- $X_7$ is a leucine residue,
- $X_8$ is a lysine residue,
- $X_9$ is a phenylalanine residue,
- $X_{10}$ is an aspartate residue,
- $X_{11}$ is a tyrosine residue,
- $X_{12}$ is a lysine residue,
- $X_{13}$ is a valine residue and
- $X_{14}$ is a leucine residue (SEQ ID NO:16).

In another aspect, the 3'-5' exonuclease domain of a thermostable or thermoactive DNA polymerase of the invention comprises an EXO II motif wherein $X_5$ is a nonpolar residue, such as an alanine residue. In one embodiment, the 3'-5' exonuclease domain of a thermostable or thermoactive DNA polymerase of the invention comprises an EXO II motif wherein $X_8$ is a lysine residue. In another embodiment, the 3'-5' exonuclease domain of a thermostable or thermoactive DNA polymerase of the invention comprises an EXO II motif wherein wherein $X_5$ is a nonpolar residue and $X_8$ is a lysine residue.

In another aspect, the 3'-5' exonuclease domain of a thermostable or thermoactive DNA polymerase of the invention comprises an EXO II motif wherein
- $X_5$ is a nonpolar residue,
- $X_6$ is an uncharged polar residue,
- $X_7$ is a cysteine or a leucine residue,
- $X_8$ is a lysine residue,
- $X_9$ is a phenylalanine or a tyrosine residue,
- $X_{10}$ is an acidic residue,
- $X_{11}$ is any amino acid residue,
- $X_{12}$ is any amino acid residue,
- $X_{13}$ is an isoleucine or a valine residue and
- $X_{14}$ is a leucine or phenylalanine amino acid residue (SEQ ID NO:17);

or wherein
- $X_5$ is an alanine residue,
- $X_6$ is an uncharged polar residue,
- $X_7$ is a cysteine or a leucine residue,
- $X_8$ is a lysine residue,
- $X_9$ is a phenylalanine or a tyrosine residue,
- $X_{10}$ is an acidic residue,
- $X_{11}$ is any amino acid residue,
- $X_{12}$ is any amino acid residue,
- $X_{13}$ is an isoleucine or a valine residue and
- $X_{14}$ is a leucine or phenylalanine amino acid residue (SEQ ID NO:18);

or wherein
- $X_5$ is an alanine residue,
- $X_6$ is an asparagine residue,
- $X_7$ is a cysteine or a leucine residue,
- $X_8$ is a lysine residue,
- $X_9$ is a phenylalanine or a tyrosine residue,
- $X_{10}$ is an aspartate residue,
- $X_{11}$ is any amino acid residue,
- $X_{12}$ is any amino acid residue,
- $X_{13}$ is an isoleucine or a valine residue and
- $X_{14}$ is a leucine or phenylalanine residue (SEQ ID NO:19).

In another aspect, the 3'-5' exonuclease domain of a thermostable or thermoactive DNA polymerase of the invention comprises an EXO II motif wherein
- $X_5$ is an alanine residue,
- $X_6$ is an asparagine residue,
- $X_7$ is a leucine residue,
- $X_8$ is a lysine residue,
- $X_9$ is a phenylalanine residue,
- $X_{10}$ is an aspartate residue,
- $X_{11}$ is a tyrosine residue,
- $X_{12}$ is a lysine residue,
- $X_{13}$ is a valine residue and
- $X_{14}$ is a leucine residue (SEQ ID NO:20).

In one embodiment, such a thermostable or thermoactive DNA polymerase comprises the amino acid sequence of the 3'-5' exonuclease domain depicted in FIG. 4A modified by a Q384A mutation (SEQ ID NO:96). In another embodiment, such a thermostable or thermoactive DNA polymerase comprises the amino acid sequence of FIG. 4A modified by a Q384A mutation (SEQ ID NO:97).

In another aspect, the 3'-5' exonuclease domain of a thermostable or thermoactive DNA polymerase of the invention comprises an EXO II motif wherein $X_6$ is a nonpolar amino acid residue.

In another aspect, the 3'-5' exonuclease domain of a thermostable or thermoactive DNA polymerase of the invention comprises an EXO II motif wherein
- $X_5$ is an uncharged polar residue,
- $X_6$ is nonpolar residue,
- $X_7$ is a cysteine or a leucine residue,
- $X_8$ is a lysine residue,
- $X_9$ is a phenylalanine or a tyrosine residue,
- $X_{10}$ is an acidic residue,
- $X_{11}$ is any amino acid residue,
- $X_{12}$ is any amino acid residue,
- $X_{13}$ is an isoleucine or a valine residue and
- $X_{14}$ is a leucine or phenylalanine amino acid residue (SEQ ID NO:21);

or wherein
- $X_5$ is a glutamine residue,
- $X_6$ is an alanine residue,
- $X_7$ is a cysteine or a leucine residue,
- $X_8$ is a lysine residue,
- $X_9$ is a phenylalanine or a tyrosine residue,
- $X_{10}$ is an aspartate residue,
- $X_{11}$ is any amino acid residue,
- $X_{12}$ is any amino acid residue,
- $X_{13}$ is an isoleucine or a valine residue and
- $X_{14}$ is a leucine or phenylalanine residue (SEQ ID NO:22).

In another aspect, the 3'-5' exonuclease domain of a thermostable or thermoactive DNA polymerase of the invention comprises an EXO II motif wherein
- $X_5$ is a glutamine residue,
- $X_6$ is an alanine residue,
- $X_7$ is a leucine residue,
- $X_8$ is a lysine residue,
- $X_9$ is a phenylalanine residue,
- $X_{10}$ is an aspartate residue,
- $X_{11}$ is a tyrosine residue,
- $X_{12}$ is a lysine residue,
- $X_{13}$ is a valine residue and
- $X_{14}$ is a leucine residue (SEQ ID NO:23).

In one embodiment, such a thermostable or thermoactive DNA polymerase comprises the amino acid sequence of the 3'-5' exonuclease domain depicted in FIG. 4A modified by a N385A mutation (SEQ ID NO:98). In another embodiment, such a thermostable or thermoactive DNA polymerase comprises the amino acid sequence of FIG. 4A modified by a N385A mutation (SEQ ID NO:99).

In another aspect, the 3'-5' exonuclease domain of a thermostable or thermoactive DNA polymerase of the invention comprises an EXO II motif wherein $X_{10}$ is a glutamate residue.

In another aspect, the 3'-5' exonuclease domain of a thermostable or thermoactive DNA polymerase of the invention comprises an EXO II motif wherein
- $X_5$ is an uncharged polar residue,
- $X_6$ is an uncharged polar residue,
- $X_7$ is a cysteine or a leucine residue,
- $X_8$ is a lysine residue,
- $X_9$ is a phenylalanine or a tyrosine residue,
- $X_{10}$ is a glutamate residue,
- $X_{11}$ is any amino acid residue,
- $X_{12}$ is any amino acid residue,
- $X_{13}$ is an isoleucine or a valine residue and
- $X_{14}$ is a leucine or phenylalanine amino acid residue (SEQ ID NO:24);

or wherein
- $X_5$ is a glutamine residue,
- $X_6$ is an asparagine residue,
- $X_7$ is a cysteine or a leucine residue,
- $X_8$ is a lysine residue,
- $X_9$ is a phenylalanine or a tyrosine residue,
- $X_{10}$ is a glutamate residue,
- $X_{11}$ is any amino acid residue,
- $X_{12}$ is any amino acid residue,
- $X_{13}$ is an isoleucine or a valine residue and
- $X_{14}$ is a leucine or phenylalanine residue (SEQ ID NO:25).

In another aspect, the 3'-5' exonuclease domain of a thermostable or thermoactive DNA polymerase of the invention comprises an EXO II motif wherein
- $X_5$ is a glutamine residue,
- $X_6$ is an asparagine residue,
- $X_7$ is a leucine residue,
- $X_8$ is a lysine residue,
- $X_9$ is a phenylalanine residue,
- $X_{10}$ is a glutamate residue,
- $X_{11}$ is a tyrosine residue,
- $X_{12}$ is a lysine residue,
- $X_{13}$ is a valine residue and
- $X_{14}$ is a leucine residue (SEQ ID NO:26).

In one embodiment, such a thermostable or thermoactive DNA polymerase comprises the amino acid sequence of the 3'-5' exonuclease domain depicted in FIG. 4A modified by a D389E mutation (SEQ ID NO: 159). In another embodiment, such a thermostable or thermoactive DNA polymerase comprises the amino acid sequence of FIG. 4A modified by a D389E mutation (SEQ ID NO:175).

In another aspect, the 3'-5' exonuclease domain of a thermostable or thermoactive DNA polymerase of the invention comprises an EXO II motif wherein $X_{10}$ is a glutamate residue.

In another aspect, the 3'-5' exonuclease domain of a thermostable or thermoactive DNA polymerase of the invention comprises an EXO II motif wherein $X_5$ is a nonpolar residue and $X_6$ is a nonpolar residue.

In another aspect, the 3'-5' exonuclease domain of a thermostable or thermoactive DNA polymerase of the invention comprises an EXO II motif wherein
- $X_5$ is a nonpolar residue,
- $X_6$ is a nonpolar residue,
- $X_7$ is a cysteine or a leucine residue,
- $X_8$ is a lysine residue,
- $X_9$ is a phenylalanine or a tyrosine residue,
- $X_{10}$ is an acidic residue,
- $X_{11}$ is any amino acid residue,
- $X_{12}$ is any amino acid residue,
- $X_{13}$ is an isoleucine or a valine residue and
- $X_{14}$ is a leucine or phenylalanine amino acid residue (SEQ ID NO:27);

or wherein
- $X_5$ is an alanine residue,
- $X_6$ is an alanine residue,
- $X_7$ is a cysteine or a leucine residue,
- $X_8$ is a lysine residue,
- $X_9$ is a phenylalanine or a tyrosine residue,
- $X_{10}$ is an aspartate residue,
- $X_{11}$ is any amino acid residue,
- $X_{12}$ is any amino acid residue,
- $X_{13}$ is an isoleucine or a valine residue and
- $X_{14}$ is a leucine or phenylalanine residue (SEQ ID NO:28).

In another aspect, the 3'-5' exonuclease domain of a thermostable or thermoactive DNA polymerase of the invention comprises an EXO II motif wherein
- $X_5$ is an alanine residue,
- $X_6$ is an alanine residue,
- $X_7$ is a leucine residue,
- $X_8$ is a lysine residue,
- $X_9$ is a phenylalanine residue,
- $X_{10}$ is an aspartate residue,
- $X_{11}$ is a tyrosine residue,
- $X_{12}$ is a lysine residue,
- $X_{13}$ is a valine residue and
- $X_{14}$ is a leucine residue (SEQ ID NO:29).

In one embodiment, such a thermostable or thermoactive DNA polymerase comprises the amino acid sequence of the 3'-5' exonuclease domain depicted in FIG. 4A modified by a Q384A N385A double mutation (SEQ ID NO:100). In another embodiment, such a thermostable or thermoactive DNA polymerase comprises the amino acid sequence of FIG. 4A modified by a Q384A N385A double mutation (SEQ ID NO:101).

In another aspect, the 3'-5' exonuclease domain of a thermostable or thermoactive DNA polymerase of the invention comprises an EXO IIA motif wherein
- D is an aspartate residue,
- $X_{15}$ is a threonine residue,
- $X_{16}$ is a methionine residue,
- $X_{17}$ is an isoleucine residue,
- $X_{18}$ is an alanine residue,
- $X_{19}$ is an alanine residue,
- Y is a tyrosine residue,
- $X_{20}$ is a leucine residue,
- $X_{21}$ is a leucine residue,
- $X_{22}$ is a glutamate residue, and
- $X_{23}$ is a proline residue (SEQ ID NO:30).

In another aspect, the 3'-5' exonuclease domain of a thermostable or thermoactive DNA polymerase of the invention comprises an EXO III motif as above wherein $X_{35}$ is an acidic amino acid residue.

In another aspect, the 3'-5' exonuclease domain of a thermostable or thermoactive DNA polymerase of the invention comprises an EXO III motif wherein
- $X_{24}$ is a proline residue,
- $X_{25}$ is a valine, leucine or isoleucine residue,
- $X_{26}$ is a glutamate, an aspartate or a proline residue,
- $X_{27}$ is a lysine, an arginine residue,
- $X_{28}$ is an alanine or a valine residue,
- $X_{29}$ is an alanine or a valine residue, $X_{30}$ is a glutamate, or an asparagine residue,
$X_{31}$ is an uncharged polar amino acid residue,
$X_{32}$ is a serine or cysteine residue,
$X_{33}$ is a cysteine or glycine residue,
$X_{34}$ is a glutamate or a threonine residue,
$X_{35}$ is an aspartate residue, and
$X_{36}$ is an alanine residue (SEQ ID NO:31)

or wherein
$X_{24}$ is a proline residue,
$X_{25}$ is a valine residue,
$X_{26}$ is a glutamate residue,
$X_{27}$ is a lysine residue,
$X_{28}$ is an alanine residue,
$X_{29}$ is an alanine residue,
$X_{30}$ is an asparagine residue,
$X_{31}$ is a tyrosine residue,
$X_{32}$ is a serine residue,
$X_{33}$ is a cysteine residue,
$X_{34}$ is a glutamate residue,
$X_{35}$ is an aspartate residue, and
$X_{36}$ is an alanine residue (SEQ ID NO:32).

In another aspect, the 3'-5' exonuclease domain of a thermostable or thermoactive DNA polymerase of the invention comprises an EXO III motif wherein $X_{31}$ is a nonpolar residue. In one embodiment, the 3'-5' exonuclease domain of a thermostable or thermoactive DNA polymerase of the invention comprises an EXO III motif wherein $X_{31}$ is a nonpolar residue and $X_{35}$ is an acidic residue.

In one aspect, the 3'-5' exonuclease domain of a thermostable or thermoactive DNA polymerase of the invention comprises an EXO III motif wherein
$X_{24}$ is a proline residue,
$X_{25}$ is a valine, leucine or isoleucine residue,
$X_{26}$ is a glutamate, an aspartate or a proline residue,
$X_{27}$ is a lysine or an arginine residue,
$X_{28}$ is an alanine or a valine residue,
$X_{29}$ is an alanine or a valine residue,
$X_{30}$ is a glutamate or an asparagine residue,
$X_{31}$ is a nonpolar residue,
$X_{32}$ is a serine or cysteine residue,
$X_{33}$ is a cysteine or a glycine residue,
$X_{34}$ is a glutamate or a threonine residue,
$X_{35}$ is an aspartate residue, and
$X_{36}$ is an alanine residue (SEQ ID NO:33).

In one aspect, the 3'-5' exonuclease domain of a thermostable or thermoactive DNA polymerase of the invention comprises an EXO III motif wherein
$X_{24}$ is a proline residue,
$X_{25}$ is a valine residue,
$X_{26}$ is a glutamate residue,
$X_{27}$ is a lysine residue,
$X_{28}$ is an alanine residue,
$X_{29}$ is an alanine residue,
$X_{30}$ is an asparagine residue,
$X_{31}$ is an alanine residue,
$X_{32}$ is a serine residue,
$X_{33}$ is a cysteine residue,
$X_{34}$ is a glutamate residue,
$X_{35}$ is an aspartate residue, and
$X_{36}$ is an alanine residue (SEQ ID NO:34).

In another aspect, the invention provides a chimeric thermostable or thermoactive DNA polymerase with an attenuated 3'-5' exonuclease activity, said polymerase comprising an amino terminal portion and a carboxy terminal portion, with the amino terminal portion derived from the amino terminal portion of a first DNA polymerase and the carboxy terminal portion derived from a second DNA polymerase. In one embodiment, said chimeric DNA polymerase with an attenuated 3'-5' exonuclease activity comprises an amino terminal portion derived from the amino terminal portion of a first thermostable or thermoactive DNA polymerase and a carboxy terminal portion derived from a second thermostable or thermoactive DNA polymerase, said second polymerase preferably being one that exhibits 3'-5' exonuclease activity. In another embodiment, in said chimeric DNA polymerase with an attenuated 3'-5' exonuclease activity, said amino terminal and/or carboxy terminal portion is derived from a DNA polymerase from a *Thermus* species. In another embodiment, in said chimeric DNA polymerase with an attenuated 3'-5' exonuclease activity, said amino terminal and/or carboxy terminal portion is derived from a DNA polymerase from a *Thermotoga* species. In another embodiment, in said chimeric DNA polymerase with an attenuated 3'-5' exonuclease activity, the amino terminal and/or carboxy terminal portion or another portion is derived from a DNA polymerase from a *Thermus* species and the other terminal portion or another portion is derived from a DNA polymerase from a *Thermotoga* species; for example, in one embodiment, the amino terminal portion is derived from a DNA polymerase from a *Thermus* species and the carboxy terminal portion is derived from a DNA polymerase from a *Thermotoga* species. In another embodiment, in said chimeric DNA polymerase with an attenuated 3'-5' exonuclease activity, the amino terminal portion is derived from a *Thermus* species and comprises a 5'-3' exonuclease domain and the carboxy terminal portion is derived from a *Thermotoga* species and comprises a 3'-5' exonuclease domain and a polymerase domain. In another embodiment, in said chimeric DNA polymerase with an attenuated 3'-5' exonuclease activity, the amino terminal portion is derived from a *Thermus* species and comprises a 5'-3' exonuclease domain and has greater than about 80% sequence identity with a corresponding amino terminal portion the DNA polymerase from the *Thermus* species and said carboxy terminal portion has greater than about 80% but less than 100% sequence identity with a corresponding carboxy terminal portion of the DNA polymerase from the *Thermotoga* species. In another embodiment, said *Thermus* species is *Thermus* sp. Z05 and said *Thermotoga* species is *Thermotoga maritima*. In another embodiment, the chimeric thermostable or thermoactive DNA polymerase comprises the amino acid sequence of FIG. 4 (SEQ ID NO:90) modified by one or more of the mutations indicated in the figure. In another embodiment, the chimeric thermostable or thermoactive DNA polymerase comprises the amino acid sequence of FIG. 5 (SEQ ID NO:107) modified by one or more of the mutations indicated in the figure. In another embodiment, the chimeric thermostable or thermoactive DNA polymerase with an attenuated 3'-5' exonuclease activity comprises an amino terminal portion, a middle portion, and a carboxy terminal portion. In another embodiment, in said chimeric DNA polymerase with an attenuated 3'-5' exonuclease activity, the amino terminal portion comprises a 5'-3' exonuclease domain. In another embodiment, in said chimeric DNA polymerase with an attenuated 3'-5' exonuclease activity, the middle portion comprises a 3'-5' exonuclease domain. In another embodiment, in said chimeric DNA polymerase with an attenuated 3'-5' exonuclease activity, the carboxy terminal portion comprises a polymerase domain. In another embodiment, in said chimeric DNA polymerase with an attenuated 3'-5' exonuclease activity, the carboxy terminal portion and the amino terminal portion are derived from a polymerase from a *Thermus* species. In another embodiment, in said chimeric DNA polymerase with an attenuated 3'-5' exonuclease activity, the amino terminus and/or the carboxy terminus have greater than 80% sequence identity with a corresponding amino and/or carboxy terminus portion of a polymerase from a *Thermus* species. In another embodiment, in said chimeric DNA polymerase with an attenuated 3'-5' exonuclease activity, the middle portion is derived from a polymerase from a *Thermotoga* species. In another embodiment, in said chimeric DNA polymerase with an attenuated 3'-5' exonuclease activity, the middle portion has greater than 80%, but less than 100%, sequence identity to the corresponding polymerase from a *Thermotoga* species. In another embodiment, in said chimeric DNA polymerase with an attenuated 3'-5' exonuclease activity, an amino portion and a carboxy portion are derived from a polymerase from a *Thermus* species and a middle portion is derived from a *Thermotoga* species. In another embodiment, in said chimeric DNA polymerase with an attenuated 3'-5' exonuclease activity, the *Thermus* species is *Thermus* sp. Z05 and the *Thermotoga* species is *Thermotoga maritima*. In another embodiment, the chimeric thermostable or thermoactive DNA polymerase comprises the amino acid sequence of FIG. 6 (SEQ ID NO:130) modified by one or more of the mutations indicated in the figure. In another embodiment, the chimeric thermostable or thermoactive DNA polymerase comprises the amino acid sequence of FIG. 7 (SEQ ID NO:148) modified by one or more of the mutations indicated in the figure.

In another aspect, an isolated thermostable or thermoactive DNA polymerase of the invention exhibiting attenuated 3'-5' activity of about 6.5 or less, but greater than 0, U/pmol, measured using the Standard Assay of Example 3, below, has greater than about 80% but less than 100% sequence identity to the 3'-5' exonuclease domain of an unmodified Tma DNA polymerase. In one embodiment, an isolated thermostable or thermoactive DNA polymerase of the invention exhibiting attenuated 3'-5' activity of about 6.5 or less, but greater than 0, U/pmol, measured using the Standard Assay of Example 3, below, has greater than about 80% but less than 100% sequence identity to an unmodified Tma DNA polymerase. The amino acid sequence of the unmodified Tma DNA polymerase can, for example, comprise the amino acid sequence of FIG. 1A (SEQ ID NO:85).

In another aspect, an isolated thermostable or thermoactive DNA polymerase of the invention exhibiting attenuated 3'-5' activity of about 6.5 or less, but greater than 0, U/pmol, measured using the Standard Assay of Example 3, below, has greater than about 80% but less than 100% sequence identity to the 3'-5' exonuclease domain of an unmodified Tne DNA polymerase. In one embodiment, the 3'-5' exonuclease domain of the unmodified Tne DNA polymerase comprises the sequence shown in FIG. 2 (SEQ ID NO:88). In another embodiment, an isolated thermostable or thermoactive DNA polymerase of the invention exhibiting attenuated 3'-5' activity of about 6.5 or less, but greater than 0, U/pmol, measured using the Standard Assay of Example 3, below, has greater than about 80% but less than 100% sequence identity to an unmodified Tne DNA polymerase. The amino acid sequence of the unmodified Tne DNA polymerase can, for example, comprise the amino acid sequence of a Tne polymerase provided in U.S. Pat. No. 5,948,614.

In another aspect, an isolated thermostable or thermoactive DNA polymerase of the invention exhibiting attenuated 3'-5' activity of about 6.5 or less, but greater than 0, U/pmol, measured using the Standard Assay of Example 3, below, has greater than about 80% but less than 100% sequence identity to the 3'-5' exonuclease domain of an unmodified Taf DNA polymerase. In one embodiment, the 3'-5' exonuclease domain of the unmodified Taf DNA polymerase comprises the sequence shown in FIG. 3 (SEQ ID NO:89). In another embodiment, an isolated thermostable or thermoactive DNA polymerase of the invention exhibiting attenuated 3'-5' activity of about 6.5 or less, but greater than 0, U/pmol, measured using the Standard Assay of Example 3, below, has greater than about 80% but less than 100% sequence identity to an unmodified Taf DNA polymerase. The amino acid sequence of the unmodified Taf DNA polymerase can, for example, comprise the amino acid sequence of a Taf DNA polymerase provided in U.S. Pat. No. 5,968,799.

In another aspect, the invention provides an isolated thermostable or thermoactive DNA polymerase having a 3'-5' exonuclease domain exhibiting attenuated 3'-5' activity wherein the ratio of 5'-3' polymerase activity in U/pmol to 3'-5' exonuclease activity in U/pmol, wherein both enzymatic activities are determined as described in Example 3, below, is between about 1 and 100 and the 3'-5' exonuclease domain has greater than about 80% but less than 100% sequence identity to the 3'-5' exonuclease domain of an unmodified Tma DNA polymerase. In one embodiment, the invention provides an isolated thermostable or thermoactive DNA polymerase having greater than about 80% but less than 100% sequence identity to an unmodified Tma DNA polymerase wherein the ratio of 5'-3' polymerase activity in U/pmol to 3'-5' exonuclease activity in U/pmol, wherein both enzymatic activities are determined as described in Example 3, below, is between about 1 and 100. The amino acid sequence of the unmodified Tma DNA polymerase can, for example, comprise the amino acid sequence of FIG. 1A (SEQ ID NO:85).

In another aspect, an isolated thermostable or thermoactive DNA polymerase of the invention has a 3'-5' exonuclease domain and exhibits attenuated 3'-5' activity wherein the ratio of 5'-3' polymerase activity in U/pmol to 3'-5' exonuclease activity in U/pmol, both enzymatic activities being measured as described in Example 3, below, is between about 1 and 100 and the 3'-5' exonuclease domain has greater than about 80% but less than 100% sequence identity to the 3'-5' exonuclease domain of an unmodified Tne DNA polymerase. In one embodiment, the 3'-5' exonuclease domain of the unmodified Tne DNA polymerase comprises the sequence shown in FIG. 2 (SEQ ID NO:88). In another embodiment, an isolated thermostable or thermoactive DNA polymerase of the invention exhibits attenuated 3'-5' activity wherein the ratio of 5'-3' polymerase activity in U/pmol to 3'-5' exonuclease activity in U/pmol is between about 1 and 100 as measured using the assays described in Example 3, and the polymerase has greater than about 80% but less than 100% sequence identity to an unmodified Tne DNA polymerase. The amino acid sequence of the unmodified Tne DNA polymerase can, for example, comprise the amino acid sequence of a Tne polymerase provided in U.S. Pat. No. 5,948,614.

In another aspect, an isolated thermostable or thermoactive DNA polymerase of the invention has a 3'-5' exonuclease domain and exhibits attenuated 3'-5' activity wherein the ratio of 5'-3' polymerase activity in U/pmol to 3'-5' exonuclease activity in U/pmol, measured using the assays described in Example 3, below, is between about 1 and 100 and the 3'-5' exonuclease domain has greater than about 80% but less than 100% sequence identity to the 3'-5' exonuclease domain of an unmodified Taf DNA polymerase. In one embodiment, the 3'-5' exonuclease domain of the unmodified Taf DNA polymerase comprises the sequence shown in FIG. 3 (SEQ ID NO:89). In another embodiment, an isolated thermostable or thermoactive DNA polymerase of the invention exhibits attenuated 3'-5' activity wherein the ratio of 5'-3' polymerase activity in U/pmol to 3'-5' exonuclease activity in U/pmol is between about 1 and 100, measured using the assays described in Example 3, below, and the polymerase has greater than about 80% but less than 100% sequence identity to an unmodified Taf DNA polymerase.comprise the amino acid sequence of a Taf DNA polymerase provided in U.S. Pat. No. 5,968,799.

In another aspect, the present invention provides for a mixture of thermostable or thermoactive DNA polymerases comprising a thermostable or thermoactive DNA polymerase of the invention exhibiting attenuated 3'-5' exonuclease activity. In one embodiment, such a mixture has a 3'-5' exonuclease activity of about 6.5 or less, but greater than 0, U/pmol, measured using the Standard Assay described in Example 3, below. In another embodiment, such a mixture has a ratio of 5'-3' polymerase activity in U/pmol to 3'-5' exonuclease activity in U/pmol that is between about 1 and 100, measured using the assays described in Example 3, below.

In another aspect, the present invention provides nucleic acids comprising a sequence that encodes a thermostable or thermoactive DNA polymerase with attenuated 3'-5' exonuclease activity. In one embodiment the present invention provides plasmids comprising a sequence that encodes a thermostable or thermoactive DNA polymerase with attenuated 3'-5' exonuclease activity. In another embodiment, the plasmid is an expression vector. In another embodiment, the expression vector allows expression of the thermostable or thermoactive DNA polymerase with attenuated 3'-5' exonuclease activity in a microorganism. In another embodiment, the microorganism is a bacterium. In another embodiment, the bacterium is *Escherichia coli*.

In another aspect, the instant invention provides cells engineered to contain and/or express a nucleic acid comprising a sequence that encodes a thermostable or thermoactive DNA polymerase with attenuated 3'-5' exonuclease activity. In one embodiment, the cell comprises a plasmid comprising a sequence that encodes the thermostable or thermoactive DNA polymerase with attenuated 3'-5' exonuclease activity. In another embodiment, the plasmid is an expression vector that allows expression of the thermostable or thermoactive DNA polymerase with attenuated 3'-5' exonuclease activity in the cell. In another embodiment, the cell is a microorganism. In another embodiment, the microorganism is a bacterium, such as *Escherichia coli*.

In another aspect, the present invention provides methods of producing a thermostable or thermoactive DNA polymerase of the invention with attenuated 3'-5' exonuclease activity comprising the steps of incubating a cell capable of expressing a nucleic acid encoding the thermoactive DNA polymerase with attenuated 3'-5' exonuclease activity under conditions that allow expression of the thermoactive DNA polymerase with attenuated 3'-5' exonuclease activity and separating the thermoactive DNA polymerases with attenuated 3'-5' exonuclease activity from the cell. In one embodiment, the cell is a microorganism. In another embodiment, the microorganism is a bacterium. In another embodiment, the bacterium is *Escherichia coli*. In another embodiment, the cell comprises an expression vector comprising the thermoactive DNA polymerases with attenuated 3'-5' exonuclease activity.

In another aspect, the present invention provides methods of replicating a DNA molecule comprising the steps of incubating the DNA molecule with a thermostable or thermoactive DNA polymerase of the invention under conditions that allow the thermostable or thermoactive DNA polymerase to replicate the DNA molecule. The DNA molecule can be any kind of DNA molecule, e.g., a cDNA molecule, a genomic DNA molecule, a single-stranded DNA molecule or a double-stranded DNA molecule. In one embodiment, the thermoactive DNA polymerase with attenuated 3'-5' exonuclease activity is used to amplify the DNA molecule, e.g., via PCR. In another embodiment, a thermostable or thermoactive DNA polymerase with a desired level of 3'-5' exonuclease activity is selected to suit the conditions of a particular application, e.g., the type and concentration of metal ion, the type and concentration of salt, the length of the target nucleic acid and/or whether the target molecule is, e.g., a single-stranded DNA, a double-stranded DNA or an RNA.

In another aspect, the instant invention provides a method of selecting a thermostable or thermoactive DNA polymerase with attenuated 3'-5' exonuclease activity, comprising the steps of assaying the 3'-5' exonuclease activity of a thermostable or thermoactive DNA polymerase and selecting the polymerase if it has an attenuated 3'-5' exonuclease activity. In one embodiment, the thermostable or thermoactive DNA polymerase is a modified thermostable or thermoactive DNA polymerase. In another embodiment, the modified thermostable or thermoactive DNA polymerase is a mutant thermostable or thermoactive DNA polymerase. In another embodiment, the thermostable or thermoactive DNA polymerase is selected if it has a level of 3'-5' exonuclease activity that is between about 0.1% and about 65% of the level of 3'-5' exonuclease activity of a reference polymerase, measured using the Standard Assay of Example 3, below. In another embodiment, the thermostable or thermoactive DNA polymerase is selected if it has a level of 3'-5' exonuclease activity that is between about 1.0% and about 30% of the level of 3'-5' exonuclease activity of the reference polymerase. In another embodiment, the thermostable or thermoactive DNA polymerase is selected if it has a level of 3'-5' exonuclease activity that is between about 3.0% and about 20% of the level of 3'-5' exonuclease activity of the reference polymerase. In another embodiment, the thermostable or thermoactive DNA polymerase is selected if it has a level of 3'-5' exonuclease activity that is between about 3.0% and about 10% of the level of 3'-5' exonuclease activity of the reference polymerase. In another embodiment, the thermostable or thermoactive DNA polymerase is selected if it has a level of 3'-5' exonuclease activity that is between about 3.0% and about 5% of the level of 3'-5' exonuclease activity of the reference polymerase. In another embodiment, the thermostable or thermoactive DNA polymerase is selected if it has a level of activity of between 6.5 or less, but greater than 0, units/pmol, as measured using the Standard Assay of Example 3. In another embodiment, the mutant thermostable or thermoactive DNA polymerase is selected if it has a ratio of 5'-3' DNA polymerase activity to 3'-5' exonuclease activity of between about 1 and 100, wherein the enzymatic activities are measured using the assays described in Example 3, below.

In another aspect, the instant invention provides kits comprising at least one thermostable or thermoactive DNA polymerase with an attenuated 3'-5' exonuclease activity. In one embodiment, the kit further comprises a reagent useful for replicating a DNA molecule. In another embodiment, the reagent is useful for replicating a DNA molecule in a PCR amplification. In another embodiment, the reagent is a buffer. In another embodiment, the reagent is a primer. In another embodiment, the reagent is a deoxyribonucleotide. In another embodiment, the reagent is a dideoxyribonucleotide.

In another aspect, the invention provides mixtures of DNA polymerases comprising a first thermostable or thermoactive DNA polymerase with an attenuated 3'-5' exonuclease activity and a second thermostable or thermoactive DNA polymerase. In one embodiment, the second thermostable or thermoactive DNA polymerase has less 3'-5' exonuclease activity than the first thermostable or thermoactive DNA polymerase. In another embodiment, the second thermostable or thermoactive DNA polymerase has essentially no 3'-5' exonuclease activity. In another embodiment, the second thermostable or thermoactive DNA polymerase has more 3'-5' exonuclease activity than the first thermostable or thermoactive DNA polymerase. In another embodiment, the mixture has a 3'-5' exonuclease activity of about 6.5 or less, but greater than 0, units/pmol, measured using the Standard Assay of Example 3, below.

In another aspect, the instant invention provides methods of replicating a DNA molecule using a mixture of thermostable or thermoactive DNA polymerases comprising the steps of incubating the DNA molecule with a first polymerase with an attenuated 3'-5' exonuclease activity and a second thermostable or thermoactive DNA polymerase under conditions that allow the DNA polymerases to replicate the DNA molecule. In one embodiment, the DNA is replicated using the mixture of polymerase in a PCR amplification.

The compositions and methods of the invention offer several advantages over previously available compositions and methods. The thermostable or thermoactive DNA polymerases of the invention are superior to thermostable or thermoactive DNA polymerases without 3'-5' exonuclease activity because the polymerases of the invention allow for higher fidelity replication and amplification of a template DNA sequence. The thermostable or thermoactive DNA polymerases of the invention are superior to thermostable or thermoactive DNA polymerases with robust 3'-5' exonuclease activities because the polymerases of the invention allow for less degradation of the template to be replicated, less degradation of the primers and/or more efficient use of dNTPs and other reaction components by reducing the occurrence of counterproductive "idling" reactions. The mutant thermostable or thermoactive DNA polymerases of the invention are superior to mixtures of thermostable or thermoactive DNA polymerases with and without 3'-5' exonuclease activities because the polymerases of the invention require less handling and less calibrating and therefore are more efficient and less costly to make and use. Also, surprisingly, it has been found that PCR requires less of the polymerases of the invention than of the mixture of enzymes used previously. The mixtures of thermostable or thermoactive enzymes of the present invention are superior to the mixtures previously available because they allow for a finer control over the ratio of template dependent 5'-3' DNA polymerase activity to 3'-5' exonuclease activity and because they allow for mixtures to be created wherein the level of ssDNA exonuclease and dsDNA exonuclease activities are independently modulated.

BRIEF DESCRIPTION OF THE FIGURES

FIG. 1A presents the amino acid sequence of the *Thermotoga maritima* (Tma) DNA polymerase (SEQ ID NO:85). The 3'-5' exonuclease domain lies within about amino acid residues 292 to 487 (SEQ ID NO:86), which residues are underlined. FIG. 1B presents the nucleic acid sequence (SEQ ID NO:87) that encodes the amino acid sequence of FIG. 1A.

FIG. 2 presents an amino acid sequence from the region of the 3'-5' exonuclease domain of *Thermotoga neapolitana* (Tne) DNA polymerase (SEQ ID NO:88).

FIG. 3 presents an amino acid sequence from the region of the 3'-5' exonuclease domain of *Thermosipho africanus* (Taf) DNA polymerase (SEQ ID NO:89).

FIG. 4A presents the amino acid sequence of the chimeric thermostable DNA polymerase CS5 (SEQ ID NO:90). The 3'-5' exonuclease domain extends from about residue 292 to about residue 487, which residues are underlined (SEQ ID NO:91). Residues 1–291 (SEQ ID NO:92) are derived from Z05 DNA polymerase and residues 292–893 (SEQ ID NO:93) are derived from Tma DNA polymerase, as indicated by the arrows. Amino acid residue substitutions introduced during the second round of mutagenesis appear directly above the residues they replaced, which are indicated in bold: L329A (3'-5' exonuclease domain, SEQ ID NO:94; entire protein, SEQ ID NO:95), Q384A (3'-5' exonuclease domain, SEQ ID NO:96; entire protein, SEQ ID NO:97), N385A (3'-5' exonuclease domain, SEQ ID NO:98; entire protein, SEQ ID NO:99), Q384A N385A (3'-5' exonuclease domain, SEQ ID NO:100; entire protein, SEQ ID NO:101), D389E (3'-5' exonuclease domain, SEQ ID NO:102; entire protein, SEQ ID NO:103), and Y464A (3'-5' exonuclease domain, SEQ ID NO:104; entire protein, SEQ ID NO:105). FIG. 4B presents the nucleic acid sequence that encodes CS5 (SEQ ID NO:106).

FIG. 5A presents the amino acid sequence of the chimeric thermostable DNA polymerase CS6 (SEQ ID NO:107). The 3'-5' exonuclease domain extends from about residue 292 to about residue 487, which residues are underlined (SEQ ID NO:108). Residues 1–291 (SEQ ID NO:109) are derived from Z05 DNA polymerase and residues 292–893 (SEQ ID NO:110) are derived from Tma DNA polymerase, as indicated by the arrows, except that residues 323–325 have been replaced with the sequence ALA. Amino acid residue substitutions introduced during the first round of mutagenesis appear directly above the residues they replaced, which are indicated in bold: DEE (3'-5' exonuclease domain, SEQ ID NO:111; entire protein, SEQ ID NO:112), DDE (3'-5' exonuclease domain, SEQ ID NO:113; entire protein, SEQ ID NO:114), DKE (3'-5' exonuclease domain, SEQ ID NO:115; entire protein, SEQ ID NO:116), DNE (3'-5' exonuclease domain, SEQ ID NO:117; entire protein, SEQ ID NO:118), DQE (3'-5' exonuclease domain, SEQ ID NO:119; entire protein, SEQ ID NO:120), DHE (3'-5' exonuclease domain, SEQ ID NO:121; entire protein, SEQ ID NO:122), DLD (3'-5' exonuclease domain, SEQ ID NO:123; entire protein, SEQ ID NO:124), ELD (3'-5' exonuclease domain, SEQ ID NO:125; entire protein, SEQ ID NO:126), ELE (3'-5' exonuclease domain, SEQ ID NO:127; entire protein, SEQ ID NO:128). FIG. 5B presents the nucleic acid sequence that encodes CS6 (SEQ ID NO:129).

FIG. 6A presents the amino acid sequence (SEQ ID NO:130) of the chimeric thermostable DNA polymerase CS7. The 3'-5' exonuclease domain extends from about residue 292 to about residue 487, which residues are underlined (SEQ ID NO:131). Residues 1–291 (SEQ ID NO:132) and 485–894 (SEQ ID NO:133) are derived from Z05 DNA polymerase and residues 292–484 (SEQ ID NO:134) are derived from Tma DNA polymerase, as indicated by the arrows. Amino acid residue substitutions analogous to those introduced into CS5 during the second round of mutagenesis appear directly above the residues they replace, which are indicated in bold:L329A (3'-5' exonuclease domain, SEQ ID NO:135; entire protein, SEQ ID NO:136), Q384A (3'-5' exonuclease domain, SEQ ID NO:137; entire protein, SEQ ID NO:138), N385A (3'-5' exonuclease domain, SEQ ID NO:139; entire protein, SEQ ID NO:140), Q384A N385A (3'-5' exonuclease domain, SEQ ID NO:141; entire protein, SEQ ID NO:142), D389E (3'-5' exonuclease domain, SEQ ID NO:143; entire protein, SEQ ID NO:144), and Y464A (3'-5' exonuclease domain, SEQ ID NO:145; entire protein, SEQ ID NO:146). FIG. 6B presents the nucleic acid sequence that encodes CS7 (SEQ ID NO:147).

FIG. 7A presents the amino acid sequence of the chimeric thermostable DNA polymerase CS8 (SEQ ID NO:148). The 3'-5' exonuclease domain extends from about residue 292 to about residue 487, which residues are underlined (SEQ ID NO:149). Residues 1–291 (SEQ ID NO:150) and 485–894 (SEQ ID NO:151) are derived from Z05 DNA polymerase and residues 292–484 (SEQ ID NO:152) are derived from Tma DNA polymerase, as indicated by the arrows, except that residues 323–325 have been replaced with residues ALA. Amino acid residue substitutions analogous to those introduced during the second round of mutagenesis of CS5 appear directly above the residues they replace, which are indicated in bold: DEE (3'-5' exonuclease domain, SEQ ID NO:153; entire protein, SEQ ID NO:154), DDE (3'-5' exonuclease domain, SEQ ID NO:155; entire protein, SEQ ID NO:156), DKE (3'-5' exonuclease domain, SEQ ID NO:157; entire protein, SEQ ID NO:158), DNE (3'-5' exonuclease domain, SEQ ID NO:159; entire protein, SEQ ID NO:160), DQE (3'-5' exonuclease domain, SEQ ID NO:161; entire protein, SEQ ID NO:162), DHE (3'-5' exonuclease domain, SEQ ID NO:163; entire protein, SEQ ID NO:164), DLD (3'-5' exonuclease domain, SEQ ID NO:165; entire protein, SEQ ID NO:166), ELD (3'-5' exonuclease domain, SEQ ID NO:167; entire protein, SEQ ID NO:168), ELE (3'-5' exonuclease domain, SEQ ID NO:169; entire protein, SEQ ID NO:170). FIG. 7B presents the nucleic acid sequence that encodes CS8 (SEQ ID NO:171).

FIG. 8 presents a sequence alignment of an amino acid sequence from the region of the 3'-5' exonuclease domain of the Eco DNA polymerase with other family A DNA polymerases: Tth (SEQ ID NO:172), Tca (SEQ ID NO:173), Z05 (SEQ ID NO:174), Taq (SEQ ID NO:175), Tfl (SEQ ID NO:176), Tfi (SEQ ID NO:177), Sps17 (SEQ ID NO:178), Dra (SEQ ID NO:179), HSP-B-7 (SEQ ID NO:180), Bst (SEQ ID NO:181), Bca (SEQ ID NO:182), *E. coli* (SEQ ID NO:183), Tma (SEQ ID NO:184), Tne (SEQ ID NO:185), Taf (SEQ ID NO:186), HSP-A (SEQ ID NO:187). The Exo I, Exo II (SEQ ID NO:188), Exo IIa (SEQ ID NO:189) and Exo III (SEQ ID NO:190) motifs are indicated in bold in the Tma sequence.

FIGS. 11A–11I present a sequence alignment of the Eco Pol II family B DNA polymerase with a number of other family B DNA polymerases (SEQ ID NOs: 191–202).

DETAILED DESCRIPTION OF THE INVENTION

Figure 9:
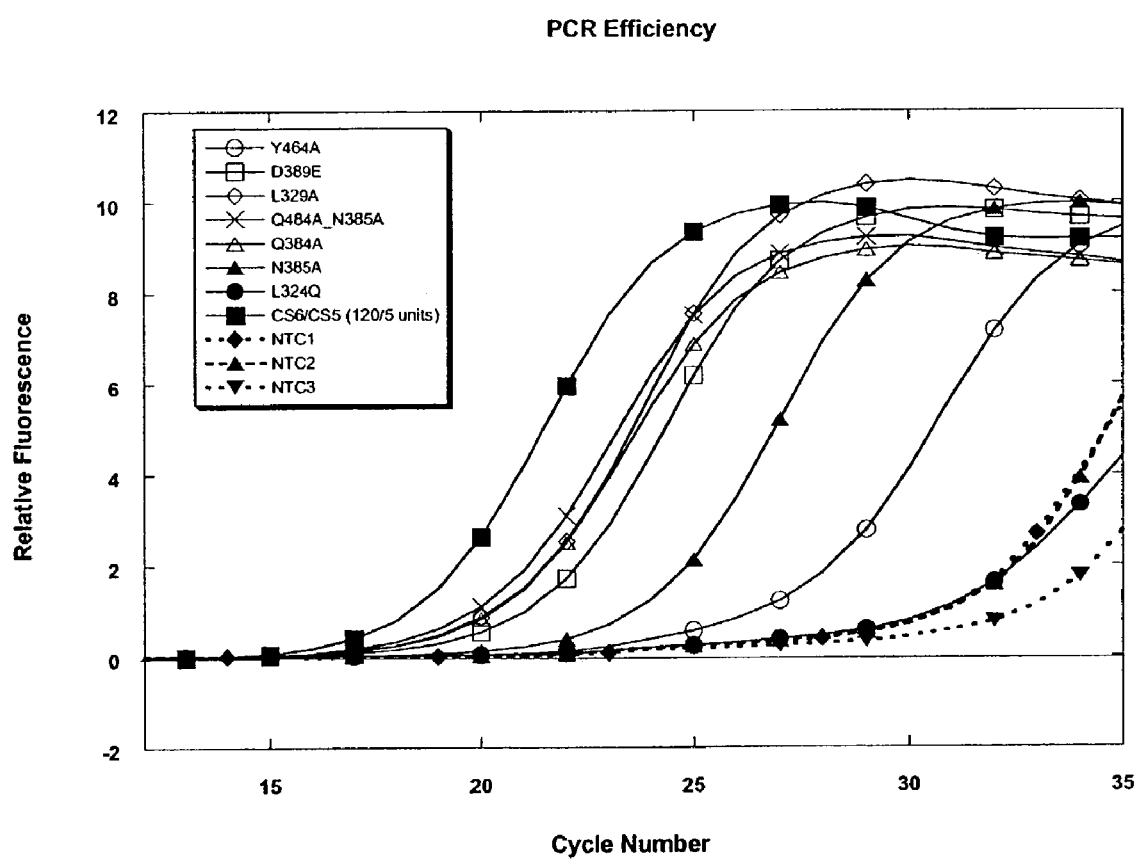
FIGS. 9A and 9B present growth curves of a reverse transcriptase/PCR amplification of a 1.7 kb HIV template using mutant DNA polymerases of the invention.
Figure 9:
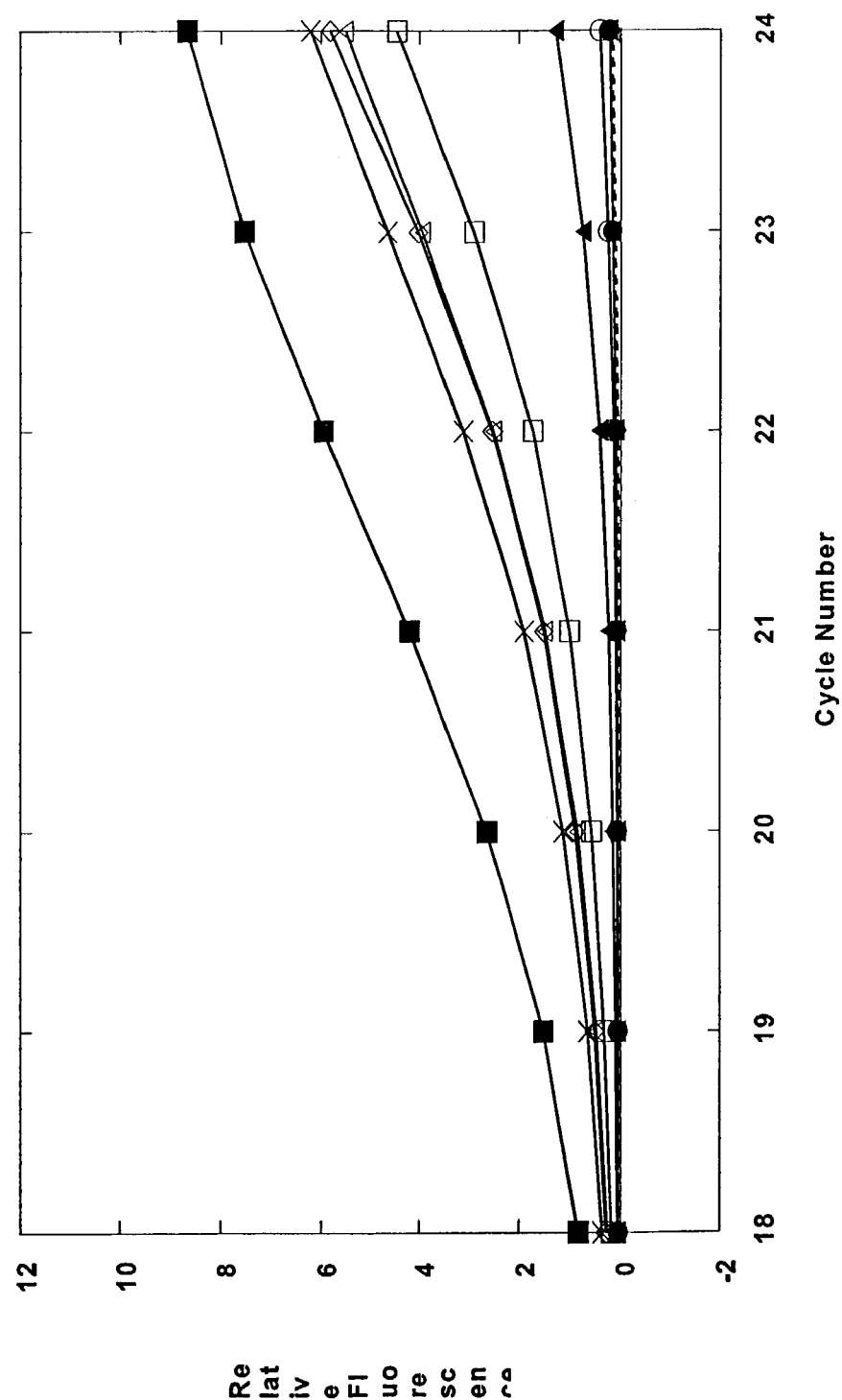

To facilitate understanding of the invention, a number of terms are defined below.

The terms "cell", "cell line", and "cell culture" can be used interchangeably and all such designations include progeny. Thus, the words "transformants" or "transformed cells" include the primary transformed cell and cultures derived from that cell without regard to the number of transfers. All progeny may not be precisely identical in DNA content, due to deliberate or inadvertent mutations. Mutant progeny that have the same functionality as screened for in the originally transformed cell are included in the definition of transformants. The cells can be prokaryotic or eukaryotic.

The term "control sequences" refers to DNA sequences necessary for the expression of an operably linked coding sequence in a particular host organism. The control sequences that are suitable for procaryotes, for example, include a promoter, optionally an operator sequence, a ribosome binding site, positive retroregulatory elements (see U.S. Pat. No. 4,666,848, incorporated herein by reference), and possibly other sequences. Eucaryotic cells are known to utilize promoters, polyadenylation signals, and enhancers.

The term "expression clone" refers to DNA sequences containing a desired coding sequence and control sequences in operable linkage, so that hosts transformed with these sequences are capable of producing the encoded proteins. The term "expression system" refers to a host transformed with an expression clone. To effect transformation, the expression clone may be included on a vector; however, the relevant DNA may also be integrated into the host chromosome.

The term "gene" refers to a DNA sequence that comprises control and coding sequences necessary for the production of a protein, polypeptide or precursor.

The term "operably linked" refers to the positioning of the coding sequence such that control sequences will function to drive expression of the protein encoded by the coding sequence. Thus, a coding sequence "operably linked" to control sequences refers to a configuration wherein the coding sequences can be expressed under the direction of a control sequence.

The term "oligonucleotide" as used herein is defined as a molecule comprised of two or more deoxyribonucleotides or ribonucleotides. The exact size will depend on many factors, which in turn depends on the ultimate function or use of the oligonucleotide. Oligonucleotides can be prepared by any suitable method, including, for example, cloning and restriction of appropriate sequences and direct chemical synthesis by a method such as the phosphotriester method of Narang et al., 1979, Meth. Enzymol. 68:90–99; the phosphodiester method of Brown et al., 1979, Meth. Enzymol. 68:109–151; the diethylphosphoramidite method of Beaucage et al., 1981, Tetrahedron Lett. 22:1859–1862; and the solid support method of U.S. Pat. No. 4,458,066, each incorporated herein by reference. A review of synthesis methods is provided in Goodchild, 1990, Bioconjugate Chemistry 1(3):165–187, incorporated herein by reference.

The term "primer" as used herein refers to an oligonucleotide which is capable of acting as a point of initiation of synthesis when placed under conditions in which primer extension is initiated. The synthesis of a primer extension product that is complementary to a nucleic acid strand is initiated in the presence of the requisite four different nucleoside triphosphates and a thermostable or thermoactive DNA polymerase in an appropriate buffer at a suitable temperature. A "buffer" includes cofactors (such as divalent metal ions) and salt (to provide the appropriate ionic strength), adjusted to the desired pH.

A primer that hybridizes to the non-coding strand of a gene sequence (equivalently, is a subsequence of the coding strand) is referred to herein as an "upstream" or "forward" primer. A primer that hybridizes to the coding strand of a gene sequence is referred to herein as an "downstream" or "reverse" primer.

The terms "restriction endonucleases" and "restriction enzymes" refer to enzymes, typically bacterial in origin, which cut double-stranded DNA at or near a specific nucleotide sequence.

Families of amino acid residues having similar side chains are defined herein. These families include amino acids with basic side chains (e.g., lysine, arginine, histidine), acidic side chains (e.g., aspartic acid, glutamic acid), uncharged polar side chains (e.g., asparagine, glutamine, serine, threonine, tyrosine), nonpolar side chains (e.g., alanine, valine, leucine, isoleucine, proline, phenylalanine, methionine, tryptophan, cysteine, glycine), beta-branched side chains (e.g., threonine, valine, isoleucine) and aromatic side chains (e.g., tyrosine, phenylalanine, tryptophan, histidine).

The term "thermostable polymerase" refers to an enzyme that is stable to heat, is heat resistant and retains sufficient activity to effect subsequent primer extension reactions after being subjected to the elevated temperatures for the time necessary to denature double-stranded nucleic acids. Heating conditions necessary for nucleic acid denaturation are well known in the art and are exemplified in U.S. Pat. Nos. 4,965,188 and 4,889,818, which are incorporated herein by reference. As used herein, a thermostable polymerase is suitable for use in a temperature cycling reaction such as PCR.

The term "thermoactive polymerase" refers to an enzyme that is active at the elevated temperatures necessary to ensure specific priming and primer extension (e.g., 55–80° C.).

The term "proofreading activity" refers to a 3'-5' exonuclease activity possessed by a molecule that also possesses a 5'-3' DNA polymerizing activity.

For a DNA polymerase activity, "enzymatic activity" refers to the catalysis of the combination of the nucleotides in the proper manner to form primer extension products that are complementary to a template nucleic acid strand. DNA polymerase activities are expressed as units/pmol as measured using the polymerase assay taught below in Example 3. One unit of polymerase activity is defined as the amount of enzyme activity required to incorporate a total of 10 nmoles dNMP into TCA-precipitable DNA product in 30 minutes using the polymerase assay conditions provided below in Example 3.

For a 3'-5' exonuclease activity, "enzymatic activity" refers to the serial removal of the 3'-most nucleotide residues of a nucleic acid strand, polynucleotide or oligomer by catalysis of the hydrolysis of the phosphodiester bond. One unit of 3'-5' exonuclease activity catalyzes the conversion of 50 pmol of single-stranded NJS40 oligonucleotide to shorter length oligonucleotides in 15 minutes under the Standard Assay conditions taught in Example 3, below.

For a 5'-3' exonuclease activity, "enzymatic activity" refers to the serial removal of the 5' most nucleotide residues of a nucleic acid strand, polynucleotide or oligonucleotide by catalysis of the hydrolysis of the phosphodiester bond. One unit of 5'-3' exonuclease activity is defined and an assay for measuring 5'-3' exonuclease activity is provided in U.S. Pat. No. 5,795,762.

As used herein, a "point mutation" in an amino acid sequence refers to either a single amino acid substitution, a single amino acid insertion or single amino acid deletion. A point mutation preferably is introduced into an amino acid sequence by a suitable codon change in the encoding DNA. Individual amino acids in a sequence are represented herein as AN, wherein A is the standard one letter symbol for the amino acid in the sequence, and N is the position in the sequence. Mutations within an amino acid sequence are represented herein as $A_1 NA_2$, wherein $A_1$ is the standard one letter symbol for the amino acid in the unmutated protein sequence, $A_2$ is the standard one letter symbol for the amino acid in the mutated protein sequence, and N is the position in the amino acid sequence. For example, a G46D mutation represents a change from glycine to an aspartate residue at amino acid position 46. When referring to mutations in a domain derived from a protein, the amino acid positions are numbered based on the full-length sequence of the protein from which the region encompassing the mutation is derived. Thus, in the present invention, mutations in the region of the protein which are derived from a *Thermus* species DNA polymerase are numbered according to the full-length *Thermus* species DNA polymerase sequence, whereas mutations in the region derived from Tma DNA polymerase are numbered according to the full-length Tma DNA polymerase sequence. Representations of nucleotides and point mutations in DNA sequences are analogous. However, when referring to a chimeric protein or a nucleic acid encoding a chimeric protein, amino acid residues or nucleic acids are numbered contiguously.

The terms "peptide," "polypeptide," and "protein" are used interchangeably. The terms "nucleic acid" and "polynucleotide" are used interchangeably. Amino acid sequences are written from amino terminus to carboxy terminus, unless otherwise indicated. Single-stranded nucleic acid sequences are written 5' to 3', unless otherwise indicated. The top strand of a double-stranded nucleic acid sequence is written 5' to 3', and the bottom strand is written 3' to 5', unless otherwise indicated.

As used herein, a "chimeric" protein refers to a protein whose amino acid sequence represents a fusion product of subsequences of the amino acid sequences from at least two distinct proteins. A chimeric protein preferably is not produced by direct manipulation of amino acid sequences, but, rather, is expressed from a "chimeric" gene that encodes the chimeric amino acid sequence. In one embodiment of the present invention, a chimeric protein is provided that consists of an amino-terminal (N-terminal) region derived from a *Thermus* species DNA polymerase and a carboxy-terminal (C-terminal) region derived from Tma DNA polymerase. The N-terminal region refers to a region extending from the N-terminus (amino acid position 1) to an internal amino acid. Similarly, the C-terminal region refers to a region extending from an internal amino acid to the C-terminus.

Unless otherwise specified, amino acid sequence identity is determined using the BLAST algorithm, described in Altschul et al., J. Mol. Biol. 215, 403–410, (1990) and Karlin et al., PNAS USA 90:5873–5787 (1993). A particularly useful BLAST program is the WU-BLAST-2 program that is described by Altschul et al., Methods in Enzymology, 266:460–480 (1996). WU-BLAST-2 uses several search parameters, most of which are set to the default values. The adjustable parameters are set with the following values: overlap span=1, overlap fraction=0.125, word threshold (T)=11. The HSP S and HSP S2 parameters are dynamic values and are established by the program itself depending upon the composition of the particular sequence and composition of the particular database against which the sequence of interest is being searched; however, the values may be adjusted to increase sensitivity. A percent amino acid sequence identity value is determined by the number of matching identical residues divided by the total number of residues of the "longer" sequence in the aligned region. The "longer" sequence is the one having the most actual residues in the aligned region (gaps introduced by WU-Blast-2 to maximize the alignment score are ignored). Percent amino acid sequence homology is determined based on the number of homologous amino acid residues in relation to the total number of amino acid residues.

Percent (%) nucleic acid sequence identity is defined as the percentage of nucleotide residues in a candidate sequence that are identical with the nucleotide residues of the sequence. Unless otherwise specified, percent nucleic acid sequence identity is calculated using the BLASTN module of WU-BLAST-2 set to the default parameters, with overlap span and overlap fraction set to 1 and 0.125, respectively. The alignment may include the introduction of gaps in the sequences to be aligned. Percent nucleic acid sequence homology is determined based on the number of homologous nucleosides in relation to the total number of nucleosides. For both nucleic acid and amino acid sequences, "% homology" and "% sequence homology" are used interchangeably with "% similarity" and "% sequence similarity."

As used herein, an activity is "attenuated" if it is less than 100% but still measureable using the Standard Assay described in Example 3, below. An activity is "inactivated" or "essentially inactivated" if reduced to less than 0.1% of the activity of the fully functional enzyme.

The Thermostable and Thermoactive DNA Polymerases of the Invention

The present invention provides novel compositions that are thermostable or thermoactive DNA polymerases with an attenuated 3'-5' exonuclease activity. The thermostable or thermoactive DNA polymerases of the invention are, for example, more suitable and desirable than previous thermostable or thermoactive DNA polymerases for use in PCR-based amplification methods, such as PCR-based amplification of a DNA fragment for cloning. Improved PCR amplification methods of the invention include the use of these thermostable or thermoactive DNA polymerases. Methods of making the thermostable or thermoactive DNA polymerases with attenuated proofreading activity, DNA sequences encoding them and vectors for expressing them also are provided.

1. Thermostable or Thermoactive DNA Polymerases with Attenuated 3'-5' Exonuclease Activity In one aspect, the present invention provides a thermostable or thermoactive DNA polymerase with an attenuated 3'-5' exonuclease activity. In one embodiment, the polymerase is from a thermophilic eubacterium. In another embodiment, the thermophilic eubacterium is a species in the genus *Thermotoga*. In another embodiment, the thermophilic eubacterium is *Thermotoga maritima* (Tma). In another embodiment, the thermophilic eubacterium is *Thermotoga neapolitana*. In another embodiment, the thermophilic eubacterium is a species in the genus *Thermosipho*. In another embodiment, the thermophilic eubacterium is *Thermosipho africanus*. In another embodiment, the thermophilic eubacterium is a species in the genus *Aquifex*. In another embodiment, the thermophilic eubacterium is *Aquifex pyrophilus*. In another embodiment, the thermophilic eubacterium is *Aquifex aeolieus*.

In another aspect, the polymerase is from a thermophilic archae. In one embodiment, the thermophilic archae is a species of the genus *Thermococcus*. In another embodiment, the thermophilic archae is *Thermococcus barossi*. In another embodiment, the thermophilic archae is *Thermococcus litoralis*. In another embodiment, the thermophilic archae is *Thermococcus gorgonarius* In another more embodiment, the thermophilic archae is a species of the genus *Pyrococcus*. In another embodiment, the thermophilic archae is *Pyrococcus furiosus*. In another embodiment, the thermophilic archae is *Pyrococcus* sp. GB-D. In another embodiment, the thermophilic archae is *Pyrococcus woesei*. In another embodiment, the thermophilic archae is *Pyrococcus abyssi*. In another embodiment, the thermophilic archae is a species of the genus *Pyrodictium*. In another embodiment, the thermophilic archae is *Pyrodictium abyssi*. In another embodiment, the thermophilic archae is *Pyrodictium occultum*.

In another aspect, the invention provides a thermostable or thermoactive DNA polymerase comprising one or more point mutations (single amino acid substitution, insertion or deletion mutations) that reduce its 3'-5' exonuclease activity. In one embodiment, the 3'-5' exonuclease activity of the mutant thermostable or thermoactive DNA polymerase is between about 0.1% and about 65% that of the wild-type DNA polymerase as measured using the Standard Assay of Example 3. In another embodiment, the 3'-5' exonuclease activity of the mutant thermostable or thermoactive DNA polymerase is between about 1.0% and about 30% that of the wild-type DNA polymerase. In another embodiment, the 3'-5' exonuclease activity of the mutant polymerase is between about 3.0% and about 20% that of the wild-type DNA polymerase. In another embodiment, the 3'-5' exonuclease activity of the mutant polymerase is between about 3.0% and about 10% that of the wild-type DNA polymerase. In another embodiment, the 3'-5' exonuclease activity of the mutant polymerase is between about 3.0% and about 5.0% that of the wild-type DNA polymerase.

In another aspect, the 3'-5' exonuclease activity of the mutant polymerase is 50% or less, but greater than 0%, that of the wild-type DNA polymerase, measured using the double-stranded DNA substrate and First Variant Assay of Example 4. In one embodiment, the 3'-5' exonuclease activity of the mutant polymerase is between about 4% and about 35% that of the wild-type DNA polymerase. In another embodiment, the 3'-5' exonuclease activity of the mutant polymerase is between about 4% and about 17% that of the wild-type DNA polymerase.

In another aspect, the 3'-5' exonuclease activity of the mutant polymerase is between about 0.1% and about 70% that of the wild-type DNA polymerase, measured using the mismatch-containing double-stranded DNA substrate and Second Variant Assay of Example 4. In one embodiment, the 3'-5' exonuclease activity of the mutant polymerase is between about 10% and about 50% that of the wild-type DNA polymerase. In another embodiment, the 3'-5' exonuclease activity of the mutant polymerase is between about 10% and about 30% that of the wild-type DNA polymerase.

In another aspect, the instant invention provides a thermostable or thermoactive DNA polymerase having a 3'-5' exonuclease activity of about 6.5 U/pmol or less, but greater than 0 U/pmol, measured using the Standard Assay of Example 3. In one embodiment, the thermostable or thermoactive DNA polymerase has a 3'-5' exonuclease activity of between about 0.4 and about 3.0 units/pmol. In another embodiment, the thermostable or thermoactive DNA polymerase has a 3'-5' exonuclease activity of between about 0.4 and about 1.6 units/pmol.

In another aspect, the instant invention provides a thermostable or thermoactive DNA polymerase having a 3'-5' exonuclease activity of about 5.5 U/pmol or less, but greater than 0 U/pmol, measured using the double-stranded DNA substrate and First Variant Assay of Example 4. In one embodiment, the thermostable or thermoactive DNA polymerase has a 3'-5' exonuclease activity of between about 0.5 and about 3.6 units/pmol. In another embodiment, the thermostable or thermoactive DNA polymerase has a 3'-5' exonuclease activity of between about 0.5 and about 1.9 units/pmol.

In another aspect, the instant invention provides a thermostable or thermoactive DNA polymerase having a 3'-5' exonuclease activity of between about 0.01 and 12.0 U/pmol, measured using the mismatch-containing double-stranded DNA substrate and Second Variant Assay of Example 4. In one embodiment, the thermostable or thermoactive DNA polymerase has a 3'-5' exonuclease activity of between about 1.0 and about 7.0 units/pmol. In another embodiment, the thermostable or thermoactive DNA polymerase has a 3'-5' exonuclease activity of between about 1.5 and about 5.0 units/pmol.

In another aspect, the instant invention provides a thermostable or thermoactive DNA polymerase having a ratio of 5'-3' template-dependent DNA polymerase activity to 3'-5' exonuclease activity of between about 1 and 100, wherein the polymerase activity and the 3'-5' exonuclease activity are measured as described in Example 3. In one embodiment, the ratio of 5'-3' template-dependent DNA polymerase activity to 3'-5' exonuclease activity is between about 3.0 and about 50. In another embodiment, the ratio of 5'-3' template-dependent DNA polymerase activity to 3'-5' exonuclease activity is between about 6.0 and about 25.0.

In another aspect, the instant invention provides a thermostable or thermoactive DNA polymerase having a ratio of 5'-3' template-dependent DNA polymerase activity to 3'-5' exonuclease activity of between about 1 and 100, wherein the polymerase activity is measured as described in Example 3 and the 3'-5' exonuclease activity is measured using the double-stranded DNA substrate and First Variant Assay of Example 4. In one embodiment, the ratio of 5'-3' template-dependent DNA polymerase activity to 3'-5' exonuclease activity is between about 2.0 and about 50. In one embodiment, the ratio of 5'-3' template-dependent DNA polymerase activity to 3'-5' exonuclease activity is between about 5.0 and about 25.0.

In another aspect, the instant invention provides a thermostable or thermoactive DNA polymerase having a ratio of 5'-3' template-dependent DNA polymerase activity to 3'-5' exonuclease activity of between about 0.75 and 10, wherein the polymerase activity is measured as described in Example 3 and the 3'-5' exonuclease activity is measured using the mismatch-containing double-stranded DNA substrate and Second Variant Assay of Example 4. In one embodiment, the ratio of 5'-3' template-dependent DNA polymerase activity to 3'-5' exonuclease activity is between about 1.2 and about 5.0. In another embodiment, the ratio of 5'-3' template-dependent DNA polymerase activity to 3'-5' exonuclease activity is between about 2.0 and about 4.5.

In another aspect of the invention, the thermostable or thermoactive DNA polymerase with attenuated 3'-5' exonuclease activity is derived from the Tma DNA polymerase. In one embodiment of the invention, the thermostable or thermoactive DNA polymerase with attenuated 3'-5' exonuclease activity is derived from a *Thermus/Thermotoga* chimeric DNA polymerase that includes a Tma 3'-5' exonuclease domain. Tma DNA polymerase is a thermostable and thermoactive enzyme with 3'-5' exonuclease activity. See U.S. Pat. No.s 5,624,833 and 5,374,553. Amino acid residues about 292 to about 484 of the Tma DNA polymerase depicted in FIG. 1 comprise the 3'-5' exonuclease domain. In another embodiment, the thermostable or thermoactive DNA polymerase of the present invention comprises one or more mutations in the 3'-5' exonuclease domain of Tma DNA polymerase. In another embodiment, the mutant Tma DNA polymerase comprises a mutation in L329. In another embodiment, the mutation is L329A. In another embodiment, the mutant Tma DNA polymerase comprises a mutation in D389. In another embodiment, the mutation is D389E. In another embodiment, the mutant Tma DNA polymerase comprises a mutation in Q384. In another embodiment, the mutation is Q384A. In another embodiment, the mutant Tma DNA polymerase comprises a mutation in N385. In another embodiment, the mutation is N385A. In another embodiment, the mutant Tma DNA polymerase comprises mutations at Q384 and N385. In another embodiment, the mutations are Q384A N385A.

Other mutations at these or other amino acid positions that result in attenuated 3'-5' exonuclease activity can be identified by creating and testing the mutants using standard techniques and the exonuclease activity assays taught herein. One method of making a mutant Tma DNA polymerase with reduced 3'-5' exonuclease activity is to either delete one or more amino acid residues or mutate them to an amino acid having a different chemical property. For example, an amino acid residue having an acidic side chain such as aspartate may be changed to a residue having a basic, uncharged polar, nonpolar, beta-branched or aromatic side chain. Substitution mutations that preserve the charge property of the amino acid also may attenuate the 3'-5' exonuclease activity, e.g., changing an aspartate residue to a glutamate residue.

Another method of generating mutant thermostable or thermoactive DNA polymerases is to make changes to the polymerase near a residue known or suspected to affect the polymerase's 3'-5' exonuclease activity. For example, one or more amino acid residues can be inserted, deleted or substituted adjacent to a critical residue in the 3'-5' exonuclease domain of the polymerase. Alternatively, one or more residues can be inserted, deleted or substituted that are not adjacent to a critical residue in the primary sequence of the protein but that are adjacent to the critical residue in the tertiary structure of the polymerase. This method is particularly favored where mutation of the critical residue itself causes a greater than desired reduction in the 3'-5' exonuclease activity of the polymerase, or causes other problems, such as misfolding of the polymerase.

As an alternative to the site-directed mutagenesis techniques described above, more random mutagenesis techniques can be used to generate the mutant thermostable or thermoactive DNA polymerases of the invention. For example, insertion, deletion and/or substitution mutations can be introduced into the Tma DNA polymerase at any position, without regard for the critical residues discussed above, or even for the domain structure of the protein. In one embodiment, mutations are introduced randomly throughout the Tma DNA polymerase 3'-5' exonuclease domain. In another embodiment, mutations are introduced randomly throughout the entire DNA polymerase molecule. Each mutagenized polymerase then can be assayed for 3'-5' exonuclease activity, as described in the examples, and mutant polymerases having the desired level of 3'-5' exonuclease activity then can be selected for use.

Mutant thermostable or thermoactive DNA polymerases according to the invention also can be made by introducing more than one mutation into Tma DNA polymerase. For example, two or more mutations, each of which on its own does not sufficiently reduce the 3'-5' exonuclease activity of the mutant polymerase, can be combined in one polymerase molecule to reduce the 3'-5' exonuclease activity to within the desired range. Alternatively, one or more mutations that preferentially reduce the 3'-5' exonuclease activity of Tma DNA polymerase on an ssDNA substrate can be combined in one polymerase molecule with one or more mutations that preferentially reduce the 3'-5' exonuclease activity of Tma DNA polymerase on a dsDNA substrate.

Mutant thermostable or thermoactive DNA polymerases according to the invention also can be made by deleting, inserting, substituting or rearranging a plurality of adjacent residues, provided that the mutant DNA polymerase has an attenuated 3'-5' exonuclease activity.

Not every mutation of every amino acid of Tma DNA polymerase will result in a mutant thermostable or thermoactive DNA polymerase with the desired level of 3'-5' exonuclease activity. Some mutations will not reduce the 3'-5' exonuclease activity sufficiently, others will reduce it too much. For example, U.S. Pat. Nos. 6,015,668; 5,939,301 and 5,948,614 describe mutations of a metal-binding aspartate to an alanine residue in the 3'-5' exonuclease domain of the Tma and Tne DNA polymerases. These mutations reduce the 3'-5' exonuclease activities of these enzymes to below detectable levels, and so are not encompassed by the present invention. Similarly, U.S. Pat. No. 5,882,904 describes an analogous aspartate-to-alanine mutation in *Thermococcus barossi*, and U.S. Pat. No. 5,489,523 teaches the double-mutant D141A E143A of the *Pyrococcus wosei* DNA polymerases. Both of these mutant polymerases have virtually no detectable 3'-5' exonuclease activity. Thus, one of skill in the art will appreciate that it is necessary to assay each mutant thermostable or thermoactive DNA polymerase to determine its 3'-5' exonuclease activity. Methods of assaying 3'-5' exonuclease activity are provided below. Other methods are well-known in the art. See, e.g., Freemont et al., 1986, Proteins 1:66; Derbyshire et al., 1991, EMBO J. 16:17 and Derbyshire et al., 1995, Methods in Enzymology 262:363–85.

In another aspect, the present invention provides a mutant Tma DNA polymerase having an attenuated 3'-5' exonuclease activity and comprising one or more mutations affecting one or more properties of Tma DNA polymerase. Examples of these properties include, but are not limited to, the ability of Tma DNA polymerase to discriminate between dNTPs and dNTP analogs or derivatives, see, e.g., U.S. Pat. No.s 5,939,292 and 5,614,365, 5'-3' exonuclease activity, see, e.g., U.S. Pat. No.s 6,228,628; 5,466,591 and 5,420,029, thermostability, cold stability, see, e.g., U.S. Pat. No. 6,214,557, ease or expense of manufacture, processivity, rate of polymerization, etc.

Mutations in the amino acid sequence are achieved by incorporating appropriate mutations in the encoding gene sequence. Such mutations in the DNA sequence are carried out using techniques well known in the art, as described further, below.

In another aspect, the present invention provides a thermostable or thermoactive DNA polymerase with attenuated 3'-5' exonuclease activity that has been chemically modified. See, e.g., U.S. Pat. No. 6,183,998. In one embodiment, the chemical modification is a post-translational modification. In another embodiment, the modified amino acid residue is one that is identified herein as being important or critical for 3'-5' exonuclease activity. The post-translational modification can be made in vitro or in vivo. Examples of post-translational modifications include, but are not limited to, processing by a protease and phosphorylation, glycosylation and acylation of amino acid residues. See, e.g., Molecular Biology of the Cell, 1994, (Alberts et al., ed.s), 3d ed., Garland Publishing, New York.

Each of the types of mutations and modifications discussed above with reference to Tma DNA polymerase can be introduced into other thermostable or thermoactive DNA polymerases to generate mutant thermostable or thermoactive DNA polymerases of the present invention. Based on amino acid sequence alignments, DNA polymerases have been classified into groups, designated families A, B, and C, according to the homology with *E. coli* DNA polymerases I, II, and III. See, e.g., Ito et al., Nucl. Acids Res. 19:4045–47, incorporated herein by reference in its entirety. The *Thermotoga* and *Thermus* species DNA polymerases are members of the family A DNA polymerases, which also includes *E. coli* DNA polymerase I. Amino acids that are conserved among family A DNA polymerases have been identified. An alignment of an amino acid sequence from the region of the 3'-5' exonuclease domain of the Tma DNA polymerase with the amino acid sequences of other family A DNA polymerases is shown in FIG. 8 (SEQ ID NO:172–187). Because of the conservation of amino acids between family A DNA polymerases, the identification of amino acids that affect 3'-5' exonuclease activity in one DNA polymerase, such as *E. coli* DNA polymerase I or Tma DNA polymerase, coupled with the teachings provided herein, allows identification of amino acids affecting 3'-5' exonuclease activity in other family A DNA polymerases based on a sequence alignment. Conserved sequence motifs Exo I, Exo II, Exo IIa and Exo III are indicated in FIG. 8. Thus, in one embodiment, the present invention provides a mutant thermostable or thermoactive family A DNA polymerase with an attenuated 3'-5' exonuclease activity. In another embodiment, the thermostable or thermoactive DNA polymerase with attenuated 3'-5' exonuclease activity has a mutation in Exo I, Exo II, Exo IIa or Exo III. In another embodiment, the mutation is in Exo I, Exo II or Exo III.

A large number of thermophilic species have been identified that have DNA polymerases with a 3'-5' exonuclease activity that can be attenuated according to the present invention. Representative eubacterial species include *Thermotoga maritima, Thermotoga neapolitina*, see, e.g., U.S. Pat. No.s 6,077,664; 6,015,668; 6,001,645 and 5,912,155, *Thermosipho africanus*, see, e.g., 5,968,799; Hot Spring family A.

Corresponding amino acids and regions within these DNA polymerases can be identified by aligning their amino acid sequences. Correspondence refers both to amino acids that are identical (conserved) among the sequences and to amino acids that are not identical, but that are aligned to maximize overall sequence similarity.

Using such alignments, one of skill in the art can determine which residues in a family A thermostable or thermoactive DNA polymerase correspond to the 3'-5' exonuclease domain or the critical residues discussed above of the Tma DNA polymerase. Thus, in one embodiment, the invention provides a mutant thermostable or thermoactive DNA polymerase comprising a mutation in a residue corresponding to the L329 residue of Tma. In another embodiment, the residue corresponding to the L329 residue of Tma is mutated to alanine. In another embodiment, the invention provides a mutant thermostable or thermoactive DNA polymerase comprising a mutation in a residue corresponding to the D389 residue of Tma. In another embodiment, the residue corresponding to the D389 residue of Tma is mutated to glutamate. In another embodiment, the invention provides a mutant thermostable or thermoactive DNA polymerase comprising a mutation in a residue corresponding to the Q384 residue of Tma. In another embodiment, the residue corresponding to the Q384 residue of Tma is mutated to alanine. In another embodiment, the invention provides a mutant thermostable or thermoactive DNA polymerase comprising a mutation in a residue corresponding to the N385 residue of Tma. In another embodiment, the residue corresponding to the N385 residue of Tma is mutated to alanine. In another embodiment, the invention provides a mutant thermostable or thermoactive DNA polymerase comprising mutations in residues corresponding to the Q384 and N385 residues of Tma. In another embodiment, each of the residues corresponding to the Q384 and N385 residues of Tma is mutated to alanine.

Additional species of thermophilic eubacteria have been identified and are available from depositories such as the American Type Culture Collection (ATCC, 10801 University Boulevard, Manassas, Va. 20110-2209) and the Deutsche Sammlung von Mikroorganismen (DSM, Macheroder Weg 1b, D-38124 Braunschweig, Germany). As discussed below, DNA polymerases and the genes encoding them can be recovered from the deposited strains and sequenced in a routine manner. A routine sequence alignment of the amino acid sequence of a thermophilic eubacterium's family A DNA polymerase with the amino acid sequence of the Tma DNA polymerase using, for example, the GAP program (Accelrys, Madison, Wis.), enables the use of the thermophilic eubacterium's DNA polymerase sequence in a mutant DNA polymerase of the present invention.

In another aspect of the present invention, a commercially available thermostable or thermoactive DNA polymerase with 3'-5' exonuclease activity is used to generate a mutant thermostable or thermoactive DNA polymerase with attenuated 3'-5' exonuclease activity. Examples of commercially available thermostable or thermoactive DNA polymerases that possess substantial 3'-5' exonuclease activity include VENT$_R$® and DEEP VENT$_R$® DNA polymerases (New England Biolabs, Beverly Mass.) and Pfu DNA polymerase (Stratagene, San Diego, Calif.).

In another aspect, the mutant thermostable or thermoactive DNA polymerase of the invention is derived from a DNA polymerase that is naturally found in a mesophilic organism and that has been mutated or engineered into a thermostable or thermoactive enzyme. See, e.g., Sanchez-Ruiz et al., 2001, Trends Biotechnol. 19:132–35; Fontana, 1991, Curr Opin Biotechnol. 2:551–60.; Nosoh et al., 1990, Trends Biotechnol. 8:16–20; Pace, 1990, Trends Biotechnol. 8:93–98 and Peters, 1998, Science 281:368–69. In one embodiment, the polymerase is a family A DNA polymerase. In another embodiment, the mesophilic organism is a mesophilic eubacterium. In another embodiment, the mesophilic eubacterium is *E. coli*. See Villbrandt et al., 2000, Protein Eng. 9:645–54.

2. Chimeric Proteins of the Invention

In another aspect, the invention provides a chimeric thermostable or thermoactive DNA polymerase with an attenuated 3'-5' exonuclease activity, said polymerase comprising an amino terminal portion and a carboxy terminal portion, with the amino terminal portion derived from the amino terminal portion of a first DNA polymerase and the carboxy terminal portion derived from a second DNA polymerase. In one embodiment, said chimeric DNA polymerase with an attenuated 3'-5' exonuclease activity comprises an amino terminal portion derived from the amino terminal portion of a first thermostable or thermoactive DNA polymerase and a carboxy terminal portion derived from a second thermostable or thermoactive DNA polymerase, said second polymerase preferably being one that exhibits 3'-5' exonuclease activity. In another embodiment, in said chimeric DNA polymerase with an attenuated 3'-5' exonuclease activity, said amino terminal and/or carboxy terminal portion is derived from a DNA polymerase from a *Thermus* species. In another embodiment, in said chimeric DNA polymerase with an attenuated 3'-5' exonuclease activity, said amino terminal and/or carboxy terminal portion is derived from a DNA polymerase from a *Thermotoga* species. In another embodiment, in said chimeric DNA polymerase with an attenuated 3'-5' exonuclease activity, the amino terminal and/or carboxy terminal portion is derived from a DNA polymerase from a *Thermus* species and the other terminal portion is derived from a DNA polymerase from a *Thermotoga* species; for example, in one embodiment, the amino terminal portion is derived from a DNA polymerase from a *Thermus* species and the carboxy terminal portion is derived from a DNA polymerase from a *Thermotoga* species. In another embodiment, in said chimeric DNA polymerase with an attenuated 3'-5' exonuclease activity, the amino terminal portion is derived from a *Thermus* species and comprises a 5'-3' exonuclease domain and the carboxy terminal portion is derived from a *Thermotoga* species and comprises a 3'-5' exonuclease domain and a polymerase domain. In another embodiment, in said chimeric DNA polymerase with an attenuated 3'-5' exonuclease activity, the amino terminal portion is derived from a *Thermus* species and comprises a 5'-3' exonuclease domain and has greater than about 80% sequence identity with a corresponding amino terminal portion the DNA polymerase from the *Thermus* species and said carboxy terminal portion has greater than about 80% sequence identity with a corresponding carboxy terminal portion of the DNA polymerase from the *Thermotoga* species. In another embodiment, said *Thermus* species is *Thermus* sp. Z05 and said *Thermotoga* species is *Thermotoga maritima*. In another embodiment, the chimeric thermostable or thermoactive DNA polymerase comprises the amino acid sequence of FIG. 4 modified by one or more of the mutations indicated in the figure. In another embodiment, the chimeric thermostable or thermoactive DNA polymerase comprises the amino acid sequence of FIG. 5 modified by one or more of the mutations indicated in the figure. In another embodiment, the chimeric thermostable or thermoactive DNA polymerase with an attenuated 3'-5' exonuclease activity comprises an amino terminal portion, a middle portion, and a carboxy terminal portion. In another embodiment, in said chimeric DNA polymerase with an attenuated 3'-5' exonuclease activity, the amino terminal portion comprises a 5'-3' exonuclease domain. In another embodiment, in said chimeric DNA polymerase with an attenuated 3'-5' exonuclease activity, the middle portion comprises a 3'-5' exonuclease domain. In another embodiment, in said chimeric DNA polymerase with an attenuated 3'-5' exonuclease activity, the carboxy terminal portion comprises a polymerase domain. In another embodiment, in said chimeric DNA polymerase with an attenuated 3'-5' exonuclease activity, the carboxy terminal portion and the amino terminal portion are derived from a polymerase from a *Thermus* species. In another embodiment, in said chimeric DNA polymerase with an attenuated 3'-5' exonuclease activity, the amino terminus and/or the carboxy terminus have greater than 80% sequence identity with a corresponding amino and/or carboxy terminus portion of a polymerase from a *Thermus* species. In another embodiment, in said chimeric DNA polymerase with an attenuated 3'-5' exonuclease activity, the middle portion is derived from a polymerase from a *Thermotoga* species. In another embodiment, in said chimeric DNA polymerase with an attenuated 3'-5' exonuclease activity, the middle portion has greater than 80%, but less than 100%, sequence identity to the corresponding polymerase from a *Thermotoga* species. In another embodiment, in said chimeric DNA polymerase with an attenuated 3'-5' exonuclease activity, an amino portion and a carboxy portion are derived from a polymerase from a *Thermus* species and a middle portion is derived from a *Thermotoga* species. In another embodiment, in said chimeric DNA polymerase with an attenuated 3'-5' exonuclease activity, the *Thermus* species is *Thermus* sp. Z05 and the *Thermotoga* species is *Thermotoga maritima*. In another embodiment, the chimeric thermostable or thermoactive DNA polymerase comprises the amino acid sequence of FIG. 6 modified by one or more of the mutations indicated in the figure. In another embodiment, the chimeric thermostable or thermoactive DNA polymerase comprises the amino acid sequence of FIG. 7 modified by one or more of the mutations indicated in the figure.

In another aspect, the chimeric DNA polymerase with an attenuated 3'-5' exonuclease activity comprises sequences from two or more thermostable or thermoactive DNA polymerases. In one embodiment, the chimeric polymerase comprises at its N-terminal end a 5'-3' exonuclease domain derived from a DNA polymerase from a first species and at its C-terminal end a DNA polymerase domain and a 3'-5' exonuclease domain from a DNA polymerase from a second species. In another embodiment, the first species and the second species are bacterial species. In another embodiment, the first species and the second species are thermophilic species. In another embodiment, the first species is a *Thermus* species. In another embodiment, the *Thermus* species is *Thermus aquaticus* (Taq). In another embodiment, the *Thermus* species is *Thermus flavus* (Tfl). In another embodiment, the *Thermus* species is *Thermus thermophilus* (Tth). In another embodiment, the *Thermus* species is *Thermus species* Z05 (TZ05). In another embodiment, the *Thermus species is Thermus* species 17 (Tsps17). In another embodiment, the *Thermus* species is *Thermus caldofilus* (Tca). In another embodiment, the second species is a *Thermotoga* species. In another embodiment, the *Thermotoga* species is *Thermotoga maritima* (Tma). In another embodiment, the first species is TZ05 and the second species is Tma.

In another aspect of the present invention, the chimeric thermostable or thermoactive DNA polymerase with attenuated 3'-5' exonuclease activity comprises sequences from a thermostable or thermoactive DNA polymerase and from another protein, wherein the sequences from the other protein confer a beneficial property to the chimeric protein. In one embodiment, the beneficial property affects the expression, purification, stability, half-life, susceptibility to proteases, post-translational modification, enzymatic activity or thermostability of the chimeric protein.

DNA polymerases from species of the genus *Thermus* and Tma DNA polymerase are similar in overall structure. In these DNA polymerases, the 5'-nuclease and DNA polymerase activities of the enzymes are present in discrete regions of the protein (the activity domains). The approximate activity domains of a representative *Thermus* species DNA polymerase, Taq DNA polymerase, and Tma DNA polymerase are shown in Table 1. See also U.S. Pat. No. 5,420,029. The difference in length between the region that encodes 3'-5' exonuclease activity in Tma DNA polymerase and the corresponding region in Taq DNA polymerase contributes or corresponds to the lack of 3'-5' exonuclease activity in Taq DNA polymerase.

TABLE 1

| Activity Domains (approximate amino acid positions) | | | |
|---|---|---|---|
| | 5'-3' exo | 3'-5' exo | Polymerase |
| Taq DNA polymerase | 1-289 | — | 423-832 |
| Tma DNA polymerase | 1-291 | 292-484 | 485-893 |

Significant amino acid sequence similarity exists between *Thermus* species DNA polymerases and Tma DNA polymerase. For example, an amino acid sequence comparison of a representative *Thermus* species DNA polymerase, Taq DNA polymerase, and Tma DNA polymerase using the GAP computer program (Accelrys, Madison, Wis.) with the default parameter values, indicates that the amino acid sequences are approximately 44% identical and 66% similar over their entire amino acid sequences.

Because of the overall structural and sequence similarity of Tma and *Thermus* species DNA polymerases, a Tma/*Thermus* chimeric enzyme can be constructed that preserves the overall structure and activity domains present in Tma DNA polymerase. In one embodiment, the chimeric enzyme comprises the C-terminal region of Tma DNA polymerase and the N-terminal region of a *Thermus* species DNA polymerase. In another embodiment, the chimeric enzyme of the present invention corresponds to a mutated Tma DNA polymerase, wherein the 5'-3' exonuclease domain has been replaced by the corresponding domain from a *Thermus* species DNA polymerase. The "corresponding domain" is defined herein by an amino acid sequence alignment, as provided in U.S. Pat. No. 6,228,628.

In another aspect of the invention, the first amino acid of the region from Tma DNA polymerase begins with the amino acid following the amino acid that corresponds to the last amino acid of the *Thermus* species DNA polymerase sequence and contains the rest (through amino acid 893) of the Tma DNA polymerase sequence. The amino acid sequence of an entire Tma DNA polymerase is provided in FIG. 1A (SEQ ID NO:85). Preferably, the amino acid sequence from the *Thermus* species DNA polymerase is joined to an amino acid sequence from Tma DNA polymerase at a point where the two amino acid sequences are identical or similar. For example, one embodiment consists of amino acids 1–190 from Taq DNA polymerase and amino acids 191–893 of Tma DNA polymerase. Amino acid 190 of Tma DNA polymerase corresponds to amino acid 190 of Taq DNA polymerase, and the Tma DNA polymerase portion of the chimeric enzyme begins with the next amino acid, amino acid 191.

In regions where the two DNA polymerases are identical, identification of the last amino acid from the *Thermus* species DNA polymerase is arbitrary within the region. For example, because amino acids 191 and 192 are identical in Taq DNA polymerase and Tma DNA polymerase (and conserved among *Thermus* species DNA polymerases), a chimeric protein that contains amino acids 1–190 of Taq DNA polymerase is indistinguishable from chimeric proteins containing amino acids 1–191 or 1–192 of Taq DNA polymerase. The embodiment of the invention described in the examples is referred to as containing amino acids 1–190 of Taq DNA polymerase in view of the original derivation of the enzyme.

In one aspect of the present invention the chimeric DNA polymerase is encoded by a chimeric gene in which the region encoding the Tma DNA polymerase sequence through at least the alternative ribosomal binding site present at about codons 133–137 in the full-length Tma DNA polymerase gene, and preferably through the methionine 140 start codon, is replaced by a gene sequence encoding the corresponding region from a *Thermus* species DNA polymerase. The presence in the full-length Tma DNA polymerase gene of this alternative ribosomal binding site and start codon results in the preferential expression of a truncated Tma DNA polymerase starting with amino acid 140. As described below, replacement of this region of the Tma DNA polymerase gene is useful for the efficient expression of the full-length chimeric protein. Thus, in one embodiment of the chimeric DNA polymerase of the invention, the N-terminal region from a *Thermus* species DNA polymerase replaces a region of Tma DNA polymerase that encompasses at least through amino acid 137, and preferably through amino acid 140.

The region of each *Thermus* species DNA polymerase that corresponds to amino acids 1–137 of Tma DNA polymerase is obtained from an amino acid sequence alignment as provided in U.S. Pat. No. 6,228,628. For example, the region of Taq DNA polymerase that corresponds to amino acids 1–137 of Tma DNA polymerase is amino acids 1–142, and the amino acid of Taq DNA polymerase that corresponds M140 of Tma DNA polymerase is L145. Thus, embodiments in which the N-terminal region is from Taq DNA polymerase comprise at least amino acids 1–142 and preferably, amino acids 1–145 of Taq DNA polymerase. Similarly, for embodiments in which the N-terminal region is from another *Thermus* species DNA polymerase, the region of the *Thermus* species DNA polymerase that corresponds to amino acids 1–137 and 140 of Tma DNA polymerase is obtained from the sequence alignment provided in U.S. Pat. No. 6,228,628.

One of skill in the art will recognize that minor mutations, additions, or deletions can be introduced into a DNA polymerase that do not alter the functional properties of the enzyme, and that such a mutated enzyme is equivalent, for all intents and purposes, to the unmutated enzyme. For example, it is known that a deletion in Taq DNA polymerase of several N-terminal amino acids does not alter the functional properties of the enzyme. Similarly, it is known that substitution mutations at many of the amino acid positions appear to have essentially no effect. For the purposes of the present invention, DNA polymerases that contain minor mutations that do not alter the functional properties of the enzyme are considered to be equivalent to the unmutated DNA polymerase.

3. Mixtures of Thermostable or Thermoactive DNA Polymerases

In another aspect, the present invention provides a mixture comprising a plurality of thermostable or thermoactive DNA polymerases, wherein at least one of the polymerases has an attenuated 3'-5' exonuclease activity, as described above. In one embodiment, at least one of the polymerases has an essentially inactivated 3'-5' exonuclease activity.

In one aspect, the mixture has a 3'-5' exonuclease activity of between about 6.5 or less, but greater than 0, units/pmol, measured using the Standard Assay described in Example 3, below. In one embodiment, the mixture has a 3'-5' exonuclease activity of between about 0.4 and 3.0 units/pmol. In another embodiment, the mixture has a 3'-5' exonuclease activity of between about 0.4 and 1.6 units/pmol.

In another aspect, the mixture has a ratio of template dependent 5'-3' DNA polymerase activity to 3'-5' exonuclease activity of between about 1 and 100, wherein the polymerase activity is measured using the polymerase assay described below in Example 3 and the 3'-5' exonuclease activity is measured using the Standard Assay described in Example 3, below. In one embodiment, the mixture has a ratio of template dependent 5'-3' DNA polymerase activity to 3'-5' exonuclease activity of between about 3.0 and 50. In another embodiment, the mixture has a ratio of template dependent 5'-3' DNA polymerase activity to 3'-5' exonuclease activity of between about 6.0 and 25.0.

4. Advantages of the DNA Polymerase of the Invention

The mutant thermostable or thermoactive DNA polymerase of the invention represents a significant improvement over thermostable or thermoactive DNA polymerases described in the literature. In particular, the DNA polymerase of the invention provides the following combination of properties:

(1) reduced degradation of primers as compared to wild-type thermostable or thermoactive DNA polymerase;

(2) more efficient use of dNTPs, reduction of unproductive "idling" reaction, as compared to wild-type thermostable or thermoactive DNA polymerases;

(3) increased fidelity of replication as compared to mutant thermostable or thermoactive DNA polymerases without a 3'-5' exonuclease activity;

(4) reduced handling and expense compared to mixtures of thermostable or thermoactive DNA polymerases;

(5) the DNA polymerase can be easily and efficiently expressed to a high level in a recombinant expression system, thereby facilitating commercial production of the enzyme; and (6) DNA polymerases of the invention readily incorporate nucleoside triphosphate analogs, in contrast to thermostable archae proofreading DNA polymerases.

The combination of properties possessed by the DNA polymerase of the invention is particularly useful in PCR, and provides significantly improved results.

(1) Reduced Degradation of Primers

In in vitro applications using a thermostable or thermoactive DNA polymerase with a robust ssDNA 3'-5' exonuclease activity, the polymerase degrades primers. This affects the reaction in two ways. First, it lowers the concentration of primers in the reaction. Second, it creates partially degraded primers of varying lengths. As the specificity of a primer for its target is directly specified by the primer's sequence and length, the shortened primers may have less specificity for their particular target sequences. This can cause simultaneously a decrease in the replication of the desired sequence and an increase in the replication of spurious or unintended sequences. Upon heating to cause DNA strand separation and duplex denaturation, the presence of the ssDNA 3'-5' exonuclease activity also may cause a reduction in length of the ends of the synthesized strands, which in subsequent rounds of polymerization act as templates. Because primers bind to these ends, a reduction in their length reduces the strength of their binding to the primers. This too can cause a decrease in the amount of the desired PCR product and an increase in the amount of spurious PCR products. These effects are particularly troublesome for PCR, wherein a decrease in the ratio of amplified target sequence to amplified spurious sequences may reduce the specificity of the reaction and thus decrease the sensitivity of target detection.

The thermostable or thermoactive DNA polymerases of the instant invention overcome this problem by having an attenuated level of 3'-5' exonuclease activity.

(2) Reduced Idling Reaction

The dsDNA exonuclease activity of thermostable or thermoactive DNA polymerases can cause the polymerase to "idle" when it reaches the end of a linear template. That is, it goes through repeated cycles of polymerizing to the end of the template, then hydrolyzing residues at the just completed end of the synthesized strand. This cycle of polymerization and hydrolysis reduces the concentration of dNTPs and increases the concentration of pyrophosphate in the reaction mix, reducng the reaction efficiency of later cycles. Product yield can be reduced as a result.

The mutant thermostable or thermoactive DNA polymerases of the present invention overcome this problem by having a reduced dsDNA 3'-5' exonuclease activity. In one embodiment, the mutant polymerases of the invention have a 3'-5' exonuclease activity that is about 0.1% to about 65% of the activity of the wild-type enzyme, as measured using the single-stranded DNA substrate and Standard Assay of Example 3. In another embodiment, the mutant polymerases of the invention have a 3'-5' exonuclease activity that is about 1% to about 30% of the activity of the wild-type enzyme. In another embodiment, the mutant polymerases of the invention have a 3'-5' exonuclease activity that is about 3% to about 20% of the activity of the wild-type enzyme. In another embodiment, the mutant polymerases of the invention have a 3'-5' exonuclease activity that is about 3% to about 10% of the activity of the wild-type enzyme. In another embodiment, the mutant polymerases of the invention have a 3'-5' exonuclease activity that is about 3% to about 5% of the activity of the wild-type enzyme.

(3) High Level of Fidelity

Previous attempts to overcome the deleterious effects of the 3'-5' exonuclease activity of thermostable or thermoactive DNA polymerases have employed mutant polymerases with no or essentially no 3'-5' exonuclease activity, or polymerases that naturally lack this activity. This approach can create its own problems. Polymerases without 3'-5' exonuclease activity have a higher error rate than polymerases with this activity. For certain applications of PCR, for example, where the amplified sequence is to be cloned, it is important that the error rate be kept low. Further, the presence of a 3'-5' exonuclease activity increases amplification and/or reverse transcriptase efficiency for longer targets because nucleotide misincorporation can be corrected. Thus, thermostable or thermoactive DNA polymerases completely lacking a proofreading activity are less suitable for these applications.

The instant invention overcomes this problem by providing isolated thermostable or thermoactive DNA polymerases that have attenuated 3'-5' exonuclease activity. It has now been determined that an attenuated level of 3'-5' activity is sufficient to enhance PCR efficiency of longer templates through efficient removal of mis-inserted dNTPs and thus facilitate longer PCR and RT-PCR.

(4) Reduced Handling

Another approach that has been used to overcome the problems associated with robust 3'-5' exonuclease activity is to mix a polymerase with a wild-type level of proofreading activity with a polymerase that has essentially no proofreading activity. One can achieve the desired ratio of proofreading activity to polymerase activity by manipulating the ratio of these two polymerases in the mixture. While this approach has been used successfully, it has its own drawbacks. The 3'-5' exonuclease and polymerase activities of both enzymes must be accurately measured for each preparation of each enzyme, then the amount of each enzyme needed calculated. Then, for each reaction, the correct amount of each enzyme must be added. This approach also requires that both enzymes have comparable storage stability. Thus, reactions using mixtures of enzymes require more manipulations, which increases costs and reduces efficiency.

The thermostable or thermoactive DNA polymerases of the instant invention overcome these problems by providing, in one embodiment, a single polymerase that has the desired ratio of proofreading activity to polymerase activity. Only one enzyme needs to be added to each reaction. Unexpectedly, it also was discovered that less total enzyme is required when the polymerases of the invention are used instead of a mixture of enzymes.

(5) Efficiency of Expression

As described above, in one aspect the present invention provides a chimeric enzyme that corresponds to a mutated Tma DNA polymerase, wherein the 5'-nuclease domain has been replaced by the corresponding domain from a *Thermus* species DNA polymerase. The enzyme is expressed from a chimeric gene that corresponds to a mutated Tma DNA polymerase gene, wherein the region of the gene that encodes the 5'-nuclease domain has been replaced by the corresponding region of the *Thermus* species DNA polymerase gene. A significant advantage of the chimeric gene is that it enables the expression of a full-length DNA polymerase in a recombinant expression system much more efficiently than is possible from the Tma DNA polymerase gene.

The expression of a full-length DNA polymerase from a recombinant expression system containing the full-length natural Tma DNA polymerase gene sequence is problematical because of the preferential expression of a truncated form of the protein. See U.S. Pat. No. 5,420,029. The truncated protein, referred to as Met140 Tma, consists of amino acids 140–893 of the full-length protein and appears to result from translation beginning at the methionine at position 140. The presence of a putative ribosomal binding site at codons 133–137 further suggests that the truncated protein results from translation beginning at the internal methionine. The preferential expression of the Met140 Tma truncated protein represents a significant difficulty in expressing and purifying a full-length Tma DNA polymerase.

In one embodiment of the present invention, the chimeric DNA polymerase gene contains a *Thermus* species DNA polymerase gene sequence in a region corresponding at least through the alternative ribosomal binding site present at about codons 133–137 in the full-length Tma DNA polymerase gene, and preferably through the internal start codon, codon 140. Thus, the Tma DNA polymerase gene sequence up through the region containing the ribosomal binding site and, preferably, the start codon responsible for the translation of Met140 Tma, is replaced by the corresponding region of a *Thermus* species DNA polymerase gene. The corresponding region of a *Thermus* species DNA polymerase gene does not provide for the undesirable internal initiation of a truncated protein. As a result, a recombinant expression system containing the chimeric DNA polymerase gene expresses a full-length chimeric DNA polymerase exclusively.

(6) Incorporation of Nucleoside Triphosphate Analogs

In another aspect, the thermostable or thermoactive proofreading DNA polymerases of this invention tolerate and readily incorporate nucleoside triphosphate analogs such as dUTP and dITP, in contrast to thermostable archae proofreading DNA polymerases (e.g., VENT™, DEEPVENT™, Pfu, Pwo, Poc, Pab, Tgo, etc.). That is, these polymerases are not inhibited by the presence of dUTP or dITP or by the presence of dUMP or dIMP in a template strand. In contrast, the aforementioned archae thermostable proofreading DNA polymerases or mixtures of DNA polymerases containing a proofreading archae DNA polymerase are inhibited by the presence of dUTP or dITP or by the presence of dUPM or dIMP in a template strand. Accordingly, the many benefits of using dUTP with or in place of dTTP or of using dITP with or in place of dGTP may be realized with enzymes of this invention, but not with archae thermostable DNA polymerases. See, e.g., *PCR Applications: Protocols for Functional Genomics,* 1999, Innis et al. (ed.s), Acaderic Press, San Diego, pages 4, 5, 142 and 143. Thus, while the previously described archae DNA polymerases or mixtures containing an archae DNA polymerase cannot carry out primer extension or PCR amplifications with dUTP or dITP, in one embodiment the thermostable and thermoactive DNA polymerases of the present invention are compatible with the use of these analogs.

5. Preparation of the DNA Polymerase of the Invention

The gene encoding Tma DNA polymerase is described in U.S. Pat. Nos. 5,420,029 and 5,466,591. The nucleotide sequence of the Tma DNA polymerase gene, as well as the full amino acid sequence of the encoded protein, are described therein. Example 5 of the '029 patent describes the construction of a variety of plasmids containing the full-length Tma DNA polymerase gene starting with plasmids pTma01 (ATCC No. 68471, deposited Nov. 7, 1990, and redeposited as ATCC No. 98764 on May 22, 1998) and pTma04 (ATCC No. 68472, deposited Nov. 7, 1990, and redeposited as ATCC No. 98765 on May 22, 1998), such as plasmids pTma12-1 and pTma13. Any of these expression vectors is suitable as a source of the Tma DNA polymerase gene.

Other thermostable or thermoactive DNA polymerases with 3'-5' exonuclease activity that can be mutated to make the polymerases of the invention include, but are not limited to, those described in U.S. Pat. No.s 6,077,664; 6,015,668; 6,001,645 and 5,912,155 (*Thermotoga neapolitina*), U.S. Pat. No.s 6,066,483; 5,874,282; 5,834,253; 5,747,298; 6,013,451 and 5,830,714, U.S. Pat. No.s 5,882,904 and 5,602,011 (*Thermococcus barossi*), U.S. Pat. No.s 5,322,785 and 5,210,036 (*Thermococcus litoralis*), U.S. Pat. No.s 5,948,663 and 5,866,395; Dabrowski et al., 1998, Protein Expr Purif 14:131–38 (*Pyrococcus furiosus*), see, e.g., U.S. Pat. No. 5,834,285 (*Pyrococcus* sp. GB-D) and Dabrowski (1998) (*Pyrococcus woesei*).

In one aspect, the DNA polymerase of the invention is a chimeric enzyme that comprises a portion derived from a *Thermus* species DNA polymerase and a portion derived from Tma DNA polymerase. In one embodiment, the DNA polymerase of the invention is a chimeric enzyme that consists of a portion derived from a *Thermus* species DNA polymerase and a portion derived from Tma DNA polymerase. The chimeric enzyme is prepared from a chimeric gene, i.e., a DNA that encodes the chimeric enzyme and consists of a portion derived from the *Thermus* species DNA polymerase gene and a portion derived from the Tma DNA polymerase gene. The chimeric gene is produced from the *Thermus* species DNA polymerase gene and the Tma DNA polymerase gene using standard gene manipulation techniques well known in the field of molecular biology, as described in detail below.

Genes encoding DNA polymerases from a number of *Thermus* species, including the nucleotide sequence of the DNA polymerase gene and the amino acid sequence of the encoded protein, have been described. A number of these genes are obtainable from publicly available plasmids. The genes from additional *Thermus* species are obtainable from the host organisms using methods described in U.S. Pat. Nos. 5,079,352; 5,618,711; 5,455,170; 5,405,774; and 5,466,591; each incorporated by reference.

The gene encoding Taq DNA polymerase is described in U.S. Pat. Nos. 5,079,352 and 5,466,591. The nucleotide sequence of the Taq DNA polymerase gene, as well as the full amino acid sequence of the encoded protein, are described therein. Examples V–VII of the '352 patent describes the construction of a variety of expression plasmids containing the full-length Taq DNA polymerase gene starting with plasmids pFC83 (ATCC No. 67422, deposited on May 29, 1987, and redeposited as ATCC No. 98763 on May 22, 1998) and pFC85 (ATCC No. 67421, deposited May 29, 1987, and redeposited as ATCC No. 98762 on May 22, 1998), such as plasmids pLSG1, pLSG2, pSYC1578, pLSG5, and pLSG6. Any of these expression vectors is suitable as a source of the Taq DNA polymerase gene.

The gene encoding Tth DNA polymerase, methods for obtaining the gene, and expression plasmids containing the gene are described in U.S. Pat. No. 5,618,711 and 5,466,591.

The gene encoding TZ05 DNA polymerase, methods for obtaining the gene, and expression plasmids containing the gene are described in U.S. Pat. No. 5,455,170 and 5,466,591.

The gene encoding Tsps17 DNA polymerase, methods for obtaining the gene, and expression plasmids containing the gene are described in U.S. Pat. No. 5,405,774 and 5,466,591.

The Tfl DNA polymerase gene is described in Akhmetzjanov et al., 1992, Nucleic Acids Research 20:5839, incorporated herein by reference in its entirety.

The Tfi DNA polymerase gene can be recovered from ATCC 43280 using the methods described in the referenced patents. See also 1984, FEMS Microbiol. Lett. 22:149–53.

The Tca DNA polymerase gene is described in Kwon, 1997, Mol. Cells 7: 264–71; and the nucleotide sequence is available under EMBL/GenBank Accession No. U62584.

Additional *Thermus* species DNA polymerase genes can be recovered using techniques described in the above cited patents from the following ATCC deposits: ATCC 43814 and 43815, see Alfredsson, 1986, Appl. Environ. Microbiol. 52:1313–16; ATCC 27978, see Ramaley, 1970, J. Bacteriol. 114:556–62; 1973; ibid. 103:527–528; ATCC 31674, see U.S. Pat. Nos. 4,442,214 and 4,480,036; ATCC 35948 (*T. ruber*, see Loginova, 1984, Int. J. Syst. Bacteriol. 34:498–99. All references are incorporated herein by reference.

Additional *Thermus* species can be recovered using techniques described in the above cited patents from the following Deutsche Sammlung von Mikroorganismen (DSM) deposits: DSM:1279 (NUM: 2244), see Loginova et al., 1975, Izv. Akad. Nauk SSSR Ser. Biol.: 304–07; DSM:579; DSM:625 (NUM: 2248), see Degryse et al., 1978, Arch. Microbiol. 189:196; DSM:1279 (NUM: 3844), see Loginova et al., 1984, Int. J. Syst. Bacteriol.:498–99; and DSM: 625(NUM: 1002), see Brock et al., 1969, J. Bacteriol.: 289–97. All references are incorporated herein by reference in their entireties.

Additional *Thermus* species which have been described include *T. oshimai*, see Williams et al., 1996, Int. J. Syst. Bacteriol. 46:403–08; *T. silvanus* and *T. chliarophilus*, see Tenreiro et al. 1995, Int. J. Syst. Bacteriol. 45:633–39; *T. scotoductus*, see Tenreiro et al., 1995, Res. Microbiol. 146: 315–24; and *T. ruber*, see Shadrina et al., 1982, Mikrobiologiia 51:611–15; all incorporated herein by reference in their entireties.

Following the guidance provided herein, and using only well known techniques, one skilled in the art will be able to prepare from the DNA polymerase genes any number of expression vectors containing a chimeric gene suitable for expressing a chimeric DNA polymerase of the invention in any of a variety of host systems.

In one aspect, the chimeric enzyme of the invention comprises amino acids 1–291 from Z05 DNA polymerase and amino acids 292–893 from Tma DNA polymerase suitably mutated to reduce associated 3'-5' exonuclease activity. In one embodiment, the chimeric enzyme of the invention consists of amino acids 1–291 from Z05 DNA polymerase and amino acids 292–893 from Tma DNA polymerase suitably mutated to reduce associated 3'-5' exonuclease activity. These embodiments can be constructed directly from the Z05 DNA polymerase and Tma DNA polymerase genes, either obtained from the deposited plasmids described above or recovered from the host organisms.

Because of the redundancy in the genetic code, typically a large number of DNA sequences encode any given amino acid sequence and are, in this sense, equivalent. As described below, it may be desirable to select one or another equivalent DNA sequences for use in a expression vector, based on the preferred codon usage of the host cell into which the expression vector will be inserted. The present invention is intended to encompass all DNA sequences that encode the chimeric enzyme. Thus, chimeric genes of the present invention are not limited to containing only sequences from a wild-type *Thermus* species and Tma DNA polymerase genes, but can contain any of the DNA sequences that encode a chimeric DNA polymerase of the present invention.

Production of the enzyme of the invention is carried out using a recombinant expression clone. The construction of the recombinant expression clone, the transformation of a host cell with the expression clone, and the culture of the transformed host cell under conditions which promote expression, can be carried out in a variety of ways using techniques of molecular biology well understood in the art. Methods for each of these steps are described in general below and specifically in the examples.

An operable expression clone is constructed by placing the coding sequence in operable linkage with a suitable control sequences in an expression vector. The vector can be designed to replicate autonomously in the host cell or to integrate into the chromosomal DNA of the host cell. The resulting clone is used to transform a suitable host, and the transformed host is cultured under conditions suitable for expression of the coding sequence. The expressed protein is isolated from the medium or from the cells, although recovery and purification of the protein may not be necessary in some instances.

Construction of suitable clones containing the coding sequence and a suitable control sequence employs standard ligation and restriction techniques that are well understood in the art. In general, isolated plasmids, DNA sequences, or synthesized oligonucleotides are cleaved, modified, and religated in the form desired. Suitable restriction sites can, if not normally available, be added to the ends of the coding sequence so as to facilitate construction of an expression clone.

Site-specific DNA cleavage is performed by treating with a suitable restriction enzyme (or enzymes) under conditions that are generally understood in the art and specified by the manufacturers of commercially available restriction enzymes. See, e.g., product catalogs from Amersham (Arlington Heights, Ill.), Roche Molecular Biochemicals (Indianapolis, Ind.), and New England Biolabs (Beverly, Mass.). In general, about 1 μg of plasmid or other DNA is cleaved by one unit of enzyme in about 20 μl of buffer solution; in the examples below, an excess of restriction enzyme is generally used to ensure complete digestion of the DNA. Incubation times of about one to two hours at a temperature which is optimal for the particular enzyme are typical. After each incubation, protein is removed by extraction with phenol and chloroform; this extraction can be followed by ether extraction and recovery of the DNA from aqueous fractions by precipitation with ethanol. If desired, size separation of the cleaved fragments may be performed by polyacrylamide gel or agarose gel electrophoresis using standard techniques. See, e.g., Maxam et al., 1980, Methods in Enzymology 65:499–560.

Restriction enzyme-cleaved DNA fragments with single-strand "overhanging" termini can be made blunt-ended (double-strand ends) by treating with the large fragment of *E. coli* DNA polymerase I (Klenow) in the presence of the four deoxynucleoside triphosphates (dNTPs) using incubation times of about 15 to 25 minutes at 20° C. to 25° C. in 50 mM Tris, pH 7.6, 50 mM NaCl, 10 mM $MgCl_2$, 10 mM DTT, and 5 to 10 μM dNTPs. The Klenow fragment fills in at 5' protruding ends, but chews back protruding 3' single strands, even though the four dNTPs are present. If desired, selective repair can be performed by supplying one or more selected dNTPs, within the limitations dictated by the nature of the protruding ends. After treatment with Klenow, the mixture is extracted with phenol/chloroform and ethanol precipitated. Similar results can be achieved using S1 nuclease, because treatment under appropriate conditions with S1 nuclease results in hydrolysis of any single-stranded portion of a nucleic acid.

Ligations are performed in 15–30 μl volumes under the following standard conditions and temperatures: 20 mM Tris-Cl, pH 7.5, 10 mM $MgCl_2$, 10 mM DTT, 33 μg/ml BSA, 10–50 mM NaCl, and either 40 μM ATP and 0.01–0.02 (Weiss) units T4 DNA ligase at 0° C. (for ligation of fragments with complementary single-stranded ends) or 1 mM ATP and 0.3–0.6 units T4 DNA ligase at 14° C. (for "blunt end" ligation). Intermolecular ligations of fragments with complementary ends are usually performed at 33–100 μg/ml total DNA concentrations (5–100 nM total ends concentration). Intermolecular blunt end ligations (usually employing a 20–30 fold molar excess of linkers, optionally) are performed at 1 μM total ends concentration.

In vector construction, the vector fragment is commonly treated with bacterial or calf intestinal alkaline phosphatase (BAP or CIAP) to remove the 5' phosphate and prevent religation and reconstruction of the vector. BAP and CIAP digestion conditions are well known in the art, and published protocols usually accompany the commercially available BAP and CIAP enzymes. To recover the nucleic acid fragments, the preparation is extracted with phenol-chloroform and ethanol precipitated to remove the phosphatase and purify the DNA. Alternatively, religation of unwanted vector fragments can be prevented by restriction enzyme digestion before or after ligation, if appropriate restriction sites are available.

Correct ligations for plasmid construction can be confirmed using any suitable method known in the art. In the construction set forth below, correct ligations for plasmid construction are confirmed by first transforming a suitable host, such as *E. coli* strain DG101 (ATCC 47043) or *E. coli* strain DG116 (ATCC 53606), with the ligation mixture. Successful transformants are selected by ampicillin, tetracycline or other antibiotic resistance or sensitivity or by using other markers, depending on the mode of plasmid construction, as is understood in the art. Plasmids from the transformants are then prepared according to the method of Clewell et al., 1969, Proc. Natl. Acad. Sci. USA 62:1159, optionally following chloramphenicol amplification. See Clewell, 1972, J. Bacteriol. 110:667. Alternatively, plasmid DNA can be prepared using the "Base-Acid" extraction method at page II of the Bethesda Research Laboratories publication *Focus* 5 (2), and very pure plasmid DNA can be obtained by replacing steps 12 through 17 of the protocol with CsCl/ethidium bromide ultracentrifugation of the DNA. As another alternative, a commercially available plasmid DNA isolation kit, e.g., HISPEED™, QIAFILTER™ and QIAGEN® plasmid DNA isolation kits (Qiagen, Valencia Calif.) can be employed following the protocols supplied by the vendor. The isolated DNA is analyzed by restriction enzyme digestion and/or sequenced by the dideoxy method of Sanger et al., 1977, Proc. Natl. Acad. Sci. USA 74:5463, as further described by Messing et al., 1981, Nuc Acids Res. 9:309, or by the method of Maxam et al., 1980, Methods in Enzymology 65:499.

The control sequences, expression vectors, and transformation methods are dependent on the type of host cell used to express the gene. Generally, procaryotic, yeast, insect, or mammalian cells are used as hosts. Procaryotic hosts are in general the most efficient and convenient for the production of recombinant proteins and are therefore preferred for the expression of the protein.

The procaryote most frequently used to express recombinant proteins is *E. coli*. However, microbial strains other than *E. coli* can also be used, such as bacilli, for example *Bacillus subtilis*, various species of *Pseudomonas* and *Salmonella*, and other bacterial strains, for recombinant expression of the protein. In such procaryotic systems, plasmid vectors that contain replication sites and control sequences derived from the host or a species compatible with the host are typically used.

For expression of constructions under control of most bacterial promoters, *E. coli* K12 strain MM294, obtained from the *E. coli* Genetic Stock Center under GCSC #6135, can be used as the host. For expression vectors with the $P_L N_{RBS}$ or $P_L T7_{RBS}$ control sequence, *E. coli* K12 strain MC1000 lambda lysogen, $N_7 N_{53} cI857$ $SusP_{80}$, ATCC 39531, may be used. *E. coli* DG116, which was deposited with the ATCC (ATCC 53606) on Apr. 7, 1987, and *E. coli* KB2, which was deposited with the ATCC (ATCC 53075) on Mar. 29, 1985, are also useful host cells. For M13 phage recombinants, *E. coli* strains susceptible to phage infection, such as *E. coli* K12 strain DG98 (ATCC 39768), are employed. The DG98 strain was deposited with the ATCC on Jul. 13, 1984.

For example, *E. coli* is typically transformed using derivatives of pBR322, described by Bolivar et al., 1977, Gene 2:95. Plasmid pBR322 contains genes for ampicillin and tetracycline resistance. These drug resistance markers can be either retained or destroyed in constructing the desired vector and so help to detect the presence of a desired recombinant. Commonly used procaryotic control sequences, i.e., a promoter for transcription initiation, optionally with an operator, along with a ribosome binding site sequence, include the β-lactamase (penicillinase) and lactose (lac) promoter systems, see Chang et al., 1977, Nature 198:1056, the tryptophan (trp) promoter system, see Goeddel et al., 1980, Nuc. Acids Res. 8:4057, and the lambda-derived $P_L$ promoter, see Shimatake et al., 1981, Nature 292:128, and gene N ribosome binding site ($N_{RBS}$). A portable control system cassette is set forth in U.S. Pat. No. 4,711,845, issued Dec. 8, 1987. This cassette comprises a $P_L$ promoter operably linked to the $N_{RBS}$ in turn positioned upstream of a third DNA sequence having at least one restriction site that permits cleavage within six base pairs 3' of the $N_{RBS}$ sequence. Also useful is the phosphatase A (phoA) system described by Chang et al., in European Patent Publication No. 196,864, published Oct. 8, 1986. However, any available promoter system compatible with procaryotes can be used to construct a expression vector of the invention.

In addition to bacteria, eucaryotic microbes, such as yeast, can also be used as recombinant host cells. Laboratory strains of *Saccharomyces cerevisiae*, Baker's yeast, are most often used, although a number of other strains are commonly available. While vectors employing the two micron origin of replication are common, see Broach, 1983, Meth. Enz. 101:307, other plasmid vectors suitable for yeast expression are known. See, e.g., Stinchcomb et al., 1979, Nature 282:39; Tschempe et al., 1980, Gene 10: 157; and Clarke et al., 1983, Meth. Enz. 101:300. Control sequences for yeast vectors include promoters for the synthesis of glycolytic enzymes. See Hess et al., 1968, J. Adv. Enzyme Reg. 7:149; Holland et al., 1978, Biotechnology 17:4900; and Holland et al., 1981, J. Biol. Chem. 256:1385. Additional promoters known in the art include the promoter for 3-phosphoglycerate kinase, see Hitzeman et al., 1980, J. Biol. Chem. 255:2073, and those for other glycolytic enzymes, such as glyceraldehyde 3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Other promoters that have the additional advantage of transcription controlled by growth conditions are the promoter regions for alcohol dehydrogenase 2, isocytochrome C, acid phosphatase, degradative enzymes associated with nitrogen metabolism, and enzymes responsible for maltose and galactose utilization (Holland, supra).

Terminator sequences may also be used to enhance expression when placed at the 3' end of the coding sequence. Such terminators are found in the 3' untranslated region following the coding sequences in yeast-derived genes. Any vector containing a yeast-compatible promoter, origin of replication, and other control sequences is suitable for use in constructing yeast expression vectors.

The coding sequence can also be expressed in eucaryotic host cell cultures derived from multicellular organisms. See, e.g., Cell & Tissue Culture: Laboratory Procedures, Wiley, Doyle et al., editors (1993). Useful host cell lines include COS-7, COS-A2, CV-1, murine cells such as murine myelomas N51 and VERO, HeLa cells, and Chinese hamster ovary (CHO) cells. Expression vectors for such cells ordinarily include promoters and control sequences compatible with mammalian cells such as, for example, the commonly used early and late promoters from Simian Virus 40 (SV 40), see Fiers et al., 1978, Nature 273:113, or other viral promoters such as those derived from polyoma, adenovirus 2, bovine papilloma virus (BPV), or avian sarcoma viruses, or immunoglobulin promoters and heat shock promoters. A system for expressing DNA in mammalian systems using a BPV vector system is disclosed in U.S. Pat. No. 4,419,446. A modification of this system is described in U.S. Pat. No. 4,601,978. General aspects of mammalian cell host system transformations have been described by Axel, U.S. Pat. No. 4,399,216. "Enhancer" regions are also important in optimizing expression; these are, generally, sequences found upstream of the promoter region. Origins of replication may be obtained, if needed, from viral sources. However, integration into the chromosome is a common mechanism for DNA replication in eucaryotes.

Plant cells can also be used as hosts, and control sequences compatible with plant cells, such as the nopaline synthase promoter and polyadenylation signal sequences, see Depicker et al., 1982, J. Mol. Appl. Gen. 1:561, are available. Expression systems employing insect cells utilizing the control systems provided by baculovirus vectors have also been described. See Miller et al., in Genetic Engineering (1986), Setlow et al., eds., Plenum Publishing, Vol. 8, pp. 277–97. Insect cell-based expression can be accomplished in *Spodoptera frugipeida*. These systems are also successful in producing recombinant enzymes.

Depending on the host cell used, transformation is done using standard techniques appropriate to such cells. The calcium treatment employing calcium chloride, as described by Cohen, 1972, Proc. Natl. Acad. Sci. USA 69:2110 is used for procaryotes or other cells that contain substantial cell wall barriers. Infection with *Agrobacterium tumefaciens*, see Shaw et al., 1983, Gene 23:315, is used for certain plant cells. For mammalian cells, the calcium phosphate precipitation method of Grahamet al., 1978, Virology 52:546 is preferred. Transformations into yeast are carried out according to the method of Van Solingen et al., 1977, J. Bact. 130:946, and Hsiao et al., 1979, Proc. Natl. Acad. Sci. USA 76:3829.

It may be desirable to modify the sequence of the DNA encoding the enzyme of the invention to provide, for example, a sequence more compatible with the codon usage of the host cell without modifying the amino acid sequence of the encoded protein. Such modifications to the initial 5–6 codons may improve expression efficiency. DNA sequences which have been modified to improve expression efficiency, but which encode the same amino acid sequence, are considered to be equivalent and encompassed by the present invention.

A variety of site-specific primer-directed mutagenesis methods are available and well-known in the art. See, e.g., Sambrook et al., Molecular Cloning: A Laboratory Manual, Cold Spring Harbor, 1989, second edition, chapter 15.51, "Oligonucleotide-mediated mutagenesis," which is incorporated herein by reference. The polymerase chain reaction (PCR) can be used to perform site-specific mutagenesis. In another technique now standard in the art, a synthetic oligonucleotide encoding the desired mutation is used as a primer to direct synthesis of a complementary nucleic acid sequence contained in a single-stranded vector, such as pBSM13+ derivatives, that serves as a template for construction of the extension product of the mutagenizing primer. The mutagenized DNA is transformed into a host bacterium, and cultures of the transformed bacteria are plated and identified. The identification of modified vectors may involve transfer of the DNA of selected transformants to a nitrocellulose filter or other membrane and the "lifts" hybridized with kinased synthetic mutagenic primer at a temperature that permits hybridization of an exact match to the modified sequence but prevents hybridization with the original unmutagenized strand. Transformants that contain DNA that hybridizes with the probe are then cultured (the sequence of the DNA is generally confirmed by sequence analysis) and serve as a reservoir of the modified DNA.

Once the protein has been expressed in a recombinant host cell, purification of the protein may be desired. A variety of purification procedures can be used to purify the recombinant thermostable or thermoactive DNA polymerase of the invention. Examples include the methods for purifying Taq DNA polymerase described in U.S. Pat. Nos. 4,889,818; 5,352,600; and 5,079,352; the methods for purifying the DNA polymerase from *Thermus thermophilis* (Tth) described in U.S. Pat. Nos. 5,618,711 and 5,310,652; the methods for purifying Tma DNA polymerase described in U.S. Pat. Nos. 5,374,553 and 5,420,029. Methods for purifying these DNA polymerases are also described in U.S. Pat. No. 5,466,591. All of the above patents are incorporated herein by reference.

In one aspect of the invention, the expression of the DNA polymerase is carried out in *E. coli*, which is a mesophilic bacterial host cell. Because most *E. coli* host proteins are heat-sensitive, the recombinant thermostable or thermoactive DNA polymerase can be substantially enriched by heat inactivating the crude lysate. This step is done in the presence of a sufficient amount of salt (typically 0.2–0.4 M ammonium sulfate) to reduce ionic interactions of the DNA polymerase with other cell lysate proteins. In one embodiment, the activity of the purified DNA polymerase is assayed using the method described below in Example 3.

For long-term stability, the purified DNA polymerase enzyme must be stored in a buffer that contains one or more non-ionic polymeric detergents. Such detergents are generally those that have a molecular weight in the range of approximately 100 to 250,00 preferably about 4,000 to 200,000 daltons and stabilize the enzyme at a pH of from about 3.5 to about 9.5, preferably from about 4 to 8.5. Examples of such detergents include those specified on pages 295–298 of McCutcheon's *Emulsifiers & Detergents*, North American edition (1983), published by the McCutcheon Division of MC Publishing Co., 175 Rock Road, Glen Rock, N.J. (USA), the entire disclosure of which is incorporated herein by reference. In one embodiment the detergents are selected from the group comprising ethoxylated fatty alcohol ethers and lauryl ethers, ethoxylated alkyl phenols, octylphenoxy polyethoxy ethanol compounds, modified oxyethylated and/or oxypropylated straight-chain alcohols, polyethylene glycol monooleate compounds, polysorbate compounds, and phenolic fatty alcohol ethers. In another embodiment the detergents are selected from the group comprising Tween 20™, a polyoxyethylated (20) sorbitan monolaurate from ICI Americas Inc. (Wilmington, Del.), and Iconol™ NP-40, an ethoxylated alkyl phenol (nonyl) from BASF Wyandotte Corp. (Parsippany, N.J.).

6. Uses of the Thermostable or Thermoactive DNA Polymerases of the Invention

The thermostable or thermoactive enzyme of this invention may be used for any purpose in which a thermostable or thermoactive DNA polymerase with an attenuated 3'-5' exonuclease activity is necessary or desired. In one embodiment, the enzyme is used for PCR. Examples of applications using the PCR include, for example, direct cloning from genomic DNA or cDNA, in vitro mutagenesis and engineering of DNA, genetic fingerprinting of forensic samples, assays for the presence of infectious agents, prenatal diagnosis of genetic diseases, analysis of allelic sequence variations, analysis of RNA transcript structure, genomic footprinting, and direct nucleotide sequencing of genomic DNA and cDNA. See, e.g., Current Protocols in Molecular Biology, 2001, Ausubel et al. (ed.s), John Wiley & Sons, Chapter 15 and *PCR Strategies,* 1995, Innis et al. (ed.s), Academic Press, Inc., incorporated herein by reference in their entireties.

7. Kits

The thermostable or thermoactive DNA polymerases of the invention are suited for the preparation of a kit. Kits comprising the mutant DNA polymerases of the invention may be used for detectably labeling DNA molecules, DNA sequencing, or amplifying DNA molecules by well known techniques, depending on the content of the kit. Such kits may comprise a carrying means being compartmentalized to receive in close confinement one or more container means such as vials, test tubes and the like. Each of such container means comprises components or a mixture of components needed to perform DNA sequencing, DNA labeling, or DNA amplification.

A kit for sequencing DNA may comprise a number of container means. A first container means may, for example, contain a substantially purified sample of a thermostable or thermoactive DNA polymerase of the invention. A second container means may contain one or a number of types of nucleotides needed to synthesize a DNA molecule complementary to DNA template. A third container means may contain one or a number different types of dideoxynucleotide triphosphates. In addition to the above container means, additional container means may be included in the kit which contain one or a number of DNA primers.

A kit used for amplifying DNA will comprise, for example, a first container means containing a substantially pure mutant DNA polymerase of the present invention and one or a number of additional container means that contain a single type of nucleotide or mixtures of nucleotides. Various primers may or may not be included in a kit for amplifying DNA.

When desired, the kit of the present invention also may include container means that contain detectably labeled nucleotides which may be used during the synthesis or sequencing of a DNA molecule. One of a number of labels may be used to detect such nucleotides. Illustrative labels include, but are not limited to, radioactive isotopes, fluorescent labels, chemiluminescent labels, bioluminescent labels and enzyme labels, or any other label for directly or indirectly labeling a nucleotide or nucleic acid.

In the following non-limiting examples, all percentages are by weight if for solids and by volume if for liquids, unless otherwise noted.

EXAMPLE 1

Mutagenesis of pCS6 and pCS5

This example describes the site directed mutagenesis of the 3'-5' exonuclease domain of a thermostable and thermoactive DNA polymerase.

In a first round of mutagenesis, a site-directed mutagenesis approach was used to alter residues in a thermostable DNA polymerase that are either homologous residues known to be important for coordinating divalent metal cations in the active site of the proofreading domain of the Klenow fragment or located between the homologous residues. See Derbyshire et al., 1995, Methods in Enzymology 262:363–85, incorporated herein by reference in its entirety. Plasmid pCS6, encoding the mutant chimeric thermostable DNA polymerase CS6, was used. See FIG. 5. CS6 is a mutant form of the chimeric thermostable DNA polymerase CS5. See FIG. 4. The N-terminal portion of CS5 is the N-terminal 291 residues of the DNA polymerase from *Thermus* species Z05, encoding its 5'-3' exonuclease activity. See U.S. Pat. No. 6,228,628. The remainder of CS5 is the C-terminal 602 residues from the Tma DNA polymerase, comprising its 3'-5' exonuclease activities and its DNA polymerase activities. CS6 is identical to CS5 except that it has the mutations D323A and E325A (the numbering of residues from the wild-type Tma enzyme are used throughout unless otherwise specified) in the 3'-5' exonuclease domain. As shown herein, these mutations cause CS6 to have no detectable 3'-5' exonuclease activity.

The acidic residues at positions 323 and 325 and the leucine residue at position 324 were targeted. Each mutation (except the D323E mutation, as explained below) was made using the same basic method. Pairs of degenerate oligonucleotides were synthesized, as shown in Table 2. One degenerate oligonucleotide of each pair was an 11-mer, the other a 17-mer. Apart from the degenerate nucleotides, the 11 mer of each pair of oligonucleotides was perfectly complementary to an 11 nucleotide subsequence of the 17mer of the pair. For the D323E mutation, a non-degenerate pair of complementary oligonucleotides was designed, as shown in Table 2. The degenerate oligonucleotides of each pair were mixed under annealing conditions such that oligonucleotides that were perfectly complementary to one another, including at their degenerate positions, annealed to form an 1-mer dsDNA strand flanked on one end by a 3'-TA overhang and on the other end by a 5'-CTAG overhang, as shown in Table 2. These ends are compatible with ends generated by the restriction enzymes SgfI and SpeI, respectively. Thus, each annealing reaction produced a mixture of perfectly complementary and annealed oligonucleotide pairs as shown in Table 2.

Five µg pCS6 were then digested in a 25 µl reaction comprising 15 units of the restriction enzyme Spe I, 50 mM Tris.HCl, 10 mM Mg Cl$_2$, 100 mM NaCl, pH 7.5 at 37° C. for 2.5 hr. The enzyme was inactivated by heating at 75° C. for 10 minutes, then cooled to room temperature. 15 units of the restriction enzyme SgfI were then added and the incubation continued for 2 hr at 37° C. The reaction was then stored overnight at 25° C. These steps linearized pCS6 and removed the codons encoding the two acidic residues at 323 and 325 (which are mutated in pCS6) and the leucine at position 324. It also left ends that were compatible with the ends of the annealed degenerate primer pairs.

In separate reactions, 0.5 pmol of each of the annealed oligonucleotide pair mixtures was mixed with 0.1 pmol of the linearized pCS6 and 0.5 units of T4 DNA ligase (Amersham Pharmacia Biotech AB, Uppsala Sweden), in the supplied buffer and incubated overnight at 4° C.

One µl (20 ng) of each ligation mix was then used to transform *E. coli* strain DG116 using a GENE PULSER™ electroporater (Bio-Rad Laboratories, Hercules Calif.) essentially according to the manufacturer's instructions. The electroporated cells were diluted with 1 ml SOC medium, then incubated for 1 hr at 30° C. with agitation. 50 or 100 µl aliquots of the resuspended cells were plated on LB plates with 100 µg/ml added ampicillin, to select for transformed cells, and incubated overnight.

For each transformation, five colonies were picked for PCR amplification and restriction analysis to determine which, if any, of the mutated pCS6 plasmids they contained. Each colony was suspended in a 50 µl master mix containing PCR buffer II (PE-Applied BioSystems, Redwood City, Calif.), 40 µM dNTP mix and 20 pmol each of the primers CS4 and CS 1A.

CS1A: GTATGTAGTACGCTTCCTTTGGTTTGAA (SEQ ID NO:35)

CS4: TGGCTTTGGGAGAAGTACGGCCT (SEQ ID NO:36)

Amplified DNA from each colony was digested with a diagnostic array of restriction enzymes, as shown in Table 3, in order to determine whether it had correctly incorporated a synthetic oligonucleotide and, if so, which mutant sequence it had incorporated. Clones that had the correct pattern of restriction sites were then sequenced in the region of the insert to ensure that each plasmid selected for further use incorporated only the desired mutations.

TABLE 2

Oligonucleotides Used In Round I

| Degenerate Oligo Pairs (degenerate positions in bold lower-case letters) | Mutation | Hybridized Mutagenic Oligo Pairs |
|---|---|---|
| CS6 5' CGACGAa/tGAGA (SEQ ID NO:37) | L324 -> E | 5' CGACGAAGAGA (SEQ ID NO:39) |
| CS7 3' TAGCTGCTt/aCTCTGATC (SEQ ID NO:38) | | 3' TAGCTGCTTCTCTGATC (SEQ ID NO:40) |
| | L324 -> D | 5' CGACGATGAGA (SEQ ID NO:41) |
| | | 3' TAGCTGCTACTCTGATC (SEQ ID NO:42) |
| C58 5' TGATa/cAGGAAA (SEQ ID NO:43) | L324 -> K | 5' TGATAAGGAAA (SEQ ID NO:45) |
| CS9 3' TAACTAt/gTCCTTTGATC (SEQ ID NO:44) | | 3' TAACTATTCCTTTGATC (SEQ ID NO:46) |
| | L324 -> Q | 5' TGATCAGGAAA (SEQ ID NO:47) |
| | | 3' TAACTAGTCCTTTGATC (SEQ ID NO:48) |
| CS10 5' CGATa/cATGAAA (SEQ ID NO:49) | L324 -> N | 5' CGATAATGAAA (SEQ ID NO:51) |
| CS11 3' TAGCTAt/gTACTTTGATC (SEQ ID NO:50) | | 3' TAGCTATTACTTTGATC (SEQ ID NO:52) |
| | L324 -> H | 5' CGATCATGAAA (SEQ ID NO:53) |
| | | 3' TAGCTAGTACTTTGATC (SEQ ID NO:54) |
| CS12 5' TGAc/gCTGGATA (SEQ ID NO:55) | E325 -> D | 5' TGACCTGGATA (SEQ ID NO:57) |
| CS13 3' TAACTg/cGACCTAAGATC (SEQ ID NO:56) | | 3' TAACTGGACCTATGATC (SEQ ID NO:58) |
| | D323 -> E; E325 -> D | 5' TGAGCTGGATA (SEQ ID NO:59) |
| | | 3' TAACTCGACCTATGATC (SEQ ID NO:60) |
| CS14 5' TGAGCTTGAGA (SEQ ID NO:61) | D323 -> E | 5' TGAGCTTGAGA (SEQ ID NO:63) |
| CS15 3' TAACTCGAACTCTGATC (SEQ ID NO:62) | | 3' TAACTCGAACTCTGATC (SEQ ID NO:64) |

TABLE 3

Restriction Enzyme Sites in Tma L324 E/D/K/N/Q/H and 323/325 Mutants

| L324 Mutant (D323 E325) | BsmAI | ClaI* | TaqI* | BclI @A321 | BclI @D323 | EarI | BspHI |
|---|---|---|---|---|---|---|---|
| E | + | − | + | + | − | + | − |
| D | + | − | + | + | − | − | − |
| K | − | − | − | − | − | − | − |
| N | − | + | + | + | − | − | − |
| Q | − | − | −− | − | + | − | − |
| H | − | + | + | + | − | − | + |
| X323L324 X325 | BstNI | AluI | SmlI | | | | |
| D-L-D | + | − | − | − | − | − | − |
| E-L-D | − | + | − | − | − | − | − |

TABLE 3-continued

Restriction Enzyme Sites in Tma L324 E/D/K/N/Q/H and 323/325 Mutants

| L324 Mutant (D323 E325) | BsmAI | ClaI* | TaqI* | BclI @A321 | BclI @D323 | EarI | BspH I |
|---|---|---|---|---|---|---|---|
| E-L-E Parents | – BsmAI BstNI | + ClaI TaqI | + SmlI | – BclI @A321 | – BclI I @D323 | – EarI | – BspH I |
| CS5(D-L-E) | – | + | – | – | – | – | – |
| CS6(A-L-A) | – | – | – | – | + also Sg/I+ | – | – |

*No in Dam+ *E. coli*; yes in PCR products and Dam– *E. coli*.

In a second round of mutagenesis, a PCR-based site-directed mutagenesis procedure was used to target residues known or suspected to contribute to the binding of substrate for the 3'-5' exonuclease activity. Primer pairs were designed for each mutagenesis, as shown in Table 4. Each primer pair allowed for the amplification of a portion of the polymerase encoding gene of pCS5. Only one primer pair was used for the L329A mutation. For this mutation, one primer of the pair introduced a mutation into the amplicon, and both primers contained restriction sites near their ends that allowed them to be subcloned into pCS5 that had been digested with the same enzymes, thus generating an expression plasmid encoding a Z05-Tma hybrid DNA polymerase with the L329A mutation. Two primer pairs were used to create each of the remaining mutations in the second round of mutagenesis. For each mutation, one primer in each pair contained the desired mutation but was otherwise complementary to pCS5. The other primer of each pair was perfectly complementary to a portion of pCS5. PCR using pCS5 as the template was carried out separately for each primer pair. These reactions produced amplicons that overlapped by approximately 35 nucleotides. The overlapping portion of the amplicons contained the desired mutation. Another PCR amplification was then done wherein the two partially overlapping amplicons were mixed and the flanking sequence primers from each pair (i.e., the respective amplification primers from each pair that did not comprise the mutant sequence) were used. This reaction resulted in one large amplicon that consisted of the two partially overlapping amplicons produced by the earlier PCRs. The flanking sequence primers were designed to be complementary to portions of the polymerase-encoding gene that had restriction sites useful for cloning. The amplicon and pCS5 were then digested with those restriction enzymes, mixed, and ligated, to produce an expression plasmid that contained the desired mutation. The ligation products were used to transform *E. coli* as described above. The success of the mutageneses was verified using the restriction sites listed in Table 5, as described above.

TABLE 4

Primers Used In Round II

| Mutation | Forward Primer (changed codon(s) in bold lower case) | Reverse Primer |
|---|---|---|
| L329A | CS20 GAAACTAGTTCCgctGATCCTTTCGA (SEQ ID NO:65) | CS36 GAAAAGAGAAGGACATGAGCTCTTGGTAA (SEQ ID NO:66) |
| | Mutagenic Primers | Flanking Sequence Primers |
| Y464A | CS21 (forward overlap primer) AGAAAAAGCtGCGAAtgcaTCCTGTGAAGA TGCAGA (SEQ ID NO:67) | CS37 TTTCCAGATCTGCCTCGTGCAGTTTTAA (SEQ ID NO:68) |
| | CS22 (reverse overlap primer) CTGCATCTTCACAGGAtgcaTTCGCaGCTT TTTCTA (SEQ ID NO:69) | CS35 ACCAAGAGCTCATGTCCTTCTCTTTTCCG (SEQ ID NO:70) |
| Q384A | CS23 (forward overlap primer) CGTTGGtgccAATTTGAAATTCGATTACAA (SEQ ID NO:71) | CS36 GAAAAGAGAAGGACATGAGCTCTTGGTAA (SEQ ID NO:66) |
| | CS24 (reverse overlap primer) TGTAATCGAATTTCAAATTggcACCAACGA (SEQ ID NO:72) | AW964 GGAAACTAGTTCCCTCGATCC (SEQ ID NO:73) |
| N385A | CS25 (forward overlap primer) CCTTGGTCAGgccTTGAAATTCGATTACAA (SEQ ID NO:74) | CS36 GAAAAGAGAAGGACATGAGCTCTTGGTAA (SEQ ID NO:66) |
| | CS26 (reverse overlap primer) TGTAATCGAATTTCAAggcCTGACCAACGA (SEQ ID NO:75) | AW964 GGAAACTAGTTCCCTCGATCC (SEQ ID NO:73) |

TABLE 4-continued

Primers Used In Round II

Mutation

Q384A  CS27 (forward overlapy primer)      CS36
N385A  CGTTGGTgccgcTcTGAAATTCGATTACAA      GAAAAGAGAAGGACATGAGCTCTTGGTAA
       (SEQ ID NO:76)                      (SEQ ID NO:66)

CS28 (reverse overlap primer)       AW964
       TGTAATCGAATTTCAgAgcggcACCAACGA      GGAAACTAGTTCCCTCCATCC
       (SEQ ID NO:77)                      (SEQ ID NO:73)

D389E  CS29 (forward overlap primer)       CS36
       TGAAATTCCAgTACAAGGTGTTGATGGTGA      GAAAAGAGAAGGACATCAGCTCTTGGTAA
       A (SEQ ID NO:78)                    (SEQ ID NO:66)

CS30 (reverse overlap primer)       AW964
       CAACACCTTGTAcTCGAATTTCAAA           GGAAACTAGTTCCCTCGATCC
       (SEQ ID NO:79)                      (SEQ ID NO:73)

TABLE 5

Round II Primers and their Restriction Sites

| Primer | | Cloning Restriction Sites | Screening Restriction Sites |
|---|---|---|---|
| CS20 | (SEQ ID NO: 65) | SpeI | MspA1I |
| CS36 | (SEQ ID NO: 66) | SacI | |
| Cs21 | (SEQ ID NO: 67) | | BsmI, NsiI |
| CS37 | (SEQ ID NO: 68) | BglII | |
| CS35 | (SEQ ID NO: 70) | SacI | |
| CS22 | (SEQ ID NO: 69) | | BsmI, NsiI |
| CS23 | (SEQ ID NO: 71) | | BanI |
| CS24 | (SEQ ID NO: 72) | | BanI |
| AW964 | (SEQ ID NO: 73) | SpeI | |
| CS25 | (SEQ TD NO: 74) | | StuI |
| CS26 | (SEQ ID NO: 75) | | StuI |
| CS27 | (SEQ ID NO: 76) | | BanI, BsrBI |
| CS28 | (SEQ ID NO: 77) | | BanI, BsrBI |
| CS29 | (SEQ ID NO: 78) | | TatI, RsaI |
| CS30 | (SEQ ID NO: 79) | | TatI, RsaI |

EXAMPLE 2

Production and Purification of Mutant Thermostable DNA Polymerases

The plasmids resulting from the ligation described above contain the polymerase gene under control of the λ $P_L$ promoter. Host cells (DG116, ATCC #53606) containing a cI857 (thermolabile) λ repressor were transformed with the plasmids. DG116 cells transformed with the plasmids containing the wild type or mutagenized polymerase gene were used to inoculate 10 ml standard flask media (SFM; comprising glucose, vitamin $B_1$, casamino acids, and minimal medium) with ampicilin (100 μg/ml) and grown overnight at 30 C, 250 rpm. 5 ml of the overnight culture was used to inoculate 450 ml SFM+ampicillin and shaken at 30 C, 250 rpm until the culture reached an $OD_{600}$ of 0.6–0.8. The culture was then transferred to 37 C and grown overnight at 250 rpm to achieve a temperature-induced expression of the polymerase. See, e.g., U.S. Pat. No.s 5,079,352, 5,420,029 and 5,618,711. The overnight growth was pelleted at 3,000×g for 15 min.

The pellets were resuspended in 30 ml lysis buffer (50 mM Tris-HCl, pH 7.5, 10 mM EDTA, 1 mM DTT, 1 mM Pefabloc, 1 μg/ml Leupeptin, 0.2 mM TLCK) and cells were lysed by french press at 16,000 psi. The lysed cell suspension was brought to 0.2M $(NH_4)_2SO_4$ and heated at 75□C. for 15 min. to inactivate and denature E. coli host proteins. The heated extracts were chilled at 0□C. for 15 min., adjusted to 0.6% polyethyleneamine to precipitate host DNA, and centrifuged at 16,000×g for 30 min. The clarified extracts were loaded onto a 2 ml Phenyl-Sepharose column pre-equilibrated with 50 mM Tris-HCl, pH 7.5, 10 mM EDTA, 1 mM DTT, 0.2M $(NH_4)_2SO_4$. The column was washed with 6 ml of equilibration buffer, followed by a 2 ml wash with 50 mM Tris-HCl, pH 7.5, 10 mM EDTA, 1 mM DTT, and a final wash with 2 ml 50 mM Tris-HCl, pH 7.5, 10 mM EDTA, 1 mM DTT, 20% ethylene glycol. The protein was eluted in 50 mM Tris-HCl, pH 7.5, 10 mM EDTA, 1 mM DTT, 2.5M urea. The eluate was adjusted to 100 mM KCl and loaded onto a 2 ml Heparin-Sepharose column pre-equilibrated with 25 mM Tris-HCl, pH 7.5, 1 mM EDTA, 1 mM DTT, 100 mM KCl. The column was washed with 6 ml equilibration buffer and eluted with 6 ml 25 mM Tris-HCl, pH 7.5, 1 mM EDTA, 1 mM DTT, 400 mM KCl. The final eluate was adjusted to 20 mM Tris-HCl, pH 8.0, 0.1 mM EDTA, 100 mM KCl, 1 mM DTT, 0.2% TWEEN 20, 50% v/v glycerol by dialysis and dilution and stored at −20° C.

EXAMPLE 3

Standard Assay for 3'-5' Exonuclease Activity

The following example provides the Standard Assay for determining the 3'-5' exonuclease activity of thermostable or thermoactive DNA polymerase and the definition of a unit of 3'-5' exonuclease activity.

To compare the 3'-5' exonuclease activities of the mutant derivatives of CS5, degradation of the carboxyfluorescein (FAM)-labeled single-stranded oligonucleotide substrate NJS40 was measured:

NJS40: FAM-GCGCTAGGGCGCTGGCAAGTG-
TAGCGGTCAC                                 (SEQ ID NO:80)

The Standard Assay (40 μl) contained 4 pmol (100 nM) FAM-labeled single-stranded NJS40 oligonucleotide in 50 mM Tricine, pH 8.3, 25 mM KOAc, 5% w/v DMSO, 0.5 mM $Mn(OAc)_2$ and 5% (v/v) contributions from enzyme storage buffer (in reaction: 1 mM Tris, pH 8.0, 5 mM KCl, 0.005 mM EDTA, 0.025% TWEEN-20, 0.05 mM DTT, 2.5% glycerol). Reactions were initiated by addition of NJS40 and the Mn(OAc)$_2$ and were incubated at 63° C. for 15 minutes. Reactions were quenched by addition of 40 µl 50 mM EDTA. The enzyme concentration and reaction times were adjusted to achieve linearity. The reaction is linear over a range of approximately 1–20% conversion of starting oligonucleotide to shorter product, corresponding to 0.5–10 milliUnits of enzyme; enzyme concentration was always less than substrate concentration. The quenched reaction solutions were diluted in formamide to 0.1 nM oligonucleotide and analyzed by capillary electrophoresis (ABI 3100, Applied Biosystems, Foster City Calif.). The peak height of the starting size and degraded oligonucleotides was determined using GENESCAN™ Software (Applied Bioystems, Foster City, Calif.). The pmol of oligonucleotide converted to shorter oligonucleotide products is equal to {1−(relative amount of P$_n$ remaining after 15 min)}× (pmol of P$_n$ at start of reaction)

where P$_n$ is the substrate oligonucleotide (NJS40) of initial length n. The relative amount of P$_n$ remaining after 15 minutes was determined by measuring the height of the peak corresponding to the starting size oligonucleotide and dividing it by the sum of all peak heights. This assay thus measures the rate of release of the 3'-terminal nucleotide from the oligonucleotide NJS40. One unit of 3'-5' exonuclease activity catalyzes the conversion of 50 pmol of single-stranded NJS40 oligonucleotide to shorter length oligonucleotides in 15 minutes under the Standard Assay conditions.

The mutant polymerases made as described above were characterized using the Standard Assay. The results of these assays are presented in Table 6 under the columns labeled "ssDNA."

The polymerase activity of each mutant enzyme was measured using the assay taught in U.S. Pat. No. 4,889,818. Briefly, an amount of enzyme stock in storage buffer (20 mM Tris, 100 mM KCl, 0.1 mM EDTA, 0.5% Tween-20, 1 mM DTT, 50% glycerol) was diluted in enzyme diluent (25 mM Tris-HCl, pH 8.0, 50 mM KCl, 1 mM β-mercaptoethanol, 0.5% Tween-20, 0.5% NP40, 100 µg/ml gelatin) to yield between about 0.02 and 0.1 units of polymerase activity per assay. Five microliters of the diluted enzyme were added to 45 µl of reaction buffer (25 mM TAPS, pH 9.4, 50 mM KCl, 2 mM MgCl$_2$, 1 mM α-mercaptoethanol, 200 µM d(GTA)TP, 100 µM α-$^{33}$P-dCTP, 30 µg activated salmon sperm DNA ("activated" DNA is a native preparation of DNA after partial hydrolysis with DNase I until 5% of the DNA was transferred to the acid-soluble fraction)). The reaction was incubated for 10 minutes at 74° C., then quenched with 10 µl of 60 mM EDTA. 50 µl from each quenched reaction was added to tubes containing 1 ml of 2 mM EDTA pH 8.0 with 50 µg/ml carrier DNA (salmon sperm DNA that has been sheared by passage through a 21 gauge needle). 1 ml of 20% trichloroacetic acid (TCA) and 2% sodium pyrophosphate was added and the tubes were gently agitated using a vortex agitator. The tubes were incubated on ice for ten to 20 minutes to allow for complete precipitation of the DNA. The precipitated DNA was collected on a GF/C filter on a vacuum filtration manifold. The filters were washed three times each in 5% TCA, 1% sodium pyrophosphate, then with 20% TCA, and finally with 95% ethanol. Two blank filters were treated similarly in order to determine the instrument's background. Radioactivity incorporated into the precipitated DNA was quantified using OMNIFLUOR® (Packard BioScience B.V., Groningen, The Netherlands) and a LS6000IC™ scintillation counter (Beckman Coulter, Fullerton Calif.). One unit of polymerase activity is defined as the amount of enzyme activity required to incorporate a total of 10 nmoles dNMP into TCA-precipitable DNA product in 30 minutes using the assay conditions provided above.

EXAMPLE 4

Variant Assays for Measuring 3'-5' Exonuclease Activity

Two variations of the Standard Assay also were used to characterize the 3'-5' exonuclease activities of the mutant thermostable or thermoactive DNA polymerases described above. These variant assays were identical to the Standard Assay except that each used a different substrate. In each variant assay, as in the Standard Assay, the rate of release of the 3'-terminal nucleotide from the oligonucleotide NJS40 was measured. However, in the variant assays, NJS40 was hybridized to a complementary oligonucleotide. The first variant assay used a double-stranded DNA substrate that was perfectly matched:

```
NJS40: 3' FAM-GCGCTAGGGCGCTGGCAAGTGTAGCGGTCAC                  (SEQ ID NO:80)

NJS43: 5' pAGCGATCCCGCGACCGTTCACATCGCCAGTGCGACGCGCATTGGTGGTGTGGGCGGCGCC   (SEQ ID NO:81)
```

Results for the mutants described above using the first variant assay are provided in Table 6 under the columns marked "dsDNA."

The second variant assay used a double-stranded DNA substrate that contained a mismatch:

```
NJS40: 3' FAM-GCGCTAGGGCGCTGGCAAGTGTAGCGGTCAC                  (SEQ ID NO:80)

NJS44: 5' pAGCGATCCCGCGACCGTTCACATCGCCAGTTCGACGCGCATTGGTGGTGTGGGCGGCGCC   (SEQ ID NO:82)
```

Results for the mutants described above using the second variant assay are provided in Table 6 under the columns marked "dsDNA with mismatch."

TABLE 6

Polymerase and 3'-5' Exonuclease Activities of Round I and Round II Mutants

| | 5'-3' Polymerase | | 3'-5' Exonuclease | | | | | | | | | |
|---|---|---|---|---|---|---|---|---|---|---|---|---|
| | | | ssDNA | | | dsDNA | | | | dsDNA with mismatch | | |
| Enzyme | Specific activity, U/pmol | Rate[#] pM/s | Specific Activity, U/pmol | % | Polymerase/ 3'Exo Ratio | Rate pM/s | Specific Activity, U/pmol | % | Polymerase/ 3'Exo Ratio | Rate, pM/s | Specific Activity, U/pmol | % | Polymerase/ 3'Exo Ratio |
| CS5 | 8.6 | 136.1 | 9.9 | 100.0 | 0.9 | 154.7 | 11.3 | 100.0 | 0.8 | 228.1 | 16.6 | 100.0 | 0.5 |
| Y464A | 14.7 | 0.2 | 0.0 | 0.1 | 1008.0 | 0.2 | 0.0 | 0.1 | 1008.0 | 0.2 | 0.01 | 0.1 | 1008.0 |
| D389E | 13.0 | 22 | 1.6 | 16.2 | 8.1 | 25.5 | 1.9 | 16.5 | 7.0 | 66.8 | 4.9 | 29.3 | 2.7 |
| L329A | 6.4 | 14.5 | 1.1 | 10.7 | 6.1 | 12.1 | 0.9 | 7.8 | 7.3 | 44.1 | 3.2 | 19.3 | 2.0 |
| Q384A_N385A | 7.7 | 5.1 | 0.4 | 3.7 | 20.9 | 6.3 | 0.5 | 4.1 | 16.9 | 24.8 | 1.8 | 10.9 | 4.3 |
| Q384A | 13.0 | 31.1 | 2.3 | 22.9 | 5.8 | 36.7 | 2.7 | 23.7 | 4.9 | 104.4 | 7.6 | 45.8 | 1.7 |
| N385A | 11.8 | 48.4 | 3.5 | 35.6 | 3.4 | 59.7 | 4.3 | 38.6 | 2.7 | 145.6 | 10.6 | 63.8 | 1.1 |
| L324Q | 8.2 | 37 | 2.7 | 27.2 | 3.0 | 49.8 | 3.6 | 32.2 | 2.3 | 94.8 | 6.9 | 41.6 | 1.2 |
| L324H | 10.3 | 46.3 | 3.4 | 34.0 | 3.1 | 54.3 | 3.9 | 35.1 | 2.6 | 99.6 | 7.2 | 43.7 | 1.4 |
| L324E | 7.1 | 65.6 | 4.8 | 48.2 | 1.5 | 56.8 | 4.1 | 36.7 | 1.7 | 102.4 | 7.4 | 44.9 | 1.0 |
| L324D | 8.6 | 83.4 | 6.1 | 61.3 | 1.4 | 61 | 4.4 | 39.4 | 1.9 | 130.6 | 9.5 | 57.3 | 0.9 |
| L324K | 8.0 | 46.9 | 3.4 | 34.5 | 2.4 | 69.4 | 5.0 | 44.9 | 1.6 | 127.1 | 9.2 | 55.7 | 0.9 |
| L324N | 8.3 | 55.1 | 4.0 | 40.5 | 2.1 | 72.7 | 5.3 | 47.0 | 1.6 | 152.4 | 11.1 | 66.8 | 0.8 |

[#]Rate is for 0.25 nM enzyme

EXAMPLE 5

Comparison of the 3'-5' Exonuclease Activities of Mutant Thermostable or Thermoactive DNA Polymerases and Mutant E. coli DNA Polymerases This example demonstrates that the 3'-5' exonuclease activity of a mutant thermostable or thermoactive DNA polymerase cannot be predicted from the enzymatic properties of analogous Eco DNA Pol I mutant polymerases. Table 7 presents a comparison of the 3'-5' exonuclease activities of the Round II polymerase mutants and of analogous E. coli Pol I mutants.

TABLE 7

Comparison of E. coli* Pol I Mutants with CS5 RoundII Mutants Residual proofreading activity † (% wild-type)

| Mutation in E. coli | Double-stranded DNA | Single-stranded DNA | Mutation in CS5 | Double-stranded DNA | Single-stranded DNA |
|---|---|---|---|---|---|
| Y497A | 5.6% | 2.9% | Y464A | 0.1% | 0.1% |
| L361A | 4.0 | 37 | L329A | 7.8 | 10.7 |
| D424E | 4.0 | 8.3 | D389E | 16.5 | 16.2 |
| Q419A | 23 | 20 | Q384A | 23.7 | 22.9 |

*based on Derbyshire et al., 1995, Methods in Enzymology 262:363–85
† from Table 6

The results presented in Table 7 show that analogous mutations in the 3'-5' exonuclease domains of the Eco and CS5 DNA polymerases frequently have different effects on the proofreading activity of the enzymes, relative to the activity of the corresponding wild-type enzyme's activity. Comparison of the Eco Q419A mutant with the CS5 Q384A mutant shows that analogous mutations in these two enzymes can affect their 3'-5' exonuclease activities similarly. However, for some analogous mutants, significant differences in enzymatic activity are observed. In some mutant pairs this difference is simply quantitative. For example, the Eco Y497A mutant has substantially more residual enzymatic activity than the CS5 Y464A mutation on both ssDNA and dsDNA substrates. Other analogous mutants additionally show qualitative differences. For example, the Eco L361A and D424E mutants both have much greater activity against a ssDNA substrate than against a dsDNA substrate. However, the analogous CS5 mutants (L329A and D389E, respectively) have similar residual enzymatic activities against both ssDNA and dsDNA substrates.

EXAMPLE 6

Use of Mutant Thermostable DNA Polymerases with Attenuated 3'-5' Exonuclease Activity for PCR The mutant enzymes Y464A, D389E, L329A, Q484A/N385A, Q384A, N385A and L324Q were tested for Reverse Transcriptase/PCR activity using an HIV drug resistance assay. A mixture of 120 units of CS6 (having no detectable 3'-5' exonuclease activity) and 5 units CS5 (having wild-type 3'-5' exonuclease activity) was used as a control. The 1.7 kb HIV[r] assay conditions were used (50 mM Tricine pH 8.3, 45 mM KOAc pH 7.5, 0.9 mM Mn(OAc)$_2$, 5% DMSO, 0.2 mM d(AGC)TP, 0.3 mM dUTP, 0.03 mM dTTP, 0.2× SYBR Green I, G46E CS5/CS6 enzyme blend (5/125 units) or 60 or 30 units of polymerase activity of each mutant enzyme, 1 unit UNG, and 0.4 M each (−1) 2'-amino modified primers (RN326 and RN328) and kinetic thermocycling, see Myers et al., 2000, Antiviral Therapy 5: Abstract 49) to specifically and sensitively amplify the protease gene and the first 400 codons of the reverse transcriptase gene of HIV.

RN326: GAGGGGTATTGACAAACTCCCACTCAGGAATCXA  (X = 2'amino-dC) (SEQ ID NO:83)

RN328: GGGAATTTTCTTCAGAGCAGACCAGAGCCAAXA  (X = 2'amino-dC) (SEQ ID NO:84)

Figure 10:
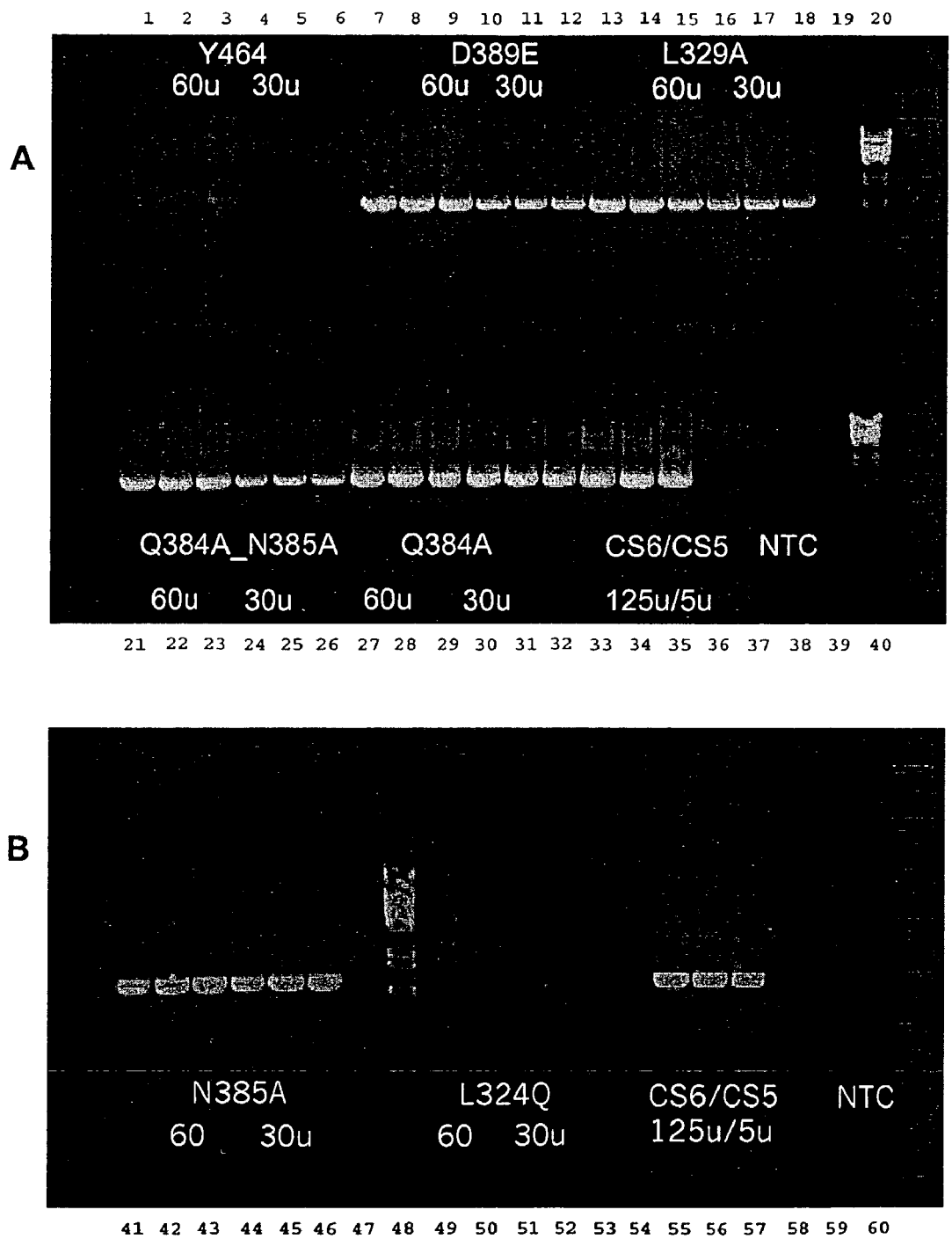
FIG. 10 presents photographs of electrophoresis analyses of the amplification products of the reverse transcriptase PCR amplifications of FIG. 9.

A GENEAMP™ 5700 SDS thermocycler (PE Biosystems, Foster City, Calif.) was used with the following thermocycling protocol: 50° C. for 2 min, 60° C. for 60 min, and 95° C. 1 min, followed by 4 cycles of 95° C., 20 sec., 58° C. 15 sec., 65° C. 1 min 45 sec, followed by 36 cycles of 90° C. 20 sec., 58° C., 15 sec., 65° C. 1 min. 45 sec., followed by 65° C. 10 min. hold. The growth curves of the PCR amplifications are shown in FIG. 9. Amplifications using the same protocol with varying amounts of enzyme also were run and analyzed using gel electrophoresis. 5 μl from each 100 μl reaction was loaded onto a 1% agarose gel following PCR which was run essentially as described in Sambrook et al., Molecular Cloning: A Laboratory Manual, Cold Spring Harbor, 1989, second edition. The gels were stained using a 1 μg/ml solution of ethidium bromide. The resulting gels are shown in FIG. 10. In FIG. 10, lanes 20, 40 and 48=Bst II digested lambda DNA (New England Biolabs, Beverly, Mass.) as a molecular weight marker; lanes 36–38 and 58–60=negative control (5 U CS5, 125 U CS6, no template); lanes 33–35 and 55–57=positive control (5 U CS5, 125 U CS6); lanes 1–3=60 U Y464A CS5; lanes 4–6=30 U Y464A CS5; lanes 7–9=60 U D389E CS5; lanes 10–12=30 U D389E CS5; lanes 13–15=60 U L329A CS5; lanes 16–18=30 U L329A CS5; lanes 21–23=60 U Q384A-N385A CS5; lanes 24–26=30 U Q384A-N385A CS5; lanes 27–29=60 U Q384A CS5; lanes 30–32=30 U Q384A CS5; lanes 41–43=60 U N385A CS5; lanes 44–46=30 U N385A CS5; lanes=49–51=60 U L324Q CS5; lanes 52–54=30 U L329Q CS5 (wherein all units refer to DNA polymerase activity).

Mutant enzymes were judged by their $C_T$ values (FIG. 9), and by their yield of specific and non-specific amplification products, detected using gel analysis of amplification products (FIG. 10). These results demonstrate that mutants with proofreading activities greater than 3% but less than 20% of wild typelevels (as measured using the Standard Assay described in Example 3, above) work well for reverse transcription PCR amplification of the 1.7 kb HIV RNA template. These mutants also had specific activities between 0.4 and 1.6 U/pmol, and a ratio of polymerase activity to 3'-5' exonuclease activity of greater than 6.0 but less than 25.0 U pol/U exo, the enzymatic activities being measured as described in Example 3, and yielded PCR results comparable to those obtained with the blend of CS5 and CS6. Q384A CS5 and N385A CS5 also work well as judged by gel analysis of their amplification products, although not as well as judged by their $C_T$ values.

EXAMPLE 7

Identification of Target Residues for Site-Specific Mutagenesis to Attenuate the 3'-5' Exonuclease Activity of Thermostable or Thermoactive Family A DNA Polymerases This example provides a method for identifying residues in thermostable or thermoactive family A DNA polymerases that can be mutated and tested to identify mutants with attenuated 3'-5' exonuclease activity.

The X-ray structure of *E. coli* Pol I complexed with DNA in the 3'-5' exonuclease site (see Brautigan et al., 1998, J. Mol. Biol. 277:363–77) was analysed using the "3D>sequence contacts" feature of the XSAE program (see Higgins et al., 1992, Cabios 8, 189–91) to identify all residues of the selected protein (Pol I; 1kfs.pdb, chain A) that are within 5 A of the DNA substrate (1kfs.pdb, chain B). Using this method, the residues in Table 8 were identified in *E. coli* Pol I. Analogous residues can be identified in a thermostable or thermoactive family A DNA polymerase by inspection of a sequence alignment of the polymerases (as shown, for example, in FIG. 8). These candidate residues then can be mutated and tested for attenuated 3'-5' exonuclease activity using, for example, the Standard Assay described in Example 3, above.

TABLE 8

| Candidate Residues in *E. coli* Pol I | |
|---|---|
| D355 | T356 |
| E357 | T358 |
| S360 | L361 |
| Q419 | N420 |
| K422 | Y423 |
| M443 | R455 |
| H456 | D457 |
| M458 | D459 |
| F473 | E474 |
| Q483 | F486 |
| Y497 | D501 |
| E541 | S658 |
| Y659 | H660 |

EXAMPLE 8

Identification of Mutants of Family B DNA Polymerase with Attenuated 3'-5' Exonuclease Activity As disclosed herein, one of skill in the art guided by the instant disclosure can readily make a mutant of a family A DNA polymerase that has an attenuated 3'-5' exonuclease activity by, for example, making mutations in its 3'-5' exonuclease domain that correspond to the mutations of the 3'-5' exonuclease domain of Tma DNA polymerase described herein. Such a sequence-based approach to designing mutants of family B DNA polymerases with attenuated proofreading activity is of only limited utility because the only region of significant sequence similarity between the Tma DNA polymerase and family B DNA polymerase 3'-5' exonuclease domains is the "DXE" metal binding motif. However, X-ray crystallographic studies have shown that the 3'-5' exonuclease domains of family A and family B polymerases have similar three-dimensional stuctures. See Zhao et al., 1999, Structure Fold Des. 7:1189–99, Karam et al, 2000, Prog Nucleic Acid Res Mol Biol. 64:65–96, Hopfner et al., 1999, Proc Natl Acad Sci USA. 96:3600–5, Wang et al., 1997, Cell 89:1087–99. A structure-based method therefore was developed to identify residues that can be mutated to produce family B DNA polymerases with attenuated proofreading activity.

FIG. 11 presents an alignment of the *E. coli* Pol II DNA polymerase, a family B polymerase, with the sequences of a number of other family B DNA polymerases. Rather than simply identify those residues that are conserved between all or almost all of these proteins on the assumption that their conservation indicates that they are important for proofreading function, the three dimensional-structure of the 3'-5' exonuclease domain of the family B DNA polymerase isolated from the bacteriophage RB69 (Shamoo et al., 1999, Cell 99:155–66; structure available from the Protein Data Bank (Berman et al., 2000, Nucleic Acids Res. 28:235–42; www.pdb.org/) under PDB ID No. 1CLQ) was examined and compared to the proofreading domain of Tma. All of the residues in each of these proteins predicted to contact the 3' terminal nucleotides of a single-stranded DNA sequence bound to the proofreading domain were identified. This information and the sequence alignment in FIG. 11 were used to identify the analogous residues in other family B DNA polymerases, as shown in Table 9, below. These data indicate that mutations at these particular positions will result in DNA polymerase molecules with attenuated 3'-5' exonuclease activity.

TABLE 9

| Residue in RB69 | Residue in Tgo | Residue in PocI | Residue in KODI | Proposed function |
|---|---|---|---|---|
| F123 | Y146 | Y191 | Y146 | Ring stacking with base of $P_{(n-1)}$ |
| F221 | F214 | F253 | F214 | Binding to sugar of $P_{(n-1)}$ |

TABLE 9-continued

| Residue in RB69 | Residue in Tgo | Residue in PocI | Residue in KODI | Proposed function |
|---|---|---|---|---|
| S287 | T272 | M309 | T272 | H-bonding to phosphodiester between $P_{(n-1)}$ and $P_{(n-2)}$ |

The foregoing examples, both prophetic and actual, are offered by way of illustration only and are not intended to limit the scope of the claimed invention in any respect.

All references cited herein are incorporated by reference in their entireties.

We claim:

1. An isolated thermostable or thermoactive DNA polymerase comprising a 3'-5' exonuclease domain and exhibiting an attenuated 3'-5' exonuclease activity of about 6.5 or less, but greater than 0, U/pmol, wherein one unit (U) of 3'-5' exonuclease activity catalyzes the conversion of 50 pmol of a labeled single-stranded oligonucleotide of SEQ ID NO:80 to shorter length oligonucleotides in 15 minutes at 63° C., the enzymatic activity being measured in a reaction mixture containing 4 pmol (100 nM) of the oligonucleotide of SEQ ID NO: 80 in 50 mM Tricine, pH 8.3, 25 mM KOAc, 5% w/v DMSO, 0.5 mM Mn(OAc)$_2$ and the polymerase, and incubated at 63° C. for 15 minutes, wherein degradation of the oligonucleotide of SEQ ID NO: 80 is measured, wherein said 3'-5' exonuclease domain comprises a sequence motif selected from the following sequence motifs:

(a) A sequence motif having the formula $DX_1EX_2X_3SX_4$, wherein
   D is an aspartate residue,
   $X_1$ is any amino acid residue
   E is a glutamate residue,
   $X_2$ is a threonine,
   $X_3$ is any amino acid residue,
   S is a serine residue, and
   $X_4$ is a leucine or an alanine, or
(b) A sequence motif having the formula $X_5X_6X_7X_8X_9X_{10}X_{11}X_{12}X_{13}X_{14}$ (SEQ ID NO:1), wherein
   $X_5$ is a glutamine or an alanine,
   $X_6$ is an asparagine or an alanine,
   $X_7$ is a cysteine or a leucine residue,
   $X_8$ is a lysine,
   $X_9$ is a phenylalanine or a tyrosine residue,
   $X_{10}$ is an aspartate or a glutamate,
   $X_{11}$ is any amino acid residue,
   $X_{12}$ is any amino acid residue,
   $X_{13}$ is an isoleucine or valine residue, and
   $X_{14}$ is a leucine or phenylalanine residue.

2. An isolated thermostable or thermoactive DNA polymerase comprising a 3'-5' exonuclease domain and having a 5'-3' polymerase activity and an attenuated 3'-5' exonuclease activity wherein the ratio of said 5'-3' polymerase activity in U/pmol to said 3'-5' exonuclease activity in U/pmol is between about 100 and 1, wherein one unit (U) of 3'-5' exonuclease activity catalyzes the conversion of 50 pmol of a labeled single-stranded oligonucleotide of SEQ ID NO:80 to shorter length oligonucleotides in 15 minutes at 63° C. wherein the 3'-5' exonuclease activity is measured in a reaction mixture containing 4 pmol (100 nM) of the oligonucleotide of SEQ ID NO: 80 in 50 mM Tricine, pH 8.3, 25 mM KOAc, 5% w/v DMSO, 0.5 mM Mn(OAc)$_2$ and the polymerase, and incubated at 63° C. for 15 minutes, wherein degradation of the oligonucleotide of SEQ ID NO: 80 is measured, and one unit of 5'-3' polymerase activity is the amount of enzyme activity required to incorporate 10 nmoles of dNMP into TCA-precipitable DNA product in 30 minutes at 74° C. wherein the 5'-3' polymerase activity is measured in a reaction mixture containing 25 mM TAPS, pH 9.4, 50 mM KCl, 2 mM MgCl$_2$, 1 mM β-mercaptoethanol, 200 µM d(GTA)TP, 100 µM α-$^{33}$P-dCTP, 30 µg activated salmon sperm DNA and the polymerase, and incubated at 74° C. for 10 minutes wherein the amount of TCA precipitable DNA is measured, set forth in Example 3 for 5'-3' polymerase activity, and said 3'-5' exonuclease domain comprises a sequence motif selected from the following sequence motifs:

(a) A sequence motif having the formula $DX_1EX_2X_3SX_4$, wherein
   D is an aspartate residue,
   $X_1$ is any amino acid residue,
   E is a glutamate residue,
   $X_2$ is a threonine,
   $X_3$ is any amino acid residue,
   S is a serine residue, and
   $X_4$ is a leucine or an alanine, or
(b) A sequence motif having the formula $X_5X_6X_7X_8X_9X_{10}X_{11}X_{12}X_{13}X_{14}$ (SEQ ID NO:1), wherein
   $X_5$ is a glutamine or an alanine,
   $X_6$ is an asparagine or an alanine,
   $X_7$ is a cysteine or a leucine residue,
   $X_8$ is a lysine,
   $X_9$ is a phenylalanine or a tyrosine residue,
   $X_{10}$ is an aspartate or a glutamate,
   $X_{11}$ is any amino acid residue,
   $X_{12}$ is any amino acid residue,
   $X_{13}$ is an isoleucine or valine residue, and
   $X_{14}$ is a leucine or phenylalanine residue.

3. An isolated modified thermostable or thermoactive DNA polymerase wherein said modified polymerase comprises a 3'-5' exonuclease domain, has about 0.1 to 65% of a 3'-5' exonuclease activity of the DNA polymerase before modification, wherein one unit (U) of 3'-5' exonuclease activity catalyzes the conversion of 50 pmol of a labeled single-stranded oligonucleotide of SEQ ID NO:80 to shorter length oligonucleotides in 15 minutes at 63° C., the enzymatic activity being measured in a reaction mixture containing 4 pmol (100 nM) of the oligonucleotide of SEQ ID NO: 80 in 50 mM Tricine, pH 8.3, 25 mM KOAc, 5% w/v DMSO, 0.5 mM Mn(OAc)$_2$ and polymerase, and incubated at 63° C. for 15 minutes, wherein degradation of the oligonucleotide of SEQ ID NO. 80 is measured, and said 3'-5' exonuclease domain comprises a sequence motif selected from the following sequence motifs:

(a) A sequence motif having the formula $DX_1EX_2X_3SX_4$, wherein

D is an aspartate residue,
$X_1$ is any amino acid residue
E is a glutamate residue,
$X_2$ is a threonine,
$X_3$ is any amino acid residue,
S is a serine residue, and
$X_4$ is a leucine or an alanine, or (b) A sequence motif having the formula $X_5X_6X_7X_8X_9X_{10}X_{11}X_{12}X_{13}X_{14}$ (SEQ ID NO:1), wherein $X_5$ is a glutamine or an alanine,
$X_6$ is an asparagine or an alanine,
$X_7$ is a cysteine or a leucine residue,
$X_8$ is a lysine,
$X_9$ is a phenylalanine or a tyrosine residue,
$X_{10}$ is an aspartate or a glutamate,
$X_{11}$ is any amino acid residue,
$X_{12}$ is any amino acid residue,
$X_{13}$ is an isoleucine or valine residue, and
$X_{14}$ is a leucine or phenylalanine residue.

* * * * *

SEQUENCE LISTING

```
<160> NUMBER OF SEQ ID NOS: 203

<210> SEQ ID NO 1
<211> LENGTH: 10
<212> TYPE: PRT
<213> ORGANISM: Artificial sequence
<220> FEATURE:
<223> OTHER INFORMATION: 3'-5' Exonuclease domain of EXO II motif
<220> FEATURE:
<221> NAME/KEY: MISC_FEATURE
<222> LOCATION: (1)..(2)
<223> OTHER INFORMATION: Xaa is any amino acid
<220> FEATURE:
<221> NAME/KEY: MISC_FEATURE
<222> LOCATION: (3)..(3)
<223> OTHER INFORMATION: Xaa is Cys or Leu
<220> FEATURE:
<221> NAME/KEY: MISC_FEATURE
<222> LOCATION: (4)..(4)
<223> OTHER INFORMATION: Xaa is any amino acid
<220> FEATURE:
<221> NAME/KEY: MISC_FEATURE
<222> LOCATION: (5)..(5)
<223> OTHER INFORMATION: Xaa is Phe or Tyr
<220> FEATURE:
<221> NAME/KEY: MISC_FEATURE
<222> LOCATION: (6)..(8)
<223> OTHER INFORMATION: Xaa is any amino acid
<220> FEATURE:
<221> NAME/KEY: MISC_FEATURE
<222> LOCATION: (9)..(9)
<223> OTHER INFORMATION: Xaa is Ile or Val
<220> FEATURE:
<221> NAME/KEY: MISC_FEATURE
<222> LOCATION: (10)..(10)
<223> OTHER INFORMATION: Xaa is Leu or Phe

<400> SEQUENCE: 1

Xaa Xaa Xaa Xaa Xaa Xaa Xaa Xaa Xaa Xaa
1               5                   10

<210> SEQ ID NO 2
<211> LENGTH: 11
<212> TYPE: PRT
<213> ORGANISM: Artificial sequence
<220> FEATURE:
<223> OTHER INFORMATION: 3'-5' Exonuclease EXOIIa motif
<220> FEATURE:
<221> NAME/KEY: MISC_FEATURE
<222> LOCATION: (2)..(2)
<223> OTHER INFORMATION: Xaa is Pro, Ala, Leu, or Thr
<220> FEATURE:
```

```
<221> NAME/KEY: MISC_FEATURE
<222> LOCATION: (3)..(3)
<223> OTHER INFORMATION: Xaa is Leu or Met
<220> FEATURE:
<221> NAME/KEY: MISC_FEATURE
<222> LOCATION: (4)..(4)
<223> OTHER INFORMATION: Xaa is Leu or Ile
<220> FEATURE:
<221> NAME/KEY: MISC_FEATURE
<222> LOCATION: (5)..(5)
<223> OTHER INFORMATION: Xaa is any amino acid
<220> FEATURE:
<221> NAME/KEY: MISC_FEATURE
<222> LOCATION: (6)..(6)
<223> OTHER INFORMATION: Xaa is Ala or Ser
<220> FEATURE:
<221> NAME/KEY: MISC_FEATURE
<222> LOCATION: (8)..(8)
<223> OTHER INFORMATION: Xaa is Leu, Ile, or Val
<220> FEATURE:
<221> NAME/KEY: MISC_FEATURE
<222> LOCATION: (9)..(9)
<223> OTHER INFORMATION: Xaa is Leu or Trp
<220> FEATURE:
<221> NAME/KEY: MISC_FEATURE
<222> LOCATION: (10)..(10)
<223> OTHER INFORMATION: Xaa is Asp, Asn, Glu, or Gln
<220> FEATURE:
<221> NAME/KEY: MISC_FEATURE
<222> LOCATION: (11)..(11)
<223> OTHER INFORMATION: Xaa is Pro, or Ser

<400> SEQUENCE: 2

Asp Xaa Xaa Xaa Xaa Xaa Tyr Xaa Xaa Xaa Xaa
1               5                   10

<210> SEQ ID NO 3
<211> LENGTH: 13
<212> TYPE: PRT
<213> ORGANISM: Artificial sequence
<220> FEATURE:
<223> OTHER INFORMATION: 3'-5' Exonuclease EXO III motif
<220> FEATURE:
<221> NAME/KEY: MISC_FEATURE
<222> LOCATION: (1)..(1)
<223> OTHER INFORMATION: Xaa is Pro, or Ala
<220> FEATURE:
<221> NAME/KEY: MISC_FEATURE
<222> LOCATION: (2)..(2)
<223> OTHER INFORMATION: Xaa is any amino acid
<220> FEATURE:
<221> NAME/KEY: MISC_FEATURE
<222> LOCATION: (3)..(3)
<223> OTHER INFORMATION: Xaa is Glu, Asp, or Pro
<220> FEATURE:
<221> NAME/KEY: MISC_FEATURE
<222> LOCATION: (4)..(4)
<223> OTHER INFORMATION: Xaa is Lys, Arg, or Glu
<220> FEATURE:
<221> NAME/KEY: MISC_FEATURE
<222> LOCATION: (5)..(6)
<223> OTHER INFORMATION: Xaa is any amino acid
<220> FEATURE:
<221> NAME/KEY: MISC_FEATURE
<222> LOCATION: (7)..(7)
<223> OTHER INFORMATION: Xaa is Glu, Arg, or Asp
<220> FEATURE:
<221> NAME/KEY: MISC_FEATURE
<222> LOCATION: (8)..(8)
<223> OTHER INFORMATION: Xaa is any amino acid
<220> FEATURE:
<221> NAME/KEY: MISC_FEATURE
<222> LOCATION: (9)..(9)
<223> OTHER INFORMATION: Xaa is Ser, Ala, or Cys
<220> FEATURE:
<221> NAME/KEY: MISC_FEATURE
<222> LOCATION: (10)..(10)
```

```
<223> OTHER INFORMATION: Xaa is any amino acid
<220> FEATURE:
<221> NAME/KEY: MISC_FEATURE
<222> LOCATION: (11)..(11)
<223> OTHER INFORMATION: Xaa is Glu or Thr
<220> FEATURE:
<221> NAME/KEY: MISC_FEATURE
<222> LOCATION: (12)..(12)
<223> OTHER INFORMATION: Xaa is any amino acid

<400> SEQUENCE: 3

Xaa Xaa Xaa Xaa Xaa Xaa Xaa Xaa Xaa Xaa Xaa Xaa Ala
1               5                   10

<210> SEQ ID NO 4
<211> LENGTH: 7
<212> TYPE: PRT
<213> ORGANISM: Artificial sequence
<220> FEATURE:
<223> OTHER INFORMATION: 3'-5' Exonuclease domain of thermostable DNA
      Polymerase
<220> FEATURE:
<221> NAME/KEY: MISC_FEATURE
<222> LOCATION: (2)..(2)
<223> OTHER INFORMATION: Xaa is any amino acid or no amino acid
<220> FEATURE:
<221> NAME/KEY: MISC_FEATURE
<222> LOCATION: (5)..(5)
<223> OTHER INFORMATION: Xaa is any amino acid
<220> FEATURE:
<221> NAME/KEY: MISC_FEATURE
<222> LOCATION: (7)..(7)
<223> OTHER INFORMATION: Xaa is any amino acid

<400> SEQUENCE: 4

Asp Xaa Glu Thr Xaa Ser Xaa
1               5

<210> SEQ ID NO 5
<211> LENGTH: 7
<212> TYPE: PRT
<213> ORGANISM: Artificial sequence
<220> FEATURE:
<223> OTHER INFORMATION: 3'-5' Exonuclease domain of thermostable DNA
      Polymerase
<220> FEATURE:
<221> NAME/KEY: MISC_FEATURE
<222> LOCATION: (2)..(2)
<223> OTHER INFORMATION: Xaa is any amino acid or no amino acid

<400> SEQUENCE: 5

Asp Xaa Glu Thr Thr Ser Leu
1               5

<210> SEQ ID NO 6
<211> LENGTH: 7
<212> TYPE: PRT
<213> ORGANISM: Artificial sequence
<220> FEATURE:
<223> OTHER INFORMATION: 3'-5' Exonuclease domain of thermostable DNA
      Polymerase
<220> FEATURE:
<221> NAME/KEY: MISC_FEATURE
<222> LOCATION: (2)..(2)
<223> OTHER INFORMATION: Xaa is any amino acid or no amino acid
<220> FEATURE:
<221> NAME/KEY: MISC_FEATURE
<222> LOCATION: (5)..(5)
<223> OTHER INFORMATION: Xaa is any amino acid

<400> SEQUENCE: 6

Asp Xaa Glu Thr Xaa Ser Leu
```

```
<210> SEQ ID NO 7
<211> LENGTH: 7
<212> TYPE: PRT
<213> ORGANISM: Artificial sequence
<220> FEATURE:
<223> OTHER INFORMATION: 3'-5' Exonuclease domain of thermostable DNA
      Polymerase
<220> FEATURE:
<221> NAME/KEY: MISC_FEATURE
<222> LOCATION: (2)..(2)
<223> OTHER INFORMATION: Xaa is any amino acid or no amino acid
<220> FEATURE:
<221> NAME/KEY: MISC_FEATURE
<222> LOCATION: (4)..(5)
<223> OTHER INFORMATION: Xaa is any amino acid

<400> SEQUENCE: 7

Asp Xaa Glu Xaa Xaa Ser Leu
1               5

<210> SEQ ID NO 8
<211> LENGTH: 7
<212> TYPE: PRT
<213> ORGANISM: Artificial sequence
<220> FEATURE:
<223> OTHER INFORMATION: 3'-5' Exonuclease domain of thermostable DNA
      Polymerase
<220> FEATURE:
<221> NAME/KEY: MISC_FEATURE
<222> LOCATION: (2)..(2)
<223> OTHER INFORMATION: Xaa is any amino acid or no amino acid
<220> FEATURE:
<221> NAME/KEY: MISC_FEATURE
<222> LOCATION: (4)..(4)
<223> OTHER INFORMATION: Xaa is any amino acid

<400> SEQUENCE: 8

Asp Xaa Glu Xaa Thr Ser Leu
1               5

<210> SEQ ID NO 9
<211> LENGTH: 7
<212> TYPE: PRT
<213> ORGANISM: Artificial sequence
<220> FEATURE:
<223> OTHER INFORMATION: 3'-5' Exonuclease domain of thermostable DNA
      Polymerase

<400> SEQUENCE: 9

Asp Leu Glu Thr Ser Ser Leu
1               5

<210> SEQ ID NO 10
<211> LENGTH: 10
<212> TYPE: PRT
<213> ORGANISM: Artificial sequence
<220> FEATURE:
<223> OTHER INFORMATION: 3'-5' Exonuclease domain of thermostable DNA
      Polymerase
<220> FEATURE:
<221> NAME/KEY: MISC_FEATURE
<222> LOCATION: (1)..(2)
<223> OTHER INFORMATION: Xaa is any amino acid
<220> FEATURE:
<221> NAME/KEY: MISC_FEATURE
<222> LOCATION: (3)..(3)
<223> OTHER INFORMATION: Xaa is Cys or Leu
<220> FEATURE:
<221> NAME/KEY: MISC_FEATURE
<222> LOCATION: (5)..(5)
```

-continued

```
<223> OTHER INFORMATION: Xaa is Phe or Tyr
<220> FEATURE:
<221> NAME/KEY: MISC_FEATURE
<222> LOCATION: (6)..(8)
<223> OTHER INFORMATION: Xaa is any amino acid
<220> FEATURE:
<221> NAME/KEY: MISC_FEATURE
<222> LOCATION: (9)..(9)
<223> OTHER INFORMATION: Xaa is Ile or Val
<220> FEATURE:
<221> NAME/KEY: MISC_FEATURE
<222> LOCATION: (10)..(10)
<223> OTHER INFORMATION: Xaa is Leu or Phe

<400> SEQUENCE: 10

Xaa Xaa Xaa Lys Xaa Xaa Xaa Xaa Xaa Xaa
1               5                   10

<210> SEQ ID NO 11
<211> LENGTH: 10
<212> TYPE: PRT
<213> ORGANISM: Artificial sequence
<220> FEATURE:
<223> OTHER INFORMATION: 3'-5' Exonuclease domain of thermostable DNA
      Polymerase
<220> FEATURE:
<221> NAME/KEY: MISC_FEATURE
<222> LOCATION: (1)..(1)
<223> OTHER INFORMATION: Xaa is any uncharged polar residue
<220> FEATURE:
<221> NAME/KEY: MISC_FEATURE
<222> LOCATION: (2)..(2)
<223> OTHER INFORMATION: Xaa is any amino acid
<220> FEATURE:
<221> NAME/KEY: MISC_FEATURE
<222> LOCATION: (3)..(3)
<223> OTHER INFORMATION: Xaa is Cys or Leu
<220> FEATURE:
<221> NAME/KEY: MISC_FEATURE
<222> LOCATION: (5)..(5)
<223> OTHER INFORMATION: Xaa is Phe or Tyr
<220> FEATURE:
<221> NAME/KEY: MISC_FEATURE
<222> LOCATION: (6)..(8)
<223> OTHER INFORMATION: Xaa is any amino acid
<220> FEATURE:
<221> NAME/KEY: MISC_FEATURE
<222> LOCATION: (9)..(9)
<223> OTHER INFORMATION: Xaa is Ile or Val
<220> FEATURE:
<221> NAME/KEY: MISC_FEATURE
<222> LOCATION: (10)..(10)
<223> OTHER INFORMATION: Xaa is Leu or Phe

<400> SEQUENCE: 11

Xaa Xaa Xaa Lys Xaa Xaa Xaa Xaa Xaa Xaa
1               5                   10

<210> SEQ ID NO 12
<211> LENGTH: 10
<212> TYPE: PRT
<213> ORGANISM: Artificial sequence
<220> FEATURE:
<223> OTHER INFORMATION: 3'-5' Exonuclease domain of thermostable DNA
      Polymerase
<220> FEATURE:
<221> NAME/KEY: MISC_FEATURE
<222> LOCATION: (1)..(2)
<223> OTHER INFORMATION: Xaa is any uncharged polar residue
<220> FEATURE:
<221> NAME/KEY: MISC_FEATURE
<222> LOCATION: (3)..(3)
<223> OTHER INFORMATION: Xaa is Cys or Leu
<220> FEATURE:
<221> NAME/KEY: MISC_FEATURE
```

```
<222> LOCATION: (5)..(5)
<223> OTHER INFORMATION: Xaa is Phe or Tyr
<220> FEATURE:
<221> NAME/KEY: MISC_FEATURE
<222> LOCATION: (6)..(8)
<223> OTHER INFORMATION: Xaa is any amino acid
<220> FEATURE:
<221> NAME/KEY: MISC_FEATURE
<222> LOCATION: (9)..(9)
<223> OTHER INFORMATION: Xaa is Ile or Val
<220> FEATURE:
<221> NAME/KEY: MISC_FEATURE
<222> LOCATION: (10)..(10)
<223> OTHER INFORMATION: Xaa is Leu or Phe

<400> SEQUENCE: 12

Xaa Xaa Xaa Lys Xaa Xaa Xaa Xaa Xaa Xaa
1               5                   10

<210> SEQ ID NO 13
<211> LENGTH: 10
<212> TYPE: PRT
<213> ORGANISM: Artificial sequence
<220> FEATURE:
<223> OTHER INFORMATION: 3'-5' Exonuclease domain of thermostable DNA
      Polymerase
<220> FEATURE:
<221> NAME/KEY: MISC_FEATURE
<222> LOCATION: (1)..(2)
<223> OTHER INFORMATION: Xaa is any uncharged polar residue
<220> FEATURE:
<221> NAME/KEY: MISC_FEATURE
<222> LOCATION: (3)..(3)
<223> OTHER INFORMATION: Xaa is Cys or Leu
<220> FEATURE:
<221> NAME/KEY: MISC_FEATURE
<222> LOCATION: (5)..(5)
<223> OTHER INFORMATION: Xaa is Phe or Tyr
<220> FEATURE:
<221> NAME/KEY: MISC_FEATURE
<222> LOCATION: (6)..(6)
<223> OTHER INFORMATION: Xaa is any acidic residue
<220> FEATURE:
<221> NAME/KEY: MISC_FEATURE
<222> LOCATION: (7)..(8)
<223> OTHER INFORMATION: Xaa is any amino acid
<220> FEATURE:
<221> NAME/KEY: MISC_FEATURE
<222> LOCATION: (9)..(9)
<223> OTHER INFORMATION: Xaa is Ile or Val
<220> FEATURE:
<221> NAME/KEY: MISC_FEATURE
<222> LOCATION: (10)..(10)
<223> OTHER INFORMATION: Xaa is Leu or Phe

<400> SEQUENCE: 13

Xaa Xaa Xaa Lys Xaa Xaa Xaa Xaa Xaa Xaa
1               5                   10

<210> SEQ ID NO 14
<211> LENGTH: 10
<212> TYPE: PRT
<213> ORGANISM: Artificial sequence
<220> FEATURE:
<223> OTHER INFORMATION: 3'-5' Exonuclease domain of thermostable DNA
      Polymerase
<220> FEATURE:
<221> NAME/KEY: MISC_FEATURE
<222> LOCATION: (1)..(2)
<223> OTHER INFORMATION: Xaa is any uncharged polar residue
<220> FEATURE:
<221> NAME/KEY: MISC_FEATURE
<222> LOCATION: (3)..(3)
<223> OTHER INFORMATION: Xaa is Cys or Leu
<220> FEATURE:
```

```
<221> NAME/KEY: MISC_FEATURE
<222> LOCATION: (5)..(5)
<223> OTHER INFORMATION: Xaa is Phe or Tyr
<220> FEATURE:
<221> NAME/KEY: MISC_FEATURE
<222> LOCATION: (6)..(6)
<223> OTHER INFORMATION: Xaa is any acidic residue
<220> FEATURE:
<221> NAME/KEY: MISC_FEATURE
<222> LOCATION: (7)..(8)
<223> OTHER INFORMATION: Xaa is any amino acid
<220> FEATURE:
<221> NAME/KEY: MISC_FEATURE
<222> LOCATION: (9)..(9)
<223> OTHER INFORMATION: Xaa is Ile or Val
<220> FEATURE:
<221> NAME/KEY: MISC_FEATURE
<222> LOCATION: (10)..(10)
<223> OTHER INFORMATION: Xaa is Leu or Phe

<400> SEQUENCE: 14

Xaa Xaa Xaa Lys Xaa Xaa Xaa Xaa Xaa Xaa
1               5                   10

<210> SEQ ID NO 15
<211> LENGTH: 10
<212> TYPE: PRT
<213> ORGANISM: Artificial sequence
<220> FEATURE:
<223> OTHER INFORMATION: 3'-5' Exonuclease domain of thermostable DNA
      Polymerase
<220> FEATURE:
<221> NAME/KEY: MISC_FEATURE
<222> LOCATION: (3)..(3)
<223> OTHER INFORMATION: Xaa is Cys or Leu
<220> FEATURE:
<221> NAME/KEY: MISC_FEATURE
<222> LOCATION: (5)..(5)
<223> OTHER INFORMATION: Xaa is Phe or Tyr
<220> FEATURE:
<221> NAME/KEY: MISC_FEATURE
<222> LOCATION: (7)..(8)
<223> OTHER INFORMATION: Xaa is any amino acid
<220> FEATURE:
<221> NAME/KEY: MISC_FEATURE
<222> LOCATION: (9)..(9)
<223> OTHER INFORMATION: Xaa is Ile or Val
<220> FEATURE:
<221> NAME/KEY: MISC_FEATURE
<222> LOCATION: (10)..(10)
<223> OTHER INFORMATION: Xaa is Leu or Phe

<400> SEQUENCE: 15

Gln Asn Xaa Lys Xaa Asp Xaa Xaa Xaa Xaa
1               5                   10

<210> SEQ ID NO 16
<211> LENGTH: 10
<212> TYPE: PRT
<213> ORGANISM: Artificial sequence
<220> FEATURE:
<223> OTHER INFORMATION: 3'-5' Exonuclease domain of thermostable DNA
      Polymerase

<400> SEQUENCE: 16

Gln Asn Leu Lys Phe Asp Tyr Lys Val Leu
1               5                   10

<210> SEQ ID NO 17
<211> LENGTH: 10
<212> TYPE: PRT
<213> ORGANISM: Artificial sequence
<220> FEATURE:
```

```
<223> OTHER INFORMATION: 3'-5' Exonuclease domain of thermostable DNA
      Polymerase
<220> FEATURE:
<221> NAME/KEY: MISC_FEATURE
<222> LOCATION: (1)..(1)
<223> OTHER INFORMATION: Xaa is any nonpolar residue
<220> FEATURE:
<221> NAME/KEY: MISC_FEATURE
<222> LOCATION: (2)..(2)
<223> OTHER INFORMATION: Xaa is any uncharged polar residue
<220> FEATURE:
<221> NAME/KEY: MISC_FEATURE
<222> LOCATION: (3)..(3)
<223> OTHER INFORMATION: Xaa is Cys or Leu
<220> FEATURE:
<221> NAME/KEY: MISC_FEATURE
<222> LOCATION: (5)..(5)
<223> OTHER INFORMATION: Xaa is Phe or Tyr
<220> FEATURE:
<221> NAME/KEY: MISC_FEATURE
<222> LOCATION: (6)..(6)
<223> OTHER INFORMATION: Xaa is any acidic residue
<220> FEATURE:
<221> NAME/KEY: MISC_FEATURE
<222> LOCATION: (7)..(8)
<223> OTHER INFORMATION: Xaa is any amino acid
<220> FEATURE:
<221> NAME/KEY: MISC_FEATURE
<222> LOCATION: (9)..(9)
<223> OTHER INFORMATION: Xaa is Ile or Val
<220> FEATURE:
<221> NAME/KEY: MISC_FEATURE
<222> LOCATION: (10)..(10)
<223> OTHER INFORMATION: Xaa is Leu or Phe

<400> SEQUENCE: 17

Xaa Xaa Xaa Lys Xaa Xaa Xaa Xaa Xaa Xaa
1               5                   10

<210> SEQ ID NO 18
<211> LENGTH: 10
<212> TYPE: PRT
<213> ORGANISM: Artificial sequence
<220> FEATURE:
<223> OTHER INFORMATION: 3'-5' Exonuclease domain of thermostable DNA
      Polymerase
<220> FEATURE:
<221> NAME/KEY: MISC_FEATURE
<222> LOCATION: (2)..(2)
<223> OTHER INFORMATION: Xaa is any uncharged polar residue
<220> FEATURE:
<221> NAME/KEY: MISC_FEATURE
<222> LOCATION: (3)..(3)
<223> OTHER INFORMATION: Xaa is Cys or Leu
<220> FEATURE:
<221> NAME/KEY: MISC_FEATURE
<222> LOCATION: (5)..(5)
<223> OTHER INFORMATION: Xaa is Phe or Tyr
<220> FEATURE:
<221> NAME/KEY: MISC_FEATURE
<222> LOCATION: (6)..(6)
<223> OTHER INFORMATION: Xaa is any acidic residue
<220> FEATURE:
<221> NAME/KEY: MISC_FEATURE
<222> LOCATION: (7)..(8)
<223> OTHER INFORMATION: Xaa is any amino acid
<220> FEATURE:
<221> NAME/KEY: MISC_FEATURE
<222> LOCATION: (9)..(9)
<223> OTHER INFORMATION: Xaa is Ile or Val
<220> FEATURE:
<221> NAME/KEY: MISC_FEATURE
<222> LOCATION: (10)..(10)
<223> OTHER INFORMATION: Xaa is Leu or Phe

<400> SEQUENCE: 18
```

```
Ala Xaa Xaa Lys Xaa Xaa Xaa Xaa Xaa Xaa
1               5                   10
```

<210> SEQ ID NO 19
<211> LENGTH: 10
<212> TYPE: PRT
<213> ORGANISM: Artificial sequence
<220> FEATURE:
<223> OTHER INFORMATION: 3'-5' Exonuclease domain of thermostable DNA
      Polymerase
<220> FEATURE:
<221> NAME/KEY: MISC_FEATURE
<222> LOCATION: (3)..(3)
<223> OTHER INFORMATION: Xaa is Cys or Leu
<220> FEATURE:
<221> NAME/KEY: MISC_FEATURE
<222> LOCATION: (5)..(5)
<223> OTHER INFORMATION: Xaa is Phe or Tyr
<220> FEATURE:
<221> NAME/KEY: MISC_FEATURE
<222> LOCATION: (7)..(8)
<223> OTHER INFORMATION: Xaa is any amino acid
<220> FEATURE:
<221> NAME/KEY: MISC_FEATURE
<222> LOCATION: (9)..(9)
<223> OTHER INFORMATION: Xaa is Ile or Val
<220> FEATURE:
<221> NAME/KEY: MISC_FEATURE
<222> LOCATION: (10)..(10)
<223> OTHER INFORMATION: Xaa is Leu or Phe

<400> SEQUENCE: 19

```
Ala Asn Xaa Lys Xaa Asp Xaa Xaa Xaa Xaa
1               5                   10
```

<210> SEQ ID NO 20
<211> LENGTH: 10
<212> TYPE: PRT
<213> ORGANISM: Artificial sequence
<220> FEATURE:
<223> OTHER INFORMATION: 3'-5' Exonuclease domain of thermostable DNA
      Polymerase

<400> SEQUENCE: 20

```
Ala Asn Leu Lys Phe Asp Tyr Lys Val Leu
1               5                   10
```

<210> SEQ ID NO 21
<211> LENGTH: 10
<212> TYPE: PRT
<213> ORGANISM: Artificial sequence
<220> FEATURE:
<223> OTHER INFORMATION: 3'-5' Exonuclease domain of thermostable DNA
      Polymerase
<220> FEATURE:
<221> NAME/KEY: MISC_FEATURE
<222> LOCATION: (1)..(1)
<223> OTHER INFORMATION: Xaa is any uncharged polar amino acid
<220> FEATURE:
<221> NAME/KEY: MISC_FEATURE
<222> LOCATION: (2)..(2)
<223> OTHER INFORMATION: Xaa is any nonpolar residue
<220> FEATURE:
<221> NAME/KEY: MISC_FEATURE
<222> LOCATION: (3)..(3)
<223> OTHER INFORMATION: Xaa is Cys or Leu
<220> FEATURE:
<221> NAME/KEY: MISC_FEATURE
<222> LOCATION: (5)..(5)
<223> OTHER INFORMATION: Xaa is Phe or Tyr
<220> FEATURE:
<221> NAME/KEY: MISC_FEATURE
<222> LOCATION: (6)..(6)
<223> OTHER INFORMATION: Xaa is any acidic residue

```
<220> FEATURE:
<221> NAME/KEY: MISC_FEATURE
<222> LOCATION: (7)..(8)
<223> OTHER INFORMATION: Xaa is any amino acid
<220> FEATURE:
<221> NAME/KEY: MISC_FEATURE
<222> LOCATION: (9)..(9)
<223> OTHER INFORMATION: Xaa is Ile or Val
<220> FEATURE:
<221> NAME/KEY: MISC_FEATURE
<222> LOCATION: (10)..(10)
<223> OTHER INFORMATION: Xaa is Leu or Phe

<400> SEQUENCE: 21

Xaa Xaa Xaa Lys Xaa Xaa Xaa Xaa Xaa Xaa
1               5                   10

<210> SEQ ID NO 22
<211> LENGTH: 10
<212> TYPE: PRT
<213> ORGANISM: Artificial sequence
<220> FEATURE:
<223> OTHER INFORMATION: 3'-5' Exonuclease domain of thermostable DNA
      Polymerase
<220> FEATURE:
<221> NAME/KEY: MISC_FEATURE
<222> LOCATION: (3)..(3)
<223> OTHER INFORMATION: Xaa is Cys or Leu
<220> FEATURE:
<221> NAME/KEY: MISC_FEATURE
<222> LOCATION: (5)..(5)
<223> OTHER INFORMATION: Xaa is Phe or Tyr
<220> FEATURE:
<221> NAME/KEY: MISC_FEATURE
<222> LOCATION: (7)..(8)
<223> OTHER INFORMATION: Xaa is any amino acid
<220> FEATURE:
<221> NAME/KEY: MISC_FEATURE
<222> LOCATION: (9)..(9)
<223> OTHER INFORMATION: Xaa is Ile or Val
<220> FEATURE:
<221> NAME/KEY: MISC_FEATURE
<222> LOCATION: (10)..(10)
<223> OTHER INFORMATION: Xaa is Leu or Phe

<400> SEQUENCE: 22

Gln Ala Xaa Lys Xaa Asp Xaa Xaa Xaa Xaa
1               5                   10

<210> SEQ ID NO 23
<211> LENGTH: 10
<212> TYPE: PRT
<213> ORGANISM: Artificial sequence
<220> FEATURE:
<223> OTHER INFORMATION: 3'-5' Exonuclease domain of thermostable DNA
      Polymerase

<400> SEQUENCE: 23

Gln Ala Leu Lys Phe Asp Tyr Lys Val Leu
1               5                   10

<210> SEQ ID NO 24
<211> LENGTH: 10
<212> TYPE: PRT
<213> ORGANISM: Artificial sequence
<220> FEATURE:
<223> OTHER INFORMATION: 3'-5' Exonuclease domain of thermostable DNA
      Polymerase
<220> FEATURE:
<221> NAME/KEY: MISC_FEATURE
<222> LOCATION: (1)..(2)
<223> OTHER INFORMATION: Xaa is any uncharged polar residue
<220> FEATURE:
```

```
<221> NAME/KEY: MISC_FEATURE
<222> LOCATION: (3)..(3)
<223> OTHER INFORMATION: Xaa is Cys or Leu
<220> FEATURE:
<221> NAME/KEY: MISC_FEATURE
<222> LOCATION: (5)..(5)
<223> OTHER INFORMATION: Xaa is Phe or Tyr
<220> FEATURE:
<221> NAME/KEY: MISC_FEATURE
<222> LOCATION: (7)..(8)
<223> OTHER INFORMATION: Xaa is any amino acid
<220> FEATURE:
<221> NAME/KEY: MISC_FEATURE
<222> LOCATION: (9)..(9)
<223> OTHER INFORMATION: Xaa is Ile or Val
<220> FEATURE:
<221> NAME/KEY: MISC_FEATURE
<222> LOCATION: (10)..(10)
<223> OTHER INFORMATION: Xaa is Leu or Phe

<400> SEQUENCE: 24

Xaa Xaa Xaa Lys Xaa Glu Xaa Xaa Xaa Xaa
1               5                   10

<210> SEQ ID NO 25
<211> LENGTH: 10
<212> TYPE: PRT
<213> ORGANISM: Artificial sequence
<220> FEATURE:
<223> OTHER INFORMATION: 3'-5' Exonuclease domain of thermostable DNA
      Polymerase
<220> FEATURE:
<221> NAME/KEY: MISC_FEATURE
<222> LOCATION: (3)..(3)
<223> OTHER INFORMATION: Xaa is Cys or Leu
<220> FEATURE:
<221> NAME/KEY: MISC_FEATURE
<222> LOCATION: (5)..(5)
<223> OTHER INFORMATION: Xaa is Phe or Tyr
<220> FEATURE:
<221> NAME/KEY: MISC_FEATURE
<222> LOCATION: (7)..(8)
<223> OTHER INFORMATION: Xaa is any amino acid
<220> FEATURE:
<221> NAME/KEY: MISC_FEATURE
<222> LOCATION: (9)..(9)
<223> OTHER INFORMATION: Xaa is Ile or Val
<220> FEATURE:
<221> NAME/KEY: MISC_FEATURE
<222> LOCATION: (10)..(10)
<223> OTHER INFORMATION: Xaa is Leu or Phe

<400> SEQUENCE: 25

Gln Asn Xaa Lys Xaa Glu Xaa Xaa Xaa Xaa
1               5                   10

<210> SEQ ID NO 26
<211> LENGTH: 10
<212> TYPE: PRT
<213> ORGANISM: Artificial sequence
<220> FEATURE:
<223> OTHER INFORMATION: 3'-5' Exonuclease domain of thermostable DNA
      Polymerase

<400> SEQUENCE: 26

Gln Asn Leu Lys Phe Glu Tyr Lys Val Leu
1               5                   10

<210> SEQ ID NO 27
<211> LENGTH: 10
<212> TYPE: PRT
<213> ORGANISM: Artificial sequence
<220> FEATURE:
```

```
<223> OTHER INFORMATION: 3'-5' Exonuclease domain of thermostable DNA
      Polymerase
<220> FEATURE:
<221> NAME/KEY: MISC_FEATURE
<222> LOCATION: (1)..(2)
<223> OTHER INFORMATION: Xaa is any nonpolar residue
<220> FEATURE:
<221> NAME/KEY: MISC_FEATURE
<222> LOCATION: (3)..(3)
<223> OTHER INFORMATION: Xaa is Cys or Leu
<220> FEATURE:
<221> NAME/KEY: MISC_FEATURE
<222> LOCATION: (5)..(5)
<223> OTHER INFORMATION: Xaa is Phe or Tyr
<220> FEATURE:
<221> NAME/KEY: MISC_FEATURE
<222> LOCATION: (6)..(6)
<223> OTHER INFORMATION: Xaa is any acidic residue
<220> FEATURE:
<221> NAME/KEY: MISC_FEATURE
<222> LOCATION: (7)..(8)
<223> OTHER INFORMATION: Xaa is any amino acid
<220> FEATURE:
<221> NAME/KEY: MISC_FEATURE
<222> LOCATION: (9)..(9)
<223> OTHER INFORMATION: Xaa is Ile or Val
<220> FEATURE:
<221> NAME/KEY: MISC_FEATURE
<222> LOCATION: (10)..(10)
<223> OTHER INFORMATION: Xaa is Leu or Phe

<400> SEQUENCE: 27

Xaa Xaa Xaa Lys Xaa Xaa Xaa Xaa Xaa Xaa
1               5                   10

<210> SEQ ID NO 28
<211> LENGTH: 10
<212> TYPE: PRT
<213> ORGANISM: Artificial sequence
<220> FEATURE:
<223> OTHER INFORMATION: 3'-5' Exonuclease domain of thermostable DNA
      Polymerase
<220> FEATURE:
<221> NAME/KEY: MISC_FEATURE
<222> LOCATION: (3)..(3)
<223> OTHER INFORMATION: Xaa is Cys or Leu
<220> FEATURE:
<221> NAME/KEY: MISC_FEATURE
<222> LOCATION: (5)..(5)
<223> OTHER INFORMATION: Xaa is Phe or Tyr
<220> FEATURE:
<221> NAME/KEY: MISC_FEATURE
<222> LOCATION: (7)..(8)
<223> OTHER INFORMATION: Xaa is any amino acid
<220> FEATURE:
<221> NAME/KEY: MISC_FEATURE
<222> LOCATION: (9)..(9)
<223> OTHER INFORMATION: Xaa is Ile or Val
<220> FEATURE:
<221> NAME/KEY: MISC_FEATURE
<222> LOCATION: (10)..(10)
<223> OTHER INFORMATION: Xaa is Leu or Phe

<400> SEQUENCE: 28

Ala Ala Xaa Lys Xaa Asp Xaa Xaa Xaa Xaa
1               5                   10

<210> SEQ ID NO 29
<211> LENGTH: 10
<212> TYPE: PRT
<213> ORGANISM: Artificial sequence
<220> FEATURE:
<223> OTHER INFORMATION: 3'-5' Exonuclease domain of thermostable DNA
      Polymerase
```

```
<400> SEQUENCE: 29

Ala Ala Leu Lys Phe Asp Tyr Lys Val Leu
 1               5                  10

<210> SEQ ID NO 30
<211> LENGTH: 11
<212> TYPE: PRT
<213> ORGANISM: Artificial sequence
<220> FEATURE:
<223> OTHER INFORMATION: 3'-5' Exonuclease domain of thermostable DNA
      Polymerase

<400> SEQUENCE: 30

Asp Thr Met Ile Ala Ala Tyr Leu Leu Glu Pro
 1               5                  10

<210> SEQ ID NO 31
<211> LENGTH: 13
<212> TYPE: PRT
<213> ORGANISM: Artificial sequence
<220> FEATURE:
<223> OTHER INFORMATION: EXO III motif of DNA polymerase of the
      invention
<220> FEATURE:
<221> NAME/KEY: MISC_FEATURE
<222> LOCATION: (2)..(2)
<223> OTHER INFORMATION: Xaa is Val Leu or Ile
<220> FEATURE:
<221> NAME/KEY: MISC_FEATURE
<222> LOCATION: (3)..(3)
<223> OTHER INFORMATION: Xaa is Glu Asp or Pro
<220> FEATURE:
<221> NAME/KEY: MISC_FEATURE
<222> LOCATION: (4)..(4)
<223> OTHER INFORMATION: Xaa is Lys or Arg
<220> FEATURE:
<221> NAME/KEY: MISC_FEATURE
<222> LOCATION: (5)..(6)
<223> OTHER INFORMATION: Xaa is Ala or Val
<220> FEATURE:
<221> NAME/KEY: MISC_FEATURE
<222> LOCATION: (7)..(7)
<223> OTHER INFORMATION: Xaa is Glu or Asp
<220> FEATURE:
<221> NAME/KEY: MISC_FEATURE
<222> LOCATION: (8)..(8)
<223> OTHER INFORMATION: Xaa is any uncharged polar amino acid
<220> FEATURE:
<221> NAME/KEY: MISC_FEATURE
<222> LOCATION: (9)..(9)
<223> OTHER INFORMATION: Xaa is Ser or Cys
<220> FEATURE:
<221> NAME/KEY: MISC_FEATURE
<222> LOCATION: (10)..(10)
<223> OTHER INFORMATION: Xaa is Cys or Gly
<220> FEATURE:
<221> NAME/KEY: MISC_FEATURE
<222> LOCATION: (11)..(11)
<223> OTHER INFORMATION: Xaa is Glu or Thr
<220> FEATURE:
<221> NAME/KEY: MISC_FEATURE
<222> LOCATION: (12)..(12)
<223> OTHER INFORMATION: Xaa is Glu or Thr

<400> SEQUENCE: 31

Pro Xaa Xaa Xaa Xaa Xaa Xaa Xaa Xaa Xaa Xaa Asp Ala
 1               5                  10

<210> SEQ ID NO 32
<211> LENGTH: 13
<212> TYPE: PRT
<213> ORGANISM: Artificial sequence
<220> FEATURE:
```

```
<223> OTHER INFORMATION: 3'-5' Exonuclease domain of thermostable DNA
      Polymerase

<400> SEQUENCE: 32

Pro Val Glu Lys Ala Ala Asp Tyr Ser Cys Glu Asp Ala
1               5                   10

<210> SEQ ID NO 33
<211> LENGTH: 13
<212> TYPE: PRT
<213> ORGANISM: Artificial sequence
<220> FEATURE:
<223> OTHER INFORMATION: 3'-5' Exonuclease domain of thermostable DNA
      Polymerase
<220> FEATURE:
<221> NAME/KEY: MISC_FEATURE
<222> LOCATION: (2)..(2)
<223> OTHER INFORMATION: Xaa is Val, Leu, or Ile
<220> FEATURE:
<221> NAME/KEY: MISC_FEATURE
<222> LOCATION: (3)..(3)
<223> OTHER INFORMATION: Xaa is Glu, Asp, or Pro
<220> FEATURE:
<221> NAME/KEY: MISC_FEATURE
<222> LOCATION: (4)..(4)
<223> OTHER INFORMATION: Xaa is Lys, or Arg
<220> FEATURE:
<221> NAME/KEY: MISC_FEATURE
<222> LOCATION: (5)..(6)
<223> OTHER INFORMATION: Xaa is Ala, or Val
<220> FEATURE:
<221> NAME/KEY: MISC_FEATURE
<222> LOCATION: (7)..(7)
<223> OTHER INFORMATION: Xaa is Glu or Asp
<220> FEATURE:
<221> NAME/KEY: MISC_FEATURE
<222> LOCATION: (8)..(8)
<223> OTHER INFORMATION: Xaa is any non polar amino acid
<220> FEATURE:
<221> NAME/KEY: MISC_FEATURE
<222> LOCATION: (9)..(9)
<223> OTHER INFORMATION: Xaa is Ser or Cys
<220> FEATURE:
<221> NAME/KEY: MISC_FEATURE
<222> LOCATION: (10)..(10)
<223> OTHER INFORMATION: Xaa is Cys or Gly
<220> FEATURE:
<221> NAME/KEY: MISC_FEATURE
<222> LOCATION: (11)..(11)
<223> OTHER INFORMATION: Xaa is Glu or Thr

<400> SEQUENCE: 33

Pro Xaa Xaa Xaa Xaa Xaa Xaa Xaa Xaa Xaa Xaa Asp Ala
1               5                   10

<210> SEQ ID NO 34
<211> LENGTH: 13
<212> TYPE: PRT
<213> ORGANISM: Artificial sequence
<220> FEATURE:
<223> OTHER INFORMATION: 3'-5' Exonuclease domain of thermostable DNA
      Polymerase

<400> SEQUENCE: 34

Pro Val Glu Lys Ala Ala Asn Ala Ser Cys Glu Asp Ala
1               5                   10

<210> SEQ ID NO 35
<211> LENGTH: 28
<212> TYPE: PRT
<213> ORGANISM: Artificial sequence
<220> FEATURE:
<223> OTHER INFORMATION: Primer
```

```
<400> SEQUENCE: 35

Gly Thr Ala Thr Gly Thr Ala Gly Thr Ala Cys Gly Cys Thr Thr Cys
1               5                   10                  15

Cys Thr Thr Thr Gly Gly Thr Thr Gly Ala Ala
            20                  25

<210> SEQ ID NO 36
<211> LENGTH: 23
<212> TYPE: PRT
<213> ORGANISM: Artificial sequence
<220> FEATURE:
<223> OTHER INFORMATION: Primer

<400> SEQUENCE: 36

Thr Gly Gly Cys Thr Thr Thr Gly Gly Gly Ala Gly Ala Ala Gly Thr
1               5                   10                  15

Ala Cys Gly Gly Cys Cys Thr
            20

<210> SEQ ID NO 37
<211> LENGTH: 11
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (7)..(7)
<223> OTHER INFORMATION: n is degenerate position, either 'a' or 't'

<400> SEQUENCE: 37
cgacgangag a                                                          11

<210> SEQ ID NO 38
<211> LENGTH: 17
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (9)..(9)
<223> OTHER INFORMATION: n is degenerate position, either 'a' or 't'

<400> SEQUENCE: 38
tagctgctnc tctgatc                                                    17

<210> SEQ ID NO 39
<211> LENGTH: 11
<212> TYPE: DNA
<213> ORGANISM: Artificial sequence
<220> FEATURE:
<223> OTHER INFORMATION: Primer

<400> SEQUENCE: 39
cgacgaagag a                                                          11

<210> SEQ ID NO 40
<211> LENGTH: 17
<212> TYPE: DNA
<213> ORGANISM: Artificial sequence
<220> FEATURE:
<223> OTHER INFORMATION: Primer

<400> SEQUENCE: 40
```

```
tagctgcttc tctgatc                                                17
```

<210> SEQ ID NO 41
<211> LENGTH: 11
<212> TYPE: DNA
<213> ORGANISM: Artificial sequence
<220> FEATURE:
<223> OTHER INFORMATION: Primer

<400> SEQUENCE: 41

```
cgacgatgag a                                                      11
```

<210> SEQ ID NO 42
<211> LENGTH: 17
<212> TYPE: DNA
<213> ORGANISM: Artificial sequence
<220> FEATURE:
<223> OTHER INFORMATION: Primer

<400> SEQUENCE: 42

```
tagctgctac tctgatc                                                17
```

<210> SEQ ID NO 43
<211> LENGTH: 11
<212> TYPE: DNA
<213> ORGANISM: Artificial sequence
<220> FEATURE:
<223> OTHER INFORMATION: Primer

<400> SEQUENCE: 43

```
tgatmaggaa a                                                      11
```

<210> SEQ ID NO 44
<211> LENGTH: 17
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (7)..(7)
<223> OTHER INFORMATION: n is degenerate position, either 'g' or 't'

<400> SEQUENCE: 44

```
taactantcc tttgatc                                                17
```

<210> SEQ ID NO 45
<211> LENGTH: 11
<212> TYPE: DNA
<213> ORGANISM: Artificial sequence
<220> FEATURE:
<223> OTHER INFORMATION: Primer

<400> SEQUENCE: 45

```
tgataaggaa a                                                      11
```

<210> SEQ ID NO 46
<211> LENGTH: 17
<212> TYPE: DNA
<213> ORGANISM: Artificial sequence
<220> FEATURE:
<223> OTHER INFORMATION: Primer

<400> SEQUENCE: 46

```
taactattcc tttgatc                                                17
```

```
<210> SEQ ID NO 47
<211> LENGTH: 11
<212> TYPE: DNA
<213> ORGANISM: Artificial sequence
<220> FEATURE:
<223> OTHER INFORMATION: Primer

<400> SEQUENCE: 47
tgatcaggaa a                                                            11

<210> SEQ ID NO 48
<211> LENGTH: 17
<212> TYPE: DNA
<213> ORGANISM: Artificial sequence
<220> FEATURE:
<223> OTHER INFORMATION: Primer

<400> SEQUENCE: 48
taactagtcc tttgatc                                                      17

<210> SEQ ID NO 49
<211> LENGTH: 11
<212> TYPE: DNA
<213> ORGANISM: Artificial sequence
<220> FEATURE:
<223> OTHER INFORMATION: Primer

<400> SEQUENCE: 49
cgatmatgaa a                                                            11

<210> SEQ ID NO 50
<211> LENGTH: 17
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (7)..(7)
<223> OTHER INFORMATION: n is degenerate position, either 't' or 'g'

<400> SEQUENCE: 50
tagctantac tttgatc                                                      17

<210> SEQ ID NO 51
<211> LENGTH: 11
<212> TYPE: DNA
<213> ORGANISM: Artificial sequence
<220> FEATURE:
<223> OTHER INFORMATION: Primer

<400> SEQUENCE: 51
cgataatgaa a                                                            11

<210> SEQ ID NO 52
<211> LENGTH: 17
<212> TYPE: DNA
<213> ORGANISM: Artificial sequence
<220> FEATURE:
<223> OTHER INFORMATION: Primer

<400> SEQUENCE: 52
tagctattac tttgatc                                                      17

<210> SEQ ID NO 53
<211> LENGTH: 11
<212> TYPE: DNA
```

```
<213> ORGANISM: Artificial sequence
<220> FEATURE:
<223> OTHER INFORMATION: Primer

<400> SEQUENCE: 53
cgatcatgaa a                                                              11

<210> SEQ ID NO 54
<211> LENGTH: 17
<212> TYPE: DNA
<213> ORGANISM: Artificial sequence
<220> FEATURE:
<223> OTHER INFORMATION: Primer

<400> SEQUENCE: 54
tagctagtac tttgatc                                                        17

<210> SEQ ID NO 55
<211> LENGTH: 11
<212> TYPE: DNA
<213> ORGANISM: Artificial sequence
<220> FEATURE:
<223> OTHER INFORMATION: Primer

<400> SEQUENCE: 55
tgasctggat a                                                              11

<210> SEQ ID NO 56
<211> LENGTH: 17
<212> TYPE: DNA
<213> ORGANISM: Artificial sequence
<220> FEATURE:
<223> OTHER INFORMATION: Primer

<400> SEQUENCE: 56
taactsgacc taagatc                                                        17

<210> SEQ ID NO 57
<211> LENGTH: 11
<212> TYPE: DNA
<213> ORGANISM: Artificial sequence
<220> FEATURE:
<223> OTHER INFORMATION: Primer

<400> SEQUENCE: 57
tgacctggat a                                                              11

<210> SEQ ID NO 58
<211> LENGTH: 17
<212> TYPE: DNA
<213> ORGANISM: Artificial sequence
<220> FEATURE:
<223> OTHER INFORMATION: Primer

<400> SEQUENCE: 58
taactggacc tatgatc                                                        17

<210> SEQ ID NO 59
<211> LENGTH: 11
<212> TYPE: DNA
<213> ORGANISM: Artificial sequence
<220> FEATURE:
<223> OTHER INFORMATION: Primer

<400> SEQUENCE: 59
tgagctggat a                                                              11
```

```
<210> SEQ ID NO 60
<211> LENGTH: 17
<212> TYPE: DNA
<213> ORGANISM: Artificial sequence
<220> FEATURE:
<223> OTHER INFORMATION: Primer

<400> SEQUENCE: 60
taactcgacc tatgatc                                                    17

<210> SEQ ID NO 61
<211> LENGTH: 11
<212> TYPE: DNA
<213> ORGANISM: Artificial sequence
<220> FEATURE:
<223> OTHER INFORMATION: Primer

<400> SEQUENCE: 61
tgagcttgag a                                                          11

<210> SEQ ID NO 62
<211> LENGTH: 17
<212> TYPE: DNA
<213> ORGANISM: Artificial sequence
<220> FEATURE:
<223> OTHER INFORMATION: Primer

<400> SEQUENCE: 62
taactcgaac tctgatc                                                    17

<210> SEQ ID NO 63
<211> LENGTH: 11
<212> TYPE: DNA
<213> ORGANISM: Artificial sequence
<220> FEATURE:
<223> OTHER INFORMATION: Primer

<400> SEQUENCE: 63
tgagcttgag a                                                          11

<210> SEQ ID NO 64
<211> LENGTH: 17
<212> TYPE: DNA
<213> ORGANISM: Artificial sequence
<220> FEATURE:
<223> OTHER INFORMATION: Primer

<400> SEQUENCE: 64
taactcgaac tctgatc                                                    17

<210> SEQ ID NO 65
<211> LENGTH: 26
<212> TYPE: DNA
<213> ORGANISM: Artificial sequence
<220> FEATURE:
<223> OTHER INFORMATION: Primer

<400> SEQUENCE: 65
gaaactagtt ccgctgatcc tt tcga                                         26

<210> SEQ ID NO 66
<211> LENGTH: 29
<212> TYPE: DNA
<213> ORGANISM: Artificial sequence
<220> FEATURE:
```

<223> OTHER INFORMATION: Primer

<400> SEQUENCE: 66
gaaaagagaa ggacatgagc tcttggtaa    29

<210> SEQ ID NO 67
<211> LENGTH: 36
<212> TYPE: DNA
<213> ORGANISM: Artificial sequence
<220> FEATURE:
<223> OTHER INFORMATION: Primer

<400> SEQUENCE: 67
agaaaaagct gcgaatgcat cctgtgaaga tgcaga    36

<210> SEQ ID NO 68
<211> LENGTH: 28
<212> TYPE: DNA
<213> ORGANISM: Artificial sequence
<220> FEATURE:
<223> OTHER INFORMATION: Primer

<400> SEQUENCE: 68
tttccagatc tgcctcgtgg agttttaa    28

<210> SEQ ID NO 69
<211> LENGTH: 36
<212> TYPE: DNA
<213> ORGANISM: Artificial sequence
<220> FEATURE:
<223> OTHER INFORMATION: Primer

<400> SEQUENCE: 69
ctgcatcttc acaggatgca ttcgcagctt tttcta    36

<210> SEQ ID NO 70
<211> LENGTH: 29
<212> TYPE: DNA
<213> ORGANISM: Artificial sequence
<220> FEATURE:
<223> OTHER INFORMATION: Primer

<400> SEQUENCE: 70
accaagagct catgtccttc tcttttccg    29

<210> SEQ ID NO 71
<211> LENGTH: 30
<212> TYPE: DNA
<213> ORGANISM: Artificial sequence
<220> FEATURE:
<223> OTHER INFORMATION: Primer

<400> SEQUENCE: 71
cgttggtgcc aatttgaaat tcgattacaa    30

<210> SEQ ID NO 72
<211> LENGTH: 30
<212> TYPE: DNA
<213> ORGANISM: Artificial sequence
<220> FEATURE:
<223> OTHER INFORMATION: Primer

<400> SEQUENCE: 72
tgtaatcgaa tttcaaattg gcaccaacga    30

<210> SEQ ID NO 73
<211> LENGTH: 21
<212> TYPE: DNA
<213> ORGANISM: Artificial sequence
<220> FEATURE:
<223> OTHER INFORMATION: Primer

<400> SEQUENCE: 73
ggaaactagt tccctcgatc c                                    21

<210> SEQ ID NO 74
<211> LENGTH: 30
<212> TYPE: DNA
<213> ORGANISM: Artificial sequence
<220> FEATURE:
<223> OTHER INFORMATION: Primer

<400> SEQUENCE: 74
cgttggtcag gccttgaaat tcgattacaa                           30

<210> SEQ ID NO 75
<211> LENGTH: 30
<212> TYPE: DNA
<213> ORGANISM: Artificial sequence
<220> FEATURE:
<223> OTHER INFORMATION: Primer

<400> SEQUENCE: 75
tgtaatcgaa tttcaaggcc tgaccaacga                           30

<210> SEQ ID NO 76
<211> LENGTH: 30
<212> TYPE: DNA
<213> ORGANISM: Artificial sequence
<220> FEATURE:
<223> OTHER INFORMATION: Primer

<400> SEQUENCE: 76
cgttggtgcc gctctgaaat tcgattacaa                           30

<210> SEQ ID NO 77
<211> LENGTH: 30
<212> TYPE: DNA
<213> ORGANISM: Artificial sequence
<220> FEATURE:
<223> OTHER INFORMATION: Primer

<400> SEQUENCE: 77
tgtaatcgaa tttcagagcg gcaccaacga                           30

<210> SEQ ID NO 78
<211> LENGTH: 31
<212> TYPE: DNA
<213> ORGANISM: Artificial sequence
<220> FEATURE:
<223> OTHER INFORMATION: Primer

<400> SEQUENCE: 78
tgaaattcga gtacaaggtg ttgatggtga a                         31

<210> SEQ ID NO 79
<211> LENGTH: 25
<212> TYPE: DNA
<213> ORGANISM: Artificial sequence
<220> FEATURE:
<223> OTHER INFORMATION: Primer

<400> SEQUENCE: 79
caacaccttg tactcgaatt tcaaa                                   25

<210> SEQ ID NO 80
<211> LENGTH: 31
<212> TYPE: DNA
<213> ORGANISM: Artificial sequence
<220> FEATURE:
<223> OTHER INFORMATION: single-stranded oligonucleotide substrate NJS40

<400> SEQUENCE: 80
gcgctagggc gctggcaagt gtagcggtca c                            31

<210> SEQ ID NO 81
<211> LENGTH: 60
<212> TYPE: DNA
<213> ORGANISM: Artificial sequence
<220> FEATURE:
<223> OTHER INFORMATION: single-stranded oligonucleotide substrate NJS43

<400> SEQUENCE: 81
agcgatcccg cgaccgttca catcgccagt gcgacgcgca ttggtggtgt gggcggcgcc    60

<210> SEQ ID NO 82
<211> LENGTH: 60
<212> TYPE: DNA
<213> ORGANISM: Artificial sequence
<220> FEATURE:
<223> OTHER INFORMATION: single-stranded oligonucleotide substrate NJS44

<400> SEQUENCE: 82
agcgatcccg cgaccgttca catcgccagt tcgacgcgca ttggtggtgt gggcggcgcc    60

<210> SEQ ID NO 83
<211> LENGTH: 34
<212> TYPE: DNA
<213> ORGANISM: Artificial sequence
<220> FEATURE:
<223> OTHER INFORMATION: Primer RN326
<220> FEATURE:
<221> NAME/KEY: misc_feature
<222> LOCATION: (33)..(33)
<223> OTHER INFORMATION: n is a 2' amino deoxy cytosine

<400> SEQUENCE: 83 gagggtatt gacaaactcc cactcaggaa tcna                          34

<210> SEQ ID NO 84
<211> LENGTH: 33
<212> TYPE: DNA
<213> ORGANISM: Artificial sequence
<220> FEATURE:
<223> OTHER INFORMATION: Primer RN328
<220> FEATURE:
<221> NAME/KEY: misc_feature
<222> LOCATION: (32)..(32)
<223> OTHER INFORMATION: n is a 2' amino deoxy cytosine

<400> SEQUENCE: 84
gggaattttc ttcagagcag accagagcca ana                          33

<210> SEQ ID NO 85
<211> LENGTH: 893
<212> TYPE: PRT
<213> ORGANISM: Thermotoga maritima

<400> SEQUENCE: 85

-continued

```
Met Ala Arg Leu Phe Leu Phe Asp Gly Thr Ala Leu Ala Tyr Arg Ala
1               5                   10                  15

Tyr Tyr Ala Leu Asp Arg Ser Leu Ser Thr Ser Thr Gly Ile Pro Thr
            20                  25                  30

Asn Ala Thr Tyr Gly Val Ala Arg Met Leu Val Arg Phe Ile Lys Asp
            35                  40                  45

His Ile Ile Val Gly Lys Asp Tyr Val Ala Val Ala Phe Asp Lys Lys
        50                  55                  60

Ala Ala Thr Phe Arg His Lys Leu Leu Glu Thr Tyr Lys Ala Gln Arg
65              70                  75                  80

Pro Lys Thr Pro Asp Leu Leu Ile Gln Gln Leu Pro Tyr Ile Lys Lys
                85                  90                  95

Leu Val Glu Ala Leu Gly Met Lys Val Leu Glu Val Glu Gly Tyr Glu
                100                 105                 110

Ala Asp Asp Ile Ile Ala Thr Leu Ala Val Lys Gly Leu Pro Leu Phe
                115                 120                 125

Asp Glu Ile Phe Ile Val Thr Gly Asp Lys Asp Met Leu Gln Leu Val
        130                 135                 140

Asn Glu Lys Ile Lys Val Trp Arg Ile Val Lys Gly Ile Ser Asp Leu
145                 150                 155                 160

Glu Leu Tyr Asp Ala Gln Lys Val Lys Glu Lys Tyr Gly Val Glu Pro
                165                 170                 175

Gln Gln Ile Pro Asp Leu Leu Ala Leu Thr Gly Asp Glu Ile Asp Asn
                180                 185                 190

Ile Pro Gly Val Thr Gly Ile Gly Glu Lys Thr Ala Val Gln Leu Leu
                195                 200                 205

Glu Lys Tyr Lys Asp Leu Glu Asp Ile Leu Asn His Val Arg Glu Leu
                210                 215                 220

Pro Gln Lys Val Arg Lys Ala Leu Leu Arg Asp Arg Glu Asn Ala Ile
225                 230                 235                 240

Leu Ser Lys Lys Leu Ala Ile Leu Glu Thr Asn Val Pro Ile Glu Ile
                245                 250                 255

Asn Trp Glu Glu Leu Arg Tyr Gln Gly Tyr Asp Arg Glu Lys Leu Leu
                260                 265                 270

Pro Leu Leu Lys Glu Leu Glu Phe Ala Ser Ile Met Lys Glu Leu Gln
                275                 280                 285

Leu Tyr Glu Glu Ser Glu Pro Val Gly Tyr Arg Ile Val Lys Asp Leu
                290                 295                 300

Val Glu Phe Glu Lys Leu Ile Glu Lys Leu Arg Glu Ser Pro Ser Phe
305                 310                 315                 320

Ala Ile Asp Leu Glu Thr Ser Ser Leu Asp Pro Phe Asp Cys Asp Ile
                325                 330                 335

Val Gly Ile Ser Val Ser Phe Lys Pro Lys Glu Ala Tyr Tyr Ile Pro
                340                 345                 350

Leu His His Arg Asn Ala Gln Asn Leu Asp Glu Lys Glu Val Leu Lys
                355                 360                 365

Lys Leu Lys Glu Ile Leu Glu Asp Pro Gly Ala Lys Ile Val Gly Gln
                370                 375                 380

Asn Leu Lys Phe Asp Tyr Lys Val Leu Met Val Lys Gly Val Glu Pro
385                 390                 395                 400

Val Pro Pro Tyr Phe Asp Thr Met Ile Ala Ala Tyr Leu Leu Glu Pro
                405                 410                 415
```

```
Asn Glu Lys Lys Phe Asn Leu Asp Asp Leu Ala Leu Lys Phe Leu Gly
            420                 425                 430

Tyr Lys Met Thr Ser Tyr Gln Glu Leu Met Ser Phe Ser Phe Pro Leu
        435                 440                 445

Phe Gly Phe Ser Phe Ala Asp Val Pro Val Glu Lys Ala Ala Asn Tyr
    450                 455                 460

Ser Cys Glu Asp Ala Asp Ile Thr Tyr Arg Leu Tyr Lys Thr Leu Ser
465                 470                 475                 480

Leu Lys Leu His Glu Ala Asp Leu Glu Asn Val Phe Tyr Lys Ile Glu
                485                 490                 495

Met Pro Leu Val Asn Val Leu Ala Arg Met Glu Leu Asn Gly Val Tyr
            500                 505                 510

Val Asp Thr Glu Phe Leu Lys Lys Leu Ser Glu Glu Tyr Gly Lys Lys
        515                 520                 525

Leu Glu Glu Leu Ala Glu Ile Tyr Arg Ile Ala Gly Glu Pro Phe
    530                 535                 540

Asn Ile Asn Ser Pro Lys Gln Val Ser Arg Ile Leu Phe Glu Lys Leu
545                 550                 555                 560

Gly Ile Lys Pro Arg Gly Lys Thr Thr Lys Thr Gly Asp Tyr Ser Thr
                565                 570                 575

Arg Ile Glu Val Leu Glu Glu Leu Ala Gly Glu His Glu Ile Ile Pro
            580                 585                 590

Leu Ile Leu Glu Tyr Arg Lys Ile Gln Lys Leu Lys Ser Thr Tyr Ile
        595                 600                 605

Asp Ala Leu Pro Lys Met Val Asn Pro Lys Thr Gly Arg Ile His Ala
    610                 615                 620

Ser Phe Asn Gln Thr Gly Thr Ala Thr Gly Arg Leu Ser Ser Ser Asp
625                 630                 635                 640

Pro Asn Leu Gln Asn Leu Pro Thr Lys Ser Glu Glu Gly Lys Glu Ile
                645                 650                 655

Arg Lys Ala Ile Val Pro Gln Asp Pro Asn Trp Trp Ile Val Ser Ala
            660                 665                 670

Asp Tyr Ser Gln Ile Glu Leu Arg Ile Leu Ala His Leu Ser Gly Asp
        675                 680                 685

Glu Asn Leu Leu Arg Ala Phe Glu Gly Ile Asp Val His Thr Leu
    690                 695                 700

Thr Ala Ser Arg Ile Phe Asn Val Lys Pro Glu Glu Val Thr Glu Glu
705                 710                 715                 720

Met Arg Arg Ala Gly Lys Met Val Asn Phe Ser Ile Ile Tyr Gly Val
                725                 730                 735

Thr Pro Tyr Gly Leu Ser Val Arg Leu Gly Val Pro Val Lys Glu Ala
            740                 745                 750

Glu Lys Met Ile Val Asn Tyr Phe Val Leu Tyr Pro Lys Val Arg Asp
        755                 760                 765

Tyr Ile Gln Arg Val Val Ser Glu Ala Lys Glu Lys Gly Tyr Val Arg
    770                 775                 780

Thr Leu Phe Gly Arg Lys Arg Asp Ile Pro Gln Leu Met Ala Arg Asp
785                 790                 795                 800

Arg Asn Thr Gln Ala Glu Gly Glu Arg Ile Ala Ile Asn Thr Pro Ile
                805                 810                 815

Gln Gly Thr Ala Ala Asp Ile Ile Lys Leu Ala Met Ile Glu Ile Asp
            820                 825                 830

Arg Glu Leu Lys Glu Arg Lys Met Arg Ser Lys Met Ile Ile Gln Val
```

-continued

```
                     835                 840                 845
His Asp Glu Leu Val Phe Glu Val Pro Asn Glu Lys Asp Ala Leu
    850                 855                 860
Val Glu Leu Val Lys Asp Arg Met Thr Asn Val Val Lys Leu Ser Val
865                 870                 875                 880
Pro Leu Glu Val Asp Val Thr Ile Gly Lys Thr Trp Ser
                885                 890

<210> SEQ ID NO 86
<211> LENGTH: 196
<212> TYPE: PRT
<213> ORGANISM: Thermotoga maritima

<400> SEQUENCE: 86

Glu Ser Glu Pro Val Gly Tyr Arg Ile Val Lys Asp Leu Val Glu Phe
1               5                   10                  15

Glu Lys Leu Ile Glu Lys Leu Arg Glu Ser Pro Ser Phe Ala Ile Asp
            20                  25                  30

Leu Glu Thr Ser Ser Leu Asp Pro Phe Asp Cys Asp Ile Val Gly Ile
        35                  40                  45

Ser Val Ser Phe Lys Pro Lys Glu Ala Tyr Tyr Ile Pro Leu His His
    50                  55                  60

Arg Asn Ala Gln Asn Leu Asp Lys Glu Val Leu Lys Lys Leu Lys
65                  70                  75                  80

Glu Ile Leu Glu Asp Pro Gly Ala Lys Ile Val Gly Gln Asn Leu Lys
                85                  90                  95

Phe Asp Tyr Lys Val Leu Met Val Lys Gly Val Glu Pro Val Pro Pro
            100                 105                 110

Tyr Phe Asp Thr Met Ile Ala Ala Tyr Leu Leu Glu Pro Asn Glu Lys
        115                 120                 125

Lys Phe Asn Leu Asp Asp Leu Ala Leu Lys Phe Leu Gly Tyr Lys Met
    130                 135                 140

Thr Ser Tyr Gln Glu Leu Met Ser Phe Ser Phe Pro Leu Phe Gly Phe
145                 150                 155                 160

Ser Phe Ala Asp Val Pro Val Glu Lys Ala Ala Asn Tyr Ser Cys Glu
                165                 170                 175

Asp Ala Asp Ile Thr Tyr Arg Leu Tyr Lys Thr Leu Ser Leu Lys Leu
            180                 185                 190

His Glu Ala Asp
        195

<210> SEQ ID NO 87
<211> LENGTH: 2682
<212> TYPE: DNA
<213> ORGANISM: Thermotoga maritima

<400> SEQUENCE: 87
atggcgagac tatttctctt tgatggaact gctctggcct acagagcgta ctatgcgctc      60
gatagatcgc tttctacttc caccggcatt cccacaaacg ccacatacgg tgtggcgagg     120
atgctggtga gattcatcaa agaccatatc attgtcggaa agactacgt tgctgtggct      180 ttcgacaaaa aagctgccac cttcagacac aagctcctcg agacttacaa ggctcaagga     240
ccaaagactc cggatctcct gattcagcag cttccgtaca taagaagct ggtcgaagcc      300 cttggaatga aagtgctgga ggtagaagga tacgaagcgg acgatataat tgccactctg     360
gctgtgaagg ggcttccgct ttttgatgaa atattcatag tgaccggaga taaagacatg     420
```

-continued

```
cttcagcttg tgaacgaaaa gatcaaggtg tggcgaatcg taaaagggat atccgatctg    480
gaactttacg atgcgcagaa ggtgaaggaa aaatacggtg ttgaacccca gcagatcccg    540
gatcttctgg ctctaaccgg agatgaaata gacaacatcc ccggtgtaac tgggataggt    600
gaaaagactg ctgttcagct tctagagaag tacaaagacc tcgaagacat actgaatcat    660
gttcgcgaac ttcctcaaaa ggtgagaaaa gccctgcttc gagacagaga aaacgccatt    720
ctcagcaaaa agctggcgat tctggaaaca acgttccca ttgaaataaa ctgggaagaa    780
cttcgctacc agggctacga cagagagaaa ctcttaccac ttttgaaaga actggaattc    840
gcatccatca tgaaggaact tcaactgtac gaagagtccg aacccgttgg atacagaata    900
gtgaaagacc tagtggaatt tgaaaaactc atagagaaac tgagagaatc cccttcgttc    960
gccatagatc ttgagacgtc ttccctcgat cctttcgact gcgacattgt cggtatctct   1020
gtgtctttca accaaagga agcgtactac ataccactcc atcatagaaa cgcccagaac   1080
ctggacgaaa agaggttct gaaaaagctc aagaaaattc tggaggaccc cggagcaaag   1140
atcgttggtc agaatttgaa attcgattac aaggtgttga tggtgaaggg tgttgaacct   1200
gttcctcctt acttcgacac gatgatagcg gcttaccttc ttgagccgaa cgaaaagaag   1260
ttcaatctgg acgatctcgc attgaaattt cttggataca aaatgacatc ttaccaagag   1320
ctcatgtcct tctcttttcc gctgtttggt ttcagtttg ccgatgttcc tgtagaaaaa   1380
gcagcgaact actcctgtga agatgcagac atcacctaca gactttacaa gaccctgagc   1440
ttaaaactcc acgaggcaga tctggaaaac gtgttctaca agatagaaat gccccttgtg   1500
aacgtgcttg cacggatgga actgaacggt gtgtatgtgg acacagagtt cctgaagaaa   1560
ctctcagaag agtacggaaa aaactcgaa gaactggcag aggaaatata caggatagct   1620
ggagagccgt tcaacataaa ctcaccgaag caggtttcaa ggatcctttt tgaaaaactc   1680
ggcataaaac cacgtggtaa aacgacgaaa acggggagact attcaacacg catagaagtc   1740
ctcgaggaac ttgccggtga acacgaaatc attcctctga ttcttgaata cagaaagata   1800
cagaaattga aatcaaccta catagacgct cttcccaaga tggtcaaccc aaagaccgga   1860
aggattcatg cttctttcaa tcaaacgggg actgccactg gaagacttag cagcagcgat   1920
cccaatcttc agaacctccc gacgaaaagt gaagagggaa aagaaatcag gaaagcgata   1980
gttcctcagg atccaaactg gtggatcgtc agtgccgact actcccaaat gaactgagg    2040 atcctcgccc atctcagtgg tgatgagaat cttttgaggg cattcgaaga gggcatcgac   2100
gtccacactc taacagcttc cagaatattc aacgtgaaac ccgaagaagt aaccgaagaa   2160
atgcgccgcg ctggtaaaat ggttaatttt tccatcatat acggtgtaac accttacggt   2220
ctgtctgtga ggcttggagt acctgtgaaa gaagcagaaa agatgatcgt caactacttc   2280
gtcctctacc caaaggtgcg cgattacatt cagagggtcg tatcggaagc gaaagaaaaa   2340
ggctatgtta gaacgctgtt tggaagaaaa agagacatac cacagctcat ggcccgggac   2400
aggaacacac aggctgaagg agaacgaatt gccataaaca ctcccataca gggtacagca   2460
gcggatataa taaagctggc tatgatagaa atagacaggg aactgaaaga aagaaaaatg   2520
agatcgaaga tgatcataca ggtccacgac gaactggttt ttgaagtgcc caatgaggaa   2580
aaggacgcgc tcgtcgagct ggtgaaagac agaatgacga atgtgtaaaa gctttcagtg   2640
ccgctcgaag tggatgtaac catcggcaaa acatggtcgt ga                      2682
```

<210> SEQ ID NO 88

```
<211> LENGTH: 196
<212> TYPE: PRT
<213> ORGANISM: Thermotoga neapolitana

<400> SEQUENCE: 88

Glu Ala Glu Pro Thr Gly Tyr Glu Ile Val Lys Asp His Lys Thr Phe
1               5                   10                  15

Glu Asp Leu Ile Glu Lys Leu Lys Glu Val Pro Ser Phe Ala Leu Asp
            20                  25                  30

Leu Glu Thr Ser Ser Leu Asp Pro Phe Asn Cys Glu Ile Val Gly Ile
        35                  40                  45

Ser Val Ser Phe Lys Pro Lys Thr Ala Tyr Tyr Ile Pro Leu His His
    50                  55                  60

Arg Asn Ala Gln Asn Leu Asp Glu Thr Leu Val Leu Ser Lys Leu Lys
65                  70                  75                  80

Glu Ile Leu Glu Asp Pro Ser Ser Lys Ile Val Gly Gln Asn Leu Lys
                85                  90                  95

Tyr Asp Tyr Lys Val Leu Met Val Lys Gly Ile Ser Pro Val Tyr Pro
            100                 105                 110

His Phe Asp Thr Met Ile Ala Ala Tyr Leu Leu Glu Pro Asn Glu Lys
        115                 120                 125

Lys Phe Asn Leu Glu Asp Leu Ser Leu Lys Phe Leu Gly Tyr Lys Met
    130                 135                 140

Thr Ser Tyr Gln Glu Leu Met Ser Phe Ser Ser Pro Leu Phe Gly Phe
145                 150                 155                 160

Ser Phe Ala Asp Val Pro Val Asp Lys Ala Ala Asn Tyr Ser Cys Glu
                165                 170                 175

Asp Ala Asp Ile Thr Tyr Arg Leu Tyr Lys Ile Leu Ser Met Lys Leu
            180                 185                 190

His Glu Ala Glu
        195

<210> SEQ ID NO 89
<211> LENGTH: 195
<212> TYPE: PRT
<213> ORGANISM: Thermosipho africanus

<400> SEQUENCE: 89

Lys Leu Glu Lys Glu Tyr Ile Leu Val Asp Asn Glu Asp Lys Leu Lys
1               5                   10                  15

Lys Leu Ala Glu Glu Ile Glu Lys Tyr Lys Thr Phe Ser Ile Asp Thr
            20                  25                  30

Glu Thr Thr Ser Leu Asp Pro Phe Glu Ala Lys Leu Val Gly Ile Ser
        35                  40                  45

Ile Ser Thr Met Glu Gly Lys Ala Tyr Tyr Ile Pro Val Ser His Phe
    50                  55                  60

Gly Ala Lys Asn Ile Ser Lys Ser Leu Ile Asp Lys Phe Leu Lys Gln
65                  70                  75                  80

Ile Leu Gln Glu Lys Asp Tyr Asn Ile Val Gly Gln Asn Leu Lys Phe
                85                  90                  95

Asp Tyr Glu Ile Phe Lys Ser Met Gly Phe Ser Pro Asn Val Pro His
            100                 105                 110

Phe Asp Thr Met Ile Ala Ala Tyr Leu Leu Asn Pro Asp Glu Lys Arg
        115                 120                 125

Phe Asn Leu Glu Glu Leu Ser Leu Lys Tyr Leu Gly Tyr Lys Met Ile
    130                 135                 140
```

```
Ser Phe Asp Glu Leu Val Asn Glu Asn Val Pro Leu Phe Gly Asn Asp
145                 150                 155                 160

Phe Ser Tyr Val Pro Leu Glu Arg Ala Val Glu Tyr Ser Cys Glu Asp
                165                 170                 175

Ala Asp Val Thr Tyr Arg Ile Phe Arg Lys Leu Gly Arg Lys Ile Tyr
                180                 185                 190

Glu Asn Glu
        195

<210> SEQ ID NO 90
<211> LENGTH: 893
<212> TYPE: PRT
<213> ORGANISM: Artificial sequence
<220> FEATURE:
<223> OTHER INFORMATION: chimeric thermostable DNA polymerase CS5

<400> SEQUENCE: 90

Met Lys Ala Met Leu Pro Leu Phe Glu Pro Lys Gly Arg Val Leu Leu
1               5                   10                  15

Val Asp Gly His His Leu Ala Tyr Arg Thr Phe Phe Ala Leu Lys Gly
                20                  25                  30

Leu Thr Thr Ser Arg Gly Glu Pro Val Gln Ala Val Tyr Gly Phe Ala
                35                  40                  45

Lys Ser Leu Leu Lys Ala Leu Lys Glu Asp Gly Tyr Lys Ala Val Phe
        50                  55                  60

Val Val Phe Asp Ala Lys Ala Pro Ser Phe Arg His Glu Ala Tyr Glu
65                  70                  75                  80

Ala Tyr Lys Ala Gly Arg Ala Pro Thr Pro Glu Asp Phe Pro Arg Gln
                85                  90                  95

Leu Ala Leu Ile Lys Glu Leu Val Asp Leu Leu Gly Phe Thr Arg Leu
                100                 105                 110

Glu Val Pro Gly Phe Glu Ala Asp Asp Val Leu Ala Thr Leu Ala Lys
                115                 120                 125

Lys Ala Glu Arg Glu Gly Tyr Glu Val Arg Ile Leu Thr Ala Asp Arg
        130                 135                 140

Asp Leu Tyr Gln Leu Val Ser Asp Arg Val Ala Val Leu His Pro Glu
145                 150                 155                 160

Gly His Leu Ile Thr Pro Glu Trp Leu Trp Glu Lys Tyr Gly Leu Lys
                165                 170                 175

Pro Glu Gln Trp Val Asp Phe Arg Ala Leu Val Gly Asp Pro Ser Asp
                180                 185                 190

Asn Leu Pro Gly Val Lys Gly Ile Gly Glu Lys Thr Ala Leu Lys Leu
                195                 200                 205

Leu Lys Glu Trp Gly Ser Leu Glu Asn Ile Leu Lys Asn Leu Asp Arg
        210                 215                 220

Val Lys Pro Glu Ser Val Arg Glu Arg Ile Lys Ala His Leu Glu Asp
225                 230                 235                 240

Leu Lys Leu Ser Leu Glu Leu Ser Arg Val Arg Ser Asp Leu Pro Leu
                245                 250                 255

Glu Val Asp Phe Ala Arg Arg Glu Pro Asp Arg Glu Gly Leu Arg
                260                 265                 270

Ala Phe Leu Glu Arg Leu Glu Phe Gly Ser Leu Leu His Glu Phe Gly
        275                 280                 285

Leu Leu Glu Glu Ser Glu Pro Val Gly Tyr Arg Ile Val Lys Asp Leu
        290                 295                 300
```

-continued

```
Val Glu Phe Glu Lys Leu Ile Glu Lys Leu Arg Glu Ser Pro Ser Phe
305                 310                 315                 320

Ala Ile Asp Leu Glu Thr Ser Ser Leu Asp Pro Phe Asp Cys Asp Ile
            325                 330                 335

Val Gly Ile Ser Val Ser Phe Lys Pro Lys Glu Ala Tyr Tyr Ile Pro
        340                 345                 350

Leu His His Arg Asn Ala Gln Asn Leu Asp Glu Lys Glu Val Leu Lys
            355                 360                 365

Lys Leu Lys Glu Ile Leu Glu Asp Pro Gly Ala Lys Ile Val Gly Gln
        370                 375                 380

Asn Leu Lys Phe Asp Tyr Lys Val Leu Met Val Lys Gly Val Glu Pro
385                 390                 395                 400

Val Pro Pro Tyr Phe Asp Thr Met Ile Ala Ala Tyr Leu Leu Glu Pro
                405                 410                 415

Asn Glu Lys Lys Phe Asn Leu Asp Asp Leu Ala Leu Lys Phe Leu Gly
            420                 425                 430

Tyr Lys Met Thr Ser Tyr Gln Glu Leu Met Ser Phe Ser Phe Pro Leu
        435                 440                 445

Phe Gly Phe Ser Phe Ala Asp Val Pro Val Glu Lys Ala Ala Asn Tyr
    450                 455                 460

Ser Cys Glu Asp Ala Asp Ile Thr Tyr Arg Leu Tyr Lys Thr Leu Ser
465                 470                 475                 480

Leu Lys Leu His Glu Ala Asp Leu Glu Asn Val Phe Tyr Lys Ile Glu
                485                 490                 495

Met Pro Leu Val Asn Val Leu Ala Arg Met Glu Leu Asn Gly Val Tyr
            500                 505                 510

Val Asp Thr Glu Phe Leu Lys Lys Leu Ser Glu Glu Tyr Gly Lys Lys
        515                 520                 525

Leu Glu Glu Leu Ala Glu Glu Ile Tyr Arg Ile Ala Gly Glu Pro Phe
    530                 535                 540

Asn Ile Asn Ser Pro Lys Gln Val Ser Arg Ile Leu Phe Glu Lys Leu
545                 550                 555                 560

Gly Ile Lys Pro Arg Gly Lys Thr Thr Lys Thr Gly Asp Tyr Ser Thr
                565                 570                 575

Arg Ile Glu Val Leu Glu Glu Leu Ala Gly Glu His Glu Ile Ile Pro
            580                 585                 590

Leu Ile Leu Glu Tyr Arg Lys Ile Gln Lys Leu Lys Ser Thr Tyr Ile
        595                 600                 605

Asp Ala Leu Pro Lys Met Val Asn Pro Lys Thr Gly Arg Ile His Ala
    610                 615                 620

Ser Phe Asn Gln Thr Gly Thr Ala Thr Gly Arg Leu Ser Ser Ser Asp
625                 630                 635                 640

Pro Asn Leu Gln Asn Leu Pro Thr Lys Ser Glu Glu Gly Lys Glu Ile
                645                 650                 655

Arg Lys Ala Ile Val Pro Gln Asp Pro Asn Trp Trp Ile Val Ser Ala
            660                 665                 670

Asp Tyr Ser Gln Ile Glu Leu Arg Ile Leu Ala His Leu Ser Gly Asp
        675                 680                 685

Glu Asn Leu Leu Arg Ala Phe Glu Glu Gly Ile Asp Val His Thr Leu
    690                 695                 700

Thr Ala Ser Arg Ile Phe Asn Val Lys Pro Glu Glu Val Thr Glu Glu
705                 710                 715                 720
```

-continued

```
Met Arg Arg Ala Gly Lys Met Val Asn Phe Ser Ile Ile Tyr Gly Val
            725                 730                 735

Thr Pro Tyr Gly Leu Ser Val Arg Leu Gly Val Pro Val Lys Glu Ala
            740                 745                 750

Glu Lys Met Ile Val Asn Tyr Phe Val Leu Tyr Pro Lys Val Arg Asp
            755                 760                 765

Tyr Ile Gln Arg Val Val Ser Glu Ala Lys Glu Lys Gly Tyr Val Arg
            770                 775                 780

Thr Leu Phe Gly Arg Lys Arg Asp Ile Pro Gln Leu Met Ala Arg Asp
785                 790                 795                 800

Arg Asn Thr Gln Ala Glu Gly Glu Arg Ile Ala Ile Asn Thr Pro Ile
                    805                 810                 815

Gln Gly Thr Ala Ala Asp Ile Ile Lys Leu Ala Met Ile Glu Ile Asp
                    820                 825                 830

Arg Glu Leu Lys Glu Arg Lys Met Arg Ser Lys Met Ile Ile Gln Val
                    835                 840                 845

His Asp Glu Leu Val Phe Glu Val Pro Asn Glu Glu Lys Asp Ala Leu
                    850                 855                 860

Val Glu Leu Val Lys Asp Arg Met Thr Asn Val Val Lys Leu Ser Val
865                 870                 875                 880

Pro Leu Glu Val Asp Val Thr Ile Gly Lys Thr Trp Ser
                    885                 890
```

<210> SEQ ID NO 91
<211> LENGTH: 196
<212> TYPE: PRT
<213> ORGANISM: Artificial sequence
<220> FEATURE:
<223> OTHER INFORMATION: Exonucleolytic domain of DNA Polymerase from chimeric thermostable DNA polymerase CS5

<400> SEQUENCE: 91

```
Glu Ser Glu Pro Val Gly Tyr Arg Ile Val Lys Asp Leu Val Glu Phe
1               5                   10                  15

Glu Lys Leu Ile Glu Lys Leu Arg Glu Ser Pro Ser Phe Ala Ile Asp
                20                  25                  30

Leu Glu Thr Ser Ser Leu Asp Pro Phe Asp Cys Asp Ile Val Gly Ile
            35                  40                  45

Ser Val Ser Phe Lys Pro Lys Glu Ala Tyr Tyr Ile Pro Leu His His
        50                  55                  60

Arg Asn Ala Gln Asn Leu Asp Glu Lys Glu Val Leu Lys Lys Leu Lys
65                  70                  75                  80

Glu Ile Leu Glu Asp Pro Gly Ala Lys Ile Val Gly Gln Asn Leu Lys
                85                  90                  95

Phe Asp Tyr Lys Val Leu Met Val Lys Gly Val Glu Pro Val Pro Pro
            100                 105                 110

Tyr Phe Asp Thr Met Ile Ala Ala Tyr Leu Leu Glu Pro Asn Glu Lys
            115                 120                 125

Lys Phe Asn Leu Asp Asp Leu Ala Leu Lys Phe Leu Gly Tyr Lys Met
        130                 135                 140

Thr Ser Tyr Gln Glu Leu Met Ser Phe Ser Phe Pro Leu Phe Gly Phe
145                 150                 155                 160

Ser Phe Ala Asp Val Pro Val Glu Lys Ala Ala Asn Tyr Ser Cys Glu
                165                 170                 175

Asp Ala Asp Ile Thr Tyr Arg Leu Tyr Lys Thr Leu Ser Leu Lys Leu
            180                 185                 190
```

```
His Glu Ala Asp
        195

<210> SEQ ID NO 92
<211> LENGTH: 291
<212> TYPE: PRT
<213> ORGANISM: Artificial sequence
<220> FEATURE:
<223> OTHER INFORMATION: Residues 1-291 of chimeric thermostable CS5 DNA
      polymerase derived from Z05 DNA polymerase

<400> SEQUENCE: 92

Met Lys Ala Met Leu Pro Leu Phe Glu Pro Lys Gly Arg Val Leu Leu
1               5                   10                  15

Val Asp Gly His His Leu Ala Tyr Arg Thr Phe Phe Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Tyr Lys Ala Val Phe
    50                  55                  60

Val Val Phe Asp Ala Lys Ala Pro Ser Phe Arg His Glu Ala Tyr Glu
65                  70                  75                  80

Ala Tyr Lys Ala Gly Arg Ala Pro Thr Pro Glu Asp Phe Pro Arg Gln
                85                  90                  95

Leu Ala Leu Ile Lys Glu Leu Val Asp Leu Leu Gly Phe Thr Arg Leu
            100                 105                 110

Glu Val Pro Gly Phe Glu Ala Asp Asp Val Leu Ala Thr Leu Ala Lys
        115                 120                 125

Lys Ala Glu Arg Glu Gly Tyr Glu Val Arg Ile Leu Thr Ala Asp Arg
    130                 135                 140

Asp Leu Tyr Gln Leu Val Ser Asp Arg Val Ala Val Leu His Pro Glu
145                 150                 155                 160

Gly His Leu Ile Thr Pro Glu Trp Leu Trp Glu Lys Tyr Gly Leu Lys
                165                 170                 175

Pro Glu Gln Trp Val Asp Phe Arg Ala Leu Val Gly Asp Pro Ser Asp
            180                 185                 190

Asn Leu Pro Gly Val Lys Gly Ile Gly Glu Lys Thr Ala Leu Lys Leu
        195                 200                 205

Leu Lys Glu Trp Gly Ser Leu Glu Asn Ile Leu Lys Asn Leu Asp Arg
    210                 215                 220

Val Lys Pro Glu Ser Val Arg Glu Arg Ile Lys Ala His Leu Glu Asp
225                 230                 235                 240

Leu Lys Leu Ser Leu Glu Leu Ser Arg Val Arg Ser Asp Leu Pro Leu
                245                 250                 255

Glu Val Asp Phe Ala Arg Arg Arg Glu Pro Asp Arg Glu Gly Leu Arg
            260                 265                 270

Ala Phe Leu Glu Arg Leu Glu Phe Gly Ser Leu Leu His Glu Phe Gly
        275                 280                 285

Leu Leu Glu
    290

<210> SEQ ID NO 93
<211> LENGTH: 602
<212> TYPE: PRT
<213> ORGANISM: Artificial sequence
<220> FEATURE:
<223> OTHER INFORMATION: Sequence 292-893 of chimeric thermostable CS5
```

DNA polymerase derived from Tma DNA polymerase

<400> SEQUENCE: 93

```
Glu Ser Glu Pro Val Gly Tyr Arg Ile Val Lys Asp Leu Val Glu Phe
1               5                   10                  15

Glu Lys Leu Ile Glu Lys Leu Arg Glu Ser Pro Ser Phe Ala Ile Asp
            20                  25                  30

Leu Glu Thr Ser Ser Leu Asp Pro Phe Asp Cys Asp Ile Val Gly Ile
        35                  40                  45

Ser Val Ser Phe Lys Pro Lys Glu Ala Tyr Tyr Ile Pro Leu His His
    50                  55                  60

Arg Asn Ala Gln Asn Leu Asp Glu Lys Glu Val Leu Lys Lys Leu Lys
65                  70                  75                  80

Glu Ile Leu Glu Asp Pro Gly Ala Lys Ile Val Gly Gln Asn Leu Lys
                85                  90                  95

Phe Asp Tyr Lys Val Leu Met Val Lys Gly Val Glu Pro Val Pro Pro
            100                 105                 110

Tyr Phe Asp Thr Met Ile Ala Ala Tyr Leu Leu Glu Pro Asn Glu Lys
        115                 120                 125

Lys Phe Asn Leu Asp Asp Leu Ala Leu Lys Phe Leu Gly Tyr Lys Met
    130                 135                 140

Thr Ser Tyr Gln Glu Leu Met Ser Phe Ser Phe Pro Leu Phe Gly Phe
145                 150                 155                 160

Ser Phe Ala Asp Val Pro Val Glu Lys Ala Ala Asn Tyr Ser Cys Glu
                165                 170                 175

Asp Ala Asp Ile Thr Tyr Arg Leu Tyr Lys Thr Leu Ser Leu Lys Leu
            180                 185                 190

His Glu Ala Asp Leu Glu Asn Val Phe Tyr Lys Ile Glu Met Pro Leu
        195                 200                 205

Val Asn Val Leu Ala Arg Met Glu Leu Asn Gly Val Tyr Val Asp Thr
    210                 215                 220

Glu Phe Leu Lys Lys Leu Ser Glu Glu Tyr Gly Lys Lys Leu Glu Glu
225                 230                 235                 240

Leu Ala Glu Glu Ile Tyr Arg Ile Ala Gly Glu Pro Phe Asn Ile Asn
                245                 250                 255

Ser Pro Lys Gln Val Ser Arg Ile Leu Phe Glu Lys Leu Gly Ile Lys
            260                 265                 270

Pro Arg Gly Lys Thr Thr Lys Thr Gly Asp Tyr Ser Thr Arg Ile Glu
        275                 280                 285

Val Leu Glu Glu Leu Ala Gly Glu His Glu Ile Ile Pro Leu Ile Leu
    290                 295                 300

Glu Tyr Arg Lys Ile Gln Lys Leu Lys Ser Thr Tyr Ile Asp Ala Leu
305                 310                 315                 320

Pro Lys Met Val Asn Pro Lys Thr Gly Arg Ile His Ala Ser Phe Asn
                325                 330                 335

Gln Thr Gly Thr Ala Thr Gly Arg Leu Ser Ser Ser Asp Pro Asn Leu
            340                 345                 350

Gln Asn Leu Pro Thr Lys Ser Glu Glu Gly Lys Glu Ile Arg Lys Ala
        355                 360                 365

Ile Val Pro Gln Asp Pro Asn Trp Trp Ile Val Ser Ala Asp Tyr Ser
    370                 375                 380

Gln Ile Glu Leu Arg Ile Leu Ala His Leu Ser Gly Asp Glu Asn Leu
385                 390                 395                 400
```

```
Leu Arg Ala Phe Glu Glu Gly Ile Asp Val His Thr Leu Thr Ala Ser
            405                 410                 415

Arg Ile Phe Asn Val Lys Pro Glu Glu Val Thr Glu Met Arg Arg
            420                 425                 430

Ala Gly Lys Met Val Asn Phe Ser Ile Ile Tyr Gly Val Thr Pro Tyr
            435                 440                 445

Gly Leu Ser Val Arg Leu Gly Val Pro Val Lys Glu Ala Glu Lys Met
    450                 455                 460

Ile Val Asn Tyr Phe Val Leu Tyr Pro Lys Val Arg Asp Tyr Ile Gln
465                 470                 475                 480

Arg Val Val Ser Glu Ala Lys Glu Lys Gly Tyr Val Arg Thr Leu Phe
                485                 490                 495

Gly Arg Lys Arg Asp Ile Pro Gln Leu Met Ala Arg Asp Arg Asn Thr
            500                 505                 510

Gln Ala Glu Gly Glu Arg Ile Ala Ile Asn Thr Pro Ile Gln Gly Thr
        515                 520                 525

Ala Ala Asp Ile Ile Lys Leu Ala Met Ile Glu Ile Asp Arg Glu Leu
    530                 535                 540

Lys Glu Arg Lys Met Arg Ser Lys Met Ile Ile Gln Val His Asp Glu
545                 550                 555                 560

Leu Val Phe Glu Val Pro Asn Glu Glu Lys Asp Ala Leu Val Glu Leu
                565                 570                 575

Val Lys Asp Arg Met Thr Asn Val Val Lys Leu Ser Val Pro Leu Glu
            580                 585                 590

Val Asp Val Thr Ile Gly Lys Thr Trp Ser
        595                 600

<210> SEQ ID NO 94
<211> LENGTH: 196
<212> TYPE: PRT
<213> ORGANISM: Artificial sequence
<220> FEATURE:
<223> OTHER INFORMATION: Exonucleolytic domain of chimeric thermostable
      DNA polymerase CS5 after second round of mutagenesis L329A
      mutation

<400> SEQUENCE: 94

Glu Ser Glu Pro Val Gly Tyr Arg Ile Val Lys Asp Leu Val Glu Phe
1               5                   10                  15

Glu Lys Leu Ile Glu Lys Leu Arg Glu Ser Pro Ser Phe Ala Ile Asp
            20                  25                  30

Leu Glu Thr Ser Ser Ala Asp Pro Phe Asp Cys Asp Ile Val Gly Ile
        35                  40                  45

Ser Val Ser Phe Lys Pro Lys Glu Ala Tyr Tyr Ile Pro Leu His His
    50                  55                  60

Arg Asn Ala Gln Asn Leu Asp Glu Lys Glu Val Leu Lys Lys Leu Lys
65                  70                  75                  80

Glu Ile Leu Glu Asp Pro Gly Ala Lys Ile Val Gly Gln Asn Leu Lys
                85                  90                  95

Phe Asp Tyr Lys Val Leu Met Val Lys Gly Val Glu Pro Val Pro Pro
            100                 105                 110

Tyr Phe Asp Thr Met Ile Ala Ala Tyr Leu Leu Glu Pro Asn Glu Lys
        115                 120                 125

Lys Phe Asn Leu Asp Asp Leu Ala Leu Lys Phe Leu Gly Tyr Lys Met
    130                 135                 140

Thr Ser Tyr Gln Glu Leu Met Ser Phe Ser Phe Pro Leu Phe Gly Phe
```

```
                145                 150                 155                 160
Ser Phe Ala Asp Val Pro Val Glu Lys Ala Ala Asn Tyr Ser Cys Glu
                165                 170                 175

Asp Ala Asp Ile Thr Tyr Arg Leu Tyr Lys Thr Leu Ser Leu Lys Leu
                180                 185                 190

His Glu Ala Asp
        195

<210> SEQ ID NO 95
<211> LENGTH: 893
<212> TYPE: PRT
<213> ORGANISM: Artificial sequence
<220> FEATURE:
<223> OTHER INFORMATION: Entire protein of chimeric thermostable DNA
      polymerase CS5 after second round of mutagenesis L329A mutation

<400> SEQUENCE: 95

Met Lys Ala Met Leu Pro Leu Phe Glu Pro Lys Gly Arg Val Leu Leu
1               5                   10                  15

Val Asp Gly His His Leu Ala Tyr Arg Thr Phe Phe Ala Leu Lys Gly
                20                  25                  30

Leu Thr Thr Ser Arg Gly Glu Pro Val Gln Ala Val Tyr Gly Phe Ala
            35                  40                  45

Lys Ser Leu Leu Lys Ala Leu Lys Glu Asp Gly Tyr Lys Ala Val Phe
50                  55                  60

Val Val Phe Asp Ala Lys Ala Pro Ser Phe Arg His Glu Ala Tyr Glu
65                  70                  75                  80

Ala Tyr Lys Ala Gly Arg Ala Pro Thr Pro Glu Asp Phe Pro Arg Gln
                85                  90                  95

Leu Ala Leu Ile Lys Glu Leu Val Asp Leu Leu Gly Phe Thr Arg Leu
            100                 105                 110

Glu Val Pro Gly Phe Glu Ala Asp Asp Val Leu Ala Thr Leu Ala Lys
        115                 120                 125

Lys Ala Glu Arg Glu Gly Tyr Glu Val Arg Ile Leu Thr Ala Asp Arg
130                 135                 140

Asp Leu Tyr Gln Leu Val Ser Asp Arg Val Ala Val Leu His Pro Glu
145                 150                 155                 160

Gly His Leu Ile Thr Pro Glu Trp Leu Trp Glu Lys Tyr Gly Leu Lys
                165                 170                 175

Pro Glu Gln Trp Val Asp Phe Arg Ala Leu Val Gly Asp Pro Ser Asp
            180                 185                 190

Asn Leu Pro Gly Val Lys Gly Ile Gly Glu Lys Thr Ala Leu Lys Leu
        195                 200                 205

Leu Lys Glu Trp Gly Ser Leu Glu Asn Ile Leu Lys Asn Leu Asp Arg
210                 215                 220

Val Lys Pro Glu Ser Val Arg Glu Arg Ile Lys Ala His Leu Glu Asp
225                 230                 235                 240

Leu Lys Leu Ser Leu Glu Leu Ser Arg Val Arg Ser Asp Leu Pro Leu
                245                 250                 255

Glu Val Asp Phe Ala Arg Arg Arg Glu Pro Asp Arg Glu Gly Leu Arg
            260                 265                 270

Ala Phe Leu Glu Arg Leu Glu Phe Gly Ser Leu Leu His Glu Phe Gly
        275                 280                 285

Leu Leu Glu Glu Ser Glu Pro Val Gly Tyr Arg Ile Val Lys Asp Leu
290                 295                 300
```

```
Val Glu Phe Glu Lys Leu Ile Glu Lys Leu Arg Ser Pro Ser Phe
305                 310                 315                 320

Ala Ile Asp Leu Glu Thr Ser Ser Ala Asp Pro Phe Asp Cys Asp Ile
            325                 330                 335

Val Gly Ile Ser Val Ser Phe Lys Pro Lys Glu Ala Tyr Tyr Ile Pro
                340                 345                 350

Leu His His Arg Asn Ala Gln Asn Leu Asp Glu Lys Glu Val Leu Lys
        355                 360                 365

Lys Leu Lys Glu Ile Leu Glu Asp Pro Gly Ala Lys Ile Val Gly Gln
    370                 375                 380

Asn Leu Lys Phe Asp Tyr Lys Val Leu Met Val Lys Gly Val Glu Pro
385                 390                 395                 400

Val Pro Pro Tyr Phe Asp Thr Met Ile Ala Ala Tyr Leu Leu Glu Pro
                405                 410                 415

Asn Glu Lys Lys Phe Asn Leu Asp Asp Leu Ala Leu Lys Phe Leu Gly
            420                 425                 430

Tyr Lys Met Thr Ser Tyr Gln Glu Leu Met Ser Phe Ser Phe Pro Leu
        435                 440                 445

Phe Gly Phe Ser Phe Ala Asp Val Pro Val Glu Lys Ala Ala Asn Tyr
    450                 455                 460

Ser Cys Glu Asp Ala Asp Ile Thr Tyr Arg Leu Tyr Lys Thr Leu Ser
465                 470                 475                 480

Leu Lys Leu His Glu Ala Asp Leu Glu Asn Val Phe Tyr Lys Ile Glu
                485                 490                 495

Met Pro Leu Val Asn Val Leu Ala Arg Met Glu Leu Asn Gly Val Tyr
            500                 505                 510

Val Asp Thr Glu Phe Leu Lys Lys Leu Ser Glu Tyr Gly Lys Lys
        515                 520                 525

Leu Glu Glu Leu Ala Glu Glu Ile Tyr Arg Ile Ala Gly Glu Pro Phe
    530                 535                 540

Asn Ile Asn Ser Pro Lys Gln Val Ser Arg Ile Leu Phe Glu Lys Leu
545                 550                 555                 560

Gly Ile Lys Pro Arg Gly Lys Thr Thr Lys Thr Gly Asp Tyr Ser Thr
                565                 570                 575

Arg Ile Glu Val Leu Glu Glu Leu Ala Gly Glu His Glu Ile Ile Pro
            580                 585                 590

Leu Ile Leu Glu Tyr Arg Lys Ile Gln Lys Leu Lys Ser Thr Tyr Ile
        595                 600                 605

Asp Ala Leu Pro Lys Met Val Asn Pro Lys Thr Gly Arg Ile His Ala
    610                 615                 620

Ser Phe Asn Gln Thr Gly Thr Ala Thr Gly Arg Leu Ser Ser Ser Asp
625                 630                 635                 640

Pro Asn Leu Gln Asn Leu Pro Thr Lys Ser Glu Glu Gly Lys Glu Ile
                645                 650                 655

Arg Lys Ala Ile Val Pro Gln Asp Pro Asn Trp Trp Ile Val Ser Ala
            660                 665                 670

Asp Tyr Ser Gln Ile Glu Leu Arg Ile Leu Ala His Leu Ser Gly Asp
        675                 680                 685

Glu Asn Leu Leu Arg Ala Phe Glu Gly Ile Asp Val His Thr Leu
    690                 695                 700

Thr Ala Ser Arg Ile Phe Asn Val Lys Pro Glu Glu Val Thr Glu Glu
705                 710                 715                 720

Met Arg Arg Ala Gly Lys Met Val Asn Phe Ser Ile Ile Tyr Gly Val
```

```
                        725                 730                 735
Thr Pro Tyr Gly Leu Ser Val Arg Leu Gly Val Pro Val Lys Glu Ala
            740                 745                 750

Glu Lys Met Ile Val Asn Tyr Phe Val Leu Tyr Pro Lys Val Arg Asp
            755                 760                 765

Tyr Ile Gln Arg Val Val Ser Glu Ala Lys Glu Lys Gly Tyr Val Arg
            770                 775                 780

Thr Leu Phe Gly Arg Lys Arg Asp Ile Pro Gln Leu Met Ala Arg Asp
785                 790                 795                 800

Arg Asn Thr Gln Ala Glu Gly Glu Arg Ile Ala Ile Asn Thr Pro Ile
            805                 810                 815

Gln Gly Thr Ala Ala Asp Ile Ile Lys Leu Ala Met Ile Glu Ile Asp
            820                 825                 830

Arg Glu Leu Lys Glu Arg Lys Met Arg Ser Lys Met Ile Ile Gln Val
            835                 840                 845

His Asp Glu Leu Val Phe Glu Val Pro Asn Glu Glu Lys Asp Ala Leu
            850                 855                 860

Val Glu Leu Val Lys Asp Arg Met Thr Asn Val Val Lys Leu Ser Val
865                 870                 875                 880

Pro Leu Glu Val Asp Val Thr Ile Gly Lys Thr Trp Ser
            885                 890

<210> SEQ ID NO 96
<211> LENGTH: 196
<212> TYPE: PRT
<213> ORGANISM: Artificial sequence
<220> FEATURE:
<223> OTHER INFORMATION: Exonucleolytic domain of chimeric thermostable
      DNA polymerase CS5 after second round of mutagenesis Q384A
      mutation

<400> SEQUENCE: 96

Glu Ser Glu Pro Val Gly Tyr Arg Ile Val Lys Asp Leu Val Glu Phe
1               5                   10                  15

Glu Lys Leu Ile Glu Lys Leu Arg Glu Ser Pro Ser Phe Ala Ile Asp
            20                  25                  30

Leu Glu Thr Ser Ser Leu Asp Pro Phe Asp Cys Asp Ile Val Gly Ile
            35                  40                  45

Ser Val Ser Phe Lys Pro Lys Glu Ala Tyr Tyr Ile Pro Leu His His
        50                  55                  60

Arg Asn Ala Gln Asn Leu Asp Glu Lys Val Leu Lys Lys Leu Lys
65                  70                  75                  80

Glu Ile Leu Glu Asp Pro Gly Ala Lys Ile Val Gly Ala Asn Leu Lys
            85                  90                  95

Phe Asp Tyr Lys Val Leu Met Val Lys Gly Val Glu Pro Val Pro Pro
            100                 105                 110

Tyr Phe Asp Thr Met Ile Ala Ala Tyr Leu Leu Glu Pro Asn Glu Lys
            115                 120                 125

Lys Phe Asn Leu Asp Asp Leu Ala Leu Lys Phe Leu Gly Tyr Lys Met
            130                 135                 140

Thr Ser Tyr Gln Glu Leu Met Ser Phe Ser Phe Pro Leu Phe Gly Phe
145                 150                 155                 160

Ser Phe Ala Asp Val Pro Val Glu Lys Ala Ala Asn Tyr Ser Cys Glu
            165                 170                 175

Asp Ala Asp Ile Thr Tyr Arg Leu Tyr Lys Thr Leu Ser Leu Lys Leu
            180                 185                 190
```

His Glu Ala Asp
    195

<210> SEQ ID NO 97
<211> LENGTH: 893
<212> TYPE: PRT
<213> ORGANISM: Artificial sequence
<220> FEATURE:
<223> OTHER INFORMATION: Entire protein of chimeric thermostable DNA
      polymerase CS5 after second round of mutagenesis Q384A mutation

<400> SEQUENCE: 97

Met Lys Ala Met Leu Pro Leu Phe Glu Pro Lys Gly Arg Val Leu Leu
1               5                   10                  15

Val Asp Gly His His Leu Ala Tyr Arg Thr Phe Phe Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Tyr Lys Ala Val Phe
    50                  55                  60

Val Val Phe Asp Ala Lys Ala Pro Ser Phe Arg His Glu Ala Tyr Glu
65                  70                  75                  80

Ala Tyr Lys Ala Gly Arg Ala Pro Thr Pro Glu Asp Phe Pro Arg Gln
                85                  90                  95

Leu Ala Leu Ile Lys Glu Leu Val Asp Leu Leu Gly Phe Thr Arg Leu
            100                 105                 110

Glu Val Pro Gly Phe Glu Ala Asp Asp Val Leu Ala Thr Leu Ala Lys
        115                 120                 125

Lys Ala Glu Arg Glu Gly Tyr Glu Val Arg Ile Leu Thr Ala Asp Arg
    130                 135                 140

Asp Leu Tyr Gln Leu Val Ser Asp Arg Val Ala Val Leu His Pro Glu
145                 150                 155                 160

Gly His Leu Ile Thr Pro Glu Trp Leu Trp Glu Lys Tyr Gly Leu Lys
                165                 170                 175

Pro Glu Gln Trp Val Asp Phe Arg Ala Leu Val Gly Asp Pro Ser Asp
            180                 185                 190

Asn Leu Pro Gly Val Lys Gly Ile Gly Glu Lys Thr Ala Leu Lys Leu
        195                 200                 205

Leu Lys Glu Trp Gly Ser Leu Glu Asn Ile Leu Lys Asn Leu Asp Arg
    210                 215                 220

Val Lys Pro Glu Ser Val Arg Glu Arg Ile Lys Ala His Leu Glu Asp
225                 230                 235                 240

Leu Lys Leu Ser Leu Glu Leu Ser Arg Val Arg Ser Asp Leu Pro Leu
                245                 250                 255

Glu Val Asp Phe Ala Arg Arg Arg Glu Pro Asp Arg Glu Gly Leu Arg
            260                 265                 270

Ala Phe Leu Glu Arg Leu Glu Phe Gly Ser Leu Leu His Glu Phe Gly
        275                 280                 285

Leu Leu Glu Glu Ser Glu Pro Val Gly Tyr Arg Ile Val Lys Asp Leu
    290                 295                 300

Val Glu Phe Glu Lys Leu Ile Glu Lys Leu Arg Glu Ser Pro Ser Phe
305                 310                 315                 320

Ala Ile Asp Leu Glu Thr Ser Ser Leu Asp Pro Phe Asp Cys Asp Ile
                325                 330                 335

Val Gly Ile Ser Val Ser Phe Lys Pro Lys Glu Ala Tyr Tyr Ile Pro

-continued

```
                    340                 345                 350
Leu His His Arg Asn Ala Gln Asn Leu Asp Glu Lys Glu Val Leu Lys
            355                 360                 365
Lys Leu Lys Glu Ile Leu Glu Asp Pro Gly Ala Lys Ile Val Gly Ala
    370                 375                 380
Asn Leu Lys Phe Asp Tyr Lys Val Leu Met Val Lys Gly Val Glu Pro
385                 390                 395                 400
Val Pro Pro Tyr Phe Asp Thr Met Ile Ala Ala Tyr Leu Leu Glu Pro
                405                 410                 415
Asn Glu Lys Lys Phe Asn Leu Asp Asp Leu Ala Leu Lys Phe Leu Gly
            420                 425                 430
Tyr Lys Met Thr Ser Tyr Gln Glu Leu Met Ser Phe Ser Phe Pro Leu
        435                 440                 445
Phe Gly Phe Ser Phe Ala Asp Val Pro Val Glu Lys Ala Ala Asn Tyr
    450                 455                 460
Ser Cys Glu Asp Ala Asp Ile Thr Tyr Arg Leu Tyr Lys Thr Leu Ser
465                 470                 475                 480
Leu Lys Leu His Glu Ala Asp Leu Glu Asn Val Phe Tyr Lys Ile Glu
                485                 490                 495
Met Pro Leu Val Asn Val Leu Ala Arg Met Glu Leu Asn Gly Val Tyr
            500                 505                 510
Val Asp Thr Glu Phe Leu Lys Lys Leu Ser Glu Glu Tyr Gly Lys Lys
        515                 520                 525
Leu Glu Glu Leu Ala Glu Ile Tyr Arg Ile Ala Gly Glu Pro Phe
    530                 535                 540
Asn Ile Asn Ser Pro Lys Gln Val Ser Arg Ile Leu Phe Glu Lys Leu
545                 550                 555                 560
Gly Ile Lys Pro Arg Gly Lys Thr Thr Lys Thr Gly Asp Tyr Ser Thr
                565                 570                 575
Arg Ile Glu Val Leu Glu Glu Leu Ala Gly Glu His Glu Ile Ile Pro
            580                 585                 590
Leu Ile Leu Glu Tyr Arg Lys Ile Gln Lys Leu Lys Ser Thr Tyr Ile
        595                 600                 605
Asp Ala Leu Pro Lys Met Val Asn Pro Lys Thr Gly Arg Ile His Ala
    610                 615                 620
Ser Phe Asn Gln Thr Gly Thr Ala Thr Gly Arg Leu Ser Ser Ser Asp
625                 630                 635                 640
Pro Asn Leu Gln Asn Leu Pro Thr Lys Ser Glu Glu Gly Lys Glu Ile
                645                 650                 655
Arg Lys Ala Ile Val Pro Gln Asp Pro Asn Trp Trp Ile Val Ser Ala
            660                 665                 670
Asp Tyr Ser Gln Ile Glu Leu Arg Ile Leu Ala His Leu Ser Gly Asp
        675                 680                 685
Glu Asn Leu Leu Arg Ala Phe Glu Glu Gly Ile Asp Val His Thr Leu
    690                 695                 700
Thr Ala Ser Arg Ile Phe Asn Val Lys Pro Glu Glu Val Thr Glu Glu
705                 710                 715                 720
Met Arg Arg Ala Gly Lys Met Val Asn Phe Ser Ile Ile Tyr Gly Val
                725                 730                 735
Thr Pro Tyr Gly Leu Ser Val Arg Leu Gly Val Pro Val Lys Glu Ala
            740                 745                 750
Glu Lys Met Ile Val Asn Tyr Phe Val Leu Tyr Pro Lys Val Arg Asp
        755                 760                 765
```

-continued

```
Tyr Ile Gln Arg Val Val Ser Glu Ala Lys Glu Lys Gly Tyr Val Arg
    770                 775                 780

Thr Leu Phe Gly Arg Lys Arg Asp Ile Pro Gln Leu Met Ala Arg Asp
785                 790                 795                 800

Arg Asn Thr Gln Ala Glu Gly Glu Arg Ile Ala Ile Asn Thr Pro Ile
                805                 810                 815

Gln Gly Thr Ala Ala Asp Ile Ile Lys Leu Ala Met Ile Glu Ile Asp
                820                 825                 830

Arg Glu Leu Lys Glu Arg Lys Met Arg Ser Lys Met Ile Ile Gln Val
                835                 840                 845

His Asp Glu Leu Val Phe Glu Val Pro Asn Glu Glu Lys Asp Ala Leu
    850                 855                 860

Val Glu Leu Val Lys Asp Arg Met Thr Asn Val Val Lys Leu Ser Val
865                 870                 875                 880

Pro Leu Glu Val Asp Val Thr Ile Gly Lys Thr Trp Ser
                885                 890
```

<210> SEQ ID NO 98
<211> LENGTH: 196
<212> TYPE: PRT
<213> ORGANISM: Artificial sequence
<220> FEATURE:
<223> OTHER INFORMATION: Exonucleolytic domain of chimeric thermostable
      DNA polymerase CS5 after second round of mutagenesis N385A
      mutation

<400> SEQUENCE: 98

```
Glu Ser Glu Pro Val Gly Tyr Arg Ile Val Lys Asp Leu Val Glu Phe
1               5                   10                  15

Glu Lys Leu Ile Glu Lys Leu Arg Glu Ser Pro Ser Phe Ala Ile Asp
                20                  25                  30

Leu Glu Thr Ser Ser Leu Asp Pro Phe Asp Cys Asp Ile Val Gly Ile
            35                  40                  45

Ser Val Ser Phe Lys Pro Lys Glu Ala Tyr Tyr Ile Pro Leu His His
    50                  55                  60

Arg Asn Ala Gln Asn Leu Asp Glu Lys Glu Val Leu Lys Lys Leu Lys
65                  70                  75                  80

Glu Ile Leu Glu Asp Pro Gly Ala Lys Ile Val Gly Gln Ala Leu Lys
                85                  90                  95

Phe Asp Tyr Lys Val Leu Met Val Lys Gly Val Glu Pro Val Pro Pro
            100                 105                 110

Tyr Phe Asp Thr Met Ile Ala Ala Tyr Leu Leu Glu Pro Asn Glu Lys
        115                 120                 125

Lys Phe Asn Leu Asp Asp Leu Ala Leu Lys Phe Leu Gly Tyr Lys Met
    130                 135                 140

Thr Ser Tyr Gln Glu Leu Met Ser Phe Ser Phe Pro Leu Phe Gly Phe
145                 150                 155                 160

Ser Phe Ala Asp Val Pro Val Glu Lys Ala Ala Asn Tyr Ser Cys Glu
                165                 170                 175

Asp Ala Asp Ile Thr Tyr Arg Leu Tyr Lys Thr Leu Ser Leu Lys Leu
            180                 185                 190

His Glu Ala Asp
        195
```

<210> SEQ ID NO 99
<211> LENGTH: 893

<212> TYPE: PRT
<213> ORGANISM: Artificial sequence
<220> FEATURE:
<223> OTHER INFORMATION: Entire protein of chimeric thermostable DNA
    polymerase CS5 after second round of mutagenesis N385A mutation

<400> SEQUENCE: 99

| Met | Lys | Ala | Met | Leu | Pro | Leu | Phe | Glu | Pro | Lys | Gly | Arg | Val | Leu | Leu |
| 1 | | | | 5 | | | | | 10 | | | | | 15 | |

| Val | Asp | Gly | His | His | Leu | Ala | Tyr | Arg | Thr | Phe | Phe | Ala | Leu | Lys | Gly |
| | | | 20 | | | | | 25 | | | | | 30 | | |

| Leu | Thr | Thr | Ser | Arg | Gly | Glu | Pro | Val | Gln | Ala | Val | Tyr | Gly | Phe | Ala |
| | | 35 | | | | | 40 | | | | | 45 | | | |

| Lys | Ser | Leu | Leu | Lys | Ala | Leu | Lys | Glu | Asp | Gly | Tyr | Lys | Ala | Val | Phe |
| 50 | | | | | 55 | | | | | 60 | | | | | |

| Val | Val | Phe | Asp | Ala | Lys | Ala | Pro | Ser | Phe | Arg | His | Glu | Ala | Tyr | Glu |
| 65 | | | | | 70 | | | | | 75 | | | | | 80 |

| Ala | Tyr | Lys | Ala | Gly | Arg | Ala | Pro | Thr | Pro | Glu | Asp | Phe | Pro | Arg | Gln |
| | | | | 85 | | | | | 90 | | | | | 95 | |

| Leu | Ala | Leu | Ile | Lys | Glu | Leu | Val | Asp | Leu | Leu | Gly | Phe | Thr | Arg | Leu |
| | | | 100 | | | | | 105 | | | | | 110 | | |

| Glu | Val | Pro | Gly | Phe | Glu | Ala | Asp | Asp | Val | Leu | Ala | Thr | Leu | Ala | Lys |
| | | 115 | | | | | 120 | | | | | 125 | | | |

| Lys | Ala | Glu | Arg | Glu | Gly | Tyr | Glu | Val | Arg | Ile | Leu | Thr | Ala | Asp | Arg |
| 130 | | | | | 135 | | | | | 140 | | | | | |

| Asp | Leu | Tyr | Gln | Leu | Val | Ser | Asp | Arg | Val | Ala | Val | Leu | His | Pro | Glu |
| 145 | | | | | 150 | | | | | 155 | | | | | 160 |

| Gly | His | Leu | Ile | Thr | Pro | Glu | Trp | Leu | Trp | Glu | Lys | Tyr | Gly | Leu | Lys |
| | | | | 165 | | | | | 170 | | | | | 175 | |

| Pro | Glu | Gln | Trp | Val | Asp | Phe | Arg | Ala | Leu | Val | Gly | Asp | Pro | Ser | Asp |
| | | | 180 | | | | | 185 | | | | | 190 | | |

| Asn | Leu | Pro | Gly | Val | Lys | Gly | Ile | Gly | Glu | Lys | Thr | Ala | Leu | Lys | Leu |
| | | 195 | | | | | 200 | | | | | 205 | | | |

| Leu | Lys | Glu | Trp | Gly | Ser | Leu | Glu | Asn | Ile | Leu | Lys | Asn | Leu | Asp | Arg |
| 210 | | | | | 215 | | | | | 220 | | | | | |

| Val | Lys | Pro | Glu | Ser | Val | Arg | Glu | Arg | Ile | Lys | Ala | His | Leu | Glu | Asp |
| 225 | | | | | 230 | | | | | 235 | | | | | 240 |

| Leu | Lys | Leu | Ser | Leu | Glu | Leu | Ser | Arg | Val | Arg | Ser | Asp | Leu | Pro | Leu |
| | | | | 245 | | | | | 250 | | | | | 255 | |

| Glu | Val | Asp | Phe | Ala | Arg | Arg | Arg | Glu | Pro | Asp | Arg | Glu | Gly | Leu | Arg |
| | | | 260 | | | | | 265 | | | | | 270 | | |

| Ala | Phe | Leu | Glu | Arg | Leu | Glu | Phe | Gly | Ser | Leu | Leu | His | Glu | Phe | Gly |
| | | 275 | | | | | 280 | | | | | 285 | | | |

| Leu | Leu | Glu | Glu | Ser | Glu | Pro | Val | Gly | Tyr | Arg | Ile | Val | Lys | Asp | Leu |
| 290 | | | | | 295 | | | | | 300 | | | | | |

| Val | Glu | Phe | Glu | Lys | Leu | Ile | Glu | Lys | Leu | Arg | Glu | Ser | Pro | Ser | Phe |
| 305 | | | | | 310 | | | | | 315 | | | | | 320 |

| Ala | Ile | Asp | Leu | Glu | Thr | Ser | Ser | Leu | Asp | Pro | Phe | Asp | Cys | Asp | Ile |
| | | | | 325 | | | | | 330 | | | | | 335 | |

| Val | Gly | Ile | Ser | Val | Ser | Phe | Lys | Pro | Lys | Glu | Ala | Tyr | Tyr | Ile | Pro |
| | | | 340 | | | | | 345 | | | | | 350 | | |

| Leu | His | His | Arg | Asn | Ala | Gln | Asn | Leu | Asp | Glu | Lys | Glu | Val | Leu | Lys |
| | | 355 | | | | | 360 | | | | | 365 | | | |

| Lys | Leu | Lys | Glu | Ile | Leu | Glu | Asp | Pro | Gly | Ala | Lys | Ile | Val | Gly | Gln |
| 370 | | | | | 375 | | | | | 380 | | | | | |

```
Ala Leu Lys Phe Asp Tyr Lys Val Leu Met Val Lys Gly Val Glu Pro
385                 390                 395                 400

Val Pro Pro Tyr Phe Asp Thr Met Ile Ala Ala Tyr Leu Leu Glu Pro
                405                 410                 415

Asn Glu Lys Lys Phe Asn Leu Asp Asp Leu Ala Leu Lys Phe Leu Gly
                420                 425                 430

Tyr Lys Met Thr Ser Tyr Gln Glu Leu Met Ser Phe Ser Phe Pro Leu
            435                 440                 445

Phe Gly Phe Ser Phe Ala Asp Val Pro Val Glu Lys Ala Ala Asn Tyr
        450                 455                 460

Ser Cys Glu Asp Ala Asp Ile Thr Tyr Arg Leu Tyr Lys Thr Leu Ser
465                 470                 475                 480

Leu Lys Leu His Glu Ala Asp Leu Glu Asn Val Phe Tyr Lys Ile Glu
                485                 490                 495

Met Pro Leu Val Asn Val Leu Ala Arg Met Glu Leu Asn Gly Val Tyr
                500                 505                 510

Val Asp Thr Glu Phe Leu Lys Lys Leu Ser Glu Glu Tyr Gly Lys Lys
            515                 520                 525

Leu Glu Glu Leu Ala Glu Glu Ile Tyr Arg Ile Ala Gly Glu Pro Phe
        530                 535                 540

Asn Ile Asn Ser Pro Lys Gln Val Ser Arg Ile Leu Phe Glu Lys Leu
545                 550                 555                 560

Gly Ile Lys Pro Arg Gly Lys Thr Thr Lys Thr Gly Asp Tyr Ser Thr
                565                 570                 575

Arg Ile Glu Val Leu Glu Glu Leu Ala Gly Glu His Glu Ile Ile Pro
                580                 585                 590

Leu Ile Leu Glu Tyr Arg Lys Ile Gln Lys Leu Lys Ser Thr Tyr Ile
            595                 600                 605

Asp Ala Leu Pro Lys Met Val Asn Pro Lys Thr Gly Arg Ile His Ala
        610                 615                 620

Ser Phe Asn Gln Thr Gly Thr Ala Thr Gly Arg Leu Ser Ser Ser Asp
625                 630                 635                 640

Pro Asn Leu Gln Asn Leu Pro Thr Lys Ser Glu Gly Lys Glu Ile
                645                 650                 655

Arg Lys Ala Ile Val Pro Gln Asp Pro Asn Trp Trp Ile Val Ser Ala
                660                 665                 670

Asp Tyr Ser Gln Ile Glu Leu Arg Ile Leu Ala His Leu Ser Gly Asp
            675                 680                 685

Glu Asn Leu Leu Arg Ala Phe Glu Glu Gly Ile Asp Val His Thr Leu
        690                 695                 700

Thr Ala Ser Arg Ile Phe Asn Val Lys Pro Glu Glu Val Thr Glu Glu
705                 710                 715                 720

Met Arg Arg Ala Gly Lys Met Val Asn Phe Ser Ile Ile Tyr Gly Val
                725                 730                 735

Thr Pro Tyr Gly Leu Ser Val Arg Leu Gly Val Pro Val Lys Glu Ala
                740                 745                 750

Glu Lys Met Ile Val Asn Tyr Phe Val Leu Tyr Pro Lys Val Arg Asp
            755                 760                 765

Tyr Ile Gln Arg Val Val Ser Glu Ala Lys Glu Lys Gly Tyr Val Arg
        770                 775                 780

Thr Leu Phe Gly Arg Lys Arg Asp Ile Pro Gln Leu Met Ala Arg Asp
785                 790                 795                 800
```

```
Arg Asn Thr Gln Ala Glu Gly Glu Arg Ile Ala Ile Asn Thr Pro Ile
                805                 810                 815

Gln Gly Thr Ala Ala Asp Ile Ile Lys Leu Ala Met Ile Glu Ile Asp
            820                 825                 830

Arg Glu Leu Lys Glu Arg Lys Met Arg Ser Lys Met Ile Ile Gln Val
            835                 840                 845

His Asp Glu Leu Val Phe Glu Val Pro Asn Glu Glu Lys Asp Ala Leu
    850                 855                 860

Val Glu Leu Val Lys Asp Arg Met Thr Asn Val Val Lys Leu Ser Val
865                 870                 875                 880

Pro Leu Glu Val Asp Val Thr Ile Gly Lys Thr Trp Ser
            885                 890
```

```
<210> SEQ ID NO 100
<211> LENGTH: 196
<212> TYPE: PRT
<213> ORGANISM: Artificial sequence
<220> FEATURE:
<223> OTHER INFORMATION: Exonucleolytic domain of chimeric thermostable
      DNA polymerase CS5 after second round of mutagenesis Q384A N385A
      mutation

<400> SEQUENCE: 100

Glu Ser Glu Pro Val Gly Tyr Arg Ile Val Lys Asp Leu Val Glu Phe
1               5                   10                  15

Glu Lys Leu Ile Glu Lys Leu Arg Glu Ser Pro Ser Phe Ala Ile Asp
            20                  25                  30

Leu Glu Thr Ser Ser Leu Asp Pro Phe Asp Cys Asp Ile Val Gly Ile
        35                  40                  45

Ser Val Ser Phe Lys Pro Lys Glu Ala Tyr Tyr Ile Pro Leu His His
    50                  55                  60

Arg Asn Ala Gln Asn Leu Asp Glu Lys Glu Val Leu Lys Lys Leu Lys
65                  70                  75                  80

Glu Ile Leu Glu Asp Pro Gly Ala Lys Ile Val Gly Ala Ala Leu Lys
                85                  90                  95

Phe Asp Tyr Lys Val Leu Met Val Lys Gly Val Glu Pro Val Pro Pro
            100                 105                 110

Tyr Phe Asp Thr Met Ile Ala Ala Tyr Leu Leu Glu Pro Asn Glu Lys
        115                 120                 125

Lys Phe Asn Leu Asp Asp Leu Ala Leu Lys Phe Leu Gly Tyr Lys Met
130                 135                 140

Thr Ser Tyr Gln Glu Leu Met Ser Phe Ser Phe Pro Leu Phe Gly Phe
145                 150                 155                 160

Ser Phe Ala Asp Val Pro Val Glu Lys Ala Ala Asn Tyr Ser Cys Glu
                165                 170                 175

Asp Ala Asp Ile Thr Tyr Arg Leu Tyr Lys Thr Leu Ser Leu Lys Leu
            180                 185                 190

His Glu Ala Asp
        195
```

```
<210> SEQ ID NO 101
<211> LENGTH: 893
<212> TYPE: PRT
<213> ORGANISM: Artificial sequence
<220> FEATURE:
<223> OTHER INFORMATION: Entire protein of chimeric thermostable DNA
      polymerase CS5 after second round of mutagenesis Q384A N385A
      mutation
```

<400> SEQUENCE: 101

```
Met Lys Ala Met Leu Pro Leu Phe Glu Pro Lys Gly Arg Val Leu Leu
1               5                   10                  15

Val Asp Gly His His Leu Ala Tyr Arg Thr Phe Phe Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Tyr Lys Ala Val Phe
    50                  55                  60

Val Val Phe Asp Ala Lys Ala Pro Ser Phe Arg His Glu Ala Tyr Glu
65                  70                  75                  80

Ala Tyr Lys Ala Gly Arg Ala Pro Thr Pro Glu Asp Phe Pro Arg Gln
                85                  90                  95

Leu Ala Leu Ile Lys Glu Leu Val Asp Leu Leu Gly Phe Thr Arg Leu
            100                 105                 110

Glu Val Pro Gly Phe Glu Ala Asp Asp Val Leu Ala Thr Leu Ala Lys
            115                 120                 125

Lys Ala Glu Arg Glu Gly Tyr Glu Val Arg Ile Leu Thr Ala Asp Arg
130                 135                 140

Asp Leu Tyr Gln Leu Val Ser Asp Arg Val Ala Val Leu His Pro Glu
145                 150                 155                 160

Gly His Leu Ile Thr Pro Glu Trp Leu Trp Glu Lys Tyr Gly Leu Lys
                165                 170                 175

Pro Glu Gln Trp Val Asp Phe Arg Ala Leu Val Gly Asp Pro Ser Asp
            180                 185                 190

Asn Leu Pro Gly Val Lys Gly Ile Gly Glu Lys Thr Ala Leu Lys Leu
            195                 200                 205

Leu Lys Glu Trp Gly Ser Leu Glu Asn Ile Leu Lys Asn Leu Asp Arg
210                 215                 220

Val Lys Pro Glu Ser Val Arg Glu Arg Ile Lys Ala His Leu Glu Asp
225                 230                 235                 240

Leu Lys Leu Ser Leu Glu Leu Ser Arg Val Arg Ser Asp Leu Pro Leu
                245                 250                 255

Glu Val Asp Phe Ala Arg Arg Glu Pro Asp Arg Glu Gly Leu Arg
            260                 265                 270

Ala Phe Leu Glu Arg Leu Glu Phe Gly Ser Leu Leu His Glu Phe Gly
            275                 280                 285

Leu Leu Glu Glu Ser Glu Pro Val Gly Tyr Arg Ile Val Lys Asp Leu
            290                 295                 300

Val Glu Phe Glu Lys Leu Ile Glu Lys Leu Arg Glu Ser Pro Ser Phe
305                 310                 315                 320

Ala Ile Asp Leu Glu Thr Ser Ser Leu Asp Pro Phe Asp Cys Asp Ile
                325                 330                 335

Val Gly Ile Ser Val Ser Phe Lys Pro Lys Glu Ala Tyr Tyr Ile Pro
            340                 345                 350

Leu His His Arg Asn Ala Gln Asn Leu Asp Glu Lys Glu Val Leu Lys
            355                 360                 365

Lys Leu Lys Glu Ile Leu Glu Asp Pro Gly Ala Lys Ile Val Gly Ala
        370                 375                 380

Ala Leu Lys Phe Asp Tyr Lys Val Leu Met Val Lys Gly Val Glu Pro
385                 390                 395                 400

Val Pro Pro Tyr Phe Asp Thr Met Ile Ala Ala Tyr Leu Leu Glu Pro
                405                 410                 415
```

```
Asn Glu Lys Lys Phe Asn Leu Asp Asp Leu Ala Leu Lys Phe Leu Gly
            420                 425                 430
Tyr Lys Met Thr Ser Tyr Gln Glu Leu Met Ser Phe Ser Phe Pro Leu
            435                 440                 445
Phe Gly Phe Ser Phe Ala Asp Val Pro Val Glu Lys Ala Ala Asn Tyr
            450                 455                 460
Ser Cys Glu Asp Ala Asp Ile Thr Tyr Arg Leu Tyr Lys Thr Leu Ser
465                 470                 475                 480
Leu Lys Leu His Glu Ala Asp Leu Glu Asn Val Phe Tyr Lys Ile Glu
                485                 490                 495
Met Pro Leu Val Asn Val Leu Ala Arg Met Glu Leu Asn Gly Val Tyr
            500                 505                 510
Val Asp Thr Glu Phe Leu Lys Lys Leu Ser Glu Glu Tyr Gly Lys Lys
            515                 520                 525
Leu Glu Glu Leu Ala Glu Glu Ile Tyr Arg Ile Ala Gly Glu Pro Phe
            530                 535                 540
Asn Ile Asn Ser Pro Lys Gln Val Ser Arg Ile Leu Phe Glu Lys Leu
545                 550                 555                 560
Gly Ile Lys Pro Arg Gly Lys Thr Thr Lys Thr Gly Asp Tyr Ser Thr
                565                 570                 575
Arg Ile Glu Val Leu Glu Glu Leu Ala Gly Glu His Glu Ile Ile Pro
            580                 585                 590
Leu Ile Leu Glu Tyr Arg Lys Ile Gln Lys Leu Lys Ser Thr Tyr Ile
            595                 600                 605
Asp Ala Leu Pro Lys Met Val Asn Pro Lys Thr Gly Arg Ile His Ala
        610                 615                 620
Ser Phe Asn Gln Thr Gly Thr Ala Thr Gly Arg Leu Ser Ser Ser Asp
625                 630                 635                 640
Pro Asn Leu Gln Asn Leu Pro Thr Lys Ser Glu Glu Gly Lys Glu Ile
                645                 650                 655
Arg Lys Ala Ile Val Pro Gln Asp Pro Asn Trp Trp Ile Val Ser Ala
            660                 665                 670
Asp Tyr Ser Gln Ile Glu Leu Arg Ile Leu Ala His Leu Ser Gly Asp
        675                 680                 685
Glu Asn Leu Leu Arg Ala Phe Glu Glu Gly Ile Asp Val His Thr Leu
    690                 695                 700
Thr Ala Ser Arg Ile Phe Asn Val Lys Pro Glu Glu Val Thr Glu Glu
705                 710                 715                 720
Met Arg Arg Ala Gly Lys Met Val Asn Phe Ser Ile Ile Tyr Gly Val
                725                 730                 735
Thr Pro Tyr Gly Leu Ser Val Arg Leu Gly Val Pro Val Lys Glu Ala
            740                 745                 750
Glu Lys Met Ile Val Asn Tyr Phe Val Leu Tyr Pro Lys Val Arg Asp
            755                 760                 765
Tyr Ile Gln Arg Val Val Ser Glu Ala Lys Glu Lys Gly Tyr Val Arg
        770                 775                 780
Thr Leu Phe Gly Arg Lys Arg Asp Ile Pro Gln Leu Met Ala Arg Asp
785                 790                 795                 800
Arg Asn Thr Gln Ala Glu Gly Glu Arg Ile Ala Ile Asn Thr Pro Ile
                805                 810                 815
Gln Gly Thr Ala Ala Asp Ile Ile Lys Leu Ala Met Ile Glu Ile Asp
            820                 825                 830
```

Arg Glu Leu Lys Glu Arg Lys Met Arg Ser Lys Met Ile Ile Gln Val
        835                 840                 845

His Asp Glu Leu Val Phe Glu Val Pro Asn Glu Glu Lys Asp Ala Leu
    850                 855                 860

Val Glu Leu Val Lys Asp Arg Met Thr Asn Val Val Lys Leu Ser Val
865                 870                 875                 880

Pro Leu Glu Val Asp Val Thr Ile Gly Lys Thr Trp Ser
            885                 890

<210> SEQ ID NO 102
<211> LENGTH: 196
<212> TYPE: PRT
<213> ORGANISM: Artificial sequence
<220> FEATURE:
<223> OTHER INFORMATION: Exonucleolytic domain of chimeric thermostable
      DNA polymerase CS5 after second round of mutagenesis D389E
      mutation

<400> SEQUENCE: 102

Glu Ser Glu Pro Val Gly Tyr Arg Ile Val Lys Asp Leu Val Glu Phe
1               5                   10                  15

Glu Lys Leu Ile Glu Lys Leu Arg Glu Ser Pro Ser Phe Ala Ile Asp
            20                  25                  30

Leu Glu Thr Ser Ser Leu Asp Pro Phe Asp Cys Asp Ile Val Gly Ile
        35                  40                  45

Ser Val Ser Phe Lys Pro Lys Glu Ala Tyr Tyr Ile Pro Leu His His
    50                  55                  60

Arg Asn Ala Gln Asn Leu Asp Glu Lys Glu Val Leu Lys Lys Leu Lys
65                  70                  75                  80

Glu Ile Leu Glu Asp Pro Gly Ala Lys Ile Val Gly Gln Asn Leu Lys
                85                  90                  95

Phe Glu Tyr Lys Val Leu Met Val Lys Gly Val Glu Pro Val Pro Pro
            100                 105                 110

Tyr Phe Asp Thr Met Ile Ala Ala Tyr Leu Leu Glu Pro Asn Glu Lys
        115                 120                 125

Lys Phe Asn Leu Asp Asp Leu Ala Leu Lys Phe Leu Gly Tyr Lys Met
    130                 135                 140

Thr Ser Tyr Gln Glu Leu Met Ser Phe Ser Phe Pro Leu Phe Gly Phe
145                 150                 155                 160

Ser Phe Ala Asp Val Pro Val Glu Lys Ala Ala Asn Tyr Ser Cys Glu
                165                 170                 175

Asp Ala Asp Ile Thr Tyr Arg Leu Tyr Lys Thr Leu Ser Leu Lys Leu
            180                 185                 190

His Glu Ala Asp
        195

<210> SEQ ID NO 103
<211> LENGTH: 893
<212> TYPE: PRT
<213> ORGANISM: Artificial sequence
<220> FEATURE:
<223> OTHER INFORMATION: Entire protein of chimeric thermostable DNA
      polymerase CS5 after second round of mutagenesis D389E mutation

<400> SEQUENCE: 103

Met Lys Ala Met Leu Pro Leu Phe Glu Pro Lys Gly Arg Val Leu Leu
1               5                   10                  15

Val Asp Gly His His Leu Ala Tyr Arg Thr Phe Phe Ala Leu Lys Gly
            20                  25                  30

-continued

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Tyr Lys Ala Val Phe
    50                  55                  60

Val Val Phe Asp Ala Lys Ala Pro Ser Phe Arg His Glu Ala Tyr Glu
65                  70                  75                  80

Ala Tyr Lys Ala Gly Arg Ala Pro Thr Pro Glu Asp Phe Pro Arg Gln
                85                  90                  95

Leu Ala Leu Ile Lys Glu Leu Val Asp Leu Leu Gly Phe Thr Arg Leu
            100                 105                 110

Glu Val Pro Gly Phe Glu Ala Asp Asp Val Leu Ala Thr Leu Ala Lys
            115                 120                 125

Lys Ala Glu Arg Glu Gly Tyr Glu Val Arg Ile Leu Thr Ala Asp Arg
            130                 135                 140

Asp Leu Tyr Gln Leu Val Ser Asp Arg Val Ala Val Leu His Pro Glu
145                 150                 155                 160

Gly His Leu Ile Thr Pro Glu Trp Leu Trp Glu Lys Tyr Gly Leu Lys
                165                 170                 175

Pro Glu Gln Trp Val Asp Phe Arg Ala Leu Val Gly Asp Pro Ser Asp
                180                 185                 190

Asn Leu Pro Gly Val Lys Gly Ile Gly Glu Lys Thr Ala Leu Lys Leu
            195                 200                 205

Leu Lys Glu Trp Gly Ser Leu Glu Asn Ile Leu Lys Asn Leu Asp Arg
            210                 215                 220

Val Lys Pro Glu Ser Val Arg Glu Arg Ile Lys Ala His Leu Glu Asp
225                 230                 235                 240

Leu Lys Leu Ser Leu Glu Leu Ser Arg Val Arg Ser Asp Leu Pro Leu
                245                 250                 255

Glu Val Asp Phe Ala Arg Arg Arg Glu Pro Asp Arg Glu Gly Leu Arg
                260                 265                 270

Ala Phe Leu Glu Arg Leu Glu Phe Gly Ser Leu Leu His Glu Phe Gly
            275                 280                 285

Leu Leu Glu Glu Ser Glu Pro Val Gly Tyr Arg Ile Val Lys Asp Leu
            290                 295                 300

Val Glu Phe Glu Lys Leu Ile Glu Lys Leu Arg Glu Ser Pro Ser Phe
305                 310                 315                 320

Ala Ile Asp Leu Glu Thr Ser Ser Leu Asp Pro Phe Asp Cys Asp Ile
                325                 330                 335

Val Gly Ile Ser Val Ser Phe Lys Pro Lys Glu Ala Tyr Tyr Ile Pro
            340                 345                 350

Leu His His Arg Asn Ala Gln Asn Leu Asp Glu Lys Glu Val Leu Lys
            355                 360                 365

Lys Leu Lys Glu Ile Leu Glu Asp Pro Gly Ala Lys Ile Val Gly Gln
            370                 375                 380

Asn Leu Lys Phe Glu Tyr Lys Val Leu Met Val Lys Gly Val Glu Pro
385                 390                 395                 400

Val Pro Pro Tyr Phe Asp Thr Met Ile Ala Ala Tyr Leu Leu Glu Pro
                405                 410                 415

Asn Glu Lys Lys Phe Asn Leu Asp Asp Leu Ala Leu Lys Phe Leu Gly
            420                 425                 430

Tyr Lys Met Thr Ser Tyr Gln Glu Leu Met Ser Phe Ser Phe Pro Leu
            435                 440                 445

```
Phe Gly Phe Ser Phe Ala Asp Val Pro Val Glu Lys Ala Ala Asn Tyr
    450                 455                 460

Ser Cys Glu Asp Ala Asp Ile Thr Tyr Arg Leu Tyr Lys Thr Leu Ser
465                 470                 475                 480

Leu Lys Leu His Glu Ala Asp Leu Glu Asn Val Phe Tyr Lys Ile Glu
                485                 490                 495

Met Pro Leu Val Asn Val Leu Ala Arg Met Glu Leu Asn Gly Val Tyr
            500                 505                 510

Val Asp Thr Glu Phe Leu Lys Lys Leu Ser Glu Glu Tyr Gly Lys Lys
        515                 520                 525

Leu Glu Glu Leu Ala Glu Glu Ile Tyr Arg Ile Ala Gly Glu Pro Phe
530                 535                 540

Asn Ile Asn Ser Pro Lys Gln Val Ser Arg Ile Leu Phe Glu Lys Leu
545                 550                 555                 560

Gly Ile Lys Pro Arg Gly Lys Thr Thr Lys Thr Gly Asp Tyr Ser Thr
                565                 570                 575

Arg Ile Glu Val Leu Glu Glu Leu Ala Gly Glu His Glu Ile Ile Pro
            580                 585                 590

Leu Ile Leu Glu Tyr Arg Lys Ile Gln Lys Leu Lys Ser Thr Tyr Ile
        595                 600                 605

Asp Ala Leu Pro Lys Met Val Asn Pro Lys Thr Gly Arg Ile His Ala
610                 615                 620

Ser Phe Asn Gln Thr Gly Thr Ala Thr Gly Arg Leu Ser Ser Ser Asp
625                 630                 635                 640

Pro Asn Leu Gln Asn Leu Pro Thr Lys Ser Glu Glu Gly Lys Glu Ile
                645                 650                 655

Arg Lys Ala Ile Val Pro Gln Asp Pro Asn Trp Trp Ile Val Ser Ala
            660                 665                 670

Asp Tyr Ser Gln Ile Glu Leu Arg Ile Leu Ala His Leu Ser Gly Asp
        675                 680                 685

Glu Asn Leu Leu Arg Ala Phe Glu Glu Gly Ile Asp Val His Thr Leu
690                 695                 700

Thr Ala Ser Arg Ile Phe Asn Val Lys Pro Glu Glu Val Thr Glu Glu
705                 710                 715                 720

Met Arg Arg Ala Gly Lys Met Val Asn Phe Ser Ile Ile Tyr Gly Val
                725                 730                 735

Thr Pro Tyr Gly Leu Ser Val Arg Leu Gly Val Pro Val Lys Glu Ala
            740                 745                 750

Glu Lys Met Ile Val Asn Tyr Phe Val Leu Tyr Pro Lys Val Arg Asp
        755                 760                 765

Tyr Ile Gln Arg Val Val Ser Glu Ala Lys Glu Lys Gly Tyr Val Arg
770                 775                 780

Thr Leu Phe Gly Arg Lys Arg Asp Ile Pro Gln Leu Met Ala Arg Asp
785                 790                 795                 800

Arg Asn Thr Gln Ala Glu Gly Glu Arg Ile Ala Ile Asn Thr Pro Ile
                805                 810                 815

Gln Gly Thr Ala Ala Asp Ile Ile Lys Leu Ala Met Ile Glu Ile Asp
            820                 825                 830

Arg Glu Leu Lys Glu Arg Lys Met Arg Ser Lys Met Ile Ile Gln Val
        835                 840                 845

His Asp Glu Leu Val Phe Glu Val Pro Asn Glu Glu Lys Asp Ala Leu
850                 855                 860

Val Glu Leu Val Lys Asp Arg Met Thr Asn Val Val Lys Leu Ser Val
```

```
                865                 870                 875                 880
Pro Leu Glu Val Asp Val Thr Ile Gly Lys Thr Trp Ser
                    885                 890

<210> SEQ ID NO 104
<211> LENGTH: 196
<212> TYPE: PRT
<213> ORGANISM: Artificial sequence
<220> FEATURE:
<223> OTHER INFORMATION: Exonucleolytic domain of chimeric thermostable
      DNA polymerase CS5 after second round of mutagenesis Y464A
      mutation

<400> SEQUENCE: 104

Glu Ser Glu Pro Val Gly Tyr Arg Ile Val Lys Asp Leu Val Glu Phe
1               5                   10                  15

Glu Lys Leu Ile Glu Lys Leu Arg Glu Ser Pro Ser Phe Ala Ile Asp
            20                  25                  30

Leu Glu Thr Ser Ser Leu Asp Pro Phe Asp Cys Asp Ile Val Gly Ile
        35                  40                  45

Ser Val Ser Phe Lys Pro Lys Glu Ala Tyr Tyr Ile Pro Leu His His
50                  55                  60

Arg Asn Ala Gln Asn Leu Asp Glu Lys Glu Val Leu Lys Lys Leu Lys
65                  70                  75                  80

Glu Ile Leu Glu Asp Pro Gly Ala Lys Ile Val Gly Gln Asn Leu Lys
                85                  90                  95

Phe Asp Tyr Lys Val Leu Met Val Lys Gly Val Glu Pro Val Pro Pro
            100                 105                 110

Tyr Phe Asp Thr Met Ile Ala Ala Tyr Leu Leu Glu Pro Asn Glu Lys
        115                 120                 125

Lys Phe Asn Leu Asp Asp Leu Ala Leu Lys Phe Leu Gly Tyr Lys Met
130                 135                 140

Thr Ser Tyr Gln Glu Leu Met Ser Phe Ser Phe Pro Leu Phe Gly Phe
145                 150                 155                 160

Ser Phe Ala Asp Val Pro Val Glu Lys Ala Ala Asn Ala Ser Cys Glu
                165                 170                 175

Asp Ala Asp Ile Thr Tyr Arg Leu Tyr Lys Thr Leu Ser Leu Lys Leu
            180                 185                 190

His Glu Ala Asp
        195

<210> SEQ ID NO 105
<211> LENGTH: 893
<212> TYPE: PRT
<213> ORGANISM: Artificial sequence
<220> FEATURE:
<223> OTHER INFORMATION: Entire protein of chimeric thermostable DNA
      polymerase CS5 after second round of mutagenesis Y464A mutation

<400> SEQUENCE: 105

Met Lys Ala Met Leu Pro Leu Phe Glu Pro Lys Gly Arg Val Leu Leu
1               5                   10                  15

Val Asp Gly His His Leu Ala Tyr Arg Thr Phe Phe Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Tyr Lys Ala Val Phe
50                  55                  60
```

```
Val Val Phe Asp Ala Lys Ala Pro Ser Phe Arg His Glu Ala Tyr Glu
 65                  70                  75                  80

Ala Tyr Lys Ala Gly Arg Ala Pro Thr Pro Glu Asp Phe Pro Arg Gln
                 85                  90                  95

Leu Ala Leu Ile Lys Glu Leu Val Asp Leu Leu Gly Phe Thr Arg Leu
            100                 105                 110

Glu Val Pro Gly Phe Glu Ala Asp Asp Val Leu Ala Thr Leu Ala Lys
            115                 120                 125

Lys Ala Glu Arg Glu Gly Tyr Glu Val Arg Ile Leu Thr Ala Asp Arg
130                 135                 140

Asp Leu Tyr Gln Leu Val Ser Asp Arg Val Ala Val Leu His Pro Glu
145                 150                 155                 160

Gly His Leu Ile Thr Pro Glu Trp Leu Trp Glu Lys Tyr Gly Leu Lys
                165                 170                 175

Pro Glu Gln Trp Val Asp Phe Arg Ala Leu Val Gly Asp Pro Ser Asp
            180                 185                 190

Asn Leu Pro Gly Val Lys Gly Ile Gly Glu Lys Thr Ala Leu Lys Leu
            195                 200                 205

Leu Lys Glu Trp Gly Ser Leu Glu Asn Ile Leu Lys Asn Leu Asp Arg
210                 215                 220

Val Lys Pro Glu Ser Val Arg Glu Arg Ile Lys Ala His Leu Glu Asp
225                 230                 235                 240

Leu Lys Leu Ser Leu Glu Leu Ser Arg Val Arg Ser Asp Leu Pro Leu
                245                 250                 255

Glu Val Asp Phe Ala Arg Arg Arg Glu Pro Asp Arg Glu Gly Leu Arg
            260                 265                 270

Ala Phe Leu Glu Arg Leu Glu Phe Gly Ser Leu Leu His Glu Phe Gly
            275                 280                 285

Leu Leu Glu Glu Ser Glu Pro Val Gly Tyr Arg Ile Val Lys Asp Leu
290                 295                 300

Val Glu Phe Glu Lys Leu Ile Glu Lys Leu Arg Glu Ser Pro Ser Phe
305                 310                 315                 320

Ala Ile Asp Leu Glu Thr Ser Ser Leu Asp Pro Phe Asp Cys Asp Ile
                325                 330                 335

Val Gly Ile Ser Val Ser Phe Lys Pro Lys Glu Ala Tyr Tyr Ile Pro
            340                 345                 350

Leu His His Arg Asn Ala Gln Asn Leu Asp Glu Lys Glu Val Leu Lys
            355                 360                 365

Lys Leu Lys Glu Ile Leu Glu Asp Pro Gly Ala Lys Ile Val Gly Gln
370                 375                 380

Asn Leu Lys Phe Asp Tyr Lys Val Leu Met Val Lys Gly Val Glu Pro
385                 390                 395                 400

Val Pro Pro Tyr Phe Asp Thr Met Ile Ala Ala Tyr Leu Leu Glu Pro
                405                 410                 415

Asn Glu Lys Lys Phe Asn Leu Asp Asp Leu Ala Leu Lys Phe Leu Gly
            420                 425                 430

Tyr Lys Met Thr Ser Tyr Gln Glu Leu Met Ser Phe Ser Phe Pro Leu
            435                 440                 445

Phe Gly Phe Ser Phe Ala Asp Val Pro Val Glu Lys Ala Ala Asn Ala
450                 455                 460

Ser Cys Glu Asp Ala Asp Ile Thr Tyr Arg Leu Tyr Lys Thr Leu Ser
465                 470                 475                 480

Leu Lys Leu His Glu Ala Asp Leu Glu Asn Val Phe Tyr Lys Ile Glu
```

```
                   485                 490                 495
Met Pro Leu Val Asn Val Leu Ala Arg Met Glu Leu Asn Gly Val Tyr
                500                 505                 510
Val Asp Thr Glu Phe Leu Lys Lys Leu Ser Glu Tyr Gly Lys Lys
            515                 520                 525
Leu Glu Glu Leu Ala Glu Ile Tyr Arg Ile Ala Gly Glu Pro Phe
        530                 535                 540
Asn Ile Asn Ser Pro Lys Gln Val Ser Arg Ile Leu Phe Glu Lys Leu
545                 550                 555                 560
Gly Ile Lys Pro Arg Gly Lys Thr Thr Lys Thr Gly Asp Tyr Ser Thr
                565                 570                 575
Arg Ile Glu Val Leu Glu Glu Leu Ala Gly Glu His Glu Ile Ile Pro
                580                 585                 590
Leu Ile Leu Glu Tyr Arg Lys Ile Gln Lys Leu Lys Ser Thr Tyr Ile
                595                 600                 605
Asp Ala Leu Pro Lys Met Val Asn Pro Lys Thr Gly Arg Ile His Ala
        610                 615                 620
Ser Phe Asn Gln Thr Gly Thr Ala Thr Gly Arg Leu Ser Ser Ser Asp
625                 630                 635                 640
Pro Asn Leu Gln Asn Leu Pro Thr Lys Ser Glu Glu Gly Lys Glu Ile
                645                 650                 655
Arg Lys Ala Ile Val Pro Gln Asp Pro Asn Trp Trp Ile Val Ser Ala
                660                 665                 670
Asp Tyr Ser Gln Ile Glu Leu Arg Ile Leu Ala His Leu Ser Gly Asp
                675                 680                 685
Glu Asn Leu Leu Arg Ala Phe Glu Glu Gly Ile Asp Val His Thr Leu
        690                 695                 700
Thr Ala Ser Arg Ile Phe Asn Val Lys Pro Glu Glu Val Thr Glu Glu
705                 710                 715                 720
Met Arg Arg Ala Gly Lys Met Val Asn Phe Ser Ile Ile Tyr Gly Val
                725                 730                 735
Thr Pro Tyr Gly Leu Ser Val Arg Leu Gly Val Pro Val Lys Glu Ala
            740                 745                 750
Glu Lys Met Ile Val Asn Tyr Phe Val Leu Tyr Pro Lys Val Arg Asp
            755                 760                 765
Tyr Ile Gln Arg Val Val Ser Glu Ala Lys Glu Lys Gly Tyr Val Arg
        770                 775                 780
Thr Leu Phe Gly Arg Lys Arg Asp Ile Pro Gln Leu Met Ala Arg Asp
785                 790                 795                 800
Arg Asn Thr Gln Ala Glu Gly Glu Arg Ile Ala Ile Asn Thr Pro Ile
                805                 810                 815
Gln Gly Thr Ala Ala Asp Ile Ile Lys Leu Ala Met Ile Glu Ile Asp
                820                 825                 830
Arg Glu Leu Lys Glu Arg Lys Met Arg Ser Lys Met Ile Ile Gln Val
            835                 840                 845
His Asp Glu Leu Val Phe Glu Val Pro Asn Glu Glu Lys Asp Ala Leu
        850                 855                 860
Val Glu Leu Val Lys Asp Arg Met Thr Asn Val Val Lys Leu Ser Val
865                 870                 875                 880
Pro Leu Glu Val Asp Val Thr Ile Gly Lys Thr Trp Ser
                885                 890

<210> SEQ ID NO 106
```

<211> LENGTH: 2682
<212> TYPE: DNA
<213> ORGANISM: Artificial sequence
<220> FEATURE:
<223> OTHER INFORMATION: Nucleic acid sequence encoding chimeric
thermostable DNA polymerase CS5 after second round of mutagenesis

<400> SEQUENCE: 106

```
atgaaagcta tgttaccatt attcgaaccc aaaggccggg tcctcctggt ggacggccac       60
cacctggcct accgcacctt cttcgccctg aagggcctca ccacgagccg ggcgaaccg       120
gtgcaggcgg tttacggctt cgccaagagc ctcctcaagg ccctgaagga ggacgggtac      180
aaggccgtct tcgtggtctt tgacgccaag gccccttcct ccgccacga ggcctacgag       240
gcctacaagg caggccgcgc cccgaccccc gaggacttcc ccggcagct cgccctcatc       300
aaggagctgg tggacctcct ggggtttact cgcctcgagg ttccgggctt tgaggcggac      360
gacgtcctcg ccaccctggc caagaaggcg gaaagggagg gtacgaggt gcgcatcctc       420
accgccgacc gggaccttta ccagctcgtc tccgaccgcg tcgccgtcct caccccgag       480
ggccacctca tcaccccgga gtggctttgg gagaagtacg ccttaagcc ggagcagtgg       540
gtggacttcc gcgccctcgt ggggaccccc tccgacaacc tccccgggt caagggcatc       600
ggggagaaga ccgccctcaa gctcctcaag gagtggggaa gcctggaaaa tatcctcaag      660
aacctggacc gggtgaagcc ggaaagcgtc cgggaaagga tcaaggccca cctggaagac      720
cttaagctct ccttggagct tccccggggtg cgctcggacc tccccctgga ggtggacttc     780
gccccggaggc gggagcctga ccgggaaggg cttcgggcct ttttgagcg cttggagttc      840
ggcagcctcc tccacgagtt cggccttcta gaggagtccg aacccgttgg gtaccgtata      900
gttaagacc tggttgaatt tgaaaaactc atagagaaac tgagagaatc tccttcgttc       960
gctatcgatt tggaaactag ttccctcgat cctttcgact gcgacattgt cggtatctct     1020
gtgtcttttca aaccaaagga agcgtactac ataccactcc atcatagaaa cgcccagaac    1080
ctggacgaaa agagggttct gaaaagctc aaagaaattc tggaggaccc cggagcaaag     1140
atcgttggtc agaatttgaa attcgattac aaggtgttga tggtgaaggg tgttgaacct    1200
gttcctcctt acttcgacac gatgatagcg gcttaccttc ttgagccgaa cgaaaagaag    1260
ttcaatctgg acgatctcgc attgaaattt cttggataca aaatgacatc ttaccaagag    1320
ctcatgtcct tctcttttcc gctgtttggt ttcagttttg ccgatgttcc tgtagaaaaa    1380
gcagcgaact actcctgtga agatgcagac atcacctaca gactttacaa gaccctgagc    1440
ttaaaactcc acgaggcaga tctggaaaac gtgttctaca agatagaaat gcccccttgtg   1500
aacgtgcttg cacggatgga actgaacggt gtgtatgtgg acacagagtt cctgaagaaa    1560
ctctcagaag agtacggaaa aaaactcgaa gaactggcag aggaaatata caggatagct    1620
ggagagccgt tcaacataaa ctcaccgaag caggtttcaa ggatcctttt tgaaaaactc    1680
ggcataaaac cacgtggtaa aacgacgaaa acgggagact attcaacacg catagaagtc   1740
ctcgaggaac ttgccggtga acacgaaatc attcctctga ttcttgaata cagaaagata   1800
cagaaattga aatcaaccta catagacgct cttcccaaga tggtcaaccc aaagaccgga   1860
aggattcatg cttctttcaa tcaaacgggg actgccactg gaagacttag cagcagcgat   1920
cccaatcttc agaacctccc gacgaaaagt gaagagggaa agaaatcag gaaagcgata    1980
gttcctcagg atccaaactg gtggatcgtc agtgccgact actcccaaat gaactgagg    2040
atcctcgccc atctcagtgg tgatgagaat cttttgaggg cattcgaaga gggcatcgac   2100
```

```
gtccacactc taacagcttc cagaatattc aacgtgaaac ccgaagaagt aaccgaagaa    2160
atgcgccgcg ctggtaaaat ggttaatttt tccatcatat acggtgtaac accttacggt    2220
ctgtctgtga ggcttggagt acctgtgaaa gaagcagaaa agatgatcgt caactacttc    2280
gtcctctacc caaaggtgcg cgattacatt cagagggtcg tatcggaagc gaaagaaaaa    2340
ggctatgtta gaacgctgtt tggaagaaaa agagacatac cacagctcat ggcccgggac    2400
aggaacacac aggctgaagg agaacgaatt gccataaaca ctcccataca gggtacagca    2460
gcggatataa taaagctggc tatgatagaa atagacaggg aactgaaaga aagaaaaatg    2520
agatcgaaga tgatcataca ggtccacgac gaactggttt ttgaagtgcc caatgaggaa    2580
aaggacgcgc tcgtcgagct ggtgaaagac agaatgacga atgtggtaaa gctttcagtg    2640
ccgctcgaag tggatgtaac catcggcaaa acatggtcgt ga                      2682
```

<210> SEQ ID NO 107
<211> LENGTH: 893
<212> TYPE: PRT
<213> ORGANISM: Artificial sequence
<220> FEATURE:
<223> OTHER INFORMATION: chimeric thermostable DNA polymerase CS6

<400> SEQUENCE: 107

```
Met Lys Ala Met Leu Pro Leu Phe Glu Pro Lys Gly Arg Val Leu Leu
1               5                   10                  15

Val Asp Gly His His Leu Ala Tyr Arg Thr Phe Phe Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Tyr Lys Ala Val Phe
    50                  55                  60

Val Val Phe Asp Ala Lys Ala Pro Ser Phe Arg His Glu Ala Tyr Glu
65                  70                  75                  80

Ala Tyr Lys Ala Gly Arg Ala Pro Thr Pro Glu Asp Phe Pro Arg Gln
                85                  90                  95

Leu Ala Leu Ile Lys Glu Leu Val Asp Leu Gly Phe Thr Arg Leu
            100                 105                 110

Glu Val Pro Gly Phe Glu Ala Asp Asp Val Leu Ala Thr Leu Ala Lys
        115                 120                 125

Lys Ala Glu Arg Glu Gly Tyr Glu Val Arg Ile Leu Thr Ala Asp Arg
    130                 135                 140

Asp Leu Tyr Gln Leu Val Ser Asp Arg Val Ala Val Leu His Pro Glu
145                 150                 155                 160

Gly His Leu Ile Thr Pro Glu Trp Leu Trp Glu Lys Tyr Gly Leu Lys
                165                 170                 175

Pro Glu Gln Trp Val Asp Phe Arg Ala Leu Val Gly Asp Pro Ser Asp
            180                 185                 190

Asn Leu Pro Gly Val Lys Gly Ile Gly Glu Lys Thr Ala Leu Lys Leu
        195                 200                 205

Leu Lys Glu Trp Gly Ser Leu Glu Asn Ile Leu Lys Asn Leu Asp Arg
    210                 215                 220

Val Lys Pro Glu Ser Val Arg Glu Arg Ile Lys Ala His Leu Glu Asp
225                 230                 235                 240

Leu Lys Leu Ser Leu Glu Leu Ser Arg Val Arg Ser Asp Leu Pro Leu
                245                 250                 255

Glu Val Asp Phe Ala Arg Arg Arg Glu Pro Asp Arg Glu Gly Leu Arg
```

-continued

```
              260                 265                 270
Ala Phe Leu Glu Arg Leu Glu Phe Gly Ser Leu Leu His Glu Phe Gly
            275                 280                 285

Leu Leu Glu Glu Ser Glu Pro Val Gly Tyr Arg Ile Val Lys Asp Leu
        290                 295                 300

Val Glu Phe Glu Lys Leu Ile Glu Lys Leu Arg Glu Ser Pro Ser Phe
305                 310                 315                 320

Ala Ile Ala Leu Ala Thr Ser Ser Leu Asp Pro Phe Asp Cys Asp Ile
                325                 330                 335

Val Gly Ile Ser Val Ser Phe Lys Pro Lys Glu Ala Tyr Tyr Ile Pro
            340                 345                 350

Leu His His Arg Asn Ala Gln Asn Leu Asp Glu Lys Glu Val Leu Lys
        355                 360                 365

Lys Leu Lys Glu Ile Leu Glu Asp Pro Gly Ala Lys Ile Val Gly Gln
    370                 375                 380

Asn Leu Lys Phe Asp Tyr Lys Val Leu Met Val Lys Gly Val Glu Pro
385                 390                 395                 400

Val Pro Pro Tyr Phe Asp Thr Met Ile Ala Ala Tyr Leu Leu Glu Pro
                405                 410                 415

Asn Glu Lys Lys Phe Asn Leu Asp Asp Leu Ala Leu Lys Phe Leu Gly
            420                 425                 430

Tyr Lys Met Thr Ser Tyr Gln Glu Leu Met Ser Phe Ser Phe Pro Leu
        435                 440                 445

Phe Gly Phe Ser Phe Ala Asp Val Pro Val Glu Lys Ala Ala Asn Tyr
    450                 455                 460

Ser Cys Glu Asp Ala Asp Ile Thr Tyr Arg Leu Tyr Lys Thr Leu Ser
465                 470                 475                 480

Leu Lys Leu His Glu Ala Asp Leu Glu Asn Val Phe Tyr Lys Ile Glu
                485                 490                 495

Met Pro Leu Val Asn Val Leu Ala Arg Met Glu Leu Asn Gly Val Tyr
            500                 505                 510

Val Asp Thr Glu Phe Leu Lys Lys Leu Ser Glu Glu Tyr Gly Lys Lys
        515                 520                 525

Leu Glu Glu Leu Ala Glu Glu Ile Tyr Arg Ile Ala Gly Glu Pro Phe
    530                 535                 540

Asn Ile Asn Ser Pro Lys Gln Val Ser Arg Ile Leu Phe Glu Lys Leu
545                 550                 555                 560

Gly Ile Lys Pro Arg Gly Lys Thr Thr Lys Thr Gly Asp Tyr Ser Thr
                565                 570                 575

Arg Ile Glu Val Leu Glu Glu Leu Ala Gly Glu His Glu Ile Ile Pro
            580                 585                 590

Leu Ile Leu Glu Tyr Arg Lys Ile Gln Lys Leu Lys Ser Thr Tyr Ile
        595                 600                 605

Asp Ala Leu Pro Lys Met Val Asn Pro Lys Thr Gly Arg Ile His Ala
    610                 615                 620

Ser Phe Asn Gln Thr Gly Thr Ala Thr Gly Arg Leu Ser Ser Ser Asp
625                 630                 635                 640

Pro Asn Leu Gln Asn Leu Pro Thr Lys Ser Glu Glu Gly Lys Glu Ile
                645                 650                 655

Arg Lys Ala Ile Val Pro Gln Asp Pro Asn Trp Trp Ile Val Ser Ala
            660                 665                 670

Asp Tyr Ser Gln Ile Glu Leu Arg Ile Leu Ala His Leu Ser Gly Asp
        675                 680                 685
```

```
Glu Asn Leu Leu Arg Ala Phe Glu Glu Gly Ile Asp Val His Thr Leu
        690                 695                 700

Thr Ala Ser Arg Ile Phe Asn Val Lys Pro Glu Val Thr Glu Glu
705                 710                 715                 720

Met Arg Arg Ala Gly Lys Met Val Asn Phe Ser Ile Ile Tyr Gly Val
                    725                 730                 735

Thr Pro Tyr Gly Leu Ser Val Arg Leu Gly Val Pro Val Lys Glu Ala
                740                 745                 750

Glu Lys Met Ile Val Asn Tyr Phe Val Leu Tyr Pro Lys Val Arg Asp
            755                 760                 765

Tyr Ile Gln Arg Val Val Ser Glu Ala Lys Glu Lys Gly Tyr Val Arg
770                 775                 780

Thr Leu Phe Gly Arg Lys Arg Asp Ile Pro Gln Leu Met Ala Arg Asp
785                 790                 795                 800

Arg Asn Thr Gln Ala Glu Gly Glu Arg Ile Ala Ile Asn Thr Pro Ile
                805                 810                 815

Gln Gly Thr Ala Ala Asp Ile Ile Lys Leu Ala Met Ile Glu Ile Asp
                820                 825                 830

Arg Glu Leu Lys Glu Arg Lys Met Arg Ser Lys Met Ile Ile Gln Val
            835                 840                 845

His Asp Glu Leu Val Phe Glu Val Pro Asn Glu Lys Asp Ala Leu
850                 855                 860

Val Glu Leu Val Lys Asp Arg Met Thr Asn Val Val Lys Leu Ser Val
865                 870                 875                 880

Pro Leu Glu Val Asp Val Thr Ile Gly Lys Thr Trp Ser
                885                 890

<210> SEQ ID NO 108
<211> LENGTH: 196
<212> TYPE: PRT
<213> ORGANISM: Artificial sequence
<220> FEATURE:
<223> OTHER INFORMATION: Exonucleolytic domain of chimeric thermostable
      DNA polymerase CS6

<400> SEQUENCE: 108

Glu Ser Glu Pro Val Gly Tyr Arg Ile Val Lys Asp Leu Val Glu Phe
1               5                   10                  15

Glu Lys Leu Ile Glu Lys Leu Arg Glu Ser Pro Ser Phe Ala Ile Ala
                20                  25                  30

Leu Ala Thr Ser Ser Leu Asp Pro Phe Asp Cys Asp Ile Val Gly Ile
            35                  40                  45

Ser Val Ser Phe Lys Pro Lys Glu Ala Tyr Tyr Ile Pro Leu His His
    50                  55                  60

Arg Asn Ala Gln Asn Leu Asp Glu Lys Glu Val Leu Lys Lys Leu Lys
65                  70                  75                  80

Glu Ile Leu Glu Asp Pro Gly Ala Lys Ile Val Gly Gln Asn Leu Lys
                85                  90                  95

Phe Asp Tyr Lys Val Leu Met Val Lys Gly Val Glu Pro Val Pro Pro
                100                 105                 110

Tyr Phe Asp Thr Met Ile Ala Ala Tyr Leu Leu Glu Pro Asn Glu Lys
            115                 120                 125

Lys Phe Asn Leu Asp Asp Leu Ala Leu Lys Phe Leu Gly Tyr Lys Met
        130                 135                 140

Thr Ser Tyr Gln Glu Leu Met Ser Phe Ser Phe Pro Leu Phe Gly Phe
```

-continued

```
                145                 150                 155                 160
Ser Phe Ala Asp Val Pro Val Glu Lys Ala Ala Asn Tyr Ser Cys Glu
                165                 170                 175

Asp Ala Asp Ile Thr Tyr Arg Leu Tyr Lys Thr Leu Ser Leu Lys Leu
                180                 185                 190

His Glu Ala Asp
        195

<210> SEQ ID NO 109
<211> LENGTH: 291
<212> TYPE: PRT
<213> ORGANISM: Artificial sequence
<220> FEATURE:
<223> OTHER INFORMATION: Residues 1-291 of thermostable chimeric DNA
      polymerase CS6 derived from Z05 DNA polymerase

<400> SEQUENCE: 109

Met Lys Ala Met Leu Pro Leu Phe Glu Pro Lys Gly Arg Val Leu Leu
1               5                   10                  15

Val Asp Gly His His Leu Ala Tyr Arg Thr Phe Phe Ala Leu Lys Gly
                20                  25                  30

Leu Thr Thr Ser Arg Gly Glu Pro Val Gln Ala Val Tyr Gly Phe Ala
            35                  40                  45

Lys Ser Leu Leu Lys Ala Leu Lys Glu Asp Gly Tyr Lys Ala Val Phe
    50                  55                  60

Val Val Phe Asp Ala Lys Ala Pro Ser Phe Arg His Glu Ala Tyr Glu
65                  70                  75                  80

Ala Tyr Lys Ala Gly Arg Ala Pro Thr Pro Glu Asp Phe Pro Arg Gln
                85                  90                  95

Leu Ala Leu Ile Lys Glu Leu Val Asp Leu Leu Gly Phe Thr Arg Leu
            100                 105                 110

Glu Val Pro Gly Phe Glu Ala Asp Asp Val Leu Ala Thr Leu Ala Lys
        115                 120                 125

Lys Ala Glu Arg Glu Gly Tyr Glu Val Arg Ile Leu Thr Ala Asp Arg
130                 135                 140

Asp Leu Tyr Gln Leu Val Ser Asp Arg Val Ala Val Leu His Pro Glu
145                 150                 155                 160

Gly His Leu Ile Thr Pro Glu Trp Leu Trp Glu Lys Tyr Gly Leu Lys
                165                 170                 175

Pro Glu Gln Trp Val Asp Phe Arg Ala Leu Val Gly Asp Pro Ser Asp
            180                 185                 190

Asn Leu Pro Gly Val Lys Gly Ile Gly Glu Lys Thr Ala Leu Lys Leu
        195                 200                 205

Leu Lys Glu Trp Gly Ser Leu Glu Asn Ile Leu Lys Asn Leu Asp Arg
    210                 215                 220

Val Lys Pro Glu Ser Val Arg Glu Arg Ile Lys Ala His Leu Glu Asp
225                 230                 235                 240

Leu Lys Leu Ser Leu Glu Leu Ser Arg Val Arg Ser Asp Leu Pro Leu
                245                 250                 255

Glu Val Asp Phe Ala Arg Arg Arg Glu Pro Asp Arg Glu Gly Leu Arg
            260                 265                 270

Ala Phe Leu Glu Arg Leu Glu Phe Gly Ser Leu Leu His Glu Phe Gly
        275                 280                 285

Leu Leu Glu
    290
```

-continued

```
<210> SEQ ID NO 110
<211> LENGTH: 602
<212> TYPE: PRT
<213> ORGANISM: Artificial sequence
<220> FEATURE:
<223> OTHER INFORMATION: Residues 292-893 of  thermostable chimeric DNA
      polymerase CS6 derived from Tma DNA polymerase

<400> SEQUENCE: 110

Glu Ser Glu Pro Val Gly Tyr Arg Ile Val Lys Asp Leu Val Glu Phe
 1               5                  10                  15

Glu Lys Leu Ile Glu Lys Leu Arg Glu Ser Pro Ser Phe Ala Ile Ala
            20                  25                  30

Leu Ala Thr Ser Ser Leu Asp Pro Phe Asp Cys Asp Ile Val Gly Ile
        35                  40                  45

Ser Val Ser Phe Lys Pro Lys Glu Ala Tyr Tyr Ile Pro Leu His His
    50                  55                  60

Arg Asn Ala Gln Asn Leu Asp Lys Glu Val Leu Lys Lys Leu Lys
 65                  70                  75                  80

Glu Ile Leu Glu Asp Pro Gly Ala Lys Ile Val Gly Gln Asn Leu Lys
                85                  90                  95

Phe Asp Tyr Lys Val Leu Met Val Lys Gly Val Glu Pro Val Pro Pro
            100                 105                 110

Tyr Phe Asp Thr Met Ile Ala Ala Tyr Leu Leu Glu Pro Asn Glu Lys
        115                 120                 125

Lys Phe Asn Leu Asp Asp Leu Ala Leu Lys Phe Leu Gly Tyr Lys Met
    130                 135                 140

Thr Ser Tyr Gln Glu Leu Met Ser Phe Ser Phe Pro Leu Phe Gly Phe
145                 150                 155                 160

Ser Phe Ala Asp Val Pro Val Glu Lys Ala Ala Asn Tyr Ser Cys Glu
                165                 170                 175

Asp Ala Asp Ile Thr Tyr Arg Leu Tyr Lys Thr Leu Ser Leu Lys Leu
            180                 185                 190

His Glu Ala Asp Leu Glu Asn Val Phe Tyr Lys Ile Glu Met Pro Leu
        195                 200                 205

Val Asn Val Leu Ala Arg Met Glu Leu Asn Gly Val Tyr Val Asp Thr
    210                 215                 220

Glu Phe Leu Lys Lys Leu Ser Glu Glu Tyr Gly Lys Lys Leu Glu Glu
225                 230                 235                 240

Leu Ala Glu Glu Ile Tyr Arg Ile Ala Gly Glu Pro Phe Asn Ile Asn
                245                 250                 255

Ser Pro Lys Gln Val Ser Arg Ile Leu Phe Glu Lys Leu Gly Ile Lys
            260                 265                 270

Pro Arg Gly Lys Thr Thr Lys Thr Gly Asp Tyr Ser Thr Arg Ile Glu
        275                 280                 285

Val Leu Glu Glu Leu Ala Gly Glu His Glu Ile Ile Pro Leu Ile Leu
    290                 295                 300

Glu Tyr Arg Lys Ile Gln Lys Leu Lys Ser Thr Tyr Ile Asp Ala Leu
305                 310                 315                 320

Pro Lys Met Val Asn Pro Lys Thr Gly Arg Ile His Ala Ser Phe Asn
                325                 330                 335

Gln Thr Gly Thr Ala Thr Gly Arg Leu Ser Ser Ser Asp Pro Asn Leu
            340                 345                 350

Gln Asn Leu Pro Thr Lys Ser Glu Glu Gly Lys Glu Ile Arg Lys Ala
        355                 360                 365
```

```
Ile Val Pro Gln Asp Pro Asn Trp Trp Ile Val Ser Ala Asp Tyr Ser
    370                 375                 380

Gln Ile Glu Leu Arg Ile Leu Ala His Leu Ser Gly Asp Glu Asn Leu
385                 390                 395                 400

Leu Arg Ala Phe Glu Glu Gly Ile Asp Val His Thr Leu Thr Ala Ser
                405                 410                 415

Arg Ile Phe Asn Val Lys Pro Glu Glu Val Thr Glu Glu Met Arg Arg
            420                 425                 430

Ala Gly Lys Met Val Asn Phe Ser Ile Ile Tyr Gly Val Thr Pro Tyr
        435                 440                 445

Gly Leu Ser Val Arg Leu Gly Val Pro Val Lys Glu Ala Glu Lys Met
    450                 455                 460

Ile Val Asn Tyr Phe Val Leu Tyr Pro Lys Val Arg Asp Tyr Ile Gln
465                 470                 475                 480

Arg Val Val Ser Glu Ala Lys Glu Lys Gly Tyr Val Arg Thr Leu Phe
                485                 490                 495

Gly Arg Lys Arg Asp Ile Pro Gln Leu Met Ala Arg Asp Arg Asn Thr
            500                 505                 510

Gln Ala Glu Gly Glu Arg Ile Ala Ile Asn Thr Pro Ile Gln Gly Thr
        515                 520                 525

Ala Ala Asp Ile Ile Lys Leu Ala Met Ile Glu Ile Asp Arg Glu Leu
    530                 535                 540

Lys Glu Arg Lys Met Arg Ser Lys Met Ile Ile Gln Val His Asp Glu
545                 550                 555                 560

Leu Val Phe Glu Val Pro Asn Glu Glu Lys Asp Ala Leu Val Glu Leu
                565                 570                 575

Val Lys Asp Arg Met Thr Asn Val Val Lys Leu Ser Val Pro Leu Glu
            580                 585                 590

Val Asp Val Thr Ile Gly Lys Thr Trp Ser
            595                 600

<210> SEQ ID NO 111
<211> LENGTH: 196
<212> TYPE: PRT
<213> ORGANISM: Artificial sequence
<220> FEATURE:
<223> OTHER INFORMATION: Exonucleolytic domain of chimeric thermostable
      DNA polymerase CS6 after first round of mutagenesis residues
      323-325 DEE substitution

<400> SEQUENCE: 111

Glu Ser Glu Pro Val Gly Tyr Arg Ile Val Lys Asp Leu Val Glu Phe
1               5                   10                  15

Glu Lys Leu Ile Glu Lys Leu Arg Glu Ser Pro Ser Phe Ala Ile Asp
            20                  25                  30

Glu Glu Thr Ser Ser Leu Asp Pro Phe Asp Cys Asp Ile Val Gly Ile
        35                  40                  45

Ser Val Ser Phe Lys Pro Lys Glu Ala Tyr Tyr Ile Pro Leu His His
    50                  55                  60

Arg Asn Ala Gln Asn Leu Asp Glu Lys Glu Val Leu Lys Lys Leu Lys
65                  70                  75                  80

Glu Ile Leu Glu Asp Pro Gly Ala Lys Ile Val Gly Gln Asn Leu Lys
                85                  90                  95

Phe Asp Tyr Lys Val Leu Met Val Lys Gly Val Glu Pro Val Pro Pro
            100                 105                 110
```

```
Tyr Phe Asp Thr Met Ile Ala Ala Tyr Leu Leu Glu Pro Asn Glu Lys
            115                 120                 125

Lys Phe Asn Leu Asp Asp Leu Ala Leu Lys Phe Leu Gly Tyr Lys Met
        130                 135                 140

Thr Ser Tyr Gln Glu Leu Met Ser Phe Ser Pro Leu Phe Gly Phe
145                 150                 155                 160

Ser Phe Ala Asp Val Pro Val Glu Lys Ala Ala Asn Tyr Ser Cys Glu
                165                 170                 175

Asp Ala Asp Ile Thr Tyr Arg Leu Tyr Lys Thr Leu Ser Leu Lys Leu
            180                 185                 190

His Glu Ala Asp
        195

<210> SEQ ID NO 112
<211> LENGTH: 893
<212> TYPE: PRT
<213> ORGANISM: Artificial sequence
<220> FEATURE:
<223> OTHER INFORMATION: chimeric thermostable DNA polymerase CS6 after
      first round of mutagenesis residues 323-325 DEE substitution

<400> SEQUENCE: 112

Met Lys Ala Met Leu Pro Leu Phe Glu Pro Lys Gly Arg Val Leu Leu
1               5                   10                  15

Val Asp Gly His His Leu Ala Tyr Arg Thr Phe Phe Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Tyr Lys Ala Val Phe
    50                  55                  60

Val Val Phe Asp Ala Lys Ala Pro Ser Phe Arg His Glu Ala Tyr Glu
65                  70                  75                  80

Ala Tyr Lys Ala Gly Arg Ala Pro Thr Pro Glu Asp Phe Pro Arg Gln
                85                  90                  95

Leu Ala Leu Ile Lys Glu Leu Val Asp Leu Leu Gly Phe Thr Arg Leu
            100                 105                 110

Glu Val Pro Gly Phe Glu Ala Asp Asp Val Leu Ala Thr Leu Ala Lys
        115                 120                 125

Lys Ala Glu Arg Glu Gly Tyr Glu Val Arg Ile Leu Thr Ala Asp Arg
    130                 135                 140

Asp Leu Tyr Gln Leu Val Ser Asp Arg Val Ala Val Leu His Pro Glu
145                 150                 155                 160

Gly His Leu Ile Thr Pro Glu Trp Leu Trp Glu Lys Tyr Gly Leu Lys
                165                 170                 175

Pro Glu Gln Trp Val Asp Phe Arg Ala Leu Val Gly Asp Pro Ser Asp
            180                 185                 190

Asn Leu Pro Gly Val Lys Gly Ile Gly Lys Thr Ala Leu Lys Leu
        195                 200                 205

Leu Lys Glu Trp Gly Ser Leu Glu Asn Ile Leu Lys Asn Leu Asp Arg
    210                 215                 220

Val Lys Pro Glu Ser Val Arg Glu Arg Ile Lys Ala His Leu Glu Asp
225                 230                 235                 240

Leu Lys Leu Ser Leu Glu Leu Ser Arg Val Arg Ser Asp Leu Pro Leu
                245                 250                 255

Glu Val Asp Phe Ala Arg Arg Arg Glu Pro Asp Arg Glu Gly Leu Arg
            260                 265                 270
```

```
Ala Phe Leu Glu Arg Leu Glu Phe Gly Ser Leu Leu His Glu Phe Gly
            275                 280                 285

Leu Leu Glu Glu Ser Glu Pro Val Gly Tyr Arg Ile Val Lys Asp Leu
        290                 295                 300

Val Glu Phe Glu Lys Leu Ile Glu Lys Leu Arg Glu Ser Pro Ser Phe
305                 310                 315                 320

Ala Ile Asp Glu Glu Thr Ser Ser Leu Asp Pro Phe Asp Cys Asp Ile
                325                 330                 335

Val Gly Ile Ser Val Ser Phe Lys Pro Lys Glu Ala Tyr Tyr Ile Pro
            340                 345                 350

Leu His His Arg Asn Ala Gln Asn Leu Asp Glu Lys Glu Val Leu Lys
            355                 360                 365

Lys Leu Lys Glu Ile Leu Glu Asp Pro Gly Ala Lys Ile Val Gly Gln
        370                 375                 380

Asn Leu Lys Phe Asp Tyr Lys Val Leu Met Val Lys Gly Val Glu Pro
385                 390                 395                 400

Val Pro Pro Tyr Phe Asp Thr Met Ile Ala Ala Tyr Leu Leu Glu Pro
                405                 410                 415

Asn Glu Lys Lys Phe Asn Leu Asp Asp Leu Ala Leu Lys Phe Leu Gly
            420                 425                 430

Tyr Lys Met Thr Ser Tyr Gln Glu Leu Met Ser Phe Ser Phe Pro Leu
            435                 440                 445

Phe Gly Phe Ser Phe Ala Asp Val Pro Val Glu Lys Ala Ala Asn Tyr
        450                 455                 460

Ser Cys Glu Asp Ala Asp Ile Thr Tyr Arg Leu Tyr Lys Thr Leu Ser
465                 470                 475                 480

Leu Lys Leu His Glu Ala Asp Leu Glu Asn Val Phe Tyr Lys Ile Glu
                485                 490                 495

Met Pro Leu Val Asn Val Leu Ala Arg Met Glu Leu Asn Gly Val Tyr
            500                 505                 510

Val Asp Thr Glu Phe Leu Lys Lys Leu Ser Glu Glu Tyr Gly Lys Lys
            515                 520                 525

Leu Glu Glu Leu Ala Glu Glu Ile Tyr Arg Ile Ala Gly Glu Pro Phe
        530                 535                 540

Asn Ile Asn Ser Pro Lys Gln Val Ser Arg Ile Leu Phe Glu Lys Leu
545                 550                 555                 560

Gly Ile Lys Pro Arg Gly Lys Thr Thr Lys Thr Gly Asp Tyr Ser Thr
                565                 570                 575

Arg Ile Glu Val Leu Glu Glu Leu Ala Gly Glu His Glu Ile Ile Pro
            580                 585                 590

Leu Ile Leu Glu Tyr Arg Lys Ile Gln Lys Leu Lys Ser Thr Tyr Ile
            595                 600                 605

Asp Ala Leu Pro Lys Met Val Asn Pro Lys Thr Gly Arg Ile His Ala
        610                 615                 620

Ser Phe Asn Gln Thr Gly Thr Ala Thr Gly Arg Leu Ser Ser Ser Asp
625                 630                 635                 640

Pro Asn Leu Gln Asn Leu Pro Thr Lys Ser Glu Glu Gly Lys Glu Ile
                645                 650                 655

Arg Lys Ala Ile Val Pro Gln Asp Pro Asn Trp Trp Ile Val Ser Ala
            660                 665                 670

Asp Tyr Ser Gln Ile Glu Leu Arg Ile Leu Ala His Leu Ser Gly Asp
            675                 680                 685
```

```
Glu Asn Leu Leu Arg Ala Phe Glu Glu Gly Ile Asp Val His Thr Leu
    690             695                 700

Thr Ala Ser Arg Ile Phe Asn Val Lys Pro Glu Glu Val Thr Glu Glu
705             710                 715                 720

Met Arg Arg Ala Gly Lys Met Val Asn Phe Ser Ile Ile Tyr Gly Val
                725                 730                 735

Thr Pro Tyr Gly Leu Ser Val Arg Leu Gly Val Pro Val Lys Glu Ala
            740                 745                 750

Glu Lys Met Ile Val Asn Tyr Phe Val Leu Tyr Pro Lys Val Arg Asp
        755                 760                 765

Tyr Ile Gln Arg Val Val Ser Glu Ala Lys Glu Lys Gly Tyr Val Arg
    770                 775                 780

Thr Leu Phe Gly Arg Lys Arg Asp Ile Pro Gln Leu Met Ala Arg Asp
785             790                 795                 800

Arg Asn Thr Gln Ala Glu Gly Glu Arg Ile Ala Ile Asn Thr Pro Ile
                805                 810                 815

Gln Gly Thr Ala Ala Asp Ile Ile Lys Leu Ala Met Ile Glu Ile Asp
            820                 825                 830

Arg Glu Leu Lys Glu Arg Lys Met Arg Ser Lys Met Ile Ile Gln Val
        835                 840                 845

His Asp Glu Leu Val Phe Glu Val Pro Asn Glu Glu Lys Asp Ala Leu
850                 855                 860

Val Glu Leu Val Lys Asp Arg Met Thr Asn Val Val Lys Leu Ser Val
865             870                 875                 880

Pro Leu Glu Val Asp Val Thr Ile Gly Lys Thr Trp Ser
                885                 890

<210> SEQ ID NO 113
<211> LENGTH: 196
<212> TYPE: PRT
<213> ORGANISM: Artificial sequence
<220> FEATURE:
<223> OTHER INFORMATION: Exonucleolytic domain of chimeric thermostable
      DNA polymerase CS6 after first round of mutagenesis residues
      323-325 DDE substitution

<400> SEQUENCE: 113

Glu Ser Glu Pro Val Gly Tyr Arg Ile Val Lys Asp Leu Val Glu Phe
1               5                   10                  15

Glu Lys Leu Ile Glu Lys Leu Arg Glu Ser Pro Ser Phe Ala Ile Asp
            20                  25                  30

Asp Glu Thr Ser Ser Leu Asp Pro Phe Asp Cys Asp Ile Val Gly Ile
        35                  40                  45

Ser Val Ser Phe Lys Pro Lys Glu Ala Tyr Tyr Ile Pro Leu His His
    50                  55                  60

Arg Asn Ala Gln Asn Leu Asp Glu Lys Val Leu Lys Lys Leu Lys
65                  70                  75                  80

Glu Ile Leu Glu Asp Pro Gly Ala Lys Ile Val Gly Gln Asn Leu Lys
            85                  90                  95

Phe Asp Tyr Lys Val Leu Met Val Lys Gly Val Glu Pro Val Pro Pro
                100                 105                 110

Tyr Phe Asp Thr Met Ile Ala Ala Tyr Leu Leu Glu Pro Asn Glu Lys
            115                 120                 125

Lys Phe Asn Leu Asp Asp Leu Ala Leu Lys Phe Leu Gly Tyr Lys Met
        130                 135                 140

Thr Ser Tyr Gln Glu Leu Met Ser Phe Ser Phe Pro Leu Phe Gly Phe
```

-continued

```
145                 150                 155                 160
Ser Phe Ala Asp Val Pro Val Glu Lys Ala Ala Asn Tyr Ser Cys Glu
                165                 170                 175

Asp Ala Asp Ile Thr Tyr Arg Leu Tyr Lys Thr Leu Ser Leu Lys Leu
            180                 185                 190

His Glu Ala Asp
        195

<210> SEQ ID NO 114
<211> LENGTH: 893
<212> TYPE: PRT
<213> ORGANISM: Artificial sequence
<220> FEATURE:
<223> OTHER INFORMATION: chimeric thermostable DNA polymerase CS6 after
      first round of mutagenesis residues 323-325 DDE substitution

<400> SEQUENCE: 114

Met Lys Ala Met Leu Pro Leu Phe Glu Pro Lys Gly Arg Val Leu Leu
1               5                   10                  15

Val Asp Gly His His Leu Ala Tyr Arg Thr Phe Phe Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Tyr Lys Ala Val Phe
50                  55                  60

Val Val Phe Asp Ala Lys Ala Pro Ser Phe Arg His Glu Ala Tyr Glu
65                  70                  75                  80

Ala Tyr Lys Ala Gly Arg Ala Pro Thr Pro Glu Asp Phe Pro Arg Gln
                85                  90                  95

Leu Ala Leu Ile Lys Glu Leu Val Asp Leu Leu Gly Phe Thr Arg Leu
            100                 105                 110

Glu Val Pro Gly Phe Glu Ala Asp Asp Val Leu Ala Thr Leu Ala Lys
        115                 120                 125

Lys Ala Glu Arg Glu Gly Tyr Glu Val Arg Ile Leu Thr Ala Asp Arg
130                 135                 140

Asp Leu Tyr Gln Leu Val Ser Asp Arg Val Ala Val Leu His Pro Glu
145                 150                 155                 160

Gly His Leu Ile Thr Pro Glu Trp Leu Trp Glu Lys Tyr Gly Leu Lys
                165                 170                 175

Pro Glu Gln Trp Val Asp Phe Arg Ala Leu Val Gly Asp Pro Ser Asp
            180                 185                 190

Asn Leu Pro Gly Val Lys Gly Ile Gly Glu Lys Thr Ala Leu Lys Leu
        195                 200                 205

Leu Lys Glu Trp Gly Ser Leu Glu Asn Ile Leu Lys Asn Leu Asp Arg
    210                 215                 220

Val Lys Pro Glu Ser Val Arg Glu Arg Ile Lys Ala His Leu Glu Asp
225                 230                 235                 240

Leu Lys Leu Ser Leu Glu Leu Ser Arg Val Arg Ser Asp Leu Pro Leu
                245                 250                 255

Glu Val Asp Phe Ala Arg Arg Arg Glu Pro Asp Arg Glu Gly Leu Arg
            260                 265                 270

Ala Phe Leu Glu Arg Leu Glu Phe Gly Ser Leu Leu His Glu Phe Gly
        275                 280                 285

Leu Leu Glu Glu Ser Glu Pro Val Gly Tyr Arg Ile Val Lys Asp Leu
    290                 295                 300
```

-continued

```
Val Glu Phe Glu Lys Leu Ile Glu Lys Leu Arg Ser Pro Ser Phe
305                 310                 315                 320

Ala Ile Asp Asp Glu Thr Ser Ser Leu Asp Pro Phe Asp Cys Asp Ile
            325                 330                 335

Val Gly Ile Ser Val Ser Phe Lys Pro Lys Glu Ala Tyr Tyr Ile Pro
            340                 345                 350

Leu His His Arg Asn Ala Gln Asn Leu Asp Glu Lys Glu Val Leu Lys
            355                 360                 365

Lys Leu Lys Glu Ile Leu Glu Asp Pro Gly Ala Lys Ile Val Gly Gln
            370                 375                 380

Asn Leu Lys Phe Asp Tyr Lys Val Leu Met Val Lys Gly Val Glu Pro
385                 390                 395                 400

Val Pro Pro Tyr Phe Asp Thr Met Ile Ala Ala Tyr Leu Leu Glu Pro
                405                 410                 415

Asn Glu Lys Lys Phe Asn Leu Asp Asp Leu Ala Leu Lys Phe Leu Gly
            420                 425                 430

Tyr Lys Met Thr Ser Tyr Gln Glu Leu Met Ser Phe Ser Phe Pro Leu
            435                 440                 445

Phe Gly Phe Ser Phe Ala Asp Val Pro Val Glu Lys Ala Ala Asn Tyr
    450                 455                 460

Ser Cys Glu Asp Ala Asp Ile Thr Tyr Arg Leu Tyr Lys Thr Leu Ser
465                 470                 475                 480

Leu Lys Leu His Glu Ala Asp Leu Glu Asn Val Phe Tyr Lys Ile Glu
            485                 490                 495

Met Pro Leu Val Asn Val Leu Ala Arg Met Glu Leu Asn Gly Val Tyr
            500                 505                 510

Val Asp Thr Glu Phe Leu Lys Lys Leu Ser Glu Tyr Gly Lys Lys
            515                 520                 525

Leu Glu Glu Leu Ala Glu Glu Ile Tyr Arg Ile Ala Gly Glu Pro Phe
            530                 535                 540

Asn Ile Asn Ser Pro Lys Gln Val Ser Arg Ile Leu Phe Glu Lys Leu
545                 550                 555                 560

Gly Ile Lys Pro Arg Gly Lys Thr Thr Lys Thr Gly Asp Tyr Ser Thr
                565                 570                 575

Arg Ile Glu Val Leu Glu Glu Leu Ala Gly Glu His Glu Ile Ile Pro
            580                 585                 590

Leu Ile Leu Glu Tyr Arg Lys Ile Gln Lys Leu Lys Ser Thr Tyr Ile
            595                 600                 605

Asp Ala Leu Pro Lys Met Val Asn Pro Lys Thr Gly Arg Ile His Ala
            610                 615                 620

Ser Phe Asn Gln Thr Gly Thr Ala Thr Gly Arg Leu Ser Ser Ser Asp
625                 630                 635                 640

Pro Asn Leu Gln Asn Leu Pro Thr Lys Ser Glu Glu Gly Lys Glu Ile
                645                 650                 655

Arg Lys Ala Ile Val Pro Gln Asp Pro Asn Trp Trp Ile Val Ser Ala
            660                 665                 670

Asp Tyr Ser Gln Ile Glu Leu Arg Ile Leu Ala His Leu Ser Gly Asp
            675                 680                 685

Glu Asn Leu Leu Arg Ala Phe Glu Gly Ile Asp Val His Thr Leu
            690                 695                 700

Thr Ala Ser Arg Ile Phe Asn Val Lys Pro Glu Glu Val Thr Glu Glu
705                 710                 715                 720

Met Arg Arg Ala Gly Lys Met Val Asn Phe Ser Ile Ile Tyr Gly Val
```

```
                         725                 730                 735
Thr Pro Tyr Gly Leu Ser Val Arg Leu Gly Val Pro Val Lys Glu Ala
                740                 745                 750

Glu Lys Met Ile Val Asn Tyr Phe Val Leu Tyr Pro Lys Val Arg Asp
            755                 760                 765

Tyr Ile Gln Arg Val Val Ser Glu Ala Lys Glu Lys Gly Tyr Val Arg
        770                 775                 780

Thr Leu Phe Gly Arg Lys Arg Asp Ile Pro Gln Leu Met Ala Arg Asp
785                 790                 795                 800

Arg Asn Thr Gln Ala Glu Gly Glu Arg Ile Ala Ile Asn Thr Pro Ile
                805                 810                 815

Gln Gly Thr Ala Ala Asp Ile Ile Lys Leu Ala Met Ile Glu Ile Asp
            820                 825                 830

Arg Glu Leu Lys Glu Arg Lys Met Arg Ser Lys Met Ile Ile Gln Val
        835                 840                 845

His Asp Glu Leu Val Phe Glu Val Pro Asn Glu Glu Lys Asp Ala Leu
    850                 855                 860

Val Glu Leu Val Lys Asp Arg Met Thr Asn Val Val Lys Leu Ser Val
865                 870                 875                 880

Pro Leu Glu Val Asp Val Thr Ile Gly Lys Thr Trp Ser
                885                 890

<210> SEQ ID NO 115
<211> LENGTH: 196
<212> TYPE: PRT
<213> ORGANISM: Artificial sequence
<220> FEATURE:
<223> OTHER INFORMATION: Exonucleolytic domain of chimeric thermostable
      DNA polymerase CS6 after first round of mutagenesis residues
      323-325 DKE substitution

<400> SEQUENCE: 115

Glu Ser Glu Pro Val Gly Tyr Arg Ile Val Lys Asp Leu Val Glu Phe
1               5                   10                  15

Glu Lys Leu Ile Glu Lys Leu Arg Glu Ser Pro Ser Phe Ala Ile Asp
            20                  25                  30

Lys Glu Thr Ser Ser Leu Asp Pro Phe Asp Cys Asp Ile Val Gly Ile
        35                  40                  45

Ser Val Ser Phe Lys Pro Lys Glu Ala Tyr Tyr Ile Pro Leu His His
    50                  55                  60

Arg Asn Ala Gln Asn Leu Asp Glu Lys Val Leu Lys Leu Lys
65                  70                  75                  80

Glu Ile Leu Glu Asp Pro Gly Ala Lys Ile Val Gly Gln Asn Leu Lys
                85                  90                  95

Phe Asp Tyr Lys Val Leu Met Val Lys Gly Val Glu Pro Val Pro Pro
            100                 105                 110

Tyr Phe Asp Thr Met Ile Ala Ala Tyr Leu Leu Glu Pro Asn Glu Lys
        115                 120                 125

Lys Phe Asn Leu Asp Asp Leu Ala Leu Lys Phe Leu Gly Tyr Lys Met
    130                 135                 140

Thr Ser Tyr Gln Glu Leu Met Ser Phe Ser Phe Pro Leu Phe Gly Phe
145                 150                 155                 160

Ser Phe Ala Asp Val Pro Val Glu Lys Ala Ala Asn Tyr Ser Cys Glu
                165                 170                 175

Asp Ala Asp Ile Thr Tyr Arg Leu Tyr Lys Thr Leu Ser Leu Lys Leu
            180                 185                 190
```

His Glu Ala Asp
        195

<210> SEQ ID NO 116
<211> LENGTH: 893
<212> TYPE: PRT
<213> ORGANISM: Artificial sequence
<220> FEATURE:
<223> OTHER INFORMATION: chimeric thermostable DNA polymerase CS6 after
      first round of mutagenesis residues 323-325 DKE substitution

<400> SEQUENCE: 116

Met Lys Ala Met Leu Pro Leu Phe Glu Pro Lys Gly Arg Val Leu Leu
1               5                   10                  15

Val Asp Gly His His Leu Ala Tyr Arg Thr Phe Phe Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Tyr Lys Ala Val Phe
    50                  55                  60

Val Val Phe Asp Ala Lys Ala Pro Ser Phe Arg His Glu Ala Tyr Glu
65                  70                  75                  80

Ala Tyr Lys Ala Gly Arg Ala Pro Thr Pro Glu Asp Phe Pro Arg Gln
                85                  90                  95

Leu Ala Leu Ile Lys Glu Leu Val Asp Leu Leu Gly Phe Thr Arg Leu
            100                 105                 110

Glu Val Pro Gly Phe Glu Ala Asp Asp Val Leu Ala Thr Leu Ala Lys
        115                 120                 125

Lys Ala Glu Arg Glu Gly Tyr Glu Val Arg Ile Leu Thr Ala Asp Arg
    130                 135                 140

Asp Leu Tyr Gln Leu Val Ser Asp Arg Val Ala Val Leu His Pro Glu
145                 150                 155                 160

Gly His Leu Ile Thr Pro Glu Trp Leu Trp Glu Lys Tyr Gly Leu Lys
                165                 170                 175

Pro Glu Gln Trp Val Asp Phe Arg Ala Leu Val Gly Asp Pro Ser Asp
            180                 185                 190

Asn Leu Pro Gly Val Lys Gly Ile Gly Glu Lys Thr Ala Leu Lys Leu
        195                 200                 205

Leu Lys Glu Trp Gly Ser Leu Glu Asn Ile Leu Lys Asn Leu Asp Arg
    210                 215                 220

Val Lys Pro Glu Ser Val Arg Glu Arg Ile Lys Ala His Leu Glu Asp
225                 230                 235                 240

Leu Lys Leu Ser Leu Glu Leu Ser Arg Val Arg Ser Asp Leu Pro Leu
                245                 250                 255

Glu Val Asp Phe Ala Arg Arg Arg Glu Pro Asp Arg Glu Gly Leu Arg
            260                 265                 270

Ala Phe Leu Glu Arg Leu Glu Phe Gly Ser Leu Leu His Glu Phe Gly
    275                 280                 285

Leu Leu Glu Glu Ser Glu Pro Val Gly Tyr Arg Ile Val Lys Asp Leu
    290                 295                 300

Val Glu Phe Glu Lys Leu Ile Glu Lys Leu Arg Glu Ser Pro Ser Phe
305                 310                 315                 320

Ala Ile Asp Lys Glu Thr Ser Ser Leu Asp Pro Phe Asp Cys Asp Ile
                325                 330                 335

Val Gly Ile Ser Val Ser Phe Lys Pro Lys Glu Ala Tyr Tyr Ile Pro

-continued

```
                340                 345                 350
Leu His His Arg Asn Ala Gln Asn Leu Asp Glu Lys Glu Val Leu Lys
            355                 360                 365
Lys Leu Lys Glu Ile Leu Glu Asp Pro Gly Ala Lys Ile Val Gly Gln
        370                 375                 380
Asn Leu Lys Phe Asp Tyr Lys Val Leu Met Val Lys Gly Val Glu Pro
385                 390                 395                 400
Val Pro Pro Tyr Phe Asp Thr Met Ile Ala Ala Tyr Leu Leu Glu Pro
                405                 410                 415
Asn Glu Lys Lys Phe Asn Leu Asp Leu Ala Leu Lys Phe Leu Gly
            420                 425                 430
Tyr Lys Met Thr Ser Tyr Gln Glu Leu Met Ser Phe Ser Phe Pro Leu
            435                 440                 445
Phe Gly Phe Ser Phe Ala Asp Val Pro Val Glu Lys Ala Ala Asn Tyr
        450                 455                 460
Ser Cys Glu Asp Ala Asp Ile Thr Tyr Arg Leu Tyr Lys Thr Leu Ser
465                 470                 475                 480
Leu Lys Leu His Glu Ala Asp Leu Glu Asn Val Phe Tyr Lys Ile Glu
                485                 490                 495
Met Pro Leu Val Asn Val Leu Ala Arg Met Glu Leu Asn Gly Val Tyr
            500                 505                 510
Val Asp Thr Glu Phe Leu Lys Lys Leu Ser Glu Glu Tyr Gly Lys Lys
        515                 520                 525
Leu Glu Glu Leu Ala Glu Ile Tyr Arg Ile Ala Gly Glu Pro Phe
        530                 535                 540
Asn Ile Asn Ser Pro Lys Gln Val Ser Arg Ile Leu Phe Glu Lys Leu
545                 550                 555                 560
Gly Ile Lys Pro Arg Gly Lys Thr Thr Lys Thr Gly Asp Tyr Ser Thr
                565                 570                 575
Arg Ile Glu Val Leu Glu Glu Leu Ala Gly His Glu Ile Ile Pro
            580                 585                 590
Leu Ile Leu Glu Tyr Arg Lys Ile Gln Lys Leu Lys Ser Thr Tyr Ile
            595                 600                 605
Asp Ala Leu Pro Lys Met Val Asn Pro Lys Thr Gly Arg Ile His Ala
        610                 615                 620
Ser Phe Asn Gln Thr Gly Thr Ala Thr Gly Arg Leu Ser Ser Ser Asp
625                 630                 635                 640
Pro Asn Leu Gln Asn Leu Pro Thr Lys Ser Glu Glu Gly Lys Glu Ile
                645                 650                 655
Arg Lys Ala Ile Val Pro Gln Asp Pro Asn Trp Trp Ile Val Ser Ala
            660                 665                 670
Asp Tyr Ser Gln Ile Glu Leu Arg Ile Leu Ala His Leu Ser Gly Asp
        675                 680                 685
Glu Asn Leu Leu Arg Ala Phe Glu Glu Gly Ile Asp Val His Thr Leu
            690                 695                 700
Thr Ala Ser Arg Ile Phe Asn Val Lys Pro Glu Glu Val Thr Glu Glu
705                 710                 715                 720
Met Arg Arg Ala Gly Lys Met Val Asn Phe Ser Ile Ile Tyr Gly Val
                725                 730                 735
Thr Pro Tyr Gly Leu Ser Val Arg Leu Gly Val Pro Val Lys Glu Ala
            740                 745                 750
Glu Lys Met Ile Val Asn Tyr Phe Val Leu Tyr Pro Lys Val Arg Asp
        755                 760                 765
```

```
Tyr Ile Gln Arg Val Val Ser Glu Ala Lys Glu Lys Gly Tyr Val Arg
    770                 775                 780

Thr Leu Phe Gly Arg Lys Arg Asp Ile Pro Gln Leu Met Ala Arg Asp
785                 790                 795                 800

Arg Asn Thr Gln Ala Glu Gly Glu Arg Ile Ala Ile Asn Thr Pro Ile
                805                 810                 815

Gln Gly Thr Ala Ala Asp Ile Ile Lys Leu Ala Met Ile Glu Ile Asp
                820                 825                 830

Arg Glu Leu Lys Glu Arg Lys Met Arg Ser Lys Met Ile Ile Gln Val
                835                 840                 845

His Asp Glu Leu Val Phe Glu Val Pro Asn Glu Glu Lys Asp Ala Leu
    850                 855                 860

Val Glu Leu Val Lys Asp Arg Met Thr Asn Val Val Lys Leu Ser Val
865                 870                 875                 880

Pro Leu Glu Val Asp Val Thr Ile Gly Lys Thr Trp Ser
                885                 890
```

```
<210> SEQ ID NO 117
<211> LENGTH: 196
<212> TYPE: PRT
<213> ORGANISM: Artificial sequence
<220> FEATURE:
<223> OTHER INFORMATION: Exonucleolytic domain of chimeric thermostable
      DNA polymerase CS6 after first round of mutagenesis residues
      323-325 DNE substitution

<400> SEQUENCE: 117

Glu Ser Glu Pro Val Gly Tyr Arg Ile Val Lys Asp Leu Val Glu Phe
1               5                   10                  15

Glu Lys Leu Ile Glu Lys Leu Arg Glu Ser Pro Ser Phe Ala Ile Asp
                20                  25                  30

Asn Glu Thr Ser Ser Leu Asp Pro Phe Asp Cys Asp Ile Val Gly Ile
            35                  40                  45

Ser Val Ser Phe Lys Pro Lys Glu Ala Tyr Tyr Ile Pro Leu His His
    50                  55                  60

Arg Asn Ala Gln Asn Leu Asp Glu Lys Glu Val Leu Lys Lys Leu Lys
65                  70                  75                  80

Glu Ile Leu Glu Asp Pro Gly Ala Lys Ile Val Gly Gln Asn Leu Lys
                85                  90                  95

Phe Asp Tyr Lys Val Leu Met Val Lys Gly Val Glu Pro Val Pro Pro
                100                 105                 110

Tyr Phe Asp Thr Met Ile Ala Ala Tyr Leu Leu Glu Pro Asn Glu Lys
            115                 120                 125

Lys Phe Asn Leu Asp Asp Leu Ala Leu Lys Phe Leu Gly Tyr Lys Met
    130                 135                 140

Thr Ser Tyr Gln Glu Leu Met Ser Phe Ser Phe Pro Leu Phe Gly Phe
145                 150                 155                 160

Ser Phe Ala Asp Val Pro Val Glu Lys Ala Ala Asn Tyr Ser Cys Glu
                165                 170                 175

Asp Ala Asp Ile Thr Tyr Arg Leu Tyr Lys Thr Leu Ser Leu Lys Leu
                180                 185                 190

His Glu Ala Asp
        195

<210> SEQ ID NO 118
<211> LENGTH: 893
```

<212> TYPE: PRT
<213> ORGANISM: Artificial sequence
<220> FEATURE:
<223> OTHER INFORMATION: chimeric thermostable DNA polymerase CS6 after first round of mutagenesis residues 323-325 DNE substitution

<400> SEQUENCE: 118

```
Met Lys Ala Met Leu Pro Leu Phe Glu Pro Lys Gly Arg Val Leu Leu
1               5                  10                  15

Val Asp Gly His His Leu Ala Tyr Arg Thr Phe Phe Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Tyr Lys Ala Val Phe
50                  55                  60

Val Val Phe Asp Ala Lys Ala Pro Ser Phe Arg His Glu Ala Tyr Glu
65                  70                  75                  80

Ala Tyr Lys Ala Gly Arg Ala Pro Thr Pro Glu Asp Phe Pro Arg Gln
                85                  90                  95

Leu Ala Leu Ile Lys Glu Leu Val Asp Leu Leu Gly Phe Thr Arg Leu
            100                 105                 110

Glu Val Pro Gly Phe Glu Ala Asp Asp Val Leu Ala Thr Leu Ala Lys
        115                 120                 125

Lys Ala Glu Arg Glu Gly Tyr Glu Val Arg Ile Leu Thr Ala Asp Arg
130                 135                 140

Asp Leu Tyr Gln Leu Val Ser Asp Arg Val Ala Val Leu His Pro Glu
145                 150                 155                 160

Gly His Leu Ile Thr Pro Glu Trp Leu Trp Glu Lys Tyr Gly Leu Lys
                165                 170                 175

Pro Glu Gln Trp Val Asp Phe Arg Ala Leu Val Gly Asp Pro Ser Asp
            180                 185                 190

Asn Leu Pro Gly Val Lys Gly Ile Gly Glu Lys Thr Ala Leu Lys Leu
        195                 200                 205

Leu Lys Glu Trp Gly Ser Leu Glu Asn Ile Leu Lys Asn Leu Asp Arg
210                 215                 220

Val Lys Pro Glu Ser Val Arg Glu Arg Ile Lys Ala His Leu Glu Asp
225                 230                 235                 240

Leu Lys Leu Ser Leu Glu Leu Ser Arg Val Arg Ser Asp Leu Pro Leu
                245                 250                 255

Glu Val Asp Phe Ala Arg Arg Arg Glu Pro Asp Arg Glu Gly Leu Arg
            260                 265                 270

Ala Phe Leu Glu Arg Leu Glu Phe Gly Ser Leu Leu His Glu Phe Gly
        275                 280                 285

Leu Leu Glu Glu Ser Glu Pro Val Gly Tyr Arg Ile Val Lys Asp Leu
290                 295                 300

Val Glu Phe Glu Lys Leu Ile Glu Lys Leu Arg Glu Ser Pro Ser Phe
305                 310                 315                 320

Ala Ile Asp Asn Glu Thr Ser Ser Leu Asp Pro Phe Asp Cys Asp Ile
                325                 330                 335

Val Gly Ile Ser Val Ser Phe Lys Pro Lys Glu Ala Tyr Tyr Ile Pro
            340                 345                 350

Leu His His Arg Asn Ala Gln Asn Leu Asp Glu Lys Glu Val Leu Lys
        355                 360                 365

Lys Leu Lys Glu Ile Leu Glu Asp Pro Gly Ala Lys Ile Val Gly Gln
370                 375                 380
```

-continued

```
Asn Leu Lys Phe Asp Tyr Lys Val Leu Met Val Lys Gly Val Glu Pro
385                 390                 395                 400

Val Pro Pro Tyr Phe Asp Thr Met Ile Ala Ala Tyr Leu Leu Glu Pro
                405                 410                 415

Asn Glu Lys Lys Phe Asn Leu Asp Asp Leu Ala Leu Lys Phe Leu Gly
            420                 425                 430

Tyr Lys Met Thr Ser Tyr Gln Glu Leu Met Ser Phe Ser Phe Pro Leu
        435                 440                 445

Phe Gly Phe Ser Phe Ala Asp Val Pro Val Glu Lys Ala Ala Asn Tyr
    450                 455                 460

Ser Cys Glu Asp Ala Asp Ile Thr Tyr Arg Leu Tyr Lys Thr Leu Ser
465                 470                 475                 480

Leu Lys Leu His Glu Ala Asp Leu Glu Asn Val Phe Tyr Lys Ile Glu
                485                 490                 495

Met Pro Leu Val Asn Val Leu Ala Arg Met Glu Leu Asn Gly Val Tyr
                500                 505                 510

Val Asp Thr Glu Phe Leu Lys Lys Leu Ser Glu Tyr Gly Lys Lys
        515                 520                 525

Leu Glu Glu Leu Ala Glu Glu Ile Tyr Arg Ile Ala Gly Glu Pro Phe
530                 535                 540

Asn Ile Asn Ser Pro Lys Gln Val Ser Arg Ile Leu Phe Glu Lys Leu
545                 550                 555                 560

Gly Ile Lys Pro Arg Gly Lys Thr Thr Lys Thr Gly Asp Tyr Ser Thr
                565                 570                 575

Arg Ile Glu Val Leu Glu Glu Leu Ala Gly Glu His Glu Ile Ile Pro
                580                 585                 590

Leu Ile Leu Glu Tyr Arg Lys Ile Gln Lys Leu Lys Ser Thr Tyr Ile
            595                 600                 605

Asp Ala Leu Pro Lys Met Val Asn Pro Lys Thr Gly Arg Ile His Ala
610                 615                 620

Ser Phe Asn Gln Thr Gly Thr Ala Thr Gly Arg Leu Ser Ser Ser Asp
625                 630                 635                 640

Pro Asn Leu Gln Asn Leu Pro Thr Lys Ser Glu Glu Gly Lys Glu Ile
            645                 650                 655

Arg Lys Ala Ile Val Pro Gln Asp Pro Asn Trp Trp Ile Val Ser Ala
                660                 665                 670

Asp Tyr Ser Gln Ile Glu Leu Arg Ile Leu Ala His Leu Ser Gly Asp
        675                 680                 685

Glu Asn Leu Leu Arg Ala Phe Glu Glu Gly Ile Asp Val His Thr Leu
    690                 695                 700

Thr Ala Ser Arg Ile Phe Asn Val Lys Pro Glu Glu Val Thr Glu Glu
705                 710                 715                 720

Met Arg Arg Ala Gly Lys Met Val Asn Phe Ser Ile Ile Tyr Gly Val
                725                 730                 735

Thr Pro Tyr Gly Leu Ser Val Arg Leu Gly Val Pro Val Lys Glu Ala
            740                 745                 750

Glu Lys Met Ile Val Asn Tyr Phe Val Leu Tyr Pro Lys Val Arg Asp
        755                 760                 765

Tyr Ile Gln Arg Val Val Ser Glu Ala Lys Glu Lys Gly Tyr Val Arg
    770                 775                 780

Thr Leu Phe Gly Arg Lys Arg Asp Ile Pro Gln Leu Met Ala Arg Asp
785                 790                 795                 800
```

```
Arg Asn Thr Gln Ala Glu Gly Glu Arg Ile Ala Ile Asn Thr Pro Ile
            805                 810                 815

Gln Gly Thr Ala Ala Asp Ile Ile Lys Leu Ala Met Ile Glu Ile Asp
        820                 825                 830

Arg Glu Leu Lys Glu Arg Lys Met Arg Ser Lys Met Ile Ile Gln Val
            835                 840                 845

His Asp Glu Leu Val Phe Glu Val Pro Asn Glu Glu Lys Asp Ala Leu
850                 855                 860

Val Glu Leu Val Lys Asp Arg Met Thr Asn Val Val Lys Leu Ser Val
865                 870                 875                 880

Pro Leu Glu Val Asp Val Thr Ile Gly Lys Thr Trp Ser
            885                 890

<210> SEQ ID NO 119
<211> LENGTH: 196
<212> TYPE: PRT
<213> ORGANISM: Artificial sequence
<220> FEATURE:
<223> OTHER INFORMATION: Exonucleolytic domain of chimeric thermostable
      DNA polymerase CS6 after first round of mutagenesis residues
      323-325 DQE substitution

<400> SEQUENCE: 119

Glu Ser Glu Pro Val Gly Tyr Arg Ile Val Lys Asp Leu Val Glu Phe
1               5                   10                  15

Glu Lys Leu Ile Glu Lys Leu Arg Glu Ser Pro Ser Phe Ala Ile Asp
            20                  25                  30

Gln Glu Thr Ser Ser Leu Asp Pro Phe Asp Cys Asp Ile Val Gly Ile
        35                  40                  45

Ser Val Ser Phe Lys Pro Lys Glu Ala Tyr Tyr Ile Pro Leu His His
50                  55                  60

Arg Asn Ala Gln Asn Leu Asp Glu Lys Val Leu Lys Lys Leu Lys
65                  70                  75                  80

Glu Ile Leu Glu Asp Pro Gly Ala Lys Ile Val Gly Gln Asn Leu Lys
            85                  90                  95

Phe Asp Tyr Lys Val Leu Met Val Lys Gly Val Glu Pro Val Pro Pro
            100                 105                 110

Tyr Phe Asp Thr Met Ile Ala Ala Tyr Leu Leu Glu Pro Asn Glu Lys
        115                 120                 125

Lys Phe Asn Leu Asp Asp Leu Ala Leu Lys Phe Leu Gly Tyr Lys Met
130                 135                 140

Thr Ser Tyr Gln Glu Leu Met Ser Phe Ser Phe Pro Leu Phe Gly Phe
145                 150                 155                 160

Ser Phe Ala Asp Val Pro Val Gly Lys Ala Ala Asn Tyr Ser Cys Glu
            165                 170                 175

Asp Ala Asp Ile Thr Tyr Arg Leu Tyr Lys Thr Leu Ser Leu Lys Leu
            180                 185                 190

His Glu Ala Asp
        195

<210> SEQ ID NO 120
<211> LENGTH: 893
<212> TYPE: PRT
<213> ORGANISM: Artificial sequence
<220> FEATURE:
<223> OTHER INFORMATION: chimeric thermostable DNA polymerase CS6 after
      first round of mutagenesis residues 323-325 DQE substitution

<400> SEQUENCE: 120
```

```
Met Lys Ala Met Leu Pro Leu Phe Glu Pro Lys Gly Arg Val Leu Leu
1               5                   10                  15

Val Asp Gly His His Leu Ala Tyr Arg Thr Phe Phe Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Tyr Lys Ala Val Phe
    50                  55                  60

Val Val Phe Asp Ala Lys Ala Pro Ser Phe Arg His Glu Ala Tyr Glu
65                  70                  75                  80

Ala Tyr Lys Ala Gly Arg Ala Pro Thr Pro Glu Asp Phe Pro Arg Gln
                85                  90                  95

Leu Ala Leu Ile Lys Glu Leu Val Asp Leu Leu Gly Phe Thr Arg Leu
            100                 105                 110

Glu Val Pro Gly Phe Glu Ala Asp Asp Val Leu Ala Thr Leu Ala Lys
            115                 120                 125

Lys Ala Glu Arg Glu Gly Tyr Glu Val Arg Ile Leu Thr Ala Asp Arg
130                 135                 140

Asp Leu Tyr Gln Leu Val Ser Asp Arg Val Ala Val Leu His Pro Glu
145                 150                 155                 160

Gly His Leu Ile Thr Pro Glu Trp Leu Trp Glu Lys Tyr Gly Leu Lys
                165                 170                 175

Pro Glu Gln Trp Val Asp Phe Arg Ala Leu Val Gly Asp Pro Ser Asp
            180                 185                 190

Asn Leu Pro Gly Val Lys Gly Ile Gly Glu Lys Thr Ala Leu Lys Leu
            195                 200                 205

Leu Lys Glu Trp Gly Ser Leu Glu Asn Ile Leu Lys Asn Leu Asp Arg
            210                 215                 220

Val Lys Pro Glu Ser Val Arg Glu Arg Ile Lys Ala His Leu Glu Asp
225                 230                 235                 240

Leu Lys Leu Ser Leu Glu Leu Ser Arg Val Arg Ser Asp Leu Pro Leu
            245                 250                 255

Glu Val Asp Phe Ala Arg Arg Arg Glu Pro Asp Arg Glu Gly Leu Arg
            260                 265                 270

Ala Phe Leu Glu Arg Leu Glu Phe Gly Ser Leu Leu His Glu Phe Gly
            275                 280                 285

Leu Leu Glu Glu Ser Glu Pro Val Gly Tyr Arg Ile Val Lys Asp Leu
            290                 295                 300

Val Glu Phe Glu Lys Leu Ile Glu Lys Leu Arg Glu Ser Pro Ser Phe
305                 310                 315                 320

Ala Ile Asp Gln Glu Thr Ser Ser Leu Asp Pro Phe Asp Cys Asp Ile
                325                 330                 335

Val Gly Ile Ser Val Ser Phe Lys Pro Lys Glu Ala Tyr Tyr Ile Pro
            340                 345                 350

Leu His His Arg Asn Ala Gln Asn Leu Asp Glu Lys Glu Val Leu Lys
            355                 360                 365

Lys Leu Lys Glu Ile Leu Glu Asp Pro Gly Ala Lys Ile Val Gly Gln
            370                 375                 380

Asn Leu Lys Phe Asp Tyr Lys Val Leu Met Val Lys Gly Val Glu Pro
385                 390                 395                 400

Val Pro Pro Tyr Phe Asp Thr Met Ile Ala Ala Tyr Leu Leu Glu Pro
                405                 410                 415
```

```
Asn Glu Lys Lys Phe Asn Leu Asp Asp Leu Ala Leu Lys Phe Leu Gly
            420                 425                 430

Tyr Lys Met Thr Ser Tyr Gln Glu Leu Met Ser Phe Ser Phe Pro Leu
        435                 440                 445

Phe Gly Phe Ser Phe Ala Asp Val Pro Val Glu Lys Ala Ala Asn Tyr
    450                 455                 460

Ser Cys Glu Asp Ala Asp Ile Thr Tyr Arg Leu Tyr Lys Thr Leu Ser
465                 470                 475                 480

Leu Lys Leu His Glu Ala Asp Leu Glu Asn Val Phe Tyr Lys Ile Glu
                485                 490                 495

Met Pro Leu Val Asn Val Leu Ala Arg Met Glu Leu Asn Gly Val Tyr
            500                 505                 510

Val Asp Thr Glu Phe Leu Lys Lys Leu Ser Glu Glu Tyr Gly Lys Lys
        515                 520                 525

Leu Glu Glu Leu Ala Glu Ile Tyr Arg Ile Ala Gly Glu Pro Phe
    530                 535                 540

Asn Ile Asn Ser Pro Lys Gln Val Ser Arg Ile Leu Phe Glu Lys Leu
545                 550                 555                 560

Gly Ile Lys Pro Arg Gly Lys Thr Thr Lys Thr Gly Asp Tyr Ser Thr
                565                 570                 575

Arg Ile Glu Val Leu Glu Glu Leu Ala Gly Glu His Glu Ile Ile Pro
            580                 585                 590

Leu Ile Leu Glu Tyr Arg Lys Ile Gln Lys Leu Lys Ser Thr Tyr Ile
        595                 600                 605

Asp Ala Leu Pro Lys Met Val Asn Pro Lys Thr Gly Arg Ile His Ala
    610                 615                 620

Ser Phe Asn Gln Thr Gly Thr Ala Thr Gly Arg Leu Ser Ser Ser Asp
625                 630                 635                 640

Pro Asn Leu Gln Asn Leu Pro Thr Lys Ser Glu Glu Gly Lys Glu Ile
                645                 650                 655

Arg Lys Ala Ile Val Pro Gln Asp Pro Asn Trp Trp Ile Val Ser Ala
            660                 665                 670

Asp Tyr Ser Gln Ile Glu Leu Arg Ile Leu Ala His Leu Ser Gly Asp
        675                 680                 685

Glu Asn Leu Leu Arg Ala Phe Glu Gly Ile Asp Val His Thr Leu
    690                 695                 700

Thr Ala Ser Arg Ile Phe Asn Val Lys Pro Glu Glu Val Thr Glu Glu
705                 710                 715                 720

Met Arg Arg Ala Gly Lys Met Val Asn Phe Ser Ile Ile Tyr Gly Val
                725                 730                 735

Thr Pro Tyr Gly Leu Ser Val Arg Leu Gly Val Pro Val Lys Glu Ala
            740                 745                 750

Glu Lys Met Ile Val Asn Tyr Phe Val Leu Tyr Pro Lys Val Arg Asp
        755                 760                 765

Tyr Ile Gln Arg Val Val Ser Glu Ala Lys Glu Lys Gly Tyr Val Arg
    770                 775                 780

Thr Leu Phe Gly Arg Lys Arg Asp Ile Pro Gln Leu Met Ala Arg Asp
785                 790                 795                 800

Arg Asn Thr Gln Ala Glu Gly Glu Arg Ile Ala Ile Asn Thr Pro Ile
                805                 810                 815

Gln Gly Thr Ala Ala Asp Ile Ile Lys Leu Ala Met Ile Glu Ile Asp
            820                 825                 830

Arg Glu Leu Lys Glu Arg Lys Met Arg Ser Lys Met Ile Ile Gln Val
```

-continued

```
                835                 840                 845
His Asp Glu Leu Val Phe Glu Val Pro Asn Glu Lys Asp Ala Leu
    850                 855                 860

Val Glu Leu Val Lys Asp Arg Met Thr Asn Val Val Lys Leu Ser Val
865                 870                 875                 880

Pro Leu Glu Val Asp Val Thr Ile Gly Lys Thr Trp Ser
                885                 890

<210> SEQ ID NO 121
<211> LENGTH: 196
<212> TYPE: PRT
<213> ORGANISM: Artificial sequence
<220> FEATURE:
<223> OTHER INFORMATION: Exonucleolytic domain of chimeric thermostable
      DNA polymerase CS6 after first round of mutagenesis residues
      323-325 DHE substitution

<400> SEQUENCE: 121

Glu Ser Glu Pro Val Gly Tyr Arg Ile Val Lys Asp Leu Val Glu Phe
1               5                   10                  15

Glu Lys Leu Ile Glu Lys Leu Arg Glu Ser Pro Ser Phe Ala Ile Asp
            20                  25                  30

His Glu Thr Ser Ser Leu Asp Pro Phe Asp Cys Asp Ile Val Gly Ile
        35                  40                  45

Ser Val Ser Phe Lys Pro Lys Glu Ala Tyr Tyr Ile Pro Leu His His
    50                  55                  60

Arg Asn Ala Gln Asn Leu Asp Lys Glu Val Leu Lys Lys Leu Lys
65                  70                  75                  80

Glu Ile Leu Glu Asp Pro Gly Ala Lys Ile Val Gly Gln Asn Leu Lys
                85                  90                  95

Phe Asp Tyr Lys Val Leu Met Val Lys Gly Val Glu Pro Val Pro Pro
            100                 105                 110

Tyr Phe Asp Thr Met Ile Ala Ala Tyr Leu Leu Glu Pro Asn Glu Lys
        115                 120                 125

Lys Phe Asn Leu Asp Asp Leu Ala Leu Lys Phe Leu Gly Tyr Lys Met
    130                 135                 140

Thr Ser Tyr Gln Glu Leu Met Ser Phe Ser Phe Pro Leu Phe Gly Phe
145                 150                 155                 160

Ser Phe Ala Asp Val Pro Val Glu Lys Ala Ala Asn Tyr Ser Cys Glu
                165                 170                 175

Asp Ala Asp Ile Thr Tyr Arg Leu Tyr Lys Thr Leu Ser Leu Lys Leu
            180                 185                 190

His Glu Ala Asp
        195

<210> SEQ ID NO 122
<211> LENGTH: 893
<212> TYPE: PRT
<213> ORGANISM: Artificial sequence
<220> FEATURE:
<223> OTHER INFORMATION: chimeric thermostable DNA polymerase CS6 after
      first round of mutagenesis residues 323-325 DHE substitution

<400> SEQUENCE: 122

Met Lys Ala Met Leu Pro Leu Phe Glu Pro Lys Gly Arg Val Leu Leu
1               5                   10                  15

Val Asp Gly His His Leu Ala Tyr Arg Thr Phe Phe Ala Leu Lys Gly
            20                  25                  30
```

-continued

Leu Thr Thr Ser Arg Gly Glu Pro Val Gln Ala Val Tyr Gly Phe Ala
         35                  40                  45

Lys Ser Leu Leu Lys Ala Leu Lys Glu Asp Gly Tyr Lys Ala Val Phe
     50                  55                  60

Val Val Phe Asp Ala Lys Ala Pro Ser Phe Arg His Glu Ala Tyr Glu
 65              70                  75                      80

Ala Tyr Lys Ala Gly Arg Ala Pro Thr Pro Glu Asp Phe Pro Arg Gln
                 85                  90                  95

Leu Ala Leu Ile Lys Glu Leu Val Asp Leu Gly Phe Thr Arg Leu
             100                 105             110

Glu Val Pro Gly Phe Glu Ala Asp Val Leu Ala Thr Leu Ala Lys
         115                 120             125

Lys Ala Glu Arg Glu Gly Tyr Glu Val Arg Ile Leu Thr Ala Asp Arg
     130                 135                 140

Asp Leu Tyr Gln Leu Val Ser Asp Arg Val Ala Val Leu His Pro Glu
145                 150                 155                 160

Gly His Leu Ile Thr Pro Glu Trp Leu Trp Glu Lys Tyr Gly Leu Lys
                 165                 170                 175

Pro Glu Gln Trp Val Asp Phe Arg Ala Leu Val Gly Asp Pro Ser Asp
             180                 185                 190

Asn Leu Pro Gly Val Lys Gly Ile Gly Glu Lys Thr Ala Leu Lys Leu
         195                 200                 205

Leu Lys Glu Trp Gly Ser Leu Glu Asn Ile Leu Lys Asn Leu Asp Arg
     210                 215                 220

Val Lys Pro Glu Ser Val Arg Glu Arg Ile Lys Ala His Leu Glu Asp
225                 230                 235                 240

Leu Lys Leu Ser Leu Glu Leu Ser Arg Val Arg Ser Asp Leu Pro Leu
                 245                 250                 255

Glu Val Asp Phe Ala Arg Arg Glu Pro Asp Arg Glu Gly Leu Arg
             260                 265                 270

Ala Phe Leu Glu Arg Leu Glu Phe Gly Ser Leu Leu His Glu Phe Gly
         275                 280                 285

Leu Leu Glu Glu Ser Glu Pro Val Gly Tyr Arg Ile Val Lys Asp Leu
     290                 295                 300

Val Glu Phe Glu Lys Leu Ile Glu Lys Leu Arg Glu Ser Pro Ser Phe
305                 310                 315                 320

Ala Ile Asp His Glu Thr Ser Ser Leu Asp Pro Phe Asp Cys Asp Ile
                 325                 330                 335

Val Gly Ile Ser Val Ser Phe Lys Pro Lys Glu Ala Tyr Tyr Ile Pro
             340                 345                 350

Leu His His Arg Asn Ala Gln Asn Leu Asp Glu Lys Glu Val Leu Lys
         355                 360                 365

Lys Leu Lys Glu Ile Leu Glu Asp Pro Gly Ala Lys Ile Val Gly Gln
     370                 375                 380

Asn Leu Lys Phe Asp Tyr Lys Val Leu Met Val Lys Gly Val Glu Pro
385                 390                 395                 400

Val Pro Pro Tyr Phe Asp Thr Met Ile Ala Ala Tyr Leu Leu Glu Pro
                 405                 410                 415

Asn Glu Lys Lys Phe Asn Leu Asp Asp Leu Ala Leu Lys Phe Leu Gly
             420                 425                 430

Tyr Lys Met Thr Ser Tyr Gln Glu Leu Met Ser Phe Ser Phe Pro Leu
         435                 440                 445

Phe Gly Phe Ser Phe Ala Asp Val Pro Val Glu Lys Ala Ala Asn Tyr

-continued

```
            450                 455                 460
Ser Cys Glu Asp Ala Asp Ile Thr Tyr Arg Leu Tyr Lys Thr Leu Ser
465                 470                 475                 480

Leu Lys Leu His Glu Ala Asp Leu Glu Asn Val Phe Tyr Lys Ile Glu
                485                 490                 495

Met Pro Leu Val Asn Val Leu Ala Arg Met Glu Leu Asn Gly Val Tyr
            500                 505                 510

Val Asp Thr Glu Phe Leu Lys Lys Leu Ser Glu Glu Tyr Gly Lys Lys
            515                 520                 525

Leu Glu Glu Leu Ala Glu Ile Tyr Arg Ile Ala Gly Glu Pro Phe
530                 535                 540

Asn Ile Asn Ser Pro Lys Gln Val Ser Arg Ile Leu Phe Glu Lys Leu
545                 550                 555                 560

Gly Ile Lys Pro Arg Gly Lys Thr Thr Lys Thr Gly Asp Tyr Ser Thr
                565                 570                 575

Arg Ile Glu Val Leu Glu Glu Leu Ala Gly His Glu Ile Ile Pro
            580                 585                 590

Leu Ile Leu Glu Tyr Arg Lys Ile Gln Lys Leu Lys Ser Thr Tyr Ile
            595                 600                 605

Asp Ala Leu Pro Lys Met Val Asn Pro Lys Thr Gly Arg Ile His Ala
610                 615                 620

Ser Phe Asn Gln Thr Gly Thr Ala Thr Gly Arg Leu Ser Ser Ser Asp
625                 630                 635                 640

Pro Asn Leu Gln Asn Leu Pro Thr Lys Ser Glu Glu Gly Lys Glu Ile
                645                 650                 655

Arg Lys Ala Ile Val Pro Gln Asp Pro Asn Trp Trp Ile Val Ser Ala
                660                 665                 670

Asp Tyr Ser Gln Ile Glu Leu Arg Ile Leu Ala His Leu Ser Gly Asp
            675                 680                 685

Glu Asn Leu Leu Arg Ala Phe Glu Glu Gly Ile Asp Val His Thr Leu
            690                 695                 700

Thr Ala Ser Arg Ile Phe Asn Val Lys Pro Glu Glu Val Thr Glu Glu
705                 710                 715                 720

Met Arg Arg Ala Gly Lys Met Val Asn Phe Ser Ile Ile Tyr Gly Val
                725                 730                 735

Thr Pro Tyr Gly Leu Ser Val Arg Leu Gly Val Pro Val Lys Glu Ala
                740                 745                 750

Glu Lys Met Ile Val Asn Tyr Phe Val Leu Tyr Pro Lys Val Arg Asp
            755                 760                 765

Tyr Ile Gln Arg Val Val Ser Glu Ala Lys Glu Lys Gly Tyr Val Arg
            770                 775                 780

Thr Leu Phe Gly Arg Lys Arg Asp Ile Pro Gln Leu Met Ala Arg Asp
785                 790                 795                 800

Arg Asn Thr Gln Ala Glu Gly Glu Arg Ile Ala Ile Asn Thr Pro Ile
                805                 810                 815

Gln Gly Thr Ala Ala Asp Ile Ile Lys Leu Ala Met Ile Glu Ile Asp
                820                 825                 830

Arg Glu Leu Lys Glu Arg Lys Met Arg Ser Lys Met Ile Ile Gln Val
                835                 840                 845

His Asp Glu Leu Val Phe Glu Val Pro Asn Glu Glu Lys Asp Ala Leu
            850                 855                 860

Val Glu Leu Val Lys Asp Arg Met Thr Asn Val Val Lys Leu Ser Val
865                 870                 875                 880
```

```
Pro Leu Glu Val Asp Val Thr Ile Gly Lys Thr Trp Ser
            885                 890
```

<210> SEQ ID NO 123
<211> LENGTH: 196
<212> TYPE: PRT
<213> ORGANISM: Artificial sequence
<220> FEATURE:
<223> OTHER INFORMATION: Exonucleolytic domain of chimeric thermostable
      DNA polymerase CS6 after first round of mutagenesis residues
      323-325 DLD substitution

<400> SEQUENCE: 123

```
Glu Ser Glu Pro Val Gly Tyr Arg Ile Val Lys Asp Leu Val Glu Phe
1               5                   10                  15

Glu Lys Leu Ile Glu Lys Leu Arg Glu Ser Pro Ser Phe Ala Ile Asp
            20                  25                  30

Leu Asp Thr Ser Ser Leu Asp Pro Phe Asp Cys Asp Ile Val Gly Ile
        35                  40                  45

Ser Val Ser Phe Lys Pro Lys Glu Ala Tyr Tyr Ile Pro Leu His His
50                  55                  60

Arg Asn Ala Gln Asn Leu Asp Glu Lys Glu Val Leu Lys Lys Leu Lys
65                  70                  75                  80

Glu Ile Leu Glu Asp Pro Gly Ala Lys Ile Val Gly Gln Asn Leu Lys
                85                  90                  95

Phe Asp Tyr Lys Val Leu Met Val Lys Gly Val Glu Pro Val Pro Pro
            100                 105                 110

Tyr Phe Asp Thr Met Ile Ala Ala Tyr Leu Leu Glu Pro Asn Glu Lys
            115                 120                 125

Lys Phe Asn Leu Asp Asp Leu Ala Leu Lys Phe Leu Gly Tyr Lys Met
        130                 135                 140

Thr Ser Tyr Gln Glu Leu Met Ser Phe Ser Phe Pro Leu Phe Gly Phe
145                 150                 155                 160

Ser Phe Ala Asp Val Pro Val Glu Lys Ala Ala Asn Tyr Ser Cys Glu
                165                 170                 175

Asp Ala Asp Ile Thr Tyr Arg Leu Tyr Lys Thr Leu Ser Leu Lys Leu
            180                 185                 190

His Glu Ala Asp
        195
```

<210> SEQ ID NO 124
<211> LENGTH: 893
<212> TYPE: PRT
<213> ORGANISM: Artificial sequence
<220> FEATURE:
<223> OTHER INFORMATION: chimeric thermostable DNA polymerase CS6 after
      first round of mutagenesis residues 323-325 DLD substitution

<400> SEQUENCE: 124

```
Met Lys Ala Met Leu Pro Leu Phe Glu Pro Lys Gly Arg Val Leu Leu
1               5                   10                  15

Val Asp Gly His His Leu Ala Tyr Arg Thr Phe Phe Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Tyr Lys Ala Val Phe
50                  55                  60

Val Val Phe Asp Ala Lys Ala Pro Ser Phe Arg His Glu Ala Tyr Glu
```

-continued

```
            65                  70                  75                  80
Ala Tyr Lys Ala Gly Arg Ala Pro Thr Pro Glu Asp Phe Pro Arg Gln
                85                  90                  95
Leu Ala Leu Ile Lys Glu Leu Val Asp Leu Leu Gly Phe Thr Arg Leu
                100                 105                 110
Glu Val Pro Gly Phe Glu Ala Asp Asp Val Leu Ala Thr Leu Ala Lys
                115                 120                 125
Lys Ala Glu Arg Glu Gly Tyr Glu Val Arg Ile Leu Thr Ala Asp Arg
                130                 135                 140
Asp Leu Tyr Gln Leu Val Ser Asp Arg Val Ala Val Leu His Pro Glu
145                 150                 155                 160
Gly His Leu Ile Thr Pro Glu Trp Leu Trp Glu Lys Tyr Gly Leu Lys
                165                 170                 175
Pro Glu Gln Trp Val Asp Phe Arg Ala Leu Val Gly Asp Pro Ser Asp
                180                 185                 190
Asn Leu Pro Gly Val Lys Gly Ile Gly Glu Lys Thr Ala Leu Lys Leu
                195                 200                 205
Leu Lys Glu Trp Gly Ser Leu Glu Asn Ile Leu Lys Asn Leu Asp Arg
                210                 215                 220
Val Lys Pro Glu Ser Val Arg Glu Arg Ile Lys Ala His Leu Glu Asp
225                 230                 235                 240
Leu Lys Leu Ser Leu Glu Leu Ser Arg Val Arg Ser Asp Leu Pro Leu
                245                 250                 255
Glu Val Asp Phe Ala Arg Arg Arg Glu Pro Asp Arg Glu Gly Leu Arg
                260                 265                 270
Ala Phe Leu Glu Arg Leu Glu Phe Gly Ser Leu Leu His Glu Phe Gly
                275                 280                 285
Leu Leu Glu Glu Ser Glu Pro Val Gly Tyr Arg Ile Val Lys Asp Leu
                290                 295                 300
Val Glu Phe Glu Lys Leu Ile Glu Lys Leu Arg Glu Ser Pro Ser Phe
305                 310                 315                 320
Ala Ile Asp Leu Asp Thr Ser Ser Leu Asp Pro Phe Asp Cys Asp Ile
                325                 330                 335
Val Gly Ile Ser Val Ser Phe Lys Pro Lys Glu Ala Tyr Tyr Ile Pro
                340                 345                 350
Leu His His Arg Asn Ala Gln Asn Leu Asp Glu Lys Glu Val Leu Lys
                355                 360                 365
Lys Leu Lys Glu Ile Leu Glu Asp Pro Gly Ala Lys Ile Val Gly Gln
                370                 375                 380
Asn Leu Lys Phe Asp Tyr Lys Val Leu Met Val Lys Gly Val Glu Pro
385                 390                 395                 400
Val Pro Pro Tyr Phe Asp Thr Met Ile Ala Ala Tyr Leu Leu Glu Pro
                405                 410                 415
Asn Glu Lys Lys Phe Asn Leu Asp Asp Leu Ala Leu Lys Phe Leu Gly
                420                 425                 430
Tyr Lys Met Thr Ser Tyr Gln Glu Leu Met Ser Phe Ser Phe Pro Leu
                435                 440                 445
Phe Gly Phe Ser Phe Ala Asp Val Pro Val Glu Lys Ala Ala Asn Tyr
                450                 455                 460
Ser Cys Glu Asp Ala Asp Ile Thr Tyr Arg Leu Tyr Lys Thr Leu Ser
465                 470                 475                 480
Leu Lys Leu His Glu Ala Asp Leu Glu Asn Val Phe Tyr Lys Ile Glu
                485                 490                 495
```

```
Met Pro Leu Val Asn Val Leu Ala Arg Met Glu Leu Asn Gly Val Tyr
            500                 505                 510
Val Asp Thr Glu Phe Leu Lys Lys Leu Ser Glu Tyr Gly Lys Lys
            515                 520                 525
Leu Glu Glu Leu Ala Glu Ile Tyr Arg Ile Ala Gly Glu Pro Phe
            530                 535                 540
Asn Ile Asn Ser Pro Lys Gln Val Ser Arg Ile Leu Phe Glu Lys Leu
545                 550                 555                 560
Gly Ile Lys Pro Arg Gly Lys Thr Thr Lys Thr Gly Asp Tyr Ser Thr
                    565                 570                 575
Arg Ile Glu Val Leu Glu Glu Leu Ala Gly Glu His Glu Ile Ile Pro
            580                 585                 590
Leu Ile Leu Glu Tyr Arg Lys Ile Gln Lys Leu Lys Ser Thr Tyr Ile
            595                 600                 605
Asp Ala Leu Pro Lys Met Val Asn Pro Lys Thr Gly Arg Ile His Ala
            610                 615                 620
Ser Phe Asn Gln Thr Gly Thr Ala Thr Gly Arg Leu Ser Ser Ser Asp
625                 630                 635                 640
Pro Asn Leu Gln Asn Leu Pro Thr Lys Ser Glu Glu Gly Lys Glu Ile
                    645                 650                 655
Arg Lys Ala Ile Val Pro Gln Asp Pro Asn Trp Trp Ile Val Ser Ala
                    660                 665                 670
Asp Tyr Ser Gln Ile Glu Leu Arg Ile Leu Ala His Leu Ser Gly Asp
                    675                 680                 685
Glu Asn Leu Leu Arg Ala Phe Glu Glu Gly Ile Asp Val His Thr Leu
            690                 695                 700
Thr Ala Ser Arg Ile Phe Asn Val Lys Pro Glu Glu Val Thr Glu Glu
705                 710                 715                 720
Met Arg Arg Ala Gly Lys Met Val Asn Phe Ser Ile Ile Tyr Gly Val
                    725                 730                 735
Thr Pro Tyr Gly Leu Ser Val Arg Leu Gly Val Pro Val Lys Glu Ala
            740                 745                 750
Glu Lys Met Ile Val Asn Tyr Phe Val Leu Tyr Pro Lys Val Arg Asp
            755                 760                 765
Tyr Ile Gln Arg Val Val Ser Glu Ala Lys Glu Lys Gly Tyr Val Arg
            770                 775                 780
Thr Leu Phe Gly Arg Lys Arg Asp Ile Pro Gln Leu Met Ala Arg Asp
785                 790                 795                 800
Arg Asn Thr Gln Ala Glu Gly Glu Arg Ile Ala Ile Asn Thr Pro Ile
                    805                 810                 815
Gln Gly Thr Ala Ala Asp Ile Ile Lys Leu Ala Met Ile Glu Ile Asp
                    820                 825                 830
Arg Glu Leu Lys Glu Arg Lys Met Arg Ser Lys Met Ile Ile Gln Val
            835                 840                 845
His Asp Glu Leu Val Phe Glu Val Pro Asn Glu Glu Lys Asp Ala Leu
            850                 855                 860
Val Glu Leu Val Lys Asp Arg Met Thr Asn Val Val Lys Leu Ser Val
865                 870                 875                 880
Pro Leu Glu Val Asp Val Thr Ile Gly Lys Thr Trp Ser
                    885                 890

<210> SEQ ID NO 125
<211> LENGTH: 196
```

```
<212> TYPE: PRT
<213> ORGANISM: Artificial sequence
<220> FEATURE:
<223> OTHER INFORMATION: Exonucleolytic domain of chimeric thermostable
      DNA polymerase CS6 after first round of mutagenesis residues
      323-325 ELD substitution

<400> SEQUENCE: 125
```

| Glu | Ser | Glu | Pro | Val | Gly | Tyr | Arg | Ile | Val | Lys | Asp | Leu | Val | Glu | Phe |
|---|---|---|---|---|---|---|---|---|---|---|---|---|---|---|---|
| 1 | | | | 5 | | | | | 10 | | | | | 15 | |

| Glu | Lys | Leu | Ile | Glu | Lys | Leu | Arg | Glu | Ser | Pro | Ser | Phe | Ala | Ile | Glu |
|---|---|---|---|---|---|---|---|---|---|---|---|---|---|---|---|
| | | | 20 | | | | | 25 | | | | | 30 | | |

| Leu | Asp | Thr | Ser | Ser | Leu | Asp | Pro | Phe | Asp | Cys | Asp | Ile | Val | Gly | Ile |
|---|---|---|---|---|---|---|---|---|---|---|---|---|---|---|---|
| | | 35 | | | | | 40 | | | | | 45 | | | |

| Ser | Val | Ser | Phe | Lys | Pro | Lys | Glu | Ala | Tyr | Tyr | Ile | Pro | Leu | His | His |
|---|---|---|---|---|---|---|---|---|---|---|---|---|---|---|---|
| | 50 | | | | | 55 | | | | | 60 | | | | |

| Arg | Asn | Ala | Gln | Asn | Leu | Asp | Glu | Lys | Glu | Val | Leu | Lys | Lys | Leu | Lys |
|---|---|---|---|---|---|---|---|---|---|---|---|---|---|---|---|
| 65 | | | | | 70 | | | | | 75 | | | | | 80 |

| Glu | Ile | Leu | Glu | Asp | Pro | Gly | Ala | Lys | Ile | Val | Gly | Gln | Asn | Leu | Lys |
|---|---|---|---|---|---|---|---|---|---|---|---|---|---|---|---|
| | | | | 85 | | | | | 90 | | | | | 95 | |

| Phe | Asp | Tyr | Lys | Val | Leu | Met | Val | Lys | Gly | Val | Glu | Pro | Val | Pro | Pro |
|---|---|---|---|---|---|---|---|---|---|---|---|---|---|---|---|
| | | | 100 | | | | | 105 | | | | | 110 | | |

| Tyr | Phe | Asp | Thr | Met | Ile | Ala | Ala | Tyr | Leu | Leu | Glu | Pro | Asn | Glu | Lys |
|---|---|---|---|---|---|---|---|---|---|---|---|---|---|---|---|
| | | 115 | | | | | 120 | | | | | 125 | | | |

| Lys | Phe | Asn | Leu | Asp | Asp | Leu | Ala | Leu | Lys | Phe | Leu | Gly | Tyr | Lys | Met |
|---|---|---|---|---|---|---|---|---|---|---|---|---|---|---|---|
| | 130 | | | | | 135 | | | | | 140 | | | | |

| Thr | Ser | Tyr | Gln | Glu | Leu | Met | Ser | Phe | Ser | Phe | Pro | Leu | Phe | Gly | Phe |
|---|---|---|---|---|---|---|---|---|---|---|---|---|---|---|---|
| 145 | | | | | 150 | | | | | 155 | | | | | 160 |

| Ser | Phe | Ala | Asp | Val | Pro | Val | Glu | Lys | Ala | Ala | Asn | Tyr | Ser | Cys | Glu |
|---|---|---|---|---|---|---|---|---|---|---|---|---|---|---|---|
| | | | | 165 | | | | | 170 | | | | | 175 | |

| Asp | Ala | Asp | Ile | Thr | Tyr | Arg | Leu | Tyr | Lys | Thr | Leu | Ser | Leu | Lys | Leu |
|---|---|---|---|---|---|---|---|---|---|---|---|---|---|---|---|
| | | 180 | | | | | 185 | | | | | 190 | | | |

| His | Glu | Ala | Asp |
|---|---|---|---|
| | 195 | | |

```
<210> SEQ ID NO 126
<211> LENGTH: 893
<212> TYPE: PRT
<213> ORGANISM: Artificial sequence
<220> FEATURE:
<223> OTHER INFORMATION: chimeric thermostable DNA polymerase CS6 after
      first round of mutagenesis residues 323-325 ELD substitution

<400> SEQUENCE: 126
```

| Met | Lys | Ala | Met | Leu | Pro | Leu | Phe | Glu | Pro | Lys | Gly | Arg | Val | Leu | Leu |
|---|---|---|---|---|---|---|---|---|---|---|---|---|---|---|---|
| 1 | | | | 5 | | | | | 10 | | | | | 15 | |

| Val | Asp | Gly | His | His | Leu | Ala | Tyr | Arg | Thr | Phe | Phe | Ala | Leu | Lys | Gly |
|---|---|---|---|---|---|---|---|---|---|---|---|---|---|---|---|
| | | | 20 | | | | | 25 | | | | | 30 | | |

| Leu | Thr | Thr | Ser | Arg | Gly | Glu | Pro | Val | Gln | Ala | Val | Tyr | Gly | Phe | Ala |
|---|---|---|---|---|---|---|---|---|---|---|---|---|---|---|---|
| | | 35 | | | | | 40 | | | | | 45 | | | |

| Lys | Ser | Leu | Leu | Lys | Ala | Leu | Lys | Glu | Asp | Gly | Tyr | Lys | Ala | Val | Phe |
|---|---|---|---|---|---|---|---|---|---|---|---|---|---|---|---|
| | 50 | | | | | 55 | | | | | 60 | | | | |

| Val | Val | Phe | Asp | Ala | Lys | Ala | Pro | Ser | Phe | Arg | His | Glu | Ala | Tyr | Glu |
|---|---|---|---|---|---|---|---|---|---|---|---|---|---|---|---|
| 65 | | | | | 70 | | | | | 75 | | | | | 80 |

| Ala | Tyr | Lys | Ala | Gly | Arg | Ala | Pro | Thr | Pro | Glu | Asp | Phe | Pro | Arg | Gln |
|---|---|---|---|---|---|---|---|---|---|---|---|---|---|---|---|
| | | | | 85 | | | | | 90 | | | | | 95 | |

| Leu | Ala | Leu | Ile | Lys | Glu | Leu | Val | Asp | Leu | Leu | Gly | Phe | Thr | Arg | Leu |
|---|---|---|---|---|---|---|---|---|---|---|---|---|---|---|---|
| | | | | 100 | | | | | 105 | | | | | 110 | |

-continued

Glu Val Pro Gly Phe Glu Ala Asp Val Leu Ala Thr Leu Ala Lys
        115                 120                 125

Lys Ala Glu Arg Glu Gly Tyr Glu Val Arg Ile Leu Thr Ala Asp Arg
130                 135                 140

Asp Leu Tyr Gln Leu Val Ser Asp Arg Val Ala Val Leu His Pro Glu
145                 150                 155                 160

Gly His Leu Ile Thr Pro Glu Trp Leu Trp Glu Lys Tyr Gly Leu Lys
                165                 170                 175

Pro Glu Gln Trp Val Asp Phe Arg Ala Leu Val Gly Asp Pro Ser Asp
            180                 185                 190

Asn Leu Pro Gly Val Lys Gly Ile Gly Glu Lys Thr Ala Leu Lys Leu
        195                 200                 205

Leu Lys Glu Trp Gly Ser Leu Glu Asn Ile Leu Lys Asn Leu Asp Arg
    210                 215                 220

Val Lys Pro Glu Ser Val Arg Glu Arg Ile Lys Ala His Leu Glu Asp
225                 230                 235                 240

Leu Lys Leu Ser Leu Glu Leu Ser Arg Val Arg Ser Asp Leu Pro Leu
                245                 250                 255

Glu Val Asp Phe Ala Arg Arg Arg Glu Pro Asp Arg Glu Gly Leu Arg
            260                 265                 270

Ala Phe Leu Glu Arg Leu Glu Phe Gly Ser Leu Leu His Glu Phe Gly
        275                 280                 285

Leu Leu Glu Glu Ser Glu Pro Val Gly Tyr Arg Ile Val Lys Asp Leu
    290                 295                 300

Val Glu Phe Glu Lys Leu Ile Glu Lys Leu Arg Glu Ser Pro Ser Phe
305                 310                 315                 320

Ala Ile Glu Leu Asp Thr Ser Ser Leu Asp Pro Phe Asp Cys Asp Ile
                325                 330                 335

Val Gly Ile Ser Val Ser Phe Lys Pro Lys Glu Ala Tyr Tyr Ile Pro
            340                 345                 350

Leu His His Arg Asn Ala Gln Asn Leu Asp Glu Lys Glu Val Leu Lys
        355                 360                 365

Lys Leu Lys Glu Ile Leu Glu Asp Pro Gly Ala Lys Ile Val Gly Gln
    370                 375                 380

Asn Leu Lys Phe Asp Tyr Lys Val Leu Met Val Lys Gly Val Glu Pro
385                 390                 395                 400

Val Pro Pro Tyr Phe Asp Thr Met Ile Ala Ala Tyr Leu Leu Glu Pro
                405                 410                 415

Asn Glu Lys Lys Phe Asn Leu Asp Asp Leu Ala Leu Lys Phe Leu Gly
            420                 425                 430

Tyr Lys Met Thr Ser Tyr Gln Glu Leu Met Ser Phe Ser Phe Pro Leu
        435                 440                 445

Phe Gly Phe Ser Phe Ala Asp Val Pro Val Glu Lys Ala Ala Asn Tyr
    450                 455                 460

Ser Cys Glu Asp Ala Asp Ile Thr Tyr Arg Leu Tyr Lys Thr Leu Ser
465                 470                 475                 480

Leu Lys Leu His Glu Ala Asp Leu Glu Asn Val Phe Tyr Lys Ile Glu
                485                 490                 495

Met Pro Leu Val Asn Val Leu Ala Arg Met Glu Leu Asn Gly Val Tyr
            500                 505                 510

Val Asp Thr Glu Phe Leu Lys Lys Leu Ser Glu Glu Tyr Gly Lys Lys
        515                 520                 525

-continued

```
Leu Glu Glu Leu Ala Glu Ile Tyr Arg Ile Ala Gly Glu Pro Phe
        530                 535                 540
Asn Ile Asn Ser Pro Lys Gln Val Ser Arg Ile Leu Phe Glu Lys Leu
545                 550                 555                 560
Gly Ile Lys Pro Arg Gly Lys Thr Thr Lys Thr Gly Asp Tyr Ser Thr
                565                 570                 575
Arg Ile Glu Val Leu Glu Glu Leu Ala Gly His Glu Ile Ile Pro
        580                 585                 590
Leu Ile Leu Glu Tyr Arg Lys Ile Gln Lys Leu Lys Ser Thr Tyr Ile
        595                 600                 605
Asp Ala Leu Pro Lys Met Val Asn Pro Lys Thr Gly Arg Ile His Ala
        610                 615                 620
Ser Phe Asn Gln Thr Gly Thr Ala Thr Gly Arg Leu Ser Ser Ser Asp
625                 630                 635                 640
Pro Asn Leu Gln Asn Leu Pro Thr Lys Ser Glu Glu Gly Lys Glu Ile
                645                 650                 655
Arg Lys Ala Ile Val Pro Gln Asp Pro Asn Trp Trp Ile Val Ser Ala
                660                 665                 670
Asp Tyr Ser Gln Ile Glu Leu Arg Ile Leu Ala His Leu Ser Gly Asp
                675                 680                 685
Glu Asn Leu Leu Arg Ala Phe Glu Gly Ile Asp Val His Thr Leu
        690                 695                 700
Thr Ala Ser Arg Ile Phe Asn Val Lys Pro Glu Glu Val Thr Glu Glu
705                 710                 715                 720
Met Arg Arg Ala Gly Lys Met Val Asn Phe Ser Ile Ile Tyr Gly Val
                725                 730                 735
Thr Pro Tyr Gly Leu Ser Val Arg Leu Gly Val Pro Val Lys Glu Ala
                740                 745                 750
Glu Lys Met Ile Val Asn Tyr Phe Val Leu Tyr Pro Lys Val Arg Asp
        755                 760                 765
Tyr Ile Gln Arg Val Val Ser Glu Ala Lys Glu Lys Gly Tyr Val Arg
770                 775                 780
Thr Leu Phe Gly Arg Lys Arg Asp Ile Pro Gln Leu Met Ala Arg Asp
785                 790                 795                 800
Arg Asn Thr Gln Ala Glu Gly Glu Arg Ile Ala Ile Asn Thr Pro Ile
                805                 810                 815
Gln Gly Thr Ala Ala Asp Ile Ile Lys Leu Ala Met Ile Glu Ile Asp
                820                 825                 830
Arg Glu Leu Lys Glu Arg Lys Met Arg Ser Lys Met Ile Ile Gln Val
        835                 840                 845
His Asp Glu Leu Val Phe Glu Val Pro Asn Glu Glu Lys Asp Ala Leu
850                 855                 860
Val Glu Leu Val Lys Asp Arg Met Thr Asn Val Val Lys Leu Ser Val
865                 870                 875                 880
Pro Leu Glu Val Asp Val Thr Ile Gly Lys Thr Trp Ser
                885                 890

<210> SEQ ID NO 127
<211> LENGTH: 196
<212> TYPE: PRT
<213> ORGANISM: Artificial sequence
<220> FEATURE:
<223> OTHER INFORMATION: Exonucleolytic domain of chimeric thermostable
      DNA polymerase CS6 after first round of mutagenesis residues
      323-325 ELE substitution
```

-continued

```
<400> SEQUENCE: 127

Glu Ser Glu Pro Val Gly Tyr Arg Ile Val Lys Asp Leu Val Glu Phe
1               5                   10                  15

Glu Lys Leu Ile Glu Lys Leu Arg Ser Pro Ser Phe Ala Ile Glu
            20                  25                  30

Leu Glu Thr Ser Ser Leu Asp Pro Phe Asp Cys Asp Ile Val Gly Ile
                35                  40                  45

Ser Val Ser Phe Lys Pro Lys Glu Ala Tyr Tyr Ile Pro Leu His His
    50                  55                  60

Arg Asn Ala Gln Asn Leu Asp Glu Lys Val Leu Lys Lys Leu Lys
65                  70                  75                  80

Glu Ile Leu Glu Asp Pro Gly Ala Lys Ile Val Gly Gln Asn Leu Lys
                85                  90                  95

Phe Asp Tyr Lys Val Leu Met Val Lys Gly Val Glu Pro Val Pro Pro
                100                 105                 110

Tyr Phe Asp Thr Met Ile Ala Ala Tyr Leu Leu Glu Pro Asn Glu Lys
                115                 120                 125

Lys Phe Asn Leu Asp Asp Leu Ala Leu Lys Phe Leu Gly Tyr Lys Met
130                 135                 140

Thr Ser Tyr Gln Glu Leu Met Ser Phe Ser Phe Pro Leu Phe Gly Phe
145                 150                 155                 160

Ser Phe Ala Asp Val Pro Val Glu Lys Ala Ala Asn Tyr Ser Cys Glu
                165                 170                 175

Asp Ala Asp Ile Thr Tyr Arg Leu Tyr Lys Thr Leu Ser Leu Lys Leu
                180                 185                 190

His Glu Ala Asp
        195

<210> SEQ ID NO 128
<211> LENGTH: 893
<212> TYPE: PRT
<213> ORGANISM: Artificial sequence
<220> FEATURE:
<223> OTHER INFORMATION: chimeric thermostable DNA polymerase CS6 after
      first round of mutagenesis 323-325 ELE substitution

<400> SEQUENCE: 128

Met Lys Ala Met Leu Pro Leu Phe Glu Pro Lys Gly Arg Val Leu Leu
1               5                   10                  15

Val Asp Gly His His Leu Ala Tyr Arg Thr Phe Phe Ala Leu Lys Gly
            20                  25                  30

Leu Thr Thr Ser Arg Gly Glu Pro Val Gln Ala Val Tyr Gly Phe Ala
                35                  40                  45

Lys Ser Leu Leu Lys Ala Leu Lys Glu Asp Gly Tyr Lys Ala Val Phe
    50                  55                  60

Val Val Phe Asp Ala Lys Ala Pro Ser Phe Arg His Glu Ala Tyr Glu
65                  70                  75                  80

Ala Tyr Lys Ala Gly Arg Ala Pro Thr Pro Glu Asp Phe Pro Arg Gln
                85                  90                  95

Leu Ala Leu Ile Lys Glu Leu Val Asp Leu Leu Gly Phe Thr Arg Leu
                100                 105                 110

Glu Val Pro Gly Phe Glu Ala Asp Asp Val Leu Ala Thr Leu Ala Lys
                115                 120                 125

Lys Ala Glu Arg Glu Gly Tyr Glu Val Arg Ile Leu Thr Ala Asp Arg
130                 135                 140
```

-continued

```
Asp Leu Tyr Gln Leu Val Ser Asp Arg Val Ala Val Leu His Pro Glu
145                 150                 155                 160

Gly His Leu Ile Thr Pro Glu Trp Leu Trp Glu Lys Tyr Gly Leu Lys
                165                 170                 175

Pro Glu Gln Trp Val Asp Phe Arg Ala Leu Val Gly Asp Pro Ser Asp
            180                 185                 190

Asn Leu Pro Gly Val Lys Gly Ile Gly Glu Lys Thr Ala Leu Lys Leu
        195                 200                 205

Leu Lys Glu Trp Gly Ser Leu Glu Asn Ile Leu Lys Asn Leu Asp Arg
    210                 215                 220

Val Lys Pro Glu Ser Val Arg Glu Arg Ile Lys Ala His Leu Glu Asp
225                 230                 235                 240

Leu Lys Leu Ser Leu Glu Leu Ser Arg Val Arg Ser Asp Leu Pro Leu
                245                 250                 255

Glu Val Asp Phe Ala Arg Arg Arg Glu Pro Asp Arg Glu Gly Leu Arg
            260                 265                 270

Ala Phe Leu Glu Arg Leu Glu Phe Gly Ser Leu Leu His Glu Phe Gly
        275                 280                 285

Leu Leu Glu Glu Ser Glu Pro Val Gly Tyr Arg Ile Val Lys Asp Leu
    290                 295                 300

Val Glu Phe Glu Lys Leu Ile Glu Lys Leu Arg Glu Ser Pro Ser Phe
305                 310                 315                 320

Ala Ile Glu Leu Glu Thr Ser Ser Leu Asp Pro Phe Asp Cys Asp Ile
                325                 330                 335

Val Gly Ile Ser Val Ser Phe Lys Pro Lys Glu Ala Tyr Tyr Ile Pro
            340                 345                 350

Leu His His Arg Asn Ala Gln Asn Leu Asp Glu Lys Glu Val Leu Lys
        355                 360                 365

Lys Leu Lys Glu Ile Leu Glu Asp Pro Gly Ala Lys Ile Val Gly Gln
    370                 375                 380

Asn Leu Lys Phe Asp Tyr Lys Val Leu Met Val Lys Gly Val Glu Pro
385                 390                 395                 400

Val Pro Pro Tyr Phe Asp Thr Met Ile Ala Ala Tyr Leu Leu Glu Pro
                405                 410                 415

Asn Glu Lys Lys Phe Asn Leu Asp Asp Leu Ala Leu Lys Phe Leu Gly
            420                 425                 430

Tyr Lys Met Thr Ser Tyr Gln Glu Leu Met Ser Phe Ser Phe Pro Leu
        435                 440                 445

Phe Gly Phe Ser Phe Ala Asp Val Pro Val Glu Lys Ala Ala Asn Tyr
    450                 455                 460

Ser Cys Glu Asp Ala Asp Ile Thr Tyr Arg Leu Tyr Lys Thr Leu Ser
465                 470                 475                 480

Leu Lys Leu His Glu Ala Asp Leu Glu Asn Val Phe Tyr Lys Ile Glu
                485                 490                 495

Met Pro Leu Val Asn Val Leu Ala Arg Met Glu Leu Asn Gly Val Tyr
            500                 505                 510

Val Asp Thr Glu Phe Leu Lys Lys Leu Ser Glu Glu Tyr Gly Lys Lys
        515                 520                 525

Leu Glu Glu Leu Ala Glu Glu Ile Tyr Arg Ile Ala Gly Glu Pro Phe
    530                 535                 540

Asn Ile Asn Ser Pro Lys Gln Val Ser Arg Ile Leu Phe Glu Lys Leu
545                 550                 555                 560

Gly Ile Lys Pro Arg Gly Lys Thr Thr Lys Thr Gly Asp Tyr Ser Thr
```

```
                  565                 570                 575
Arg Ile Glu Val Leu Glu Leu Ala Gly Glu His Glu Ile Ile Pro
        580                 585                 590
Leu Ile Leu Glu Tyr Arg Lys Ile Gln Lys Leu Lys Ser Thr Tyr Ile
    595                 600                 605
Asp Ala Leu Pro Lys Met Val Asn Pro Lys Thr Gly Arg Ile His Ala
610                 615                 620
Ser Phe Asn Gln Thr Gly Thr Ala Thr Gly Arg Leu Ser Ser Ser Asp
625                 630                 635                 640
Pro Asn Leu Gln Asn Leu Pro Thr Lys Ser Glu Glu Gly Lys Glu Ile
            645                 650                 655
Arg Lys Ala Ile Val Pro Gln Asp Pro Asn Trp Trp Ile Val Ser Ala
            660                 665                 670
Asp Tyr Ser Gln Ile Glu Leu Arg Ile Leu Ala His Leu Ser Gly Asp
            675                 680                 685
Glu Asn Leu Leu Arg Ala Phe Glu Glu Gly Ile Asp Val His Thr Leu
    690                 695                 700
Thr Ala Ser Arg Ile Phe Asn Val Lys Pro Glu Glu Val Thr Glu Glu
705                 710                 715                 720
Met Arg Arg Ala Gly Lys Met Val Asn Phe Ser Ile Ile Tyr Gly Val
            725                 730                 735
Thr Pro Tyr Gly Leu Ser Val Arg Leu Gly Val Pro Val Lys Glu Ala
            740                 745                 750
Glu Lys Met Ile Val Asn Tyr Phe Val Leu Tyr Pro Lys Val Arg Asp
            755                 760                 765
Tyr Ile Gln Arg Val Val Ser Glu Ala Lys Glu Lys Gly Tyr Val Arg
    770                 775                 780
Thr Leu Phe Gly Arg Lys Arg Asp Ile Pro Gln Leu Met Ala Arg Asp
785                 790                 795                 800
Arg Asn Thr Gln Ala Glu Gly Glu Arg Ile Ala Ile Asn Thr Pro Ile
                805                 810                 815
Gln Gly Thr Ala Ala Asp Ile Ile Lys Leu Ala Met Ile Glu Ile Asp
            820                 825                 830
Arg Glu Leu Lys Glu Arg Lys Met Arg Ser Lys Met Ile Ile Gln Val
        835                 840                 845
His Asp Glu Leu Val Phe Glu Val Pro Asn Glu Glu Lys Asp Ala Leu
    850                 855                 860
Val Glu Leu Val Lys Asp Arg Met Thr Asn Val Val Lys Leu Ser Val
865                 870                 875                 880
Pro Leu Glu Val Asp Val Thr Ile Gly Lys Thr Trp Ser
                885                 890

<210> SEQ ID NO 129
<211> LENGTH: 2682
<212> TYPE: DNA
<213> ORGANISM: Artificial sequence
<220> FEATURE:
<223> OTHER INFORMATION: Nucleic acid sequence encoding thermostable
      chimeric DNA polymerase CS6

<400> SEQUENCE: 129
atgaaagcta tgttaccatt attcgaaccc aaaggccggg tcctcctggt ggacggccac      60
cacctggcct accgcacctt cttcgccctg aagggcctca ccacgagccg ggcgaaccg     120 gtgcaggcgg tttacggctt cgccaagagc ctcctcaagg ccctgaagga ggacgggtac     180
```

-continued

```
aaggccgtct tcgtggtctt tgacgccaag gccccttcct tccgccacga ggcctacgag      240
gcctacaagg caggccgcgc cccgacccc gaggacttcc cccggcagct cgccctcatc       300
aaggagctgg tggacctcct ggggtttact cgcctcgagg ttccgggctt tgaggcggac      360
gacgtcctcg ccaccctggc caagaaggcg aaagggagg ggtacgaggt gcgcatcctc       420
accgccgacc gggacctta ccagctcgtc tccgaccgcg tcgccgtcct ccaccccgag       480
ggccacctca tcaccccgga gtggctttgg agaagtacg gccttaagcc ggagcagtgg      540
gtggacttcc gcgccctcgt gggggacccc tccgacaacc tccccggggt caagggcatc     600
ggggagaaga ccgccctcaa gctcctcaag gagtggggaa gcctggaaaa tatcctcaag     660
aacctggacc gggtgaagcc ggaaagcgtc cgggaaagga tcaaggccca cctggaagac    720
cttaagctct ccttggagct ttcccgggtg cgctcggacc tcccccctgga ggtggacttc    780 gcccggaggc gggagcctga ccgggaaggg cttcgggcct ttttggagcg cttggagttc     840
ggcagcctcc tccacgagtt cggccttcta gaggagtccg aacccgttgg gtaccgtata    900
gttaaagacc tggttgaatt tgaaaaactc atagagaaac tgagagaatc tccttcgttc    960
gcgatcgctc ttgcgactag ttccctcgat cctttcgact gcgacattgt cggtatctct    1020
gtgtctttca aaccaaagga agcgtactac ataccactcc atcatagaaa cgcccagaac    1080
ctggacgaaa aagaggttct gaaaagctc aagaaattc tggaggaccc cggagcaaag     1140
atcgttggtc agaatttgaa attcgattac aaggtgttga tggtgaaggg tgttgaacct    1200
gttcctcctt acttcgacac gatgatagcg gcttaccttc ttgagccgaa cgaaaagaag    1260
ttcaatctgg acgatctcgc attgaaattt cttggataca aaatgacatc ttaccaagag    1320
ctcatgtcct tctcttttcc gctgtttggt ttcagttttg ccgatgttcc tgtagaaaaa    1380
gcagcgaact actcctgtga agatgcagac atcacctaca gactttacaa gaccctgagc    1440
ttaaaactcc acgaggcaga tctggaaaac gtgttctaca agatagaaat gccccttgtg    1500
aacgtgcttg cacggatgga actgaacggt gtgtatgtgg acacagagtt cctgaagaaa    1560
ctctcagaag agtacggaaa aaactcgaa gaactggcag aggaaatata caggatagct     1620
ggagagccgt tcaacataaa ctcaccgaag caggtttcaa ggatccttt tgaaaaactc     1680 ggcataaaac cacgtggtaa aacgacgaaa acgggagact attcaacacg catagaagtc    1740
ctcgaggaac ttgccggtga acacgaaatc attcctctga ttcttgaata cagaaagata    1800
cagaaattga atcaaccta catagacgct cttcccaaga tggtcaaccc aaagaccgga    1860
aggattcatg cttcttttcaa tcaaacgggg actgccactg gaagacttag cagcagcgat    1920
cccaatcttc agaacctccc gacgaaaagt gaagagggaa aagaaatcag gaaagcgata    1980
gttcctcagg atccaaactg gtggatcgtc agtgccgact actcccaaat gaactgagg    2040 atcctcgccc atctcagtgg tgatgagaat cttttgaggg cattcgaaga gggcatcgac    2100
gtccacactc taacagcttc cagaatattc aacgtgaaac ccgaagaagt aaccgaagaa    2160
atgcgccgcg ctggtaaaat ggttaatttt tccatcatat acggtgtaac accttacggt    2220
ctgtctgtga ggcttggagt acctgtgaaa gaagcagaaa agatgatcgt caactacttc    2280
gtcctctacc caaaggtgcg cgattacatt cagagggtcg tatcggaagc gaaagaaaaa    2340
ggctatgtta aacgctgtt tggaagaaaa agagacatac cacagctcat ggcccgggac    2400
aggaacacac aggctgaagg agaacgaatt gccataaaca ctcccataca gggtacagca    2460
gcggatataa taaagctggc tatgatagaa atagacaggg aactgaaaga aagaaaaatg    2520
agatcgaaga tgatcataca ggtccacgac gaactggttt ttgaagtgcc caatgaggaa    2580
```

-continued

```
aaggacgcgc tcgtcgagct ggtgaaagac agaatgacga atgtggtaaa gctttcagtg    2640
ccgctcgaag tggatgtaac catcggcaaa acatggtcgt ga                       2682
```

<210> SEQ ID NO 130
<211> LENGTH: 894
<212> TYPE: PRT
<213> ORGANISM: Artificial sequence
<220> FEATURE:
<223> OTHER INFORMATION: Amino acid sequence encoding thermostable chimeric DNA polymerase CS7

<400> SEQUENCE: 130

```
Met Lys Ala Met Leu Pro Leu Phe Glu Pro Lys Gly Arg Val Leu Leu
1               5                   10                  15

Val Asp Gly His His Leu Ala Tyr Arg Thr Phe Phe Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Tyr Lys Ala Val Phe
    50                  55                  60

Val Val Phe Asp Ala Lys Ala Pro Ser Phe Arg His Glu Ala Tyr Glu
65                  70                  75                  80

Ala Tyr Lys Ala Gly Arg Ala Pro Thr Pro Glu Asp Phe Pro Arg Gln
                85                  90                  95

Leu Ala Leu Ile Lys Glu Leu Val Asp Leu Leu Gly Phe Thr Arg Leu
            100                 105                 110

Glu Val Pro Gly Phe Glu Ala Asp Asp Val Leu Ala Thr Leu Ala Lys
        115                 120                 125

Lys Ala Glu Arg Glu Gly Tyr Glu Val Arg Ile Leu Thr Ala Asp Arg
    130                 135                 140

Asp Leu Tyr Gln Leu Val Ser Asp Arg Val Ala Val Leu His Pro Glu
145                 150                 155                 160

Gly His Leu Ile Thr Pro Glu Trp Leu Trp Glu Lys Tyr Gly Leu Lys
                165                 170                 175

Pro Glu Gln Trp Val Asp Phe Arg Ala Leu Val Gly Asp Pro Ser Asp
            180                 185                 190

Asn Leu Pro Gly Val Lys Gly Ile Gly Glu Lys Thr Ala Leu Lys Leu
        195                 200                 205

Leu Lys Glu Trp Gly Ser Leu Glu Asn Ile Leu Lys Asn Leu Asp Arg
    210                 215                 220

Val Lys Pro Glu Ser Val Arg Glu Arg Ile Lys Ala His Leu Glu Asp
225                 230                 235                 240

Leu Lys Leu Ser Leu Glu Leu Ser Arg Val Arg Ser Asp Leu Pro Leu
                245                 250                 255

Glu Val Asp Phe Ala Arg Arg Arg Glu Pro Asp Arg Glu Gly Leu Arg
            260                 265                 270

Ala Phe Leu Glu Arg Leu Glu Phe Gly Ser Leu Leu His Glu Phe Gly
        275                 280                 285

Leu Leu Glu Glu Ser Glu Pro Val Gly Tyr Arg Ile Val Lys Asp Leu
    290                 295                 300

Val Glu Phe Glu Lys Leu Ile Glu Lys Leu Arg Glu Ser Pro Ser Phe
305                 310                 315                 320

Ala Ile Asp Leu Glu Thr Ser Ser Leu Asp Pro Phe Asp Cys Asp Ile
                325                 330                 335
```

-continued

```
Val Gly Ile Ser Val Ser Phe Lys Pro Lys Glu Ala Tyr Tyr Ile Pro
            340                 345                 350
Leu His His Arg Asn Ala Gln Asn Leu Asp Glu Lys Glu Val Leu Lys
        355                 360                 365
Lys Leu Lys Glu Ile Leu Glu Asp Pro Gly Ala Lys Ile Val Gly Gln
    370                 375                 380
Asn Leu Lys Phe Asp Tyr Lys Val Leu Met Val Lys Gly Val Glu Pro
385                 390                 395                 400
Val Pro Pro Tyr Phe Asp Thr Met Ile Ala Ala Tyr Leu Leu Glu Pro
            405                 410                 415
Asn Glu Lys Lys Phe Asn Leu Asp Asp Leu Ala Leu Lys Phe Leu Gly
        420                 425                 430
Tyr Lys Met Thr Ser Tyr Gln Glu Leu Met Ser Phe Ser Phe Pro Leu
    435                 440                 445
Phe Gly Phe Ser Phe Ala Asp Val Pro Val Glu Lys Ala Ala Asn Tyr
450                 455                 460
Ser Cys Glu Asp Ala Asp Ile Thr Tyr Arg Leu Tyr Lys Thr Leu Ser
465                 470                 475                 480
Leu Lys Leu His Glu Glu Lys Leu Leu Trp Leu Tyr Gln Glu Val Glu
            485                 490                 495
Lys Pro Leu Ser Arg Val Leu Ala His Met Glu Ala Thr Gly Val Arg
        500                 505                 510
Leu Asp Val Ala Tyr Leu Lys Ala Leu Ser Leu Glu Leu Ala Glu Glu
    515                 520                 525
Ile Arg Arg Leu Glu Glu Glu Val Phe Arg Leu Ala Gly His Pro Phe
530                 535                 540
Asn Leu Asn Ser Arg Asp Gln Leu Glu Arg Val Leu Phe Asp Glu Leu
545                 550                 555                 560
Arg Leu Pro Ala Leu Gly Lys Thr Gln Lys Thr Gly Lys Arg Ser Thr
            565                 570                 575
Ser Ala Ala Val Leu Glu Ala Leu Arg Glu Ala His Pro Ile Val Glu
        580                 585                 590
Lys Ile Leu Gln His Arg Glu Leu Thr Lys Leu Lys Asn Thr Tyr Val
    595                 600                 605
Asp Pro Leu Pro Gly Leu Val His Pro Arg Thr Gly Arg Leu His Thr
610                 615                 620
Arg Phe Asn Gln Thr Ala Thr Ala Thr Gly Arg Leu Ser Ser Ser Asp
625                 630                 635                 640
Pro Asn Leu Gln Asn Ile Pro Ile Arg Thr Pro Leu Gly Gln Arg Ile
            645                 650                 655
Arg Arg Ala Phe Val Ala Glu Ala Gly Trp Ala Leu Val Ala Leu Asp
        660                 665                 670
Tyr Ser Gln Ile Glu Leu Arg Val Leu Ala His Leu Ser Gly Asp Glu
    675                 680                 685
Asn Leu Ile Arg Val Phe Gln Glu Gly Lys Asp Ile His Thr Gln Thr
690                 695                 700
Ala Ser Trp Met Phe Gly Val Ser Pro Glu Ala Val Asp Pro Leu Met
705                 710                 715                 720
Arg Arg Ala Ala Lys Thr Val Asn Phe Gly Val Leu Tyr Gly Met Ser
            725                 730                 735
Ala His Arg Leu Ser Gln Glu Leu Ala Ile Pro Tyr Glu Glu Ala Val
        740                 745                 750
Ala Phe Ile Glu Arg Tyr Phe Gln Ser Phe Pro Lys Val Arg Ala Trp
```

```
                755                 760                 765
Ile Glu Lys Thr Leu Glu Gly Arg Lys Arg Gly Tyr Val Glu Thr
            770                 775                 780

Leu Phe Gly Arg Arg Tyr Val Pro Asp Leu Asn Ala Arg Val Lys
785                 790                 795                 800

Ser Val Arg Glu Ala Glu Arg Met Ala Phe Asn Met Pro Val Gln
                805                 810                 815

Gly Thr Ala Ala Asp Leu Met Lys Leu Ala Met Val Lys Leu Phe Pro
                820                 825                 830

His Leu Arg Glu Met Gly Ala Arg Met Leu Leu Gln Val His Asp Glu
            835                 840                 845

Leu Leu Leu Glu Ala Pro Gln Ala Arg Ala Glu Glu Val Ala Ala Leu
850                 855                 860

Ala Lys Glu Ala Met Glu Lys Ala Tyr Pro Leu Ala Val Pro Leu Glu
865                 870                 875                 880

Val Glu Val Gly Ile Gly Glu Asp Trp Leu Ser Ala Lys Gly
                885                 890

<210> SEQ ID NO 131
<211> LENGTH: 196
<212> TYPE: PRT
<213> ORGANISM: Artificial sequence
<220> FEATURE:
<223> OTHER INFORMATION: Exonucleolytic domain of thermostable chimeric
      DNA polymerase CS7

<400> SEQUENCE: 131

Glu Ser Glu Pro Val Gly Tyr Arg Ile Val Lys Asp Leu Val Glu Phe
1               5                   10                  15

Glu Lys Leu Ile Glu Lys Leu Arg Glu Ser Pro Ser Phe Ala Ile Asp
                20                  25                  30

Leu Glu Thr Ser Ser Leu Asp Pro Phe Asp Cys Asp Ile Val Gly Ile
            35                  40                  45

Ser Val Ser Phe Lys Pro Lys Glu Ala Tyr Tyr Ile Pro Leu His His
        50                  55                  60

Arg Asn Ala Gln Asn Leu Asp Glu Lys Glu Val Leu Lys Lys Leu Lys
65                  70                  75                  80

Glu Ile Leu Glu Asp Pro Gly Ala Lys Ile Val Gly Gln Asn Leu Lys
                85                  90                  95

Phe Asp Tyr Lys Val Leu Met Val Lys Gly Val Glu Pro Val Pro Pro
            100                 105                 110

Tyr Phe Asp Thr Met Ile Ala Ala Tyr Leu Leu Glu Pro Asn Glu Lys
        115                 120                 125

Lys Phe Asn Leu Asp Asp Leu Ala Leu Lys Phe Leu Gly Tyr Lys Met
    130                 135                 140

Thr Ser Tyr Gln Glu Leu Met Ser Phe Ser Phe Pro Leu Phe Gly Phe
145                 150                 155                 160

Ser Phe Ala Asp Val Pro Val Glu Lys Ala Ala Asn Tyr Ser Cys Glu
                165                 170                 175

Asp Ala Asp Ile Thr Tyr Arg Leu Tyr Lys Thr Leu Ser Leu Lys Leu
            180                 185                 190

His Glu Glu Lys
        195

<210> SEQ ID NO 132
<211> LENGTH: 291
```

<212> TYPE: PRT
<213> ORGANISM: Artificial sequence
<220> FEATURE:
<223> OTHER INFORMATION: Residues 1-291 of thermostable chimeric DNA
    polymerase CS7 derived from Z05 DNA polymerase

<400> SEQUENCE: 132

Met Lys Ala Met Leu Pro Leu Phe Glu Pro Lys Gly Arg Val Leu Leu
1               5                   10                  15

Val Asp Gly His His Leu Ala Tyr Arg Thr Phe Phe Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Tyr Lys Ala Val Phe
    50                  55                  60

Val Val Phe Asp Ala Lys Ala Pro Ser Phe Arg His Glu Ala Tyr Glu
65                  70                  75                  80

Ala Tyr Lys Ala Gly Arg Ala Pro Thr Pro Glu Asp Phe Pro Arg Gln
                85                  90                  95

Leu Ala Leu Ile Lys Glu Leu Val Asp Leu Leu Gly Phe Thr Arg Leu
            100                 105                 110

Glu Val Pro Gly Phe Glu Ala Asp Asp Val Leu Ala Thr Leu Ala Lys
        115                 120                 125

Lys Ala Glu Arg Glu Gly Tyr Glu Val Arg Ile Leu Thr Ala Asp Arg
    130                 135                 140

Asp Leu Tyr Gln Leu Val Ser Asp Arg Val Ala Val Leu His Pro Glu
145                 150                 155                 160

Gly His Leu Ile Thr Pro Glu Trp Leu Trp Glu Lys Tyr Gly Leu Lys
                165                 170                 175

Pro Glu Gln Trp Val Asp Phe Arg Ala Leu Val Gly Asp Pro Ser Asp
            180                 185                 190

Asn Leu Pro Gly Val Lys Gly Ile Gly Glu Lys Thr Ala Leu Lys Leu
        195                 200                 205

Leu Lys Glu Trp Gly Ser Leu Glu Asn Ile Leu Lys Asn Leu Asp Arg
    210                 215                 220

Val Lys Pro Glu Ser Val Arg Glu Arg Ile Lys Ala His Leu Glu Asp
225                 230                 235                 240

Leu Lys Leu Ser Leu Glu Leu Ser Arg Val Arg Ser Asp Leu Pro Leu
                245                 250                 255

Glu Val Asp Phe Ala Arg Arg Arg Glu Pro Asp Arg Glu Gly Leu Arg
            260                 265                 270

Ala Phe Leu Glu Arg Leu Glu Phe Gly Ser Leu Leu His Glu Phe Gly
        275                 280                 285

Leu Leu Glu
    290

<210> SEQ ID NO 133
<211> LENGTH: 409
<212> TYPE: PRT
<213> ORGANISM: Artificial sequence
<220> FEATURE:
<223> OTHER INFORMATION: Residues 485-894 of thermostable chimeric DNA
    polymerase CS7 derived from Z05 DNA polymerase

<400> SEQUENCE: 133

Glu Lys Leu Leu Trp Leu Tyr Gln Glu Val Glu Lys Pro Leu Ser Arg
1               5                   10                  15

-continued

Val Leu Ala His Met Glu Ala Thr Gly Val Arg Leu Asp Val Ala Tyr
             20                  25                  30

Leu Lys Ala Leu Ser Leu Glu Leu Ala Glu Glu Ile Arg Arg Leu Glu
         35                  40                  45

Glu Glu Val Phe Arg Leu Ala Gly His Pro Phe Asn Leu Asn Ser Arg
     50                  55                  60

Asp Gln Leu Glu Arg Val Leu Phe Asp Glu Leu Arg Leu Pro Ala Leu
 65                  70                  75                  80

Gly Lys Thr Gln Lys Thr Gly Lys Arg Ser Thr Ser Ala Ala Val Leu
                 85                  90                  95

Glu Ala Leu Arg Glu Ala His Pro Ile Val Glu Lys Ile Leu Gln His
             100                 105                 110

Arg Glu Leu Thr Lys Leu Lys Asn Thr Tyr Val Asp Pro Leu Pro Gly
         115                 120                 125

Leu Val His Pro Arg Thr Gly Arg Leu His Thr Arg Phe Asn Gln Thr
130                 135                 140

Ala Thr Ala Thr Gly Arg Leu Ser Ser Ser Asp Pro Asn Leu Gln Asn
145                 150                 155                 160

Ile Pro Ile Arg Thr Pro Leu Gly Gln Arg Ile Arg Arg Ala Phe Val
                165                 170                 175

Ala Glu Ala Gly Trp Ala Leu Val Ala Leu Asp Tyr Ser Gln Ile Glu
            180                 185                 190

Leu Arg Val Leu Ala His Leu Ser Gly Asp Glu Asn Leu Ile Arg Val
        195                 200                 205

Phe Gln Glu Gly Lys Asp Ile His Thr Gln Thr Ala Ser Trp Met Phe
210                 215                 220

Gly Val Ser Pro Glu Ala Val Asp Pro Leu Met Arg Arg Ala Ala Lys
225                 230                 235                 240

Thr Val Asn Phe Gly Val Leu Tyr Gly Met Ser Ala His Arg Leu Ser
                245                 250                 255

Gln Glu Leu Ala Ile Pro Tyr Glu Glu Ala Val Ala Phe Ile Glu Arg
            260                 265                 270

Tyr Phe Gln Ser Phe Pro Lys Val Arg Ala Trp Ile Glu Lys Thr Leu
        275                 280                 285

Glu Glu Gly Arg Lys Arg Gly Tyr Val Glu Thr Leu Phe Gly Arg Arg
    290                 295                 300

Arg Tyr Val Pro Asp Leu Asn Ala Arg Val Lys Ser Val Arg Glu Ala
305                 310                 315                 320

Ala Glu Arg Met Ala Phe Asn Met Pro Val Gln Gly Thr Ala Ala Asp
                325                 330                 335

Leu Met Lys Leu Ala Met Val Lys Leu Phe Pro His Leu Arg Glu Met
            340                 345                 350

Gly Ala Arg Met Leu Leu Gln Val His Asp Glu Leu Leu Leu Glu Ala
        355                 360                 365

Pro Gln Ala Arg Ala Glu Val Ala Leu Ala Lys Glu Ala Met
    370                 375                 380

Glu Lys Ala Tyr Pro Leu Ala Val Pro Leu Glu Val Glu Val Gly Ile
385                 390                 395                 400

Gly Glu Asp Trp Leu Ser Ala Lys Gly
                405

<210> SEQ ID NO 134
<211> LENGTH: 193
<212> TYPE: PRT

<213> ORGANISM: Artificial sequence
<220> FEATURE:
<223> OTHER INFORMATION: Residues 292-484 of thermostable chimeric DNA
      polymerase CS7 derived from Tma DNA polymerase

<400> SEQUENCE: 134

Glu Ser Glu Pro Val Gly Tyr Arg Ile Val Lys Asp Leu Val Glu Phe
1               5                   10                  15

Glu Lys Leu Ile Glu Lys Leu Arg Glu Ser Pro Ser Phe Ala Ile Asp
            20                  25                  30

Leu Glu Thr Ser Ser Leu Asp Pro Phe Asp Cys Asp Ile Val Gly Ile
        35                  40                  45

Ser Val Ser Phe Lys Pro Lys Glu Ala Tyr Tyr Ile Pro Leu His His
    50                  55                  60

Arg Asn Ala Gln Asn Leu Asp Glu Lys Val Leu Lys Lys Leu Lys
65                  70                  75                  80

Glu Ile Leu Glu Asp Pro Gly Ala Lys Ile Val Gly Gln Asn Leu Lys
                85                  90                  95

Phe Asp Tyr Lys Val Leu Met Val Lys Gly Val Glu Pro Val Pro Pro
            100                 105                 110

Tyr Phe Asp Thr Met Ile Ala Ala Tyr Leu Leu Glu Pro Asn Glu Lys
        115                 120                 125

Lys Phe Asn Leu Asp Asp Leu Ala Leu Lys Phe Leu Gly Tyr Lys Met
    130                 135                 140

Thr Ser Tyr Gln Glu Leu Met Ser Phe Ser Phe Pro Leu Phe Gly Phe
145                 150                 155                 160

Ser Phe Ala Asp Val Pro Val Glu Lys Ala Ala Asn Tyr Ser Cys Glu
                165                 170                 175

Asp Ala Asp Ile Thr Tyr Arg Leu Tyr Lys Thr Leu Ser Leu Lys Leu
                180                 185                 190

His

<210> SEQ ID NO 135
<211> LENGTH: 196
<212> TYPE: PRT
<213> ORGANISM: Artificial sequence
<220> FEATURE:
<223> OTHER INFORMATION: Exonucleolytic domain of thermostable DNA
      polymerase CS7 after second round of mutagenesis L329A
      substitution

<400> SEQUENCE: 135

Glu Ser Glu Pro Val Gly Tyr Arg Ile Val Lys Asp Leu Val Glu Phe
1               5                   10                  15

Glu Lys Leu Ile Glu Lys Leu Arg Glu Ser Pro Ser Phe Ala Ile Asp
            20                  25                  30

Leu Glu Thr Ser Ser Ala Asp Pro Phe Asp Cys Asp Ile Val Gly Ile
        35                  40                  45

Ser Val Ser Phe Lys Pro Lys Glu Ala Tyr Tyr Ile Pro Leu His His
    50                  55                  60

Arg Asn Ala Gln Asn Leu Asp Glu Lys Val Leu Lys Lys Leu Lys
65                  70                  75                  80

Glu Ile Leu Glu Asp Pro Gly Ala Lys Ile Val Gly Gln Asn Leu Lys
                85                  90                  95

Phe Asp Tyr Lys Val Leu Met Val Lys Gly Val Glu Pro Val Pro Pro
            100                 105                 110

Tyr Phe Asp Thr Met Ile Ala Ala Tyr Leu Leu Glu Pro Asn Glu Lys

-continued

```
            115                 120                 125
Lys Phe Asn Leu Asp Asp Leu Ala Leu Lys Phe Leu Gly Tyr Lys Met
        130                 135                 140

Thr Ser Tyr Gln Glu Leu Met Ser Phe Ser Phe Pro Leu Phe Gly Phe
145                 150                 155                 160

Ser Phe Ala Asp Val Pro Val Glu Lys Ala Ala Asn Tyr Ser Cys Glu
                165                 170                 175

Asp Ala Asp Ile Thr Tyr Arg Leu Tyr Lys Thr Leu Ser Leu Lys Leu
            180                 185                 190

His Glu Glu Lys
        195

<210> SEQ ID NO 136
<211> LENGTH: 894
<212> TYPE: PRT
<213> ORGANISM: Artificial sequence
<220> FEATURE:
<223> OTHER INFORMATION: thermostable DNA polymerase CS7 after second
      round of mutagenesis L329A substitution

<400> SEQUENCE: 136

Met Lys Ala Met Leu Pro Leu Phe Glu Pro Lys Gly Arg Val Leu Leu
1               5                   10                  15

Val Asp Gly His His Leu Ala Tyr Arg Thr Phe Phe Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Tyr Lys Ala Val Phe
    50                  55                  60

Val Val Phe Asp Ala Lys Ala Pro Ser Phe Arg His Glu Ala Tyr Glu
65                  70                  75                  80

Ala Tyr Lys Ala Gly Arg Ala Pro Thr Pro Glu Asp Phe Pro Arg Gln
                85                  90                  95

Leu Ala Leu Ile Lys Glu Leu Val Asp Leu Leu Gly Phe Thr Arg Leu
            100                 105                 110

Glu Val Pro Gly Phe Glu Ala Asp Asp Val Leu Ala Thr Leu Ala Lys
        115                 120                 125

Lys Ala Glu Arg Glu Gly Tyr Glu Val Arg Ile Leu Thr Ala Asp Arg
    130                 135                 140

Asp Leu Tyr Gln Leu Val Ser Asp Arg Val Ala Val Leu His Pro Glu
145                 150                 155                 160

Gly His Leu Ile Thr Pro Glu Trp Leu Trp Glu Lys Tyr Gly Leu Lys
                165                 170                 175

Pro Glu Gln Trp Val Asp Phe Arg Ala Leu Val Gly Asp Pro Ser Asp
            180                 185                 190

Asn Leu Pro Gly Val Lys Gly Ile Gly Glu Lys Thr Ala Leu Lys Leu
        195                 200                 205

Leu Lys Glu Trp Gly Ser Leu Glu Asn Ile Leu Lys Asn Leu Asp Arg
    210                 215                 220

Val Lys Pro Glu Ser Val Arg Glu Arg Ile Lys Ala His Leu Glu Asp
225                 230                 235                 240

Leu Lys Leu Ser Leu Glu Leu Ser Arg Val Arg Ser Asp Leu Pro Leu
                245                 250                 255

Glu Val Asp Phe Ala Arg Arg Arg Glu Pro Asp Arg Glu Gly Leu Arg
            260                 265                 270
```

-continued

```
Ala Phe Leu Glu Arg Leu Glu Phe Gly Ser Leu Leu His Glu Phe Gly
        275                 280                 285

Leu Leu Glu Glu Ser Glu Pro Val Gly Tyr Arg Ile Val Lys Asp Leu
    290                 295                 300

Val Glu Phe Glu Lys Leu Ile Glu Lys Leu Arg Glu Ser Pro Ser Phe
305                 310                 315                 320

Ala Ile Asp Leu Glu Thr Ser Ser Ala Asp Pro Phe Asp Cys Asp Ile
                325                 330                 335

Val Gly Ile Ser Val Ser Phe Lys Pro Lys Glu Ala Tyr Tyr Ile Pro
            340                 345                 350

Leu His His Arg Asn Ala Gln Asn Leu Asp Glu Lys Glu Val Leu Lys
        355                 360                 365

Lys Leu Lys Glu Ile Leu Glu Asp Pro Gly Ala Lys Ile Val Gly Gln
    370                 375                 380

Asn Leu Lys Phe Asp Tyr Lys Val Leu Met Val Lys Gly Val Glu Pro
385                 390                 395                 400

Val Pro Pro Tyr Phe Asp Thr Met Ile Ala Ala Tyr Leu Leu Glu Pro
                405                 410                 415

Asn Glu Lys Lys Phe Asn Leu Asp Asp Leu Ala Leu Lys Phe Leu Gly
            420                 425                 430

Tyr Lys Met Thr Ser Tyr Gln Glu Leu Met Ser Phe Ser Phe Pro Leu
        435                 440                 445

Phe Gly Phe Ser Phe Ala Asp Val Pro Val Glu Lys Ala Ala Asn Tyr
    450                 455                 460

Ser Cys Glu Asp Ala Asp Ile Thr Tyr Arg Leu Tyr Lys Thr Leu Ser
465                 470                 475                 480

Leu Lys Leu His Glu Glu Lys Leu Leu Trp Leu Tyr Gln Glu Val Glu
                485                 490                 495

Lys Pro Leu Ser Arg Val Leu Ala His Met Glu Ala Thr Gly Val Arg
            500                 505                 510

Leu Asp Val Ala Tyr Leu Lys Ala Leu Ser Leu Glu Leu Ala Glu Glu
        515                 520                 525

Ile Arg Arg Leu Glu Glu Glu Val Phe Arg Leu Ala Gly His Pro Phe
    530                 535                 540

Asn Leu Asn Ser Arg Asp Gln Leu Glu Arg Val Leu Phe Asp Glu Leu
545                 550                 555                 560

Arg Leu Pro Ala Leu Gly Lys Thr Gln Lys Thr Gly Lys Arg Ser Thr
                565                 570                 575

Ser Ala Ala Val Leu Glu Ala Leu Arg Glu Ala His Pro Ile Val Glu
            580                 585                 590

Lys Ile Leu Gln His Arg Glu Leu Thr Lys Leu Lys Asn Thr Tyr Val
        595                 600                 605

Asp Pro Leu Pro Gly Leu Val His Pro Arg Thr Gly Arg Leu His Thr
    610                 615                 620

Arg Phe Asn Gln Thr Ala Thr Ala Thr Gly Arg Leu Ser Ser Ser Asp
625                 630                 635                 640

Pro Asn Leu Gln Asn Ile Pro Ile Arg Thr Pro Leu Gly Gln Arg Ile
                645                 650                 655

Arg Arg Ala Phe Val Ala Glu Ala Gly Trp Ala Leu Val Ala Leu Asp
            660                 665                 670

Tyr Ser Gln Ile Glu Leu Arg Val Leu Ala His Leu Ser Gly Asp Glu
        675                 680                 685

Asn Leu Ile Arg Val Phe Gln Glu Gly Lys Asp Ile His Thr Gln Thr
```

```
                690                 695                 700
Ala Ser Trp Met Phe Gly Val Ser Pro Glu Ala Val Asp Pro Leu Met
705                     710                     715                 720

Arg Arg Ala Ala Lys Thr Val Asn Phe Gly Val Leu Tyr Gly Met Ser
                725                     730                     735

Ala His Arg Leu Ser Gln Glu Leu Ala Ile Pro Tyr Glu Glu Ala Val
            740                     745                 750

Ala Phe Ile Glu Arg Tyr Phe Gln Ser Phe Pro Lys Val Arg Ala Trp
        755                     760                 765

Ile Glu Lys Thr Leu Glu Gly Arg Lys Arg Gly Tyr Val Glu Thr
770                     775                     780

Leu Phe Gly Arg Arg Tyr Val Pro Asp Leu Asn Ala Arg Val Lys
785                 790                     795                 800

Ser Val Arg Glu Ala Glu Arg Met Ala Phe Asn Met Pro Val Gln
                805                     810                     815

Gly Thr Ala Ala Asp Leu Met Lys Leu Ala Met Val Lys Leu Phe Pro
            820                     825                 830

His Leu Arg Glu Met Gly Ala Arg Met Leu Leu Gln Val His Asp Glu
        835                     840                     845

Leu Leu Leu Glu Ala Pro Gln Ala Arg Ala Glu Glu Val Ala Ala Leu
850                     855                     860

Ala Lys Glu Ala Met Glu Lys Ala Tyr Pro Leu Ala Val Pro Leu Glu
865                 870                     875                 880

Val Glu Val Gly Ile Gly Glu Asp Trp Leu Ser Ala Lys Gly
                885                     890

<210> SEQ ID NO 137
<211> LENGTH: 196
<212> TYPE: PRT
<213> ORGANISM: Artificial sequence
<220> FEATURE:
<223> OTHER INFORMATION: Exonucleolytic domain of thermostable DNA
      polymerase CS7 after second round of mutagenesis Q384A
      substitution

<400> SEQUENCE: 137

Glu Ser Glu Pro Val Gly Tyr Arg Ile Val Lys Asp Leu Val Glu Phe
1               5                   10                  15

Glu Lys Leu Ile Glu Lys Leu Arg Glu Ser Pro Ser Phe Ala Ile Asp
            20                  25                  30

Leu Glu Thr Ser Ser Leu Asp Pro Phe Asp Cys Asp Ile Val Gly Ile
        35                  40                  45

Ser Val Ser Phe Lys Pro Lys Glu Ala Tyr Tyr Ile Pro Leu His His
    50                  55                  60

Arg Asn Ala Gln Asn Leu Asp Glu Lys Glu Val Leu Lys Lys Leu Lys
65                  70                  75                  80

Glu Ile Leu Glu Asp Pro Gly Ala Lys Ile Val Gly Ala Asn Leu Lys
                85                  90                  95

Phe Asp Tyr Lys Val Leu Met Val Lys Gly Val Glu Pro Val Pro Pro
            100                 105                 110

Tyr Phe Asp Thr Met Ile Ala Ala Tyr Leu Leu Glu Pro Asn Glu Lys
        115                 120                 125

Lys Phe Asn Leu Asp Asp Leu Ala Leu Lys Phe Leu Gly Tyr Lys Met
    130                 135                 140

Thr Ser Tyr Gln Glu Leu Met Ser Phe Ser Phe Pro Leu Phe Gly Phe
145                 150                 155                 160
```

```
Ser Phe Ala Asp Val Pro Val Glu Lys Ala Ala Asn Tyr Ser Cys Glu
            165                 170                 175

Asp Ala Asp Ile Thr Tyr Arg Leu Tyr Lys Thr Leu Ser Leu Lys Leu
        180                 185                 190

His Glu Glu Lys
        195

<210> SEQ ID NO 138
<211> LENGTH: 894
<212> TYPE: PRT
<213> ORGANISM: Artificial sequence
<220> FEATURE:
<223> OTHER INFORMATION: thermostable DNA polymerase CS7 after second
      round of mutagenesis Q384A substitution

<400> SEQUENCE: 138

Met Lys Ala Met Leu Pro Leu Phe Glu Pro Lys Gly Arg Val Leu Leu
1               5                   10                  15

Val Asp Gly His His Leu Ala Tyr Arg Thr Phe Phe Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Tyr Lys Ala Val Phe
50                  55                  60

Val Val Phe Asp Ala Lys Ala Pro Ser Phe Arg His Glu Ala Tyr Glu
65                  70                  75                  80

Ala Tyr Lys Ala Gly Arg Ala Pro Thr Pro Glu Asp Phe Pro Arg Gln
                85                  90                  95

Leu Ala Leu Ile Lys Glu Leu Val Asp Leu Leu Gly Phe Thr Arg Leu
            100                 105                 110

Glu Val Pro Gly Phe Glu Ala Asp Asp Val Leu Ala Thr Leu Ala Lys
        115                 120                 125

Lys Ala Glu Arg Glu Gly Tyr Glu Val Arg Ile Leu Thr Ala Asp Arg
    130                 135                 140

Asp Leu Tyr Gln Leu Val Ser Asp Arg Val Ala Val Leu His Pro Glu
145                 150                 155                 160

Gly His Leu Ile Thr Pro Glu Trp Leu Trp Glu Lys Tyr Gly Leu Lys
                165                 170                 175

Pro Glu Gln Trp Val Asp Phe Arg Ala Leu Val Gly Asp Pro Ser Asp
            180                 185                 190

Asn Leu Pro Gly Val Lys Gly Ile Gly Glu Lys Thr Ala Leu Lys Leu
        195                 200                 205

Leu Lys Glu Trp Gly Ser Leu Glu Asn Ile Leu Lys Asn Leu Asp Arg
    210                 215                 220

Val Lys Pro Glu Ser Val Arg Glu Arg Ile Lys Ala His Leu Glu Asp
225                 230                 235                 240

Leu Lys Leu Ser Leu Glu Leu Ser Arg Val Arg Ser Asp Leu Pro Leu
                245                 250                 255

Glu Val Asp Phe Ala Arg Arg Arg Glu Pro Asp Arg Glu Gly Leu Arg
            260                 265                 270

Ala Phe Leu Glu Arg Leu Glu Phe Gly Ser Leu Leu His Glu Phe Gly
        275                 280                 285

Leu Leu Glu Glu Ser Glu Pro Val Gly Tyr Arg Ile Val Lys Asp Leu
    290                 295                 300

Val Glu Phe Glu Lys Leu Ile Glu Lys Leu Arg Glu Ser Pro Ser Phe
```

```
                305                 310                 315                 320
        Ala Ile Asp Leu Glu Thr Ser Ser Leu Asp Pro Phe Asp Cys Asp Ile
                        325                 330                 335
        Val Gly Ile Ser Val Ser Phe Lys Pro Lys Glu Ala Tyr Tyr Ile Pro
                        340                 345                 350
        Leu His His Arg Asn Ala Gln Asn Leu Asp Glu Lys Glu Val Leu Lys
                        355                 360                 365
        Lys Leu Lys Glu Ile Leu Glu Asp Pro Gly Ala Lys Ile Val Gly Ala
                370                 375                 380
        Asn Leu Lys Phe Asp Tyr Lys Val Leu Met Val Lys Gly Val Glu Pro
        385                 390                 395                 400
        Val Pro Pro Tyr Phe Asp Thr Met Ile Ala Ala Tyr Leu Leu Glu Pro
                        405                 410                 415
        Asn Glu Lys Lys Phe Asn Leu Asp Asp Leu Ala Leu Lys Phe Leu Gly
                        420                 425                 430
        Tyr Lys Met Thr Ser Tyr Gln Glu Leu Met Ser Phe Ser Phe Pro Leu
                        435                 440                 445
        Phe Gly Phe Ser Phe Ala Asp Val Pro Val Glu Lys Ala Ala Asn Tyr
                450                 455                 460
        Ser Cys Glu Asp Ala Asp Ile Thr Tyr Arg Leu Tyr Lys Thr Leu Ser
        465                 470                 475                 480
        Leu Lys Leu His Glu Glu Lys Leu Leu Trp Leu Tyr Gln Glu Val Glu
                        485                 490                 495
        Lys Pro Leu Ser Arg Val Leu Ala His Met Glu Ala Thr Gly Val Arg
                        500                 505                 510
        Leu Asp Val Ala Tyr Leu Lys Ala Leu Ser Leu Glu Leu Ala Glu Glu
                        515                 520                 525
        Ile Arg Arg Leu Glu Glu Val Phe Arg Leu Ala Gly His Pro Phe
                530                 535                 540
        Asn Leu Asn Ser Arg Asp Gln Leu Glu Arg Val Leu Phe Asp Glu Leu
        545                 550                 555                 560
        Arg Leu Pro Ala Leu Gly Lys Thr Gln Lys Thr Gly Lys Arg Ser Thr
                        565                 570                 575
        Ser Ala Ala Val Leu Glu Ala Leu Arg Glu Ala His Pro Ile Val Glu
                        580                 585                 590
        Lys Ile Leu Gln His Arg Glu Leu Thr Lys Leu Lys Asn Thr Tyr Val
                        595                 600                 605
        Asp Pro Leu Pro Gly Leu Val His Pro Arg Thr Gly Arg Leu His Thr
                        610                 615                 620
        Arg Phe Asn Gln Thr Ala Thr Ala Thr Gly Arg Leu Ser Ser Ser Asp
        625                 630                 635                 640
        Pro Asn Leu Gln Asn Ile Pro Ile Arg Thr Pro Leu Gly Gln Arg Ile
                        645                 650                 655
        Arg Arg Ala Phe Val Ala Glu Ala Gly Trp Ala Leu Val Ala Leu Asp
                        660                 665                 670
        Tyr Ser Gln Ile Glu Leu Arg Val Leu Ala His Leu Ser Gly Asp Glu
                        675                 680                 685
        Asn Leu Ile Arg Val Phe Gln Glu Gly Lys Asp Ile His Thr Gln Thr
                        690                 695                 700
        Ala Ser Trp Met Phe Gly Val Ser Pro Glu Ala Val Asp Pro Leu Met
        705                 710                 715                 720
        Arg Arg Ala Ala Lys Thr Val Asn Phe Gly Val Leu Tyr Gly Met Ser
                        725                 730                 735
```

```
Ala His Arg Leu Ser Gln Glu Leu Ala Ile Pro Tyr Glu Glu Ala Val
            740                 745                 750

Ala Phe Ile Glu Arg Tyr Phe Gln Ser Phe Pro Lys Val Arg Ala Trp
            755                 760                 765

Ile Glu Lys Thr Leu Glu Gly Arg Lys Arg Gly Tyr Val Glu Thr
            770                 775                 780

Leu Phe Gly Arg Arg Tyr Val Pro Asp Leu Asn Ala Arg Val Lys
785                 790                 795                 800

Ser Val Arg Glu Ala Glu Arg Met Ala Phe Asn Met Pro Val Gln
                805                 810                 815

Gly Thr Ala Ala Asp Leu Met Lys Leu Ala Met Val Lys Leu Phe Pro
            820                 825                 830

His Leu Arg Glu Met Gly Ala Arg Met Leu Leu Gln Val His Asp Glu
            835                 840                 845

Leu Leu Leu Glu Ala Pro Gln Ala Arg Ala Glu Val Ala Ala Leu
            850                 855                 860

Ala Lys Glu Ala Met Glu Lys Ala Tyr Pro Leu Ala Val Pro Leu Glu
865                 870                 875                 880

Val Glu Val Gly Ile Gly Glu Asp Trp Leu Ser Ala Lys Gly
                885                 890

<210> SEQ ID NO 139
<211> LENGTH: 196
<212> TYPE: PRT
<213> ORGANISM: Artificial sequence
<220> FEATURE:
<223> OTHER INFORMATION: Exonucleolytic domain of thermostable DNA
      polymerase CS7 after second round of mutagenesis N385A
      substitution

<400> SEQUENCE: 139

Glu Ser Glu Pro Val Gly Tyr Arg Ile Val Lys Asp Leu Val Glu Phe
1               5                   10                  15

Glu Lys Leu Ile Glu Lys Leu Arg Glu Ser Pro Ser Phe Ala Ile Asp
            20                  25                  30

Leu Glu Thr Ser Ser Leu Asp Pro Phe Asp Cys Asp Ile Val Gly Ile
        35                  40                  45

Ser Val Ser Phe Lys Pro Lys Glu Ala Tyr Tyr Ile Pro Leu His His
    50                  55                  60

Arg Asn Ala Gln Asn Leu Asp Glu Lys Glu Val Leu Lys Lys Leu Lys
65                  70                  75                  80

Glu Ile Leu Glu Asp Pro Gly Ala Lys Ile Val Gly Gln Ala Leu Lys
                85                  90                  95

Phe Asp Tyr Lys Val Leu Met Val Lys Gly Val Glu Pro Val Pro Pro
            100                 105                 110

Tyr Phe Asp Thr Met Ile Ala Ala Tyr Leu Leu Glu Pro Asn Glu Lys
        115                 120                 125

Lys Phe Asn Leu Asp Asp Leu Ala Leu Lys Phe Leu Gly Tyr Lys Met
    130                 135                 140

Thr Ser Tyr Gln Glu Leu Met Ser Phe Ser Phe Pro Leu Phe Gly Phe
145                 150                 155                 160

Ser Phe Ala Asp Val Pro Val Glu Lys Ala Ala Asn Tyr Ser Cys Glu
                165                 170                 175

Asp Ala Asp Ile Thr Tyr Arg Leu Tyr Lys Thr Leu Ser Leu Lys Leu
            180                 185                 190
```

His Glu Glu Lys
        195

<210> SEQ ID NO 140
<211> LENGTH: 894
<212> TYPE: PRT
<213> ORGANISM: Artificial sequence
<220> FEATURE:
<223> OTHER INFORMATION: thermostable DNA polymerase CS7 after second
      round of mutagenesis N385A substitution

<400> SEQUENCE: 140

Met Lys Ala Met Leu Pro Leu Phe Glu Pro Lys Gly Arg Val Leu Leu
1               5                   10                  15

Val Asp Gly His His Leu Ala Tyr Arg Thr Phe Phe Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Tyr Lys Ala Val Phe
    50                  55                  60

Val Val Phe Asp Ala Lys Ala Pro Ser Phe Arg His Glu Ala Tyr Glu
65                  70                  75                  80

Ala Tyr Lys Ala Gly Arg Ala Pro Thr Pro Glu Asp Phe Pro Arg Gln
                85                  90                  95

Leu Ala Leu Ile Lys Glu Leu Val Asp Leu Leu Gly Phe Thr Arg Leu
            100                 105                 110

Glu Val Pro Gly Phe Glu Ala Asp Asp Val Leu Ala Thr Leu Ala Lys
        115                 120                 125

Lys Ala Glu Arg Glu Gly Tyr Glu Val Arg Ile Leu Thr Ala Asp Arg
    130                 135                 140

Asp Leu Tyr Gln Leu Val Ser Asp Arg Val Ala Val Leu His Pro Glu
145                 150                 155                 160

Gly His Leu Ile Thr Pro Glu Trp Leu Trp Glu Lys Tyr Gly Leu Lys
                165                 170                 175

Pro Glu Gln Trp Val Asp Phe Arg Ala Leu Val Gly Asp Pro Ser Asp
            180                 185                 190

Asn Leu Pro Gly Val Lys Gly Ile Gly Glu Lys Thr Ala Leu Lys Leu
        195                 200                 205

Leu Lys Glu Trp Gly Ser Leu Glu Asn Ile Leu Lys Asn Leu Asp Arg
    210                 215                 220

Val Lys Pro Glu Ser Val Arg Glu Arg Ile Lys Ala His Leu Glu Asp
225                 230                 235                 240

Leu Lys Leu Ser Leu Glu Leu Ser Arg Val Arg Ser Asp Leu Pro Leu
                245                 250                 255

Glu Val Asp Phe Ala Arg Arg Glu Pro Asp Arg Glu Gly Leu Arg
            260                 265                 270

Ala Phe Leu Glu Arg Leu Glu Phe Gly Ser Leu Leu His Glu Phe Gly
    275                 280                 285

Leu Leu Glu Glu Ser Glu Pro Val Gly Tyr Arg Ile Val Lys Asp Leu
    290                 295                 300

Val Glu Phe Glu Lys Leu Ile Glu Lys Leu Arg Glu Ser Pro Ser Phe
305                 310                 315                 320

Ala Ile Asp Leu Glu Thr Ser Ser Leu Asp Pro Phe Asp Cys Asp Ile
                325                 330                 335

Val Gly Ile Ser Val Ser Phe Lys Pro Lys Glu Ala Tyr Tyr Ile Pro
            340                 345                 350

```
Leu His His Arg Asn Ala Gln Asn Leu Asp Glu Lys Glu Val Leu Lys
        355                 360                 365

Lys Leu Lys Glu Ile Leu Glu Asp Pro Gly Ala Lys Ile Val Gly Gln
        370                 375                 380

Ala Leu Lys Phe Asp Tyr Lys Val Leu Met Val Lys Gly Val Glu Pro
385                 390                 395                 400

Val Pro Pro Tyr Phe Asp Thr Met Ile Ala Ala Tyr Leu Leu Glu Pro
                405                 410                 415

Asn Glu Lys Lys Phe Asn Leu Asp Asp Leu Ala Leu Lys Phe Leu Gly
            420                 425                 430

Tyr Lys Met Thr Ser Tyr Gln Glu Leu Met Ser Phe Ser Phe Pro Leu
            435                 440                 445

Phe Gly Phe Ser Phe Ala Asp Val Pro Val Glu Lys Ala Ala Asn Tyr
        450                 455                 460

Ser Cys Glu Asp Ala Asp Ile Thr Tyr Arg Leu Tyr Lys Thr Leu Ser
465                 470                 475                 480

Leu Lys Leu His Glu Glu Lys Leu Leu Trp Leu Tyr Gln Glu Val Glu
                485                 490                 495

Lys Pro Leu Ser Arg Val Leu Ala His Met Glu Ala Thr Gly Val Arg
            500                 505                 510

Leu Asp Val Ala Tyr Leu Lys Ala Leu Ser Leu Glu Leu Ala Glu Glu
            515                 520                 525

Ile Arg Arg Leu Glu Glu Glu Val Phe Arg Leu Ala Gly His Pro Phe
        530                 535                 540

Asn Leu Asn Ser Arg Asp Gln Leu Glu Arg Val Leu Phe Asp Glu Leu
545                 550                 555                 560

Arg Leu Pro Ala Leu Gly Lys Thr Gln Lys Thr Gly Lys Arg Ser Thr
                565                 570                 575

Ser Ala Ala Val Leu Glu Ala Leu Arg Glu Ala His Pro Ile Val Glu
            580                 585                 590

Lys Ile Leu Gln His Arg Glu Leu Thr Lys Leu Lys Asn Thr Tyr Val
        595                 600                 605

Asp Pro Leu Pro Gly Leu Val His Pro Arg Thr Gly Arg Leu His Thr
        610                 615                 620

Arg Phe Asn Gln Thr Ala Thr Ala Thr Gly Arg Leu Ser Ser Ser Asp
625                 630                 635                 640

Pro Asn Leu Gln Asn Ile Pro Ile Arg Thr Pro Leu Gly Gln Arg Ile
                645                 650                 655

Arg Arg Ala Phe Val Ala Glu Ala Gly Trp Ala Leu Val Ala Leu Asp
            660                 665                 670

Tyr Ser Gln Ile Glu Leu Arg Val Leu Ala His Leu Ser Gly Asp Glu
        675                 680                 685

Asn Leu Ile Arg Val Phe Gln Glu Gly Lys Asp Ile His Thr Gln Thr
        690                 695                 700

Ala Ser Trp Met Phe Gly Val Ser Pro Glu Ala Val Asp Pro Leu Met
705                 710                 715                 720

Arg Arg Ala Ala Lys Thr Val Asn Phe Gly Val Leu Tyr Gly Met Ser
                725                 730                 735

Ala His Arg Leu Ser Gln Glu Leu Ala Ile Pro Tyr Glu Glu Ala Val
            740                 745                 750

Ala Phe Ile Glu Arg Tyr Phe Gln Ser Phe Pro Lys Val Arg Ala Trp
        755                 760                 765
```

-continued

Ile Glu Lys Thr Leu Glu Glu Gly Arg Lys Arg Gly Tyr Val Glu Thr
    770                 775                 780

Leu Phe Gly Arg Arg Arg Tyr Val Pro Asp Leu Asn Ala Arg Val Lys
785                 790                 795                 800

Ser Val Arg Glu Ala Ala Glu Arg Met Ala Phe Asn Met Pro Val Gln
                805                 810                 815

Gly Thr Ala Ala Asp Leu Met Lys Leu Ala Met Val Lys Leu Phe Pro
            820                 825                 830

His Leu Arg Glu Met Gly Ala Arg Met Leu Leu Gln Val His Asp Glu
        835                 840                 845

Leu Leu Leu Glu Ala Pro Gln Ala Arg Ala Glu Val Ala Ala Leu
    850                 855                 860

Ala Lys Glu Ala Met Glu Lys Ala Tyr Pro Leu Ala Val Pro Leu Glu
865                 870                 875                 880

Val Glu Val Gly Ile Gly Glu Asp Trp Leu Ser Ala Lys Gly
                885                 890

<210> SEQ ID NO 141
<211> LENGTH: 196
<212> TYPE: PRT
<213> ORGANISM: Artificial sequence
<220> FEATURE:
<223> OTHER INFORMATION: Exonucleolytic domain of thermostable DNA
      polymerase CS7 after second round of mutagenesis Q384A N385A
      substitution

<400> SEQUENCE: 141

Glu Ser Glu Pro Val Gly Tyr Arg Ile Val Lys Asp Leu Val Glu Phe
1               5                   10                  15

Glu Lys Leu Ile Glu Lys Leu Arg Glu Ser Pro Ser Phe Ala Ile Asp
            20                  25                  30

Leu Glu Thr Ser Ser Leu Asp Pro Phe Asp Cys Asp Ile Val Gly Ile
        35                  40                  45

Ser Val Ser Phe Lys Pro Lys Glu Ala Tyr Tyr Ile Pro Leu His His
    50                  55                  60

Arg Asn Ala Gln Asn Leu Asp Glu Lys Glu Val Leu Lys Lys Leu Lys
65                  70                  75                  80

Glu Ile Leu Glu Asp Pro Gly Ala Lys Ile Val Gly Ala Ala Leu Lys
                85                  90                  95

Phe Asp Tyr Lys Val Leu Met Val Lys Gly Val Glu Pro Val Pro Pro
            100                 105                 110

Tyr Phe Asp Thr Met Ile Ala Ala Tyr Leu Leu Glu Pro Asn Glu Lys
        115                 120                 125

Lys Phe Asn Leu Asp Asp Leu Ala Leu Lys Phe Leu Gly Tyr Lys Met
    130                 135                 140

Thr Ser Tyr Gln Glu Leu Met Ser Phe Ser Phe Pro Leu Phe Gly Phe
145                 150                 155                 160

Ser Phe Ala Asp Val Pro Val Glu Lys Ala Ala Asn Tyr Ser Cys Glu
                165                 170                 175

Asp Ala Asp Ile Thr Tyr Arg Leu Tyr Lys Thr Leu Ser Leu Lys Leu
            180                 185                 190

His Glu Glu Lys
        195

<210> SEQ ID NO 142
<211> LENGTH: 894
<212> TYPE: PRT

<213> ORGANISM: Artificial sequence
<220> FEATURE:
<223> OTHER INFORMATION: thermostable DNA polymerase CS7 after second
      round of mutagenesis Q384A N385A substitution

<400> SEQUENCE: 142

| | | | | | | | | | | | | | | |
|---|---|---|---|---|---|---|---|---|---|---|---|---|---|---|
| Met | Lys | Ala | Met | Leu | Pro | Leu | Phe | Glu | Pro | Lys | Gly | Arg | Val | Leu | Leu |
| 1 | | | | 5 | | | | | 10 | | | | | 15 | |
| Val | Asp | Gly | His | His | Leu | Ala | Tyr | Arg | Thr | Phe | Phe | Ala | Leu | Lys | Gly |
| | | | 20 | | | | | 25 | | | | | 30 | | |
| Leu | Thr | Thr | Ser | Arg | Gly | Glu | Pro | Val | Gln | Ala | Val | Tyr | Gly | Phe | Ala |
| | | | | 35 | | | | | 40 | | | | | 45 | |
| Lys | Ser | Leu | Leu | Lys | Ala | Leu | Lys | Glu | Asp | Gly | Tyr | Lys | Ala | Val | Phe |
| | 50 | | | | | 55 | | | | | 60 | | | | |
| Val | Val | Phe | Asp | Ala | Lys | Ala | Pro | Ser | Phe | Arg | His | Glu | Ala | Tyr | Glu |
| 65 | | | | | 70 | | | | | 75 | | | | | 80 |
| Ala | Tyr | Lys | Ala | Gly | Arg | Ala | Pro | Thr | Pro | Glu | Asp | Phe | Pro | Arg | Gln |
| | | | | 85 | | | | | 90 | | | | | 95 | |
| Leu | Ala | Leu | Ile | Lys | Glu | Leu | Val | Asp | Leu | Leu | Gly | Phe | Thr | Arg | Leu |
| | | | 100 | | | | | 105 | | | | | 110 | | |
| Glu | Val | Pro | Gly | Phe | Glu | Ala | Asp | Asp | Val | Leu | Ala | Thr | Leu | Ala | Lys |
| | | | | 115 | | | | | 120 | | | | | 125 | |
| Lys | Ala | Glu | Arg | Glu | Gly | Tyr | Glu | Val | Arg | Ile | Leu | Thr | Ala | Asp | Arg |
| | 130 | | | | | 135 | | | | | 140 | | | | |
| Asp | Leu | Tyr | Gln | Leu | Val | Ser | Asp | Arg | Val | Ala | Val | Leu | His | Pro | Glu |
| 145 | | | | | 150 | | | | | 155 | | | | | 160 |
| Gly | His | Leu | Ile | Thr | Pro | Glu | Trp | Leu | Trp | Glu | Lys | Tyr | Gly | Leu | Lys |
| | | | | 165 | | | | | 170 | | | | | 175 | |
| Pro | Glu | Gln | Trp | Val | Asp | Phe | Arg | Ala | Leu | Val | Gly | Asp | Pro | Ser | Asp |
| | | | 180 | | | | | 185 | | | | | 190 | | |
| Asn | Leu | Pro | Gly | Val | Lys | Gly | Ile | Gly | Glu | Lys | Thr | Ala | Leu | Lys | Leu |
| | | | | 195 | | | | | 200 | | | | | 205 | |
| Leu | Lys | Glu | Trp | Gly | Ser | Leu | Glu | Asn | Ile | Leu | Lys | Asn | Leu | Asp | Arg |
| | 210 | | | | | 215 | | | | | 220 | | | | |
| Val | Lys | Pro | Glu | Ser | Val | Arg | Glu | Arg | Ile | Lys | Ala | His | Leu | Glu | Asp |
| 225 | | | | | 230 | | | | | 235 | | | | | 240 |
| Leu | Lys | Leu | Ser | Leu | Glu | Leu | Ser | Arg | Val | Arg | Ser | Asp | Leu | Pro | Leu |
| | | | | 245 | | | | | 250 | | | | | 255 | |
| Glu | Val | Asp | Phe | Ala | Arg | Arg | Arg | Glu | Pro | Asp | Arg | Glu | Gly | Leu | Arg |
| | | | 260 | | | | | 265 | | | | | 270 | | |
| Ala | Phe | Leu | Glu | Arg | Leu | Glu | Phe | Gly | Ser | Leu | Leu | His | Glu | Phe | Gly |
| | | 275 | | | | | 280 | | | | | 285 | | | |
| Leu | Leu | Glu | Glu | Ser | Glu | Pro | Val | Gly | Tyr | Arg | Ile | Val | Lys | Asp | Leu |
| | 290 | | | | | 295 | | | | | 300 | | | | |
| Val | Glu | Phe | Glu | Lys | Leu | Ile | Glu | Lys | Leu | Arg | Glu | Ser | Pro | Ser | Phe |
| 305 | | | | | 310 | | | | | 315 | | | | | 320 |
| Ala | Ile | Asp | Leu | Glu | Thr | Ser | Ser | Leu | Asp | Pro | Phe | Asp | Cys | Asp | Ile |
| | | | | 325 | | | | | 330 | | | | | 335 | |
| Val | Gly | Ile | Ser | Val | Ser | Phe | Lys | Pro | Lys | Glu | Ala | Tyr | Tyr | Ile | Pro |
| | | | 340 | | | | | 345 | | | | | 350 | | |
| Leu | His | His | Arg | Asn | Ala | Gln | Asn | Leu | Asp | Glu | Lys | Glu | Val | Leu | Lys |
| | | | | 355 | | | | | 360 | | | | | 365 | |
| Lys | Leu | Lys | Glu | Ile | Leu | Glu | Asp | Pro | Gly | Ala | Lys | Ile | Val | Gly | Ala |
| | 370 | | | | | 375 | | | | | 380 | | | | |

```
Ala Leu Lys Phe Asp Tyr Lys Val Leu Met Val Lys Gly Val Glu Pro
385                 390                 395                 400

Val Pro Pro Tyr Phe Asp Thr Met Ile Ala Ala Tyr Leu Leu Glu Pro
                405                 410                 415

Asn Glu Lys Lys Phe Asn Leu Asp Asp Leu Ala Leu Lys Phe Leu Gly
            420                 425                 430

Tyr Lys Met Thr Ser Tyr Gln Glu Leu Met Ser Phe Ser Phe Pro Leu
        435                 440                 445

Phe Gly Phe Ser Phe Ala Asp Val Pro Val Glu Lys Ala Ala Asn Tyr
    450                 455                 460

Ser Cys Glu Asp Ala Asp Ile Thr Tyr Arg Leu Tyr Lys Thr Leu Ser
465                 470                 475                 480

Leu Lys Leu His Glu Glu Lys Leu Leu Trp Leu Tyr Gln Glu Val Glu
                485                 490                 495

Lys Pro Leu Ser Arg Val Leu Ala His Met Glu Ala Thr Gly Val Arg
            500                 505                 510

Leu Asp Val Ala Tyr Leu Lys Ala Leu Ser Leu Glu Leu Ala Glu Glu
        515                 520                 525

Ile Arg Arg Leu Glu Glu Val Phe Arg Leu Ala Gly His Pro Phe
530                 535                 540

Asn Leu Asn Ser Arg Asp Gln Leu Glu Arg Val Leu Phe Asp Glu Leu
545                 550                 555                 560

Arg Leu Pro Ala Leu Gly Lys Thr Gln Lys Thr Gly Lys Arg Ser Thr
                565                 570                 575

Ser Ala Ala Val Leu Glu Ala Leu Arg Glu Ala His Pro Ile Val Glu
            580                 585                 590

Lys Ile Leu Gln His Arg Glu Leu Thr Lys Leu Lys Asn Thr Tyr Val
        595                 600                 605

Asp Pro Leu Pro Gly Leu Val His Pro Arg Thr Gly Arg Leu His Thr
610                 615                 620

Arg Phe Asn Gln Thr Ala Thr Ala Thr Gly Arg Leu Ser Ser Ser Asp
625                 630                 635                 640

Pro Asn Leu Gln Asn Ile Pro Ile Arg Thr Pro Leu Gly Gln Arg Ile
                645                 650                 655

Arg Arg Ala Phe Val Ala Glu Ala Gly Trp Ala Leu Val Ala Leu Asp
            660                 665                 670

Tyr Ser Gln Ile Glu Leu Arg Val Leu Ala His Leu Ser Gly Asp Glu
        675                 680                 685

Asn Leu Ile Arg Val Phe Gln Glu Gly Lys Asp Ile His Thr Gln Thr
690                 695                 700

Ala Ser Trp Met Phe Gly Val Ser Pro Glu Ala Val Asp Pro Leu Met
705                 710                 715                 720

Arg Arg Ala Ala Lys Thr Val Asn Phe Gly Val Leu Tyr Gly Met Ser
                725                 730                 735

Ala His Arg Leu Ser Gln Glu Leu Ala Ile Pro Tyr Glu Glu Ala Val
            740                 745                 750

Ala Phe Ile Glu Arg Tyr Phe Gln Ser Phe Pro Lys Val Arg Ala Trp
        755                 760                 765

Ile Glu Lys Thr Leu Glu Glu Gly Arg Lys Arg Gly Tyr Val Glu Thr
770                 775                 780

Leu Phe Gly Arg Arg Arg Tyr Val Pro Asp Leu Asn Ala Arg Val Lys
785                 790                 795                 800

Ser Val Arg Glu Ala Ala Glu Arg Met Ala Phe Asn Met Pro Val Gln
```

```
                805                 810                 815
Gly Thr Ala Ala Asp Leu Met Lys Leu Ala Met Val Lys Leu Phe Pro
            820                 825                 830

His Leu Arg Glu Met Gly Ala Arg Met Leu Leu Gln Val His Asp Glu
            835                 840                 845

Leu Leu Leu Glu Ala Pro Gln Ala Arg Ala Glu Glu Val Ala Ala Leu
            850                 855                 860

Ala Lys Glu Ala Met Glu Lys Ala Tyr Pro Leu Ala Val Pro Leu Glu
865                 870                 875                 880

Val Glu Val Gly Ile Gly Glu Asp Trp Leu Ser Ala Lys Gly
                885                 890
```

<210> SEQ ID NO 143
<211> LENGTH: 196
<212> TYPE: PRT
<213> ORGANISM: Artificial sequence
<220> FEATURE:
<223> OTHER INFORMATION: Exonucleolytic domain of thermostable DNA
      polymerase CS7 after second round of mutagenesis D389E
      substitution

<400> SEQUENCE: 143

```
Glu Ser Glu Pro Val Gly Tyr Arg Ile Val Lys Asp Leu Val Glu Phe
1               5                   10                  15

Glu Lys Leu Ile Glu Lys Leu Arg Glu Ser Pro Ser Phe Ala Ile Asp
            20                  25                  30

Leu Glu Thr Ser Ser Leu Asp Pro Phe Asp Cys Asp Ile Val Gly Ile
        35                  40                  45

Ser Val Ser Phe Lys Pro Lys Glu Ala Tyr Tyr Ile Pro Leu His His
    50                  55                  60

Arg Asn Ala Gln Asn Leu Asp Glu Lys Glu Val Leu Lys Lys Leu Lys
65                  70                  75                  80

Glu Ile Leu Glu Asp Pro Gly Ala Lys Ile Val Gly Gln Asn Leu Lys
                85                  90                  95

Phe Glu Tyr Lys Val Leu Met Val Lys Gly Val Glu Pro Val Pro Pro
            100                 105                 110

Tyr Phe Asp Thr Met Ile Ala Ala Tyr Leu Leu Glu Pro Asn Glu Lys
        115                 120                 125

Lys Phe Asn Leu Asp Asp Leu Ala Leu Lys Phe Leu Gly Tyr Lys Met
    130                 135                 140

Thr Ser Tyr Gln Glu Leu Met Ser Phe Ser Phe Pro Leu Phe Gly Phe
145                 150                 155                 160

Ser Phe Ala Asp Val Pro Val Glu Lys Ala Ala Asn Tyr Ser Cys Glu
                165                 170                 175

Asp Ala Asp Ile Thr Tyr Arg Leu Tyr Lys Thr Leu Ser Leu Lys Leu
            180                 185                 190

His Glu Glu Lys
        195
```

<210> SEQ ID NO 144
<211> LENGTH: 894
<212> TYPE: PRT
<213> ORGANISM: Artificial sequence
<220> FEATURE:
<223> OTHER INFORMATION: thermostable DNA polymerase CS7 after second
      round of mutagenesis D389E substitution

<400> SEQUENCE: 144

-continued

```
Met Lys Ala Met Leu Pro Leu Phe Glu Pro Lys Gly Arg Val Leu Leu
1               5                   10                  15

Val Asp Gly His His Leu Ala Tyr Arg Thr Phe Ala Leu Lys Gly
            20                  25              30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Tyr Lys Ala Val Phe
50                      55                  60

Val Val Phe Asp Ala Lys Ala Pro Ser Phe Arg His Glu Ala Tyr Glu
65                  70                  75                  80

Ala Tyr Lys Ala Gly Arg Ala Pro Thr Pro Glu Asp Phe Pro Arg Gln
                85                  90                  95

Leu Ala Leu Ile Lys Glu Leu Val Asp Leu Leu Gly Phe Thr Arg Leu
            100                 105                 110

Glu Val Pro Gly Phe Glu Ala Asp Asp Val Leu Ala Thr Leu Ala Lys
            115                 120                 125

Lys Ala Glu Arg Glu Gly Tyr Glu Val Arg Ile Leu Thr Ala Asp Arg
130                 135                 140

Asp Leu Tyr Gln Leu Val Ser Asp Arg Val Ala Val Leu His Pro Glu
145                 150                 155                 160

Gly His Leu Ile Thr Pro Glu Trp Leu Trp Glu Lys Tyr Gly Leu Lys
                165                 170                 175

Pro Glu Gln Trp Val Asp Phe Arg Ala Leu Val Gly Asp Pro Ser Asp
            180                 185                 190

Asn Leu Pro Gly Val Lys Gly Ile Gly Glu Lys Thr Ala Leu Lys Leu
            195                 200                 205

Leu Lys Glu Trp Gly Ser Leu Glu Asn Ile Leu Lys Asn Leu Asp Arg
210                 215                 220

Val Lys Pro Glu Ser Val Arg Glu Arg Ile Lys Ala His Leu Glu Asp
225                 230                 235                 240

Leu Lys Leu Ser Leu Glu Leu Ser Arg Val Arg Ser Asp Leu Pro Leu
            245                 250                 255

Glu Val Asp Phe Ala Arg Arg Arg Glu Pro Asp Arg Glu Gly Leu Arg
            260                 265                 270

Ala Phe Leu Glu Arg Leu Glu Phe Gly Ser Leu Leu His Glu Phe Gly
            275                 280                 285

Leu Leu Glu Glu Ser Glu Pro Val Gly Tyr Arg Ile Val Lys Asp Leu
            290                 295                 300

Val Glu Phe Glu Lys Leu Ile Glu Lys Leu Arg Glu Ser Pro Ser Phe
305                 310                 315                 320

Ala Ile Asp Leu Glu Thr Ser Ser Leu Asp Pro Phe Asp Cys Asp Ile
                325                 330                 335

Val Gly Ile Ser Val Ser Phe Lys Pro Lys Glu Ala Tyr Tyr Ile Pro
            340                 345                 350

Leu His His Arg Asn Ala Gln Asn Leu Asp Glu Lys Glu Val Leu Lys
            355                 360                 365

Lys Leu Lys Glu Ile Leu Glu Asp Pro Gly Ala Lys Ile Val Gly Gln
370                 375                 380

Asn Leu Lys Phe Glu Tyr Lys Val Leu Met Val Lys Gly Val Glu Pro
385                 390                 395                 400

Val Pro Pro Tyr Phe Asp Thr Met Ile Ala Ala Tyr Leu Leu Glu Pro
                405                 410                 415

Asn Glu Lys Lys Phe Asn Leu Asp Asp Leu Ala Leu Lys Phe Leu Gly
```

-continued

```
                420                 425                 430
Tyr Lys Met Thr Ser Tyr Gln Glu Leu Met Ser Phe Ser Phe Pro Leu
            435                 440                 445

Phe Gly Phe Ser Phe Ala Asp Val Pro Val Glu Lys Ala Ala Asn Tyr
        450                 455                 460

Ser Cys Glu Asp Ala Asp Ile Thr Tyr Arg Leu Tyr Lys Thr Leu Ser
465                 470                 475                 480

Leu Lys Leu His Glu Glu Lys Leu Leu Trp Leu Tyr Gln Glu Val Glu
                485                 490                 495

Lys Pro Leu Ser Arg Val Leu Ala His Met Glu Ala Thr Gly Val Arg
            500                 505                 510

Leu Asp Val Ala Tyr Leu Lys Ala Leu Ser Leu Glu Leu Ala Glu Glu
        515                 520                 525

Ile Arg Arg Leu Glu Glu Val Phe Arg Leu Ala Gly His Pro Phe
    530                 535                 540

Asn Leu Asn Ser Arg Asp Gln Leu Glu Arg Val Leu Phe Asp Glu Leu
545                 550                 555                 560

Arg Leu Pro Ala Leu Gly Lys Thr Gln Lys Thr Gly Lys Arg Ser Thr
                565                 570                 575

Ser Ala Ala Val Leu Glu Ala Leu Arg Glu Ala His Pro Ile Val Glu
            580                 585                 590

Lys Ile Leu Gln His Arg Glu Leu Thr Lys Leu Lys Asn Thr Tyr Val
        595                 600                 605

Asp Pro Leu Pro Gly Leu Val His Pro Arg Thr Gly Arg Leu His Thr
    610                 615                 620

Arg Phe Asn Gln Thr Ala Thr Ala Thr Gly Arg Leu Ser Ser Ser Asp
625                 630                 635                 640

Pro Asn Leu Gln Asn Ile Pro Ile Arg Thr Pro Leu Gly Gln Arg Ile
                645                 650                 655

Arg Arg Ala Phe Val Ala Glu Ala Gly Trp Ala Leu Val Ala Leu Asp
            660                 665                 670

Tyr Ser Gln Ile Glu Leu Arg Val Leu Ala His Leu Ser Gly Asp Glu
        675                 680                 685

Asn Leu Ile Arg Val Phe Gln Glu Gly Lys Asp Ile His Thr Gln Thr
    690                 695                 700

Ala Ser Trp Met Phe Gly Val Ser Pro Glu Ala Val Asp Pro Leu Met
705                 710                 715                 720

Arg Arg Ala Ala Lys Thr Val Asn Phe Gly Val Leu Tyr Gly Met Ser
                725                 730                 735

Ala His Arg Leu Ser Gln Glu Leu Ala Ile Pro Tyr Glu Glu Ala Val
            740                 745                 750

Ala Phe Ile Glu Arg Tyr Phe Gln Ser Phe Pro Lys Val Arg Ala Trp
        755                 760                 765

Ile Glu Lys Thr Leu Glu Glu Gly Arg Lys Arg Gly Tyr Val Glu Thr
    770                 775                 780

Leu Phe Gly Arg Arg Tyr Val Pro Asp Leu Asn Ala Arg Val Lys
785                 790                 795                 800

Ser Val Arg Glu Ala Ala Glu Arg Met Ala Phe Asn Met Pro Val Gln
                805                 810                 815

Gly Thr Ala Ala Asp Leu Met Lys Leu Ala Met Val Lys Leu Phe Pro
            820                 825                 830

His Leu Arg Glu Met Gly Ala Arg Met Leu Leu Gln Val His Asp Glu
        835                 840                 845
```

```
Leu Leu Leu Glu Ala Pro Gln Ala Arg Ala Glu Val Ala Ala Leu
        850                 855                 860

Ala Lys Glu Ala Met Glu Lys Ala Tyr Pro Leu Ala Val Pro Leu Glu
865                 870                 875                 880

Val Glu Val Gly Ile Gly Glu Asp Trp Leu Ser Ala Lys Gly
                885                 890
```

<210> SEQ ID NO 145
<211> LENGTH: 196
<212> TYPE: PRT
<213> ORGANISM: Artificial sequence
<220> FEATURE:
<223> OTHER INFORMATION: Exonucleolytic domain of thermostable DNA polymerase CS7 after second round of mutagenesis Y464A substitution

<400> SEQUENCE: 145

```
Glu Ser Glu Pro Val Gly Tyr Arg Ile Val Lys Asp Leu Val Glu Phe
1               5                   10                  15

Glu Lys Leu Ile Glu Lys Leu Arg Glu Ser Pro Ser Phe Ala Ile Asp
            20                  25                  30

Leu Glu Thr Ser Ser Leu Asp Pro Phe Asp Cys Asp Ile Val Gly Ile
        35                  40                  45

Ser Val Ser Phe Lys Pro Lys Glu Ala Tyr Tyr Ile Pro Leu His His
    50                  55                  60

Arg Asn Ala Gln Asn Leu Asp Glu Lys Glu Val Leu Lys Lys Leu Lys
65                  70                  75                  80

Glu Ile Leu Glu Asp Pro Gly Ala Lys Ile Val Gly Gln Asn Leu Lys
                85                  90                  95

Phe Asp Tyr Lys Val Leu Met Val Lys Gly Val Glu Pro Val Pro Pro
            100                 105                 110

Tyr Phe Asp Thr Met Ile Ala Ala Tyr Leu Leu Glu Pro Asn Glu Lys
        115                 120                 125

Lys Phe Asn Leu Asp Asp Leu Ala Leu Lys Phe Leu Gly Tyr Lys Met
    130                 135                 140

Thr Ser Tyr Gln Glu Leu Met Ser Phe Ser Phe Pro Leu Phe Gly Phe
145                 150                 155                 160

Ser Phe Ala Asp Val Pro Val Glu Lys Ala Ala Asn Ala Ser Cys Glu
                165                 170                 175

Asp Ala Asp Ile Thr Tyr Arg Leu Tyr Lys Thr Leu Ser Leu Lys Leu
            180                 185                 190

His Glu Glu Lys
        195
```

<210> SEQ ID NO 146
<211> LENGTH: 894
<212> TYPE: PRT
<213> ORGANISM: Artificial sequence
<220> FEATURE:
<223> OTHER INFORMATION: thermostable DNA polymerase CS7 after second round of mutagenesis Y464A substitution

<400> SEQUENCE: 146

```
Met Lys Ala Met Leu Pro Leu Phe Glu Pro Lys Gly Arg Val Leu Leu
1               5                   10                  15

Val Asp Gly His His Leu Ala Tyr Arg Thr Phe Phe Ala Leu Lys Gly
            20                  25                  30

Leu Thr Thr Ser Arg Gly Glu Pro Val Gln Ala Val Tyr Gly Phe Ala
```

-continued

```
                    35                  40                  45
Lys Ser Leu Leu Lys Ala Leu Lys Glu Asp Gly Tyr Lys Ala Val Phe
 50                  55                  60
Val Val Phe Asp Ala Lys Ala Pro Ser Phe Arg His Glu Ala Tyr Glu
 65                  70                  75                  80
Ala Tyr Lys Ala Gly Arg Ala Pro Thr Pro Glu Asp Phe Pro Arg Gln
                 85                  90                  95
Leu Ala Leu Ile Lys Glu Leu Val Asp Leu Leu Gly Phe Thr Arg Leu
                100                 105                 110
Glu Val Pro Gly Phe Glu Ala Asp Val Leu Ala Thr Leu Ala Lys
                115                 120                 125
Lys Ala Glu Arg Glu Gly Tyr Glu Val Arg Ile Leu Thr Ala Asp Arg
130                 135                 140
Asp Leu Tyr Gln Leu Val Ser Asp Arg Val Ala Val Leu His Pro Glu
145                 150                 155                 160
Gly His Leu Ile Thr Pro Glu Trp Leu Trp Glu Lys Tyr Gly Leu Lys
                165                 170                 175
Pro Glu Gln Trp Val Asp Phe Arg Ala Leu Val Gly Asp Pro Ser Asp
                180                 185                 190
Asn Leu Pro Gly Val Lys Gly Ile Gly Glu Lys Thr Ala Leu Lys Leu
                195                 200                 205
Leu Lys Glu Trp Gly Ser Leu Glu Asn Ile Leu Lys Asn Leu Asp Arg
            210                 215                 220
Val Lys Pro Glu Ser Val Arg Glu Arg Ile Lys Ala His Leu Glu Asp
225                 230                 235                 240
Leu Lys Leu Ser Leu Glu Leu Ser Arg Val Arg Ser Asp Leu Pro Leu
                245                 250                 255
Glu Val Asp Phe Ala Arg Arg Glu Pro Asp Arg Glu Gly Leu Arg
                260                 265                 270
Ala Phe Leu Glu Arg Leu Glu Phe Gly Ser Leu Leu His Glu Phe Gly
            275                 280                 285
Leu Leu Glu Glu Ser Glu Pro Val Gly Tyr Arg Ile Val Lys Asp Leu
            290                 295                 300
Val Glu Phe Glu Lys Leu Ile Glu Lys Leu Arg Glu Ser Pro Ser Phe
305                 310                 315                 320
Ala Ile Asp Leu Glu Thr Ser Ser Leu Asp Pro Phe Asp Cys Asp Ile
                325                 330                 335
Val Gly Ile Ser Val Ser Phe Lys Pro Lys Glu Ala Tyr Tyr Ile Pro
            340                 345                 350
Leu His His Arg Asn Ala Gln Asn Leu Asp Glu Lys Glu Val Leu Lys
            355                 360                 365
Lys Leu Lys Glu Ile Leu Glu Asp Pro Gly Ala Lys Ile Val Gly Gln
            370                 375                 380
Asn Leu Lys Phe Asp Tyr Lys Val Leu Met Val Lys Gly Val Glu Pro
385                 390                 395                 400
Val Pro Pro Tyr Phe Asp Thr Met Ile Ala Ala Tyr Leu Leu Glu Pro
                405                 410                 415
Asn Glu Lys Lys Phe Asn Leu Asp Asp Leu Ala Leu Lys Phe Leu Gly
            420                 425                 430
Tyr Lys Met Thr Ser Tyr Gln Glu Leu Met Ser Phe Ser Phe Pro Leu
            435                 440                 445
Phe Gly Phe Ser Phe Ala Asp Val Pro Val Glu Lys Ala Ala Asn Ala
450                 455                 460
```

```
Ser Cys Glu Asp Ala Asp Ile Thr Tyr Arg Leu Tyr Lys Thr Leu Ser
465                 470                 475                 480

Leu Lys Leu His Glu Glu Lys Leu Leu Trp Leu Tyr Gln Glu Val Glu
                485                 490                 495

Lys Pro Leu Ser Arg Val Leu Ala His Met Glu Ala Thr Gly Val Arg
            500                 505                 510

Leu Asp Val Ala Tyr Leu Lys Ala Leu Ser Leu Glu Leu Ala Glu Glu
                515                 520                 525

Ile Arg Arg Leu Glu Glu Val Phe Arg Leu Ala Gly His Pro Phe
    530                 535                 540

Asn Leu Asn Ser Arg Asp Gln Leu Glu Arg Val Leu Phe Asp Glu Leu
545                 550                 555                 560

Arg Leu Pro Ala Leu Gly Lys Thr Gln Lys Thr Gly Lys Arg Ser Thr
                565                 570                 575

Ser Ala Ala Val Leu Glu Ala Leu Arg Glu Ala His Pro Ile Val Glu
            580                 585                 590

Lys Ile Leu Gln His Arg Glu Leu Thr Lys Leu Lys Asn Thr Tyr Val
595                 600                 605

Asp Pro Leu Pro Gly Leu Val His Pro Arg Thr Gly Arg Leu His Thr
    610                 615                 620

Arg Phe Asn Gln Thr Ala Thr Ala Thr Gly Arg Leu Ser Ser Ser Asp
625                 630                 635                 640

Pro Asn Leu Gln Asn Ile Pro Ile Arg Thr Pro Leu Gly Gln Arg Ile
                645                 650                 655

Arg Arg Ala Phe Val Ala Glu Ala Gly Trp Ala Leu Val Ala Leu Asp
            660                 665                 670

Tyr Ser Gln Ile Glu Leu Arg Val Leu Ala His Leu Ser Gly Asp Glu
            675                 680                 685

Asn Leu Ile Arg Val Phe Gln Glu Gly Lys Asp Ile His Thr Gln Thr
690                 695                 700

Ala Ser Trp Met Phe Gly Val Ser Pro Glu Ala Val Asp Pro Leu Met
705                 710                 715                 720

Arg Arg Ala Ala Lys Thr Val Asn Phe Gly Val Leu Tyr Gly Met Ser
                725                 730                 735

Ala His Arg Leu Ser Gln Glu Leu Ala Ile Pro Tyr Glu Glu Ala Val
            740                 745                 750

Ala Phe Ile Glu Arg Tyr Phe Gln Ser Phe Pro Lys Val Arg Ala Trp
            755                 760                 765

Ile Glu Lys Thr Leu Glu Glu Gly Arg Lys Arg Gly Tyr Val Glu Thr
770                 775                 780

Leu Phe Gly Arg Arg Arg Tyr Val Pro Asp Leu Asn Ala Arg Val Lys
785                 790                 795                 800

Ser Val Arg Glu Ala Glu Arg Met Ala Phe Asn Met Pro Val Gln
                805                 810                 815

Gly Thr Ala Ala Asp Leu Met Lys Leu Ala Met Val Lys Leu Phe Pro
                820                 825                 830

His Leu Arg Glu Met Gly Ala Arg Met Leu Leu Gln Val His Asp Glu
            835                 840                 845

Leu Leu Leu Glu Ala Pro Gln Ala Arg Ala Glu Val Ala Ala Leu
    850                 855                 860

Ala Lys Glu Ala Met Glu Lys Ala Tyr Pro Leu Ala Val Pro Leu Glu
865                 870                 875                 880
```

-continued

Val Glu Val Gly Ile Gly Glu Asp Trp Leu Ser Ala Lys Gly
      885                 890

<210> SEQ ID NO 147
<211> LENGTH: 2685
<212> TYPE: DNA
<213> ORGANISM: Artificial sequence
<220> FEATURE:
<223> OTHER INFORMATION: nucleic acid sequence that encodes chimeric
       thermostable DNA polymerase CS7

<400> SEQUENCE: 147

| | |
|---|---|
| atgaaagcta tgttaccatt attcgaaccc aaaggccggg tcctcctggt ggacggccac | 60 |
| cacctggcct accgcacctt cttcgccctg aagggcctca ccacgagccg ggcgaaccg | 120 |
| gtgcaggcgg tttacggctt cgccaagagc ctcctcaagg ccctgaagga ggacgggtac | 180 |
| aaggccgtct tcgtggtctt tgacgccaag gccccttcct ccgccacga ggcctacgag | 240 |
| gcctacaagg caggccgcgc cccgaccccc gaggacttcc ccggcagct cgccctcatc | 300 |
| aaggagctgg tggacctcct ggggtttact cgcctcgagg ttccgggctt tgaggcggac | 360 |
| gacgtcctcg ccaccctggc caagaaggcg aaagggaggg gtacgaggt gcgcatcctc | 420 |
| accgccgacc gggaccttta ccagctcgtc tccgaccgcg tcgccgtcct caccccgag | 480 |
| ggccacctca tcaccccgga gtggcttttg gagaagtacg ccttaagcc ggagcagtgg | 540 |
| gtggacttcc gcgccctcgt gggggacccc tccgacaacc tccccggggt caaggggcatc | 600 |
| ggggagaaga ccgccctcaa gctcctcaag gagtggggaa gcctggaaaa tatcctcaag | 660 |
| aacctggacc gggtgaagcc ggaaagcgtc cgggaaagga tcaaggccca cctggaagac | 720 |
| cttaagctct ccttggagct ttcccgggtg cgctcggacc tcccctgga ggtggacttc | 780 |
| gcccggaggc gggagcctga ccgggaaggg cttcgggcct ttttggagcg cttggagttc | 840 |
| ggcagcctcc tccacgagtt cggccttcta gaggagtccg aacccgttgg gtaccgtata | 900 |
| gttaaagacc tggttgaatt tgaaaaactc atagagaaac tgagagaatc tccttcgttc | 960 |
| gctatcgatt tggaaactag ttccctcgat cctttcgact gcgacattgt cggtatctct | 1020 |
| gtgtctttca aaccaaagga agcgtactac ataccactcc atcatagaaa cgcccagaac | 1080 |
| ctggacgaaa aagaggttct gaaaaagctc aaagaaattc tggaggaccc cggagcaaag | 1140 |
| atcgttggtc agaatttgaa attcgattac aaggtgttga tggtgaaggg tgttgaacct | 1200 |
| gttcctcctt acttcgacac gatgatagcg gcttaccttc ttgagccgaa cgaaaagaag | 1260 |
| ttcaatctgg acgatctcgc attgaaattt cttggataca aaatgacatc ttaccaagag | 1320 |
| ctcatgtcct ctctctttcc gctgtttggt ttcagttttg ccgatgttcc tgtagaaaaa | 1380 |
| gcagcgaact actcctgtga agatgcagac atcacctaca actttacaa gaccctgagc | 1440 |
| ttaaaactcc acgaggaaaa gcttctttgg ctctaccaag aggtggaaaa gcccctctcc | 1500 |
| cgggtcctgg cccacatgga ggccaccggg gtaaggctgg acgtggccta tctaaaggcc | 1560 |
| cttttccctg gagcttgcgga ggagattcgc cgcctcgagg aggaggtctt ccgcctggcg | 1620 |
| ggccaccccct tcaacctgaa ctcccgtgac cagctagagc gggtgctctt tgacgagctt | 1680 |
| aggcttcccg ccctgggcaa gacgcaaaag acggggaagc gctccaccag cgccgcggtg | 1740 |
| ctggaggccc tcagggaggc caccccatc gtggagaaga tcctccagca ccgggagctc | 1800 |
| accaagctca agaacaccta cgtggacccc ctcccgggcc tcgtccaccc gaggacgggc | 1860 |
| cgcctccaca cccgcttcaa ccagacagcc acggccacgg gaaggctctc tagctccgac | 1920 |
| cccaacctgc agaacatccc catccgcacc cccttgggcc agaggatccg ccgggccttc | 1980 |

```
gtggccgagg cgggatgggc gttggtggcc ctggactata gccagataga gctccgggtc    2040
ctcgcccacc tctccgggga cgagaacctg atcagggtct tccaggaggg gaaggacatc    2100
cacacccaga ccgcaagctg gatgttcggc gtctccccgg aggccgtgga ccccctgatg    2160
cgccgggcgg ccaagacggt gaacttcggc gtcctctacg gcatgtccgc ccataggctc    2220
tcccaggagc ttgccatccc ctacgaggag gcggtggcct ttatagagcg ctacttccaa    2280
agcttcccca aggtgcgggc ctggatagaa aagaccctgg aggaggggag gaagcggggc    2340
tacgtggaaa ccctcttcgg aagaaggcgc tacgtgcccg acctcaacgc ccgggtgaag    2400
agcgtcaggg aggccgcgga gcgcatggcc ttcaacatgc ccgtccaggg caccgccgcc    2460
gacctcatga agctcgccat ggtgaagctc ttcccccacc tccgggagat ggggccccgc    2520
atgctcctcc aggtccacga cgagctcctc ctggaggccc ccaagcgcgg ggccgaggag    2580
gtggcggctt tggccaagga ggccatggag aaggcctatc ccctcgccgt gccccctggag   2640 gtggaggtgg ggatcgggga ggactggctt tccgccaagg gctga                    2685
```

<210> SEQ ID NO 148
<211> LENGTH: 894
<212> TYPE: PRT
<213> ORGANISM: Artificial sequence
<220> FEATURE:
<223> OTHER INFORMATION: thermostable chimeric DNA polymerase CS8

<400> SEQUENCE: 148

```
Met Lys Ala Met Leu Pro Leu Phe Glu Pro Lys Gly Arg Val Leu Leu
1               5                   10                  15

Val Asp Gly His His Leu Ala Tyr Arg Thr Phe Phe Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Tyr Lys Ala Val Phe
    50                  55                  60

Val Val Phe Asp Ala Lys Ala Pro Ser Phe Arg His Glu Ala Tyr Glu
65                  70                  75                  80

Ala Tyr Lys Ala Gly Arg Ala Pro Thr Pro Glu Asp Phe Pro Arg Gln
                85                  90                  95

Leu Ala Leu Ile Lys Glu Leu Val Asp Leu Leu Gly Phe Thr Arg Leu
            100                 105                 110

Glu Val Pro Gly Phe Glu Ala Asp Asp Val Leu Ala Thr Leu Ala Lys
        115                 120                 125

Lys Ala Glu Arg Glu Gly Tyr Glu Val Arg Ile Leu Thr Ala Asp Arg
    130                 135                 140

Asp Leu Tyr Gln Leu Val Ser Asp Arg Val Ala Val Leu His Pro Glu
145                 150                 155                 160

Gly His Leu Ile Thr Pro Glu Trp Leu Trp Glu Lys Tyr Gly Leu Lys
                165                 170                 175

Pro Glu Gln Trp Val Asp Phe Arg Ala Leu Val Gly Asp Pro Ser Asp
            180                 185                 190

Asn Leu Pro Gly Val Lys Gly Ile Gly Glu Lys Thr Ala Leu Lys Leu
        195                 200                 205

Leu Lys Glu Trp Gly Ser Leu Glu Asn Ile Leu Lys Asn Leu Asp Arg
    210                 215                 220

Val Lys Pro Glu Ser Val Arg Glu Arg Ile Lys Ala His Leu Glu Asp
225                 230                 235                 240
```

-continued

```
Leu Lys Leu Ser Leu Glu Leu Ser Arg Val Arg Ser Asp Leu Pro Leu
            245                 250                 255
Glu Val Asp Phe Ala Arg Arg Glu Pro Asp Arg Glu Gly Leu Arg
        260                 265                 270
Ala Phe Leu Glu Arg Leu Glu Phe Gly Ser Leu Leu His Glu Phe Gly
        275                 280                 285
Leu Leu Glu Glu Ser Glu Pro Val Gly Tyr Arg Ile Val Lys Asp Leu
    290                 295                 300
Val Glu Phe Glu Lys Leu Ile Glu Lys Leu Arg Glu Ser Pro Ser Phe
305                 310                 315                 320
Ala Ile Ala Leu Ala Thr Ser Ser Leu Asp Pro Phe Asp Cys Asp Ile
                325                 330                 335
Val Gly Ile Ser Val Ser Phe Lys Pro Lys Glu Ala Tyr Tyr Ile Pro
            340                 345                 350
Leu His His Arg Asn Ala Gln Asn Leu Asp Glu Lys Glu Val Leu Lys
        355                 360                 365
Lys Leu Lys Glu Ile Leu Glu Asp Pro Gly Ala Lys Ile Val Gly Gln
    370                 375                 380
Asn Leu Lys Phe Asp Tyr Lys Val Leu Met Val Lys Gly Val Glu Pro
385                 390                 395                 400
Val Pro Pro Tyr Phe Asp Thr Met Ile Ala Ala Tyr Leu Leu Glu Pro
                405                 410                 415
Asn Glu Lys Lys Phe Asn Leu Asp Asp Leu Ala Leu Lys Phe Leu Gly
            420                 425                 430
Tyr Lys Met Thr Ser Tyr Gln Glu Leu Met Ser Phe Ser Phe Pro Leu
        435                 440                 445
Phe Gly Phe Ser Phe Ala Asp Val Pro Val Glu Lys Ala Ala Asn Tyr
    450                 455                 460
Ser Cys Glu Asp Ala Asp Ile Thr Tyr Arg Leu Tyr Lys Thr Leu Ser
465                 470                 475                 480
Leu Lys Leu His Glu Glu Lys Leu Leu Trp Leu Tyr Gln Glu Val Glu
                485                 490                 495
Lys Pro Leu Ser Arg Val Leu Ala His Met Glu Ala Thr Gly Val Arg
            500                 505                 510
Leu Asp Val Ala Tyr Leu Lys Ala Leu Ser Leu Glu Leu Ala Glu Glu
        515                 520                 525
Ile Arg Arg Leu Glu Glu Glu Val Phe Arg Leu Ala Gly His Pro Phe
    530                 535                 540
Asn Leu Asn Ser Arg Asp Gln Leu Glu Arg Val Leu Phe Asp Glu Leu
545                 550                 555                 560
Arg Leu Pro Ala Leu Gly Lys Thr Gln Lys Thr Gly Lys Arg Ser Thr
                565                 570                 575
Ser Ala Ala Val Leu Glu Ala Leu Arg Glu Ala His Pro Ile Val Glu
            580                 585                 590
Lys Ile Leu Gln His Arg Glu Leu Thr Lys Leu Lys Asn Thr Tyr Val
        595                 600                 605
Asp Pro Leu Pro Gly Leu Val His Pro Arg Thr Gly Arg Leu His Thr
    610                 615                 620
Arg Phe Asn Gln Thr Ala Thr Ala Thr Gly Arg Leu Ser Ser Ser Asp
625                 630                 635                 640
Pro Asn Leu Gln Asn Ile Pro Ile Arg Thr Pro Leu Gly Gln Arg Ile
                645                 650                 655
```

```
Arg Arg Ala Phe Val Ala Glu Ala Gly Trp Ala Leu Val Ala Leu Asp
            660                 665                 670

Tyr Ser Gln Ile Glu Leu Arg Val Leu Ala His Leu Ser Gly Asp Glu
        675                 680                 685

Asn Leu Ile Arg Val Phe Gln Glu Gly Lys Asp Ile His Thr Gln Thr
    690                 695                 700

Ala Ser Trp Met Phe Gly Val Ser Pro Glu Ala Val Asp Pro Leu Met
705                 710                 715                 720

Arg Arg Ala Ala Lys Thr Val Asn Phe Gly Val Leu Tyr Gly Met Ser
                725                 730                 735

Ala His Arg Leu Ser Gln Glu Leu Ala Ile Pro Tyr Glu Glu Ala Val
            740                 745                 750

Ala Phe Ile Glu Arg Tyr Phe Gln Ser Phe Pro Lys Val Arg Ala Trp
        755                 760                 765

Ile Glu Lys Thr Leu Glu Glu Gly Arg Lys Arg Gly Tyr Val Glu Thr
    770                 775                 780

Leu Phe Gly Arg Arg Arg Tyr Val Pro Asp Leu Asn Ala Arg Val Lys
785                 790                 795                 800

Ser Val Arg Glu Ala Ala Glu Arg Met Ala Phe Asn Met Pro Val Gln
                805                 810                 815

Gly Thr Ala Ala Asp Leu Met Lys Leu Ala Met Val Lys Leu Phe Pro
            820                 825                 830

His Leu Arg Glu Met Gly Ala Arg Met Leu Leu Gln Val His Asp Glu
        835                 840                 845

Leu Leu Leu Glu Ala Pro Gln Ala Arg Ala Glu Glu Val Ala Ala Leu
    850                 855                 860

Ala Lys Glu Ala Met Glu Lys Ala Tyr Pro Leu Ala Val Pro Leu Glu
865                 870                 875                 880

Val Glu Val Gly Ile Gly Glu Asp Trp Leu Ser Ala Lys Gly
                885                 890

<210> SEQ ID NO 149
<211> LENGTH: 197
<212> TYPE: PRT
<213> ORGANISM: Artificial sequence
<220> FEATURE:
<223> OTHER INFORMATION: 3'-5' exonuclease domain of chimeric
      thermostable DNA polymerase CS8

<400> SEQUENCE: 149

Glu Glu Ser Glu Pro Val Gly Tyr Arg Ile Val Lys Asp Leu Val Glu
1               5                   10                  15

Phe Glu Lys Leu Ile Glu Lys Leu Arg Glu Ser Pro Ser Phe Ala Ile
            20                  25                  30

Ala Leu Ala Thr Ser Ser Leu Asp Pro Phe Asp Cys Asp Ile Val Gly
        35                  40                  45

Ile Ser Val Ser Phe Lys Pro Lys Glu Ala Tyr Tyr Ile Pro Leu His
    50                  55                  60

His Arg Asn Ala Gln Asn Leu Asp Glu Lys Glu Val Leu Lys Lys Leu
65                  70                  75                  80

Lys Glu Ile Leu Glu Asp Pro Gly Ala Lys Ile Val Gly Gln Asn Leu
                85                  90                  95

Lys Phe Asp Tyr Lys Val Leu Met Val Lys Gly Val Glu Pro Val Pro
            100                 105                 110

Pro Tyr Phe Asp Thr Met Ile Ala Ala Tyr Leu Leu Glu Pro Asn Glu
        115                 120                 125
```

-continued

```
Lys Lys Phe Asn Leu Asp Asp Leu Ala Leu Lys Phe Leu Gly Tyr Lys
    130                 135                 140

Met Thr Ser Tyr Gln Glu Leu Met Ser Phe Ser Phe Pro Leu Phe Gly
145                 150                 155                 160

Phe Ser Phe Ala Asp Val Pro Val Glu Lys Ala Ala Asn Tyr Ser Cys
                165                 170                 175

Glu Asp Ala Asp Ile Thr Tyr Arg Leu Tyr Lys Thr Leu Ser Leu Lys
                180                 185                 190

Leu His Glu Glu Lys
        195

<210> SEQ ID NO 150
<211> LENGTH: 291
<212> TYPE: PRT
<213> ORGANISM: Artificial sequence
<220> FEATURE:
<223> OTHER INFORMATION: Residues 1-291 of thermostable chimeric DNA
      polymerase CS8 Sequence derived from Z05 DNA polymerase

<400> SEQUENCE: 150

Met Lys Ala Met Leu Pro Leu Phe Glu Pro Lys Gly Arg Val Leu Leu
1               5                   10                  15

Val Asp Gly His His Leu Ala Tyr Arg Thr Phe Phe Ala Leu Lys Gly
                20                  25                  30

Leu Thr Thr Ser Arg Gly Glu Pro Val Gln Ala Val Tyr Gly Phe Ala
            35                  40                  45

Lys Ser Leu Leu Lys Ala Leu Lys Glu Asp Gly Tyr Lys Ala Val Phe
    50                  55                  60

Val Val Phe Asp Ala Lys Ala Pro Ser Phe Arg His Glu Ala Tyr Glu
65                  70                  75                  80

Ala Tyr Lys Ala Gly Arg Ala Pro Thr Pro Glu Asp Phe Pro Arg Gln
                85                  90                  95

Leu Ala Leu Ile Lys Glu Leu Val Asp Leu Leu Gly Phe Thr Arg Leu
            100                 105                 110

Glu Val Pro Gly Phe Glu Ala Asp Asp Val Leu Ala Thr Leu Ala Lys
        115                 120                 125

Lys Ala Glu Arg Glu Gly Tyr Glu Val Arg Ile Leu Thr Ala Asp Arg
    130                 135                 140

Asp Leu Tyr Gln Leu Val Ser Asp Arg Val Ala Val Leu His Pro Glu
145                 150                 155                 160

Gly His Leu Ile Thr Pro Glu Trp Leu Trp Glu Lys Tyr Gly Leu Lys
                165                 170                 175

Pro Glu Gln Trp Val Asp Phe Arg Ala Leu Val Gly Asp Pro Ser Asp
            180                 185                 190

Asn Leu Pro Gly Val Lys Gly Ile Gly Glu Lys Thr Ala Leu Lys Leu
        195                 200                 205

Leu Lys Glu Trp Gly Ser Leu Glu Asn Ile Leu Lys Asn Leu Asp Arg
    210                 215                 220

Val Lys Pro Glu Ser Val Arg Glu Arg Ile Lys Ala His Leu Glu Asp
225                 230                 235                 240

Leu Lys Leu Ser Leu Glu Leu Ser Arg Val Arg Ser Asp Leu Pro Leu
                245                 250                 255

Glu Val Asp Phe Ala Arg Arg Glu Pro Asp Arg Glu Gly Leu Arg
            260                 265                 270

Ala Phe Leu Glu Arg Leu Glu Phe Gly Ser Leu Leu His Glu Phe Gly
```

```
              275                 280                 285
Leu Leu Glu
    290

<210> SEQ ID NO 151
<211> LENGTH: 409
<212> TYPE: PRT
<213> ORGANISM: Artificial sequence
<220> FEATURE:
<223> OTHER INFORMATION: Residues 485-894 of thermostable chimeric DNA
      polymerase CS8 Sequence derived from Z05 DNA polymerase

<400> SEQUENCE: 151

Glu Lys Leu Leu Trp Leu Tyr Gln Glu Val Glu Lys Pro Leu Ser Arg
1               5                   10                  15

Val Leu Ala His Met Glu Ala Thr Gly Val Arg Leu Asp Val Ala Tyr
            20                  25                  30

Leu Lys Ala Leu Ser Leu Glu Leu Ala Glu Glu Ile Arg Arg Leu Glu
        35                  40                  45

Glu Glu Val Phe Arg Leu Ala Gly His Pro Phe Asn Leu Asn Ser Arg
    50                  55                  60

Asp Gln Leu Glu Arg Val Leu Phe Asp Glu Leu Arg Leu Pro Ala Leu
65                  70                  75                  80

Gly Lys Thr Gln Lys Thr Gly Lys Arg Ser Thr Ser Ala Ala Val Leu
                85                  90                  95

Glu Ala Leu Arg Glu Ala His Pro Ile Val Glu Lys Ile Leu Gln His
            100                 105                 110

Arg Glu Leu Thr Lys Leu Lys Asn Thr Tyr Val Asp Pro Leu Pro Gly
        115                 120                 125

Leu Val His Pro Arg Thr Gly Arg Leu His Thr Arg Phe Asn Gln Thr
    130                 135                 140

Ala Thr Ala Thr Gly Arg Leu Ser Ser Ser Asp Pro Asn Leu Gln Asn
145                 150                 155                 160

Ile Pro Ile Arg Thr Pro Leu Gly Gln Arg Ile Arg Arg Ala Phe Val
                165                 170                 175

Ala Glu Ala Gly Trp Ala Leu Val Ala Leu Asp Tyr Ser Gln Ile Glu
            180                 185                 190

Leu Arg Val Leu Ala His Leu Ser Gly Asp Glu Asn Leu Ile Arg Val
        195                 200                 205

Phe Gln Glu Gly Lys Asp Ile His Thr Gln Thr Ala Ser Trp Met Phe
    210                 215                 220

Gly Val Ser Pro Glu Ala Val Asp Pro Leu Met Arg Arg Ala Ala Lys
225                 230                 235                 240

Thr Val Asn Phe Gly Val Leu Tyr Gly Met Ser Ala His Arg Leu Ser
                245                 250                 255

Gln Glu Leu Ala Ile Pro Tyr Glu Glu Ala Val Ala Phe Ile Glu Arg
            260                 265                 270

Tyr Phe Gln Ser Phe Pro Lys Val Arg Ala Trp Ile Glu Lys Thr Leu
        275                 280                 285

Glu Glu Gly Arg Lys Arg Gly Tyr Val Glu Thr Leu Phe Gly Arg Arg
    290                 295                 300

Arg Tyr Val Pro Asp Leu Asn Ala Arg Val Lys Ser Val Arg Glu Ala
305                 310                 315                 320

Ala Glu Arg Met Ala Phe Asn Met Pro Val Gln Gly Thr Ala Ala Asp
                325                 330                 335
```

```
Leu Met Lys Leu Ala Met Val Lys Leu Phe Pro His Leu Arg Glu Met
            340                 345                 350

Gly Ala Arg Met Leu Leu Gln Val His Asp Glu Leu Leu Leu Glu Ala
            355                 360                 365

Pro Gln Ala Arg Ala Glu Val Ala Ala Leu Ala Lys Glu Ala Met
            370                 375                 380

Glu Lys Ala Tyr Pro Leu Ala Val Pro Leu Glu Val Glu Val Gly Ile
385                 390                 395                 400

Gly Glu Asp Trp Leu Ser Ala Lys Gly
            405

<210> SEQ ID NO 152
<211> LENGTH: 193
<212> TYPE: PRT
<213> ORGANISM: Artificial sequence
<220> FEATURE:
<223> OTHER INFORMATION: Residues 292-484 of thermostable chimeric DNA
      polymerase CS8 Sequence derived from Tma DNA polymerase

<400> SEQUENCE: 152

Glu Ser Glu Pro Val Gly Tyr Arg Ile Val Lys Asp Leu Val Glu Phe
1               5                   10                  15

Glu Lys Leu Ile Glu Lys Leu Arg Glu Ser Pro Ser Phe Ala Ile Ala
            20                  25                  30

Leu Ala Thr Ser Ser Leu Asp Pro Phe Asp Cys Asp Ile Val Gly Ile
            35                  40                  45

Ser Val Ser Phe Lys Pro Lys Glu Ala Tyr Tyr Ile Pro Leu His His
50                  55                  60

Arg Asn Ala Gln Asn Leu Asp Glu Lys Glu Val Leu Lys Lys Leu Lys
65                  70                  75                  80

Glu Ile Leu Glu Asp Pro Gly Ala Lys Ile Val Gly Gln Asn Leu Lys
            85                  90                  95

Phe Asp Tyr Lys Val Leu Met Val Lys Gly Val Glu Pro Val Pro Pro
            100                 105                 110

Tyr Phe Asp Thr Met Ile Ala Ala Tyr Leu Leu Glu Pro Asn Glu Lys
            115                 120                 125

Lys Phe Asn Leu Asp Asp Leu Ala Leu Lys Phe Leu Gly Tyr Lys Met
            130                 135                 140

Thr Ser Tyr Gln Glu Leu Met Ser Phe Ser Phe Pro Leu Phe Gly Phe
145                 150                 155                 160

Ser Phe Ala Asp Val Pro Val Glu Lys Ala Ala Asn Tyr Ser Cys Glu
            165                 170                 175

Asp Ala Asp Ile Thr Tyr Arg Leu Tyr Lys Thr Leu Ser Leu Lys Leu
            180                 185                 190

His

<210> SEQ ID NO 153
<211> LENGTH: 197
<212> TYPE: PRT
<213> ORGANISM: Artificial sequence
<220> FEATURE:
<223> OTHER INFORMATION: Exonucleolytic domain of chimeric DNA
      polymerase CS8 after second round of mutagenesis residues
      323-325 DEE substitution

<400> SEQUENCE: 153

Glu Glu Ser Glu Pro Val Gly Tyr Arg Ile Val Lys Asp Leu Val Glu
1               5                   10                  15
```

```
Phe Glu Lys Leu Ile Glu Lys Leu Arg Glu Ser Pro Ser Phe Ala Ile
            20                  25                  30

Asp Glu Glu Thr Ser Ser Leu Asp Pro Phe Asp Cys Asp Ile Val Gly
        35                  40                  45

Ile Ser Val Ser Phe Lys Pro Lys Glu Ala Tyr Tyr Ile Pro Leu His
    50                  55                  60

His Arg Asn Ala Gln Asn Leu Asp Glu Lys Glu Val Leu Lys Lys Leu
65                  70                  75                  80

Lys Glu Ile Leu Glu Asp Pro Gly Ala Lys Ile Val Gly Gln Asn Leu
                85                  90                  95

Lys Phe Asp Tyr Lys Val Leu Met Val Lys Gly Val Glu Pro Val Pro
            100                 105                 110

Pro Tyr Phe Asp Thr Met Ile Ala Ala Tyr Leu Leu Glu Pro Asn Glu
        115                 120                 125

Lys Lys Phe Asn Leu Asp Asp Leu Ala Leu Lys Phe Leu Gly Tyr Lys
    130                 135                 140

Met Thr Ser Tyr Gln Glu Leu Met Ser Phe Ser Pro Leu Phe Gly
145                 150                 155                 160

Phe Ser Phe Ala Asp Val Pro Val Glu Lys Ala Ala Asn Tyr Ser Cys
            165                 170                 175

Glu Asp Ala Asp Ile Thr Tyr Arg Leu Tyr Lys Thr Leu Ser Leu Lys
        180                 185                 190

Leu His Glu Glu Lys
        195

<210> SEQ ID NO 154
<211> LENGTH: 894
<212> TYPE: PRT
<213> ORGANISM: Artificial sequence
<220> FEATURE:
<223> OTHER INFORMATION: chimeric DNA polymerase CS8 after second round
      of mutagenesis residues 323-325 DEE substitution

<400> SEQUENCE: 154

Met Lys Ala Met Leu Pro Leu Phe Glu Pro Lys Gly Arg Val Leu Leu
1               5                   10                  15

Val Asp Gly His His Leu Ala Tyr Arg Thr Phe Phe Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Tyr Lys Ala Val Phe
    50                  55                  60

Val Val Phe Asp Ala Lys Ala Pro Ser Phe Arg His Glu Ala Tyr Glu
65                  70                  75                  80

Ala Tyr Lys Ala Gly Arg Ala Pro Thr Pro Glu Asp Phe Pro Arg Gln
                85                  90                  95

Leu Ala Leu Ile Lys Glu Leu Val Asp Leu Leu Gly Phe Thr Arg Leu
            100                 105                 110

Glu Val Pro Gly Phe Glu Ala Asp Asp Val Leu Ala Thr Leu Ala Lys
        115                 120                 125

Lys Ala Glu Arg Glu Gly Tyr Glu Val Arg Ile Leu Thr Ala Asp Arg
    130                 135                 140

Asp Leu Tyr Gln Leu Val Ser Asp Arg Val Ala Val Leu His Pro Glu
145                 150                 155                 160

Gly His Leu Ile Thr Pro Glu Trp Leu Trp Glu Lys Tyr Gly Leu Lys
                165                 170                 175
```

```
Pro Glu Gln Trp Val Asp Phe Arg Ala Leu Val Gly Asp Pro Ser Asp
            180                 185                 190

Asn Leu Pro Gly Val Lys Gly Ile Gly Glu Lys Thr Ala Leu Lys Leu
            195                 200                 205

Leu Lys Glu Trp Gly Ser Leu Glu Asn Ile Leu Lys Asn Leu Asp Arg
            210                 215                 220

Val Lys Pro Glu Ser Val Arg Glu Arg Ile Lys Ala His Leu Glu Asp
225                 230                 235                 240

Leu Lys Leu Ser Leu Glu Leu Ser Arg Val Arg Ser Asp Leu Pro Leu
                245                 250                 255

Glu Val Asp Phe Ala Arg Arg Arg Glu Pro Asp Arg Glu Gly Leu Arg
            260                 265                 270

Ala Phe Leu Glu Arg Leu Glu Phe Gly Ser Leu Leu His Glu Phe Gly
            275                 280                 285

Leu Leu Glu Glu Ser Glu Pro Val Gly Tyr Arg Ile Val Lys Asp Leu
            290                 295                 300

Val Glu Phe Glu Lys Leu Ile Glu Lys Leu Arg Glu Ser Pro Ser Phe
305                 310                 315                 320

Ala Ile Asp Glu Glu Thr Ser Ser Leu Asp Pro Phe Asp Cys Asp Ile
                325                 330                 335

Val Gly Ile Ser Val Ser Phe Lys Pro Lys Glu Ala Tyr Tyr Ile Pro
            340                 345                 350

Leu His His Arg Asn Ala Gln Asn Leu Asp Glu Lys Glu Val Leu Lys
            355                 360                 365

Lys Leu Lys Glu Ile Leu Glu Asp Pro Gly Ala Lys Ile Val Gly Gln
            370                 375                 380

Asn Leu Lys Phe Asp Tyr Lys Val Leu Met Val Lys Gly Val Glu Pro
385                 390                 395                 400

Val Pro Pro Tyr Phe Asp Thr Met Ile Ala Ala Tyr Leu Leu Glu Pro
                405                 410                 415

Asn Glu Lys Lys Phe Asn Leu Asp Asp Leu Ala Leu Lys Phe Leu Gly
            420                 425                 430

Tyr Lys Met Thr Ser Tyr Gln Glu Leu Met Ser Phe Ser Phe Pro Leu
            435                 440                 445

Phe Gly Phe Ser Phe Ala Asp Val Pro Val Glu Lys Ala Ala Asn Tyr
            450                 455                 460

Ser Cys Glu Asp Ala Asp Ile Thr Tyr Arg Leu Tyr Lys Thr Leu Ser
465                 470                 475                 480

Leu Lys Leu His Glu Glu Lys Leu Leu Trp Leu Tyr Gln Glu Val Glu
                485                 490                 495

Lys Pro Leu Ser Arg Val Leu Ala His Met Glu Ala Thr Gly Val Arg
            500                 505                 510

Leu Asp Val Ala Tyr Leu Lys Ala Leu Ser Leu Glu Leu Ala Glu Glu
            515                 520                 525

Ile Arg Arg Leu Glu Glu Glu Val Phe Arg Leu Ala Gly His Pro Phe
            530                 535                 540

Asn Leu Asn Ser Arg Asp Gln Leu Glu Arg Val Leu Phe Asp Glu Leu
545                 550                 555                 560

Arg Leu Pro Ala Leu Gly Lys Thr Gln Lys Thr Gly Lys Arg Ser Thr
                565                 570                 575

Ser Ala Ala Val Leu Glu Ala Leu Arg Glu Ala His Pro Ile Val Glu
            580                 585                 590
```

Lys Ile Leu Gln His Arg Glu Leu Thr Lys Leu Lys Asn Thr Tyr Val
            595                 600                 605

Asp Pro Leu Pro Gly Leu Val His Pro Arg Thr Gly Arg Leu His Thr
        610                 615                 620

Arg Phe Asn Gln Thr Ala Thr Ala Thr Gly Arg Leu Ser Ser Ser Asp
625                 630                 635                 640

Pro Asn Leu Gln Asn Ile Pro Ile Arg Thr Pro Leu Gly Gln Arg Ile
                645                 650                 655

Arg Arg Ala Phe Val Ala Glu Ala Gly Trp Ala Leu Val Ala Leu Asp
            660                 665                 670

Tyr Ser Gln Ile Glu Leu Arg Val Leu Ala His Leu Ser Gly Asp Glu
        675                 680                 685

Asn Leu Ile Arg Val Phe Gln Glu Gly Lys Asp Ile His Thr Gln Thr
    690                 695                 700

Ala Ser Trp Met Phe Gly Val Ser Pro Glu Ala Val Asp Pro Leu Met
705                 710                 715                 720

Arg Arg Ala Ala Lys Thr Val Asn Phe Gly Val Leu Tyr Gly Met Ser
                725                 730                 735

Ala His Arg Leu Ser Gln Glu Leu Ala Ile Pro Tyr Glu Glu Ala Val
            740                 745                 750

Ala Phe Ile Glu Arg Tyr Phe Gln Ser Phe Pro Lys Val Arg Ala Trp
        755                 760                 765

Ile Glu Lys Thr Leu Glu Glu Gly Arg Lys Arg Gly Tyr Val Glu Thr
    770                 775                 780

Leu Phe Gly Arg Arg Arg Tyr Val Pro Asp Leu Asn Ala Arg Val Lys
785                 790                 795                 800

Ser Val Arg Glu Ala Ala Glu Arg Met Ala Phe Asn Met Pro Val Gln
                805                 810                 815

Gly Thr Ala Ala Asp Leu Met Lys Leu Ala Met Val Lys Leu Phe Pro
            820                 825                 830

His Leu Arg Glu Met Gly Ala Arg Met Leu Leu Gln Val His Asp Glu
        835                 840                 845

Leu Leu Leu Glu Ala Pro Gln Ala Arg Ala Glu Val Ala Ala Leu
    850                 855                 860

Ala Lys Glu Ala Met Glu Lys Ala Tyr Pro Leu Ala Val Pro Leu Glu
865                 870                 875                 880

Val Glu Val Gly Ile Gly Glu Asp Trp Leu Ser Ala Lys Gly
                885                 890

<210> SEQ ID NO 155
<211> LENGTH: 197
<212> TYPE: PRT
<213> ORGANISM: Artificial sequence
<220> FEATURE:
<223> OTHER INFORMATION: Exonucleolytic domain of chimeric DNA
      polymerase CS8 after second round of mutagenesis residues 323-325
      DDE substitution

<400> SEQUENCE: 155

Glu Glu Ser Glu Pro Val Gly Tyr Arg Ile Val Lys Asp Leu Val Glu
1               5                   10                  15

Phe Glu Lys Leu Ile Glu Lys Leu Arg Glu Ser Pro Ser Phe Ala Ile
                20                  25                  30

Asp Asp Glu Thr Ser Ser Leu Asp Pro Phe Asp Cys Asp Ile Val Gly
            35                  40                  45

Ile Ser Val Ser Phe Lys Pro Lys Glu Ala Tyr Tyr Ile Pro Leu His

```
                50              55              60
His Arg Asn Ala Gln Asn Leu Asp Glu Lys Glu Val Leu Lys Lys Leu
 65                  70                  75                  80

Lys Glu Ile Leu Glu Asp Pro Gly Ala Lys Ile Val Gly Gln Asn Leu
                 85                  90                  95

Lys Phe Asp Tyr Lys Val Leu Met Val Lys Gly Val Glu Pro Val Pro
                100                 105                 110

Pro Tyr Phe Asp Thr Met Ile Ala Ala Tyr Leu Leu Glu Pro Asn Glu
                115                 120                 125

Lys Lys Phe Asn Leu Asp Asp Leu Ala Leu Lys Phe Leu Gly Tyr Lys
130                 135                 140

Met Thr Ser Tyr Gln Glu Leu Met Ser Phe Ser Phe Pro Leu Phe Gly
145                 150                 155                 160

Phe Ser Phe Ala Asp Val Pro Val Glu Lys Ala Ala Asn Tyr Ser Cys
                165                 170                 175

Glu Asp Ala Asp Ile Thr Tyr Arg Leu Tyr Lys Thr Leu Ser Leu Lys
                180                 185                 190

Leu His Glu Glu Lys
            195

<210> SEQ ID NO 156
<211> LENGTH: 894
<212> TYPE: PRT
<213> ORGANISM: Artificial sequence
<220> FEATURE:
<223> OTHER INFORMATION: chimeric DNA polymerase CS8 after second round
      of mutagenesis residues 323-325 DDE substitution

<400> SEQUENCE: 156

Met Lys Ala Met Leu Pro Leu Phe Glu Pro Lys Gly Arg Val Leu Leu
 1               5                  10                  15

Val Asp Gly His His Leu Ala Tyr Arg Thr Phe Phe Ala Leu Lys Gly
                 20                  25                  30

Leu Thr Thr Ser Arg Gly Glu Pro Val Gln Ala Val Tyr Gly Phe Ala
             35                  40                  45

Lys Ser Leu Leu Lys Ala Leu Lys Glu Asp Gly Tyr Lys Ala Val Phe
 50                  55                  60

Val Val Phe Asp Ala Lys Ala Pro Ser Phe Arg His Glu Ala Tyr Glu
 65                  70                  75                  80

Ala Tyr Lys Ala Gly Arg Ala Pro Thr Pro Glu Asp Phe Pro Arg Gln
                 85                  90                  95

Leu Ala Leu Ile Lys Glu Leu Val Asp Leu Leu Gly Phe Thr Arg Leu
                100                 105                 110

Glu Val Pro Gly Phe Glu Ala Asp Asp Val Leu Ala Thr Leu Ala Lys
                115                 120                 125

Lys Ala Glu Arg Glu Gly Tyr Glu Val Arg Ile Leu Thr Ala Asp Arg
130                 135                 140

Asp Leu Tyr Gln Leu Val Ser Asp Arg Val Ala Val Leu His Pro Glu
145                 150                 155                 160

Gly His Leu Ile Thr Pro Glu Trp Leu Trp Glu Lys Tyr Gly Leu Lys
                165                 170                 175

Pro Glu Gln Trp Val Asp Phe Arg Ala Leu Val Gly Asp Pro Ser Asp
                180                 185                 190

Asn Leu Pro Gly Val Lys Gly Ile Gly Glu Lys Thr Ala Leu Lys Leu
                195                 200                 205
```

```
Leu Lys Glu Trp Gly Ser Leu Glu Asn Ile Leu Lys Asn Leu Asp Arg
    210                 215                 220

Val Lys Pro Glu Ser Val Arg Glu Arg Ile Lys Ala His Leu Glu Asp
225                 230                 235                 240

Leu Lys Leu Ser Leu Glu Leu Ser Arg Val Arg Ser Asp Leu Pro Leu
                245                 250                 255

Glu Val Asp Phe Ala Arg Arg Arg Glu Pro Asp Arg Glu Gly Leu Arg
            260                 265                 270

Ala Phe Leu Glu Arg Leu Glu Phe Gly Ser Leu Leu His Glu Phe Gly
        275                 280                 285

Leu Leu Glu Glu Ser Glu Pro Val Gly Tyr Arg Ile Val Lys Asp Leu
    290                 295                 300

Val Glu Phe Glu Lys Leu Ile Glu Lys Leu Arg Glu Ser Pro Ser Phe
305                 310                 315                 320

Ala Ile Asp Asp Glu Thr Ser Ser Leu Asp Pro Phe Asp Cys Asp Ile
                325                 330                 335

Val Gly Ile Ser Val Ser Phe Lys Pro Lys Glu Ala Tyr Tyr Ile Pro
            340                 345                 350

Leu His His Arg Asn Ala Gln Asn Leu Asp Glu Lys Glu Val Leu Lys
        355                 360                 365

Lys Leu Lys Glu Ile Leu Glu Asp Pro Gly Ala Lys Ile Val Gly Gln
    370                 375                 380

Asn Leu Lys Phe Asp Tyr Lys Val Leu Met Val Lys Gly Val Glu Pro
385                 390                 395                 400

Val Pro Pro Tyr Phe Asp Thr Met Ile Ala Ala Tyr Leu Leu Glu Pro
                405                 410                 415

Asn Glu Lys Lys Phe Asn Leu Asp Asp Leu Ala Leu Lys Phe Leu Gly
            420                 425                 430

Tyr Lys Met Thr Ser Tyr Gln Glu Leu Met Ser Phe Ser Phe Pro Leu
        435                 440                 445

Phe Gly Phe Ser Phe Ala Asp Val Pro Val Glu Lys Ala Ala Asn Tyr
    450                 455                 460

Ser Cys Glu Asp Ala Asp Ile Thr Tyr Arg Leu Tyr Lys Thr Leu Ser
465                 470                 475                 480

Leu Lys Leu His Glu Glu Lys Leu Leu Trp Leu Tyr Gln Glu Val Glu
                485                 490                 495

Lys Pro Leu Ser Arg Val Leu Ala His Met Glu Ala Thr Gly Val Arg
            500                 505                 510

Leu Asp Val Ala Tyr Leu Lys Ala Leu Ser Leu Glu Leu Ala Glu Glu
        515                 520                 525

Ile Arg Arg Leu Glu Glu Glu Val Phe Arg Leu Ala Gly His Pro Phe
    530                 535                 540

Asn Leu Asn Ser Arg Asp Gln Leu Glu Arg Val Leu Phe Asp Glu Leu
545                 550                 555                 560

Arg Leu Pro Ala Leu Gly Lys Thr Gln Lys Thr Gly Lys Arg Ser Thr
                565                 570                 575

Ser Ala Ala Val Leu Glu Ala Leu Arg Glu Ala His Pro Ile Val Glu
            580                 585                 590

Lys Ile Leu Gln His Arg Glu Leu Thr Lys Leu Lys Asn Thr Tyr Val
        595                 600                 605

Asp Pro Leu Pro Gly Leu Val His Pro Arg Thr Gly Arg Leu His Thr
    610                 615                 620

Arg Phe Asn Gln Thr Ala Thr Ala Thr Gly Arg Leu Ser Ser Ser Asp
```

```
               625                 630                 635                 640
Pro Asn Leu Gln Asn Ile Pro Ile Arg Thr Pro Leu Gly Gln Arg Ile
                    645                 650                 655
Arg Arg Ala Phe Val Ala Glu Ala Gly Trp Ala Leu Val Ala Leu Asp
                660                 665                 670
Tyr Ser Gln Ile Glu Leu Arg Val Leu Ala His Leu Ser Gly Asp Glu
            675                 680                 685
Asn Leu Ile Arg Val Phe Gln Glu Gly Lys Asp Ile His Thr Gln Thr
        690                 695                 700
Ala Ser Trp Met Phe Gly Val Ser Pro Glu Ala Val Asp Pro Leu Met
705                 710                 715                 720
Arg Arg Ala Ala Lys Thr Val Asn Phe Gly Val Leu Tyr Gly Met Ser
                725                 730                 735
Ala His Arg Leu Ser Gln Glu Leu Ala Ile Pro Tyr Glu Glu Ala Val
                740                 745                 750
Ala Phe Ile Glu Arg Tyr Phe Gln Ser Phe Pro Lys Val Arg Ala Trp
                755                 760                 765
Ile Glu Lys Thr Leu Glu Glu Gly Arg Lys Arg Gly Tyr Val Glu Thr
        770                 775                 780
Leu Phe Gly Arg Arg Tyr Val Pro Asp Leu Asn Ala Arg Val Lys
785                 790                 795                 800
Ser Val Arg Glu Ala Ala Glu Arg Met Ala Phe Asn Met Pro Val Gln
                805                 810                 815
Gly Thr Ala Ala Asp Leu Met Lys Leu Ala Met Val Lys Leu Phe Pro
                820                 825                 830
His Leu Arg Glu Met Gly Ala Arg Met Leu Leu Gln Val His Asp Glu
                835                 840                 845
Leu Leu Leu Glu Ala Pro Gln Ala Arg Ala Glu Val Ala Ala Leu
        850                 855                 860
Ala Lys Glu Ala Met Glu Lys Ala Tyr Pro Leu Ala Val Pro Leu Glu
865                 870                 875                 880
Val Glu Val Gly Ile Gly Glu Asp Trp Leu Ser Ala Lys Gly
                885                 890

<210> SEQ ID NO 157
<211> LENGTH: 197
<212> TYPE: PRT
<213> ORGANISM: Artificial sequence
<220> FEATURE:
<223> OTHER INFORMATION: Exonucleolytic domain of chimeric DNA
      polymerase CS8 after second round of mutagenesis residues 323-325
      DKE substitution

<400> SEQUENCE: 157

Glu Glu Ser Glu Pro Val Gly Tyr Arg Ile Val Lys Asp Leu Val Glu
1               5                   10                  15
Phe Glu Lys Leu Ile Glu Lys Leu Arg Glu Ser Pro Ser Phe Ala Ile
                20                  25                  30
Asp Lys Glu Thr Ser Ser Leu Asp Pro Phe Asp Cys Asp Ile Val Gly
            35                  40                  45
Ile Ser Val Ser Phe Lys Pro Lys Glu Ala Tyr Tyr Ile Pro Leu His
        50                  55                  60
His Arg Asn Ala Gln Asn Leu Asp Glu Lys Glu Val Leu Lys Lys Leu
65                  70                  75                  80
Lys Glu Ile Leu Glu Asp Pro Gly Ala Lys Ile Val Gly Gln Asn Leu
                85                  90                  95
```

-continued

```
Lys Phe Asp Tyr Lys Val Leu Met Val Lys Gly Val Glu Pro Val Pro
            100                 105                 110

Pro Tyr Phe Asp Thr Met Ile Ala Ala Tyr Leu Leu Glu Pro Asn Glu
        115                 120                 125

Lys Lys Phe Asn Leu Asp Asp Leu Ala Leu Lys Phe Leu Gly Tyr Lys
    130                 135                 140

Met Thr Ser Tyr Gln Glu Leu Met Ser Phe Ser Phe Pro Leu Phe Gly
145                 150                 155                 160

Phe Ser Phe Ala Asp Val Pro Val Lys Ala Ala Asn Tyr Ser Cys
                165                 170                 175

Glu Asp Ala Asp Ile Thr Tyr Arg Leu Tyr Lys Thr Leu Ser Leu Lys
                180                 185                 190

Leu His Glu Glu Lys
        195

<210> SEQ ID NO 158
<211> LENGTH: 894
<212> TYPE: PRT
<213> ORGANISM: Artificial sequence
<220> FEATURE:
<223> OTHER INFORMATION: chimeric DNA polymerase CS8 after second round
      of mutagenesis residues 323-325 DKE substitution

<400> SEQUENCE: 158

Met Lys Ala Met Leu Pro Leu Phe Glu Pro Lys Gly Arg Val Leu Leu
1               5                   10                  15

Val Asp Gly His His Leu Ala Tyr Arg Thr Phe Phe Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Tyr Lys Ala Val Phe
    50                  55                  60

Val Val Phe Asp Ala Lys Ala Pro Ser Phe Arg His Glu Ala Tyr Glu
65                  70                  75                  80

Ala Tyr Lys Ala Gly Arg Ala Pro Thr Pro Glu Asp Phe Pro Arg Gln
                85                  90                  95

Leu Ala Leu Ile Lys Glu Leu Val Asp Leu Leu Gly Phe Thr Arg Leu
            100                 105                 110

Glu Val Pro Gly Phe Glu Ala Asp Asp Val Leu Ala Thr Leu Ala Lys
        115                 120                 125

Lys Ala Glu Arg Glu Gly Tyr Glu Val Arg Ile Leu Thr Ala Asp Arg
    130                 135                 140

Asp Leu Tyr Gln Leu Val Ser Asp Arg Val Ala Val Leu His Pro Glu
145                 150                 155                 160

Gly His Leu Ile Thr Pro Glu Trp Leu Trp Glu Lys Tyr Gly Leu Lys
                165                 170                 175

Pro Glu Gln Trp Val Asp Phe Arg Ala Leu Val Gly Asp Pro Ser Asp
            180                 185                 190

Asn Leu Pro Gly Val Lys Gly Ile Gly Glu Lys Thr Ala Leu Lys Leu
        195                 200                 205

Leu Lys Glu Trp Gly Ser Leu Glu Asn Ile Leu Lys Asn Leu Asp Arg
    210                 215                 220

Val Lys Pro Glu Ser Val Arg Glu Arg Ile Lys Ala His Leu Glu Asp
225                 230                 235                 240

Leu Lys Leu Ser Leu Glu Leu Ser Arg Val Arg Ser Asp Leu Pro Leu
```

-continued

```
                245                 250                 255
Glu Val Asp Phe Ala Arg Arg Arg Glu Pro Asp Arg Glu Gly Leu Arg
            260                 265                 270

Ala Phe Leu Glu Arg Leu Glu Phe Gly Ser Leu Leu His Glu Phe Gly
            275                 280                 285

Leu Leu Glu Glu Ser Glu Pro Val Gly Tyr Arg Ile Val Lys Asp Leu
            290                 295                 300

Val Glu Phe Glu Lys Leu Ile Glu Lys Leu Arg Glu Ser Pro Ser Phe
305                 310                 315                 320

Ala Ile Asp Lys Glu Thr Ser Ser Leu Asp Pro Phe Asp Cys Asp Ile
            325                 330                 335

Val Gly Ile Ser Val Ser Phe Lys Pro Lys Glu Ala Tyr Tyr Ile Pro
            340                 345                 350

Leu His His Arg Asn Ala Gln Asn Leu Asp Glu Lys Glu Val Leu Lys
            355                 360                 365

Lys Leu Lys Glu Ile Leu Glu Asp Pro Gly Ala Lys Ile Val Gly Gln
            370                 375                 380

Asn Leu Lys Phe Asp Tyr Lys Val Leu Met Val Lys Gly Val Glu Pro
385                 390                 395                 400

Val Pro Pro Tyr Phe Asp Thr Met Ile Ala Ala Tyr Leu Leu Glu Pro
            405                 410                 415

Asn Glu Lys Lys Phe Asn Leu Asp Asp Leu Ala Leu Lys Phe Leu Gly
            420                 425                 430

Tyr Lys Met Thr Ser Tyr Gln Glu Leu Met Ser Phe Ser Phe Pro Leu
            435                 440                 445

Phe Gly Phe Ser Phe Ala Asp Val Pro Val Glu Lys Ala Ala Asn Tyr
            450                 455                 460

Ser Cys Glu Asp Ala Asp Ile Thr Tyr Arg Leu Tyr Lys Thr Leu Ser
465                 470                 475                 480

Leu Lys Leu His Glu Glu Lys Leu Leu Trp Leu Tyr Gln Glu Val Glu
            485                 490                 495

Lys Pro Leu Ser Arg Val Leu Ala His Met Glu Ala Thr Gly Val Arg
            500                 505                 510

Leu Asp Val Ala Tyr Leu Lys Ala Leu Ser Leu Glu Leu Ala Glu Glu
            515                 520                 525

Ile Arg Arg Leu Glu Glu Glu Val Phe Arg Leu Ala Gly His Pro Phe
            530                 535                 540

Asn Leu Asn Ser Arg Asp Gln Leu Glu Arg Val Leu Phe Asp Glu Leu
545                 550                 555                 560

Arg Leu Pro Ala Leu Gly Lys Thr Gln Lys Thr Gly Lys Arg Ser Thr
            565                 570                 575

Ser Ala Ala Val Leu Glu Ala Leu Arg Glu Ala His Pro Ile Val Glu
            580                 585                 590

Lys Ile Leu Gln His Arg Glu Leu Thr Lys Leu Lys Asn Thr Tyr Val
            595                 600                 605

Asp Pro Leu Pro Gly Leu Val His Pro Arg Thr Gly Arg Leu His Thr
            610                 615                 620

Arg Phe Asn Gln Thr Ala Thr Ala Thr Gly Arg Leu Ser Ser Ser Asp
625                 630                 635                 640

Pro Asn Leu Gln Asn Ile Pro Ile Arg Thr Pro Leu Gly Gln Arg Ile
            645                 650                 655

Arg Arg Ala Phe Val Ala Glu Ala Gly Trp Ala Leu Val Ala Leu Asp
            660                 665                 670
```

-continued

```
Tyr Ser Gln Ile Glu Leu Arg Val Leu Ala His Leu Ser Gly Asp Glu
            675                 680                 685
Asn Leu Ile Arg Val Phe Gln Glu Gly Lys Asp Ile His Thr Gln Thr
        690                 695                 700
Ala Ser Trp Met Phe Gly Val Ser Pro Glu Ala Val Asp Pro Leu Met
705                 710                 715                 720
Arg Arg Ala Ala Lys Thr Val Asn Phe Gly Val Leu Tyr Gly Met Ser
                725                 730                 735
Ala His Arg Leu Ser Gln Glu Leu Ala Ile Pro Tyr Glu Glu Ala Val
            740                 745                 750
Ala Phe Ile Glu Arg Tyr Phe Gln Ser Phe Pro Lys Val Arg Ala Trp
            755                 760                 765
Ile Glu Lys Thr Leu Glu Glu Gly Arg Lys Arg Gly Tyr Val Glu Thr
            770                 775                 780
Leu Phe Gly Arg Arg Tyr Val Pro Asp Leu Asn Ala Arg Val Lys
785                 790                 795                 800
Ser Val Arg Glu Ala Glu Arg Met Ala Phe Asn Met Pro Val Gln
                805                 810                 815
Gly Thr Ala Ala Asp Leu Met Lys Leu Ala Met Val Lys Leu Phe Pro
            820                 825                 830
His Leu Arg Glu Met Gly Ala Arg Met Leu Leu Gln Val His Asp Glu
            835                 840                 845
Leu Leu Leu Glu Ala Pro Gln Ala Arg Ala Glu Glu Val Ala Ala Leu
850                 855                 860
Ala Lys Glu Ala Met Glu Lys Ala Tyr Pro Leu Ala Val Pro Leu Glu
865                 870                 875                 880
Val Glu Val Gly Ile Gly Glu Asp Trp Leu Ser Ala Lys Gly
                885                 890

<210> SEQ ID NO 159
<211> LENGTH: 197
<212> TYPE: PRT
<213> ORGANISM: Artificial sequence
<220> FEATURE:
<223> OTHER INFORMATION: Exonucleolytic domain of chimeric DNA
      polymerase CS8 after second round of mutagenesis residues 323-325
      DNE substitution

<400> SEQUENCE: 159

Glu Glu Ser Glu Pro Val Gly Tyr Arg Ile Val Lys Asp Leu Val Glu
1               5                   10                  15
Phe Glu Lys Leu Ile Glu Lys Leu Arg Glu Ser Pro Ser Phe Ala Ile
            20                  25                  30
Asp Asn Glu Thr Ser Ser Leu Asp Pro Phe Asp Cys Asp Ile Val Gly
        35                  40                  45
Ile Ser Val Ser Phe Lys Pro Lys Glu Ala Tyr Tyr Ile Pro Leu His
    50                  55                  60
His Arg Asn Ala Gln Asn Leu Asp Glu Lys Glu Val Leu Lys Lys Leu
65                  70                  75                  80
Lys Glu Ile Leu Glu Asp Pro Gly Ala Lys Ile Val Gly Gln Asn Leu
                85                  90                  95
Lys Phe Asp Tyr Lys Val Leu Met Val Lys Gly Val Glu Pro Val Pro
            100                 105                 110
Pro Tyr Phe Asp Thr Met Ile Ala Ala Tyr Leu Leu Glu Pro Asn Glu
        115                 120                 125
```

```
Lys Lys Phe Asn Leu Asp Asp Leu Ala Leu Lys Phe Leu Gly Tyr Lys
    130                 135                 140

Met Thr Ser Tyr Gln Glu Leu Met Ser Phe Ser Phe Pro Leu Phe Gly
145                 150                 155                 160

Phe Ser Phe Ala Asp Val Pro Val Glu Lys Ala Ala Asn Tyr Ser Cys
                165                 170                 175

Glu Asp Ala Asp Ile Thr Tyr Arg Leu Tyr Lys Thr Leu Ser Leu Lys
                180                 185                 190

Leu His Glu Glu Lys
        195

<210> SEQ ID NO 160
<211> LENGTH: 894
<212> TYPE: PRT
<213> ORGANISM: Artificial sequence
<220> FEATURE:
<223> OTHER INFORMATION: chimeric DNA polymerase CS8 after second round
      of mutagenesis residues 323-325 DNE substitution

<400> SEQUENCE: 160

Met Lys Ala Met Leu Pro Leu Phe Glu Pro Lys Gly Arg Val Leu Leu
1               5                   10                  15

Val Asp Gly His His Leu Ala Tyr Arg Thr Phe Phe Ala Leu Lys Gly
                20                  25                  30

Leu Thr Thr Ser Arg Gly Glu Pro Val Gln Ala Val Tyr Gly Phe Ala
            35                  40                  45

Lys Ser Leu Leu Lys Ala Leu Lys Glu Asp Gly Tyr Lys Ala Val Phe
    50                  55                  60

Val Val Phe Asp Ala Lys Ala Pro Ser Phe Arg His Glu Ala Tyr Glu
65                  70                  75                  80

Ala Tyr Lys Ala Gly Arg Ala Pro Thr Pro Glu Asp Phe Pro Arg Gln
                85                  90                  95

Leu Ala Leu Ile Lys Glu Leu Val Asp Leu Leu Gly Phe Thr Arg Leu
                100                 105                 110

Glu Val Pro Gly Phe Glu Ala Asp Asp Val Leu Ala Thr Leu Ala Lys
            115                 120                 125

Lys Ala Glu Arg Glu Gly Tyr Glu Val Arg Ile Leu Thr Ala Asp Arg
    130                 135                 140

Asp Leu Tyr Gln Leu Val Ser Asp Arg Val Ala Val Leu His Pro Glu
145                 150                 155                 160

Gly His Leu Ile Thr Pro Glu Trp Leu Trp Glu Lys Tyr Gly Leu Lys
                165                 170                 175

Pro Glu Gln Trp Val Asp Phe Arg Ala Leu Val Gly Asp Pro Ser Asp
                180                 185                 190

Asn Leu Pro Gly Val Lys Gly Ile Gly Glu Lys Thr Ala Leu Lys Leu
            195                 200                 205

Leu Lys Glu Trp Gly Ser Leu Glu Asn Ile Leu Lys Asn Leu Asp Arg
    210                 215                 220

Val Lys Pro Glu Ser Val Arg Glu Arg Ile Lys Ala His Leu Glu Asp
225                 230                 235                 240

Leu Lys Leu Ser Leu Glu Leu Ser Arg Val Arg Ser Asp Leu Pro Leu
                245                 250                 255

Glu Val Asp Phe Ala Arg Arg Glu Pro Asp Arg Glu Gly Leu Arg
                260                 265                 270

Ala Phe Leu Glu Arg Leu Glu Phe Gly Ser Leu Leu His Glu Phe Gly
    275                 280                 285
```

-continued

```
Leu Leu Glu Glu Ser Glu Pro Val Gly Tyr Arg Ile Val Lys Asp Leu
    290                 295                 300
Val Glu Phe Glu Lys Leu Ile Glu Lys Leu Arg Glu Ser Pro Ser Phe
305                 310                 315                 320
Ala Ile Asp Asn Glu Thr Ser Ser Leu Asp Pro Phe Asp Cys Asp Ile
                325                 330                 335
Val Gly Ile Ser Val Ser Phe Lys Pro Lys Glu Ala Tyr Tyr Ile Pro
            340                 345                 350
Leu His His Arg Asn Ala Gln Asn Leu Asp Glu Lys Glu Val Leu Lys
        355                 360                 365
Lys Leu Lys Glu Ile Leu Glu Asp Pro Gly Ala Lys Ile Val Gly Gln
    370                 375                 380
Asn Leu Lys Phe Asp Tyr Lys Val Leu Met Val Lys Gly Val Glu Pro
385                 390                 395                 400
Val Pro Pro Tyr Phe Asp Thr Met Ile Ala Ala Tyr Leu Leu Glu Pro
                405                 410                 415
Asn Glu Lys Lys Phe Asn Leu Asp Asp Leu Ala Leu Lys Phe Leu Gly
            420                 425                 430
Tyr Lys Met Thr Ser Tyr Gln Glu Leu Met Ser Phe Ser Phe Pro Leu
        435                 440                 445
Phe Gly Phe Ser Phe Ala Asp Val Pro Val Glu Lys Ala Ala Asn Tyr
    450                 455                 460
Ser Cys Glu Asp Ala Asp Ile Thr Tyr Arg Leu Tyr Lys Thr Leu Ser
465                 470                 475                 480
Leu Lys Leu His Glu Glu Lys Leu Leu Trp Leu Tyr Gln Glu Val Glu
                485                 490                 495
Lys Pro Leu Ser Arg Val Leu Ala His Met Glu Ala Thr Gly Val Arg
            500                 505                 510
Leu Asp Val Ala Tyr Leu Lys Ala Leu Ser Leu Glu Leu Ala Glu Glu
        515                 520                 525
Ile Arg Arg Leu Glu Glu Glu Val Phe Arg Leu Ala Gly His Pro Phe
    530                 535                 540
Asn Leu Asn Ser Arg Asp Gln Leu Glu Arg Val Leu Phe Asp Glu Leu
545                 550                 555                 560
Arg Leu Pro Ala Leu Gly Lys Thr Gln Lys Thr Gly Lys Arg Ser Thr
                565                 570                 575
Ser Ala Ala Val Leu Glu Ala Leu Arg Glu Ala His Pro Ile Val Glu
            580                 585                 590
Lys Ile Leu Gln His Arg Glu Leu Thr Lys Leu Lys Asn Thr Tyr Val
        595                 600                 605
Asp Pro Leu Pro Gly Leu Val His Pro Arg Thr Gly Arg Leu His Thr
    610                 615                 620
Arg Phe Asn Gln Thr Ala Thr Ala Thr Gly Arg Leu Ser Ser Ser Asp
625                 630                 635                 640
Pro Asn Leu Gln Asn Ile Pro Ile Arg Thr Pro Leu Gly Gln Arg Ile
                645                 650                 655
Arg Arg Ala Phe Val Ala Glu Ala Gly Trp Ala Leu Val Ala Leu Asp
            660                 665                 670
Tyr Ser Gln Ile Glu Leu Arg Val Leu Ala His Leu Ser Gly Asp Glu
        675                 680                 685
Asn Leu Ile Arg Val Phe Gln Glu Gly Lys Asp Ile His Thr Gln Thr
    690                 695                 700
```

```
Ala Ser Trp Met Phe Gly Val Ser Pro Glu Ala Val Asp Pro Leu Met
705                 710                 715                 720

Arg Arg Ala Ala Lys Thr Val Asn Phe Gly Val Leu Tyr Gly Met Ser
            725                 730                 735

Ala His Arg Leu Ser Gln Glu Leu Ala Ile Pro Tyr Glu Glu Ala Val
        740                 745                 750

Ala Phe Ile Glu Arg Tyr Phe Gln Ser Phe Pro Lys Val Arg Ala Trp
    755                 760                 765

Ile Glu Lys Thr Leu Glu Gly Arg Lys Arg Gly Tyr Val Glu Thr
770                 775                 780

Leu Phe Gly Arg Arg Tyr Val Pro Asp Leu Asn Ala Arg Val Lys
785             790                 795                 800

Ser Val Arg Glu Ala Glu Arg Met Ala Phe Asn Met Pro Val Gln
            805                 810                 815

Gly Thr Ala Ala Asp Leu Met Lys Leu Ala Met Val Lys Leu Phe Pro
        820                 825                 830

His Leu Arg Glu Met Gly Ala Arg Met Leu Leu Gln Val His Asp Glu
    835                 840                 845

Leu Leu Leu Glu Ala Pro Gln Ala Arg Ala Glu Val Ala Ala Leu
850                 855                 860

Ala Lys Glu Ala Met Glu Lys Ala Tyr Pro Leu Ala Val Pro Leu Glu
865                 870                 875                 880

Val Glu Val Gly Ile Gly Glu Asp Trp Leu Ser Ala Lys Gly
            885                 890

<210> SEQ ID NO 161
<211> LENGTH: 197
<212> TYPE: PRT
<213> ORGANISM: Artificial sequence
<220> FEATURE:
<223> OTHER INFORMATION: Exonucleolytic domain of chimeric DNA
      polymerase CS8 after second round of mutagenesis residues 323-325
      DQE substitution

<400> SEQUENCE: 161

Glu Glu Ser Glu Pro Val Gly Tyr Arg Ile Val Lys Asp Leu Val Glu
1               5                   10                  15

Phe Glu Lys Leu Ile Glu Lys Leu Arg Glu Ser Pro Ser Phe Ala Ile
            20                  25                  30

Asp Gln Glu Thr Ser Ser Leu Asp Pro Phe Asp Cys Asp Ile Val Gly
        35                  40                  45

Ile Ser Val Ser Phe Lys Pro Lys Glu Ala Tyr Tyr Ile Pro Leu His
    50                  55                  60

His Arg Asn Ala Gln Asn Leu Asp Glu Lys Glu Val Leu Lys Lys Leu
65                  70                  75                  80

Lys Glu Ile Leu Glu Asp Pro Gly Ala Lys Ile Val Gly Gln Asn Leu
                85                  90                  95

Lys Phe Asp Tyr Lys Val Leu Met Val Lys Gly Val Glu Pro Val Pro
            100                 105                 110

Pro Tyr Phe Asp Thr Met Ile Ala Ala Tyr Leu Leu Glu Pro Asn Glu
        115                 120                 125

Lys Lys Phe Asn Leu Asp Asp Leu Ala Leu Lys Phe Leu Gly Tyr Lys
    130                 135                 140

Met Thr Ser Tyr Gln Glu Leu Met Ser Phe Ser Phe Pro Leu Phe Gly
145                 150                 155                 160

Phe Ser Phe Ala Asp Val Pro Val Glu Lys Ala Ala Asn Tyr Ser Cys
```

-continued

```
                165                 170                 175
Glu Asp Ala Asp Ile Thr Tyr Arg Leu Tyr Lys Thr Leu Ser Leu Lys
            180                 185                 190

Leu His Glu Glu Lys
        195
```

<210> SEQ ID NO 162
<211> LENGTH: 894
<212> TYPE: PRT
<213> ORGANISM: Artificial sequence
<220> FEATURE:
<223> OTHER INFORMATION: chimeric DNA polymerase CS8 after second round of mutagenesis residues 323-325 DQE substitution

<400> SEQUENCE: 162

```
Met Lys Ala Met Leu Pro Leu Phe Glu Pro Lys Gly Arg Val Leu Leu
1               5                   10                  15

Val Asp Gly His His Leu Ala Tyr Arg Thr Phe Phe Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Tyr Lys Ala Val Phe
    50                  55                  60

Val Val Phe Asp Ala Lys Ala Pro Ser Phe Arg His Glu Ala Tyr Glu
65                  70                  75                  80

Ala Tyr Lys Ala Gly Arg Ala Pro Thr Pro Glu Asp Phe Pro Arg Gln
                85                  90                  95

Leu Ala Leu Ile Lys Glu Leu Val Asp Leu Leu Gly Phe Thr Arg Leu
            100                 105                 110

Glu Val Pro Gly Phe Glu Ala Asp Asp Val Leu Ala Thr Leu Ala Lys
        115                 120                 125

Lys Ala Glu Arg Glu Gly Tyr Glu Val Arg Ile Leu Thr Ala Asp Arg
    130                 135                 140

Asp Leu Tyr Gln Leu Val Ser Asp Arg Val Ala Val Leu His Pro Glu
145                 150                 155                 160

Gly His Leu Ile Thr Pro Glu Trp Leu Trp Glu Lys Tyr Gly Leu Lys
                165                 170                 175

Pro Glu Gln Trp Val Asp Phe Arg Ala Leu Val Gly Asp Pro Ser Asp
            180                 185                 190

Asn Leu Pro Gly Val Lys Gly Ile Gly Glu Lys Thr Ala Leu Lys Leu
        195                 200                 205

Leu Lys Glu Trp Gly Ser Leu Glu Asn Ile Leu Lys Asn Leu Asp Arg
    210                 215                 220

Val Lys Pro Glu Ser Val Arg Glu Arg Ile Lys Ala His Leu Glu Asp
225                 230                 235                 240

Leu Lys Leu Ser Leu Glu Leu Ser Arg Val Arg Ser Asp Leu Pro Leu
                245                 250                 255

Glu Val Asp Phe Ala Arg Arg Arg Glu Pro Asp Arg Glu Gly Leu Arg
            260                 265                 270

Ala Phe Leu Glu Arg Leu Glu Phe Gly Ser Leu Leu His Glu Phe Gly
        275                 280                 285

Leu Leu Glu Glu Ser Glu Pro Val Gly Tyr Arg Ile Val Lys Asp Leu
    290                 295                 300

Val Glu Phe Glu Lys Leu Ile Glu Lys Leu Arg Glu Ser Pro Ser Phe
305                 310                 315                 320
```

-continued

```
Ala Ile Asp Gln Glu Thr Ser Ser Leu Asp Pro Phe Asp Cys Asp Ile
                325                 330                 335

Val Gly Ile Ser Val Ser Phe Lys Pro Lys Glu Ala Tyr Tyr Ile Pro
            340                 345                 350

Leu His His Arg Asn Ala Gln Asn Leu Asp Glu Lys Glu Val Leu Lys
        355                 360                 365

Lys Leu Lys Glu Ile Leu Glu Asp Pro Gly Ala Lys Ile Val Gly Gln
    370                 375                 380

Asn Leu Lys Phe Asp Tyr Lys Val Leu Met Val Lys Gly Val Glu Pro
385                 390                 395                 400

Val Pro Pro Tyr Phe Asp Thr Met Ile Ala Ala Tyr Leu Leu Glu Pro
                405                 410                 415

Asn Glu Lys Lys Phe Asn Leu Asp Asp Leu Ala Leu Lys Phe Leu Gly
            420                 425                 430

Tyr Lys Met Thr Ser Tyr Gln Glu Leu Met Ser Phe Ser Phe Pro Leu
        435                 440                 445

Phe Gly Phe Ser Phe Ala Asp Val Pro Val Glu Lys Ala Ala Asn Tyr
    450                 455                 460

Ser Cys Glu Asp Ala Asp Ile Thr Tyr Arg Leu Tyr Lys Thr Leu Ser
465                 470                 475                 480

Leu Lys Leu His Glu Glu Lys Leu Leu Trp Leu Tyr Gln Glu Val Glu
                485                 490                 495

Lys Pro Leu Ser Arg Val Leu Ala His Met Glu Ala Thr Gly Val Arg
            500                 505                 510

Leu Asp Val Ala Tyr Leu Lys Ala Leu Ser Leu Glu Leu Ala Glu Glu
        515                 520                 525

Ile Arg Arg Leu Glu Glu Glu Val Phe Arg Leu Ala Gly His Pro Phe
    530                 535                 540

Asn Leu Asn Ser Arg Asp Gln Leu Glu Arg Val Leu Phe Asp Glu Leu
545                 550                 555                 560

Arg Leu Pro Ala Leu Gly Lys Thr Gln Lys Thr Gly Lys Arg Ser Thr
                565                 570                 575

Ser Ala Ala Val Leu Glu Ala Leu Arg Glu Ala His Pro Ile Val Glu
            580                 585                 590

Lys Ile Leu Gln His Arg Glu Leu Thr Lys Leu Lys Asn Thr Tyr Val
    595                 600                 605

Asp Pro Leu Pro Gly Leu Val His Pro Arg Thr Gly Arg Leu His Thr
610                 615                 620

Arg Phe Asn Gln Thr Ala Thr Ala Thr Gly Arg Leu Ser Ser Ser Asp
625                 630                 635                 640

Pro Asn Leu Gln Asn Ile Pro Ile Arg Thr Pro Leu Gly Gln Arg Ile
                645                 650                 655

Arg Arg Ala Phe Val Ala Glu Ala Gly Trp Ala Leu Val Ala Leu Asp
            660                 665                 670

Tyr Ser Gln Ile Glu Leu Arg Val Leu Ala His Leu Ser Gly Asp Glu
        675                 680                 685

Asn Leu Ile Arg Val Phe Gln Glu Gly Lys Asp Ile His Thr Gln Thr
    690                 695                 700

Ala Ser Trp Met Phe Gly Val Ser Pro Glu Ala Val Asp Pro Leu Met
705                 710                 715                 720

Arg Arg Ala Ala Lys Thr Val Asn Phe Gly Val Leu Tyr Gly Met Ser
                725                 730                 735

Ala His Arg Leu Ser Gln Glu Leu Ala Ile Pro Tyr Glu Glu Ala Val
```

```
                    740                 745                 750
Ala Phe Ile Glu Arg Tyr Phe Gln Ser Phe Pro Lys Val Arg Ala Trp
                755                 760                 765
Ile Glu Lys Thr Leu Glu Glu Gly Arg Lys Arg Gly Tyr Val Glu Thr
770                 775                 780
Leu Phe Gly Arg Arg Tyr Val Pro Asp Leu Asn Ala Arg Val Lys
785                 790                 795                 800
Ser Val Arg Glu Ala Glu Arg Met Ala Phe Asn Met Pro Val Gln
                805                 810                 815
Gly Thr Ala Ala Asp Leu Met Lys Leu Ala Met Val Lys Leu Phe Pro
                820                 825                 830
His Leu Arg Glu Met Gly Ala Arg Met Leu Leu Gln Val His Asp Glu
                835                 840                 845
Leu Leu Leu Glu Ala Pro Gln Ala Arg Ala Glu Val Ala Ala Leu
850                 855                 860
Ala Lys Glu Ala Met Glu Lys Ala Tyr Pro Leu Ala Val Pro Leu Glu
865                 870                 875                 880
Val Glu Val Gly Ile Gly Glu Asp Trp Leu Ser Ala Lys Gly
                885                 890

<210> SEQ ID NO 163
<211> LENGTH: 197
<212> TYPE: PRT
<213> ORGANISM: Artificial sequence
<220> FEATURE:
<223> OTHER INFORMATION: Exonucleolytic domain of chimeric DNA
      polymerase CS8 after second round of mutagenesis residues 323-325
      DHE substitution

<400> SEQUENCE: 163

Glu Glu Ser Glu Pro Val Gly Tyr Arg Ile Val Lys Asp Leu Val Glu
1               5                   10                  15
Phe Glu Lys Leu Ile Glu Lys Leu Arg Glu Ser Pro Ser Phe Ala Ile
                20                  25                  30
Asp His Glu Thr Ser Ser Leu Asp Pro Phe Asp Cys Asp Ile Val Gly
            35                  40                  45
Ile Ser Val Ser Phe Lys Pro Lys Glu Ala Tyr Tyr Ile Pro Leu His
50                  55                  60
His Arg Asn Ala Gln Asn Leu Asp Glu Lys Glu Val Leu Lys Lys Leu
65                  70                  75                  80
Lys Glu Ile Leu Glu Asp Pro Gly Ala Lys Ile Val Gly Gln Asn Leu
                85                  90                  95
Lys Phe Asp Tyr Lys Val Leu Met Val Lys Gly Val Glu Pro Val Pro
            100                 105                 110
Pro Tyr Phe Asp Thr Met Ile Ala Ala Tyr Leu Leu Glu Pro Asn Glu
        115                 120                 125
Lys Lys Phe Asn Leu Asp Asp Leu Ala Leu Lys Phe Leu Gly Tyr Lys
    130                 135                 140
Met Thr Ser Tyr Gln Glu Leu Met Ser Phe Ser Phe Pro Leu Phe Gly
145                 150                 155                 160
Phe Ser Phe Ala Asp Val Pro Val Glu Lys Ala Ala Asn Tyr Ser Cys
                165                 170                 175
Glu Asp Ala Asp Ile Thr Tyr Arg Leu Tyr Lys Thr Leu Ser Leu Lys
            180                 185                 190
Leu His Glu Glu Lys
        195
```

<210> SEQ ID NO 164
<211> LENGTH: 894
<212> TYPE: PRT
<213> ORGANISM: Artificial sequence
<220> FEATURE:
<223> OTHER INFORMATION: chimeric DNA polymerase CS8 after second round
of mutagenesis residues 323-325 DHE substitution

<400> SEQUENCE: 164

```
Met Lys Ala Met Leu Pro Leu Phe Glu Pro Lys Gly Arg Val Leu Leu
1               5                   10                  15

Val Asp Gly His His Leu Ala Tyr Arg Thr Phe Phe Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Tyr Lys Ala Val Phe
    50                  55                  60

Val Val Phe Asp Ala Lys Ala Pro Ser Phe Arg His Glu Ala Tyr Glu
65                  70                  75                  80

Ala Tyr Lys Ala Gly Arg Ala Pro Thr Pro Glu Asp Phe Pro Arg Gln
                85                  90                  95

Leu Ala Leu Ile Lys Glu Leu Val Asp Leu Leu Gly Phe Thr Arg Leu
            100                 105                 110

Glu Val Pro Gly Phe Glu Ala Asp Asp Val Leu Ala Thr Leu Ala Lys
        115                 120                 125

Lys Ala Glu Arg Glu Gly Tyr Glu Val Arg Ile Leu Thr Ala Asp Arg
    130                 135                 140

Asp Leu Tyr Gln Leu Val Ser Asp Arg Val Ala Val Leu His Pro Glu
145                 150                 155                 160

Gly His Leu Ile Thr Pro Glu Trp Leu Trp Glu Lys Tyr Gly Leu Lys
                165                 170                 175

Pro Glu Gln Trp Val Asp Phe Arg Ala Leu Val Gly Asp Pro Ser Asp
            180                 185                 190

Asn Leu Pro Gly Val Lys Gly Ile Gly Glu Lys Thr Ala Leu Lys Leu
        195                 200                 205

Leu Lys Glu Trp Gly Ser Leu Glu Asn Ile Leu Lys Asn Leu Asp Arg
    210                 215                 220

Val Lys Pro Glu Ser Val Arg Glu Arg Ile Lys Ala His Leu Glu Asp
225                 230                 235                 240

Leu Lys Leu Ser Leu Glu Leu Ser Arg Val Arg Ser Asp Leu Pro Leu
                245                 250                 255

Glu Val Asp Phe Ala Arg Arg Arg Glu Pro Asp Arg Glu Gly Leu Arg
            260                 265                 270

Ala Phe Leu Glu Arg Leu Glu Phe Gly Ser Leu Leu His Glu Phe Gly
        275                 280                 285

Leu Leu Glu Glu Ser Glu Pro Val Gly Tyr Arg Ile Val Lys Asp Leu
    290                 295                 300

Val Glu Phe Glu Lys Leu Ile Glu Lys Leu Arg Glu Ser Pro Ser Phe
305                 310                 315                 320

Ala Ile Asp His Glu Thr Ser Ser Leu Asp Pro Phe Asp Cys Asp Ile
                325                 330                 335

Val Gly Ile Ser Val Ser Phe Lys Pro Lys Glu Ala Tyr Tyr Ile Pro
            340                 345                 350

Leu His His Arg Asn Ala Gln Asn Leu Asp Glu Lys Glu Val Leu Lys
```

```
            355                 360                 365
Lys Leu Lys Glu Ile Leu Glu Asp Pro Gly Ala Lys Ile Val Gly Gln
            370                 375                 380

Asn Leu Lys Phe Asp Tyr Lys Val Leu Met Val Lys Gly Val Glu Pro
385                 390                 395                 400

Val Pro Pro Tyr Phe Asp Thr Met Ile Ala Ala Tyr Leu Leu Glu Pro
                    405                 410                 415

Asn Glu Lys Lys Phe Asn Leu Asp Asp Leu Ala Leu Lys Phe Leu Gly
                420                 425                 430

Tyr Lys Met Thr Ser Tyr Gln Glu Leu Met Ser Phe Ser Phe Pro Leu
            435                 440                 445

Phe Gly Phe Ser Phe Ala Asp Val Pro Val Glu Lys Ala Ala Asn Tyr
        450                 455                 460

Ser Cys Glu Asp Ala Asp Ile Thr Tyr Arg Leu Tyr Lys Thr Leu Ser
465                 470                 475                 480

Leu Lys Leu His Glu Glu Lys Leu Leu Trp Leu Tyr Gln Glu Val Glu
                    485                 490                 495

Lys Pro Leu Ser Arg Val Leu Ala His Met Glu Ala Thr Gly Val Arg
                500                 505                 510

Leu Asp Val Ala Tyr Leu Lys Ala Leu Ser Leu Glu Leu Ala Glu Glu
            515                 520                 525

Ile Arg Arg Leu Glu Glu Glu Val Phe Arg Leu Ala Gly His Pro Phe
        530                 535                 540

Asn Leu Asn Ser Arg Asp Gln Leu Glu Arg Val Leu Phe Asp Glu Leu
545                 550                 555                 560

Arg Leu Pro Ala Leu Gly Lys Thr Gln Lys Thr Gly Lys Arg Ser Thr
                    565                 570                 575

Ser Ala Ala Val Leu Glu Ala Leu Arg Glu Ala His Pro Ile Val Glu
                580                 585                 590

Lys Ile Leu Gln His Arg Glu Leu Thr Lys Leu Lys Asn Thr Tyr Val
            595                 600                 605

Asp Pro Leu Pro Gly Leu Val His Pro Arg Thr Gly Arg Leu His Thr
        610                 615                 620

Arg Phe Asn Gln Thr Ala Thr Ala Thr Gly Arg Leu Ser Ser Ser Asp
625                 630                 635                 640

Pro Asn Leu Gln Asn Ile Pro Ile Arg Thr Pro Leu Gly Gln Arg Ile
                    645                 650                 655

Arg Arg Ala Phe Val Ala Glu Ala Gly Trp Ala Leu Val Ala Leu Asp
                660                 665                 670

Tyr Ser Gln Ile Glu Leu Arg Val Leu Ala His Leu Ser Gly Asp Glu
            675                 680                 685

Asn Leu Ile Arg Val Phe Gln Glu Gly Lys Asp Ile His Thr Gln Thr
        690                 695                 700

Ala Ser Trp Met Phe Gly Val Ser Pro Glu Ala Val Asp Pro Leu Met
705                 710                 715                 720

Arg Arg Ala Ala Lys Thr Val Asn Phe Gly Val Leu Tyr Gly Met Ser
                    725                 730                 735

Ala His Arg Leu Ser Gln Glu Leu Ala Ile Pro Tyr Glu Glu Ala Val
                740                 745                 750

Ala Phe Ile Glu Arg Tyr Phe Gln Ser Phe Pro Lys Val Arg Ala Trp
            755                 760                 765

Ile Glu Lys Thr Leu Glu Glu Gly Arg Lys Arg Gly Tyr Val Glu Thr
        770                 775                 780
```

```
Leu Phe Gly Arg Arg Arg Tyr Val Pro Asp Leu Asn Ala Arg Val Lys
785                 790                 795                 800

Ser Val Arg Glu Ala Ala Glu Arg Met Ala Phe Asn Met Pro Val Gln
            805                 810                 815

Gly Thr Ala Ala Asp Leu Met Lys Leu Ala Met Val Lys Leu Phe Pro
        820                 825                 830

His Leu Arg Glu Met Gly Ala Arg Met Leu Leu Gln Val His Asp Glu
    835                 840                 845

Leu Leu Leu Glu Ala Pro Gln Ala Arg Ala Glu Val Ala Ala Leu
850                 855                 860

Ala Lys Glu Ala Met Glu Lys Ala Tyr Pro Leu Ala Val Pro Leu Glu
865                 870                 875                 880

Val Glu Val Gly Ile Gly Glu Asp Trp Leu Ser Ala Lys Gly
                885                 890

<210> SEQ ID NO 165
<211> LENGTH: 197
<212> TYPE: PRT
<213> ORGANISM: Artificial sequence
<220> FEATURE:
<223> OTHER INFORMATION: Exonucleolytic domain of chimeric DNA
      polymerase CS8 after second round of mutagenesis residues 323-325
      DLD substitution

<400> SEQUENCE: 165

Glu Glu Ser Glu Pro Val Gly Tyr Arg Ile Val Lys Asp Leu Val Glu
1               5                   10                  15

Phe Glu Lys Leu Ile Glu Lys Leu Arg Glu Ser Pro Ser Phe Ala Ile
            20                  25                  30

Asp Leu Asp Thr Ser Ser Leu Asp Pro Phe Asp Cys Asp Ile Val Gly
        35                  40                  45

Ile Ser Val Ser Phe Lys Pro Lys Glu Ala Tyr Tyr Ile Pro Leu His
50                  55                  60

His Arg Asn Ala Gln Asn Leu Asp Glu Lys Glu Val Leu Lys Lys Leu
65                  70                  75                  80

Lys Glu Ile Leu Glu Asp Pro Gly Ala Lys Ile Val Gly Gln Asn Leu
            85                  90                  95

Lys Phe Asp Tyr Lys Val Leu Met Val Lys Gly Val Glu Pro Val Pro
            100                 105                 110

Pro Tyr Phe Asp Thr Met Ile Ala Ala Tyr Leu Leu Glu Pro Asn Glu
        115                 120                 125

Lys Lys Phe Asn Leu Asp Asp Leu Ala Leu Lys Phe Leu Gly Tyr Lys
130                 135                 140

Met Thr Ser Tyr Gln Glu Leu Met Ser Phe Ser Phe Pro Leu Phe Gly
145                 150                 155                 160

Phe Ser Phe Ala Asp Val Pro Val Glu Lys Ala Ala Asn Tyr Ser Cys
                165                 170                 175

Glu Asp Ala Asp Ile Thr Tyr Arg Leu Tyr Lys Thr Leu Ser Leu Lys
            180                 185                 190

Leu His Glu Glu Lys
        195

<210> SEQ ID NO 166
<211> LENGTH: 894
<212> TYPE: PRT
<213> ORGANISM: Artificial sequence
<220> FEATURE:
```

<223> OTHER INFORMATION: chimeric DNA polymerase CS8 after second round
      of mutagenesis residues 323-325 DLD substitution

<400> SEQUENCE: 166

| | | | | | | | | | | | | | | |
|---|---|---|---|---|---|---|---|---|---|---|---|---|---|---|
| Met | Lys | Ala | Met | Leu | Pro | Leu | Phe | Glu | Pro | Lys | Gly | Arg | Val | Leu | Leu |
| 1 | | | | 5 | | | | | 10 | | | | | 15 | |
| Val | Asp | Gly | His | His | Leu | Ala | Tyr | Arg | Thr | Phe | Phe | Ala | Leu | Lys | Gly |
| | | | 20 | | | | | 25 | | | | | 30 | | |
| Leu | Thr | Thr | Ser | Arg | Gly | Glu | Pro | Val | Gln | Ala | Val | Tyr | Gly | Phe | Ala |
| | | | 35 | | | | 40 | | | | | 45 | | | |
| Lys | Ser | Leu | Leu | Lys | Ala | Leu | Lys | Glu | Asp | Gly | Tyr | Lys | Ala | Val | Phe |
| | 50 | | | | | 55 | | | | | 60 | | | | |
| Val | Val | Phe | Asp | Ala | Lys | Ala | Pro | Ser | Phe | Arg | His | Glu | Ala | Tyr | Glu |
| 65 | | | | | 70 | | | | | 75 | | | | | 80 |
| Ala | Tyr | Lys | Ala | Gly | Arg | Ala | Pro | Thr | Pro | Glu | Asp | Phe | Pro | Arg | Gln |
| | | | | 85 | | | | | 90 | | | | | 95 | |
| Leu | Ala | Leu | Ile | Lys | Glu | Leu | Val | Asp | Leu | Leu | Gly | Phe | Thr | Arg | Leu |
| | | | 100 | | | | | 105 | | | | | 110 | | |
| Glu | Val | Pro | Gly | Phe | Glu | Ala | Asp | Asp | Val | Leu | Ala | Thr | Leu | Ala | Lys |
| | | | 115 | | | | | 120 | | | | | 125 | | |
| Lys | Ala | Glu | Arg | Glu | Gly | Tyr | Glu | Val | Arg | Ile | Leu | Thr | Ala | Asp | Arg |
| | 130 | | | | | 135 | | | | | 140 | | | | |
| Asp | Leu | Tyr | Gln | Leu | Val | Ser | Asp | Arg | Val | Ala | Val | Leu | His | Pro | Glu |
| 145 | | | | | 150 | | | | | 155 | | | | | 160 |
| Gly | His | Leu | Ile | Thr | Pro | Glu | Trp | Leu | Trp | Glu | Lys | Tyr | Gly | Leu | Lys |
| | | | | 165 | | | | | 170 | | | | | 175 | |
| Pro | Glu | Gln | Trp | Val | Asp | Phe | Arg | Ala | Leu | Val | Gly | Asp | Pro | Ser | Asp |
| | | | 180 | | | | | 185 | | | | | 190 | | |
| Asn | Leu | Pro | Gly | Val | Lys | Gly | Ile | Gly | Glu | Lys | Thr | Ala | Leu | Lys | Leu |
| | | 195 | | | | | 200 | | | | | 205 | | | |
| Leu | Lys | Glu | Trp | Gly | Ser | Leu | Glu | Asn | Ile | Leu | Lys | Asn | Leu | Asp | Arg |
| | 210 | | | | | 215 | | | | | 220 | | | | |
| Val | Lys | Pro | Glu | Ser | Val | Arg | Glu | Arg | Ile | Lys | Ala | His | Leu | Glu | Asp |
| 225 | | | | | 230 | | | | | 235 | | | | | 240 |
| Leu | Lys | Leu | Ser | Leu | Glu | Leu | Ser | Arg | Val | Arg | Ser | Asp | Leu | Pro | Leu |
| | | | 245 | | | | | 250 | | | | | 255 | | |
| Glu | Val | Asp | Phe | Ala | Arg | Arg | Arg | Glu | Pro | Asp | Arg | Glu | Gly | Leu | Arg |
| | | | 260 | | | | | 265 | | | | | 270 | | |
| Ala | Phe | Leu | Glu | Arg | Leu | Glu | Phe | Gly | Ser | Leu | Leu | His | Glu | Phe | Gly |
| | | 275 | | | | | 280 | | | | | 285 | | | |
| Leu | Leu | Glu | Glu | Ser | Glu | Pro | Val | Gly | Tyr | Arg | Ile | Val | Lys | Asp | Leu |
| | 290 | | | | | 295 | | | | | 300 | | | | |
| Val | Glu | Phe | Glu | Lys | Leu | Ile | Glu | Lys | Leu | Arg | Glu | Ser | Pro | Ser | Phe |
| 305 | | | | | 310 | | | | | 315 | | | | | 320 |
| Ala | Ile | Asp | Leu | Asp | Thr | Ser | Ser | Leu | Asp | Pro | Phe | Asp | Cys | Asp | Ile |
| | | | | 325 | | | | | 330 | | | | | 335 | |
| Val | Gly | Ile | Ser | Val | Ser | Phe | Lys | Pro | Lys | Glu | Ala | Tyr | Tyr | Ile | Pro |
| | | | 340 | | | | | 345 | | | | | 350 | | |
| Leu | His | His | Arg | Asn | Ala | Gln | Asn | Leu | Asp | Glu | Lys | Glu | Val | Leu | Lys |
| | | | 355 | | | | | 360 | | | | | 365 | | |
| Lys | Leu | Lys | Glu | Ile | Leu | Glu | Asp | Pro | Gly | Ala | Lys | Ile | Val | Gly | Gln |
| | 370 | | | | | 375 | | | | | 380 | | | | |
| Asn | Leu | Lys | Phe | Asp | Tyr | Lys | Val | Leu | Met | Val | Lys | Gly | Val | Glu | Pro |
| 385 | | | | | 390 | | | | | 395 | | | | | 400 |

-continued

```
Val Pro Pro Tyr Phe Asp Thr Met Ile Ala Ala Tyr Leu Leu Glu Pro
            405                 410                 415
Asn Glu Lys Lys Phe Asn Leu Asp Asp Leu Ala Leu Lys Phe Leu Gly
        420                 425                 430
Tyr Lys Met Thr Ser Tyr Gln Glu Leu Met Ser Phe Ser Phe Pro Leu
            435                 440                 445
Phe Gly Phe Ser Phe Ala Asp Val Pro Val Lys Ala Ala Asn Tyr
450                 455                 460
Ser Cys Glu Asp Ala Asp Ile Thr Tyr Arg Leu Tyr Lys Thr Leu Ser
465                 470                 475                 480
Leu Lys Leu His Glu Lys Leu Leu Trp Leu Tyr Gln Glu Val Glu
            485                 490                 495
Lys Pro Leu Ser Arg Val Leu Ala His Met Glu Ala Thr Gly Val Arg
            500                 505                 510
Leu Asp Val Ala Tyr Leu Lys Ala Leu Ser Leu Glu Leu Ala Glu Glu
            515                 520                 525
Ile Arg Arg Leu Glu Glu Val Phe Arg Leu Ala Gly His Pro Phe
530                 535                 540
Asn Leu Asn Ser Arg Asp Gln Leu Glu Arg Val Leu Phe Asp Glu Leu
545                 550                 555                 560
Arg Leu Pro Ala Leu Gly Lys Thr Gln Lys Thr Gly Lys Arg Ser Thr
            565                 570                 575
Ser Ala Ala Val Leu Glu Ala Leu Arg Glu Ala His Pro Ile Val Glu
            580                 585                 590
Lys Ile Leu Gln His Arg Glu Leu Thr Lys Leu Lys Asn Thr Tyr Val
            595                 600                 605
Asp Pro Leu Pro Gly Leu Val His Pro Arg Thr Gly Arg Leu His Thr
            610                 615                 620
Arg Phe Asn Gln Thr Ala Thr Ala Thr Gly Arg Leu Ser Ser Ser Asp
625                 630                 635                 640
Pro Asn Leu Gln Asn Ile Pro Ile Arg Thr Pro Leu Gly Gln Arg Ile
                645                 650                 655
Arg Arg Ala Phe Val Ala Glu Ala Gly Trp Ala Leu Val Ala Leu Asp
                660                 665                 670
Tyr Ser Gln Ile Glu Leu Arg Val Leu Ala His Leu Ser Gly Asp Glu
            675                 680                 685
Asn Leu Ile Arg Val Phe Gln Glu Gly Lys Asp Ile His Thr Gln Thr
            690                 695                 700
Ala Ser Trp Met Phe Gly Val Ser Pro Glu Ala Val Asp Pro Leu Met
705                 710                 715                 720
Arg Arg Ala Ala Lys Thr Val Asn Phe Gly Val Leu Tyr Gly Met Ser
                725                 730                 735
Ala His Arg Leu Ser Gln Glu Leu Ala Ile Pro Tyr Glu Glu Ala Val
                740                 745                 750
Ala Phe Ile Glu Arg Tyr Phe Gln Ser Phe Pro Lys Val Arg Ala Trp
            755                 760                 765
Ile Glu Lys Thr Leu Glu Glu Gly Arg Lys Arg Gly Tyr Val Glu Thr
            770                 775                 780
Leu Phe Gly Arg Arg Arg Tyr Val Pro Asp Leu Asn Ala Arg Val Lys
785                 790                 795                 800
Ser Val Arg Glu Ala Ala Glu Arg Met Ala Phe Asn Met Pro Val Gln
                805                 810                 815
```

Gly Thr Ala Ala Asp Leu Met Lys Leu Ala Met Val Lys Leu Phe Pro
            820                 825                 830

His Leu Arg Glu Met Gly Ala Arg Met Leu Leu Gln Val His Asp Glu
        835                 840                 845

Leu Leu Leu Glu Ala Pro Gln Ala Arg Ala Glu Val Ala Ala Leu
    850                 855                 860

Ala Lys Glu Ala Met Glu Lys Ala Tyr Pro Leu Ala Val Pro Leu Glu
865                 870                 875                 880

Val Glu Val Gly Ile Gly Glu Asp Trp Leu Ser Ala Lys Gly
                885                 890

<210> SEQ ID NO 167
<211> LENGTH: 197
<212> TYPE: PRT
<213> ORGANISM: Artificial sequence
<220> FEATURE:
<223> OTHER INFORMATION: Exonucleolytic domain of chimeric DNA
      polymerase CS8 after second round of mutagenesis residues 323-325
      ELD substitution

<400> SEQUENCE: 167

Glu Glu Ser Glu Pro Val Gly Tyr Arg Ile Val Lys Asp Leu Val Glu
1               5                   10                  15

Phe Glu Lys Leu Ile Glu Lys Leu Arg Glu Ser Pro Ser Phe Ala Ile
            20                  25                  30

Glu Leu Asp Thr Ser Ser Leu Asp Pro Phe Asp Cys Asp Ile Val Gly
        35                  40                  45

Ile Ser Val Ser Phe Lys Pro Lys Glu Ala Tyr Tyr Ile Pro Leu His
    50                  55                  60

His Arg Asn Ala Gln Asn Leu Asp Glu Lys Glu Val Leu Lys Lys Leu
65                  70                  75                  80

Lys Glu Ile Leu Glu Asp Pro Gly Ala Lys Ile Val Gly Gln Asn Leu
            85                  90                  95

Lys Phe Asp Tyr Lys Val Leu Met Val Lys Gly Val Glu Pro Val Pro
            100                 105                 110

Pro Tyr Phe Asp Thr Met Ile Ala Ala Tyr Leu Leu Glu Pro Asn Glu
        115                 120                 125

Lys Lys Phe Asn Leu Asp Asp Leu Ala Leu Lys Phe Leu Gly Tyr Lys
    130                 135                 140

Met Thr Ser Tyr Gln Glu Leu Met Ser Phe Ser Phe Pro Leu Phe Gly
145                 150                 155                 160

Phe Ser Phe Ala Asp Val Pro Val Glu Lys Ala Ala Asn Tyr Ser Cys
                165                 170                 175

Glu Asp Ala Asp Ile Thr Tyr Arg Leu Tyr Lys Thr Leu Ser Leu Lys
            180                 185                 190

Leu His Glu Glu Lys
        195

<210> SEQ ID NO 168
<211> LENGTH: 894
<212> TYPE: PRT
<213> ORGANISM: Artificial sequence
<220> FEATURE:
<223> OTHER INFORMATION: chimeric DNA polymerase CS8 after second round
      of mutagenesis residues 323-325 ELD substitution

<400> SEQUENCE: 168

Met Lys Ala Met Leu Pro Leu Phe Glu Pro Lys Gly Arg Val Leu Leu
1               5                   10                  15

-continued

```
Val Asp Gly His His Leu Ala Tyr Arg Thr Phe Phe Ala Leu Lys Gly
         20                  25                  30

Leu Thr Thr Ser Arg Gly Glu Pro Val Gln Ala Val Tyr Gly Phe Ala
             35                  40                  45

Lys Ser Leu Leu Lys Ala Leu Lys Glu Asp Gly Tyr Lys Ala Val Phe
 50                  55                  60

Val Val Phe Asp Ala Lys Ala Pro Ser Phe Arg His Glu Ala Tyr Glu
 65                  70                  75                  80

Ala Tyr Lys Ala Gly Arg Ala Pro Thr Pro Glu Asp Phe Pro Arg Gln
                 85                  90                  95

Leu Ala Leu Ile Lys Glu Leu Val Asp Leu Leu Gly Phe Thr Arg Leu
            100                 105                 110

Glu Val Pro Gly Phe Glu Ala Asp Asp Val Leu Ala Thr Leu Ala Lys
            115                 120                 125

Lys Ala Glu Arg Glu Gly Tyr Glu Val Arg Ile Leu Thr Ala Asp Arg
130                 135                 140

Asp Leu Tyr Gln Leu Val Ser Asp Arg Val Ala Val Leu His Pro Glu
145                 150                 155                 160

Gly His Leu Ile Thr Pro Glu Trp Leu Trp Glu Lys Tyr Gly Leu Lys
                165                 170                 175

Pro Glu Gln Trp Val Asp Phe Arg Ala Leu Val Gly Asp Pro Ser Asp
            180                 185                 190

Asn Leu Pro Gly Val Lys Gly Ile Gly Glu Lys Thr Ala Leu Lys Leu
            195                 200                 205

Leu Lys Glu Trp Gly Ser Leu Glu Asn Ile Leu Lys Asn Leu Asp Arg
210                 215                 220

Val Lys Pro Glu Ser Val Arg Glu Arg Ile Lys Ala His Leu Glu Asp
225                 230                 235                 240

Leu Lys Leu Ser Leu Glu Leu Ser Arg Val Arg Ser Asp Leu Pro Leu
                245                 250                 255

Glu Val Asp Phe Ala Arg Arg Glu Pro Asp Arg Glu Gly Leu Arg
            260                 265                 270

Ala Phe Leu Glu Arg Leu Glu Phe Gly Ser Leu Leu His Glu Phe Gly
            275                 280                 285

Leu Leu Glu Glu Ser Glu Pro Val Gly Tyr Arg Ile Val Lys Asp Leu
            290                 295                 300

Val Glu Phe Glu Lys Leu Ile Glu Lys Leu Arg Glu Ser Pro Ser Phe
305                 310                 315                 320

Ala Ile Glu Leu Asp Thr Ser Ser Leu Asp Pro Phe Asp Cys Asp Ile
                325                 330                 335

Val Gly Ile Ser Val Ser Phe Lys Pro Lys Glu Ala Tyr Tyr Ile Pro
            340                 345                 350

Leu His His Arg Asn Ala Gln Asn Leu Asp Glu Lys Glu Val Leu Lys
            355                 360                 365

Lys Leu Lys Glu Ile Leu Glu Asp Pro Gly Ala Lys Ile Val Gly Gln
370                 375                 380

Asn Leu Lys Phe Asp Tyr Lys Val Leu Met Val Lys Gly Val Glu Pro
385                 390                 395                 400

Val Pro Pro Tyr Phe Asp Thr Met Ile Ala Ala Tyr Leu Leu Glu Pro
                405                 410                 415

Asn Glu Lys Lys Phe Asn Leu Asp Asp Leu Ala Leu Lys Phe Leu Gly
            420                 425                 430
```

```
Tyr Lys Met Thr Ser Tyr Gln Glu Leu Met Ser Phe Ser Phe Pro Leu
        435                 440                 445

Phe Gly Phe Ser Phe Ala Asp Val Pro Val Glu Lys Ala Ala Asn Tyr
        450                 455                 460

Ser Cys Glu Asp Ala Asp Ile Thr Tyr Arg Leu Tyr Lys Thr Leu Ser
465                 470                 475                 480

Leu Lys Leu His Glu Glu Lys Leu Leu Trp Leu Tyr Gln Glu Val Glu
            485                 490                 495

Lys Pro Leu Ser Arg Val Leu Ala His Met Glu Ala Thr Gly Val Arg
                500                 505                 510

Leu Asp Val Ala Tyr Leu Lys Ala Leu Ser Leu Glu Leu Ala Glu Glu
        515                 520                 525

Ile Arg Arg Leu Glu Glu Val Phe Arg Leu Ala Gly His Pro Phe
        530                 535                 540

Asn Leu Asn Ser Arg Asp Gln Leu Glu Arg Val Leu Phe Asp Glu Leu
545                 550                 555                 560

Arg Leu Pro Ala Leu Gly Lys Thr Gln Lys Thr Gly Lys Arg Ser Thr
                565                 570                 575

Ser Ala Ala Val Leu Glu Ala Leu Arg Glu Ala His Pro Ile Val Glu
            580                 585                 590

Lys Ile Leu Gln His Arg Glu Leu Thr Lys Leu Lys Asn Thr Tyr Val
        595                 600                 605

Asp Pro Leu Pro Gly Leu Val His Pro Arg Thr Gly Arg Leu His Thr
        610                 615                 620

Arg Phe Asn Gln Thr Ala Thr Ala Thr Gly Arg Leu Ser Ser Ser Asp
625                 630                 635                 640

Pro Asn Leu Gln Asn Ile Pro Ile Arg Thr Pro Leu Gly Gln Arg Ile
                645                 650                 655

Arg Arg Ala Phe Val Ala Glu Ala Gly Trp Ala Leu Val Ala Leu Asp
            660                 665                 670

Tyr Ser Gln Ile Glu Leu Arg Val Leu Ala His Leu Ser Gly Asp Glu
        675                 680                 685

Asn Leu Ile Arg Val Phe Gln Glu Gly Lys Asp Ile His Thr Gln Thr
        690                 695                 700

Ala Ser Trp Met Phe Gly Val Ser Pro Glu Ala Val Asp Pro Leu Met
705                 710                 715                 720

Arg Arg Ala Ala Lys Thr Val Asn Phe Gly Val Leu Tyr Gly Met Ser
                725                 730                 735

Ala His Arg Leu Ser Gln Glu Leu Ala Ile Pro Tyr Glu Glu Ala Val
            740                 745                 750

Ala Phe Ile Glu Arg Tyr Phe Gln Ser Phe Pro Lys Val Arg Ala Trp
        755                 760                 765

Ile Glu Lys Thr Leu Glu Glu Gly Arg Lys Arg Gly Tyr Val Glu Thr
        770                 775                 780

Leu Phe Gly Arg Arg Arg Tyr Val Pro Asp Leu Asn Ala Arg Val Lys
785                 790                 795                 800

Ser Val Arg Glu Ala Ala Glu Arg Met Ala Phe Asn Met Pro Val Gln
                805                 810                 815

Gly Thr Ala Ala Asp Leu Met Lys Leu Ala Met Val Lys Leu Phe Pro
            820                 825                 830

His Leu Arg Glu Met Gly Ala Arg Met Leu Leu Gln Val His Asp Glu
        835                 840                 845

Leu Leu Leu Glu Ala Pro Gln Ala Arg Ala Glu Glu Val Ala Ala Leu
```

```
                850                 855                 860
Ala Lys Glu Ala Met Glu Lys Ala Tyr Pro Leu Ala Val Pro Leu Glu
865                 870                 875                 880

Val Glu Val Gly Ile Gly Glu Asp Trp Leu Ser Ala Lys Gly
                885                 890
```

<210> SEQ ID NO 169
<211> LENGTH: 197
<212> TYPE: PRT
<213> ORGANISM: Artificial sequence
<220> FEATURE:
<223> OTHER INFORMATION: Exonucleolytic domain of chimeric DNA
      polymerase CS8 after second round of mutagenesis residues 323-325
      ELE substitution

<400> SEQUENCE: 169

```
Glu Glu Ser Glu Pro Val Gly Tyr Arg Ile Val Lys Asp Leu Val Glu
1               5                   10                  15

Phe Glu Lys Leu Ile Glu Lys Leu Arg Glu Ser Pro Ser Phe Ala Ile
                20                  25                  30

Glu Leu Glu Thr Ser Ser Leu Asp Pro Phe Asp Cys Asp Ile Val Gly
            35                  40                  45

Ile Ser Val Ser Phe Lys Pro Lys Glu Ala Tyr Tyr Ile Pro Leu His
        50                  55                  60

His Arg Asn Ala Gln Asn Leu Asp Glu Lys Glu Val Leu Lys Lys Leu
65                  70                  75                  80

Lys Glu Ile Leu Glu Asp Pro Gly Ala Lys Ile Val Gly Gln Asn Leu
                85                  90                  95

Lys Phe Asp Tyr Lys Val Leu Met Val Lys Gly Val Glu Pro Val Pro
            100                 105                 110

Pro Tyr Phe Asp Thr Met Ile Ala Ala Tyr Leu Leu Glu Pro Asn Glu
        115                 120                 125

Lys Lys Phe Asn Leu Asp Asp Leu Ala Leu Lys Phe Leu Gly Tyr Lys
    130                 135                 140

Met Thr Ser Tyr Gln Glu Leu Met Ser Phe Ser Phe Pro Leu Phe Gly
145                 150                 155                 160

Phe Ser Phe Ala Asp Val Pro Val Glu Lys Ala Ala Asn Tyr Ser Cys
                165                 170                 175

Glu Asp Ala Asp Ile Thr Tyr Arg Leu Tyr Lys Thr Leu Ser Leu Lys
            180                 185                 190

Leu His Glu Glu Lys
        195
```

<210> SEQ ID NO 170
<211> LENGTH: 894
<212> TYPE: PRT
<213> ORGANISM: Artificial sequence
<220> FEATURE:
<223> OTHER INFORMATION: chimeric DNA polymerase CS8 after second round
      of mutagenesis residues 323-325 ELE substitution

<400> SEQUENCE: 170

```
Met Lys Ala Met Leu Pro Leu Phe Glu Pro Lys Gly Arg Val Leu Leu
1               5                   10                  15

Val Asp Gly His His Leu Ala Tyr Arg Thr Phe Phe Ala Leu Lys Gly
                20                  25                  30

Leu Thr Thr Ser Arg Gly Glu Pro Val Gln Ala Val Tyr Gly Phe Ala
            35                  40                  45
```

```
Lys Ser Leu Leu Lys Ala Leu Lys Glu Asp Gly Tyr Lys Ala Val Phe
    50                  55                  60

Val Val Phe Asp Ala Lys Ala Pro Ser Phe Arg His Glu Ala Tyr Glu
65                  70                  75                  80

Ala Tyr Lys Ala Gly Arg Ala Pro Thr Pro Glu Asp Phe Pro Arg Gln
                85                  90                  95

Leu Ala Leu Ile Lys Glu Leu Val Asp Leu Leu Gly Phe Thr Arg Leu
            100                 105                 110

Glu Val Pro Gly Phe Glu Ala Asp Asp Val Leu Ala Thr Leu Ala Lys
        115                 120                 125

Lys Ala Glu Arg Glu Gly Tyr Glu Val Arg Ile Leu Thr Ala Asp Arg
130                 135                 140

Asp Leu Tyr Gln Leu Val Ser Asp Arg Val Ala Val Leu His Pro Glu
145                 150                 155                 160

Gly His Leu Ile Thr Pro Glu Trp Leu Trp Glu Lys Tyr Gly Leu Lys
                165                 170                 175

Pro Glu Gln Trp Val Asp Phe Arg Ala Leu Val Gly Asp Pro Ser Asp
            180                 185                 190

Asn Leu Pro Gly Val Lys Gly Ile Gly Glu Lys Thr Ala Leu Lys Leu
        195                 200                 205

Leu Lys Glu Trp Gly Ser Leu Glu Asn Ile Leu Lys Asn Leu Asp Arg
210                 215                 220

Val Lys Pro Glu Ser Val Arg Glu Arg Ile Lys Ala His Leu Glu Asp
225                 230                 235                 240

Leu Lys Leu Ser Leu Glu Leu Ser Arg Val Arg Ser Asp Leu Pro Leu
                245                 250                 255

Glu Val Asp Phe Ala Arg Arg Arg Glu Pro Asp Arg Glu Gly Leu Arg
            260                 265                 270

Ala Phe Leu Glu Arg Leu Glu Phe Gly Ser Leu Leu His Glu Phe Gly
        275                 280                 285

Leu Leu Glu Glu Ser Glu Pro Val Gly Tyr Arg Ile Val Lys Asp Leu
290                 295                 300

Val Glu Phe Glu Lys Leu Ile Glu Lys Leu Arg Glu Ser Pro Ser Phe
305                 310                 315                 320

Ala Ile Glu Leu Glu Thr Ser Ser Leu Asp Pro Phe Asp Cys Asp Ile
                325                 330                 335

Val Gly Ile Ser Val Ser Phe Lys Pro Lys Glu Ala Tyr Tyr Ile Pro
            340                 345                 350

Leu His His Arg Asn Ala Gln Asn Leu Asp Glu Lys Glu Val Leu Lys
        355                 360                 365

Lys Leu Lys Glu Ile Leu Glu Asp Pro Gly Ala Lys Ile Val Gly Gln
370                 375                 380

Asn Leu Lys Phe Asp Tyr Lys Val Leu Met Val Lys Gly Val Glu Pro
385                 390                 395                 400

Val Pro Pro Tyr Phe Asp Thr Met Ile Ala Ala Tyr Leu Leu Glu Pro
                405                 410                 415

Asn Glu Lys Lys Phe Asn Leu Asp Asp Leu Ala Leu Lys Phe Leu Gly
            420                 425                 430

Tyr Lys Met Thr Ser Tyr Gln Glu Leu Met Ser Phe Ser Phe Pro Leu
        435                 440                 445

Phe Gly Phe Ser Phe Ala Asp Val Pro Val Glu Lys Ala Ala Asn Tyr
450                 455                 460

Ser Cys Glu Asp Ala Asp Ile Thr Tyr Arg Leu Tyr Lys Thr Leu Ser
```

-continued

```
            465                 470                 475                 480
Leu Lys Leu His Glu Glu Lys Leu Leu Trp Leu Tyr Gln Glu Val Glu
                    485                 490                 495
Lys Pro Leu Ser Arg Val Leu Ala His Met Glu Ala Thr Gly Val Arg
                500                 505                 510
Leu Asp Val Ala Tyr Leu Lys Ala Leu Ser Leu Glu Leu Ala Glu Glu
            515                 520                 525
Ile Arg Arg Leu Glu Glu Val Phe Arg Leu Ala Gly His Pro Phe
        530                 535                 540
Asn Leu Asn Ser Arg Asp Gln Leu Glu Arg Val Leu Phe Asp Glu Leu
545                 550                 555                 560
Arg Leu Pro Ala Leu Gly Lys Thr Gln Lys Thr Gly Lys Arg Ser Thr
                565                 570                 575
Ser Ala Ala Val Leu Glu Ala Leu Arg Glu Ala His Pro Ile Val Glu
                580                 585                 590
Lys Ile Leu Gln His Arg Glu Leu Thr Lys Leu Lys Asn Thr Tyr Val
            595                 600                 605
Asp Pro Leu Pro Gly Leu Val His Pro Arg Thr Gly Arg Leu His Thr
        610                 615                 620
Arg Phe Asn Gln Thr Ala Thr Ala Thr Gly Arg Leu Ser Ser Ser Asp
625                 630                 635                 640
Pro Asn Leu Gln Asn Ile Pro Ile Arg Thr Pro Leu Gly Gln Arg Ile
                645                 650                 655
Arg Arg Ala Phe Val Ala Glu Ala Gly Trp Ala Leu Val Ala Leu Asp
                660                 665                 670
Tyr Ser Gln Ile Glu Leu Arg Val Leu Ala His Leu Ser Gly Asp Glu
            675                 680                 685
Asn Leu Ile Arg Val Phe Gln Glu Gly Lys Asp Ile His Thr Gln Thr
        690                 695                 700
Ala Ser Trp Met Phe Gly Val Ser Pro Glu Ala Val Asp Pro Leu Met
705                 710                 715                 720
Arg Arg Ala Ala Lys Thr Val Asn Phe Gly Val Leu Tyr Gly Met Ser
                725                 730                 735
Ala His Arg Leu Ser Gln Glu Leu Ala Ile Pro Tyr Glu Glu Ala Val
                740                 745                 750
Ala Phe Ile Glu Arg Tyr Phe Gln Ser Phe Pro Lys Val Arg Ala Trp
            755                 760                 765
Ile Glu Lys Thr Leu Glu Glu Gly Arg Lys Arg Gly Tyr Val Glu Thr
        770                 775                 780
Leu Phe Gly Arg Arg Arg Tyr Val Pro Asp Leu Asn Ala Arg Val Lys
785                 790                 795                 800
Ser Val Arg Glu Ala Ala Glu Arg Met Ala Phe Asn Met Pro Val Gln
                805                 810                 815
Gly Thr Ala Ala Asp Leu Met Lys Leu Ala Met Val Lys Leu Phe Pro
                820                 825                 830
His Leu Arg Glu Met Gly Ala Arg Met Leu Leu Gln Val His Asp Glu
            835                 840                 845
Leu Leu Leu Glu Ala Pro Gln Ala Arg Ala Glu Glu Val Ala Ala Leu
        850                 855                 860
Ala Lys Glu Ala Met Glu Lys Ala Tyr Pro Leu Ala Val Pro Leu Glu
865                 870                 875                 880
Val Glu Val Gly Ile Gly Glu Asp Trp Leu Ser Ala Lys Gly
                885                 890
```

-continued

<210> SEQ ID NO 171
<211> LENGTH: 2685
<212> TYPE: DNA
<213> ORGANISM: Artificial sequence
<220> FEATURE:
<223> OTHER INFORMATION: Nucleic acid encoding chimeric thermostable DNA
      polymerase CS8

<400> SEQUENCE: 171

| | | | | | |
|---|---|---|---|---|---|
| atgaaagcta | tgttaccatt | attcgaaccc | aaaggccggg | tcctcctggt | ggacggccac | 60 |
| cacctggcct | accgcacctt | cttcgccctg | aagggcctca | ccacgagccg | ggcgaaccg | 120 |
| gtgcaggcgg | tttacggctt | cgccaagagc | ctcctcaagg | ccctgaagga | ggacgggtac | 180 |
| aaggccgtct | tcgtggtctt | tgacgccaag | gcccccttcct | tccgccacga | ggcctacgag | 240 |
| gcctacaagg | caggccgcgc | ccgaccccc | gaggacttcc | ccggcagct | cgccctcatc | 300 |
| aaggagctgt | ggacctcct | ggggtttact | cgcctcgagg | ttccgggctt | tgaggcggac | 360 |
| gacgtcctcg | ccaccctggc | caagaaggcg | gaaagggagg | ggtacgaggt | gcgcatcctc | 420 |
| accgccgacc | gggaccttta | ccagctcgtc | tccgaccgcg | tcgccgtcct | caccccgag | 480 |
| ggccacctca | tcaccccgga | gtggcttgg | gagaagtacg | gccttaagcc | ggagcagtgg | 540 |
| gtggacttcc | gcgccctcgt | gggggacccc | tccgacaacc | tccccgggtg | caagggcatc | 600 |
| ggggagaaga | ccgccctcaa | gctcctcaag | gagtggggaa | gcctggaaaa | tatcctcaag | 660 |
| aacctggacc | gggtgaagcc | ggaaagcgtc | cgggaaagga | tcaaggccca | cctgaagac | 720 |
| cttaagctct | ccttggagct | tcccgggtg | cgctcggacc | tccccctgga | ggtggacttc | 780 |
| gcccggaggc | gggagcctga | ccgggaaggg | cttcgggcct | ttttggagcg | cttggagttc | 840 |
| ggcagcctcc | tccacgagtt | cggccttcta | gaggagtccg | aacccgttgg | gtaccgtata | 900 |
| gttaaagacc | tggttgaatt | tgaaaaactc | atagagaaac | tgagagaatc | tccttcgttc | 960 |
| gcgatcgctc | ttgcgactag | ttccctcgat | cctttcgact | gcgacattgt | cggtatctct | 1020 |
| gtgtctttca | accaaagga | agcgtactac | ataccactcc | atcatagaaa | cgcccagaac | 1080 |
| ctggacgaaa | aagaggttct | gaaaaagctc | aaagaaattc | tggaggaccc | cggagcaaag | 1140 |
| atcgttggtc | agaatttgaa | attcgattac | aaggtgttga | tggtgaaggg | tgttgaacct | 1200 |
| gttcctcctt | acttcgacac | gatgatagcg | gcttaccttc | ttgagccgaa | cgaaaagaag | 1260 |
| ttcaatctgg | acgatctcgc | attgaaattt | cttggataca | aaatgacatc | ttaccaagag | 1320 |
| ctcatgtcct | tctctttcc | gctgtttggt | ttcagttttg | ccgatgttcc | tgtagaaaaa | 1380 |
| gcagcgaact | actcctgtga | agatgcagac | atcactaca | gactttacaa | gaccctgagc | 1440 |
| ttaaaactcc | acgaggaaaa | gcttctttgg | ctctaccaag | aggtggaaaa | gcccctctcc | 1500 |
| cgggtcctgg | cccacatgga | ggccaccggg | gtaaggctgg | acgtggccta | tctaaaggcc | 1560 |
| cttttccctgg | agcttgcgga | ggagattcgc | cgcctcgagg | aggaggtctt | ccgcctggcg | 1620 |
| ggccaccct | tcaacctgaa | ctcccgtgac | cagctagagc | gggtgctctt | tgacgagctt | 1680 |
| aggcttcccg | ccctgggcaa | gacgcaaaag | acggggaagc | gctccaccag | cgccgcggtg | 1740 |
| ctggaggccc | tcagggaggc | ccaccccatc | gtggagaaga | tcctccagca | ccgggagctc | 1800 |
| accaagctca | gaacacccta | cgtggacccc | tccccgggcc | tcgtccaccc | gaggacgggc | 1860 |
| cgcctccaca | cccgcttcaa | ccagacagcc | acggccacgg | gaaggctctc | tagctccgac | 1920 |
| cccaacctgc | agaacatccc | catccgcacc | cccttgggcc | agaggatccg | ccgggccttc | 1980 |
| gtggccgagg | cgggatgggc | gttggtggcc | ctggactata | gccagataga | gctccgggtc | 2040 |

```
ctcgcccacc tctccgggga cgagaacctg atcagggtct tccaggaggg gaaggacatc    2100
cacacccaga ccgcaagctg gatgttcggc gtctccccgg aggccgtgga ccccctgatg    2160
cgccgggcgg ccaagacggt gaacttcggc gtcctctacg gcatgtccgc catagggctc   2220
tcccaggagc ttgccatccc ctacgaggag gcggtggcct ttatagagcg ctacttccaa    2280 agcttccccca aggtgcgggc ctggataaga aagaccctgg aggaggggag gaagcggggc    2340
tacgtggaaa ccctcttcgg aagaaggcgc tacgtgcccg acctcaacgc ccgggtgaag    2400
agcgtcaggg aggccgcgga gcgcatggcc ttcaacatgc ccgtccaggg caccgccgcc    2460
gacctcatga agctcgccat ggtgaagctc ttccccccacc tccgggagat ggggggccccgc    2520 atgctcctcc aggtccacga cgagctcctc ctggaggccc cccaagcgcg ggccgaggag   2580
gtggcggctt tggccaagga ggccatggag aaggcctatc ccctcgccgt gcccctggag    2640
gtggaggtgg ggatcgggga ggactggctt tccgccaagg gctga                    2685
```

```
<210> SEQ ID NO 172
<211> LENGTH: 100
<212> TYPE: PRT
<213> ORGANISM: Thermus thermophilus

<400> SEQUENCE: 172

Ala Ala Cys Arg Asp Gly Arg Val His Arg Ala Asp Pro Leu Ala
1               5                  10                  15

Gly Leu Lys Asp Leu Lys Glu Val Arg Gly Leu Leu Ala Lys Asp Leu
            20                  25                  30

Ala Val Leu Ala Ser Arg Glu Gly Leu Asp Leu Val Pro Gly Asp Asp
        35                  40                  45

Pro Met Leu Leu Ala Tyr Leu Leu Asp Pro Ser Asn Thr Thr Pro Glu
    50                  55                  60

Gly Val Ala Arg Arg Tyr Gly Gly Glu Trp Thr Glu Asp Ala Ala His
65                  70                  75                  80

Arg Ala Leu Leu Ser Glu Arg Leu His Arg Asn Leu Leu Lys Arg Leu
                85                  90                  95

Glu Gly Glu Glu
            100
```

```
<210> SEQ ID NO 173
<211> LENGTH: 100
<212> TYPE: PRT
<213> ORGANISM: Thermus caldofilus

<400> SEQUENCE: 173

Ala Ala Cys Arg Asp Gly Arg Val His Arg Ala Asp Pro Leu Ala
1               5                  10                  15

Gly Leu Lys Asp Leu Lys Glu Val Arg Gly Leu Leu Ala Lys Asp Leu
            20                  25                  30

Ala Val Leu Ala Ser Arg Glu Gly Leu Asp Leu Val Pro Gly Asp Asp
        35                  40                  45

Pro Met Leu Leu Ala Tyr Leu Leu Asp Pro Ser Asn Thr Thr Pro Glu
    50                  55                  60

Gly Val Ala Arg Arg Tyr Gly Gly Glu Trp Thr Glu Asp Ala Ala His
65                  70                  75                  80

Arg Ala Leu Leu Ser Glu Arg Leu His Arg Asn Leu Leu Lys Arg Leu
                85                  90                  95

Gln Gly Glu Glu
```

<210> SEQ ID NO 174
<211> LENGTH: 100
<212> TYPE: PRT
<213> ORGANISM: Artificial sequence
<220> FEATURE:
<223> OTHER INFORMATION: DNA Polymerase from Z05

<400> SEQUENCE: 174

```
Ala Ala Cys Lys Glu Gly Arg Val His Arg Ala Lys Asp Pro Leu Ala
1               5                   10                  15
Gly Leu Lys Asp Leu Lys Glu Val Arg Gly Leu Leu Ala Lys Asp Leu
                20                  25                  30
Ala Val Leu Ala Leu Arg Glu Gly Leu Asp Leu Ala Pro Ser Asp Asp
            35                  40                  45
Pro Met Leu Leu Ala Tyr Leu Leu Asp Pro Ser Asn Thr Thr Pro Glu
    50                  55                  60
Gly Val Ala Arg Arg Tyr Gly Gly Glu Trp Thr Glu Asp Ala Ala His
65                  70                  75                  80
Arg Ala Leu Leu Ala Glu Arg Leu Gln Gln Asn Leu Leu Glu Arg Leu
                85                  90                  95
Lys Gly Glu Glu
            100
```

<210> SEQ ID NO 175
<211> LENGTH: 100
<212> TYPE: PRT
<213> ORGANISM: Thermus aquaticus

<400> SEQUENCE: 175

```
Ala Ala Ala Arg Gly Gly Arg Val His Arg Ala Pro Glu Pro Tyr Lys
1               5                   10                  15
Ala Leu Arg Asp Leu Lys Glu Ala Arg Gly Leu Leu Ala Lys Asp Leu
                20                  25                  30
Ser Val Leu Ala Leu Arg Glu Gly Leu Gly Leu Pro Pro Gly Asp Asp
            35                  40                  45
Pro Met Leu Leu Ala Tyr Leu Leu Asp Pro Ser Asn Thr Thr Pro Glu
    50                  55                  60
Gly Val Ala Arg Arg Tyr Gly Gly Glu Trp Thr Glu Glu Ala Gly Glu
65                  70                  75                  80
Arg Ala Ala Leu Ser Glu Arg Leu Phe Ala Asn Leu Trp Gly Arg Leu
                85                  90                  95
Glu Gly Glu Glu
            100
```

<210> SEQ ID NO 176
<211> LENGTH: 100
<212> TYPE: PRT
<213> ORGANISM: Thermus flavus

<400> SEQUENCE: 176

```
Ala Gly Ala Trp Glu Gly Arg Leu His Arg Ala Gln Asp Pro Leu Arg
1               5                   10                  15
Gly Leu Arg Asp Leu Lys Gly Val Arg Gly Ile Leu Ala Lys Asp Leu
                20                  25                  30
Ala Val Leu Ala Leu Arg Glu Gly Leu Asp Leu Phe Pro Glu Asp Asp
            35                  40                  45
```

```
Pro Met Leu Leu Ala Tyr Leu Leu Asp Pro Ser Asn Thr Thr Pro Glu
    50                  55                  60

Gly Val Ala Arg Arg Tyr Gly Gly Glu Trp Thr Glu Asp Ala Gly Glu
65                  70                  75                  80

Arg Ala Leu Leu Ala Glu Arg Leu Phe Gln Thr Leu Lys Glu Arg Leu
                85                  90                  95

Lys Gly Glu Glu
            100

<210> SEQ ID NO 177
<211> LENGTH: 100
<212> TYPE: PRT
<213> ORGANISM: Artificial sequence
<220> FEATURE:
<223> OTHER INFORMATION: DNA polymerase Tfi

<400> SEQUENCE: 177

Ala Gly Ala Lys Glu Gly Arg Val His Arg Ala Glu Asp Pro Val Gly
1               5                   10                  15

Ala Leu Lys Asp Leu Lys Glu Ile Arg Gly Leu Leu Ala Lys Asp Leu
            20                  25                  30

Ser Val Leu Ala Leu Arg Glu Gly Arg Glu Ile Pro Pro Gly Asp Asp
        35                  40                  45

Pro Met Leu Leu Ala Tyr Leu Leu Asp Pro Gly Asn Thr Asn Pro Glu
    50                  55                  60

Gly Val Ala Arg Arg Tyr Gly Gly Glu Trp Lys Glu Asp Ala Ala Ala
65                  70                  75                  80

Arg Ala Leu Leu Ser Glu Arg Leu Trp Gln Ala Leu Tyr Pro Arg Val
                85                  90                  95

Ala Glu Glu Glu
            100

<210> SEQ ID NO 178
<211> LENGTH: 100
<212> TYPE: PRT
<213> ORGANISM: Artificial sequence
<220> FEATURE:
<223> OTHER INFORMATION: DNA polymerase Sps17

<400> SEQUENCE: 178

Ala Gly Ala Lys Glu Gly Arg Val His Arg Ala Glu Asp Pro Val Gly
1               5                   10                  15

Ala Leu Lys Asp Leu Lys Glu Ile Arg Gly Leu Leu Ala Lys Asp Leu
            20                  25                  30

Ser Val Leu Ala Leu Arg Glu Gly Arg Glu Ile Pro Pro Gly Asp Asp
        35                  40                  45

Pro Met Leu Leu Ala Tyr Leu Leu Asp Pro Gly Asn Thr Asn Pro Glu
    50                  55                  60

Gly Val Ala Arg Arg Tyr Gly Gly Glu Trp Lys Glu Asp Ala Ala Ala
65                  70                  75                  80

Arg Ala Leu Leu Ser Glu Arg Leu Trp Gln Ala Leu Tyr Pro Arg Val
                85                  90                  95

Ala Glu Glu Glu
            100

<210> SEQ ID NO 179
<211> LENGTH: 118
<212> TYPE: PRT
<213> ORGANISM: Artificial sequence
```

<220> FEATURE:
<223> OTHER INFORMATION: DNA polymerase Dra

<400> SEQUENCE: 179

Thr Lys Lys Glu Gln Lys Ala Leu Glu Lys Ala Gln Lys Asp Ala Glu
1               5                   10                  15

Lys Ala Arg Ala Lys Leu Arg Glu Gln Phe Pro Ala Thr Val Asp Glu
            20                  25                  30

Ala Glu Phe Val Gly Gln Arg Thr Val Thr Ala Ala Ala Lys Ala
        35                  40                  45

Leu Ala Ala His Leu Ser Val Arg Gly Thr Val Glu Pro Gly Asp
    50                  55                  60

Asp Pro Leu Leu Tyr Ala Tyr Leu Leu Asp Pro Ala Asn Thr Asn Met
65                  70                  75                  80

Pro Val Val Ala Lys Arg Tyr Leu Asp Arg Glu Trp Pro Ala Asp Ala
                85                  90                  95

Pro Thr Arg Ala Ala Ile Thr Gly His Leu Val Arg Glu Leu Pro Pro
            100                 105                 110

Leu Leu Asp Asp Ala Arg
        115

<210> SEQ ID NO 180
<211> LENGTH: 129
<212> TYPE: PRT
<213> ORGANISM: Artificial sequence
<220> FEATURE:
<223> OTHER INFORMATION: DNA polymerase HSP-B-7

<400> SEQUENCE: 180

Asn Arg Leu Arg Asp Ala Thr Leu His Gly Val Ala Leu Ala Val Ala
1               5                   10                  15

Ser Asp Arg Ala Val Trp Leu Glu Leu Gly Gly Ser Leu Phe Leu Pro
            20                  25                  30

Glu Pro Leu Thr Arg Leu Leu Asn Asp Pro Gln Arg Ala Arg Ala Val
        35                  40                  45

Trp Asp Leu Lys Thr Glu Cys Leu Leu Leu Arg Gly Ala Gly Ile Asp
    50                  55                  60

Ala Arg Pro Ala His Phe Asp Ala Leu Leu Ala Ala Tyr Leu Trp Gln
65                  70                  75                  80

Pro Ser Arg Ala Ala Tyr Thr Leu Asp Trp Leu Cys Glu Asp Val Leu
                85                  90                  95

Arg Leu Arg Leu Pro Asp Asp Pro Ala Arg Pro Ala Ala Glu Ala
            100                 105                 110

Cys Ala Leu Leu Met Leu Gln Pro Arg Leu Arg Asp Ile Leu His Arg
        115                 120                 125

Glu

<210> SEQ ID NO 181
<211> LENGTH: 153
<212> TYPE: PRT
<213> ORGANISM: Artificial sequence
<220> FEATURE:
<223> OTHER INFORMATION: DNA polymerase Bst

<400> SEQUENCE: 181

Ala Leu Val Val Glu Val Val Gly Asp Asn Tyr His His Ala Pro Ile
1               5                   10                  15

Val Gly Ile Ala Leu Ala Asn Glu Arg Gly Arg Phe Phe Leu Arg Pro

```
               20                  25                  30
Glu Thr Ala Leu Ala Asp Pro Lys Phe Leu Ala Trp Leu Gly Asp Glu
            35                  40                  45

Thr Lys Lys Lys Thr Met Phe Asp Ser Lys Arg Ala Ala Val Ala Leu
 50                  55                  60

Lys Trp Lys Gly Ile Glu Leu Arg Gly Val Val Phe Asp Leu Leu Leu
 65                  70                  75                  80

Ala Ala Tyr Leu Leu Asp Pro Ala Gln Ala Gly Asp Val Ala Ala
            85                  90                  95

Val Ala Lys Met His Gln Tyr Glu Ala Val Arg Ser Asp Glu Ala Val
               100                 105                 110

Tyr Gly Lys Gly Ala Lys Arg Thr Val Pro Asp Glu Pro Thr Leu Ala
            115                 120                 125

Glu His Leu Ala Arg Lys Ala Ala Ile Trp Ala Leu Glu Glu Pro
        130                 135                 140

Leu Met Asp Glu Leu Arg Arg Asn Glu
145                 150
```

<210> SEQ ID NO 182
<211> LENGTH: 153
<212> TYPE: PRT
<213> ORGANISM: Artificial sequence
<220> FEATURE:
<223> OTHER INFORMATION: DNA polymerase Bca

<400> SEQUENCE: 182

```
Ala Leu Val Val Glu Val Val Glu Glu Asn Tyr His Asp Ala Pro Ile
 1               5                  10                  15

Val Gly Ile Ala Val Val Asn Glu His Gly Arg Phe Phe Leu Arg Pro
            20                  25                  30

Glu Thr Ala Leu Ala Asp Pro Gln Phe Val Ala Trp Leu Gly Asp Glu
            35                  40                  45

Thr Lys Lys Lys Ser Met Phe Asp Ser Lys Arg Ala Ala Val Ala Leu
 50                  55                  60

Lys Trp Lys Gly Ile Glu Leu Cys Gly Val Ser Phe Asp Leu Leu Leu
 65                  70                  75                  80

Ala Ala Tyr Leu Leu Asp Pro Ala Gln Gly Val Asp Asp Val Ala Ala
            85                  90                  95

Ala Ala Lys Met Lys Gln Tyr Glu Ala Val Arg Pro Asp Glu Ala Val
               100                 105                 110

Tyr Gly Lys Gly Ala Lys Arg Ala Val Pro Asp Glu Pro Val Leu Ala
            115                 120                 125

Glu His Leu Val Arg Lys Ala Ala Ile Trp Ala Leu Glu Arg Pro
        130                 135                 140

Phe Leu Asp Glu Leu Arg Arg Asn Glu
145                 150
```

<210> SEQ ID NO 183
<211> LENGTH: 174
<212> TYPE: PRT
<213> ORGANISM: Escherichia coli

<400> SEQUENCE: 183

```
Glu Lys Ala Pro Val Phe Ala Phe Asp Thr Glu Thr Asp Ser Leu Asp
 1               5                  10                  15

Asn Ile Ser Ala Asn Leu Val Gly Leu Ser Phe Ala Ile Glu Pro Gly
            20                  25                  30
```

```
Val Ala Ala Tyr Ile Pro Val Ala His Asp Tyr Leu Asp Ala Pro Asp
            35                  40                  45

Gln Ile Ser Arg Glu Arg Ala Leu Glu Leu Leu Lys Pro Leu Leu Glu
     50                  55                  60

Asp Glu Lys Ala Leu Lys Val Gly Gln Asn Leu Lys Tyr Asp Arg Gly
 65                  70                  75                  80

Ile Leu Ala Asn Tyr Gly Ile Glu Leu Arg Gly Ile Ala Phe Asp Thr
                 85                  90                  95

Met Leu Glu Ser Tyr Ile Leu Asn Ser Val Ala Gly Arg His Asp Met
            100                 105                 110

Asp Ser Leu Ala Glu Arg Trp Leu Lys His Lys Thr Ile Thr Phe Glu
        115                 120                 125

Glu Ile Ala Gly Lys Gly Lys Asn Gln Leu Thr Phe Asn Gln Ile Ala
    130                 135                 140

Leu Glu Glu Ala Gly Arg Tyr Ala Ala Glu Asp Ala Asp Val Thr Leu
145                 150                 155                 160

Gln Leu His Leu Lys Met Trp Pro Asp Leu Gln Lys His Lys
                165                 170

<210> SEQ ID NO 184
<211> LENGTH: 173
<212> TYPE: PRT
<213> ORGANISM: Artificial sequence
<220> FEATURE:
<223> OTHER INFORMATION: Thermatoga maritima

<400> SEQUENCE: 184

Arg Glu Ser Pro Ser Phe Ala Ile Asp Leu Glu Thr Ser Ser Leu Asp
1               5                   10                  15

Pro Phe Asp Cys Asp Ile Val Gly Ile Ser Val Ser Phe Lys Pro Lys
            20                  25                  30

Glu Ala Tyr Tyr Ile Pro Leu His His Arg Asn Ala Gln Asn Leu Asp
         35                  40                  45

Glu Lys Glu Val Leu Lys Lys Leu Lys Glu Ile Leu Glu Asp Pro Gly
     50                  55                  60

Ala Lys Ile Val Gly Gln Asn Leu Lys Phe Asp Tyr Lys Val Leu Met
 65                  70                  75                  80

Val Lys Gly Val Glu Pro Val Pro Pro Tyr Phe Asp Thr Met Ile Ala
                 85                  90                  95

Ala Tyr Leu Leu Glu Pro Asn Glu Lys Lys Phe Asn Leu Asp Asp Leu
            100                 105                 110

Ala Leu Lys Phe Leu Gly Tyr Lys Met Thr Ser Tyr Gln Glu Leu Met
        115                 120                 125

Ser Phe Ser Phe Pro Leu Phe Gly Phe Ser Phe Ala Asp Val Pro Val
    130                 135                 140

Glu Lys Ala Ala Asn Tyr Ser Cys Glu Asp Ala Asp Ile Thr Tyr Arg
145                 150                 155                 160

Leu Tyr Lys Thr Leu Ser Leu Lys Leu His Glu Ala Asp
                165                 170

<210> SEQ ID NO 185
<211> LENGTH: 173
<212> TYPE: PRT
<213> ORGANISM: Thermotoga neapolitana

<400> SEQUENCE: 185
```

```
Lys Glu Val Pro Ser Phe Ala Leu Asp Leu Glu Thr Ser Ser Leu Asp
1               5                   10                  15

Pro Phe Asn Cys Glu Ile Val Gly Ile Ser Val Ser Phe Lys Pro Lys
            20                  25                  30

Thr Ala Tyr Tyr Ile Pro Leu His His Arg Asn Ala His Asn Leu Asp
        35                  40                  45

Glu Thr Leu Val Leu Ser Lys Leu Lys Glu Ile Leu Glu Asp Pro Ser
    50                  55                  60

Ser Lys Ile Val Gly Gln Asn Leu Lys Tyr Asp Tyr Lys Val Leu Met
65                  70                  75                  80

Val Lys Gly Ile Ser Pro Val Tyr Pro His Phe Asp Thr Met Ile Ala
                85                  90                  95

Ala Tyr Leu Leu Glu Pro Asn Glu Lys Lys Phe Asn Leu Glu Asp Leu
            100                 105                 110

Ser Leu Lys Phe Leu Gly Tyr Lys Met Thr Ser Tyr Gln Glu Leu Met
            115                 120                 125

Ser Phe Ser Ser Pro Leu Phe Gly Phe Ser Phe Ala Asp Val Pro Val
        130                 135                 140

Asp Lys Ala Ala Glu Tyr Ser Cys Glu Asp Ala Asp Ile Thr Tyr Arg
145                 150                 155                 160

Leu Tyr Lys Ile Leu Ser Met Lys Leu His Glu Ala Glu
                165                 170

<210> SEQ ID NO 186
<211> LENGTH: 173
<212> TYPE: PRT
<213> ORGANISM: Thermosipho africanus

<400> SEQUENCE: 186

Glu Lys Tyr Lys Thr Phe Ser Ile Asp Thr Glu Thr Thr Ser Leu Asp
1               5                   10                  15

Pro Phe Glu Ala Lys Leu Val Gly Ile Ser Ile Ser Thr Met Glu Gly
            20                  25                  30

Lys Ala Tyr Tyr Ile Pro Val Ser His Phe Gly Ala Lys Asn Ile Ser
        35                  40                  45

Lys Ser Leu Ile Asp Lys Phe Leu Lys Gln Ile Leu Gln Glu Lys Asp
    50                  55                  60

Tyr Asn Ile Val Gly Gln Asn Leu Lys Phe Asp Tyr Glu Ile Phe Lys
65                  70                  75                  80

Ser Met Gly Phe Ser Pro Asn Val Pro His Phe Asp Thr Met Ile Ala
                85                  90                  95

Ala Tyr Leu Leu Asn Pro Asp Glu Lys Arg Phe Asn Leu Glu Glu Leu
            100                 105                 110

Ser Leu Lys Tyr Leu Gly Tyr Lys Met Ile Ser Phe Asp Glu Leu Val
            115                 120                 125

Asn Glu Asn Val Pro Leu Phe Gly Asn Asp Phe Ser Tyr Val Pro Leu
        130                 135                 140

Glu Arg Ala Val Glu Tyr Ser Cys Glu Asp Ala Asp Val Thr Tyr Arg
145                 150                 155                 160

Ile Phe Arg Lys Leu Gly Arg Lys Ile Tyr Glu Asn Glu
                165                 170

<210> SEQ ID NO 187
<211> LENGTH: 168
<212> TYPE: PRT
<213> ORGANISM: Artificial sequence
```

```
<220> FEATURE:
<223> OTHER INFORMATION: DNA polymerase HSP-A

<400> SEQUENCE: 187

Leu Ala Cys Ser Gly Ile Val Ala Trp Asp Thr Glu Thr Thr Ser Leu
1               5                   10                  15

Asp Pro Arg Asp Ala Gln Leu Val Gly Ile Gly Cys Cys Trp Ser Glu
            20                  25                  30

Arg Asp Val Ala Tyr Leu Pro Ile Gly His Arg Gln Gly Ser Asn Leu
        35                  40                  45

Asp Trp Asn Leu Val Lys Gln Ser Leu Gln Pro Ile Trp Glu Asp Pro
    50                  55                  60

Ser Arg Pro Lys Ser Leu Gln Asn Cys Lys Tyr Asp Leu Ser Ile Phe
65                  70                  75                  80

Arg Ala His Gly Ile Arg Leu Gln Gly Ile Gln Phe Asp Pro Met Leu
                85                  90                  95

Ala Ser Tyr Val Leu Asn Pro Glu Ala Ser His Asn Leu Ala Asp Leu
            100                 105                 110

Ala Ala Thr Tyr Leu Asn Leu Pro Thr Thr Ala Ser His Glu Leu Leu
        115                 120                 125

Gly Lys Ala Glu Ser Ile Ala Asp Leu Pro Ile Pro Lys Val Ala Glu
    130                 135                 140

Tyr Cys Gly Thr Asp Ala Tyr Cys Ala Tyr Arg Leu Val Pro Ile Leu
145                 150                 155                 160

Thr Glu Lys Leu Gln Gln Thr Asp
                165

<210> SEQ ID NO 188
<211> LENGTH: 9
<212> TYPE: PRT
<213> ORGANISM: Artificial sequence
<220> FEATURE:
<223> OTHER INFORMATION: EXO II motif from Tma DNA polymerase

<400> SEQUENCE: 188

Gln Asn Leu Lys Phe Asp Tyr Lys Val
1               5

<210> SEQ ID NO 189
<211> LENGTH: 11
<212> TYPE: PRT
<213> ORGANISM: Artificial sequence
<220> FEATURE:
<223> OTHER INFORMATION: EXO IIa motif from Tma DNA polymerase

<400> SEQUENCE: 189

Asp Thr Met Ile Ala Ala Tyr Leu Leu Glu Pro
1               5                   10

<210> SEQ ID NO 190
<211> LENGTH: 13
<212> TYPE: PRT
<213> ORGANISM: Artificial sequence
<220> FEATURE:
<223> OTHER INFORMATION: EXO III motif from Tma DNA polymerase

<400> SEQUENCE: 190

Pro Val Glu Lys Ala Ala Asn Tyr Ser Cys Glu Asp Ala
1               5                   10

<210> SEQ ID NO 191
```

-continued

```
<211> LENGTH: 773
<212> TYPE: PRT
<213> ORGANISM: Thermococcus gorgonarius

<400> SEQUENCE: 191

Met Ile Leu Asp Thr Asp Tyr Ile Thr Glu Asp Gly Lys Pro Val Ile
1               5                   10                  15

Arg Ile Phe Lys Lys Glu Asn Gly Glu Phe Lys Ile Asp Tyr Asp Arg
            20                  25                  30

Asn Phe Glu Pro Tyr Ile Tyr Ala Leu Leu Lys Asp Asp Ser Ala Ile
        35                  40                  45

Glu Asp Val Lys Lys Ile Thr Ala Glu Arg His Gly Thr Thr Val Arg
    50                  55                  60

Val Val Arg Ala Glu Lys Val Lys Lys Phe Leu Gly Arg Pro Ile
65                  70                  75                  80

Glu Val Trp Lys Leu Tyr Phe Thr His Pro Gln Asp Val Pro Ala Ile
                85                  90                  95

Arg Asp Lys Ile Lys Glu His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Lys Met Leu Ala Phe Asp Ile Glu Thr
    130                 135                 140

Leu Tyr His Glu Gly Glu Glu Phe Ala Glu Gly Pro Ile Leu Met Ile
145                 150                 155                 160

Ser Tyr Ala Asp Glu Glu Gly Ala Arg Val Ile Thr Trp Lys Asn Ile
                165                 170                 175

Asp Leu Pro Tyr Val Asp Val Val Ser Thr Glu Lys Glu Met Ile Lys
            180                 185                 190

Arg Phe Leu Lys Val Val Lys Glu Lys Asp Pro Asp Val Leu Ile Thr
        195                 200                 205

Tyr Asn Gly Asp Asn Phe Asp Phe Ala Tyr Leu Lys Lys Arg Ser Glu
    210                 215                 220

Lys Leu Gly Val Lys Phe Ile Leu Gly Arg Glu Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Ile Phe Gly Gln Pro Lys Glu
        275                 280                 285

Lys Val Tyr Ala Glu Glu Ile Ala Gln Ala Trp Glu Thr Gly Glu Gly
    290                 295                 300

Leu Glu Arg Val Ala Arg Tyr Ser Met Glu Asp Ala Lys Val Thr Tyr
305                 310                 315                 320

Glu Leu Gly Lys Glu Phe Phe Pro Met Glu Ala Gln Leu Ser Arg Leu
                325                 330                 335

Val Gly Gln Ser Leu Trp Asp Val Ser Arg Ser Ser Thr Gly Asn Leu
            340                 345                 350

Val Glu Trp Phe Leu Leu Arg Lys Ala Tyr Glu Arg Asn Glu Leu Ala
        355                 360                 365

Pro Asn Lys Pro Asp Glu Arg Glu Leu Ala Arg Arg Arg Glu Ser Tyr
    370                 375                 380

Ala Gly Gly Tyr Val Lys Glu Pro Glu Arg Gly Leu Trp Glu Asn Ile
```

```
                385                 390                 395                 400
Val Tyr Leu Asp Phe Arg Ser Leu Tyr Pro Ser Ile Ile Ile Thr His
                    405                 410                 415
Asn Val Ser Pro Asp Thr Leu Asn Arg Glu Gly Cys Glu Glu Tyr Asp
                420                 425                 430
Val Ala Pro Gln Val Gly His Lys Phe Cys Lys Asp Phe Pro Gly Phe
            435                 440                 445
Ile Pro Ser Leu Leu Gly Asp Leu Leu Glu Glu Arg Gln Lys Val Lys
        450                 455                 460
Lys Lys Met Lys Ala Thr Ile Asp Pro Ile Glu Lys Lys Leu Leu Asp
465                 470                 475                 480
Tyr Arg Gln Arg Ala Ile Lys Ile Leu Ala Asn Ser Phe Tyr Gly Tyr
                485                 490                 495
Tyr Gly Tyr Ala Lys Ala Arg Trp Tyr Cys Lys Glu Cys Ala Glu Ser
                500                 505                 510
Val Thr Ala Trp Gly Arg Gln Tyr Ile Glu Thr Thr Ile Arg Glu Ile
            515                 520                 525
Glu Glu Lys Phe Gly Phe Lys Val Leu Tyr Ala Asp Thr Asp Gly Phe
        530                 535                 540
Phe Ala Thr Ile Pro Gly Ala Asp Ala Glu Thr Val Lys Lys Lys Ala
545                 550                 555                 560
Lys Glu Phe Leu Asp Tyr Ile Asn Ala Lys Leu Pro Gly Leu Leu Glu
                565                 570                 575
Leu Glu Tyr Glu Gly Phe Tyr Lys Arg Gly Phe Phe Val Thr Lys Lys
                580                 585                 590
Lys Tyr Ala Val Ile Asp Glu Glu Asp Lys Ile Thr Thr Arg Gly Leu
            595                 600                 605
Glu Ile Val Arg Arg Asp Trp Ser Glu Ile Ala Lys Glu Thr Gln Ala
        610                 615                 620
Arg Val Leu Glu Ala Ile Leu Lys His Gly Asp Val Glu Glu Ala Val
625                 630                 635                 640
Arg Ile Val Lys Glu Val Thr Glu Lys Leu Ser Lys Tyr Glu Val Pro
                645                 650                 655
Pro Glu Lys Leu Val Ile Tyr Glu Gln Ile Thr Arg Asp Leu Lys Asp
                660                 665                 670
Tyr Lys Ala Thr Gly Pro His Val Ala Val Ala Lys Arg Leu Ala Ala
            675                 680                 685
Arg Gly Ile Lys Ile Arg Pro Gly Thr Val Ile Ser Tyr Ile Val Leu
        690                 695                 700
Lys Gly Ser Gly Arg Ile Gly Asp Arg Ala Ile Pro Phe Asp Glu Phe
705                 710                 715                 720
Asp Pro Ala Lys His Lys Tyr Asp Ala Glu Tyr Tyr Ile Glu Asn Gln
                725                 730                 735
Val Leu Pro Ala Val Glu Arg Ile Leu Arg Ala Phe Gly Tyr Arg Lys
                740                 745                 750
Glu Asp Leu Arg Tyr Gln Lys Thr Arg Gln Val Gly Leu Gly Ala Trp
            755                 760                 765
Leu Lys Pro Lys Thr
    770

<210> SEQ ID NO 192
<211> LENGTH: 863
<212> TYPE: PRT
<213> ORGANISM: Pyrococcus furiosus
```

```
<220> FEATURE:
<221> NAME/KEY: misc_feature
<222> LOCATION: (789)..(789)
<223> OTHER INFORMATION: Xaa can be any naturally occurring amino acid
<220> FEATURE:
<221> NAME/KEY: misc_feature
<222> LOCATION: (795)..(795)
<223> OTHER INFORMATION: Xaa can be any naturally occurring amino acid
<220> FEATURE:
<221> NAME/KEY: misc_feature
<222> LOCATION: (804)..(804)
<223> OTHER INFORMATION: Xaa can be any naturally occurring amino acid
<220> FEATURE:
<221> NAME/KEY: misc_feature
<222> LOCATION: (832)..(832)
<223> OTHER INFORMATION: Xaa can be any naturally occurring amino acid

<400> SEQUENCE: 192

Met Ile Leu Asp Val Asp Tyr Ile Thr Glu Glu Gly Lys Pro Val Ile
1               5                   10                  15

Arg Leu Phe Lys Lys Glu Asn Gly Lys Phe Lys Ile Glu His Asp Arg
            20                  25                  30

Thr Phe Arg Pro Tyr Ile Tyr Ala Leu Leu Arg Asp Asp Ser Lys Ile
        35                  40                  45

Glu Glu Val Lys Lys Ile Thr Gly Glu Arg His Gly Lys Ile Val Arg
    50                  55                  60

Ile Val Asp Val Glu Lys Val Glu Lys Phe Leu Gly Lys Pro Ile
65                  70                  75                  80

Thr Val Trp Lys Leu Tyr Leu Glu His Pro Gln Asp Val Pro Thr Ile
                85                  90                  95

Arg Glu Lys Val Arg Glu His Pro Ala Val Val Asp Ile Phe Glu Tyr
            100                 105                 110

Asp Ile Pro Phe Ala Lys Arg Tyr Leu Ile Asp Lys Gly Leu Ile Pro
        115                 120                 125

Met Glu Gly Glu Glu Leu Lys Ile Leu Ala Phe Asp Ile Glu Thr
    130                 135                 140

Leu Tyr His Glu Gly Glu Glu Phe Gly Lys Gly Pro Ile Ile Met Ile
145                 150                 155                 160

Ser Tyr Ala Asp Glu Asn Glu Ala Lys Val Ile Thr Trp Lys Asn Ile
                165                 170                 175

Asp Leu Pro Tyr Val Glu Val Val Ser Ser Glu Arg Glu Met Ile Lys
            180                 185                 190

Arg Phe Leu Arg Ile Ile Arg Glu Lys Asp Pro Asp Ile Ile Val Thr
        195                 200                 205

Tyr Asn Gly Asp Ser Phe Asp Phe Pro Tyr Leu Ala Lys Arg Ala Glu
    210                 215                 220

Lys Leu Gly Ile Lys Leu Thr Ile Gly Arg Asp Gly Ser Glu Pro Lys
225                 230                 235                 240

Met Gln Arg Ile Gly Asp Met Thr Ala Val Glu Val Lys Gly Arg Ile
                245                 250                 255

His Phe Asp Leu Tyr His Val Ile Thr Arg Thr Ile Asn Leu Pro Thr
            260                 265                 270

Tyr Thr Leu Glu Ala Val Tyr Glu Ala Ile Phe Gly Lys Pro Lys Glu
        275                 280                 285

Lys Val Tyr Ala Asp Glu Ile Ala Lys Ala Trp Glu Ser Gly Glu Asn
    290                 295                 300

Leu Glu Arg Val Ala Lys Tyr Ser Met Glu Asp Ala Lys Ala Thr Tyr
305                 310                 315                 320
```

-continued

```
Glu Leu Gly Lys Glu Phe Leu Pro Met Glu Ile Gln Leu Ser Arg Leu
            325                 330                 335

Val Gly Gln Pro Leu Trp Asp Val Ser Arg Ser Ser Thr Gly Asn Leu
        340                 345                 350

Val Glu Trp Phe Leu Leu Arg Lys Ala Tyr Glu Arg Asn Glu Val Ala
            355                 360                 365

Pro Asn Lys Pro Ser Glu Glu Tyr Gln Arg Arg Leu Arg Glu Ser
    370                 375                 380

Tyr Thr Gly Gly Phe Val Lys Glu Pro Glu Lys Gly Leu Trp Glu Asn
385                 390                 395                 400

Ile Val Tyr Leu Asp Phe Arg Ala Leu Tyr Pro Ser Ile Ile Ile Thr
                405                 410                 415

His Asn Val Ser Pro Asp Thr Leu Asn Leu Glu Gly Cys Lys Asn Tyr
            420                 425                 430

Asp Ile Ala Pro Gln Val Gly His Lys Phe Cys Lys Asp Ile Pro Gly
        435                 440                 445

Phe Ile Pro Ser Leu Leu Gly His Leu Leu Glu Glu Arg Gln Lys Ile
    450                 455                 460

Lys Thr Lys Met Lys Glu Thr Gln Asp Pro Ile Glu Lys Ile Leu Leu
465                 470                 475                 480

Asp Tyr Arg Gln Lys Ala Ile Lys Leu Leu Ala Asn Ser Phe Tyr Gly
                485                 490                 495

Tyr Tyr Gly Tyr Ala Lys Ala Arg Trp Tyr Cys Lys Glu Cys Ala Glu
            500                 505                 510

Ser Val Thr Ala Trp Gly Arg Lys Tyr Ile Glu Leu Val Trp Lys Glu
        515                 520                 525

Leu Glu Glu Lys Phe Gly Phe Lys Val Leu Tyr Ile Asp Thr Asp Gly
    530                 535                 540

Leu Tyr Ala Thr Ile Pro Gly Gly Glu Ser Glu Glu Ile Lys Lys Lys
545                 550                 555                 560

Ala Leu Glu Phe Val Lys Tyr Ile Asn Ser Lys Leu Pro Gly Leu Leu
                565                 570                 575

Glu Leu Glu Tyr Glu Gly Phe Tyr Lys Arg Gly Phe Phe Val Thr Lys
            580                 585                 590

Lys Arg Tyr Ala Val Ile Asp Glu Glu Gly Lys Val Ile Thr Arg Gly
        595                 600                 605

Leu Glu Ile Val Arg Arg Asp Trp Ser Glu Ile Ala Lys Glu Thr Gln
    610                 615                 620

Ala Arg Val Leu Glu Thr Ile Leu Lys His Gly Asp Val Glu Glu Ala
625                 630                 635                 640

Val Arg Ile Val Lys Glu Val Ile Gln Lys Leu Ala Asn Tyr Glu Ile
                645                 650                 655

Pro Pro Glu Lys Leu Ala Ile Tyr Glu Gln Ile Thr Arg Pro Leu His
            660                 665                 670

Glu Tyr Lys Ala Ile Gly Pro His Val Ala Val Ala Lys Lys Leu Ala
        675                 680                 685

Ala Lys Gly Val Lys Ile Lys Pro Gly Met Val Ile Gly Tyr Ile Val
    690                 695                 700

Leu Arg Gly Asp Gly Pro Ile Ser Asn Arg Ala Ile Leu Ala Glu Glu
705                 710                 715                 720

Tyr Asp Pro Lys Lys His Lys Tyr Asp Ala Glu Tyr Tyr Ile Glu Asn
                725                 730                 735

Gln Val Leu Pro Ala Val Leu Arg Ile Leu Glu Gly Phe Gly Tyr Arg
```

```
                    740                 745                 750
Lys Glu Asp Leu Arg Tyr Gln Lys Thr Arg Gln Val Gly Leu Thr Ser
            755                 760                 765

Trp Leu Asn Ile Lys Lys Ser Thr Pro Trp Arg Lys Ile Asn Gly Trp
        770                 775                 780

Ile Thr His Phe Xaa Leu Leu Ser Glu Gln Xaa Glu Asn Cys Glu Ser
785                 790                 795                 800

Ser Glu Gln Xaa Glu Asn Cys Glu Ile Asn Ala Leu Ile Gly Asn Met
            805                 810                 815

Glu Asn Thr Ser Glu Thr Gly Thr Arg Cys His Glu Ser Glu Gln Xaa
            820                 825                 830

Glu Asn Cys Glu Ala Asn Ala Leu Tyr Ser Ile Ser Trp Glu Ile Asn
            835                 840                 845

Thr Glu Arg Phe Ala Cys Glu Met Ala Ile Asn Pro Ala Gly Glu
            850                 855                 860

<210> SEQ ID NO 193
<211> LENGTH: 775
<212> TYPE: PRT
<213> ORGANISM: Artificial sequence
<220> FEATURE:
<223> OTHER INFORMATION: DNA polymerase of Thermus sp. 9oN-7

<400> SEQUENCE: 193

Met Ile Leu Asp Thr Asp Tyr Ile Thr Glu Asn Gly Lys Pro Val Ile
1               5                   10                  15

Arg Val Phe Lys Lys Glu Asn Gly Glu Phe Lys Ile Glu Tyr Asp Arg
                20                  25                  30

Thr Phe Glu Pro Tyr Phe Tyr Ala Leu Leu Lys Asp Asp Ser Ala Ile
            35                  40                  45

Glu Asp Val Lys Lys Val Thr Ala Lys Arg His Gly Thr Val Val Lys
        50                  55                  60

Val Lys Arg Ala Glu Lys Val Gln Lys Lys Phe Leu Gly Arg Pro Ile
65                  70                  75                  80

Glu Val Trp Lys Leu Tyr Phe Asn His Pro Gln Asp Val Pro Ala Ile
                85                  90                  95

Arg Asp Arg Ile Arg Ala His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Thr Met Leu Ala Phe Asp Ile Glu Thr
    130                 135                 140

Leu Tyr His Glu Gly Glu Glu Phe Gly Thr Gly Pro Ile Leu Met Ile
145                 150                 155                 160

Ser Tyr Ala Asp Gly Ser Glu Ala Arg Val Ile Thr Trp Lys Lys Ile
                165                 170                 175

Asp Leu Pro Tyr Val Asp Val Val Ser Thr Glu Lys Glu Met Ile Lys
            180                 185                 190

Arg Phe Leu Arg Val Val Arg Glu Lys Asp Pro Asp Val Leu Ile Thr
        195                 200                 205

Tyr Asn Gly Asp Asn Phe Asp Phe Ala Tyr Leu Lys Lys Arg Cys Glu
    210                 215                 220

Glu Leu Gly Ile Lys Phe Thr Leu Gly Arg Asp Gly Ser Glu Pro Lys
225                 230                 235                 240

Ile Gln Arg Met Gly Asp Arg Phe Ala Val Glu Val Lys Gly Arg Ile
```

```
                    245                 250                 255
His Phe Asp Leu Tyr Pro Val Ile Arg Arg Thr Ile Asn Leu Pro Thr
                260                 265                 270
Tyr Thr Leu Glu Ala Val Tyr Glu Ala Val Phe Gly Lys Pro Lys Glu
                275                 280                 285
Lys Val Tyr Ala Glu Glu Ile Ala Gln Ala Trp Glu Ser Gly Glu Gly
                290                 295                 300
Leu Glu Arg Val Ala Arg Tyr Ser Met Glu Asp Ala Lys Val Thr Tyr
305                 310                 315                 320
Glu Leu Gly Arg Glu Phe Phe Pro Met Glu Ala Gln Leu Ser Arg Leu
                    325                 330                 335
Ile Gly Gln Ser Leu Trp Asp Val Ser Arg Ser Ser Thr Gly Asn Leu
                340                 345                 350
Val Glu Trp Phe Leu Leu Arg Lys Ala Tyr Lys Arg Asn Glu Leu Ala
                355                 360                 365
Pro Asn Lys Pro Asp Glu Arg Glu Leu Ala Arg Arg Gly Gly Tyr
                370                 375                 380
Ala Gly Gly Tyr Val Lys Glu Pro Glu Arg Gly Leu Trp Asp Asn Ile
385                 390                 395                 400
Val Tyr Leu Asp Phe Arg Ser Leu Tyr Pro Ser Ile Ile Thr His
                    405                 410                 415
Asn Val Ser Pro Asp Thr Leu Asn Arg Glu Gly Cys Lys Glu Tyr Asp
                420                 425                 430
Val Ala Pro Glu Val Gly His Lys Phe Cys Lys Asp Phe Pro Gly Phe
                435                 440                 445
Ile Pro Ser Leu Leu Gly Asp Leu Leu Glu Glu Arg Gln Lys Ile Lys
450                 455                 460
Arg Lys Met Lys Ala Thr Val Asp Pro Leu Glu Lys Lys Leu Leu Asp
465                 470                 475                 480
Tyr Arg Gln Arg Ala Ile Lys Ile Leu Ala Asn Ser Phe Tyr Gly Tyr
                    485                 490                 495
Tyr Gly Tyr Ala Lys Ala Arg Trp Tyr Cys Lys Glu Cys Ala Glu Ser
                500                 505                 510
Val Thr Ala Trp Gly Arg Glu Tyr Ile Glu Met Val Ile Arg Glu Leu
                515                 520                 525
Glu Glu Lys Phe Gly Phe Lys Val Leu Tyr Ala Asp Thr Asp Gly Leu
                530                 535                 540
His Ala Thr Ile Pro Gly Ala Asp Ala Glu Thr Val Lys Lys Lys Ala
545                 550                 555                 560
Lys Glu Phe Leu Lys Tyr Ile Asn Pro Lys Leu Pro Gly Leu Leu Glu
                    565                 570                 575
Leu Glu Tyr Glu Gly Phe Tyr Val Arg Gly Phe Phe Val Thr Lys Lys
                580                 585                 590
Lys Tyr Ala Val Ile Asp Glu Glu Gly Lys Ile Thr Thr Arg Gly Leu
                595                 600                 605
Glu Ile Val Arg Arg Asp Trp Ser Glu Ile Ala Lys Glu Thr Gln Ala
                610                 615                 620
Arg Val Leu Glu Ala Ile Leu Lys His Gly Asp Val Glu Glu Ala Val
625                 630                 635                 640
Arg Ile Val Lys Glu Val Thr Glu Lys Leu Ser Lys Tyr Glu Val Pro
                    645                 650                 655
Pro Glu Lys Leu Val Ile His Glu Gln Ile Thr Arg Asp Leu Arg Asp
                660                 665                 670
```

-continued

Tyr Lys Ala Thr Gly Pro His Val Ala Val Ala Lys Arg Leu Ala Ala
            675                 680                 685

Arg Gly Val Lys Ile Arg Pro Gly Thr Val Ile Ser Tyr Ile Val Leu
        690                 695                 700

Lys Gly Ser Gly Arg Ile Gly Asp Arg Ala Ile Pro Ala Asp Glu Phe
705                 710                 715                 720

Asp Pro Thr Lys His Arg Tyr Asp Ala Glu Tyr Tyr Ile Glu Asn Gln
                725                 730                 735

Val Leu Pro Ala Val Glu Arg Ile Leu Lys Ala Phe Gly Tyr Arg Lys
            740                 745                 750

Glu Asp Leu Arg Tyr Gln Lys Thr Lys Gln Val Gly Leu Gly Ala Trp
        755                 760                 765

Leu Lys Val Lys Gly Lys Lys
        770                 775

<210> SEQ ID NO 194
<211> LENGTH: 774
<212> TYPE: PRT
<213> ORGANISM: Thermococcus litoralis

<400> SEQUENCE: 194

Met Ile Leu Asp Thr Asp Tyr Ile Thr Lys Asp Gly Lys Pro Ile Ile
1               5                   10                  15

Arg Ile Phe Lys Lys Glu Asn Gly Glu Phe Lys Ile Glu Leu Asp Pro
            20                  25                  30

His Phe Gln Pro Tyr Ile Tyr Ala Leu Leu Lys Asp Asp Ser Ala Ile
        35                  40                  45

Glu Glu Ile Lys Ala Ile Lys Gly Glu Arg His Gly Lys Thr Val Arg
    50                  55                  60

Val Leu Asp Ala Val Lys Val Arg Lys Lys Phe Leu Gly Arg Glu Val
65                  70                  75                  80

Glu Val Trp Lys Leu Ile Phe Glu His Pro Gln Asp Val Pro Ala Met
                85                  90                  95

Arg Gly Lys Ile Arg Glu His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Lys Leu Leu Ala Phe Asp Ile Glu Thr
    130                 135                 140

Phe Tyr His Glu Gly Asp Glu Phe Gly Lys Gly Glu Ile Ile Met Ile
145                 150                 155                 160

Ser Tyr Ala Asp Glu Glu Ala Arg Val Ile Thr Trp Lys Asn Ile
                165                 170                 175

Asp Leu Pro Tyr Val Asp Val Val Ser Asn Glu Arg Glu Met Ile Lys
            180                 185                 190

Arg Phe Val Gln Val Val Lys Glu Lys Asp Pro Asp Val Ile Ile Thr
        195                 200                 205

Tyr Asn Gly Asp Asn Phe Asp Leu Pro Tyr Leu Ile Lys Arg Ala Glu
    210                 215                 220

Lys Leu Gly Val Arg Leu Val Leu Gly Arg Asp Lys Glu His Pro Glu
225                 230                 235                 240

Pro Lys Ile Gln Arg Met Gly Asp Ser Phe Ala Val Glu Ile Lys Gly
                245                 250                 255

Arg Ile His Phe Asp Leu Phe Pro Val Val Arg Arg Thr Ile Asn Leu

-continued

```
                260                 265                 270
Pro Thr Tyr Thr Leu Glu Ala Val Tyr Glu Ala Val Leu Gly Lys Thr
            275                 280                 285
Lys Ser Lys Leu Gly Ala Glu Glu Ile Ala Ala Ile Trp Glu Thr Glu
        290                 295                 300
Glu Ser Met Lys Lys Leu Ala Gln Tyr Ser Met Glu Asp Ala Arg Ala
305                 310                 315                 320
Thr Tyr Glu Leu Gly Lys Glu Phe Phe Pro Met Glu Ala Glu Leu Ala
                325                 330                 335
Lys Leu Ile Gly Gln Ser Val Trp Asp Val Ser Arg Ser Ser Thr Gly
            340                 345                 350
Asn Leu Val Glu Trp Tyr Leu Leu Arg Val Ala Tyr Ala Arg Asn Glu
        355                 360                 365
Leu Ala Pro Asn Lys Pro Asp Glu Glu Tyr Lys Arg Arg Leu Arg
370                 375                 380
Thr Thr Tyr Leu Gly Gly Tyr Val Lys Glu Pro Glu Lys Gly Leu Trp
385                 390                 395                 400
Glu Asn Ile Ile Tyr Leu Asp Phe Arg Ser Leu Tyr Pro Ser Ile Ile
                405                 410                 415
Val Thr His Asn Val Ser Pro Asp Thr Leu Glu Lys Glu Gly Cys Lys
            420                 425                 430
Asn Tyr Asp Val Ala Pro Ile Val Gly Tyr Arg Phe Cys Lys Asp Phe
        435                 440                 445
Pro Gly Phe Ile Pro Ser Ile Leu Gly Asp Leu Ile Ala Met Arg Gln
    450                 455                 460
Asp Ile Lys Lys Met Lys Ser Thr Ile Asp Pro Ile Glu Lys Lys
465                 470                 475                 480
Met Leu Asp Tyr Arg Gln Arg Ala Ile Lys Leu Leu Ala Asn Ser Tyr
                485                 490                 495
Tyr Gly Tyr Met Gly Tyr Pro Lys Ala Arg Trp Tyr Ser Lys Glu Cys
            500                 505                 510
Ala Glu Ser Val Thr Ala Trp Gly Arg His Tyr Ile Glu Met Thr Ile
        515                 520                 525
Arg Glu Ile Glu Glu Lys Phe Gly Phe Lys Val Leu Tyr Ala Asp Thr
    530                 535                 540
Asp Gly Phe Tyr Ala Thr Ile Pro Gly Glu Lys Pro Glu Leu Ile Lys
545                 550                 555                 560
Lys Lys Ala Lys Glu Phe Leu Asn Tyr Ile Asn Ser Lys Leu Pro Gly
                565                 570                 575
Leu Leu Glu Leu Glu Tyr Glu Gly Phe Tyr Leu Arg Gly Phe Phe Val
            580                 585                 590
Thr Lys Lys Arg Tyr Ala Val Ile Asp Glu Glu Gly Arg Ile Thr Thr
        595                 600                 605
Arg Gly Leu Glu Val Val Arg Arg Asp Trp Ser Glu Ile Ala Lys Glu
    610                 615                 620
Thr Gln Ala Lys Val Leu Glu Ala Ile Leu Lys Glu Gly Ser Val Glu
625                 630                 635                 640
Lys Ala Val Glu Val Val Arg Asp Val Glu Lys Ile Ala Lys Tyr
                645                 650                 655
Arg Val Pro Leu Glu Lys Leu Val Ile His Glu Gln Ile Thr Arg Asp
            660                 665                 670
Leu Lys Asp Tyr Lys Ala Ile Gly Pro His Val Ala Ile Ala Lys Arg
        675                 680                 685
```

-continued

```
Leu Ala Ala Arg Gly Ile Lys Val Lys Pro Gly Thr Ile Ile Ser Tyr
    690                 695                 700
Ile Val Leu Lys Gly Ser Gly Lys Ile Ser Asp Arg Val Ile Leu Leu
705                 710                 715                 720
Thr Glu Tyr Asp Pro Arg Lys His Lys Tyr Asp Pro Asp Tyr Tyr Ile
                725                 730                 735
Glu Asn Gln Val Leu Pro Ala Val Leu Arg Ile Leu Glu Ala Phe Gly
            740                 745                 750
Tyr Arg Lys Glu Asp Leu Arg Tyr Gln Ser Ser Lys Gln Thr Gly Leu
        755                 760                 765
Asp Ala Trp Leu Lys Arg
    770
```

<210> SEQ ID NO 195
<211> LENGTH: 887
<212> TYPE: PRT
<213> ORGANISM: Methanococcus voltae
<220> FEATURE:
<221> NAME/KEY: misc_feature
<222> LOCATION: (838)..(838)
<223> OTHER INFORMATION: Xaa can be any naturally occurring amino acid
<220> FEATURE:
<221> NAME/KEY: misc_feature
<222> LOCATION: (844)..(844)
<223> OTHER INFORMATION: Xaa can be any naturally occurring amino acid
<220> FEATURE:
<221> NAME/KEY: misc_feature
<222> LOCATION: (853)..(853)
<223> OTHER INFORMATION: Xaa can be any naturally occurring amino acid

<400> SEQUENCE: 195

```
Met Asp Leu Asp Tyr Asn Ser Lys Asp Leu Cys Ile Asp Met Tyr Tyr
1               5                   10                  15
Lys Asn Cys Gly Leu Lys Lys Pro Glu Ile Asn Leu Gln Lys Glu Cys
            20                  25                  30
Glu Phe Lys Pro Tyr Phe Tyr Val Asp Thr Ser Glu Pro Lys Glu Ile
        35                  40                  45
Tyr Asp Tyr Leu Asp Gly Leu Asn Gln Glu Ile Asp Leu Lys Lys Leu
50                  55                  60
Glu Pro Glu Phe Glu Asn Asn Thr Ser Leu Lys Val Gln Asp Leu Ile
65                  70                  75                  80
Thr Asn Ile Glu Ile Ile Glu Lys Ile Val Tyr Ser Asp Tyr Ile Leu
                85                  90                  95
Asn Gly Lys Asp Ile Ser Glu Val Ser Asp Phe Lys Asn Lys Lys Glu
            100                 105                 110
Arg Lys Ile Cys Lys Val Tyr Val Lys Tyr Pro Asn His Val Lys Ile
        115                 120                 125
Ile Arg Glu Tyr Phe Lys Glu Phe Gly Lys Ser Tyr Glu Phe Asp Ile
    130                 135                 140
Pro Phe Leu Arg Arg Tyr Met Ile Asp Gln Asp Ile Val Pro Ser Ala
145                 150                 155                 160
Lys Tyr Ser Glu Asp Asn Lys Ile Asp Asn Ser Ile Pro Glu Leu Asn
                165                 170                 175
Cys Ile Ala Phe Asp Met Glu Leu Tyr Cys Lys Lys Glu Pro Asn Ala
            180                 185                 190
Lys Lys Asp Pro Ile Ile Met Val Asn Leu Phe Ser Lys Asp Tyr Gln
        195                 200                 205
Lys Val Ile Thr Tyr Lys Lys Phe Glu Asn Ser Glu Tyr Asn Gly Cys
```

```
              210                 215                 220
Val Asp Tyr Val Lys Asp Glu Lys Glu Leu Ile Gln Lys Thr Ile Glu
225                 230                 235                 240

Ile Leu Lys Gln Tyr Asp Val Ile Tyr Thr Tyr Asn Gly Asp Asn Phe
                245                 250                 255

Asp Phe Pro Tyr Leu Lys Lys Arg Ala Asn Ile Tyr Glu Ile Glu Leu
            260                 265                 270

Asp Phe Asp Asn Ala Ser Asn Ser Gln Gln Pro Gln Ile Ile Lys Ile
        275                 280                 285

Ser Lys Gly Gly Ile Asn Arg Lys Ser Lys Ile Pro Gly Ile Ile His
    290                 295                 300

Ile Asp Leu Tyr Pro Ile Ala Arg Lys Leu Leu Asn Leu Thr Lys Tyr
305                 310                 315                 320

Lys Leu Glu Asn Val Val Gln Glu Leu Phe Lys Ile Asn Lys Glu Ala
                325                 330                 335

Val Asp Tyr Gly Asp Ile Pro Lys Met Trp Glu Thr Glu Asp Thr Thr
            340                 345                 350

Leu Leu Arg Tyr Ala Tyr Glu Asp Ala Leu Tyr Thr Tyr Lys Met Gly
        355                 360                 365

Asn Tyr Phe Leu Pro Leu Glu Ile Met Phe Ser Arg Ile Val Asn Gln
    370                 375                 380

Pro Leu Tyr Asp Thr Ser Arg Met Asn Ser Ser Gln Met Val Glu Phe
385                 390                 395                 400

Leu Leu Leu Lys Arg Ser Phe Glu Gln Asn Met Ile Ser Pro Asn Arg
                405                 410                 415

Pro Ser Ser Ser Tyr Arg Glu Arg Ala Lys Phe Ser Tyr Glu Gly
            420                 425                 430

Gly Tyr Val Arg Glu Pro Leu Lys Gly Ile Gln Glu Asp Ile Val Ser
        435                 440                 445

Leu Asp Phe Met Ser Leu Tyr Pro Ser Ile Leu Ile Ser His Asn Ile
    450                 455                 460

Ser Pro Glu Thr Val Ile Tyr Glu Glu Lys Glu Arg Glu Asn Met Glu
465                 470                 475                 480

Leu Gly Ile Ile Pro Lys Thr Leu Asn Glu Leu Leu Ser Arg Arg Lys
                485                 490                 495

His Ile Lys Met Leu Leu Lys Asp Lys Ile Gln Lys Asn Glu Phe Asp
            500                 505                 510

Glu Glu Tyr Ser Arg Leu Glu His Glu Gln Lys Ser Ile Lys Val Leu
        515                 520                 525

Ala Asn Ser His Tyr Gly Tyr Leu Ala Phe Pro Met Ala Arg Trp Tyr
    530                 535                 540

Ser Asp Lys Cys Ala Glu Met Val Thr Gly Leu Gly Arg Lys Tyr Ile
545                 550                 555                 560

Gln Glu Thr Ile Glu Lys Ala Glu Glu Phe Gly Phe Lys Val Ile Tyr
                565                 570                 575

Ala Asp Thr Asp Gly Phe Tyr Ala Lys Trp Asp Tyr Asp Lys Leu Gln
            580                 585                 590

Lys Gly Lys Lys Glu Glu Asn Asp Lys Ser Asp Lys Leu Ser Asn Leu
        595                 600                 605

Pro Lys Leu Ser Lys Glu Glu Leu Ile Ile Leu Thr Lys Lys Phe Leu
    610                 615                 620

Lys Gly Ile Asn Glu Glu Leu Pro Glu Gly Met Glu Leu Glu Phe Glu
625                 630                 635                 640
```

```
Gly His Phe Lys Arg Gly Leu Phe Val Thr Lys Lys Tyr Ala Leu
            645                 650                 655

Ile Glu Asp Asp Gly His Ile Val Val Lys Gly Leu Glu Val Val Arg
            660                 665                 670

Arg Asp Trp Ser Asn Ile Ala Lys Asp Thr Gln Gln Ala Val Ile Arg
            675                 680                 685

Ala Leu Leu Glu Asp Gly Asp Val Asn Leu Ala Lys Lys Ile Ile Lys
            690                 695                 700

Asn Thr Ile Asp Asn Leu Lys Lys Gly Asn Ile Asp Lys Asn Asp Leu
705                 710                 715                 720

Leu Ile His Thr Gln Leu Thr Lys Asn Ile Glu Glu Tyr Lys Ser Thr
                725                 730                 735

Ala Pro His Ile Glu Val Ala Lys Lys Ile Lys Gln Arg Gly Asp Ser
            740                 745                 750

Val Arg Val Gly Asp Val Ile Ser Tyr Ile Ile Val Lys Gly Ser Arg
            755                 760                 765

Ser Ile Ser Glu Arg Ala Glu Leu Leu Glu Tyr Ala Gly Asp Tyr Asp
            770                 775                 780

Ile Asn Tyr Tyr Ile Asp Asn Gln Val Leu Pro Pro Val Ile Arg Ile
785                 790                 795                 800

Met Glu Ser Leu Gly Ile Ser Glu Asp Glu Leu Lys Asn Ser Gly Lys
                805                 810                 815

Gln Phe Lys Leu Asp Gln Phe Met Thr Pro Trp Arg Lys Ile Asn Gly
            820                 825                 830

Trp Ile Thr His Phe Xaa Leu Leu Ser Glu Gln Xaa Glu Asn Cys Glu
            835                 840                 845

Ser Ser Glu Gln Xaa Glu Asn Cys Glu Ile Asn Ala Leu Ile Gly Asn
850                 855                 860

Met Glu Asn Thr Ser Glu Thr Gly Thr Gly Cys Gly Leu Ala Ser Thr
865                 870                 875                 880

Ser Arg Ser Pro Ala Gly Glu
            885

<210> SEQ ID NO 196
<211> LENGTH: 856
<212> TYPE: PRT
<213> ORGANISM: Bacteriophage RB69

<400> SEQUENCE: 196

Met Lys Glu Phe Tyr Leu Thr Val Glu Gln Ile Gly Asp Ser Ile Phe
1               5                   10                  15

Glu Arg Tyr Ile Asp Ser Asn Gly Arg Glu Arg Thr Arg Glu Val Glu
            20                  25                  30

Tyr Lys Pro Ser Leu Phe Ala His Cys Pro Glu Ser Gln Ala Thr Lys
        35                  40                  45

Tyr Phe Asp Ile Tyr Gly Lys Pro Cys Thr Arg Lys Leu Phe Ala Asn
    50                  55                  60

Met Arg Asp Ala Ser Gln Trp Ile Lys Arg Met Glu Asp Ile Gly Leu
65                  70                  75                  80

Glu Ala Leu Gly Met Asp Asp Phe Lys Leu Ala Tyr Leu Ser Asp Thr
                85                  90                  95

Tyr Asn Tyr Glu Ile Lys Tyr Asp His Thr Lys Ile Arg Val Ala Asn
            100                 105                 110

Phe Asp Ile Glu Val Thr Ser Pro Asp Gly Phe Pro Glu Pro Ser Gln
```

-continued

```
            115                 120                 125
Ala Lys His Pro Ile Asp Ala Ile Thr His Tyr Asp Ser Ile Asp Asp
    130                 135                 140

Arg Phe Tyr Val Phe Asp Leu Leu Asn Ser Pro Tyr Gly Asn Val Glu
145                 150                 155                 160

Glu Trp Ser Ile Glu Ile Ala Ala Lys Leu Gln Glu Gln Gly Gly Asp
                165                 170                 175

Glu Val Pro Ser Glu Ile Ile Asp Lys Ile Ile Tyr Met Pro Phe Asp
            180                 185                 190

Asn Glu Lys Glu Leu Leu Met Glu Tyr Leu Asn Phe Trp Gln Gln Lys
        195                 200                 205

Thr Pro Val Ile Leu Thr Gly Trp Asn Val Glu Ser Phe Asp Ile Pro
    210                 215                 220

Tyr Val Tyr Asn Arg Ile Lys Asn Ile Phe Gly Glu Ser Thr Ala Lys
225                 230                 235                 240

Arg Leu Ser Pro His Arg Lys Thr Arg Val Lys Val Ile Glu Asn Met
                245                 250                 255

Tyr Gly Ser Arg Glu Ile Ile Thr Leu Phe Gly Ile Ser Val Leu Asp
            260                 265                 270

Tyr Ile Asp Leu Tyr Lys Lys Phe Ser Phe Thr Asn Gln Pro Ser Tyr
        275                 280                 285

Ser Leu Asp Tyr Ile Ser Glu Phe Glu Leu Asn Val Gly Lys Leu Lys
    290                 295                 300

Tyr Asp Gly Pro Ile Ser Lys Leu Arg Glu Ser Asn His Gln Arg Tyr
305                 310                 315                 320

Ile Ser Tyr Asn Ile Ile Asp Val Tyr Arg Val Leu Gln Ile Asp Ala
                325                 330                 335

Lys Arg Gln Phe Ile Asn Leu Ser Leu Asp Met Gly Tyr Tyr Ala Lys
            340                 345                 350

Ile Gln Ile Gln Ser Val Phe Ser Pro Ile Lys Thr Trp Asp Ala Ile
        355                 360                 365

Ile Phe Asn Ser Leu Lys Glu Gln Asn Lys Val Ile Pro Gln Gly Arg
    370                 375                 380

Ser His Pro Val Gln Pro Tyr Pro Gly Ala Phe Val Lys Glu Pro Ile
385                 390                 395                 400

Pro Asn Arg Tyr Lys Tyr Val Met Ser Phe Asp Leu Thr Ser Leu Tyr
                405                 410                 415

Pro Ser Ile Ile Arg Gln Val Asn Ile Ser Pro Glu Thr Ile Ala Gly
            420                 425                 430

Thr Phe Lys Val Ala Pro Leu His Asp Tyr Ile Asn Ala Val Ala Glu
        435                 440                 445

Arg Pro Ser Asp Val Tyr Ser Cys Ser Pro Asn Gly Met Met Tyr Tyr
    450                 455                 460

Lys Asp Arg Asp Gly Val Val Pro Thr Glu Ile Thr Lys Val Phe Asn
465                 470                 475                 480

Gln Arg Lys Glu His Lys Gly Tyr Met Leu Ala Ala Gln Arg Asn Gly
                485                 490                 495

Glu Ile Ile Lys Glu Ala Leu His Asn Pro Asn Leu Ser Val Asp Glu
            500                 505                 510

Pro Leu Asp Val Asp Tyr Arg Phe Asp Phe Ser Asp Glu Ile Lys Glu
        515                 520                 525

Lys Ile Lys Lys Leu Ser Ala Lys Ser Leu Asn Glu Met Leu Phe Arg
    530                 535                 540
```

```
Ala Gln Arg Thr Glu Val Ala Gly Met Thr Ala Gln Ile Asn Arg Lys
545                 550                 555                 560

Leu Leu Ile Asn Ser Leu Tyr Gly Ala Leu Gly Asn Val Trp Phe Arg
                565                 570                 575

Tyr Tyr Asp Leu Arg Asn Ala Thr Ala Ile Thr Thr Phe Gly Gln Met
            580                 585                 590

Ala Leu Gln Trp Ile Glu Arg Lys Val Asn Glu Tyr Leu Asn Glu Val
        595                 600                 605

Cys Gly Thr Glu Gly Glu Ala Phe Val Leu Tyr Gly Asp Thr Asp Ser
    610                 615                 620

Ile Tyr Val Ser Ala Asp Lys Ile Ile Asp Lys Val Gly Glu Ser Lys
625                 630                 635                 640

Phe Arg Asp Thr Asn His Trp Val Asp Phe Leu Asp Lys Phe Ala Arg
                645                 650                 655

Glu Arg Met Glu Pro Ala Ile Asp Arg Gly Phe Arg Glu Met Cys Glu
            660                 665                 670

Tyr Met Asn Asn Lys Gln His Leu Met Phe Met Asp Arg Glu Ala Ile
        675                 680                 685

Ala Gly Pro Pro Leu Gly Ser Lys Gly Ile Gly Gly Phe Trp Thr Gly
    690                 695                 700

Lys Lys Arg Tyr Ala Leu Asn Val Trp Asp Met Glu Gly Thr Arg Tyr
705                 710                 715                 720

Ala Glu Pro Phe Arg Gln Leu Asn Tyr Ile Ser Ile Ala Ser Val Ser
                725                 730                 735

Ser Ala Asn Asn Ile Ala Lys Tyr Asp Val Gly Gly Phe Pro Gly Pro
            740                 745                 750

Lys Cys Pro Phe His Ile Arg Gly Ile Leu Thr Tyr Asn Arg Ala Ile
        755                 760                 765

Lys Gly Asn Ile Asp Ala Pro Gln Val Val Glu Gly Glu Lys Val Tyr
    770                 775                 780

Val Leu Pro Leu Arg Glu Gly Asn Pro Phe Gly Asp Lys Cys Ile Ala
785                 790                 795                 800

Trp Pro Ser Gly Thr Glu Ile Thr Asp Leu Ile Lys Asp Asp Val Leu
                805                 810                 815

His Trp Met Asp Tyr Thr Val Leu Leu Glu Lys Thr Phe Ile Lys Pro
            820                 825                 830

Leu Glu Gly Phe Thr Ser Ala Ala Lys Leu Asp Tyr Glu Lys Lys Ala
        835                 840                 845

Ser Leu Phe Asp Met Phe Asp Phe
    850                 855

<210> SEQ ID NO 197
<211> LENGTH: 898
<212> TYPE: PRT
<213> ORGANISM: Bacteriophage T4

<400> SEQUENCE: 197

Met Lys Glu Phe Tyr Ile Ser Ile Glu Thr Val Gly Asn Asn Ile Val
1               5                   10                  15

Glu Arg Tyr Ile Asp Glu Asn Gly Lys Glu Arg Thr Arg Glu Val Glu
            20                  25                  30

Tyr Leu Pro Thr Met Phe Arg His Cys Lys Glu Glu Ser Lys Tyr Lys
        35                  40                  45

Asp Ile Tyr Gly Lys Asn Cys Ala Pro Gln Lys Phe Pro Ser Met Lys
```

```
                50                  55                  60
Asp Ala Arg Asp Trp Met Lys Arg Met Glu Asp Ile Gly Leu Glu Ala
 65                  70                  75                  80

Leu Gly Met Asn Asp Phe Lys Leu Ala Tyr Ile Ser Asp Thr Tyr Gly
                 85                  90                  95

Ser Glu Ile Val Tyr Asp Arg Lys Phe Val Arg Val Ala Asn Cys Asp
                100                 105                 110

Ile Glu Val Thr Gly Asp Lys Phe Pro Asp Pro Met Lys Ala Glu Tyr
                115                 120                 125

Glu Ile Asp Ala Ile Thr His Tyr Asp Ser Ile Asp Asp Arg Phe Tyr
130                 135                 140

Val Phe Asp Leu Leu Asn Ser Met Tyr Gly Ser Val Ser Lys Trp Asp
145                 150                 155                 160

Ala Lys Leu Ala Ala Lys Leu Asp Cys Glu Gly Gly Asp Glu Val Pro
                165                 170                 175

Gln Glu Ile Leu Asp Arg Val Ile Tyr Met Pro Phe Asp Asn Glu Arg
                180                 185                 190

Asp Met Leu Met Glu Tyr Ile Asn Leu Trp Glu Gln Lys Arg Pro Ala
                195                 200                 205

Ile Phe Thr Gly Trp Asn Ile Glu Gly Phe Asp Val Pro Tyr Ile Met
210                 215                 220

Asn Arg Val Lys Met Ile Leu Gly Glu Arg Ser Met Lys Arg Phe Ser
225                 230                 235                 240

Pro Ile Gly Arg Val Lys Ser Lys Leu Ile Gln Asn Met Tyr Gly Ser
                245                 250                 255

Lys Glu Ile Tyr Ser Ile Asp Gly Val Ser Ile Leu Asp Tyr Leu Asp
                260                 265                 270

Leu Tyr Lys Lys Phe Ala Phe Thr Asn Leu Pro Ser Phe Ser Leu Glu
                275                 280                 285

Ser Val Ala Gln His Glu Thr Lys Lys Gly Lys Leu Pro Tyr Asp Gly
290                 295                 300

Pro Ile Asn Lys Leu Arg Glu Thr Asn His Gln Arg Tyr Ile Ser Tyr
305                 310                 315                 320

Asn Ile Ile Asp Val Glu Ser Val Gln Ala Ile Asp Lys Ile Arg Gly
                325                 330                 335

Phe Ile Asp Leu Val Leu Ser Met Ser Tyr Tyr Ala Lys Met Pro Phe
                340                 345                 350

Ser Gly Val Met Ser Pro Ile Lys Thr Trp Asp Ala Ile Ile Phe Asn
                355                 360                 365

Ser Leu Lys Gly Glu His Lys Val Ile Pro Gln Gln Gly Ser His Val
370                 375                 380

Lys Gln Ser Phe Pro Gly Ala Phe Val Phe Glu Pro Lys Pro Ile Ala
385                 390                 395                 400

Arg Arg Tyr Ile Met Ser Phe Asp Leu Thr Ser Leu Tyr Pro Ser Ile
                405                 410                 415

Ile Arg Gln Val Asn Ile Ser Pro Glu Thr Ile Arg Gly Gln Phe Lys
                420                 425                 430

Val His Pro Ile His Glu Tyr Ile Ala Gly Thr Ala Pro Lys Pro Ser
                435                 440                 445

Asp Glu Tyr Ser Cys Ser Pro Asn Gly Trp Met Tyr Asp Lys His Gln
                450                 455                 460

Glu Gly Ile Ile Pro Lys Glu Ile Ala Lys Val Phe Phe Gln Arg Lys
465                 470                 475                 480
```

```
Asp Trp Lys Lys Lys Met Phe Ala Glu Glu Met Asn Ala Glu Ala Ile
            485                 490                 495

Lys Lys Ile Ile Met Lys Gly Ala Gly Ser Cys Ser Thr Lys Pro Glu
            500                 505                 510

Val Glu Arg Tyr Val Lys Phe Ser Asp Asp Phe Leu Asn Glu Leu Ser
            515                 520                 525

Asn Tyr Thr Glu Ser Val Leu Asn Ser Leu Ile Glu Glu Cys Glu Lys
            530                 535                 540

Ala Ala Thr Leu Ala Asn Thr Asn Gln Leu Asn Arg Lys Ile Leu Ile
545                 550                 555                 560

Asn Ser Leu Tyr Gly Ala Leu Gly Asn Ile His Phe Arg Tyr Tyr Asp
            565                 570                 575

Leu Arg Asn Ala Thr Ala Ile Thr Ile Phe Gly Gln Val Gly Ile Gln
            580                 585                 590

Trp Ile Ala Arg Lys Ile Asn Glu Tyr Leu Asn Lys Val Cys Gly Thr
            595                 600                 605

Asn Asp Glu Asp Phe Ile Ala Ala Gly Asp Thr Asp Ser Val Tyr Val
            610                 615                 620

Cys Val Asp Lys Val Ile Glu Lys Val Gly Leu Asp Arg Phe Lys Glu
625                 630                 635                 640

Gln Asn Asp Leu Val Glu Phe Met Asn Gln Phe Gly Lys Lys Lys Met
            645                 650                 655

Glu Pro Met Ile Asp Val Ala Tyr Arg Glu Leu Cys Asp Tyr Met Asn
            660                 665                 670

Asn Arg Glu His Leu Met His Met Asp Arg Glu Ala Ile Ser Cys Pro
            675                 680                 685

Pro Leu Gly Ser Lys Gly Val Gly Gly Phe Trp Lys Ala Lys Lys Arg
            690                 695                 700

Tyr Ala Leu Asn Val Tyr Asp Met Glu Asp Lys Arg Phe Ala Glu Pro
705                 710                 715                 720

His Leu Lys Ile Met Gly Met Glu Thr Gln Gln Ser Ser Thr Pro Lys
            725                 730                 735

Ala Val Gln Glu Ala Leu Glu Glu Ser Ile Arg Arg Ile Leu Gln Glu
            740                 745                 750

Gly Glu Glu Ser Val Gln Glu Tyr Tyr Lys Asn Phe Glu Lys Glu Tyr
            755                 760                 765

Arg Gln Leu Asp Tyr Lys Val Ile Ala Glu Val Lys Thr Ala Asn Asp
770                 775                 780

Ile Ala Lys Tyr Asp Asp Lys Gly Trp Pro Gly Phe Lys Cys Pro Phe
785                 790                 795                 800

His Ile Arg Gly Val Leu Thr Tyr Arg Arg Ala Val Ser Gly Leu Gly
            805                 810                 815

Val Ala Pro Ile Leu Asp Gly Asn Lys Val Met Val Leu Pro Leu Arg
            820                 825                 830

Glu Gly Asn Pro Phe Gly Asp Lys Cys Ile Ala Trp Pro Ser Gly Thr
            835                 840                 845

Glu Leu Pro Lys Glu Ile Arg Ser Asp Val Leu Ser Trp Ile Asp His
            850                 855                 860

Ser Thr Leu Phe Gln Lys Ser Phe Val Lys Pro Leu Ala Gly Met Cys
865                 870                 875                 880

Glu Ser Ala Gly Met Asp Tyr Glu Glu Lys Ala Ser Leu Asp Phe Leu
            885                 890                 895
```

Phe Gly

<210> SEQ ID NO 198
<211> LENGTH: 759
<212> TYPE: PRT
<213> ORGANISM: Escherichia coli

<400> SEQUENCE: 198

```
Met Ala Gln Ala Gly Phe Ile Leu Thr Arg His Trp Arg Asp Thr Pro
1               5                   10                  15

Gln Gly Thr Glu Val Ser Phe Trp Leu Ala Thr Asp Asn Gly Pro Leu
            20                  25                  30

Gln Val Thr Leu Ala Pro Gln Glu Ser Val Ala Phe Ile Pro Ala Asp
        35                  40                  45

Gln Val Pro Arg Ala Gln His Ile Leu Gln Gly Glu Gln Gly Phe Arg
    50                  55                  60

Leu Thr Pro Leu Ala Leu Lys Asp Phe His Arg Gln Pro Val Tyr Gly
65                  70                  75                  80

Leu Tyr Cys Arg Ala His Arg Gln Leu Met Asn Tyr Glu Lys Arg Leu
                85                  90                  95

Arg Glu Gly Gly Val Thr Val Tyr Glu Ala Asp Val Arg Pro Pro Glu
            100                 105                 110

Arg Tyr Leu Met Glu Arg Phe Ile Thr Ser Pro Val Trp Val Glu Gly
        115                 120                 125

Asp Met His Asn Gly Thr Ile Val Asn Ala Arg Leu Lys Pro His Pro
130                 135                 140

Asp Tyr Arg Pro Pro Leu Lys Trp Val Ser Ile Asp Ile Glu Thr Thr
145                 150                 155                 160

Arg His Gly Glu Leu Tyr Cys Ile Gly Leu Glu Ala Cys Gly Gln Arg
                165                 170                 175

Ile Val Tyr Met Leu Gly Pro Glu Asn Gly Asp Ala Ser Ser Leu Asp
            180                 185                 190

Phe Glu Leu Glu Tyr Val Ala Ser Arg Pro Gln Leu Leu Glu Lys Leu
        195                 200                 205

Asn Ala Trp Phe Ala Asn Tyr Asp Pro Asp Val Ile Ile Gly Trp Asn
210                 215                 220

Val Val Gln Phe Asp Leu Arg Met Leu Gln Lys His Ala Glu Arg Tyr
225                 230                 235                 240

Arg Leu Pro Leu Arg Leu Gly Arg Asp Asn Ser Glu Leu Glu Trp Arg
                245                 250                 255

Glu His Gly Phe Lys Asn Gly Val Phe Phe Ala Gln Ala Lys Gly Arg
            260                 265                 270

Leu Ile Ile Asp Gly Ile Glu Ala Leu Lys Ser Ala Phe Trp Asn Phe
        275                 280                 285

Ser Ser Phe Ser Leu Glu Thr Val Ala Gln Glu Leu Leu Gly Glu Gly
    290                 295                 300

Lys Ser Ile Asp Asn Pro Trp Asp Arg Met Asp Glu Ile Asp Arg Arg
305                 310                 315                 320

Phe Ala Glu Asp Lys Pro Ala Leu Ala Thr Tyr Asn Leu Lys Asp Cys
                325                 330                 335

Glu Leu Val Thr Gln Ile Phe His Lys Thr Glu Ile Met Pro Phe Leu
            340                 345                 350

Leu Glu Arg Ala Thr Val Asn Gly Leu Pro Val Asp Arg His Gly Gly
        355                 360                 365
```

Ser Val Ala Ala Phe Gly His Leu Tyr Phe Pro Arg Met His Arg Ala
370                 375                 380

Gly Tyr Val Ala Pro Asn Leu Gly Glu Val Pro Pro His Ala Ser Pro
385                 390                 395                 400

Gly Gly Tyr Val Met Asp Ser Arg Pro Gly Leu Tyr Asp Ser Val Leu
            405                 410                 415

Val Leu Asp Tyr Lys Ser Leu Tyr Pro Ser Ile Ile Arg Thr Phe Leu
        420                 425                 430

Ile Asp Pro Val Gly Leu Val Glu Gly Met Ala Gln Pro Asp Pro Glu
            435                 440                 445

His Ser Thr Glu Gly Phe Leu Asp Ala Trp Phe Ser Arg Glu Lys His
    450                 455                 460

Cys Leu Pro Glu Ile Val Thr Asn Ile Trp His Gly Arg Asp Glu Ala
465                 470                 475                 480

Lys Arg Gln Gly Asn Lys Pro Leu Ser Gln Ala Leu Lys Ile Ile Met
                485                 490                 495

Asn Ala Phe Tyr Gly Val Leu Gly Thr Thr Ala Cys Arg Phe Phe Asp
            500                 505                 510

Pro Arg Leu Ala Ser Ser Ile Thr Met Arg Gly His Gln Ile Met Arg
        515                 520                 525

Gln Thr Lys Ala Leu Ile Glu Ala Gln Gly Tyr Asp Val Ile Tyr Gly
530                 535                 540

Asp Thr Asp Ser Thr Phe Val Trp Leu Lys Gly Ala His Ser Glu Glu
545                 550                 555                 560

Glu Ala Ala Lys Ile Gly Arg Ala Leu Val Gln His Val Asn Ala Trp
                565                 570                 575

Trp Ala Glu Thr Leu Gln Lys Gln Arg Leu Thr Ser Ala Leu Glu Leu
            580                 585                 590

Glu Tyr Glu Thr His Phe Cys Arg Phe Leu Met Pro Thr Ile Arg Gly
        595                 600                 605

Ala Asp Thr Gly Ser Lys Lys Arg Tyr Ala Gly Leu Ile Gln Glu Gly
            610                 615                 620

Asp Lys Gln Arg Met Val Phe Lys Gly Leu Glu Thr Val Arg Thr Asp
625                 630                 635                 640

Trp Thr Pro Leu Ala Gln Gln Phe Gln Gln Glu Leu Tyr Leu Arg Ile
                645                 650                 655

Phe Arg Asn Glu Pro Tyr Gln Glu Tyr Val Arg Glu Thr Ile Asp Lys
            660                 665                 670

Leu Met Ala Gly Glu Leu Asp Ala Arg Leu Val Tyr Arg Lys Arg Leu
        675                 680                 685

Arg Arg Pro Leu Ser Glu Tyr Gln Arg Asn Val Pro Pro His Val Arg
    690                 695                 700

Ala Ala Arg Leu Ala Asp Glu Glu Asn Gln Lys Arg Gly Arg Pro Leu
705                 710                 715                 720

Gln Tyr Gln Asn Arg Gly Thr Ile Lys Tyr Val Trp Thr Thr Thr Gly
                725                 730                 735

Pro Glu Pro Pro Gly Leu Pro Thr Phe Thr Thr Gly Leu Arg Thr Leu
            740                 745                 750

Ser Asp Pro Pro Pro Phe Tyr
            755

<210> SEQ ID NO 199
<211> LENGTH: 1170
<212> TYPE: PRT

```
<213> ORGANISM: Homo sapiens
<220> FEATURE:
<221> NAME/KEY: misc_feature
<222> LOCATION: (1121)..(1121)
<223> OTHER INFORMATION: Xaa can be any naturally occurring amino acid
<220> FEATURE:
<221> NAME/KEY: misc_feature
<222> LOCATION: (1127)..(1127)
<223> OTHER INFORMATION: Xaa can be any naturally occurring amino acid
<220> FEATURE:
<221> NAME/KEY: misc_feature
<222> LOCATION: (1136)..(1136)
<223> OTHER INFORMATION: Xaa can be any naturally occurring amino acid

<400> SEQUENCE: 199

Met Asp Gly Lys Arg Arg Pro Gly Pro Gly Val Pro Pro Lys
1               5                  10                  15

Arg Ala Arg Gly Gly Leu Trp Asp Asp Asp Ala Pro Trp Pro Ser
            20                  25                  30

Gln Phe Glu Glu Asp Leu Ala Leu Met Glu Glu Met Glu Ala Glu His
        35                  40                  45

Arg Leu Gln Glu Gln Glu Glu Glu Leu Gln Ser Val Leu Glu Gly
    50                  55                  60

Val Ala Asp Gly Gln Val Pro Pro Ser Ala Ile Asp Pro Arg Trp Leu
65                  70                  75                  80

Arg Pro Thr Pro Pro Ala Leu Asp Pro Gln Thr Glu Pro Leu Ile Phe
                85                  90                  95

Gln Gln Leu Glu Ile Asp His Tyr Val Gly Pro Ala Gln Pro Val Pro
            100                 105                 110

Gly Gly Pro Pro Pro Ser Arg Gly Ser Val Pro Val Leu Arg Ala Phe
        115                 120                 125

Gly Val Thr Asp Glu Gly Phe Ser Val Cys Cys His Ile His Gly Phe
130                 135                 140

Ala Pro Tyr Phe Tyr Thr Pro Ala Pro Pro Gly Phe Gly Pro Glu His
145                 150                 155                 160

Met Gly Asp Leu Gln Arg Glu Leu Asn Leu Ala Ile Ser Arg Asp Ser
                165                 170                 175

Arg Gly Gly Arg Glu Leu Thr Gly Pro Ala Val Leu Ala Val Glu Leu
            180                 185                 190

Cys Ser Arg Glu Ser Met Phe Gly Tyr His Gly His Gly Pro Ser Pro
        195                 200                 205

Phe Leu Arg Ile Thr Val Ala Leu Pro Arg Leu Val Ala Pro Ala Arg
210                 215                 220

Arg Leu Leu Glu Gln Gly Ile Arg Val Ala Gly Leu Gly Thr Pro Ser
225                 230                 235                 240

Phe Ala Pro Tyr Glu Ala Asn Val Asp Phe Glu Ile Arg Phe Met Val
                245                 250                 255

Asp Thr Asp Ile Val Gly Cys Asn Trp Leu Glu Leu Pro Ala Gly Lys
            260                 265                 270

Tyr Ala Leu Arg Leu Lys Glu Lys Ala Thr Gln Cys Gln Leu Glu Ala
        275                 280                 285

Asp Val Leu Trp Ser Asp Val Val Ser His Pro Pro Glu Gly Pro Trp
    290                 295                 300

Gln Arg Ile Ala Pro Leu Arg Val Leu Ser Phe Asp Ile Glu Cys Ala
305                 310                 315                 320

Gly Arg Lys Gly Ile Phe Pro Glu Pro Glu Arg Asp Pro Val Ile Gln
                325                 330                 335
```

-continued

```
Ile Cys Ser Leu Gly Leu Arg Trp Gly Glu Pro Phe Leu Arg
            340                 345             350

Leu Ala Leu Thr Leu Arg Pro Cys Ala Pro Ile Leu Gly Ala Lys Val
            355                 360             365

Gln Ser Tyr Glu Lys Glu Asp Leu Leu Gln Ala Trp Ser Thr Phe
    370             375                 380

Ile Arg Ile Met Asp Pro Asp Val Ile Thr Gly Tyr Asn Ile Gln Asn
385             390                 395                 400

Phe Asp Leu Pro Tyr Leu Ile Ser Arg Ala Gln Thr Leu Lys Val Gln
                405                 410              415

Thr Phe Pro Phe Leu Gly Arg Val Ala Gly Leu Cys Ser Asn Ile Arg
            420                 425                 430

Asp Ser Ser Phe Gln Ser Lys Gln Thr Gly Arg Arg Asp Thr Lys Val
        435                 440                 445

Val Ser Met Val Gly Arg Val Gln Met Asp Met Leu Gln Val Leu Leu
    450                 455                 460

Arg Glu Tyr Lys Leu Arg Ser His Thr Leu Asn Ala Val Ser Phe His
465                 470                 475                 480

Phe Leu Gly Glu Gln Lys Glu Asp Val Gln His Ser Ile Ile Thr Asp
                485                 490                 495

Leu Gln Asn Gly Asn Asp Gln Thr Arg Arg Leu Ala Val Tyr Cys
            500                 505             510

Leu Lys Asp Ala Tyr Leu Pro Leu Arg Leu Glu Arg Leu Met Val
        515                 520             525

Leu Val Asn Ala Val Glu Met Ala Arg Val Thr Gly Val Pro Leu Ser
    530                 535                 540

Tyr Leu Leu Ser Arg Gly Gln Gln Val Lys Val Val Ser Gln Leu Leu
545                 550                 555                 560

Arg Gln Ala Met His Glu Gly Leu Leu Met Pro Val Lys Ser Glu
                565                 570             575

Gly Gly Glu Asp Tyr Thr Gly Ala Thr Val Ile Glu Pro Leu Lys Gly
                580             585                 590

Tyr Tyr Asp Val Pro Ile Ala Thr Leu Asp Phe Ser Ser Leu Tyr Pro
        595                 600                 605

Ser Ile Met Met Ala His Asn Leu Cys Tyr Thr Thr Leu Leu Arg Pro
    610                 615                 620

Gly Thr Ala Gln Lys Leu Gly Leu Thr Glu Asp Gln Phe Ile Arg Thr
625                 630                 635                 640

Pro Thr Gly Asp Glu Phe Val Lys Thr Ser Val Arg Lys Gly Leu Leu
                645                 650                 655

Pro Gln Ile Leu Glu Asn Leu Leu Ser Ala Arg Lys Arg Ala Lys Ala
            660                 665                 670

Glu Leu Ala Lys Glu Thr Asp Pro Leu Arg Arg Gln Val Leu Asp Gly
        675                 680                 685

Arg Gln Leu Ala Leu Lys Val Ser Ala Asn Ser Val Tyr Gly Phe Thr
    690                 695                 700

Gly Ala Gln Val Gly Lys Leu Pro Cys Leu Glu Ile Ser Gln Ser Val
705                 710                 715                 720

Thr Gly Phe Gly Arg Gln Met Ile Glu Lys Thr Lys Gln Leu Val Glu
                725                 730                 735

Ser Lys Tyr Thr Val Glu Asn Gly Tyr Ser Thr Ser Ala Lys Val Val
            740                 745                 750

Tyr Gly Asp Thr Asp Ser Val Met Cys Arg Phe Gly Val Ser Ser Val
```

755                 760                 765
Ala Glu Ala Met Ala Leu Gly Arg Glu Ala Ala Asp Trp Val Ser Gly
    770                 775                 780

His Phe Pro Ser Pro Ile Arg Leu Glu Phe Glu Lys Val Tyr Phe Pro
785                 790                 795                 800

Tyr Leu Leu Ile Ser Lys Lys Tyr Ala Gly Leu Leu Phe Ser Ser
                805                 810                 815

Arg Pro Asp Ala His Asp Arg Met Asp Cys Lys Gly Leu Glu Ala Val
                820                 825                 830

Arg Arg Asp Asn Cys Pro Leu Val Ala Asn Leu Val Thr Ala Ser Leu
            835                 840                 845

Arg Arg Leu Leu Ile Asp Arg Asp Pro Glu Gly Ala Val Ala His Ala
    850                 855                 860

Gln Asp Val Ile Ser Asp Leu Leu Cys Asn Arg Ile Asp Ile Ser Gln
865                 870                 875                 880

Leu Val Ile Thr Lys Glu Leu Thr Arg Ala Ala Ser Asp Tyr Ala Gly
                885                 890                 895

Lys Gln Ala His Val Glu Leu Ala Glu Arg Met Arg Lys Arg Asp Pro
                900                 905                 910

Gly Ser Ala Pro Ser Leu Gly Asp Arg Val Pro Tyr Val Ile Ile Ser
            915                 920                 925

Ala Ala Lys Gly Val Ala Ala Tyr Met Lys Ser Glu Asp Pro Leu Phe
    930                 935                 940

Val Leu Glu His Ser Leu Pro Ile Asp Thr Gln Tyr Tyr Leu Glu Gln
945                 950                 955                 960

Gln Leu Ala Lys Pro Leu Leu Arg Ile Phe Glu Pro Ile Leu Gly Glu
                965                 970                 975

Gly Arg Ala Glu Ala Val Leu Leu Arg Gly Asp His Thr Arg Cys Lys
            980                 985                 990

Thr Val Leu Thr Gly Lys Val Gly Gly Leu Leu Ala Phe Ala Lys Arg
        995                 1000                1005

Arg Asn Cys Cys Ile Gly Cys Arg Thr Val Leu Ser His Gln Gly
    1010                1015                1020

Ala Val Cys Glu Phe Cys Gln Pro Arg Glu Ser Glu Leu Tyr Gln
    1025                1030                1035

Lys Glu Val Ser His Leu Asn Ala Leu Glu Glu Arg Phe Ser Arg
    1040                1045                1050

Leu Trp Thr Gln Cys Gln Arg Cys Gln Gly Ser Leu His Glu Asp
    1055                1060                1065

Val Ile Cys Thr Ser Arg Asp Cys Pro Ile Phe Tyr Met Arg Lys
    1070                1075                1080

Lys Val Arg Lys Asp Leu Glu Asp Gln Glu Gln Leu Leu Arg Arg
    1085                1090                1095

Phe Gly Pro Pro Gly Pro Glu Ala Trp Thr Pro Trp Arg Lys Ile
    1100                1105                1110

Asn Gly Trp Ile Thr His Phe Xaa Leu Leu Ser Glu Gln Xaa Glu
    1115                1120                1125

Asn Cys Glu Ser Ser Glu Gln Xaa Glu Asn Cys Glu Ile Asn Ala
    1130                1135                1140

Leu Ile Gly Asn Met Glu Asn Thr Ser Glu Thr Gly Thr Gly Cys
    1145                1150                1155

Gly Leu Ala Ser Thr Ser Arg Ser Pro Ala Gly Glu
    1160                1165                1170

-continued

<210> SEQ ID NO 200
<211> LENGTH: 774
<212> TYPE: PRT
<213> ORGANISM: Pyrococcus kodakaraensis

<400> SEQUENCE: 200

Met Ile Leu Asp Thr Asp Tyr Ile Thr Glu Asp Gly Lys Pro Val Ile
1               5                   10                  15

Arg Ile Phe Lys Lys Glu Asn Gly Glu Phe Lys Ile Glu Tyr Asp Arg
            20                  25                  30

Thr Phe Glu Pro Tyr Phe Tyr Ala Leu Leu Lys Asp Asp Ser Ala Ile
        35                  40                  45

Glu Glu Val Lys Lys Ile Thr Ala Glu Arg His Gly Thr Val Val Thr
    50                  55                  60

Val Lys Arg Val Glu Lys Val Gln Lys Phe Leu Gly Arg Pro Val
65                  70                  75                  80

Glu Val Trp Lys Leu Tyr Phe Thr His Pro Gln Asp Val Pro Ala Ile
                85                  90                  95

Arg Asp Lys Ile Arg Glu His Pro Ala Val Ile Asp Ile Tyr Glu Tyr
            100                 105                 110

Asp Ile Pro Phe Ala Lys Arg Tyr Leu Ile Asp Lys Gly Leu Val Pro
        115                 120                 125

Met Glu Gly Asp Glu Glu Leu Lys Met Leu Ala Phe Asp Ile Glu Thr
130                 135                 140

Leu Tyr His Glu Gly Glu Glu Phe Ala Glu Gly Pro Ile Leu Met Ile
145                 150                 155                 160

Ser Tyr Ala Asp Glu Glu Gly Ala Arg Val Ile Thr Trp Lys Asn Val
                165                 170                 175

Asp Leu Pro Tyr Val Asp Val Val Ser Thr Glu Arg Glu Met Ile Lys
            180                 185                 190

Arg Phe Leu Arg Val Val Lys Glu Lys Asp Pro Asp Val Leu Ile Thr
        195                 200                 205

Tyr Asn Gly Asp Asn Phe Asp Phe Ala Tyr Leu Lys Lys Arg Cys Glu
    210                 215                 220

Lys Leu Gly Ile Asn Phe Ala Leu Gly Arg Asp Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Val Phe Gly Gln Pro Lys Glu
        275                 280                 285

Lys Val Tyr Ala Glu Glu Ile Thr Thr Ala Trp Glu Thr Gly Glu Asn
    290                 295                 300

Leu Glu Arg Val Ala Arg Tyr Ser Met Glu Asp Ala Lys Val Thr Tyr
305                 310                 315                 320

Glu Leu Gly Lys Glu Phe Leu Pro Met Glu Ala Gln Leu Ser Arg Leu
                325                 330                 335

Ile Gly Gln Ser Leu Trp Asp Val Ser Arg Ser Ser Thr Gly Asn Leu
            340                 345                 350

Val Glu Trp Phe Leu Leu Arg Lys Ala Tyr Glu Arg Asn Glu Leu Ala
        355                 360                 365

Pro Asn Lys Pro Asp Glu Lys Glu Leu Ala Arg Arg Arg Gln Ser Tyr

-continued

```
            370                 375                 380
Glu Gly Gly Tyr Val Lys Glu Pro Glu Arg Gly Leu Trp Glu Asn Ile
385                 390                 395                 400

Val Tyr Leu Asp Phe Arg Ser Leu Tyr Pro Ser Ile Ile Thr His
                405                 410                 415

Asn Val Ser Pro Asp Thr Leu Asn Arg Glu Gly Cys Lys Glu Tyr Asp
                420                 425                 430

Val Ala Pro Gln Val Gly His Arg Phe Cys Lys Asp Phe Pro Gly Phe
                435                 440                 445

Ile Pro Ser Leu Leu Gly Asp Leu Leu Glu Arg Gln Lys Ile Lys
450                 455                 460

Lys Lys Met Lys Ala Thr Ile Asp Pro Ile Glu Arg Lys Leu Leu Asp
465                 470                 475                 480

Tyr Arg Gln Arg Ala Ile Lys Ile Leu Ala Asn Ser Tyr Tyr Gly Tyr
                485                 490                 495

Tyr Gly Tyr Ala Arg Ala Arg Trp Tyr Cys Lys Glu Cys Ala Glu Ser
                500                 505                 510

Val Thr Ala Trp Gly Arg Glu Tyr Ile Thr Met Thr Ile Lys Glu Ile
                515                 520                 525

Glu Glu Lys Tyr Gly Phe Lys Val Ile Tyr Ser Asp Thr Asp Gly Phe
530                 535                 540

Phe Ala Thr Ile Pro Gly Ala Asp Ala Glu Thr Val Lys Lys Lys Ala
545                 550                 555                 560

Met Glu Phe Leu Lys Tyr Ile Asn Ala Lys Leu Pro Gly Ala Leu Glu
                565                 570                 575

Leu Glu Tyr Glu Gly Phe Tyr Lys Arg Gly Phe Phe Val Thr Lys Lys
                580                 585                 590

Lys Tyr Ala Val Ile Asp Glu Glu Gly Lys Ile Thr Thr Arg Gly Leu
                595                 600                 605

Glu Ile Val Arg Arg Asp Trp Ser Glu Ile Ala Lys Glu Thr Gln Ala
                610                 615                 620

Arg Val Leu Glu Ala Leu Leu Lys Asp Gly Asp Val Glu Lys Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile His Glu Gln Ile Thr Arg Asp Leu Lys Asp
                660                 665                 670

Tyr Lys Ala Thr Gly Pro His Val Ala Val Ala Lys Arg Leu Ala Ala
                675                 680                 685

Arg Gly Val Lys Ile Arg Pro Gly Thr Val Ile Ser Tyr Ile Val Leu
690                 695                 700

Lys Gly Ser Gly Arg Ile Gly Asp Arg Ala Ile Pro Phe Asp Glu Phe
705                 710                 715                 720

Asp Pro Thr Lys His Lys Tyr Asp Ala Glu Tyr Tyr Ile Glu Asn Gln
                725                 730                 735

Val Leu Pro Ala Val Glu Arg Ile Leu Arg Ala Phe Gly Tyr Arg Lys
                740                 745                 750

Glu Asp Leu Arg Tyr Gln Lys Thr Arg Gln Val Gly Leu Ser Ala Trp
                755                 760                 765

Leu Lys Pro Lys Gly Thr
770

<210> SEQ ID NO 201
```

```
<211> LENGTH: 804
<212> TYPE: PRT
<213> ORGANISM: Pyrococcus abyssei
<220> FEATURE:
<221> NAME/KEY: misc_feature
<222> LOCATION: (804)..(804)
<223> OTHER INFORMATION: Xaa can be any naturally occurring amino acid

<400> SEQUENCE: 201
```

| | | | | | | | | | | | | | | | |
|---|---|---|---|---|---|---|---|---|---|---|---|---|---|---|---|
| Met | Pro | Glu | Ala | Ile | Glu | Phe | Val | Leu | Leu | Asp | Ser | Ser | Tyr | Glu | Ile |
| 1 | | | | 5 | | | | | 10 | | | | | 15 | |
| Val | Gly | Lys | Glu | Pro | Val | Ile | Ile | Leu | Trp | Gly | Val | Thr | Leu | Asp | Gly |
| | | | 20 | | | | | 25 | | | | | 30 | | |
| Lys | Arg | Ile | Val | Leu | Leu | Asp | Arg | Arg | Phe | Arg | Pro | Tyr | Phe | Tyr | Ala |
| | | | 35 | | | | | 40 | | | | | 45 | | |
| Leu | Ile | Ser | Arg | Asp | Tyr | Glu | Gly | Lys | Ala | Glu | Glu | Val | Val | Ala | Ala |
| | 50 | | | | | 55 | | | | | 60 | | | | |
| Ile | Arg | Arg | Leu | Ser | Met | Ala | Lys | Ser | Pro | Ile | Ile | Glu | Ala | Lys | Val |
| 65 | | | | | 70 | | | | | 75 | | | | | 80 |
| Val | Ser | Lys | Lys | Tyr | Phe | Gly | Arg | Pro | Arg | Lys | Ala | Val | Lys | Val | Thr |
| | | | | 85 | | | | | 90 | | | | | 95 | |
| Thr | Val | Ile | Pro | Glu | Ser | Val | Arg | Glu | Tyr | Arg | Glu | Ala | Val | Lys | Lys |
| | | | 100 | | | | | 105 | | | | | 110 | | |
| Leu | Glu | Gly | Val | Glu | Asp | Ser | Leu | Glu | Ala | Asp | Ile | Arg | Phe | Ala | Met |
| | | 115 | | | | | 120 | | | | | 125 | | | |
| Arg | Tyr | Leu | Ile | Asp | Lys | Lys | Leu | Tyr | Pro | Phe | Thr | Ala | Tyr | Arg | Val |
| | 130 | | | | | 135 | | | | | 140 | | | | |
| Arg | Ala | Glu | Asn | Ala | Gly | Arg | Ser | Pro | Gly | Phe | Arg | Val | Asp | Ser | Val |
| 145 | | | | | 150 | | | | | 155 | | | | | 160 |
| Tyr | Thr | Ile | Val | Glu | Asp | Pro | Glu | Pro | Ile | Ala | Asp | Ile | Thr | Ser | Ile |
| | | | | 165 | | | | | 170 | | | | | 175 | |
| Asp | Ile | Pro | Glu | Met | Arg | Val | Leu | Ala | Phe | Asp | Ile | Glu | Val | Tyr | Ser |
| | | | 180 | | | | | 185 | | | | | 190 | | |
| Lys | Arg | Gly | Ser | Pro | Asn | Pro | Ser | Arg | Asp | Pro | Val | Ile | Ile | Ile | Ser |
| | | 195 | | | | | 200 | | | | | 205 | | | |
| Ile | Lys | Asp | Ser | Lys | Gly | Asn | Glu | Lys | Leu | Leu | Glu | Ala | Asn | Asn | Tyr |
| | 210 | | | | | 215 | | | | | 220 | | | | |
| Asp | Asp | Arg | Asn | Val | Leu | Arg | Glu | Phe | Ile | Glu | Tyr | Ile | Arg | Ser | Phe |
| 225 | | | | | 230 | | | | | 235 | | | | | 240 |
| Asp | Pro | Asp | Ile | Ile | Val | Gly | Tyr | Asn | Ser | Asn | Asn | Phe | Asp | Trp | Pro |
| | | | | 245 | | | | | 250 | | | | | 255 | |
| Tyr | Leu | Ile | Glu | Arg | Ala | His | Arg | Ile | Gly | Val | Lys | Leu | Asp | Val | Thr |
| | | | 260 | | | | | 265 | | | | | 270 | | |
| Arg | Arg | Val | Gly | Ala | Glu | Pro | Ser | Met | Ser | Val | Tyr | Gly | His | Val | Ser |
| | | 275 | | | | | 280 | | | | | 285 | | | |
| Val | Gln | Gly | Arg | Leu | Asn | Val | Asp | Leu | Tyr | Asn | Tyr | Val | Glu | Glu | Met |
| | 290 | | | | | 295 | | | | | 300 | | | | |
| His | Glu | Ile | Lys | Val | Lys | Thr | Leu | Glu | Glu | Val | Ala | Glu | Tyr | Leu | Gly |
| 305 | | | | | 310 | | | | | 315 | | | | | 320 |
| Val | Met | Arg | Lys | Ser | Glu | Arg | Val | Leu | Ile | Glu | Trp | Trp | Arg | Ile | Pro |
| | | | | 325 | | | | | 330 | | | | | 335 | |
| Asp | Tyr | Trp | Asp | Asp | Glu | Lys | Lys | Arg | Pro | Leu | Leu | Lys | Arg | Tyr | Ala |
| | | | 340 | | | | | 345 | | | | | 350 | | |
| Leu | Asp | Asp | Val | Arg | Ala | Thr | Tyr | Gly | Leu | Ala | Glu | Lys | Ile | Leu | Pro |
| | | 355 | | | | | 360 | | | | | 365 | | | |

-continued

```
Phe Ala Ile Gln Leu Ser Thr Val Thr Gly Val Pro Leu Asp Gln Val
    370                 375                 380
Gly Ala Met Gly Val Gly Phe Arg Leu Glu Trp Tyr Leu Met Arg Ala
385                 390                 395                 400
Ala His Asp Met Asn Glu Leu Val Pro Asn Arg Val Lys Arg Arg Glu
                405                 410                 415
Glu Ser Tyr Lys Gly Ala Val Val Leu Lys Pro Leu Lys Gly Val His
            420                 425                 430
Glu Asn Val Val Val Leu Asp Phe Ser Ser Met Tyr Pro Asn Ile Met
        435                 440                 445
Ile Lys Tyr Asn Val Gly Pro Asp Thr Ile Ile Asp Asp Pro Ser Glu
    450                 455                 460
Cys Glu Lys Tyr Ser Gly Cys Tyr Val Ala Pro Glu Val Gly His Met
465                 470                 475                 480
Phe Arg Arg Ser Pro Ser Gly Phe Phe Lys Thr Val Leu Glu Asn Leu
                485                 490                 495
Ile Ala Leu Arg Lys Gln Val Arg Glu Lys Met Lys Glu Phe Pro Pro
            500                 505                 510
Asp Ser Pro Glu Tyr Arg Ile Tyr Asp Glu Arg Gln Lys Ala Leu Lys
        515                 520                 525
Val Leu Ala Asn Ala Ser Tyr Gly Tyr Met Gly Trp Val His Ala Arg
    530                 535                 540
Trp Tyr Cys Lys Arg Cys Ala Glu Ala Val Thr Ala Trp Gly Arg Asn
545                 550                 555                 560
Leu Ile Leu Ser Ala Ile Glu Tyr Ala Arg Lys Leu Gly Leu Lys Val
                565                 570                 575
Ile Tyr Gly Asp Thr Asp Ser Leu Phe Val Thr Tyr Asp Ile Glu Lys
            580                 585                 590
Val Lys Lys Leu Ile Glu Phe Val Glu Lys Gln Leu Gly Phe Glu Ile
        595                 600                 605
Lys Ile Asp Lys Val Tyr Lys Arg Val Phe Phe Thr Glu Ala Lys Lys
    610                 615                 620
Arg Tyr Val Gly Leu Leu Glu Asp Gly Arg Met Asp Ile Val Gly Phe
625                 630                 635                 640
Glu Ala Val Arg Gly Asp Trp Cys Glu Leu Ala Lys Glu Val Gln Glu
                645                 650                 655
Lys Val Ala Glu Ile Ile Leu Lys Thr Gly Asp Ile Asn Arg Ala Ile
            660                 665                 670
Ser Tyr Ile Arg Glu Val Val Arg Lys Leu Arg Glu Gly Lys Ile Pro
        675                 680                 685
Ile Thr Lys Leu Val Ile Trp Lys Thr Leu Thr Lys Arg Ile Glu Glu
    690                 695                 700
Tyr Glu His Glu Ala Pro His Val Thr Ala Ala Arg Arg Met Lys Glu
705                 710                 715                 720
Ala Gly Tyr Asp Val Ala Pro Gly Asp Lys Ile Gly Tyr Ile Ile Val
                725                 730                 735
Lys Gly His Gly Ser Ile Ser Ser Arg Ala Tyr Pro Tyr Phe Met Val
            740                 745                 750
Asp Ser Ser Lys Val Asp Thr Glu Tyr Tyr Ile Asp His Gln Ile Val
        755                 760                 765
Pro Ala Ala Met Arg Ile Leu Ser Tyr Phe Gly Val Thr Glu Lys Gln
    770                 775                 780
Leu Lys Ala Ala Ser Ser Gly His Arg Ser Leu Phe Asp Phe Phe Ala
```

Ala Lys Lys Xaa

<210> SEQ ID NO 202
<211> LENGTH: 804
<212> TYPE: PRT
<213> ORGANISM: Pyrococcus occultum
<220> FEATURE:
<221> NAME/KEY: misc_feature
<222> LOCATION: (804)..(804)
<223> OTHER INFORMATION: Xaa can be any naturally occurring amino acid

<400> SEQUENCE: 202

| | | | | | | | | | | | | | | |
|---|---|---|---|---|---|---|---|---|---|---|---|---|---|---|
| Met | Thr | Glu | Thr | Ile | Glu | Phe | Val | Leu | Leu | Asp | Ser | Ser | Tyr | Glu | Ile |
| 1 | | | | 5 | | | | | 10 | | | | | 15 | |
| Leu | Gly | Lys | Glu | Pro | Val | Val | Ile | Leu | Trp | Gly | Ile | Thr | Leu | Asp | Gly |
| | | | 20 | | | | | 25 | | | | | 30 | | |
| Lys | Arg | Val | Val | Leu | Leu | Asp | His | Arg | Phe | Arg | Pro | Tyr | Phe | Tyr | Ala |
| | | | 35 | | | | | 40 | | | | 45 | | | |
| Leu | Ile | Ala | Arg | Gly | Tyr | Glu | Asp | Met | Val | Glu | Ile | Ala | Ala | Ser | |
| | 50 | | | | | 55 | | | | | 60 | | | | |
| Ile | Arg | Arg | Leu | Ser | Val | Val | Lys | Ser | Pro | Ile | Ile | Asp | Ala | Lys | Pro |
| 65 | | | | | 70 | | | | | 75 | | | | | 80 |
| Leu | Asp | Lys | Arg | Tyr | Phe | Gly | Arg | Pro | Arg | Lys | Ala | Val | Lys | Ile | Thr |
| | | | | 85 | | | | | 90 | | | | | 95 | |
| Thr | Met | Ile | Pro | Glu | Ser | Val | Arg | His | Tyr | Arg | Glu | Ala | Val | Lys | Lys |
| | | | 100 | | | | | 105 | | | | | 110 | | |
| Ile | Glu | Gly | Val | Glu | Asp | Ser | Leu | Glu | Ala | Asp | Ile | Arg | Phe | Ala | Met |
| | | | 115 | | | | | 120 | | | | | 125 | | |
| Arg | Tyr | Leu | Ile | Asp | Lys | Arg | Leu | Tyr | Pro | Phe | Thr | Val | Tyr | Arg | Ile |
| | 130 | | | | | 135 | | | | | 140 | | | | |
| Pro | Val | Glu | Asp | Ala | Gly | Arg | Asn | Pro | Gly | Phe | Arg | Val | Asp | Arg | Val |
| 145 | | | | | 150 | | | | | 155 | | | | | 160 |
| Tyr | Lys | Val | Ala | Gly | Asp | Pro | Glu | Pro | Leu | Ala | Asp | Ile | Thr | Arg | Ile |
| | | | | 165 | | | | | 170 | | | | | 175 | |
| Asp | Leu | Pro | Pro | Met | Arg | Leu | Val | Ala | Phe | Asp | Ile | Glu | Val | Tyr | Ser |
| | | | 180 | | | | | 185 | | | | | 190 | | |
| Arg | Arg | Gly | Ser | Pro | Asn | Pro | Ala | Arg | Asp | Pro | Val | Ile | Ile | Val | Ser |
| | | | 195 | | | | | 200 | | | | | 205 | | |
| Leu | Arg | Asp | Ser | Glu | Gly | Lys | Glu | Arg | Leu | Ile | Glu | Ala | Glu | Gly | His |
| | 210 | | | | | 215 | | | | | 220 | | | | |
| Asp | Asp | Arg | Arg | Val | Leu | Arg | Glu | Phe | Val | Glu | Tyr | Val | Arg | Ala | Phe |
| 225 | | | | | 230 | | | | | 235 | | | | | 240 |
| Asp | Pro | Asp | Ile | Ile | Val | Gly | Tyr | Asn | Ser | Asn | His | Phe | Asp | Trp | Pro |
| | | | | 245 | | | | | 250 | | | | | 255 | |
| Tyr | Leu | Met | Glu | Arg | Ala | Arg | Leu | Gly | Ile | Lys | Leu | Asp | Val | Thr | |
| | | | 260 | | | | | 265 | | | | | 270 | | |
| Arg | Arg | Val | Gly | Ala | Glu | Pro | Thr | Thr | Ser | Val | Tyr | Gly | His | Val | Ser |
| | | | 275 | | | | | 280 | | | | | 285 | | |
| Val | Gln | Gly | Arg | Leu | Asn | Val | Asp | Leu | Tyr | Asp | Tyr | Ala | Glu | Glu | Met |
| | 290 | | | | | 295 | | | | | 300 | | | | |
| Pro | Glu | Ile | Lys | Met | Lys | Thr | Leu | Glu | Glu | Val | Ala | Glu | Tyr | Leu | Gly |
| 305 | | | | | 310 | | | | | 315 | | | | | 320 |
| Val | Met | Lys | Lys | Ser | Glu | Arg | Val | Ile | Ile | Glu | Trp | Trp | Arg | Ile | Pro |
| | | | | 325 | | | | | 330 | | | | | 335 | |

-continued

```
Glu Tyr Trp Asp Asp Glu Lys Lys Arg Gln Leu Leu Glu Arg Tyr Ala
                340                 345                 350

Leu Asp Asp Val Arg Ala Thr Tyr Gly Leu Ala Glu Lys Met Leu Pro
            355                 360                 365

Phe Ala Ile Gln Leu Ser Thr Val Thr Gly Val Pro Leu Asp Gln Val
        370                 375                 380

Gly Ala Met Gly Val Gly Phe Arg Leu Glu Trp Tyr Leu Met Arg Ala
385                 390                 395                 400

Ala Tyr Asp Met Asn Glu Leu Val Pro Asn Arg Val Glu Arg Arg Gly
                405                 410                 415

Glu Ser Tyr Lys Gly Ala Val Val Leu Lys Pro Leu Lys Gly Val His
            420                 425                 430

Glu Asn Val Val Val Leu Asp Phe Ser Ser Met Tyr Pro Ser Ile Met
        435                 440                 445

Ile Lys Tyr Asn Val Gly Pro Asp Thr Ile Val Asp Asp Pro Ser Glu
    450                 455                 460

Cys Pro Lys Tyr Gly Gly Cys Tyr Val Ala Pro Glu Val Gly His Arg
465                 470                 475                 480

Phe Arg Arg Ser Pro Pro Gly Phe Phe Lys Thr Val Leu Glu Asn Leu
                485                 490                 495

Leu Lys Leu Arg Arg Gln Val Lys Glu Lys Met Lys Glu Phe Pro Pro
            500                 505                 510

Asp Ser Pro Glu Tyr Arg Leu Tyr Asp Glu Arg Gln Lys Ala Leu Lys
        515                 520                 525

Val Leu Ala Asn Ala Ser Tyr Gly Tyr Met Gly Trp Ser His Ala Arg
    530                 535                 540

Trp Tyr Cys Lys Arg Cys Ala Glu Ala Val Thr Ala Trp Gly Arg Asn
545                 550                 555                 560

Leu Ile Leu Thr Ala Ile Glu Tyr Ala Arg Lys Leu Gly Leu Lys Val
                565                 570                 575

Ile Tyr Gly Asp Thr Asp Ser Leu Phe Val Val Tyr Asp Lys Glu Lys
            580                 585                 590

Val Glu Lys Leu Ile Glu Phe Val Glu Lys Glu Leu Gly Phe Glu Ile
        595                 600                 605

Lys Ile Asp Lys Ile Tyr Lys Lys Val Phe Phe Thr Glu Ala Lys Lys
    610                 615                 620

Arg Tyr Val Gly Leu Leu Glu Asp Gly Arg Ile Asp Ile Val Gly Phe
625                 630                 635                 640

Glu Ala Val Arg Gly Asp Trp Cys Glu Leu Ala Lys Glu Val Gln Glu
                645                 650                 655

Lys Ala Ala Glu Ile Val Leu Asn Thr Gly Asn Val Asp Lys Ala Ile
            660                 665                 670

Ser Tyr Ile Arg Glu Val Ile Lys Gln Leu Arg Glu Gly Lys Val Pro
        675                 680                 685

Ile Thr Lys Leu Ile Ile Trp Lys Thr Leu Ser Lys Arg Ile Glu Glu
    690                 695                 700

Tyr Glu His Asp Ala Pro His Val Met Ala Ala Arg Arg Met Lys Glu
705                 710                 715                 720

Ala Gly Tyr Glu Val Ser Pro Gly Asp Lys Val Gly Tyr Val Ile Val
                725                 730                 735

Lys Gly Ser Gly Ser Val Ser Ser Arg Ala Tyr Pro Tyr Phe Met Val
            740                 745                 750

Asp Pro Ser Thr Ile Asp Val Asn Tyr Tyr Ile Asp His Gln Ile Val
```

```
                    755                 760                 765
Pro Ala Ala Leu Arg Ile Leu Ser Tyr Phe Gly Val Thr Glu Lys Gln
        770                 775                 780

Leu Lys Ala Ala Ala Thr Val Gln Arg Ser Leu Phe Asp Phe Ala
785                 790                 795                 800

Ser Lys Lys Xaa

<210> SEQ ID NO 203
<211> LENGTH: 7
<212> TYPE: PRT
<213> ORGANISM: Artificial sequence
<220> FEATURE:
<223> OTHER INFORMATION: EXO I motif from Tma DNA polymerase

<400> SEQUENCE: 203

Asp Leu Glu Thr Ser Ser Leu
1               5
```